US009719098B2

(12) United States Patent
Argyros et al.

(10) Patent No.: US 9,719,098 B2
(45) Date of Patent: Aug. 1, 2017

(54) METHODS FOR THE IMPROVEMENT OF PRODUCT YIELD AND PRODUCTION IN A MICROORGANISM THROUGH THE ADDITION OF ALTERNATE ELECTRON ACCEPTORS

(71) Applicant: LALLEMAND HUNGARY LIQUIDITY MANAGEMENT LLC, Budapest (HU)

(72) Inventors: Aaron Argyros, White River Junction, VT (US); William Ryan Sillers, Lebanon, NH (US); Trisha Barrett, Bradford, VT (US); Nicky Caiazza, Lebanon, NH (US); Arthur J. Shaw, IV, Grantham, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 344 days.

(21) Appl. No.: 14/624,163

(22) Filed: Feb. 17, 2015

(65) Prior Publication Data

US 2015/0232863 A1 Aug. 20, 2015

Related U.S. Application Data

(63) Continuation of application No. 14/110,075, filed as application No. PCT/US2012/032443 on Apr. 5, 2012, now Pat. No. 8,956,851.

(60) Provisional application No. 61/472,085, filed on Apr. 5, 2011.

(51) Int. Cl.

| | |
|---|---|
| ***C12N 9/88*** | (2006.01) |
| ***C12N 15/52*** | (2006.01) |
| ***C12N 15/81*** | (2006.01) |
| ***C12N 9/10*** | (2006.01) |
| ***C12N 9/02*** | (2006.01) |

(52) U.S. Cl.

CPC ........... *C12N 15/81* (2013.01); *C12N 9/0008* (2013.01); *C12N 9/1029* (2013.01); *C12Y 102/0101* (2013.01); *C12Y 203/01054* (2013.01)

(58) Field of Classification Search

None

See application file for complete search history.

(56) References Cited

U.S. PATENT DOCUMENTS

| | | | |
|---|---|---|---|
| 5,422,267 | A | 6/1995 | Yocum et al. |
| 7,226,776 | B2 | 6/2007 | Ingram et al. |
| 7,846,712 | B2 | 12/2010 | Zhang et al. |
| 2005/0106734 | A1 | 5/2005 | Richard et al. |
| 2006/0257983 | A1 | 11/2006 | Bro et al. |
| 2010/0009418 | A1 | 1/2010 | San et al. |
| 2010/0062505 | A1 | 3/2010 | Gunawardena et al. |
| 2011/0189744 | A1 | 8/2011 | Mcbride et al. |
| 2011/0312054 | A1 | 12/2011 | Brevnova et al. |
| 2012/0003701 | A1 | 1/2012 | Brevnova et al. |

FOREIGN PATENT DOCUMENTS

| | | | |
|---|---|---|---|
| EP | 2 277 989 | A1 | 1/2011 |
| WO | 03/089626 | A1 | 10/2003 |
| WO | 2006/009434 | A1 | 1/2006 |
| WO | 2007/026957 | A2 | 3/2007 |
| WO | 2009/138877 | A2 | 11/2009 |
| WO | 2010/019882 | A1 | 2/2010 |
| WO | 2010/056805 | A2 | 5/2010 |
| WO | 2010/060056 | A2 | 5/2010 |
| WO | 2010/075529 | A2 | 7/2010 |
| WO | 2010/140386 | A1 | 12/2010 |
| WO | 2011/153516 | A2 | 12/2011 |
| WO | 2012/019175 | A2 | 2/2012 |
| WO | 2012/067510 | A1 | 5/2012 |

OTHER PUBLICATIONS

U.S. Appl. No. 14/110,075, filed Mar. 21, 2014, Methods for the Improvement of Product Yield and Production in a Microorganism Through the Addition of Alternate Electron Acceptors.

Somogyi, M., "Notes on Sugar Determination," J. Biol. Chem. 195:19-23, American Society for Biochemistry and Molecular Biology, United States (1952).

Stairs, C.W., et al.,"Eukaryotic pyruvate formate lyase and its activating enzyme were acquired laterally from a firmicute," Molecular Biology and Evolution, Advanced Access published Feb. 3, 2011, 42 pages, Oxford University Press, England (Feb. 2011).

Szybalski, W., "Use of the HPRT Gene and the HAT Selection Technique in DNA-Mediated Transformation of Mammalian Cells: First Steps Toward Developing Hybridoma Techniques and Gene Therapy," BioEssays 14(7):495-500, The Company of Biologists Limited, England (1992).

(Continued)

*Primary Examiner* — Kagnew H Gebreyesus

(74) *Attorney, Agent, or Firm* — Nutter McClennen & Fish LLP

(57) ABSTRACT

The present invention provides for novel metabolic pathways to reduce or eliminate glycerol production and increase product formation. More specifically, the invention provides for a recombinant microorganism comprising a deletion of one or more native enzymes that function to produce glycerol and/or regulate glycerol synthesis and one or more native and/or heterologous enzymes that function in one or more engineered metabolic pathways to convert a carbohydrate source, such as lignocellulose, to a product, such as ethanol, wherein the one or more native and/or heterologous enzymes is activated, upregulated, or downregulated. The invention also provides for a recombinant microorganism comprising one or more heterologous enzymes that function to regulate glycerol synthesis and one or more native and/or heterologous enzymes that function in one or more engineered metabolic pathways to convert a carbohydrate source to ethanol, wherein said one or more native and/or heterologous enzymes is activated, upregulated or downregulated.

31 Claims, 63 Drawing Sheets

(56) References Cited

OTHER PUBLICATIONS

Tamás, M.J., et al., "Fps1p controls the accumulation and release of the compatible solute glycerol in yeast osmoregulation," Molecular Microbiology, 31(4):1087-1104, Blackwell Science Ltd, England (1999).
Valadi, H., et al., "Improved ethanol production by glycerol-3-phosphate dehydrogenase mutants of *Saccharomyces cerevisiae*," Appl. Microbiol. Biotechnol. 50:434-39, Springer-Verlag, Germany (1998).
Vallee, B.L. and Hoch, F.L., "Zinc, A Component of Yeast Alcohol Dehydrogenase," PNAS 41(6):327-38, National Academy of Sciences, United States (1995).
van Walsum et al., "Allocation of ATP to synthesis of cells and hydrolytic enzymes in cellulolytic fermentative microorganisms: Bioenergetics, kinetics, and bioprocessing," Biotech. Bioeng., 58:316-320, (1998).
Wach, A., et al., "New Heterologous Modules for Classical or PCR-based Gene Disruptions in *Saccharomyces cerevisiae*," Yeast 10:1793-1808, John Wiley & Sons Ltd, England (1994).
Waks, Z. and Silver, P. A., "Engineering a Synthetic Dual-Organism System for Hydrogen Production," Appl.. Env. Microbiol., 75(7):1867-1875, American Society for Microbiology, United States (Apr. 2009).
Watanabe, S., et al., "Cloning, Expression, and Characterization of Bacterial L-Arabinose 1-Dehydrogenase Involved in an Alternative Pathway of L-Arabinose Metabolism," J. Biol. Chem., 281(5):2612-2623, American Society for Biochemistry and Molecular Biology, United States (2006).
Yu, K.O., et al., "Improvement of Ethanol Yield from Glycerol via Conversion of Pyruvate to Ethanol in Metabolically Engineered *Saccharomyces cerevisiae*," Appl. Biochem. Biotechnol. 166:856-65, Springer Science+Business Media, LLC, United States (2012).
Yu, K.O., et al., "Reduction of glycerol production to improve ethanol yield in an engineered *Saccharomyces cerevisiae* using glycerol as a substrate," J. Biotechnol. 2010,150:209-14.
[No Author Listed] "Backtranslation tool citations" accessed at www.entelechon.com/2008/1 0/backtranslation-tool/ on Mar. 21, 2014, (2 pages).
[No Author Listed] "backtranseq" accessed at emboss.bioinformatics.nl/cgi/bin/emboss/backtranseq on Mar. 28, 2013 (1 page).
[No Author Listed] "Codon Usage Database" accessed at http://www.kazusa.or.jp/codon/ on Apr. 23, 2013 (1 page).
[No Author Listed] Locus tag No. JDM1_2085, NCBI Database, accessed at http://www.ncbi.nlm.nih.gov/gene/?term=JDM1_2087 on May 1, 2013 (3 pages).
[No Author Listed] Locus tag No. JDM1_2087, NCBI Database, accessed at http://www.ncbi.nlm.nih.gov/gene/8188856 on Dec. 11, 2013, (2 pages).
[No Author Listed] Locus tag No. JDMI 2660, NCBI Database, accessed at http://www.ncbi.nlm.nih.gov/gene/?term=JDMI 2660 on Dec. 11, 2013,(2 pages).
[No Author Listed] Locus tag No. JDM1_2695, NCBI Database, accessed at http://www.ncbi.nlm.nih.gov/gene/?term=JDMI 2695 on May 1, 2013, 3 pages.
[No Author Listed] Locus tag No. Ip_2596, NCBI Database, accessed at http://www.ncbi.nlm.nih.gov/gene/?term=Ip_2596 on Dec. 11, 2013, (3 pages).
[No Author Listed] Locus tag No. Ip_2598, NCBI Database, accessed at http://www.ncbi.nlm.nih.gov/gene/?term=Ip_2598 on May 1, 2013, (3 pages).
[No Author Listed] Locus tag No. Ip_3313, NCBI Database, accessed at http://www.ncbi.nlm.nih.gov/gene/?term=IP_3313 on May 1, 2013, (3 pages).
[No Author Listed] Locus tag No. Ip 3314, NCBI Database, accessed at http://www.ncbi.nlm.nih.gov/gene/?term=IP 3314 on Dec. 11, 2013, (2 pages).
[No Author Listed] National Microbial Pathogen Data Resource, SEED Subsystem: L-Arabinose_utilization, accessed at http://www.nmpdr.org/FIG/subsys.cgi?user=&ssa_name=L-Arabinose_utilization&request=show.ssa, accessed on Jun. 11, 2013 (7 pages).
[No Author Listed] Phibro Animal Health Corporation, "Performance Products: Ethanol Red® (*Saccharomyces cerevisiae*)," accessed at http://www.pahc.com/Phibro/Performance-Products/Catalog/23/Ethanol-Red.html on Dec. 11, 2013, (1 page).
Ansell, R., et al., "The two isoenzymes for yeast NAD -dependent glycerol 3-phosphate dehydrogenase encoded by GDP1 and GDP2 have distinct roles in osmoadaptation and redox regulation," The EMBO Journal 16(9):2719-2187, Nature Publishing Group, England (1997).
Bro, C., et al., "In silico aided metabolic engineering of *Saccharomyces cerevisiae* for improved bioethanol production," Metabolic Engineering 8:102-111, Elsevier Inc., United States (2006).
Cavanaugh, M., "GenBank Release 128.0 Available," published Feb. 21, 2002, accessed at http://www.bio.net/bionet/mm/genbankb/2002-February/000110.html on Nov. 25, 2013, 3 pages.
Czako, M. and Marton, L., "The Herpes Simplex Virus Thymidine Kinase Gene as a Conditional Negative-Selection Marker Gene in *Arabidopsis thaliana*," Plant Physiol. 104:1067-71, American Society of Plant Physiologists, United States (1994).
Desai, S.G., et al., "Cloning of L-lactate dehydrogenase and elimination of lactic acid production via gene knockout in *Thermoanaerobacterium saccharolyticum* JW/SL-YS485," Appl Microbiol Biotechnol. Oct. 2004;65(5):600-5. Epub Mar. 6, 2004.
Gardiner, D.M. and Howlett, B.J., "Negative selection using thymidine kinase increases the efficiency of recovery of trans formants with targeted genes in the filamentous fungus *Leptosphaeria maculans*," Curr. Genet. 45:249-55, Springer-Verlag, Germany (2004).
Goldstein, A.L. and McCusker, J.H., "Three New Dominant Drug Resistance Cassettes for Gene Disruption in *Saccharomyces cerevisiae*," Yeast 15:1541-53, John Wiley & Sons, Ltd., England (1999).
Güldener, U., et al., "A new efficient gene disruption cassette for repeated use in budding yeast," Nucleic Acids Research 24(13):2519-24, Oxford University Press, England (1996).
Guo, Z.P., et al., "Improving ethanol productivity by modification of glycolytic redox factor generation in glycerol-3-phosphate dehydrogenase mutants of an industrial ethanol yeast," J Ind Microbiol. Biotechnol. 38:935-43, Springer, Germany (2011).
Guo, Z-P., et al., "Minimization of glycerol synthesis in industrial ethanol yeast without influencing its fermentation performance," Metabol. Eng. 1 3(1):49-59, Elsevier, Inc., United States (2010).
Hartzog, P.E., etal., "Cytosine deaminase MX cassettes as positive/negative markers in *Saccharomyces cerevisiae*," Yeast 22:789-98, Wiley InterScience, England (2005).
International Search Report for International Application No. PCT/US2012/032443, European Patent Office, Rijswijk, Netherlands, mailed on Jul. 2, 2012. (6 pages).
International Preliminary Report on Patentability, including the Written Opinion of the International Searching Authority, for International Application No. PCT/US2012/032443, The International Bureau of WIPO, Geneva, Switzerland, issued on Oct. 8, 2013. 8 pages).
Ito-Harashima, S. and McCusker, J.H., "Positive and negative selection LYS5MX gene replacement cassettes for use in *Saccharomyces cerevisiae*," Yeast 21:53-61, John Wiley & Sons, Ltd., England (2004).
Jain, V.K., etal., "Effect of alternative NAD+-regenerating pathways on the formation of primary and secondary aroma compounds in a *Saccharomyces cerevisiae* glycerol-defective mutant," Appl. Microbial. Biotechnol. 93:131-41, Springer-Verlag, Germany (2012).
Jeppsson, M., et al., "Reduced Oxidative Pentose Phosphate Pathway Flux in Recombinant Xylose-Utilizing *Saccharomyces cerevisiae* Strains Improves the Ethanol Yield from Xylose," Appl. Environ. Microbial. 68(4):1604-09, American Society for Microbiology, United States (2002).

(56) References Cited

OTHER PUBLICATIONS

Karhumaa, K., et al., "Comparison of xylose reductase-xylitol dehydrogenase and the xylose isomerase pathways for xylose fermentation by recombinant *Saccharomyces cerevisiae*," Microbial Cell Factories 6(5):1-10, BioMed Central, England (2007).
Karlgren, S., et al., "Conditional Osmotic Stress in Yeast: A System to Study Transport through Aquaglyceroporins and Osmostress Signaling," J. Biol. Chem. 280(8):7186-93, The American Society for Biochemistry and Molecular Biology, Inc., United States (2005).
Khang, C.H., et al., "A dual selection based, targeted gene replacement tool for *Magnoporthe grisea* and *Fusarium oxysporum*," Fungal Genetics and Biology 42:483-92, Elsevier Inc., United States (2005).
Kuyper, M., et al., "Evolutionary engineering of mixed-sugar utilization by a xylose-fermenting *Saccharomyces cerevisiae* strain," FEMS Yeast Res. Jul. 2005;5(10):925-34.
Kuyper M., et al., "Metabolic engineering of a xylose-isomerase-expressing *Saccharomyces cerevisiae* strain for rapid anaerobic xylose fermentation," FEMS Yeast Res. Feb. 2005;5(4-5):399-409.
Kuyper M., et al, "Minimal metabolic engineering of *Saccharomyces cerevisiae* for efficient anaerobic xylose fermentation: a proof of principle," FEMS Yeast Res. Mar. 2004;4(6):655-64.
Leal, T.F. and Sa-Nogueira, "Purification, characterization and functional analysis of an endo-arabinanase (AbnA) from *Bacillus subtilis*," FEMS Microbial. Let. 241:41-48, Elsevier, B.V., Netherlands (2004).
Liden, G., et al., "A Glycerol-3-Phosphate Dehydrogenase-Deficient Mutant of *Saccharomyces cerevisiae* Expressing the Heterologous XYLI Gene," Appl. Environ. Microbial. 62(10):3894-96, American Society for Microbiology, United States (1996).
Lynd, L.R., et al., "Microbial Cellulose Utilization: Fundamentals and Biotechnology," Microbiology and Molecular Biology Reviews, 66(3):506-577, American Society for Microbiology, United States (2002).
McLaughlin, S.B., et al., "High-value renewable energy from prairie grasses," Environ Sci Technol. May 15, 2002;36(10):2122-29.
Medina, V.G., et al.,"Elimination of Glycerol Production in Anaerobic Cultures of a *Saccharomyces cerevisiae* Strain Engineered to Use Acetic Acid As an Electron Acceptor," Applied and Environmental Microbiology, 76(1):190-195, American Society for Microbiology., United States (Jan. 2010).
Michnick, S. etal., "Modulation of Glycerol and Ethanol Yields During Alcoholic Fermentation in *Saccharomyces cerevisiae* Strains Overexpressed or Disrupted for GPDJ Encoding Glycerol 3-Phosphate Dehydrogenase," Yeast 13:783-93, John Wiley & Sons, England (1997).
Mollapour, M. and Piper, P.W., "Hog1 Mitogen-Activated Protein Kinase Phosphorylation Targets the Yeast Fps 1 Aquaglyceroporin for Endocytosis, Thereby Rendering Cells Resistant to Acetic Acid," Mol. Cell. Biol. 27 (18):6446-56, American Society for Microbiology, United States (2007).
Mota, L.J., et al., "Control of the Arabinose Regulation in *Bacillus subtilis* by AraR In Vivo: Crucial Roles of Operators, Cooperativity, and DNA Looping," J. Bacteriol., 183(14):4190-4201, American Society for Microbiology, United States (2001).
Mota, L.J., et al., "Mode of action of AraR, the key regulator of L-Arabinose metabolism in *Bacillus subtilis*," Molec. Microbiol., 33(3):476-489, Blackwell Science Ltd., England (1999).
Nakamura, Y., et al.,"Codon Usage Tabulated from International DNA Sequence Databases: Status for the Year 2000," Nucl. Acids Res., 28:292, Oxford University Press, United Kingdom (2000).
Nevoigt, E. "Progress in Metabolic Engineering of *Saccharomyces cerevisiae*," Microbial. Mol. Biol. Rev. 72(3):379-412, American Society for Microbiology, United States (2008).
Påhlman, A-K., et al., "The Yeast Glycerol 3-Phosphatases Gpp1p and Gpp2p Are Required for Glycerol Biosynthesis and Differentially Involved in the Cellular Response to Osmotic, Anaerobic, and Oxidative Stress," J. Biol. Chem., 276(5):3555-3563, American Society for Biochemistry and Molecular Biology, United States (2001).
Remize, F., et al., "Glycerol Export and Glycerol-3-phosphate Dehydrogenase, but Not Glycerol Phosphatase, Are Rate Limiting for Glycerol Production in *Saccharomyces cerevisiae*," Metab. Eng. 3:301-12, Academic Press, United States (2001).
Sá-Nogueira, I., et al, "The *Bacillus subtilis* L-arabinose (ara) operon: nucleotide sequence, genetic organization and expression," Microbiology, 143:957-969, Society for General Microbiology, Great Britain (1997).
Schleif, R., "Regulation of the L-arabinose operon of *Escherichia coli*," Trends in Genet. 16(1 2):559-65, Elsevier Science, Ltd., England (2000).

Figure 12 (cont'd)

```
                      (387) 387         400       410       420       430       440       450       460       470         483
   B. adolescentis pflB(315) IIDNLVMKLRIVRFLRTKDYDAIFSGDPYWATWSDAGFGDDGRTMVTKTSFRLLNTLTLEHLGPGPEPNITIFWDPKLPEAYKRFCARISIDTSAIQ
    C. reinhardtii pflB(379) LIDHFVMKLRIVRQLRTPEYNALFAGDPTWVTCVLGGTDASGKAMVTKTSFRLLN--TLYNLGPAPEPNLTVLWNDNLPAPFKEFCAKVSLDTSSIQ
         Piromyces pflB(355) IIDNLILKLRFARHLRTPEYNDLFAGDPTWVTMSLGGMGSDGRTLVTKTSFRVLN--TLYNLGPAPEPNITVLWNKALPKNFKDFATKVSIDTSSIQ
 C. cellulolyticum pflB(293) LVDHFVMKLRLVRFLRTPEYEKLFSGDPTWITESIGGMGLDGRTLVTKNSFRMLH--TLFNLGHAPEPNMTVLWSVHLPDGFKKYCSYVSINTSSIQ
            E. coli pflB(305) MVDHLVMKLRMVRFLRTPEYDELFSGDPIWATESIGGMGLDGRTLVTKNSFRFLN--TLYTMGPSPEPNMTILWSEKLPLNFKKFAAKVSIDTSSLQ
           L. casei pflB(302) LIDHLVMKLRMVRFIRTEEYNSLFSGDPIWATLSLAGMGNDGRHHVTKTAFRFLK--TLDNMGAAPEPNITLLWSERLPEGFKRYATEVSIQSSTIQ
           Consensus(387) LIDHLVMKLRIVRFLRTPEYNALFSGDPTWAT SLGGMG DGRTLVTKTSFRLLN  TLYNLGPAPEPNITVLWSEKLPEGFKKFCAKVSIDTSSIQ

                      (485) 485 490       500       510       520       530       540       550       560       570         581
   B. adolescentis pflB(413) ESDKEIRSHWG-DDAAIACCVSPMRVGKQMQFFAARVNSAKALLYAINGGRDEMTGMQVIDKGVIDPIKPEADGTLDYEKVKANYEKALEWLSETYV
    C. reinhardtii pflB(475) ESDNLMSKLFG-SDYSIACCVSAMRVGKDMQYFGARANLPKLLLYTLNGGRDEVSGDQVGPK--FAPVRSPT-APLDYEEVKAKIEDGMEWLASMYA
         Piromyces pflB(451) ESDALMSARFG-DDYGIACCVSAMRIGKDMQFFGARCNLAKLMLYVLNHGKDERTGKQVGPD--FGPVPE---GPIPFDWMWETYDKAMDWIAKLYV
 C. cellulolyticum pflB(389) ESDDIMRYYWG-DDYGIACCVSAMRIGKQMQFFGARCNMAKALLYAINGGRDEKSGVQVGPI--MQAIET---EYLDYDDVIKRFDAVLTWVARLYI
            E. coli pflB(401) ENDDLMRPDFNNDDYAIACCVSPMIVGKQMQFFGARANLAKTMLYAINGGVDEKLKMQVGPK--SEPIKG---DVLNYDEVMERMDHFMDWLAKQYI
           L. casei pflB(398) ENDDLMRNEWGTDYYGIACCVSAQPIADGVQYFGARANLAKTVLYAINGGKDEIQEAQVGPE--YAPITS---DYIDYKEFMNKFDKMMDWLADTYV
           Consensus(485) ESDDLMR   FG DDYGIACCVSAMRIGKQMQFFGARANLAK LLYAINGGRDEMSGMQVGPK  FAPIKS   G LDYDEVM KFDKAMDWLAKLYV

                      (581) 581      590       600       610       620       630       640       650       660              677
   B. adolescentis pflB(508) VMALNIIHYMHDKYAYESIEMALHDKEVYRTLGCGMSGLSIAADSLSACKYAKVYPIYNKDAKTTPGHENEYVEGADDDLIVGYRTEG-DFPLYGND
    C. reinhardtii pflB(567) ANTMNIIHYMHDKYDYERLQMALHDTHVRRLLAFGISGLSVVTDSLSAIKYAQVTPVIDER-----------------GLMTDFKVEG-SFPKYGND
         Piromyces pflB(541) VNTMNVIHFCHDQYCYESLQMALHDTDVRRLMAFGVAGLSVVADSFSAIKYAKVTPVRDAKT----------------GLTVDFKIEG-EFPKFGND
 C. cellulolyticum pflB(479) INTLNIIHYMHDKYAYERLQMALHDKDILRTMACGIAGLSVVADSLSAIKYAKVKVIRNEE-----------------GLAVDYDIEG-DYPKFGNN
            E. coli pflB(492) ITALNIIHYMHDKYSYEASLMALHDRDVIRTMACGIAGLSVAADSLSAIKYAKVKPIRDED-----------------GLAIDFEIEG-EYPQFGNN
           L. casei pflB(489) VNALNVIHYMHDKYYYEAAQLALKDTQLNRTFATGISGLSHAVDSISAIKYGHVKAIRDEN-----------------GVAVDFVADNDDYPRYGNN
           Consensus(581) VNTLNIIHYMHDKYAYEALQMALHDTDV RTMACGIAGLSVVADSLSAIKYAKVKPIRDED                  GLAVDFKIEG DFPKFGNN

                      (678) 678         690       700       710       720       730       740       750       760         774
   B. adolescentis pflB(604) DDRADDIAKWVVSTVMGQVKRLPVYRDAVPTQSILTITSNVEYGKATGAFPSGHKKGTPYAPGANPENGMDSHGMLPSMFSVGKIDYNDALDGISLT
    C. reinhardtii pflB(646) DDRVDEIAEWVVSTFSSKLAKQHTYRNSVPTLSVLTITSNVVYGKKTGSTPDGRKKGEPFAPGANPLHGRDAHGALASLNSVAKLPYTMCLDGISNT
         Piromyces pflB(621) DDRVDFFARTVTDKLINKLRKTPTYRGATHTLSILTITSNVVYGKKTGSTPDGRKAGQPFAPGCNPMHGREFSGAVASLSSVAKVNYDSCMDGISNT
 C. cellulolyticum pflB(558) DDRVDNIAVMLVKSFMEKLEKQRTYRHSVPTLSILTITSNVVYGAKTGNTPDGRKAGEPFGPGANPMHGRDLNGALAVLKSISKLPYQFAQDGISYT
            E. coli pflB(571) DPRVDDLAVDLVERFMKKIQKLHTYRDAIPTQSVLTITSNVVYGKKTGNTPDGRRAGAPFGPGANPMHGRDQKGAVASLTSVAKLPFAYAKDGISYT
           L. casei pflB(569) DDRADDIAKWLVKTFYNKMNTHHLYRGAKLSTSVLTITSNVVYGKNTGTTPNGRQKGEPFSPGANPAYGAEKNGALASLMSTAKIPYHYATDGISNT
           Consensus(678) DDRVDDIAKWLV TFM KL K HTYR AVPTLSILTITSNVVYGKKTGSTPDGRKKGEPFAPGANPMHGRD GALASL SVAKLPY YALDGISNT
                                                                         *                               *
```

Figure 12 (cont'd)

```
                      (775) 775  780       790       800       810       820       830       840       850       860         871
  B. adolescentis pflB(701) NTITPDGLGRD-EEERIGNLVGILDAGNG-----HGLYHANINVLRKEQLEDAVEHPEKYPHLTVRVSGYAVNFVKLTKEQQLDVISRTFHQGAVVD
     C. reinhardtii pflB(743) FSLIPQVLGRGGEHERATNLASILDGYFA-----NGGHHINVNVLNRSMLMDAVEHPEKYPNLTIRVSGYAVHFARLTREQQLEVIARTFHDTM---
        Piromyces pflB(718) FSIVPNTIGKS-LQERQGNLSGLLDGYFT-----KGAHHLNVNVLKRETLEDAMAHPENYPNLTIRVSGYAVNFVKLTPQQQKEVIARTFHEKM---
C. cellulolyticum pflB(655) FSIVPKALGKE-EDTRINNLVSLLDSYFK-----EGGHHINININVFEREMLLDAMDHPEKYPQLTIRVSGYAVNFIKLTREQQLDVINRTIHENI---
           E. coli pflB(668) FSIVPNALGKD-DEVRKTNLAGLMDGYFHHEASIEGGQHLNVNVMNREMLLDAMENPEKYPQLTIRVSGYAVRFNSLTKEQQQDVITRTFTQSM---
          L. casei pflB(666) FGVTPNTLGHD-DETRKDTLVHMVDGYME-----NSGMHLNINVFNKETLIDAQKHPEEYPTLTVRVSGYCVYFADLTKEQQDDVIARTFFEEM---
            Consensus(775) FSIVPNALGKD EEER  NLVGLLDGYF       GGHHLNINVLNREMLLDAMEHPEKYPNLTIRVSGYAVNFVKLTKEQQLDVIARTFHE M
                                                                                                             *
```

AdhE: alcohol dehydrogenase activity

SEQUENCE LISTING

```
<160> NUMBER OF SEQ ID NOS: 191

<210> SEQ ID NO 1
<211> LENGTH: 3599
<212> TYPE: DNA
<213> ORGANISM: Saccharomyces cerevisiae
<220> FEATURE:
<221> NAME/KEY: misc_feature
<223> OTHER INFORMATION: FPS1
<220> FEATURE:
<221> NAME/KEY: misc_feature
<222> LOCATION: (801)..(2810)
<223> OTHER INFORMATION: coding sequence

<400> SEQUENCE: 1

ttgacggcag ttctcatagc atctcaaagc aatagcagtg caaaagtaca taaccgtagg     60

aaggtacgcg gtaggtattt gagttcgttg gtggttatcc tccgcaaggc gcttcggcgg    120

ttatttgttg atagtcgaag aacaccaaaa aaaatgctgt tattgctttc tccgtaaaca    180

ataaaacccg gtagcgggat aacgcggctg atgcttttat ttaggaagga atacttacat    240

tatcatgaga acattgtcaa gggcattctg atacgggcct tccatcgcaa gaaaaaggca    300

gcaacggact gagggacgga gagagttacg gcataagaag tagtaggaga gcagagtgtc    360

ataaagttat attattctcg tcctaaagtc aattagttct gttgcgcttg acaatatatg    420

tcgtgtaata ccgtccctta gcagaagaaa gaaagacgga tccatatatg ttaaaatgct    480

tcagagatgt ttctttaatg tgccgtccaa caaaggtatc ttctgtagct tcctctattt    540

tcgatcagat ctcatagtga gaaggcgcaa ttcagtagtt aaaagcgggg aacagtgtga    600

atccggagac ggcaagattg cccggccctt tttgcggaaa agataaaaca agatatattg    660

cactttttcc accaagaaaa acaggaagtg gattaaaaaa tcaacaaagt ataacgccta    720

ttgtcccaat aagcgtcggt tgttcttctt tattatttta ccaagtacgc tcgagggtac    780

attctaatgc attaaaagac atgagtaatc ctcaaaaagc tctaaacgac tttctgtcca    840

gtgaatctgt tcatacacat gatagttcta ggaaacaatc taataagcag tcatccgacg    900

aaggacgctc ttcatcacaa ccttcacatc atcactctgg tggtactaac aacaataata    960

acaataataa taataataat aacagtaaca acaacaacaa cggcaacgat gggggaaatg   1020

atgacgacta tgattatgaa atgcaagatt atagaccttc tccgcaaagt gcgcggccta   1080

ctcccacgta tgttccacaa tattctgtag aaagtgggac tgctttcccg attcaagagg   1140

ttattcctag cgcatacatt aacacacaag atataaacca taaagataac ggtccgccga   1200
```

-continued

```
gtgcaagcag taatagagca ttcaggccta gagggcagac cacagtgtcg gccaacgtgc   1260
ttaacattga agatttttac aaaaatgcag acgatgcgca taccatcccg gagtcacatt   1320
tatcgagaag gagaagtagg tcgagggcta cgagtaatgc tgggcacagt gccaatacag   1380
gcgccacgaa tggcaggact actggtgccc aaactaatat ggaaagcaat gaatcaccac   1440
gtaacgtccc cattatggtg aagccaaaga cattatacca gaaccctcaa acacctacag   1500
tcttgccctc cacataccat ccaattaata aatggtcttc cgtcaaaaac acttatttga   1560
aggaattttt agccgagttt atgggaacaa tggttatgat tattttcggt agtgctgttg   1620
tttgtcaggt caatgttgct gggaaaatac agcaggacaa tttcaacgtg gctttggata   1680
accttaacgt taccgggtct tctgcagaaa cgatagacgc tatgaagagt ttaacatcct   1740
tggtttcatc cgttgcgggc ggtacctttg atgatgtggc attgggctgg gctgctgccg   1800
tggtgatggg ctatttctgc gctggtggta gtgccatctc aggtgctcat ttgaatccgt   1860
ctattacatt agccaatttg gtgtatagag gttttcccct gaagaaagtt ccttattact   1920
ttgctggaca attgatcggt gccttcacag gcgctttgat cttgtttatt tggtacaaaa   1980
gggtgttaca agaggcatat agcgattggt ggatgaatga aagtgttgcg ggaatgtttt   2040
gcgtttttcc aaagccttat ctaagttcag gacggcaatt tttttccgaa tttttatgtg   2100
gagctatgtt acaagcagga acatttgcgc tgaccgatcc ttatacgtgt ttgtcctctg   2160
atgttttccc attgatgatg tttattttga ttttcattat caatgcttcc atggcttatc   2220
agacaggtac agcaatgaat ttggctcgtg atctgggccc acgtcttgca ctatatgcag   2280
ttggatttga tcataaaatg ctttgggtgc atcatcatca tttcttttgg gttcccatgg   2340
taggcccatt tattggtgcg ttaatggggg ggttggttta cgatgtctgt atttatcagg   2400
gtcatgaatc tccagtcaac tggtctttac cagtttataa ggaaatgatt atgagagcct   2460
ggtttagaag gcctggttgg aagaagagaa atagagcaag aagaacatcg gacctgagtg   2520
acttctcata caataacgat gatgatgagg aatttggaga aagaatggct cttcaaaaga   2580
caaagaccaa gtcatctatt tcagacaacg aaaatgaagc aggagaaaag aaagtgcaat   2640
ttaaatctgt tcagcgcggc aaaagaacgt ttggtggtat accaacaatt cttgaagaag   2700
aagattccat tgaaactgct tcgctaggtg cgacgacgac tgattctatt gggttatccg   2760
acacatcatc agaagattcg cattatggta atgctaagaa ggtaacatga gaaaacagac   2820
aagaaaaaga aacaaataat atagactgat agaaaaaaat actgcttact accgccggta   2880
taatatatat atatatatat atttacatag atgattgcat agtgttttaa aaagctttcc   2940
taggttaagc tatgaatctt cataacctaa ccaactaaat atgaaaatac tgacccatcg   3000
tcttaagtaa gttgacatga actcagcctg gtcacctact atacatgatg tatcgcatgg   3060
atggaaagaa taccaaacgc taccttccag gttaatgata gtatccaaac ctagttggaa   3120
tttgccttga acatcaagca gcgattcgat atcagttggg agcatcaatt tggtcattgg   3180
aataccatct atgcttttct cctcccatat tcgcaaaagt agtaagggct cgttatatac   3240
ttttgaatat gtaagatata attctatatg atttagtaat ttattttcta tacgctcagt   3300
atttttctgc agttgtcgag taggtattaa acgcaaaaga agtccatcct tttcatcatt   3360
caaatggaca tcttggcaaa gggcccagtt atggaaaatc tgggagtcat acaacgattg   3420
cagttggcta tgccactcct ggtaaggaat catcaagtct gataattctg tttttttagcc   3480
cttttttttt ttttttcatg gtgttctctt ctcattgctt ttcaatttta agttcgttac   3540
ctttcatata gagtttctta acagaaattt cacaacgaaa atataattaa ctacaggca    3599
```

<210> SEQ ID NO 2
<211> LENGTH: 669
<212> TYPE: PRT
<213> ORGANISM: Saccharomyces cerevisiae
<220> FEATURE:
<221> NAME/KEY: MISC_FEATURE
<223> OTHER INFORMATION: FPS1

<400> SEQUENCE: 2

```
Met Ser Asn Pro Gln Lys Ala Leu Asn Asp Phe Leu Ser Ser Glu Ser
1               5                   10                  15

Val His Thr His Asp Ser Ser Arg Lys Gln Ser Asn Lys Gln Ser Ser
            20                  25                  30

Asp Glu Gly Arg Ser Ser Ser Gln Pro Ser His His His Ser Gly Gly
        35                  40                  45

Thr Asn Asn Asn Asn Asn Asn Asn Asn Asn Asn Asn Asn Ser Asn Asn
    50                  55                  60

Asn Asn Asn Gly Asn Asp Gly Gly Asn Asp Asp Asp Tyr Asp Tyr Glu
65                  70                  75                  80

Met Gln Asp Tyr Arg Pro Ser Pro Gln Ser Ala Arg Pro Thr Pro Thr
                85                  90                  95

Tyr Val Pro Gln Tyr Ser Val Glu Ser Gly Thr Ala Phe Pro Ile Gln
            100                 105                 110

Glu Val Ile Pro Ser Ala Tyr Ile Asn Thr Gln Asp Ile Asn His Lys
        115                 120                 125

Asp Asn Gly Pro Pro Ser Ala Ser Ser Asn Arg Ala Phe Arg Pro Arg
    130                 135                 140

Gly Gln Thr Thr Val Ser Ala Asn Val Leu Asn Ile Glu Asp Phe Tyr
145                 150                 155                 160

Lys Asn Ala Asp Asp Ala His Thr Ile Pro Glu Ser His Leu Ser Arg
                165                 170                 175

Arg Arg Ser Arg Ser Arg Ala Thr Ser Asn Ala Gly His Ser Ala Asn
            180                 185                 190

Thr Gly Ala Thr Asn Gly Arg Thr Thr Gly Ala Gln Thr Asn Met Glu
        195                 200                 205

Ser Asn Glu Ser Pro Arg Asn Val Pro Ile Met Val Lys Pro Lys Thr
    210                 215                 220

Leu Tyr Gln Asn Pro Gln Thr Pro Thr Val Leu Pro Ser Thr Tyr His
225                 230                 235                 240

Pro Ile Asn Lys Trp Ser Ser Val Lys Asn Thr Tyr Leu Lys Glu Phe
                245                 250                 255

Leu Ala Glu Phe Met Gly Thr Met Val Met Ile Ile Phe Gly Ser Ala
            260                 265                 270

Val Val Cys Gln Val Asn Val Ala Gly Lys Ile Gln Gln Asp Asn Phe
        275                 280                 285

Asn Val Ala Leu Asp Asn Leu Asn Val Thr Gly Ser Ser Ala Glu Thr
    290                 295                 300

Ile Asp Ala Met Lys Ser Leu Thr Ser Leu Val Ser Ser Val Ala Gly
305                 310                 315                 320

Gly Thr Phe Asp Asp Val Ala Leu Gly Trp Ala Ala Ala Val Val Met
                325                 330                 335

Gly Tyr Phe Cys Ala Gly Gly Ser Ala Ile Ser Gly Ala His Leu Asn
            340                 345                 350

Pro Ser Ile Thr Leu Ala Asn Leu Val Tyr Arg Gly Phe Pro Leu Lys
```

```
        355                 360                 365

Lys Val Pro Tyr Tyr Phe Ala Gly Gln Leu Ile Gly Ala Phe Thr Gly
    370                 375                 380

Ala Leu Ile Leu Phe Ile Trp Tyr Lys Arg Val Leu Gln Glu Ala Tyr
385                 390                 395                 400

Ser Asp Trp Trp Met Asn Glu Ser Val Ala Gly Met Phe Cys Val Phe
                405                 410                 415

Pro Lys Pro Tyr Leu Ser Ser Gly Arg Gln Phe Phe Ser Glu Phe Leu
            420                 425                 430

Cys Gly Ala Met Leu Gln Ala Gly Thr Phe Ala Leu Thr Asp Pro Tyr
        435                 440                 445

Thr Cys Leu Ser Ser Asp Val Phe Pro Leu Met Met Phe Ile Leu Ile
    450                 455                 460

Phe Ile Ile Asn Ala Ser Met Ala Tyr Gln Thr Gly Thr Ala Met Asn
465                 470                 475                 480

Leu Ala Arg Asp Leu Gly Pro Arg Leu Ala Leu Tyr Ala Val Gly Phe
                485                 490                 495

Asp His Lys Met Leu Trp Val His His His His Phe Phe Trp Val Pro
            500                 505                 510

Met Val Gly Pro Phe Ile Gly Ala Leu Met Gly Gly Leu Val Tyr Asp
        515                 520                 525

Val Cys Ile Tyr Gln Gly His Glu Ser Pro Val Asn Trp Ser Leu Pro
    530                 535                 540

Val Tyr Lys Glu Met Ile Met Arg Ala Trp Phe Arg Arg Pro Gly Trp
545                 550                 555                 560

Lys Lys Arg Asn Arg Ala Arg Arg Thr Ser Asp Leu Ser Asp Phe Ser
                565                 570                 575

Tyr Asn Asn Asp Asp Asp Glu Glu Phe Gly Glu Arg Met Ala Leu Gln
            580                 585                 590

Lys Thr Lys Thr Lys Ser Ser Ile Ser Asp Asn Glu Asn Glu Ala Gly
        595                 600                 605

Glu Lys Lys Val Gln Phe Lys Ser Val Gln Arg Gly Lys Arg Thr Phe
    610                 615                 620

Gly Gly Ile Pro Thr Ile Leu Glu Glu Glu Asp Ser Ile Glu Thr Ala
625                 630                 635                 640

Ser Leu Gly Ala Thr Thr Thr Asp Ser Ile Gly Leu Ser Asp Thr Ser
                645                 650                 655

Ser Glu Asp Ser His Tyr Gly Asn Ala Lys Lys Val Thr
            660                 665
```

<210> SEQ ID NO 3
<211> LENGTH: 759
<212> TYPE: DNA
<213> ORGANISM: Bacillus licheniformis
<220> FEATURE:
<221> NAME/KEY: misc_feature
<223> OTHER INFORMATION: DSM13

<400> SEQUENCE: 3

```
atggatggaa atattcattc gatcgaaaca ttcggcaccg ttgacggtcc aggcatcagg      60

tatgtcgtct tcacacaagg ctgcctgatg cgctgtcaat tttgccataa tgctgatact     120

tgggaaatcg gaaccggaaa acaaatgacg gtttccgaaa tcgttcagga tgtccagcat     180

tatctcccgt ttattcaatc atcgggcgga ggcatcaccg tgagcggagg cgagccgctt     240

ttacaactgc cgtttttaat cgagctgttc aaagcatgca aaagcctcgg cattcacacg     300
```

```
gcactcgatt cgtccggcgg atgctattcg gctgcgccgg catttcaaga gcagatcaaa    360

gaactgatcc agtatacaga ccttgttttg cttgacctca agcatcacaa cagaaaaaaa    420

catatcaacc tgacaggaat gccgaatgac cacattttag aatttgcccg gtttctcgct    480

gaacatcaag ttcccgtctg gatccgccac gtactggttc cggggatctc cgatatcgat    540

gccgatttaa cggccctcgg cacgtttatc ggcacgcttg cgaacgttca gaaggtggag    600

gttcttcctt atcacaagct cggcgtctac aaatgggaag cgcttggcct ggattatccg    660

ttaaaagggg ttgaaccgcc aagtgccgac agggccgaaa atgcgtacag actgctcacc    720

gcacacttgc aaggcggatc cttgctgcaa gagacataa                           759
```

```
<210> SEQ ID NO 4
<211> LENGTH: 252
<212> TYPE: PRT
<213> ORGANISM: Bacillus licheniformis
<220> FEATURE:
<221> NAME/KEY: MISC_FEATURE
<223> OTHER INFORMATION: DSM13

<400> SEQUENCE: 4

Met Asp Gly Asn Ile His Ser Ile Glu Thr Phe Gly Thr Val Asp Gly
1               5                   10                  15

Pro Gly Ile Arg Tyr Val Val Phe Thr Gln Gly Cys Leu Met Arg Cys
            20                  25                  30

Gln Phe Cys His Asn Ala Asp Thr Trp Glu Ile Gly Thr Gly Lys Gln
        35                  40                  45

Met Thr Val Ser Glu Ile Val Gln Asp Val Gln His Tyr Leu Pro Phe
    50                  55                  60

Ile Gln Ser Ser Gly Gly Gly Ile Thr Val Ser Gly Gly Glu Pro Leu
65                  70                  75                  80

Leu Gln Leu Pro Phe Leu Ile Glu Leu Phe Lys Ala Cys Lys Ser Leu
                85                  90                  95

Gly Ile His Thr Ala Leu Asp Ser Ser Gly Gly Cys Tyr Ser Ala Ala
            100                 105                 110

Pro Ala Phe Gln Glu Gln Ile Lys Glu Leu Ile Gln Tyr Thr Asp Leu
        115                 120                 125

Val Leu Leu Asp Leu Lys His His Asn Arg Lys Lys His Ile Asn Leu
    130                 135                 140

Thr Gly Met Pro Asn Asp His Ile Leu Glu Phe Ala Arg Phe Leu Ala
145                 150                 155                 160

Glu His Gln Val Pro Val Trp Ile Arg His Val Leu Val Pro Gly Ile
                165                 170                 175

Ser Asp Ile Asp Ala Asp Leu Thr Ala Leu Gly Thr Phe Ile Gly Thr
            180                 185                 190

Leu Ala Asn Val Gln Lys Val Glu Val Leu Pro Tyr His Lys Leu Gly
        195                 200                 205

Val Tyr Lys Trp Glu Ala Leu Gly Leu Asp Tyr Pro Leu Lys Gly Val
    210                 215                 220

Glu Pro Pro Ser Ala Asp Arg Ala Glu Asn Ala Tyr Arg Leu Leu Thr
225                 230                 235                 240

Ala His Leu Gln Gly Gly Ser Leu Leu Gln Glu Thr
                245                 250


<210> SEQ ID NO 5
<211> LENGTH: 759
```

<212> TYPE: DNA
<213> ORGANISM: Bacillus licheniformis
<220> FEATURE:
<221> NAME/KEY: misc_feature
<223> OTHER INFORMATION: ATCC14580

<400> SEQUENCE: 5

```
atggatggaa atattcattc gatcgaaaca ttcggcaccg ttgacggtcc aggcatcagg      60

tatgtcgtct tcacacaagg ctgcctgatg cgctgtcaat tttgccataa tgctgatact     120

tgggaaatcg gaaccggaaa acaaatgacg gtttccgaaa tcgttcagga tgtccagcat     180

tatctcccgt ttattcaatc atcgggcgga ggcatcaccg tgagcggagg cgagccgctt     240

ttacaactgc cgtttttaat cgagctgttc aaagcatgca aaagcctcgg cattcacacg     300

gcactcgatt cgtccggcgg atgctattcg gctgcgccgg catttcaaga gcagatcaaa     360

gaactgatcc agtatacaga ccttgttttg cttgacctca agcatcacaa cagaaaaaaa     420

catatcaacc tgacaggaat gccgaatgac cacattttag aatttgcccg gtttctcgct     480

gaacatcaag ttcccgtctg gatccgccac gtactggttc cggggatctc cgatatcgat     540

gccgatttaa cggccctcgg cacgtttatc ggcacgcttg cgaacgttca gaaggtggag     600

gttcttcctt atcacaagct cggcgtctac aaatgggaag cgcttggcct ggattatccg     660

ttaaaagggg ttgaaccgcc aagtgccgac agggccgaaa atgcgtacag actgctcacc     720

gcacacttgc aaggcggatc cttgctgcaa gagacataa                            759
```

<210> SEQ ID NO 6
<211> LENGTH: 252
<212> TYPE: PRT
<213> ORGANISM: Bacillus licheniformis
<220> FEATURE:
<221> NAME/KEY: MISC_FEATURE
<223> OTHER INFORMATION: ATCC14580

<400> SEQUENCE: 6

```
Met Asp Gly Asn Ile His Ser Ile Glu Thr Phe Gly Thr Val Asp Gly
1               5                   10                  15

Pro Gly Ile Arg Tyr Val Val Phe Thr Gln Gly Cys Leu Met Arg Cys
            20                  25                  30

Gln Phe Cys His Asn Ala Asp Thr Trp Glu Ile Gly Thr Gly Lys Gln
        35                  40                  45

Met Thr Val Ser Glu Ile Val Gln Asp Val Gln His Tyr Leu Pro Phe
    50                  55                  60

Ile Gln Ser Ser Gly Gly Gly Ile Thr Val Ser Gly Gly Glu Pro Leu
65                  70                  75                  80

Leu Gln Leu Pro Phe Leu Ile Glu Leu Phe Lys Ala Cys Lys Ser Leu
                85                  90                  95

Gly Ile His Thr Ala Leu Asp Ser Ser Gly Gly Cys Tyr Ser Ala Ala
            100                 105                 110

Pro Ala Phe Gln Glu Gln Ile Lys Glu Leu Ile Gln Tyr Thr Asp Leu
        115                 120                 125

Val Leu Leu Asp Leu Lys His His Asn Arg Lys Lys His Ile Asn Leu
    130                 135                 140

Thr Gly Met Pro Asn Asp His Ile Leu Glu Phe Ala Arg Phe Leu Ala
145                 150                 155                 160

Glu His Gln Val Pro Val Trp Ile Arg His Val Leu Val Pro Gly Ile
                165                 170                 175

Ser Asp Ile Asp Ala Asp Leu Thr Ala Leu Gly Thr Phe Ile Gly Thr
```

-continued

```
            180                 185                 190

Leu Ala Asn Val Gln Lys Val Glu Val Leu Pro Tyr His Lys Leu Gly
        195                 200                 205

Val Tyr Lys Trp Glu Ala Leu Gly Leu Asp Tyr Pro Leu Lys Gly Val
    210                 215                 220

Glu Pro Pro Ser Ala Asp Arg Ala Glu Asn Ala Tyr Arg Leu Leu Thr
225                 230                 235                 240

Ala His Leu Gln Gly Gly Ser Leu Leu Gln Glu Thr
                245                 250


<210> SEQ ID NO 7
<211> LENGTH: 801
<212> TYPE: DNA
<213> ORGANISM: Streptococcus thermophilus
<220> FEATURE:
<221> NAME/KEY: misc_feature
<223> OTHER INFORMATION: CNRZ1066

<400> SEQUENCE: 7

atggcagaaa ttgattacag tcaggtgact ggacttgttc attcaaccga aagtttcgga      60

tccgtagatg gtcctggtat ccgttttatt gtgtttatgc aaggctgtaa gctgcgttgc     120

caatattgtc ataacccaga tacttgggcc atgaagtcaa ataaggctgt tgaacgtaca     180

gttgaagatg tcttagaaga ggctcttcgc ttccgtcatt tctggggtga gcatggtgga     240

atcactgtat caggtggtga agccatgctt cagattgatt ttgtcactgc cctctttaca     300

gaggctaaga agttagggat tcactgtacg cttgatacgt gtggcttgtc ttatcgtaat     360

actccagagt atcatgaagt tgtcgacaaa cttttggctg taactgactt ggttctactg     420

gatatcaaag agattgaccc cgaacaacac aagtttgtga cccgtcaacc taataagaat     480

atcttggaat ttgctcaata tctgtctgat aaacaagttc cggtctggat tcgtcatgtc     540

ttggtacctg gtttgacaga ttttgacgaa cacttggtta agctcggcga gtttgtaaag     600

accttgaaaa atgtcgataa atttgaaatt cttccatatc atacgatggg ggaattcaag     660

tggcgtgaac ttggcatccc ttatccattg gaaggtgtca aaccaccaac tgcagatcgt     720

gttaaaaatg ctaaggctct tatgcatacg gaaacttatc aagagtataa gaatcgtatc     780

ggggttaaaa ccttggatta a                                               801


<210> SEQ ID NO 8
<211> LENGTH: 266
<212> TYPE: PRT
<213> ORGANISM: Streptococcus thermophilus
<220> FEATURE:
<221> NAME/KEY: MISC_FEATURE
<223> OTHER INFORMATION: CNRZ1066

<400> SEQUENCE: 8

Met Ala Glu Ile Asp Tyr Ser Gln Val Thr Gly Leu Val His Ser Thr
1               5                   10                  15

Glu Ser Phe Gly Ser Val Asp Gly Pro Gly Ile Arg Phe Ile Val Phe
            20                  25                  30

Met Gln Gly Cys Lys Leu Arg Cys Gln Tyr Cys His Asn Pro Asp Thr
        35                  40                  45

Trp Ala Met Lys Ser Asn Lys Ala Val Glu Arg Thr Val Glu Asp Val
    50                  55                  60

Leu Glu Glu Ala Leu Arg Phe Arg His Phe Trp Gly Glu His Gly Gly
65                  70                  75                  80
```

-continued

```
Ile Thr Val Ser Gly Gly Glu Ala Met Leu Gln Ile Asp Phe Val Thr
                85                  90                  95

Ala Leu Phe Thr Glu Ala Lys Lys Leu Gly Ile His Cys Thr Leu Asp
            100                 105                 110

Thr Cys Gly Leu Ser Tyr Arg Asn Thr Pro Glu Tyr His Glu Val Val
        115                 120                 125

Asp Lys Leu Leu Ala Val Thr Asp Leu Val Leu Leu Asp Ile Lys Glu
    130                 135                 140

Ile Asp Pro Glu Gln His Lys Phe Val Thr Arg Gln Pro Asn Lys Asn
145                 150                 155                 160

Ile Leu Glu Phe Ala Gln Tyr Leu Ser Asp Lys Gln Val Pro Val Trp
                165                 170                 175

Ile Arg His Val Leu Val Pro Gly Leu Thr Asp Phe Asp Glu His Leu
            180                 185                 190

Val Lys Leu Gly Glu Phe Val Lys Thr Leu Lys Asn Val Asp Lys Phe
        195                 200                 205

Glu Ile Leu Pro Tyr His Thr Met Gly Glu Phe Lys Trp Arg Glu Leu
    210                 215                 220

Gly Ile Pro Tyr Pro Leu Glu Gly Val Lys Pro Pro Thr Ala Asp Arg
225                 230                 235                 240

Val Lys Asn Ala Lys Ala Leu Met His Thr Glu Thr Tyr Gln Glu Tyr
                245                 250                 255

Lys Asn Arg Ile Gly Val Lys Thr Leu Asp
            260                 265
```

<210> SEQ ID NO 9
<211> LENGTH: 801
<212> TYPE: DNA
<213> ORGANISM: Streptococcus thermophilus
<220> FEATURE:
<221> NAME/KEY: misc_feature
<223> OTHER INFORMATION: LMG18311

<400> SEQUENCE: 9

```
atggcagaaa ttgattacag tcaggtgact ggacttgttc attcaaccga aagtttcgga      60

tccgtagatg gtcctggtat ccgttttatt gtgtttatgc aaggctgtaa gctgcgttgc     120

caatattgtc ataacccaga tacttgggcc atgaagtcaa ataaggctgt tgaacgtaca     180

gttgaagatg tcttagaaga ggctcttcgc ttccgtcatt tctggggtga gcatggtgga     240

atcactgtat caggtggtga agccatgctt cagattgatt ttgtcactgc cctctttaca     300

gaggctaaga agttagggat tcactgtacg cttgatacgt gtggcttgtc ttatcgtaat     360

actccagagt atcatgaagt tgtcgacaaa cttttggctg taactgactt ggttctactg     420

gatatcaaag agattgaccc cgaacaacac aagtttgtga cccgtcaacc taataagaat     480

atcttggaat ttgctcaata tctgtctgat aaacaagttc cggtctggat tcgtcatgtc     540

ttggtacctg gtttgacaga ttttgacgaa cacttggtta agctcggcga gtttgtaaag     600

accttgaaaa atgtcgataa atttgaaatt cttccatatc atacgatggg ggaattcaag     660

tggcgtgaac ttggcatccc ttatccattg gaaggtgtca aaccaccaac tgcagatcgt     720

gttaaaaatg ctaaggctct tatgcatacg gaaacttatc aagagtataa gaatcgtatc     780

ggggttaaaa ccttggatta a                                               801
```

<210> SEQ ID NO 10
<211> LENGTH: 266
<212> TYPE: PRT

```
<213> ORGANISM: Streptococcus thermophilus
<220> FEATURE:
<221> NAME/KEY: MISC_FEATURE
<223> OTHER INFORMATION: LMG18311

<400> SEQUENCE: 10

Met Ala Glu Ile Asp Tyr Ser Gln Val Thr Gly Leu Val His Ser Thr
1               5                   10                  15

Glu Ser Phe Gly Ser Val Asp Gly Pro Gly Ile Arg Phe Ile Val Phe
            20                  25                  30

Met Gln Gly Cys Lys Leu Arg Cys Gln Tyr Cys His Asn Pro Asp Thr
        35                  40                  45

Trp Ala Met Lys Ser Asn Lys Ala Val Glu Arg Thr Val Glu Asp Val
    50                  55                  60

Leu Glu Glu Ala Leu Arg Phe Arg His Phe Trp Gly Glu His Gly Gly
65                  70                  75                  80

Ile Thr Val Ser Gly Gly Glu Ala Met Leu Gln Ile Asp Phe Val Thr
                85                  90                  95

Ala Leu Phe Thr Glu Ala Lys Lys Leu Gly Ile His Cys Thr Leu Asp
            100                 105                 110

Thr Cys Gly Leu Ser Tyr Arg Asn Thr Pro Glu Tyr His Glu Val Val
        115                 120                 125

Asp Lys Leu Leu Ala Val Thr Asp Leu Val Leu Leu Asp Ile Lys Glu
    130                 135                 140

Ile Asp Pro Glu Gln His Lys Phe Val Thr Arg Gln Pro Asn Lys Asn
145                 150                 155                 160

Ile Leu Glu Phe Ala Gln Tyr Leu Ser Asp Lys Gln Val Pro Val Trp
                165                 170                 175

Ile Arg His Val Leu Val Pro Gly Leu Thr Asp Phe Asp Glu His Leu
            180                 185                 190

Val Lys Leu Gly Glu Phe Val Lys Thr Leu Lys Asn Val Asp Lys Phe
        195                 200                 205

Glu Ile Leu Pro Tyr His Thr Met Gly Glu Phe Lys Trp Arg Glu Leu
    210                 215                 220

Gly Ile Pro Tyr Pro Leu Glu Gly Val Lys Pro Pro Thr Ala Asp Arg
225                 230                 235                 240

Val Lys Asn Ala Lys Ala Leu Met His Thr Glu Thr Tyr Gln Glu Tyr
                245                 250                 255

Lys Asn Arg Ile Gly Val Lys Thr Leu Asp
            260                 265


<210> SEQ ID NO 11
<211> LENGTH: 801
<212> TYPE: DNA
<213> ORGANISM: Streptococcus thermophilus
<220> FEATURE:
<221> NAME/KEY: misc_feature
<223> OTHER INFORMATION: LMD-9

<400> SEQUENCE: 11

atggcagaaa ttgattacag tcaggtgact ggacttgttc attcaaccga aagtttcgga      60

tccgtagatg gtcctggtat ccgttttatt gtgtttatgc aaggctgtaa gctgcgttgc     120

caatattgtc ataacccaga tacttgggcc atgaagtcaa ataaggctgt tgaacgtaca     180

gttgaagatg tcttagaaga ggctcttcgc ttccgtcatt tctggggtga gcatggtgga     240

atcactgtat caggtggtga agccatgctt cagattgatt ttgtcactgc cctctttaca     300
```

```
gaggctaaga agttagggat tcactgtacg cttgatacgt gtggcttgtc ttatcgtaat    360

actccagagt atcatgaagt tgtcgacaaa cttttggctg taactgactt ggttctactg    420

gatatcaaag agattgaccc cgaacaacac aagtttgtga cccgtcaacc taataagaat    480

atcttggaat ttgctcaata tctgtctgat aaacaagttc cggtctggat tcgtcatgtc    540

ttggtacctg gtttgacaga ttttgacgaa cacttggtta agctcggcga gtttgtaaag    600

accttgaaaa atgtcgataa atttgaaatt cttccatatc atacgatggg ggaattcaag    660

tggcgtgaac ttggcatccc ttatccattg gaaggtgtca aaccaccaac tgcagatcgt    720

gttaaaaatg ctaaggctct tatgcatacg gaaacttatc aagagtataa gaatcgtatc    780

ggggttaaaa ccttggatta a                                              801
```

```
<210> SEQ ID NO 12
<211> LENGTH: 266
<212> TYPE: PRT
<213> ORGANISM: Streptococcus thermophilus
<220> FEATURE:
<221> NAME/KEY: MISC_FEATURE
<223> OTHER INFORMATION: LMD-9

<400> SEQUENCE: 12

Met Ala Glu Ile Asp Tyr Ser Gln Val Thr Gly Leu Val His Ser Thr
1               5                   10                  15

Glu Ser Phe Gly Ser Val Asp Gly Pro Gly Ile Arg Phe Ile Val Phe
            20                  25                  30

Met Gln Gly Cys Lys Leu Arg Cys Gln Tyr Cys His Asn Pro Asp Thr
        35                  40                  45

Trp Ala Met Lys Ser Asn Lys Ala Val Glu Arg Thr Val Glu Asp Val
    50                  55                  60

Leu Glu Glu Ala Leu Arg Phe Arg His Phe Trp Gly Glu His Gly Gly
65                  70                  75                  80

Ile Thr Val Ser Gly Gly Glu Ala Met Leu Gln Ile Asp Phe Val Thr
                85                  90                  95

Ala Leu Phe Thr Glu Ala Lys Lys Leu Gly Ile His Cys Thr Leu Asp
            100                 105                 110

Thr Cys Gly Leu Ser Tyr Arg Asn Thr Pro Glu Tyr His Glu Val Val
        115                 120                 125

Asp Lys Leu Leu Ala Val Thr Asp Leu Val Leu Leu Asp Ile Lys Glu
    130                 135                 140

Ile Asp Pro Glu Gln His Lys Phe Val Thr Arg Gln Pro Asn Lys Asn
145                 150                 155                 160

Ile Leu Glu Phe Ala Gln Tyr Leu Ser Asp Lys Gln Val Pro Val Trp
                165                 170                 175

Ile Arg His Val Leu Val Pro Gly Leu Thr Asp Phe Asp Glu His Leu
            180                 185                 190

Val Lys Leu Gly Glu Phe Val Lys Thr Leu Lys Asn Val Asp Lys Phe
        195                 200                 205

Glu Ile Leu Pro Tyr His Thr Met Gly Glu Phe Lys Trp Arg Glu Leu
    210                 215                 220

Gly Ile Pro Tyr Pro Leu Glu Gly Val Lys Pro Pro Thr Ala Asp Arg
225                 230                 235                 240

Val Lys Asn Ala Lys Ala Leu Met His Thr Glu Thr Tyr Gln Glu Tyr
                245                 250                 255

Lys Asn Arg Ile Gly Val Lys Thr Leu Asp
            260                 265
```

<210> SEQ ID NO 13
<211> LENGTH: 804
<212> TYPE: DNA
<213> ORGANISM: Lactobacillus plantarum
<220> FEATURE:
<221> NAME/KEY: misc_feature
<223> OTHER INFORMATION: WCFS1

<400> SEQUENCE: 13
atgccaacga tcacaactaa gacgcccgta aaaggactaa tatttaacat tcaaaaattt 60
agtatcaatg atggaccagg tattcgaaca gtagttttct ttaaagggtg cccgttacgc 120
tgcaagtggt gttctaatcc agaatcacaa tcaggtgagc aagaatcaat gtatgatgaa 180
cagaccgcca agcaaaccat cgtcggtgat tatatgacgg ttgatgatat tatgaaagtt 240
attctacaag ataaagactt ctatgaagag tctggcggtg gggtaacctt ctctggtggt 300
gaagttcttt ttcaagcttc ctttgcgatt gagcttgcta aggcagttaa agcagctggc 360
attaatttag cctgtgagac aactggttac gcacggccta aggtttttaa tgaattcatg 420
tcttatatgg acttcatgta ttatgactgt aaacaatggg acccagccca acatcgaatc 480
ggaacgggtg ccgataacgg ggtaatttta cgtaacttag caactgcagt gcaagctcat 540
caaaagatga tggttcggat tccggttatt ccaggtttta attatacatt gaatgacgcg 600
gatcattttg gacaactatt taatcagatt ggcgtaaccg aagttgaatt attgccattt 660
caccagtttg ggttgaaaaa gtatcaagat ttgggccgaa aatatgcgct agttaatgtt 720
aaacagttac aagcggatga cttaattgat tatgctgaac atattcgtgc acatggtgtt 780
aaagtacggg tgaatgggtg gtaa 804

<210> SEQ ID NO 14
<211> LENGTH: 267
<212> TYPE: PRT
<213> ORGANISM: Lactobacillus plantarum
<220> FEATURE:
<221> NAME/KEY: MISC_FEATURE
<223> OTHER INFORMATION: WCFS1

<400> SEQUENCE: 14

Met Pro Thr Ile Thr Thr Lys Thr Pro Val Lys Gly Leu Ile Phe Asn
1 5 10 15

Ile Gln Lys Phe Ser Ile Asn Asp Gly Pro Gly Ile Arg Thr Val Val
20 25 30

Phe Phe Lys Gly Cys Pro Leu Arg Cys Lys Trp Cys Ser Asn Pro Glu
35 40 45

Ser Gln Ser Gly Glu Gln Glu Ser Met Tyr Asp Glu Gln Thr Ala Lys
50 55 60

Gln Thr Ile Val Gly Asp Tyr Met Thr Val Asp Asp Ile Met Lys Val
65 70 75 80

Ile Leu Gln Asp Lys Asp Phe Tyr Glu Glu Ser Gly Gly Gly Val Thr
85 90 95

Phe Ser Gly Gly Glu Val Leu Phe Gln Ala Ser Phe Ala Ile Glu Leu
100 105 110

Ala Lys Ala Val Lys Ala Ala Gly Ile Asn Leu Ala Cys Glu Thr Thr
115 120 125

Gly Tyr Ala Arg Pro Lys Val Phe Asn Glu Phe Met Ser Tyr Met Asp
130 135 140

Phe Met Tyr Tyr Asp Cys Lys Gln Trp Asp Pro Ala Gln His Arg Ile

-continued

```
145                 150                 155                 160

Gly Thr Gly Ala Asp Asn Gly Val Ile Leu Arg Asn Leu Ala Thr Ala
                165                 170                 175

Val Gln Ala His Gln Lys Met Met Val Arg Ile Pro Val Ile Pro Gly
            180                 185                 190

Phe Asn Tyr Thr Leu Asn Asp Ala Asp His Phe Gly Gln Leu Phe Asn
        195                 200                 205

Gln Ile Gly Val Thr Glu Val Glu Leu Leu Pro Phe His Gln Phe Gly
    210                 215                 220

Leu Lys Lys Tyr Gln Asp Leu Gly Arg Lys Tyr Ala Leu Val Asn Val
225                 230                 235                 240

Lys Gln Leu Gln Ala Asp Asp Leu Ile Asp Tyr Ala Glu His Ile Arg
                245                 250                 255

Ala His Gly Val Lys Val Arg Val Asn Gly Trp
            260                 265


<210> SEQ ID NO 15
<211> LENGTH: 822
<212> TYPE: DNA
<213> ORGANISM: Lactobacillus plantarum
<220> FEATURE:
<221> NAME/KEY: misc_feature
<223> OTHER INFORMATION: WCFS1

<400> SEQUENCE: 15

atggaaaaca aacaagtttc aacaacgcaa gcggcggcaa aggagccttt gataggctac     60

gttcactcca tcgaaacgtt tggctccgtt gacggaccag gtatccgtta cgtggcattc    120

cttcaaggat gccacatgcg ttgccaatac tgtcacaacc ctgatacttg gaaactcaac    180

gttggcgatc aaatgacggc cgacgagatt ctcgaagacg cggctaaata ccgggctttc    240

tggggcaaga cgggtggcat cacagtcagt ggtggtgaat cactggtaca aatcgacttc    300

atcttagact tattcgaaaa agccaaggcg atgaatatca gtacttgtct ggatacctct    360

ggacagcctt ttacccgaga acaacctttc tttgacaagt tcgaacgtct aatgaaggtc    420

acggacattt cgttggtcga cattaagcac atcgattctg ccaaacacaa gcagttgacc    480

cagtatggga acgaaaatat cttggatatg attcagtaca tggcccaaca ccacgatgat    540

atgtggattc gtcacgtcct ggttccccaa cggactgatt acgatgaaga cttgaagaaa    600

ctcggcgatt acattgctaa aattccaaac gacgtcgttc aaaaagtcga agtattgccg    660

taccatactt tgggcgttaa aaaatatcat gaaatgaaga tcaagtaccg gcttgaagga    720

atcgagtctc caacccaaga tcgggtggca aatgccgaaa agctactgca cactgctgat    780

tacaacgggt acaagacatg gatgccattg ccaaaacttt aa                       822


<210> SEQ ID NO 16
<211> LENGTH: 273
<212> TYPE: PRT
<213> ORGANISM: Lactobacillus plantarum
<220> FEATURE:
<221> NAME/KEY: MISC_FEATURE
<223> OTHER INFORMATION: WCFS1

<400> SEQUENCE: 16

Met Glu Asn Lys Gln Val Ser Thr Thr Gln Ala Ala Ala Lys Glu Pro
1               5                   10                  15

Leu Ile Gly Tyr Val His Ser Ile Glu Thr Phe Gly Ser Val Asp Gly
            20                  25                  30
```

```
Pro Gly Ile Arg Tyr Val Ala Phe Leu Gln Gly Cys His Met Arg Cys
        35                  40                  45

Gln Tyr Cys His Asn Pro Asp Thr Trp Lys Leu Asn Val Gly Asp Gln
    50                  55                  60

Met Thr Ala Asp Glu Ile Leu Glu Asp Ala Ala Lys Tyr Arg Ala Phe
65                  70                  75                  80

Trp Gly Lys Thr Gly Gly Ile Thr Val Ser Gly Gly Glu Ser Leu Val
                85                  90                  95

Gln Ile Asp Phe Ile Leu Asp Leu Phe Glu Lys Ala Lys Ala Met Asn
            100                 105                 110

Ile Ser Thr Cys Leu Asp Thr Ser Gly Gln Pro Phe Thr Arg Glu Gln
        115                 120                 125

Pro Phe Phe Asp Lys Phe Glu Arg Leu Met Lys Val Thr Asp Ile Ser
    130                 135                 140

Leu Val Asp Ile Lys His Ile Asp Ser Ala Lys His Lys Gln Leu Thr
145                 150                 155                 160

Gln Tyr Gly Asn Glu Asn Ile Leu Asp Met Ile Gln Tyr Met Ala Gln
                165                 170                 175

His His Asp Asp Met Trp Ile Arg His Val Leu Val Pro Gln Arg Thr
            180                 185                 190

Asp Tyr Asp Glu Asp Leu Lys Lys Leu Gly Asp Tyr Ile Ala Lys Ile
        195                 200                 205

Pro Asn Asp Val Val Gln Lys Val Glu Val Leu Pro Tyr His Thr Leu
    210                 215                 220

Gly Val Lys Lys Tyr His Glu Met Lys Ile Lys Tyr Arg Leu Glu Gly
225                 230                 235                 240

Ile Glu Ser Pro Thr Gln Asp Arg Val Ala Asn Ala Glu Lys Leu Leu
                245                 250                 255

His Thr Ala Asp Tyr Asn Gly Tyr Lys Thr Trp Met Pro Leu Pro Lys
            260                 265                 270

Leu


<210> SEQ ID NO 17
<211> LENGTH: 822
<212> TYPE: DNA
<213> ORGANISM: Lactobacillus plantarum
<220> FEATURE:
<221> NAME/KEY: misc_feature
<223> OTHER INFORMATION: JDM1

<400> SEQUENCE: 17

atggaaaaca aacaagtttc aacaacgcaa gcggcggcaa aagagccttt gataggctac      60

gttcactcca tcgaaacgtt tggctccgtt gacggaccag gtatccgtta cgtggcattc     120

cttcaaggat gccacatgcg ttgccaatac tgtcacaacc ctgatacttg gaaactcaac     180

gttggcgatc aaatgacggc cgacgagatt ctcgaagacg cggctaaata ccgggctttc     240

tggggcaaga cgggtggcat cacagtcagt ggtggtgaat cactggtaca aatcgacttc     300

atcttagact tattcgaaaa agccaaggcg atgaatatca gtacttgtct ggatacctct     360

ggacagcctt ttacccgaga acaacctttc tttgacaagt tcgaacgtct aatgaaggtc     420

acggacattt cgttggtcga cattaagcac atcgattctg ccaaacacaa gcagttgacc     480

cagtatggga acgaaaatat cttggatatg attcagtaca tggcccaaca ccacgatgat     540

atgtggattc gtcacgtcct ggttccccaa cggactgatt acgatgaaga cttgaagaaa     600

ctcggcgatt acattgctaa gattccaaac gacgtcgttc aaaaagtcga agtattgccg     660
```

```
taccatactt tgggcgttaa aaaatatcat gaaatgaaga tcaagtaccg gcttgaagga    720

atcgagtctc caacccaaga tcgggtggca aatgccgaaa agctactgca cactgctgat    780

tacaacgggt acaagacatg gatgccattg ccaaaacttt aa                       822


<210> SEQ ID NO 18
<211> LENGTH: 273
<212> TYPE: PRT
<213> ORGANISM: Lactobacillus plantarum
<220> FEATURE:
<221> NAME/KEY: MISC_FEATURE
<223> OTHER INFORMATION: JDM1

<400> SEQUENCE: 18

Met Glu Asn Lys Gln Val Ser Thr Thr Gln Ala Ala Ala Lys Glu Pro
1               5                   10                  15

Leu Ile Gly Tyr Val His Ser Ile Glu Thr Phe Gly Ser Val Asp Gly
            20                  25                  30

Pro Gly Ile Arg Tyr Val Ala Phe Leu Gln Gly Cys His Met Arg Cys
        35                  40                  45

Gln Tyr Cys His Asn Pro Asp Thr Trp Lys Leu Asn Val Gly Asp Gln
    50                  55                  60

Met Thr Ala Asp Glu Ile Leu Glu Asp Ala Ala Lys Tyr Arg Ala Phe
65                  70                  75                  80

Trp Gly Lys Thr Gly Gly Ile Thr Val Ser Gly Gly Glu Ser Leu Val
                85                  90                  95

Gln Ile Asp Phe Ile Leu Asp Leu Phe Glu Lys Ala Lys Ala Met Asn
            100                 105                 110

Ile Ser Thr Cys Leu Asp Thr Ser Gly Gln Pro Phe Thr Arg Glu Gln
        115                 120                 125

Pro Phe Phe Asp Lys Phe Glu Arg Leu Met Lys Val Thr Asp Ile Ser
    130                 135                 140

Leu Val Asp Ile Lys His Ile Asp Ser Ala Lys His Lys Gln Leu Thr
145                 150                 155                 160

Gln Tyr Gly Asn Glu Asn Ile Leu Asp Met Ile Gln Tyr Met Ala Gln
                165                 170                 175

His His Asp Asp Met Trp Ile Arg His Val Leu Val Pro Gln Arg Thr
            180                 185                 190

Asp Tyr Asp Glu Asp Leu Lys Lys Leu Gly Asp Tyr Ile Ala Lys Ile
        195                 200                 205

Pro Asn Asp Val Val Gln Lys Val Glu Val Leu Pro Tyr His Thr Leu
    210                 215                 220

Gly Val Lys Lys Tyr His Glu Met Lys Ile Lys Tyr Arg Leu Glu Gly
225                 230                 235                 240

Ile Glu Ser Pro Thr Gln Asp Arg Val Ala Asn Ala Glu Lys Leu Leu
                245                 250                 255

His Thr Ala Asp Tyr Asn Gly Tyr Lys Thr Trp Met Pro Leu Pro Lys
            260                 265                 270

Leu


<210> SEQ ID NO 19
<211> LENGTH: 804
<212> TYPE: DNA
<213> ORGANISM: Lactobacillus plantarum
<220> FEATURE:
<221> NAME/KEY: misc_feature
<223> OTHER INFORMATION: JDM1
```

<400> SEQUENCE: 19

```
atgccaacga tcacaactaa gacgcccgta aaaggactaa tatttaacat tcaaaaattt     60
agtatcaatg atggaccagg tattcgaaca gtagttttct ttaaagggtg cccgttacgc    120
tgcaagtggt gttctaatcc agaatcacaa tcaggtgagc aagaatcaat gtatgatgaa    180
cagaccgcca agcaaaccat cgtcggtgat tatatgacgg ttgatgatat tatgaaagtt    240
attctacaag ataaagactt ctatgaagag tctggcggtg gggtaacctt ctctggtggt    300
gaagttcttt ttcaagcttc ctttgcgatt gagcttgcta aggcagttaa agcagctggc    360
attaatttag cctgtgagac aactggttac gcacggccta aggtttttaa tgaattcatg    420
tcttatatgg acttcatgta ttatgactgt aaacaatggg acccagccca acatcgaatc    480
ggaacgggtg ccgataacgg ggtaatttta cgtaacttag caactgcagt gcaagctcat    540
caaaagatga tggttcggat tccggttatt ccaggtttta attatacatt gaatgacgcg    600
gatcattttg gacaactatt taatcagatt ggcgtaaccg aagttgaatt attgccattt    660
caccagtttg ggttgaaaaa gtatcaagat ttgggccgaa aatatgcgct agttaatgtt    720
aaacagttac aagcggatga cttaattgat tatgctgaac atattcgtgc acatggtgtt    780
aaagtacggg tgaatgggtg gtaa                                           804
```

<210> SEQ ID NO 20
<211> LENGTH: 267
<212> TYPE: PRT
<213> ORGANISM: Lactobacillus plantarum
<220> FEATURE:
<221> NAME/KEY: MISC_FEATURE
<223> OTHER INFORMATION: JDM1

<400> SEQUENCE: 20

```
Met Pro Thr Ile Thr Thr Lys Thr Pro Val Lys Gly Leu Ile Phe Asn
1               5                   10                  15

Ile Gln Lys Phe Ser Ile Asn Asp Gly Pro Gly Ile Arg Thr Val Val
            20                  25                  30

Phe Phe Lys Gly Cys Pro Leu Arg Cys Lys Trp Cys Ser Asn Pro Glu
        35                  40                  45

Ser Gln Ser Gly Glu Gln Glu Ser Met Tyr Asp Glu Gln Thr Ala Lys
    50                  55                  60

Gln Thr Ile Val Gly Asp Tyr Met Thr Val Asp Asp Ile Met Lys Val
65                  70                  75                  80

Ile Leu Gln Asp Lys Asp Phe Tyr Glu Glu Ser Gly Gly Gly Val Thr
                85                  90                  95

Phe Ser Gly Gly Glu Val Leu Phe Gln Ala Ser Phe Ala Ile Glu Leu
            100                 105                 110

Ala Lys Ala Val Lys Ala Ala Gly Ile Asn Leu Ala Cys Glu Thr Thr
        115                 120                 125

Gly Tyr Ala Arg Pro Lys Val Phe Asn Glu Phe Met Ser Tyr Met Asp
    130                 135                 140

Phe Met Tyr Tyr Asp Cys Lys Gln Trp Asp Pro Ala Gln His Arg Ile
145                 150                 155                 160

Gly Thr Gly Ala Asp Asn Gly Val Ile Leu Arg Asn Leu Ala Thr Ala
                165                 170                 175

Val Gln Ala His Gln Lys Met Met Val Arg Ile Pro Val Ile Pro Gly
            180                 185                 190

Phe Asn Tyr Thr Leu Asn Asp Ala Asp His Phe Gly Gln Leu Phe Asn
```

```
        195                 200                 205

Gln Ile Gly Val Thr Glu Val Glu Leu Leu Pro Phe His Gln Phe Gly
    210                 215                 220

Leu Lys Lys Tyr Gln Asp Leu Gly Arg Lys Tyr Ala Leu Val Asn Val
225                 230                 235                 240

Lys Gln Leu Gln Ala Asp Asp Leu Ile Asp Tyr Ala Glu His Ile Arg
                245                 250                 255

Ala His Gly Val Lys Val Arg Val Asn Gly Trp
            260                 265


<210> SEQ ID NO 21
<211> LENGTH: 852
<212> TYPE: DNA
<213> ORGANISM: Lactobacillus casei
<220> FEATURE:
<221> NAME/KEY: misc_feature
<223> OTHER INFORMATION: bl23

<400> SEQUENCE: 21

atgaaactca tcgatcagtc acaaagccca ttaaatatct tagaacaagt tggtcaggat      60

catgatggcc cgatcaaagg gtatgttcac tcggtcgaaa gttttggttc ggtcgatggc     120

cctggtattc gcttcgttgt ctttatgcaa gggtgtcgca tgcgttgcca gtattgtcac     180

aaccctgaca cctggaacat tggggttggt gaagaaatga cggccgatca aattttggcg     240

gatgcccagc gctataaagc attctggggt gaccaagggg gtattacctg cagtggcggt     300

gagagtttgg tacaaatcga tttcattctc gaactcttca ccaaggctaa ggcactggga     360

atttcgactt gcctcgatac gtcaggtggc cccttcacgc gtgaccaacc gtggtttggc     420

cagtttgaaa agctgatggc tgttactgac atctcattag ttgatattaa acacattgat     480

tcggccgagc ataaaaagct caccggtttt cctaatgaga atattttgga tatggtgcag     540

tatatgtcgg cgcatggtga tgacatgtgg attcgccacg ttctggtccc ggaacgcact     600

gactttgacc cttatctcaa acggttaggg gactatattg cgacattgga caaaaacgtg     660

gtccaaaaag ttgagattct gccgtatcac acgttaggcg ttaaaaagta tcacgagctt     720

ggcattacgt acccgcttga aggcatcgaa ccgccgtctg ccgaacgcgt taagaatgca     780

gagaatctgc tgcacgttaa ggattatacc ggatggcaaa gctggcgtcc gaaaccagtt     840

gcgagcaact ga                                                         852


<210> SEQ ID NO 22
<211> LENGTH: 283
<212> TYPE: PRT
<213> ORGANISM: Lactobacillus casei
<220> FEATURE:
<221> NAME/KEY: MISC_FEATURE
<223> OTHER INFORMATION: bl23

<400> SEQUENCE: 22

Met Lys Leu Ile Asp Gln Ser Gln Ser Pro Leu Asn Ile Leu Glu Gln
1               5                   10                  15

Val Gly Gln Asp His Asp Gly Pro Ile Lys Gly Tyr Val His Ser Val
            20                  25                  30

Glu Ser Phe Gly Ser Val Asp Gly Pro Gly Ile Arg Phe Val Val Phe
        35                  40                  45

Met Gln Gly Cys Arg Met Arg Cys Gln Tyr Cys His Asn Pro Asp Thr
    50                  55                  60

Trp Asn Ile Gly Val Gly Glu Glu Met Thr Ala Asp Gln Ile Leu Ala
```

-continued

```
65                  70                  75                  80

Asp Ala Gln Arg Tyr Lys Ala Phe Trp Gly Asp Gln Gly Gly Ile Thr
                85                  90                  95

Cys Ser Gly Gly Glu Ser Leu Val Gln Ile Asp Phe Ile Leu Glu Leu
            100                 105                 110

Phe Thr Lys Ala Lys Ala Leu Gly Ile Ser Thr Cys Leu Asp Thr Ser
        115                 120                 125

Gly Gly Pro Phe Thr Arg Asp Gln Pro Trp Phe Gly Gln Phe Glu Lys
    130                 135                 140

Leu Met Ala Val Thr Asp Ile Ser Leu Val Asp Ile Lys His Ile Asp
145                 150                 155                 160

Ser Ala Glu His Lys Lys Leu Thr Gly Phe Pro Asn Glu Asn Ile Leu
                165                 170                 175

Asp Met Val Gln Tyr Met Ser Ala His Gly Asp Asp Met Trp Ile Arg
            180                 185                 190

His Val Leu Val Pro Glu Arg Thr Asp Phe Asp Pro Tyr Leu Lys Arg
        195                 200                 205

Leu Gly Asp Tyr Ile Ala Thr Leu Asp Lys Asn Val Val Gln Lys Val
    210                 215                 220

Glu Ile Leu Pro Tyr His Thr Leu Gly Val Lys Lys Tyr His Glu Leu
225                 230                 235                 240

Gly Ile Thr Tyr Pro Leu Glu Gly Ile Glu Pro Pro Ser Ala Glu Arg
                245                 250                 255

Val Lys Asn Ala Glu Asn Leu Leu His Val Lys Asp Tyr Thr Gly Trp
            260                 265                 270

Gln Ser Trp Arg Pro Lys Pro Val Ala Ser Asn
        275                 280
```

<210> SEQ ID NO 23
<211> LENGTH: 852
<212> TYPE: DNA
<213> ORGANISM: Lactobacillus casei
<220> FEATURE:
<221> NAME/KEY: misc_feature
<223> OTHER INFORMATION: ATCC 334

<400> SEQUENCE: 23

```
atgaaactca tcgatcagtc acaaagccca ttaaatatct tagaacaagt tggtcaggat     60

catgatggcc cgatcaaagg gtatgttcac tcggtcgaaa gttttggttc ggtcgatggc    120

cctggtattc gcttcgttgt ctttatgcaa gggtgtcgca tgcgttgcca gtattgtcac    180

aaccctgaca cctggaacat tggggttggt gaagaaatga cggccgatca aattttggcg    240

gatgcccagc gctataaagc attctggggt gaccaagggg gtattacgtg cagtggcggt    300

gagagtttgg tacaaatcga tttcattctc gaactcttca ccaaggctaa ggcactggga    360

atttcgactt gcctcgatac gtcaggcggc cccttcacgc gtgaccaacc gtggtttggc    420

cagtttgaaa agctgatggc tgttactgac atctcattag ttgatattaa acacatcgat    480

tcggccgagc ataaaaagct caccggtttt cctaatgaaa atattttaga tatggtgcag    540

tatatgtcgg cgcatggtga tgacatgtgg attcgccacg ttctggtccc ggaacgcact    600

gactttgacc cttatctcaa acgattaggg gactatattg cgacattgga caaaaacgtg    660

gtccaaaaag ttgagattct gccgtatcac acgttaggcg ttaaaaagta tcacgagctt    720

ggcattacgt acccgcttga aggcatcgaa ccgccgtctg ccgatcgcgt taagaatgca    780

gagaatctgc tgcacgttaa ggattatacc ggatggcaaa gctggcgtcc gaaaccagtt    840
```

```
gcgagcaact ga                                                       852


<210> SEQ ID NO 24
<211> LENGTH: 283
<212> TYPE: PRT
<213> ORGANISM: Lactobacillus casei
<220> FEATURE:
<221> NAME/KEY: MISC_FEATURE
<223> OTHER INFORMATION: ATCC 334

<400> SEQUENCE: 24

Met Lys Leu Ile Asp Gln Ser Gln Ser Pro Leu Asn Ile Leu Glu Gln
1               5                   10                  15

Val Gly Gln Asp His Asp Gly Pro Ile Lys Gly Tyr Val His Ser Val
            20                  25                  30

Glu Ser Phe Gly Ser Val Asp Gly Pro Gly Ile Arg Phe Val Val Phe
        35                  40                  45

Met Gln Gly Cys Arg Met Arg Cys Gln Tyr Cys His Asn Pro Asp Thr
    50                  55                  60

Trp Asn Ile Gly Val Gly Glu Glu Met Thr Ala Asp Gln Ile Leu Ala
65                  70                  75                  80

Asp Ala Gln Arg Tyr Lys Ala Phe Trp Gly Asp Gln Gly Gly Ile Thr
                85                  90                  95

Cys Ser Gly Gly Glu Ser Leu Val Gln Ile Asp Phe Ile Leu Glu Leu
            100                 105                 110

Phe Thr Lys Ala Lys Ala Leu Gly Ile Ser Thr Cys Leu Asp Thr Ser
        115                 120                 125

Gly Gly Pro Phe Thr Arg Asp Gln Pro Trp Phe Gly Gln Phe Glu Lys
    130                 135                 140

Leu Met Ala Val Thr Asp Ile Ser Leu Val Asp Ile Lys His Ile Asp
145                 150                 155                 160

Ser Ala Glu His Lys Lys Leu Thr Gly Phe Pro Asn Glu Asn Ile Leu
                165                 170                 175

Asp Met Val Gln Tyr Met Ser Ala His Gly Asp Asp Met Trp Ile Arg
            180                 185                 190

His Val Leu Val Pro Glu Arg Thr Asp Phe Asp Pro Tyr Leu Lys Arg
        195                 200                 205

Leu Gly Asp Tyr Ile Ala Thr Leu Asp Lys Asn Val Val Gln Lys Val
    210                 215                 220

Glu Ile Leu Pro Tyr His Thr Leu Gly Val Lys Lys Tyr His Glu Leu
225                 230                 235                 240

Gly Ile Thr Tyr Pro Leu Glu Gly Ile Glu Pro Pro Ser Ala Asp Arg
                245                 250                 255

Val Lys Asn Ala Glu Asn Leu Leu His Val Lys Asp Tyr Thr Gly Trp
            260                 265                 270

Gln Ser Trp Arg Pro Lys Pro Val Ala Ser Asn
        275                 280


<210> SEQ ID NO 25
<211> LENGTH: 879
<212> TYPE: DNA
<213> ORGANISM: Bifidobacterium adolescentis

<400> SEQUENCE: 25

atgtctgaac atattttccg ttccacgacc agacacatgc tgagggattc caaggactac      60

gtcaatcaga cgctgatggg aggcctgtcc ggattcgaat cgccaatcgg cttggaccgt     120
```

-continued

```
ctcgaccgca tcaaggcgtt gaaaagcggc gatatcggtt tcgtgcactc gtgggacatc    180

aacacttccg tggatggtcc tggcaccaga atgaccgtgt tcatgagcgg atgccctctg    240

cgctgccagt actgccagaa tccggatact tggaagatgc gcgacggcaa gcccgtctac    300

tacgaagcca tggtcaagaa aatcgagcgg tatgccgatt tattcaaggc caccggcggc    360

ggcatcactt tctccggcgg cgaatccatg atgcagccgg ctttcgtgtc acgcgtgttc    420

catgccgcca agcagatggg agtgcatacc tgcctcgaca cgtccggatt cctcggggcg    480

agctacaccg atgacatggt ggatgacatc gacctgtgcc tgcttgacgt caaatccggc    540

gatgaggaga cctaccataa ggtgaccggc ggcatcctgc agccgaccat cgacttcgga    600

cagcgtctgg ccaaggcagg caagaagatc tgggtgcgtt tcgtgctcgt gccgggcctc    660

acatcctccg aagaaaacgt cgagaacgtg gcgaagatct gcgagacctt cggcgacgcg    720

ttggaacata tcgacgtatt gcccttccac cagcttggcc gtccgaagtg gcacatgctg    780

aacatcccat acccgttgga ggaccagaaa ggcccgtccg cggcaatgaa acaacgtgtg    840

gtcgagcagt tccagtcgca cggcttcacc gtgtactaa                           879
```

<210> SEQ ID NO 26
<211> LENGTH: 292
<212> TYPE: PRT
<213> ORGANISM: Bifidobacterium adolescentis

<400> SEQUENCE: 26

```
Met Ser Glu His Ile Phe Arg Ser Thr Thr Arg His Met Leu Arg Asp
1               5                   10                  15

Ser Lys Asp Tyr Val Asn Gln Thr Leu Met Gly Gly Leu Ser Gly Phe
            20                  25                  30

Glu Ser Pro Ile Gly Leu Asp Arg Leu Asp Arg Ile Lys Ala Leu Lys
        35                  40                  45

Ser Gly Asp Ile Gly Phe Val His Ser Trp Asp Ile Asn Thr Ser Val
    50                  55                  60

Asp Gly Pro Gly Thr Arg Met Thr Val Phe Met Ser Gly Cys Pro Leu
65                  70                  75                  80

Arg Cys Gln Tyr Cys Gln Asn Pro Asp Thr Trp Lys Met Arg Asp Gly
                85                  90                  95

Lys Pro Val Tyr Tyr Glu Ala Met Val Lys Lys Ile Glu Arg Tyr Ala
            100                 105                 110

Asp Leu Phe Lys Ala Thr Gly Gly Gly Ile Thr Phe Ser Gly Gly Glu
        115                 120                 125

Ser Met Met Gln Pro Ala Phe Val Ser Arg Val Phe His Ala Ala Lys
    130                 135                 140

Gln Met Gly Val His Thr Cys Leu Asp Thr Ser Gly Phe Leu Gly Ala
145                 150                 155                 160

Ser Tyr Thr Asp Asp Met Val Asp Asp Ile Asp Leu Cys Leu Leu Asp
                165                 170                 175

Val Lys Ser Gly Asp Glu Glu Thr Tyr His Lys Val Thr Gly Gly Ile
            180                 185                 190

Leu Gln Pro Thr Ile Asp Phe Gly Gln Arg Leu Ala Lys Ala Gly Lys
        195                 200                 205

Lys Ile Trp Val Arg Phe Val Leu Val Pro Gly Leu Thr Ser Ser Glu
    210                 215                 220

Glu Asn Val Glu Asn Val Ala Lys Ile Cys Glu Thr Phe Gly Asp Ala
225                 230                 235                 240
```

-continued

```
Leu Glu His Ile Asp Val Leu Pro Phe His Gln Leu Gly Arg Pro Lys
                245                 250                 255

Trp His Met Leu Asn Ile Pro Tyr Pro Leu Glu Asp Gln Lys Gly Pro
            260                 265                 270

Ser Ala Ala Met Lys Gln Arg Val Val Glu Gln Phe Gln Ser His Gly
        275                 280                 285

Phe Thr Val Tyr
    290


<210> SEQ ID NO 27
<211> LENGTH: 882
<212> TYPE: DNA
<213> ORGANISM: Bifidobacterium longum
<220> FEATURE:
<221> NAME/KEY: misc_feature
<223> OTHER INFORMATION: NCC2705

<400> SEQUENCE: 27

atgcccgcaa cacccacgtt ccgcaccacg accaggcata tgctcaagga atcgaagacc      60

tatgcctcgc agactttgat gggcggcctt tccggctttg aatccccaat cggactcgac     120

cgacgtgacc gcctttccgc cctgaaatcc ggcgatatcg gcttcgtcca ctcttgggac     180

atcaacacct ccgtggacgg accgggcacc cgtatgaccg tgttcatgtc cggctgcccg     240

ctgcgctgcc agtactgcca gaacccggac acttggaaga tgcgcgacgg caagcccgtc     300

taccttgacg ccatgatcaa gaaggtcgat cgttacaagg acctgttcaa ggccacgcat     360

ggcggtatca ccttctccgg cggcgaatcc atgatgcagc ccgccttcgt ctcgcgtgtg     420

ttccatgccg ccaaggagat gggcgtgcac acctgcctcg acacgtccgg cttcctcaac     480

acgaattaca ccgacgagat gctcgaggac atcgacctgt gtctgctcga cgtcaaatcc     540

ggcgacgagg agacctatca caaggtcacc ggcggcacct tgcagcccac catcgatttt     600

ggccagcgac tggccaaggc cggcaagaag atctgggtgc gatttgtgct cgtgccgggc     660

ctgaccgact ccgaagagaa cgtcgaaaac gtggcgaaga tctgcgagtc cttcggcgat     720

gccgtcgaac acatcgacgt gctgggattc caccagcttg gccgcccgaa gtggcacgaa     780

ctgcgcatcc catacccgct ggagaaccag aagggaccca acgccgccac ccgcgaacgg     840

gtggccaacc agttcaagga ccacggcttc accgtgtatt aa                        882


<210> SEQ ID NO 28
<211> LENGTH: 293
<212> TYPE: PRT
<213> ORGANISM: Bifidobacterium longum
<220> FEATURE:
<221> NAME/KEY: MISC_FEATURE
<223> OTHER INFORMATION: NCC2705

<400> SEQUENCE: 28

Met Pro Ala Thr Pro Thr Phe Arg Thr Thr Thr Arg His Met Leu Lys
1               5                   10                  15

Glu Ser Lys Thr Tyr Ala Ser Gln Thr Leu Met Gly Gly Leu Ser Gly
            20                  25                  30

Phe Glu Ser Pro Ile Gly Leu Asp Arg Arg Asp Arg Leu Ser Ala Leu
        35                  40                  45

Lys Ser Gly Asp Ile Gly Phe Val His Ser Trp Asp Ile Asn Thr Ser
    50                  55                  60

Val Asp Gly Pro Gly Thr Arg Met Thr Val Phe Met Ser Gly Cys Pro
65                  70                  75                  80
```

```
Leu Arg Cys Gln Tyr Cys Gln Asn Pro Asp Thr Trp Lys Met Arg Asp
                85                  90                  95

Gly Lys Pro Val Tyr Leu Asp Ala Met Ile Lys Lys Val Asp Arg Tyr
            100                 105                 110

Lys Asp Leu Phe Lys Ala Thr His Gly Gly Ile Thr Phe Ser Gly Gly
        115                 120                 125

Glu Ser Met Met Gln Pro Ala Phe Val Ser Arg Val Phe His Ala Ala
    130                 135                 140

Lys Glu Met Gly Val His Thr Cys Leu Asp Thr Ser Gly Phe Leu Asn
145                 150                 155                 160

Thr Asn Tyr Thr Asp Glu Met Leu Glu Asp Ile Asp Leu Cys Leu Leu
                165                 170                 175

Asp Val Lys Ser Gly Asp Glu Glu Thr Tyr His Lys Val Thr Gly Gly
            180                 185                 190

Thr Leu Gln Pro Thr Ile Asp Phe Gly Gln Arg Leu Ala Lys Ala Gly
        195                 200                 205

Lys Lys Ile Trp Val Arg Phe Val Leu Val Pro Gly Leu Thr Asp Ser
    210                 215                 220

Glu Glu Asn Val Glu Asn Val Ala Lys Ile Cys Glu Ser Phe Gly Asp
225                 230                 235                 240

Ala Val Glu His Ile Asp Val Leu Gly Phe His Gln Leu Gly Arg Pro
                245                 250                 255

Lys Trp His Glu Leu Arg Ile Pro Tyr Pro Leu Glu Asn Gln Lys Gly
            260                 265                 270

Pro Asn Ala Ala Thr Arg Glu Arg Val Ala Asn Gln Phe Lys Asp His
        275                 280                 285

Gly Phe Thr Val Tyr
    290
```

<210> SEQ ID NO 29
<211> LENGTH: 882
<212> TYPE: DNA
<213> ORGANISM: Bifidobacterium longum
<220> FEATURE:
<221> NAME/KEY: misc_feature
<223> OTHER INFORMATION: DJO10A

<400> SEQUENCE: 29

```
atgcccgcaa cacccacgtt ccgcaccacg accaggcata tgctcaagga atcgaagacc     60

tatgcctcgc agactttgat gggtggcctt tccggctttg aatccccaat cggactcgac    120

cgacgtgacc gcctttccgc cctgaaatcc ggtgatatcg gcttcgtcca ctcttgggac    180

atcaacacct ccgtggatgg accgggcacc cgcatgaccg tgttcatgtc cggctgcccg    240

ctgcgctgcc agtactgcca gaacccggac acttggaaga tgcgcgacgg caagcccgtc    300

taccttgacg ccatgatcaa gaaggtcgat cgttacaagg acctgttcaa ggccacgcat    360

ggcggtatca ccttctccgg cggcgaatcc atgatgcagc ccgccttcgt ctcgcgtgtg    420

ttccatgccg ccaaggagat gggcgtgcac acctgcctcg atacgtccgg cttcctcaac    480

acgaattaca ccgacgagat gctcgaggac atcgacctgt gtctgctcga cgtcaaatcc    540

ggcgacgagg agacctatca caaggtcacc ggcggcacct tgcagcccac catcgatttt    600

ggccagcgac tggccaaggc cggcaagaag atctgggtgc gatttgtgct cgtgccgggc    660

ctgaccgact ccgaagagaa cgtcgaaaac gtggcgaaga tctgcgagtc cttcggtgat    720

gccgtcgaac acatcgacgt gctgggattc caccagcttg gccgcccgaa gtggcacgaa    780
```

ctgcgtatcc catacccgct ggagaaccag aagggaccca acgccgccac ccgcgaacgg 840
gtgaccaacc agttcaagga ccacggcttc accgtgtatt aa 882

<210> SEQ ID NO 30
<211> LENGTH: 293
<212> TYPE: PRT
<213> ORGANISM: Bifidobacterium longum
<220> FEATURE:
<221> NAME/KEY: MISC_FEATURE
<223> OTHER INFORMATION: DJO10A

<400> SEQUENCE: 30

Met Pro Ala Thr Pro Thr Phe Arg Thr Thr Thr Arg His Met Leu Lys
1 5 10 15

Glu Ser Lys Thr Tyr Ala Ser Gln Thr Leu Met Gly Gly Leu Ser Gly
20 25 30

Phe Glu Ser Pro Ile Gly Leu Asp Arg Arg Asp Arg Leu Ser Ala Leu
35 40 45

Lys Ser Gly Asp Ile Gly Phe Val His Ser Trp Asp Ile Asn Thr Ser
50 55 60

Val Asp Gly Pro Gly Thr Arg Met Thr Val Phe Met Ser Gly Cys Pro
65 70 75 80

Leu Arg Cys Gln Tyr Cys Gln Asn Pro Asp Thr Trp Lys Met Arg Asp
85 90 95

Gly Lys Pro Val Tyr Leu Asp Ala Met Ile Lys Lys Val Asp Arg Tyr
100 105 110

Lys Asp Leu Phe Lys Ala Thr His Gly Gly Ile Thr Phe Ser Gly Gly
115 120 125

Glu Ser Met Met Gln Pro Ala Phe Val Ser Arg Val Phe His Ala Ala
130 135 140

Lys Glu Met Gly Val His Thr Cys Leu Asp Thr Ser Gly Phe Leu Asn
145 150 155 160

Thr Asn Tyr Thr Asp Glu Met Leu Glu Asp Ile Asp Leu Cys Leu Leu
165 170 175

Asp Val Lys Ser Gly Asp Glu Glu Thr Tyr His Lys Val Thr Gly Gly
180 185 190

Thr Leu Gln Pro Thr Ile Asp Phe Gly Gln Arg Leu Ala Lys Ala Gly
195 200 205

Lys Lys Ile Trp Val Arg Phe Val Leu Val Pro Gly Leu Thr Asp Ser
210 215 220

Glu Glu Asn Val Glu Asn Val Ala Lys Ile Cys Glu Ser Phe Gly Asp
225 230 235 240

Ala Val Glu His Ile Asp Val Leu Gly Phe His Gln Leu Gly Arg Pro
245 250 255

Lys Trp His Glu Leu Arg Ile Pro Tyr Pro Leu Glu Asn Gln Lys Gly
260 265 270

Pro Asn Ala Ala Thr Arg Glu Arg Val Thr Asn Gln Phe Lys Asp His
275 280 285

Gly Phe Thr Val Tyr
290

<210> SEQ ID NO 31
<211> LENGTH: 903
<212> TYPE: DNA
<213> ORGANISM: Bifidobacterium animalis
<220> FEATURE:

-continued

<221> NAME/KEY: misc_feature
<223> OTHER INFORMATION: DSM 10140

<400> SEQUENCE: 31

```
atgtcgaatt cagagtcgaa tcacggtgca tccgcattcc gcaccacgac gcggcacatg     60

ctcaagtcgt cgaaggagta ccagcgcaag acgctcatgg gcggtctgtc aggattcgaa    120

tcgcccatcg gactcgatcg gcgtgaccgc atcaatgcgt tgaaaaccgg cgacataggt    180

tttgtgcatt cctgggacat caatacgtcg gtggacggcc cgggcacccg catgacggta    240

ttcctgagcg gctgcccact gcgctgccag tactgccaga accccgacac ctggaagatg    300

cgcgacggca agccggtgta cctcgatgcc atggtggtca agatcgaacg gtacaaggac    360

ctgttcgaag ccacgaaagg cggcatcacc ttctcgggcg gcgagtccat gatgcagccg    420

gcattcgtgt cgcgggtgtt ccgggcggcc aaggagatgg gtgtgcacac ctgccttgat    480

acttcgggct tcctcaacgc caactattcg gatgaaatga tcgacgacat cgatctgtgc    540

ctgctcgatg tgaagtccgg agacgaggag acctacaagc gggtaaccgg gggagtgctc    600

cagcccacca tcgatttcgg acagcggttg aacaggaggg gcaagaagat ctgggtgcgc    660

ttcgtgctgg ttcccgggct cacctcgtcg gaggagaacg tggagaatgt ggcccgcatc    720

tgtgagagct tcggcgacgc ggtggagcat atagacgtgc tgccgttcca ccagctcggg    780

cgtccgaagt ggcatgagct gcgaatccct tacccgttgg aggaccagaa gggaccttcc    840

caggcgttgc gcgaccgcgt gcgccagcag ttcgagagcc acggattcac ggtctacgtc    900

taa                                                                  903
```

<210> SEQ ID NO 32
<211> LENGTH: 300
<212> TYPE: PRT
<213> ORGANISM: Bifidobacterium animalis
<220> FEATURE:
<221> NAME/KEY: MISC_FEATURE
<223> OTHER INFORMATION: DSM 10140

<400> SEQUENCE: 32

```
Met Ser Asn Ser Glu Ser Asn His Gly Ala Ser Ala Phe Arg Thr Thr
1               5                   10                  15

Thr Arg His Met Leu Lys Ser Ser Lys Glu Tyr Gln Arg Lys Thr Leu
            20                  25                  30

Met Gly Gly Leu Ser Gly Phe Glu Ser Pro Ile Gly Leu Asp Arg Arg
        35                  40                  45

Asp Arg Ile Asn Ala Leu Lys Thr Gly Asp Ile Gly Phe Val His Ser
    50                  55                  60

Trp Asp Ile Asn Thr Ser Val Asp Gly Pro Gly Thr Arg Met Thr Val
65                  70                  75                  80

Phe Leu Ser Gly Cys Pro Leu Arg Cys Gln Tyr Cys Gln Asn Pro Asp
                85                  90                  95

Thr Trp Lys Met Arg Asp Gly Lys Pro Val Tyr Leu Asp Ala Met Val
            100                 105                 110

Val Lys Ile Glu Arg Tyr Lys Asp Leu Phe Glu Ala Thr Lys Gly Gly
        115                 120                 125

Ile Thr Phe Ser Gly Gly Glu Ser Met Met Gln Pro Ala Phe Val Ser
    130                 135                 140

Arg Val Phe Arg Ala Ala Lys Glu Met Gly Val His Thr Cys Leu Asp
145                 150                 155                 160

Thr Ser Gly Phe Leu Asn Ala Asn Tyr Ser Asp Glu Met Ile Asp Asp
```

165 170 175

Ile Asp Leu Cys Leu Leu Asp Val Lys Ser Gly Asp Glu Glu Thr Tyr
180 185 190

Lys Arg Val Thr Gly Gly Val Leu Gln Pro Thr Ile Asp Phe Gly Gln
195 200 205

Arg Leu Asn Arg Arg Gly Lys Lys Ile Trp Val Arg Phe Val Leu Val
210 215 220

Pro Gly Leu Thr Ser Ser Glu Glu Asn Val Glu Asn Val Ala Arg Ile
225 230 235 240

Cys Glu Ser Phe Gly Asp Ala Val Glu His Ile Asp Val Leu Pro Phe
245 250 255

His Gln Leu Gly Arg Pro Lys Trp His Glu Leu Arg Ile Pro Tyr Pro
260 265 270

Leu Glu Asp Gln Lys Gly Pro Ser Gln Ala Leu Arg Asp Arg Val Arg
275 280 285

Gln Gln Phe Glu Ser His Gly Phe Thr Val Tyr Val
290 295 300

<210> SEQ ID NO 33
<211> LENGTH: 720
<212> TYPE: DNA
<213> ORGANISM: Clostridium cellulolyticum

<400> SEQUENCE: 33
atggagatta aagggaggat acattcattt gagacatttg ggaccgtgga cggtcccgga 60
attagattta ttgtgtttct gaagggctgc ccgcttcgct gtaagtactg ccacaacaga 120
gatgcatgga gttcagaggg tgcaaaactg tacagtcctc aagaggtgtt gaaggaaatc 180
cagaaataca ggaattttat agatgcctct catggaggaa taacagtcag cgggggagaa 240
cctttaattc agcatgaatt tgtaaaggaa ctatttaaat tatgtcgtga agctgggata 300
cataccgctg tggacacttc cggctacgtc aatgtggaag atgtaaagga cacactagag 360
tatacagacc ttgttcttct tgatttaaag caggcaaatg cacagaagca tttggaattg 420
acaggagtgg agaataagcg tatcaagctg tttacaacct acctgggtga aatcggaaaa 480
cctgtttgga taagatatgt gcttataccg ggttatacag atggtgaaga ggatttgctg 540
gcagcataca attatttaaa gggatttaaa aatatagaga aaatagaggt tcttccatat 600
cacataatgg gaaaggcaaa atgggagaag ctgaacgtac aatatcccct ggagggagtt 660
ccttccccta cacaggaaga ggtggacagg gccaaaaaca tcctgactac aggaaaaccg 720

<210> SEQ ID NO 34
<211> LENGTH: 240
<212> TYPE: PRT
<213> ORGANISM: Clostridium cellulolyticum

<400> SEQUENCE: 34

Met Glu Ile Lys Gly Arg Ile His Ser Phe Glu Thr Phe Gly Thr Val
1 5 10 15

Asp Gly Pro Gly Ile Arg Phe Ile Val Phe Leu Lys Gly Cys Pro Leu
20 25 30

Arg Cys Lys Tyr Cys His Asn Arg Asp Ala Trp Ser Ser Glu Gly Ala
35 40 45

Lys Leu Tyr Ser Pro Gln Glu Val Leu Lys Glu Ile Gln Lys Tyr Arg
50 55 60

Asn Phe Ile Asp Ala Ser His Gly Gly Ile Thr Val Ser Gly Gly Glu

```
65                  70                  75                  80

Pro Leu Ile Gln His Glu Phe Val Lys Glu Leu Phe Lys Leu Cys Arg
                85                  90                  95

Glu Ala Gly Ile His Thr Ala Val Asp Thr Ser Gly Tyr Val Asn Val
            100                 105                 110

Glu Asp Val Lys Asp Thr Leu Glu Tyr Thr Asp Leu Val Leu Leu Asp
        115                 120                 125

Leu Lys Gln Ala Asn Ala Gln Lys His Leu Glu Leu Thr Gly Val Glu
    130                 135                 140

Asn Lys Arg Ile Lys Leu Phe Thr Thr Tyr Leu Gly Glu Ile Gly Lys
145                 150                 155                 160

Pro Val Trp Ile Arg Tyr Val Leu Ile Pro Gly Tyr Thr Asp Gly Glu
                165                 170                 175

Glu Asp Leu Leu Ala Ala Tyr Asn Tyr Leu Lys Gly Phe Lys Asn Ile
            180                 185                 190

Glu Lys Ile Glu Val Leu Pro Tyr His Ile Met Gly Lys Ala Lys Trp
        195                 200                 205

Glu Lys Leu Asn Val Gln Tyr Pro Leu Glu Gly Val Pro Ser Pro Thr
    210                 215                 220

Gln Glu Glu Val Asp Arg Ala Lys Asn Ile Leu Thr Thr Gly Lys Pro
225                 230                 235                 240
```

<210> SEQ ID NO 35
<211> LENGTH: 741
<212> TYPE: DNA
<213> ORGANISM: Escherichia coli

<400> SEQUENCE: 35

```
atgtcagtta ttggtcgcat tcactccttt gaatcctgtg gaaccgtaga cggcccaggt     60

attcgcttta tcaccttttt ccagggctgc ctgatgcgct gcctgtattg tcataaccgc    120

gacacctggg acacgcatgg cggtaaagaa gttaccgttg aagatttgat gaaggaagtg    180

gtgacctatc gccactttat gaacgcttcc ggcggcggcg ttaccgcatc cggcggtgaa    240

gcaatcctgc aagctgagtt tgttcgtgac tggttccgcg cctgcaaaaa agaaggcatt    300

catacctgtc tggacaccaa cggttttgtt cgtcgttacg atccggtgat tgatgaactg    360

ctggaagtaa ccgacctggt aatgctcgat ctcaaacaga tgaacgacga gatccaccaa    420

aatctggttg gagtttccaa ccaccgcacg ctggagttcg ctaaatatct ggcgaacaaa    480

aatgtgaagg tgtggatccg ctacgttgtt gtcccaggct ggtctgacga tgacgattca    540

gcgcatcgcc tcggtgaatt tacccgtgat atgggcaacg ttgagaaaat cgagcttctc    600

ccctaccacg agctgggcaa acacaaatgg gtggcaatgg gtgaagagta caaactcgac    660

ggtgttaaac caccgaagaa agagaccatg gaacgcgtga aaggcattct tgagcagtac    720

ggtcataagg taatgttcta a                                              741
```

<210> SEQ ID NO 36
<211> LENGTH: 246
<212> TYPE: PRT
<213> ORGANISM: Escherichia coli

<400> SEQUENCE: 36

```
Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
            20                  25                  30
```

```
Arg Cys Leu Tyr Cys His Asn Arg Asp Thr Trp Asp Thr His Gly Gly
        35                  40                  45

Lys Glu Val Thr Val Glu Asp Leu Met Lys Glu Val Val Thr Tyr Arg
    50                  55                  60

His Phe Met Asn Ala Ser Gly Gly Gly Val Thr Ala Ser Gly Gly Glu
65                  70                  75                  80

Ala Ile Leu Gln Ala Glu Phe Val Arg Asp Trp Phe Arg Ala Cys Lys
                85                  90                  95

Lys Glu Gly Ile His Thr Cys Leu Asp Thr Asn Gly Phe Val Arg Arg
            100                 105                 110

Tyr Asp Pro Val Ile Asp Glu Leu Leu Glu Val Thr Asp Leu Val Met
        115                 120                 125

Leu Asp Leu Lys Gln Met Asn Asp Glu Ile His Gln Asn Leu Val Gly
    130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Val Pro Gly Trp Ser Asp
                165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
        195                 200                 205

Lys Trp Val Ala Met Gly Glu Glu Tyr Lys Leu Asp Gly Val Lys Pro
    210                 215                 220

Pro Lys Lys Glu Thr Met Glu Arg Val Lys Gly Ile Leu Glu Gln Tyr
225                 230                 235                 240

Gly His Lys Val Met Phe
                245
```

<210> SEQ ID NO 37
<211> LENGTH: 2226
<212> TYPE: DNA
<213> ORGANISM: Bacillus licheniformis
<220> FEATURE:
<221> NAME/KEY: misc_feature
<223> OTHER INFORMATION: DSM13

<400> SEQUENCE: 37

```
atggaacaat ggaaaggttt caccacaaac gtttggcaaa aagaagtcaa tgtccgcgat      60

tttattctct cgaactttga gccatatcaa ggtgacgaat cgtttctcga acctccgacg     120

gaagctacat cggcattatg ggatcatgta atggatttga caaaaaaaga gcgtgaaaac     180

ggaggcgtcc ttgatatgga tacagagatc gtctcaacga tcacctcgca cggtcccgga     240

tatttgaaca aagacctgga aaaagtcgtc ggcgttcaaa ccgatgagcc gtttaaacgg     300

tcgcttcagc ctttcggcgg catccgaatg gcaaagcagg catgcgaatc ctatggtttt     360

aaactgaatg aagaagtgga aaggatcttt accgattacc gcaaaactca taaccaaggc     420

gtgtttgacg catatacgga cgaaatgaag ctcgcccgaa aagtcggaat cattaccgga     480

ctgcctgatg cttacgggcg cgggcgcatc atcggtgatt accggagagt ggcgctttac     540

ggcgtggatt tcttgatcga tgaaaagaaa aaagatgcgg ccggcacctc tcgggtgatg     600

tctgaagaaa acatccgcct tcgtgaagaa ctgtcagaac aaatccgagc attgaacgaa     660

cttaaagcgc ttgcaaaaag ctatgggttt gacatttcca agcctgcggc gaatgcaaga     720

gaagcatttc aatggctgta ttttgcctat ttggctgcca ttaaagagca aaacggagca     780
```

-continued

```
gcaatgagcc ttggccgcgt gtccacgttc cttgatattt acatcgaaag agatttgaaa    840

acgggcgtat taacagagcg tgaagcccaa gagcttgtcg accatttcgt catgaagctg    900

cgtttggtca aattcgcgcg cacacctgac tacaatgaac tgttcagcgg cgatccgacg    960

tgggtgacag aatcaatcgg cggaatggcg cacgacggac gcgccctggt gacgaaaaac   1020

tcgttccgtt tcctgcatac gcttgacaat ttaggcccgg cgcctgaacc gaatttaacc   1080

gttctttggt ctgtcagact gccgcaaaag tttaaaaact actgtgccaa aatgtcgatt   1140

aaaacaagct cgatccaata cgaaaatgac gatatcatgc gtccagaata cggtgatgac   1200

tacggaatcg cctgctgtgt atcggcaatg gcaatcggca aacaaatgca gttcttcgga   1260

gcacgcgcca acttggcgaa agctctttta tatgcgatta acggcggaaa agacgaaaag   1320

cataaaatgc aagtcggtcc ggaaatgccg ccggttgctt ccgacgtgct ggactatgac   1380

gaagtgatgc ataaattcga tcagacgatg gaatggctcg caggcttgta catcaacacg   1440

ctcaatgtca ttcactacat gcatgataaa tattgctatg aaagaattga aatggccctg   1500

cacgacacgg aaattttgcg gacgatggcc actgggatcg ccggcttgag tgttgtcgcc   1560

gattcattaa gcgctgtcaa atatgccaaa gtcagcgtgg tccgcgatga aaacggcatt   1620

gcggtcgatt ttgaaacaga aggcgacttt cctaagtacg gaaataacga tgaccgcgtc   1680

gacgcgatcg ccgttgacat tgtcaagcgc tttatgaaaa aactgcgcaa gcatcagaca   1740

tatcgccagt ccgttcagac catgtcaatt ttaacgatca cgtcaaacgt cgtttacggc   1800

aagaaaaccg gaaatacgcc ggatggacgc cgcgcgggag aaccgtttgc tccaggtgcg   1860

aatccgatgc acggccgcga tactaaaggg acgcttgcat cgctgtcttc agtggcaaag   1920

ctgccttaca gctatgcgct cgacggcatt tccaacacct tttcaatcgt cccgaaagcg   1980

cttggcaaag acgaagagag ccgcgccgcc aatttgtcaa gcatccttga cggatatgcc   2040

gcaaaaacag gacatcactt aaatgtaaac gtatttaaca gagagacact gctcgacgcc   2100

atggaacatc cagaggaata tccgcagtta acgattcgcg tctcaggcta tgcggtcaac   2160

tttattaagc tgacgaaaga acagcagtta gacgtcatca gcagaacctt ccatgaatcg   2220

atgtag                                                              2226
```

<210> SEQ ID NO 38
<211> LENGTH: 741
<212> TYPE: PRT
<213> ORGANISM: Bacillus licheniformis
<220> FEATURE:
<221> NAME/KEY: MISC_FEATURE
<223> OTHER INFORMATION: DSM13

<400> SEQUENCE: 38

```
Met Glu Gln Trp Lys Gly Phe Thr Thr Asn Val Trp Gln Lys Glu Val
1               5                   10                  15

Asn Val Arg Asp Phe Ile Leu Ser Asn Phe Glu Pro Tyr Gln Gly Asp
            20                  25                  30

Glu Ser Phe Leu Glu Pro Pro Thr Glu Ala Thr Ser Ala Leu Trp Asp
        35                  40                  45

His Val Met Asp Leu Thr Lys Lys Glu Arg Glu Asn Gly Gly Val Leu
    50                  55                  60

Asp Met Asp Thr Glu Ile Val Ser Thr Ile Thr Ser His Gly Pro Gly
65                  70                  75                  80

Tyr Leu Asn Lys Asp Leu Glu Lys Val Val Gly Val Gln Thr Asp Glu
                85                  90                  95
```

-continued

```
Pro Phe Lys Arg Ser Leu Gln Pro Phe Gly Gly Ile Arg Met Ala Lys
            100                 105                 110

Gln Ala Cys Glu Ser Tyr Gly Phe Lys Leu Asn Glu Glu Val Glu Arg
        115                 120                 125

Ile Phe Thr Asp Tyr Arg Lys Thr His Asn Gln Gly Val Phe Asp Ala
    130                 135                 140

Tyr Thr Asp Glu Met Lys Leu Ala Arg Lys Val Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Phe Leu Ile Asp Glu Lys Lys Lys Asp
            180                 185                 190

Ala Ala Gly Thr Ser Arg Val Met Ser Glu Glu Asn Ile Arg Leu Arg
        195                 200                 205

Glu Glu Leu Ser Glu Gln Ile Arg Ala Leu Asn Glu Leu Lys Ala Leu
    210                 215                 220

Ala Lys Ser Tyr Gly Phe Asp Ile Ser Lys Pro Ala Ala Asn Ala Arg
225                 230                 235                 240

Glu Ala Phe Gln Trp Leu Tyr Phe Ala Tyr Leu Ala Ala Ile Lys Glu
                245                 250                 255

Gln Asn Gly Ala Ala Met Ser Leu Gly Arg Val Ser Thr Phe Leu Asp
            260                 265                 270

Ile Tyr Ile Glu Arg Asp Leu Lys Thr Gly Val Leu Thr Glu Arg Glu
        275                 280                 285

Ala Gln Glu Leu Val Asp His Phe Val Met Lys Leu Arg Leu Val Lys
    290                 295                 300

Phe Ala Arg Thr Pro Asp Tyr Asn Glu Leu Phe Ser Gly Asp Pro Thr
305                 310                 315                 320

Trp Val Thr Glu Ser Ile Gly Gly Met Ala His Asp Gly Arg Ala Leu
                325                 330                 335

Val Thr Lys Asn Ser Phe Arg Phe Leu His Thr Leu Asp Asn Leu Gly
            340                 345                 350

Pro Ala Pro Glu Pro Asn Leu Thr Val Leu Trp Ser Val Arg Leu Pro
        355                 360                 365

Gln Lys Phe Lys Asn Tyr Cys Ala Lys Met Ser Ile Lys Thr Ser Ser
    370                 375                 380

Ile Gln Tyr Glu Asn Asp Asp Ile Met Arg Pro Glu Tyr Gly Asp Asp
385                 390                 395                 400

Tyr Gly Ile Ala Cys Cys Val Ser Ala Met Ala Ile Gly Lys Gln Met
                405                 410                 415

Gln Phe Phe Gly Ala Arg Ala Asn Leu Ala Lys Ala Leu Leu Tyr Ala
            420                 425                 430

Ile Asn Gly Gly Lys Asp Glu Lys His Lys Met Gln Val Gly Pro Glu
        435                 440                 445

Met Pro Pro Val Ala Ser Asp Val Leu Asp Tyr Asp Glu Val Met His
    450                 455                 460

Lys Phe Asp Gln Thr Met Glu Trp Leu Ala Gly Leu Tyr Ile Asn Thr
465                 470                 475                 480

Leu Asn Val Ile His Tyr Met His Asp Lys Tyr Cys Tyr Glu Arg Ile
                485                 490                 495

Glu Met Ala Leu His Asp Thr Glu Ile Leu Arg Thr Met Ala Thr Gly
            500                 505                 510
```

-continued

```
Ile Ala Gly Leu Ser Val Val Ala Asp Ser Leu Ser Ala Val Lys Tyr
        515                 520                 525

Ala Lys Val Ser Val Val Arg Asp Glu Asn Gly Ile Ala Val Asp Phe
    530                 535                 540

Glu Thr Glu Gly Asp Phe Pro Lys Tyr Gly Asn Asn Asp Asp Arg Val
545                 550                 555                 560

Asp Ala Ile Ala Val Asp Ile Val Lys Arg Phe Met Lys Lys Leu Arg
                565                 570                 575

Lys His Gln Thr Tyr Arg Gln Ser Val Gln Thr Met Ser Ile Leu Thr
            580                 585                 590

Ile Thr Ser Asn Val Val Tyr Gly Lys Lys Thr Gly Asn Thr Pro Asp
        595                 600                 605

Gly Arg Arg Ala Gly Glu Pro Phe Ala Pro Gly Ala Asn Pro Met His
    610                 615                 620

Gly Arg Asp Thr Lys Gly Thr Leu Ala Ser Leu Ser Ser Val Ala Lys
625                 630                 635                 640

Leu Pro Tyr Ser Tyr Ala Leu Asp Gly Ile Ser Asn Thr Phe Ser Ile
                645                 650                 655

Val Pro Lys Ala Leu Gly Lys Asp Glu Glu Ser Arg Ala Ala Asn Leu
            660                 665                 670

Ser Ser Ile Leu Asp Gly Tyr Ala Ala Lys Thr Gly His His Leu Asn
        675                 680                 685

Val Asn Val Phe Asn Arg Glu Thr Leu Leu Asp Ala Met Glu His Pro
    690                 695                 700

Glu Glu Tyr Pro Gln Leu Thr Ile Arg Val Ser Gly Tyr Ala Val Asn
705                 710                 715                 720

Phe Ile Lys Leu Thr Lys Glu Gln Gln Leu Asp Val Ile Ser Arg Thr
                725                 730                 735

Phe His Glu Ser Met
            740


<210> SEQ ID NO 39
<211> LENGTH: 2226
<212> TYPE: DNA
<213> ORGANISM: Bacillus licheniformis
<220> FEATURE:
<221> NAME/KEY: misc_feature
<223> OTHER INFORMATION: ATCC14580

<400> SEQUENCE: 39

atggaacaat ggaaaggttt caccacaaac gtttggcaaa aagaagtcaa tgtccgcgat      60

tttattctct cgaactttga gccatatcaa ggtgacgaat cgtttctcga acctccgacg     120

gaagctacat cggcattatg ggatcatgta atggatttga caaaaaaaga gcgtgaaaac     180

ggaggcgtcc ttgatatgga tacagagatc gtctcaacga tcacctcgca cggtcccgga     240

tatttgaaca aagacctgga aaaagtcgtc ggcgttcaaa ccgatgagcc gtttaaacgg     300

tcgcttcagc ctttcggcgg catccgaatg gcaaagcagg catgcgaatc ctatggtttt     360

aaactgaatg aagaagtgga aaggatcttt accgattacc gcaaaactca taaccaaggc     420

gtgtttgacg catatacgga cgaaatgaag ctcgcccgaa aagtcggaat cattaccgga     480

ctgcctgatg cttacgggcg cgggcgcatc atcggtgatt accggagagt ggcgctttac     540

ggcgtggatt tcttgatcga tgaaaagaaa aaagatgcgg ccggcacctc tcgggtgatg     600

tctgaagaaa acatccgcct tcgtgaagaa ctgtcagaac aaatccgagc attgaacgaa     660

cttaaagcgc ttgcaaaaag ctatgggttt gacatttcca agcctgcggc gaatgcaaga     720
```

-continued

```
gaagcatttc aatggctgta ttttgcctat ttggctgcca ttaaagagca aaacggagca    780
gcaatgagcc ttggccgcgt gtccacgttc cttgatattt acatcgaaag agatttgaaa    840
acgggcgtat taacagagcg tgaagcccaa gagcttgtcg accatttcgt catgaagctg    900
cgtttggtca aattcgcgcg cacacctgac tacaatgaac tgttcagcgg cgatccgacg    960
tgggtgacag aatcaatcgg cggaatggcg cacgacggac gcgccctggt gacgaaaaac   1020
tcgttccgtt tcctgcatac gcttgacaat ttaggcccgg cgcctgaacc gaatttaacc   1080
gttctttggt ctgtcagact gccgcaaaag tttaaaaact actgtgccaa aatgtcgatt   1140
aaaacaagct cgatccaata cgaaaatgac gatatcatgc gtccagaata cggtgatgac   1200
tacggaatcg cctgctgtgt atcggcaatg gcaatcggca aacaaatgca gttcttcgga   1260
gcacgcgcca acttggcgaa agctctttta tatgcgatta acggcggaaa agacgaaaag   1320
cataaaatgc aagtcggtcc ggaaatgccg ccggttgctt ccgacgtgct ggactatgac   1380
gaagtgatgc ataaattcga tcagacgatg gaatggctcg caggcttgta catcaacacg   1440
ctcaatgtca ttcactacat gcatgataaa tattgctatg aaagaattga aatggccctg   1500
cacgacacgg aaattttgcg gacgatggcc actgggatcg ccggcttgag tgttgtcgcc   1560
gattcattaa gcgctgtcaa atatgccaaa gtcagcgtgg tccgcgatga aaacggcatt   1620
gcggtcgatt ttgaaacaga aggcgacttt cctaagtacg gaaataacga tgaccgcgtc   1680
gacgcgatcg ccgttgacat tgtcaagcgc tttatgaaaa aactgcgcaa gcatcagaca   1740
tatcgccagt ccgttcagac catgtcaatt ttaacgatca cgtcaaacgt cgtttacggc   1800
aagaaaaccg gaaatacgcc ggatggacgc cgcgcgggag aaccgtttgc tccaggtgcg   1860
aatccgatgc acggccgcga tactaaaggg acgcttgcat cgctgtcttc agtggcaaag   1920
ctgccttaca gctatgcgct cgacggcatt tccaacacct tttcaatcgt cccgaaagcg   1980
cttggcaaag acgaagagag ccgcgccgcc aatttgtcaa gcatccttga cggatatgcc   2040
gcaaaaacag gacatcactt aaatgtaaac gtatttaaca gagagacact gctcgacgcc   2100
atggaacatc cagaggaata tccgcagtta acgattcgcg tctcaggcta tgcggtcaac   2160
tttattaagc tgacgaaaga acagcagtta gacgtcatca gcagaacctt ccatgaatcg   2220
atgtag                                                              2226
```

<210> SEQ ID NO 40
<211> LENGTH: 741
<212> TYPE: PRT
<213> ORGANISM: Bacillus licheniformis
<220> FEATURE:
<221> NAME/KEY: MISC_FEATURE
<223> OTHER INFORMATION: ATCC14580

<400> SEQUENCE: 40

```
Met Glu Gln Trp Lys Gly Phe Thr Thr Asn Val Trp Gln Lys Glu Val
1               5                   10                  15

Asn Val Arg Asp Phe Ile Leu Ser Asn Phe Glu Pro Tyr Gln Gly Asp
            20                  25                  30

Glu Ser Phe Leu Glu Pro Pro Thr Glu Ala Thr Ser Ala Leu Trp Asp
        35                  40                  45

His Val Met Asp Leu Thr Lys Lys Glu Arg Glu Asn Gly Gly Val Leu
    50                  55                  60

Asp Met Asp Thr Glu Ile Val Ser Thr Ile Thr Ser His Gly Pro Gly
65                  70                  75                  80
```

```
Tyr Leu Asn Lys Asp Leu Glu Lys Val Val Gly Val Gln Thr Asp Glu
                85                  90                  95

Pro Phe Lys Arg Ser Leu Gln Pro Phe Gly Gly Ile Arg Met Ala Lys
            100                 105                 110

Gln Ala Cys Glu Ser Tyr Gly Phe Lys Leu Asn Glu Glu Val Glu Arg
        115                 120                 125

Ile Phe Thr Asp Tyr Arg Lys Thr His Asn Gln Gly Val Phe Asp Ala
    130                 135                 140

Tyr Thr Asp Glu Met Lys Leu Ala Arg Lys Val Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Phe Leu Ile Asp Glu Lys Lys Lys Asp
            180                 185                 190

Ala Ala Gly Thr Ser Arg Val Met Ser Glu Glu Asn Ile Arg Leu Arg
        195                 200                 205

Glu Glu Leu Ser Glu Gln Ile Arg Ala Leu Asn Glu Leu Lys Ala Leu
    210                 215                 220

Ala Lys Ser Tyr Gly Phe Asp Ile Ser Lys Pro Ala Ala Asn Ala Arg
225                 230                 235                 240

Glu Ala Phe Gln Trp Leu Tyr Phe Ala Tyr Leu Ala Ala Ile Lys Glu
                245                 250                 255

Gln Asn Gly Ala Ala Met Ser Leu Gly Arg Val Ser Thr Phe Leu Asp
            260                 265                 270

Ile Tyr Ile Glu Arg Asp Leu Lys Thr Gly Val Leu Thr Glu Arg Glu
        275                 280                 285

Ala Gln Glu Leu Val Asp His Phe Val Met Lys Leu Arg Leu Val Lys
    290                 295                 300

Phe Ala Arg Thr Pro Asp Tyr Asn Glu Leu Phe Ser Gly Asp Pro Thr
305                 310                 315                 320

Trp Val Thr Glu Ser Ile Gly Gly Met Ala His Asp Gly Arg Ala Leu
                325                 330                 335

Val Thr Lys Asn Ser Phe Arg Phe Leu His Thr Leu Asp Asn Leu Gly
            340                 345                 350

Pro Ala Pro Glu Pro Asn Leu Thr Val Leu Trp Ser Val Arg Leu Pro
        355                 360                 365

Gln Lys Phe Lys Asn Tyr Cys Ala Lys Met Ser Ile Lys Thr Ser Ser
    370                 375                 380

Ile Gln Tyr Glu Asn Asp Asp Ile Met Arg Pro Glu Tyr Gly Asp Asp
385                 390                 395                 400

Tyr Gly Ile Ala Cys Cys Val Ser Ala Met Ala Ile Gly Lys Gln Met
                405                 410                 415

Gln Phe Phe Gly Ala Arg Ala Asn Leu Ala Lys Ala Leu Leu Tyr Ala
            420                 425                 430

Ile Asn Gly Gly Lys Asp Glu Lys His Lys Met Gln Val Gly Pro Glu
        435                 440                 445

Met Pro Pro Val Ala Ser Asp Val Leu Asp Tyr Asp Glu Val Met His
    450                 455                 460

Lys Phe Asp Gln Thr Met Glu Trp Leu Ala Gly Leu Tyr Ile Asn Thr
465                 470                 475                 480

Leu Asn Val Ile His Tyr Met His Asp Lys Tyr Cys Tyr Glu Arg Ile
                485                 490                 495

Glu Met Ala Leu His Asp Thr Glu Ile Leu Arg Thr Met Ala Thr Gly
```

```
            500                 505                 510

Ile Ala Gly Leu Ser Val Val Ala Asp Ser Leu Ser Ala Val Lys Tyr
        515                 520                 525

Ala Lys Val Ser Val Val Arg Asp Glu Asn Gly Ile Ala Val Asp Phe
    530                 535                 540

Glu Thr Glu Gly Asp Phe Pro Lys Tyr Gly Asn Asn Asp Asp Arg Val
545                 550                 555                 560

Asp Ala Ile Ala Val Asp Ile Val Lys Arg Phe Met Lys Lys Leu Arg
                565                 570                 575

Lys His Gln Thr Tyr Arg Gln Ser Val Gln Thr Met Ser Ile Leu Thr
            580                 585                 590

Ile Thr Ser Asn Val Val Tyr Gly Lys Lys Thr Gly Asn Thr Pro Asp
        595                 600                 605

Gly Arg Arg Ala Gly Glu Pro Phe Ala Pro Gly Ala Asn Pro Met His
    610                 615                 620

Gly Arg Asp Thr Lys Gly Thr Leu Ala Ser Leu Ser Ser Val Ala Lys
625                 630                 635                 640

Leu Pro Tyr Ser Tyr Ala Leu Asp Gly Ile Ser Asn Thr Phe Ser Ile
                645                 650                 655

Val Pro Lys Ala Leu Gly Lys Asp Glu Glu Ser Arg Ala Ala Asn Leu
            660                 665                 670

Ser Ser Ile Leu Asp Gly Tyr Ala Ala Lys Thr Gly His His Leu Asn
        675                 680                 685

Val Asn Val Phe Asn Arg Glu Thr Leu Leu Asp Ala Met Glu His Pro
    690                 695                 700

Glu Glu Tyr Pro Gln Leu Thr Ile Arg Val Ser Gly Tyr Ala Val Asn
705                 710                 715                 720

Phe Ile Lys Leu Thr Lys Glu Gln Gln Leu Asp Val Ile Ser Arg Thr
                725                 730                 735

Phe His Glu Ser Met
            740


<210> SEQ ID NO 41
<211> LENGTH: 2310
<212> TYPE: DNA
<213> ORGANISM: Streptococcus thermophilus
<220> FEATURE:
<221> NAME/KEY: misc_feature
<223> OTHER INFORMATION: CNRZ1066

<400> SEQUENCE: 41

atggcaacgg ttaaaactaa cacagatgtt tttgaaaaag cgtgggaagg ctttaaagga      60

actgactgga aagaaaaagc aagtgtgtct cgcttcgtac aagcaaacta cacaccatat     120

gatggtgatg aaagcttcct tgcaggacca actgaacgct cacttaaaat caaaaaaatc     180

attgaagaaa ctaaagccca ctacgaagaa actcgtttcc caatggatac tcgtccgaca     240

tcaatcgcag atattcctgc cggctatatt tcaaaagacg acgaactaat ctacggtatt     300

caaaatgatg agttattcaa attgaatttc atgccaaaag gcggaattcg tatggcagaa     360

acagctctca aggaacatgg ctatgaacct gatccagctg ttcacgaaat ttttacaaaa     420

catgtaacta cagtaaatga cggtatcttc cgtgcttata catcaaatat ccgtcgtgca     480

cgtcacgcac acactataac tggacttcca gatgcttact ctcgtggacg tatcatcggt     540

gtttatgctc gccttgctct ttacggtgct gacttcttga tgcaagaaaa agtaaacgac     600

tggaactcta tcgaagaaat caacgaagaa actattcgtc ttcgtgaaga agttaacctt     660
```

```
caataccaag cacttcaaga tgttgttcgc cttggtgacc tttacggtgt agatgttcgt    720
cgtccagcct tcgatactaa agaagctatc caatggacaa acattgcttt tatggctgta    780
tgtcgtgtta tcaatggtgc ggctacttca cttggtcgtg tgccaatcgt ccttgacata    840
tatgcagaac gtgaccttgc tcgtggtact tacactgaat cagaaatcca agaattcgtt    900
gatgattttg tcttgaaact tcgtactgta aaattcgcac gtacaaaagc ttacgacgaa    960
ctttactcag gtgacccaac attcatcaca acttctatgg ctggtatggg tgctgacgga   1020
cgtcaccgtg ttactaaaat ggactaccgt ttcttgaaca cacttgataa tattggtaat   1080
gctccagaac caaacttgac agttctttgg tctgacaaat tgccttactc attccgtcgc   1140
tactgtatgc acatgagtca caagcactct tctattcaat acgaaggtgt gactactatg   1200
gctaaagacg gatacggtga aatgagctgt atctcatgtt gtgtatcacc acttgaccca   1260
gaaaacgaag aacaacgcca caacatccaa tacttcggtg ctcgtgttaa cgtacttaaa   1320
gcccttctta ctggtttgaa cggtggttac gacgatgttc ataaagacta caaagtattt   1380
gacatcgatc cagtccgtga tgaagttctt gactttgaca ctgttaaagc taacttcgaa   1440
aaatctcttg actggttgac tgacacttat gtagatgccc ttaacatcat ccactacatg   1500
actgataagt acaactacga agctgttcaa atggccttct tgccaactaa acaacgtgct   1560
aacatgggat tcggtatctg tggtttcgca aatactgttg atacattgtc agctatcaag   1620
tacgctacag ttaaaccaat ccgtgacgaa gatggctaca tctacgacta cgaaacaatc   1680
ggtgaatacc cacgttgggg tgaagatgac ccacgttcaa acgaattggc agaatggttg   1740
attgaagctt acactactcg tcttcgtagc cataaactct acaaagatgc agaagctaca   1800
gtttcacttc ttacaatcac ttcgaacgtt gcttactcta aacaaactgg taactctcca   1860
gttcacaaag ggtatacct caacgaagat ggttcagtga acttgtccaa attggaattc   1920
ttctcaccag gtgctaaccc atctaacaaa gctaaaggtg gatggttgca aaacttgaac   1980
tcacttgcaa gccttgactt cggttatgca gctgacggta tctcacttac tactcaagta   2040
tcacctcgtg cccttggtaa gactcgcgac gaacaagttg ataacctcgt aactatcctt   2100
gacggatact tcgaaaacgg tggacaacac cttaacttga acgttatgga cttgtcagct   2160
gtttacaaaa agatcatgag cggtgaagat gttatcgtac gtatctctgg atactgtgta   2220
aacactaaat acctcactcc agaacaaaaa actgaattga cacaacgtgt cttccacgaa   2280
gttctttcaa cggacgatgc tatgggataa                                    2310
```

<210> SEQ ID NO 42
<211> LENGTH: 769
<212> TYPE: PRT
<213> ORGANISM: Streptococcus thermophilus
<220> FEATURE:
<221> NAME/KEY: MISC_FEATURE
<223> OTHER INFORMATION: CNRZ1066

<400> SEQUENCE: 42

```
Met Ala Thr Val Lys Thr Asn Thr Asp Val Phe Glu Lys Ala Trp Glu
1               5                   10                  15

Gly Phe Lys Gly Thr Asp Trp Lys Glu Lys Ala Ser Val Ser Arg Phe
            20                  25                  30

Val Gln Ala Asn Tyr Thr Pro Tyr Asp Gly Asp Glu Ser Phe Leu Ala
        35                  40                  45

Gly Pro Thr Glu Arg Ser Leu Lys Ile Lys Lys Ile Ile Glu Glu Thr
    50                  55                  60
```

-continued

```
Lys Ala His Tyr Glu Glu Thr Arg Phe Pro Met Asp Thr Arg Pro Thr
65                  70                  75                  80

Ser Ile Ala Asp Ile Pro Ala Gly Tyr Ile Ser Lys Asp Asp Glu Leu
                85                  90                  95

Ile Tyr Gly Ile Gln Asn Asp Glu Leu Phe Lys Leu Asn Phe Met Pro
            100                 105                 110

Lys Gly Gly Ile Arg Met Ala Glu Thr Ala Leu Lys Glu His Gly Tyr
        115                 120                 125

Glu Pro Asp Pro Ala Val His Glu Ile Phe Thr Lys His Val Thr Thr
    130                 135                 140

Val Asn Asp Gly Ile Phe Arg Ala Tyr Thr Ser Asn Ile Arg Arg Ala
145                 150                 155                 160

Arg His Ala His Thr Ile Thr Gly Leu Pro Asp Ala Tyr Ser Arg Gly
                165                 170                 175

Arg Ile Ile Gly Val Tyr Ala Arg Leu Ala Leu Tyr Gly Ala Asp Phe
            180                 185                 190

Leu Met Gln Glu Lys Val Asn Asp Trp Asn Ser Ile Glu Glu Ile Asn
        195                 200                 205

Glu Glu Thr Ile Arg Leu Arg Glu Glu Val Asn Leu Gln Tyr Gln Ala
    210                 215                 220

Leu Gln Asp Val Val Arg Leu Gly Asp Leu Tyr Gly Val Asp Val Arg
225                 230                 235                 240

Arg Pro Ala Phe Asp Thr Lys Glu Ala Ile Gln Trp Thr Asn Ile Ala
                245                 250                 255

Phe Met Ala Val Cys Arg Val Ile Asn Gly Ala Ala Thr Ser Leu Gly
            260                 265                 270

Arg Val Pro Ile Val Leu Asp Ile Tyr Ala Glu Arg Asp Leu Ala Arg
        275                 280                 285

Gly Thr Tyr Thr Glu Ser Glu Ile Gln Glu Phe Val Asp Asp Phe Val
    290                 295                 300

Leu Lys Leu Arg Thr Val Lys Phe Ala Arg Thr Lys Ala Tyr Asp Glu
305                 310                 315                 320

Leu Tyr Ser Gly Asp Pro Thr Phe Ile Thr Thr Ser Met Ala Gly Met
                325                 330                 335

Gly Ala Asp Gly Arg His Arg Val Thr Lys Met Asp Tyr Arg Phe Leu
            340                 345                 350

Asn Thr Leu Asp Asn Ile Gly Asn Ala Pro Glu Pro Asn Leu Thr Val
        355                 360                 365

Leu Trp Ser Asp Lys Leu Pro Tyr Ser Phe Arg Arg Tyr Cys Met His
    370                 375                 380

Met Ser His Lys His Ser Ser Ile Gln Tyr Glu Gly Val Thr Thr Met
385                 390                 395                 400

Ala Lys Asp Gly Tyr Gly Glu Met Ser Cys Ile Ser Cys Cys Val Ser
                405                 410                 415

Pro Leu Asp Pro Glu Asn Glu Glu Gln Arg His Asn Ile Gln Tyr Phe
            420                 425                 430

Gly Ala Arg Val Asn Val Leu Lys Ala Leu Leu Thr Gly Leu Asn Gly
        435                 440                 445

Gly Tyr Asp Asp Val His Lys Asp Tyr Lys Val Phe Asp Ile Asp Pro
    450                 455                 460

Val Arg Asp Glu Val Leu Asp Phe Asp Thr Val Lys Ala Asn Phe Glu
465                 470                 475                 480
```

Lys Ser Leu Asp Trp Leu Thr Asp Thr Tyr Val Asp Ala Leu Asn Ile
485 490 495

Ile His Tyr Met Thr Asp Lys Tyr Asn Tyr Glu Ala Val Gln Met Ala
500 505 510

Phe Leu Pro Thr Lys Gln Arg Ala Asn Met Gly Phe Gly Ile Cys Gly
515 520 525

Phe Ala Asn Thr Val Asp Thr Leu Ser Ala Ile Lys Tyr Ala Thr Val
530 535 540

Lys Pro Ile Arg Asp Glu Asp Gly Tyr Ile Tyr Asp Tyr Glu Thr Ile
545 550 555 560

Gly Glu Tyr Pro Arg Trp Gly Glu Asp Asp Pro Arg Ser Asn Glu Leu
565 570 575

Ala Glu Trp Leu Ile Glu Ala Tyr Thr Thr Arg Leu Arg Ser His Lys
580 585 590

Leu Tyr Lys Asp Ala Glu Ala Thr Val Ser Leu Leu Thr Ile Thr Ser
595 600 605

Asn Val Ala Tyr Ser Lys Gln Thr Gly Asn Ser Pro Val His Lys Gly
610 615 620

Val Tyr Leu Asn Glu Asp Gly Ser Val Asn Leu Ser Lys Leu Glu Phe
625 630 635 640

Phe Ser Pro Gly Ala Asn Pro Ser Asn Lys Ala Lys Gly Gly Trp Leu
645 650 655

Gln Asn Leu Asn Ser Leu Ala Ser Leu Asp Phe Gly Tyr Ala Ala Asp
660 665 670

Gly Ile Ser Leu Thr Thr Gln Val Ser Pro Arg Ala Leu Gly Lys Thr
675 680 685

Arg Asp Glu Gln Val Asp Asn Leu Val Thr Ile Leu Asp Gly Tyr Phe
690 695 700

Glu Asn Gly Gly Gln His Leu Asn Leu Asn Val Met Asp Leu Ser Ala
705 710 715 720

Val Tyr Lys Lys Ile Met Ser Gly Glu Asp Val Ile Val Arg Ile Ser
725 730 735

Gly Tyr Cys Val Asn Thr Lys Tyr Leu Thr Pro Glu Gln Lys Thr Glu
740 745 750

Leu Thr Gln Arg Val Phe His Glu Val Leu Ser Thr Asp Asp Ala Met
755 760 765

Gly

<210> SEQ ID NO 43
<211> LENGTH: 2310
<212> TYPE: DNA
<213> ORGANISM: Streptococcus thermophilus
<220> FEATURE:
<221> NAME/KEY: MISC_FEATURE
<223> OTHER INFORMATION: LMG18311

<400> SEQUENCE: 43
atggcaacgg ttaaaactaa cacagatgtt tttgaaaaag cgtgggaagg ctttaaagga 60
actgactgga aagaaaaagc aagtgtgtct cgcttcgtac aagcaaacta cacaccatat 120
gatggtgatg aaagcttcct tgcaggacca actgaacgct cacttaaaat caaaaaaatc 180
attgaagaaa ctaaagctca ctacgaagaa actcgtttcc caatggatac tcgtccgaca 240
tcaatcgcag atattcctgc cggctatatt tcaaaagacg acgaactaat ctacggtatt 300
caaaatgatg agttattcaa attgaatttc atgccaaaag gcggaattcg tatggcagaa 360

-continued acagctctca aggaacatgg ctatgaacct gatccagctg ttcacgaaat ttttacaaaa 420
catgtaacta cagtaaatga cggtatcttc cgtgcttata catcaaatat ccgtcgtgca 480
cgtcacgcac acactataac tggacttcca gatgcttact ctcgtggacg tatcatcggt 540
gtttatgctc gccttgctct ttacggtgct gacttcttga tgcaagaaaa agtaaacgac 600
tggaactcta tcgaagaaat caacgaagaa actattcgtc ttcgtgaaga agttaacctt 660
caataccaag cacttcaaga tgttgttcgc cttggtgacc tttacggtgt agatgttcgt 720
cgtccagcct tcgatactaa agaagctatc caatggacaa acattgcttt tatggctgta 780
tgtcgtgtta tcaatggtgc ggctacttca cttggtcgtg tgccaatcgt ccttgacata 840
tatgcagaac gtgaccttgc tcgtggtact tacactgaat cagaaatcca agaattcgtt 900
gatgattttg tcttgaaact tcgtactgta aaattcgcac gtacaaaagc ttacgacgaa 960
ctttactcag gtgacccaac attcatcaca acttctatgg ctggtatggg tgctgacgga 1020
cgtcaccgtg ttactaaaat ggactaccgt ttcttgaaca cacttgataa tattggtaat 1080
gctccagaac caaacttgac agttctttgg tctgacaaat tgccttactc attccgtcgc 1140
tactgtatgc acatgagtca caagcactct tctattcaat acgaaggtgt gactactatg 1200
gctaaagacg gatacggtga aatgagctgt atctcatgtt gtgtatcacc acttgaccca 1260
gaaaacgaag aacaacgcca caacatccaa tacttcggtg ctcgtgttaa cgtacttaaa 1320
gcccttctta ctggtttgaa cggtggttac gacgatgttc ataaagacta caaagtattt 1380
gacatcgatc cagtccgtga tgaagttctt gactttgaca ctgttaaagc taacttcgaa 1440
aaatctcttg actggttgac tgacacttat gtagatgccc ttaacatcat ccactacatg 1500
actgataagt acaactacga agctgttcaa atggccttct tgccaactaa acaacgtgct 1560
aacatgggat tcggtatctg tggtttcgca aatactgttg atacattgtc agctatcaag 1620
tacgctacag ttaaaccaat ccgtgacgaa gatggctaca tctacgacta cgaaacaatc 1680
ggtgaatacc cacgttgggg tgaagatgac ccacgttcaa acgaattggc agaatggttg 1740
attgaagctt acactactcg tcttcgtagc cataaactct acaaagatgc agaagctaca 1800
gtttcacttc ttacaatcac ttcgaacgtt gcttactcta aacaaactgg taactctcca 1860
gttcacaaag ggtatacct caacgaagat ggttcagtga acttgtctaa attggaattc 1920
ttctcaccag gtgctaaccc atctaacaaa gctaaaggtg gatggttgca aaacttgaac 1980
tcacttgcaa gccttgactt cggttatgca gctgacggta tctcacttac tactcaagta 2040
tcacctcgtg cccttggtaa gactcgcgac gaacaagttg ataacctcgt aactatcctt 2100
gacggatact tcgaaaacgg tggacaacac cttaacttga acgttatgga cttgtcagct 2160
gtttacaaaa agatcatgag cggtgaagat gttatcgtac gtatctctgg atactgtgta 2220
aacactaaat acctcactcc agaacaaaaa actgaattga cacaacgtgt cttccacgaa 2280
gttctttcaa cggacgatgc tatgggataa 2310

<210> SEQ ID NO 44
<211> LENGTH: 769
<212> TYPE: PRT
<213> ORGANISM: Streptococcus thermophilus
<220> FEATURE:
<221> NAME/KEY: MISC_FEATURE
<223> OTHER INFORMATION: LMG18311

<400> SEQUENCE: 44

Met Ala Thr Val Lys Thr Asn Thr Asp Val Phe Glu Lys Ala Trp Glu
1 5 10 15

```
Gly Phe Lys Gly Thr Asp Trp Lys Glu Lys Ala Ser Val Ser Arg Phe
            20                  25                  30

Val Gln Ala Asn Tyr Thr Pro Tyr Asp Gly Asp Glu Ser Phe Leu Ala
        35                  40                  45

Gly Pro Thr Glu Arg Ser Leu Lys Ile Lys Lys Ile Ile Glu Glu Thr
    50                  55                  60

Lys Ala His Tyr Glu Glu Thr Arg Phe Pro Met Asp Thr Arg Pro Thr
65                  70                  75                  80

Ser Ile Ala Asp Ile Pro Ala Gly Tyr Ile Ser Lys Asp Asp Glu Leu
                85                  90                  95

Ile Tyr Gly Ile Gln Asn Asp Glu Leu Phe Lys Leu Asn Phe Met Pro
            100                 105                 110

Lys Gly Gly Ile Arg Met Ala Glu Thr Ala Leu Lys Glu His Gly Tyr
        115                 120                 125

Glu Pro Asp Pro Ala Val His Glu Ile Phe Thr Lys His Val Thr Thr
    130                 135                 140

Val Asn Asp Gly Ile Phe Arg Ala Tyr Thr Ser Asn Ile Arg Arg Ala
145                 150                 155                 160

Arg His Ala His Thr Ile Thr Gly Leu Pro Asp Ala Tyr Ser Arg Gly
                165                 170                 175

Arg Ile Ile Gly Val Tyr Ala Arg Leu Ala Leu Tyr Gly Ala Asp Phe
            180                 185                 190

Leu Met Gln Glu Lys Val Asn Asp Trp Asn Ser Ile Glu Glu Ile Asn
        195                 200                 205

Glu Glu Thr Ile Arg Leu Arg Glu Glu Val Asn Leu Gln Tyr Gln Ala
    210                 215                 220

Leu Gln Asp Val Val Arg Leu Gly Asp Leu Tyr Gly Val Asp Val Arg
225                 230                 235                 240

Arg Pro Ala Phe Asp Thr Lys Glu Ala Ile Gln Trp Thr Asn Ile Ala
                245                 250                 255

Phe Met Ala Val Cys Arg Val Ile Asn Gly Ala Ala Thr Ser Leu Gly
            260                 265                 270

Arg Val Pro Ile Val Leu Asp Ile Tyr Ala Glu Arg Asp Leu Ala Arg
        275                 280                 285

Gly Thr Tyr Thr Glu Ser Glu Ile Gln Glu Phe Val Asp Asp Phe Val
    290                 295                 300

Leu Lys Leu Arg Thr Val Lys Phe Ala Arg Thr Lys Ala Tyr Asp Glu
305                 310                 315                 320

Leu Tyr Ser Gly Asp Pro Thr Phe Ile Thr Thr Ser Met Ala Gly Met
                325                 330                 335

Gly Ala Asp Gly Arg His Arg Val Thr Lys Met Asp Tyr Arg Phe Leu
            340                 345                 350

Asn Thr Leu Asp Asn Ile Gly Asn Ala Pro Glu Pro Asn Leu Thr Val
        355                 360                 365

Leu Trp Ser Asp Lys Leu Pro Tyr Ser Phe Arg Arg Tyr Cys Met His
    370                 375                 380

Met Ser His Lys His Ser Ser Ile Gln Tyr Glu Gly Val Thr Thr Met
385                 390                 395                 400

Ala Lys Asp Gly Tyr Gly Glu Met Ser Cys Ile Ser Cys Cys Val Ser
                405                 410                 415

Pro Leu Asp Pro Glu Asn Glu Glu Gln Arg His Asn Ile Gln Tyr Phe
            420                 425                 430
```

-continued

```
Gly Ala Arg Val Asn Val Leu Lys Ala Leu Leu Thr Gly Leu Asn Gly
        435                 440                 445

Gly Tyr Asp Asp Val His Lys Asp Tyr Lys Val Phe Asp Ile Asp Pro
    450                 455                 460

Val Arg Asp Glu Val Leu Asp Phe Asp Thr Val Lys Ala Asn Phe Glu
465                 470                 475                 480

Lys Ser Leu Asp Trp Leu Thr Asp Thr Tyr Val Asp Ala Leu Asn Ile
                485                 490                 495

Ile His Tyr Met Thr Asp Lys Tyr Asn Tyr Glu Ala Val Gln Met Ala
            500                 505                 510

Phe Leu Pro Thr Lys Gln Arg Ala Asn Met Gly Phe Gly Ile Cys Gly
        515                 520                 525

Phe Ala Asn Thr Val Asp Thr Leu Ser Ala Ile Lys Tyr Ala Thr Val
    530                 535                 540

Lys Pro Ile Arg Asp Glu Asp Gly Tyr Ile Tyr Asp Tyr Glu Thr Ile
545                 550                 555                 560

Gly Glu Tyr Pro Arg Trp Gly Glu Asp Asp Pro Arg Ser Asn Glu Leu
                565                 570                 575

Ala Glu Trp Leu Ile Glu Ala Tyr Thr Thr Arg Leu Arg Ser His Lys
            580                 585                 590

Leu Tyr Lys Asp Ala Glu Ala Thr Val Ser Leu Leu Thr Ile Thr Ser
        595                 600                 605

Asn Val Ala Tyr Ser Lys Gln Thr Gly Asn Ser Pro Val His Lys Gly
    610                 615                 620

Val Tyr Leu Asn Glu Asp Gly Ser Val Asn Leu Ser Lys Leu Glu Phe
625                 630                 635                 640

Phe Ser Pro Gly Ala Asn Pro Ser Asn Lys Ala Lys Gly Gly Trp Leu
                645                 650                 655

Gln Asn Leu Asn Ser Leu Ala Ser Leu Asp Phe Gly Tyr Ala Ala Asp
            660                 665                 670

Gly Ile Ser Leu Thr Thr Gln Val Ser Pro Arg Ala Leu Gly Lys Thr
        675                 680                 685

Arg Asp Glu Gln Val Asp Asn Leu Val Thr Ile Leu Asp Gly Tyr Phe
    690                 695                 700

Glu Asn Gly Gly Gln His Leu Asn Leu Asn Val Met Asp Leu Ser Ala
705                 710                 715                 720

Val Tyr Lys Lys Ile Met Ser Gly Glu Asp Val Ile Val Arg Ile Ser
                725                 730                 735

Gly Tyr Cys Val Asn Thr Lys Tyr Leu Thr Pro Glu Gln Lys Thr Glu
            740                 745                 750

Leu Thr Gln Arg Val Phe His Glu Val Leu Ser Thr Asp Asp Ala Met
        755                 760                 765

Gly
```

<210> SEQ ID NO 45
<211> LENGTH: 2310
<212> TYPE: DNA
<213> ORGANISM: Streptococcus thermophilus
<220> FEATURE:
<221> NAME/KEY: misc_feature
<223> OTHER INFORMATION: LMD-9

<400> SEQUENCE: 45

```
atggcaacgg ttaaaactaa cacagatgtt tttgaaaaag cgtgggaagg ctttaaagga      60

actgactgga aagaaaaagc aagtgtgtct cgcttcgtac aagcaaacta cacaccatat     120
```

```
gatggtgatg aaagcttcct tgcaggacca actgaacgct cacttaaaat caaaaaaatc    180
attgaagaaa ctaaagctca ctacgaagaa actcgtttcc caatggatac tcgtccgaca    240
tcaatcgcag atattcctgc cggctatatt tcaaaagacg acgaactaat ctacggtatt    300
caaaatgatg agttattcaa attgaatttc atgccaaaag gcggaattcg tatggcagaa    360
acagctctca aggaacatgg ctatgaacct gatccagctg ttcacgaaat ttttacaaaa    420
catgtaacta cagtaaatga cggtatcttc cgtgcttata catcaaatat ccgtcgtgca    480
cgtcacgcac acactataac tggacttcca gatgcttact ctcgtggacg tatcatcggt    540
gtttatgctc gccttgctct ttacggtgct gacttcttga tgcaagaaaa agtaaacgac    600
tggaactcta tcgaagaaat caacgaagaa actattcgtc ttcgtgaaga agttaacctt    660
caataccaag cacttcaaga tgttgttcgc cttggtgacc tttacggtgt agatgttcgt    720
cgtccagcct tcgatactaa agaagctatc caatggacaa acattgcttt tatggctgta    780
tgtcgtgtta tcaatggtgc ggctacttca cttggtcgtg tgccaatcgt ccttgacata    840
tatgcagaac gtgaccttgc tcgtggtact tacactgaat cagaaatcca agaattcgtt    900
gatgattttg tcttgaaact tcgtactgta aaattcgcac gtacaaaagc ttacgacgaa    960
ctttactcag gtgacccaac attcatcaca acttctatgg ctggtatggg tgctgacgga   1020
cgtcaccgtg ttactaaaat ggactaccgt ttcttgaaca cacttgataa tattggtaat   1080
gctccagaac caaacttgac agttctttgg tctgacaaat tgccttactc attccgtcgc   1140
tactgtatgc acatgagtca caagcactct tctattcaat acgaaggtgt gactactatg   1200
gctaaagacg gatacggtga aatgagctgt atctcatgtt gtgtatcacc acttgaccca   1260
gaaaacgaag aacaacgcca caacatccaa tacttcggtg ctcgtgttaa cgtacttaaa   1320
gcccttctta ctggtttgaa cggtggttac gacgatgttc ataaagacta caaagtattt   1380
gacatcgatc cagtccgtga tgaagttctt gactttgaca ctgttaaagc taacttcgaa   1440
aaatctcttg actggttgac tgacacttat gtagatgccc ttaacatcat ccactacatg   1500
actgataagt acaactacga agctgttcaa atggccttct tgccaactaa acaacgtgct   1560
aacatgggat tcggtatctg tggtttcgca aatactgttg atacattgtc agctatcaag   1620
tacgctacag ttaaaccaat ccgtgacgaa gatggctaca tctacgacta cgaaacaatc   1680
ggtgaatacc cacgttgggg tgaagatgac ccacgttcaa acgaattggc agaatggttg   1740
attgaagctt acactactcg tcttcgtagc cataaactct acaaagatgc agaagctaca   1800
gtttcacttc ttacaatcac ttcgaacgtt gcttactcta aacaaactgg taactctcca   1860
gttcacaaag ggtatacct caacgaagat ggttcagtga acttgtctaa attggaattc    1920
ttctcaccag gtgctaaccc atctaacaaa gctaaaggtg gatggttgca aaacttgaac   1980
tcacttgcaa gccttgactt cggttatgca gctgacggta tctcgcttac tactcaagta   2040
tcacctcgtg cccttggtaa gactcgcgac gaacaagttg ataacctcgt aactatcctt   2100
gacggatact tcgaaaacgg tggacaacac cttaacttga acgttatgga cttgtcagct   2160
gtttacaaaa agatcatgag cggtgaagat gttatcgtac gtatctctgg atactgtgta   2220
aacactaaat acctcactcc agaacaaaaa actgaattga cacaacgtgt cttccacgaa   2280
gttctttcaa cggacgatgc tatgggataa                                    2310
```

<210> SEQ ID NO 46
<211> LENGTH: 769
<212> TYPE: PRT

```
<213> ORGANISM: Streptococcus thermophilus
<220> FEATURE:
<221> NAME/KEY: MISC_FEATURE
<223> OTHER INFORMATION: LMD-9

<400> SEQUENCE: 46

Met Ala Thr Val Lys Thr Asn Thr Asp Val Phe Glu Lys Ala Trp Glu
1               5                   10                  15

Gly Phe Lys Gly Thr Asp Trp Lys Glu Lys Ala Ser Val Ser Arg Phe
            20                  25                  30

Val Gln Ala Asn Tyr Thr Pro Tyr Asp Gly Asp Glu Ser Phe Leu Ala
        35                  40                  45

Gly Pro Thr Glu Arg Ser Leu Lys Ile Lys Lys Ile Ile Glu Glu Thr
    50                  55                  60

Lys Ala His Tyr Glu Glu Thr Arg Phe Pro Met Asp Thr Arg Pro Thr
65                  70                  75                  80

Ser Ile Ala Asp Ile Pro Ala Gly Tyr Ile Ser Lys Asp Asp Glu Leu
                85                  90                  95

Ile Tyr Gly Ile Gln Asn Asp Glu Leu Phe Lys Leu Asn Phe Met Pro
            100                 105                 110

Lys Gly Gly Ile Arg Met Ala Glu Thr Ala Leu Lys Glu His Gly Tyr
        115                 120                 125

Glu Pro Asp Pro Ala Val His Glu Ile Phe Thr Lys His Val Thr Thr
    130                 135                 140

Val Asn Asp Gly Ile Phe Arg Ala Tyr Thr Ser Asn Ile Arg Arg Ala
145                 150                 155                 160

Arg His Ala His Thr Ile Thr Gly Leu Pro Asp Ala Tyr Ser Arg Gly
                165                 170                 175

Arg Ile Ile Gly Val Tyr Ala Arg Leu Ala Leu Tyr Gly Ala Asp Phe
            180                 185                 190

Leu Met Gln Glu Lys Val Asn Asp Trp Asn Ser Ile Glu Glu Ile Asn
        195                 200                 205

Glu Glu Thr Ile Arg Leu Arg Glu Glu Val Asn Leu Gln Tyr Gln Ala
    210                 215                 220

Leu Gln Asp Val Val Arg Leu Gly Asp Leu Tyr Gly Val Asp Val Arg
225                 230                 235                 240

Arg Pro Ala Phe Asp Thr Lys Glu Ala Ile Gln Trp Thr Asn Ile Ala
                245                 250                 255

Phe Met Ala Val Cys Arg Val Ile Asn Gly Ala Ala Thr Ser Leu Gly
            260                 265                 270

Arg Val Pro Ile Val Leu Asp Ile Tyr Ala Glu Arg Asp Leu Ala Arg
        275                 280                 285

Gly Thr Tyr Thr Glu Ser Glu Ile Gln Glu Phe Val Asp Asp Phe Val
    290                 295                 300

Leu Lys Leu Arg Thr Val Lys Phe Ala Arg Thr Lys Ala Tyr Asp Glu
305                 310                 315                 320

Leu Tyr Ser Gly Asp Pro Thr Phe Ile Thr Thr Ser Met Ala Gly Met
                325                 330                 335

Gly Ala Asp Gly Arg His Arg Val Thr Lys Met Asp Tyr Arg Phe Leu
            340                 345                 350

Asn Thr Leu Asp Asn Ile Gly Asn Ala Pro Glu Pro Asn Leu Thr Val
        355                 360                 365

Leu Trp Ser Asp Lys Leu Pro Tyr Ser Phe Arg Arg Tyr Cys Met His
    370                 375                 380
```

```
Met Ser His Lys His Ser Ser Ile Gln Tyr Glu Gly Val Thr Thr Met
385                 390                 395                 400

Ala Lys Asp Gly Tyr Gly Glu Met Ser Cys Ile Ser Cys Cys Val Ser
                405                 410                 415

Pro Leu Asp Pro Glu Asn Glu Glu Gln Arg His Asn Ile Gln Tyr Phe
            420                 425                 430

Gly Ala Arg Val Asn Val Leu Lys Ala Leu Leu Thr Gly Leu Asn Gly
        435                 440                 445

Gly Tyr Asp Asp Val His Lys Asp Tyr Lys Val Phe Asp Ile Asp Pro
    450                 455                 460

Val Arg Asp Glu Val Leu Asp Phe Asp Thr Val Lys Ala Asn Phe Glu
465                 470                 475                 480

Lys Ser Leu Asp Trp Leu Thr Asp Thr Tyr Val Asp Ala Leu Asn Ile
                485                 490                 495

Ile His Tyr Met Thr Asp Lys Tyr Asn Tyr Glu Ala Val Gln Met Ala
            500                 505                 510

Phe Leu Pro Thr Lys Gln Arg Ala Asn Met Gly Phe Gly Ile Cys Gly
        515                 520                 525

Phe Ala Asn Thr Val Asp Thr Leu Ser Ala Ile Lys Tyr Ala Thr Val
    530                 535                 540

Lys Pro Ile Arg Asp Glu Asp Gly Tyr Ile Tyr Asp Tyr Glu Thr Ile
545                 550                 555                 560

Gly Glu Tyr Pro Arg Trp Gly Glu Asp Asp Pro Arg Ser Asn Glu Leu
                565                 570                 575

Ala Glu Trp Leu Ile Glu Ala Tyr Thr Thr Arg Leu Arg Ser His Lys
            580                 585                 590

Leu Tyr Lys Asp Ala Glu Ala Thr Val Ser Leu Leu Thr Ile Thr Ser
        595                 600                 605

Asn Val Ala Tyr Ser Lys Gln Thr Gly Asn Ser Pro Val His Lys Gly
    610                 615                 620

Val Tyr Leu Asn Glu Asp Gly Ser Val Asn Leu Ser Lys Leu Glu Phe
625                 630                 635                 640

Phe Ser Pro Gly Ala Asn Pro Ser Asn Lys Ala Lys Gly Gly Trp Leu
                645                 650                 655

Gln Asn Leu Asn Ser Leu Ala Ser Leu Asp Phe Gly Tyr Ala Ala Asp
            660                 665                 670

Gly Ile Ser Leu Thr Thr Gln Val Ser Pro Arg Ala Leu Gly Lys Thr
        675                 680                 685

Arg Asp Glu Gln Val Asp Asn Leu Val Thr Ile Leu Asp Gly Tyr Phe
    690                 695                 700

Glu Asn Gly Gly Gln His Leu Asn Leu Asn Val Met Asp Leu Ser Ala
705                 710                 715                 720

Val Tyr Lys Lys Ile Met Ser Gly Glu Asp Val Ile Val Arg Ile Ser
                725                 730                 735

Gly Tyr Cys Val Asn Thr Lys Tyr Leu Thr Pro Glu Gln Lys Thr Glu
            740                 745                 750

Leu Thr Gln Arg Val Phe His Glu Val Leu Ser Thr Asp Asp Ala Met
        755                 760                 765

Gly
```

<210> SEQ ID NO 47
<211> LENGTH: 2445
<212> TYPE: DNA
<213> ORGANISM: Lactobacillus plantarum
<220> FEATURE:
<221> NAME/KEY: misc_feature
<223> OTHER INFORMATION: WCFS1

<400> SEQUENCE: 47

```
atgatcatgt ctgaaacttt aactaaaaca acgacaacta ttaaccactt cggtaaattg     60
acgccaatga tggatcgctt acgcgatagc atcattgatg caaaacctta tgtcgatcca    120
gaacgggcga ttctcacaac cgaaacttat cgacaacacc aagacgaaca agtcgatata    180
ttacgggcta aaatgcttga acacgttctt gataaaatga gtatcttcat tgaagatgat    240
actttaattg ttggtaacca agcacgccaa aatcgttggg caccagtatt ccctgagtat    300
tctatgaatt gggtcattga tgaattagat acatttgaga agcgtcctgg tgacgttttc    360
tatattacgg agaaatccaa ggaagaactt cgtgcgattg cgcctttctg gaaacataat    420
accttggaag accgcggcta cgctagtttt ccagaagcaa gtcgtatttt ttatgattta    480
ggtattattg gagccgatgg taatatcact tctggtgatg gtcacattgc ggtcgactat    540
aaaaacgttg ttaataaggg acttaaatgg tatgaagacc gcattaagac agcacttgct    600
aatcttgacc ttactgattt taaccagcaa aaacaatact atttctataa agcgggccta    660
attgtaattg atgccattca caattttgct aaacgttacg cccaattagc gtccaagcaa    720
gctcaaaaca cgacatccgc aactcgcaaa gcacaacttg aaaaaatcgc ccaaattcta    780
aacaaggttc cttacgaacc tgcaaattca ttttatgaag cgattcaagc tgtctggtta    840
gttcatctga ccttacaaat cgaatccaac ggtcattctg tctcatatgg tcgtctagat    900
cagtacctag ctccattcta tgagcacgat ttaaaaactg gtgctattga cgccaacggt    960
gcaaccgaat tactcacaaa cttatgtctt aagacgttaa cgattaataa agtacgctca   1020
tggcaacata ctgaattttc tgcagggagt cccctctacc aaaacattac gattggtggt   1080
caaacaccag atggtaaaga tgccgttaat ccgacgtcct atctgatttt acgagcaatt   1140
gcgcaagcac atttaccaca acccaactta acggtccgtt atcaccatgg cttaagcgat   1200
aagtttatgc gtgaatgtgt cgaagttatt aaacaaggct taggtatgcc tgcgtttaat   1260
aacgacgaaa ttattattcc gtcgtttatt cgtcgtggcg tcaagaaaga agacgcctat   1320
aattacagtg ccatcggttg tgtcgaaaca gcgatccctg gaaaatgggg ctatcgttgc   1380
accgggatga gcttcattaa cttcccacgc gttctcttac tcattatgaa tggtggcatt   1440
gatcctgaat ctggcaaacg gttattaccc gattatggta agttcactga tatgacttct   1500
tttgatcaac ttatgactgc ttgggacaaa gcgctccgtg aaatgacacg acaaagtgtg   1560
attatcgaaa atagttgtga tttggctttg gaacaaaatt atcctgatat tctctgctcc   1620
gttttaaccg acgattgtat cggtcgtggt aagaccatta aagaaggtgg cgcggtatac   1680
gactttatca gtggattaca agttggtatt gctaacctag cggactccct agctgcaatc   1740
aagaaacttg tctttgaaga aaagaagttg acaacaaccc aactttggca cgcacttacc   1800
actgattttg cggatgaaga tggtgaaaag attcggcaga tgctcattaa tgatgcccca   1860
aagtatggta acgatgatga ttatgttgat gatttgattg ttgaagctta taaaccatat   1920
attgatgaaa ttgccaagta caaaaacacg cgctacggtc gcggccctat tggtggcttg   1980
cgctacgcag gaacctcttc tatttcggcc aacgttggtc aagggcacag cactttggct   2040
acaccagatg gtcggcacgc tcggacacca ttagccgaag gttgctcacc agaacatgca   2100
atggatactg atggcccaac tgctgtgttc aaatcagttt ccaaattatc cactaaggac   2160
atcactggtg gcgtattact gaaccaaaag atgtcaccac aaattctacg gagtgatgaa   2220
```

-continued

```
agctgcatga aattggttgc actactacgg accttcttca atcgacttca tggttaccat   2280

gtccaataca acattgtttc acgggatacc ttgattgatg cacagaacca tcctgacaag   2340

caccgtgact tgattgttcg ggttgctgga tattccgcct tcttcgtggg cctatccaaa   2400

gaaacccaag atgatattat cgaacggacg gagcagtctc tataa                    2445


<210> SEQ ID NO 48
<211> LENGTH: 814
<212> TYPE: PRT
<213> ORGANISM: Lactobacillus plantarum
<220> FEATURE:
<221> NAME/KEY: MISC_FEATURE
<223> OTHER INFORMATION: WCFS1

<400> SEQUENCE: 48

Met Ile Met Ser Glu Thr Leu Thr Lys Thr Thr Thr Thr Ile Asn His
1               5                   10                  15

Phe Gly Lys Leu Thr Pro Met Met Asp Arg Leu Arg Asp Ser Ile Ile
            20                  25                  30

Asp Ala Lys Pro Tyr Val Asp Pro Glu Arg Ala Ile Leu Thr Thr Glu
        35                  40                  45

Thr Tyr Arg Gln His Gln Asp Glu Gln Val Asp Ile Leu Arg Ala Lys
    50                  55                  60

Met Leu Glu His Val Leu Asp Lys Met Ser Ile Phe Ile Glu Asp Asp
65                  70                  75                  80

Thr Leu Ile Val Gly Asn Gln Ala Arg Gln Asn Arg Trp Ala Pro Val
                85                  90                  95

Phe Pro Glu Tyr Ser Met Asn Trp Val Ile Asp Glu Leu Asp Thr Phe
            100                 105                 110

Glu Lys Arg Pro Gly Asp Val Phe Tyr Ile Thr Glu Lys Ser Lys Glu
        115                 120                 125

Glu Leu Arg Ala Ile Ala Pro Phe Trp Lys His Asn Thr Leu Glu Asp
    130                 135                 140

Arg Gly Tyr Ala Ser Phe Pro Glu Ala Ser Arg Ile Phe Tyr Asp Leu
145                 150                 155                 160

Gly Ile Ile Gly Ala Asp Gly Asn Ile Thr Ser Gly Asp Gly His Ile
                165                 170                 175

Ala Val Asp Tyr Lys Asn Val Val Asn Lys Gly Leu Lys Trp Tyr Glu
            180                 185                 190

Asp Arg Ile Lys Thr Ala Leu Ala Asn Leu Asp Leu Thr Asp Phe Asn
        195                 200                 205

Gln Gln Lys Gln Tyr Tyr Phe Tyr Lys Ala Gly Leu Ile Val Ile Asp
    210                 215                 220

Ala Ile His Asn Phe Ala Lys Arg Tyr Ala Gln Leu Ala Ser Lys Gln
225                 230                 235                 240

Ala Gln Asn Thr Thr Ser Ala Thr Arg Lys Ala Gln Leu Glu Lys Ile
                245                 250                 255

Ala Gln Ile Leu Asn Lys Val Pro Tyr Glu Pro Ala Asn Ser Phe Tyr
            260                 265                 270

Glu Ala Ile Gln Ala Val Trp Leu Val His Leu Thr Leu Gln Ile Glu
        275                 280                 285

Ser Asn Gly His Ser Val Ser Tyr Gly Arg Leu Asp Gln Tyr Leu Ala
    290                 295                 300

Pro Phe Tyr Glu His Asp Leu Lys Thr Gly Ala Ile Asp Ala Asn Gly
305                 310                 315                 320
```

```
Ala Thr Glu Leu Leu Thr Asn Leu Cys Leu Lys Thr Leu Thr Ile Asn
                325                 330                 335

Lys Val Arg Ser Trp Gln His Thr Glu Phe Ser Ala Gly Ser Pro Leu
            340                 345                 350

Tyr Gln Asn Ile Thr Ile Gly Gly Gln Thr Pro Asp Gly Lys Asp Ala
        355                 360                 365

Val Asn Pro Thr Ser Tyr Leu Ile Leu Arg Ala Ile Ala Gln Ala His
    370                 375                 380

Leu Pro Gln Pro Asn Leu Thr Val Arg Tyr His His Gly Leu Ser Asp
385                 390                 395                 400

Lys Phe Met Arg Glu Cys Val Glu Val Ile Lys Gln Gly Leu Gly Met
                405                 410                 415

Pro Ala Phe Asn Asn Asp Glu Ile Ile Ile Pro Ser Phe Ile Arg Arg
            420                 425                 430

Gly Val Lys Lys Glu Asp Ala Tyr Asn Tyr Ser Ala Ile Gly Cys Val
        435                 440                 445

Glu Thr Ala Ile Pro Gly Lys Trp Gly Tyr Arg Cys Thr Gly Met Ser
    450                 455                 460

Phe Ile Asn Phe Pro Arg Val Leu Leu Leu Ile Met Asn Gly Gly Ile
465                 470                 475                 480

Asp Pro Glu Ser Gly Lys Arg Leu Leu Pro Asp Tyr Gly Lys Phe Thr
                485                 490                 495

Asp Met Thr Ser Phe Asp Gln Leu Met Thr Ala Trp Asp Lys Ala Leu
            500                 505                 510

Arg Glu Met Thr Arg Gln Ser Val Ile Ile Glu Asn Ser Cys Asp Leu
        515                 520                 525

Ala Leu Glu Gln Asn Tyr Pro Asp Ile Leu Cys Ser Val Leu Thr Asp
    530                 535                 540

Asp Cys Ile Gly Arg Gly Lys Thr Ile Lys Glu Gly Gly Ala Val Tyr
545                 550                 555                 560

Asp Phe Ile Ser Gly Leu Gln Val Gly Ile Ala Asn Leu Ala Asp Ser
                565                 570                 575

Leu Ala Ala Ile Lys Lys Leu Val Phe Glu Glu Lys Lys Leu Thr Thr
            580                 585                 590

Thr Gln Leu Trp His Ala Leu Thr Thr Asp Phe Ala Asp Glu Asp Gly
        595                 600                 605

Glu Lys Ile Arg Gln Met Leu Ile Asn Asp Ala Pro Lys Tyr Gly Asn
    610                 615                 620

Asp Asp Asp Tyr Val Asp Asp Leu Ile Val Glu Ala Tyr Lys Pro Tyr
625                 630                 635                 640

Ile Asp Glu Ile Ala Lys Tyr Lys Asn Thr Arg Tyr Gly Arg Gly Pro
                645                 650                 655

Ile Gly Gly Leu Arg Tyr Ala Gly Thr Ser Ser Ile Ser Ala Asn Val
            660                 665                 670

Gly Gln Gly His Ser Thr Leu Ala Thr Pro Asp Gly Arg His Ala Arg
        675                 680                 685

Thr Pro Leu Ala Glu Gly Cys Ser Pro Glu His Ala Met Asp Thr Asp
    690                 695                 700

Gly Pro Thr Ala Val Phe Lys Ser Val Ser Lys Leu Ser Thr Lys Asp
705                 710                 715                 720

Ile Thr Gly Gly Val Leu Leu Asn Gln Lys Met Ser Pro Gln Ile Leu
                725                 730                 735
```

-continued

```
Arg Ser Asp Glu Ser Cys Met Lys Leu Val Ala Leu Leu Arg Thr Phe
            740                 745                 750

Phe Asn Arg Leu His Gly Tyr His Val Gln Tyr Asn Ile Val Ser Arg
        755                 760                 765

Asp Thr Leu Ile Asp Ala Gln Asn His Pro Asp Lys His Arg Asp Leu
    770                 775                 780

Ile Val Arg Val Ala Gly Tyr Ser Ala Phe Phe Val Gly Leu Ser Lys
785                 790                 795                 800

Glu Thr Gln Asp Asp Ile Ile Glu Arg Thr Glu Gln Ser Leu
                805                 810


<210> SEQ ID NO 49
<211> LENGTH: 2259
<212> TYPE: DNA
<213> ORGANISM: Lactobacillus plantarum
<220> FEATURE:
<221> NAME/KEY: misc_feature
<223> OTHER INFORMATION: WCFS1

<400> SEQUENCE: 49

atgattacat cagaaaagac aacaaaacca gcagcttgga aaggtttcaa aggcgggcac     60

tggcaggaag aaatcaacat tcgtgatttt attcaaaata acttcacaca gtacaatggc    120

gacgaaagct tcctggccgg accaacagcc gctactaaga ccttgaatga caaagtctta    180

gaattaaaga aacaagaacg tgccgctggt ggtgtgttgg atgctgatac taaagtcgtt    240

gcaacgatta cttcacacgg ccctggttat attcaaaaag atctcgaaaa gattgttggt    300

ctccagactg acaagccttt gaagcgggcc ttcatgccat ttggtggtat tcgaatggct    360

gatgacgctt tgaaatcata cggttatacc cctgatgaag aaaacgacaa gattttcact    420

gaatatcgca agactcataa ccaaggcgtc ttcgatgttt atactcctga catgcggaaa    480

gcacgtcact acaagatcat caccggacta ccagatgcat acgcacgtgg ccgtctcatt    540

cctgatcttc cacgggtcgc tgtttatggg atcgatcgtt taatggaaga caaagctaat    600

gactttgccc acattggtga tggtgaattg actgatgatg ttattcgcct ccgtgaagaa    660

gttcaagatc aataccgtgc tttagcagat atgaagaaga tggctgccag ttatggctac    720

gatattagca agcctgcaac taatgctcaa gaagctattc aatggatgta cttcgcttac    780

ttagctgcta tcaagaccca aaacggcgct gcaatgtccg ttggccggat tgatacaacg    840

atggacatct tcatccaacg tgacttggac aatggtgttc tggacgaaag ccaagctcaa    900

gaattaattg atcaattcgt catgaaacta cggatggttc ggttcatccg tactgaagaa    960

tacaattctc tcttctctgg tgacccaatc tgggcaacct tatcaatgtg tggtttaggc   1020

gtcgacggtc aacaccatgt gactaagact gctttccgga ttttaaagac tttggacaac   1080

atgggcgccg caccagaacc aaacatcacg attttatggt cagaccgctt accagaagac   1140

ttcaaacgtt acgcaactga agtttcaatc gacagttcaa ccattcagta tgaaaatgat   1200

gacttgatgc gggtacaatg gggtaccgat tattatggca ttgcttgctg tgtttccgca   1260

caaccaattg ctgatggaat ccagtacttc ggtgcccggg caaacttagc caaagcgatt   1320

ctttatgcca tcaatggtgg ccgcgacgaa attgctggag atcaagttgg ccctgcttac   1380

gaaccaatta cttcagaata catcgattac gacgaattca tgaagaaatt agacaagcaa   1440

atggattggt tagctgacac ttacgttaac tcactgaatg caattcatta tatgcatgat   1500

aagtactact atgaagctgc ccaattagct ttgaagaata ctgatcttga tcggaccttt   1560

gcaactggga tttctggctt atcacatgcc gcggattcaa tctcagctat caagtatggt   1620
```

```
cacgttaaag taattcgtga cgaacgtggt atcgccgttg acttcaaagc cgacaatgac   1680

tacccacgtt atgggaacaa tgacgatcgc gctgatgaca ttgctaaatg gttagtcaaa   1740

gaattataca gcaagatgaa cacgcatcac ctctatcgga atgccaaact ttcaacttct   1800

gttttgacga ttacctccaa cgttgtttat ggtaagaaca ctggtaccac gccaaatggc   1860

cgtcaaaaag gcgaaccatt ctcaccaggt gctaaccctg catacggtgc tgaaaagagt   1920

ggtgcattag cttcacttct ttcaactgcc aaattaccat accgttacgc aactgacggg   1980

atttccaaca cgttcggcgt taccccctaac acgttaggcc atgacctcga atcacggaaa   2040

gacacgttag taaacatgtt agacggttac atgaagaacg atgggatgca cttgaacatc   2100

aacgtcttca ataaagacac tttgattgat gctcagaaac accctgaaga atacccaaca   2160

ttaacggttc gggtttctgg ctattgtgtc tacttcgcag atttaaccaa ggaacaacaa   2220

gatgacgtta tttcacggac attcttcgaa tcaatgtaa                         2259
```

<210> SEQ ID NO 50
<211> LENGTH: 752
<212> TYPE: PRT
<213> ORGANISM: Lactobacillus plantarum
<220> FEATURE:
<221> NAME/KEY: MISC_FEATURE
<223> OTHER INFORMATION: WCFS1

<400> SEQUENCE: 50

```
Met Ile Thr Ser Glu Lys Thr Thr Lys Pro Ala Ala Trp Lys Gly Phe
1               5                   10                  15

Lys Gly Gly His Trp Gln Glu Glu Ile Asn Ile Arg Asp Phe Ile Gln
            20                  25                  30

Asn Asn Phe Thr Gln Tyr Asn Gly Asp Glu Ser Phe Leu Ala Gly Pro
        35                  40                  45

Thr Ala Ala Thr Lys Thr Leu Asn Asp Lys Val Leu Glu Leu Lys Lys
    50                  55                  60

Gln Glu Arg Ala Ala Gly Gly Val Leu Asp Ala Asp Thr Lys Val Val
65                  70                  75                  80

Ala Thr Ile Thr Ser His Gly Pro Gly Tyr Ile Gln Lys Asp Leu Glu
                85                  90                  95

Lys Ile Val Gly Leu Gln Thr Asp Lys Pro Leu Lys Arg Ala Phe Met
            100                 105                 110

Pro Phe Gly Gly Ile Arg Met Ala Asp Asp Ala Leu Lys Ser Tyr Gly
        115                 120                 125

Tyr Thr Pro Asp Glu Glu Asn Asp Lys Ile Phe Thr Glu Tyr Arg Lys
    130                 135                 140

Thr His Asn Gln Gly Val Phe Asp Val Tyr Thr Pro Asp Met Arg Lys
145                 150                 155                 160

Ala Arg His Tyr Lys Ile Ile Thr Gly Leu Pro Asp Ala Tyr Ala Arg
                165                 170                 175

Gly Arg Leu Ile Pro Asp Leu Pro Arg Val Ala Val Tyr Gly Ile Asp
            180                 185                 190

Arg Leu Met Glu Asp Lys Ala Asn Asp Phe Ala His Ile Gly Asp Gly
        195                 200                 205

Glu Leu Thr Asp Asp Val Ile Arg Leu Arg Glu Glu Val Gln Asp Gln
    210                 215                 220

Tyr Arg Ala Leu Ala Asp Met Lys Lys Met Ala Ala Ser Tyr Gly Tyr
225                 230                 235                 240
```

```
Asp Ile Ser Lys Pro Ala Thr Asn Ala Gln Glu Ala Ile Gln Trp Met
                245                 250                 255

Tyr Phe Ala Tyr Leu Ala Ala Ile Lys Thr Gln Asn Gly Ala Ala Met
            260                 265                 270

Ser Val Gly Arg Ile Asp Thr Thr Met Asp Ile Phe Ile Gln Arg Asp
        275                 280                 285

Leu Asp Asn Gly Val Leu Asp Glu Ser Gln Ala Gln Glu Leu Ile Asp
    290                 295                 300

Gln Phe Val Met Lys Leu Arg Met Val Arg Phe Ile Arg Thr Glu Glu
305                 310                 315                 320

Tyr Asn Ser Leu Phe Ser Gly Asp Pro Ile Trp Ala Thr Leu Ser Met
                325                 330                 335

Cys Gly Leu Gly Val Asp Gly Gln His His Val Thr Lys Thr Ala Phe
            340                 345                 350

Arg Ile Leu Lys Thr Leu Asp Asn Met Gly Ala Ala Pro Glu Pro Asn
        355                 360                 365

Ile Thr Ile Leu Trp Ser Asp Arg Leu Pro Glu Asp Phe Lys Arg Tyr
    370                 375                 380

Ala Thr Glu Val Ser Ile Asp Ser Ser Thr Ile Gln Tyr Glu Asn Asp
385                 390                 395                 400

Asp Leu Met Arg Val Gln Trp Gly Thr Asp Tyr Tyr Gly Ile Ala Cys
                405                 410                 415

Cys Val Ser Ala Gln Pro Ile Ala Asp Gly Ile Gln Tyr Phe Gly Ala
            420                 425                 430

Arg Ala Asn Leu Ala Lys Ala Ile Leu Tyr Ala Ile Asn Gly Gly Arg
        435                 440                 445

Asp Glu Ile Ala Gly Asp Gln Val Gly Pro Ala Tyr Glu Pro Ile Thr
    450                 455                 460

Ser Glu Tyr Ile Asp Tyr Asp Glu Phe Met Lys Lys Leu Asp Lys Gln
465                 470                 475                 480

Met Asp Trp Leu Ala Asp Thr Tyr Val Asn Ser Leu Asn Ala Ile His
                485                 490                 495

Tyr Met His Asp Lys Tyr Tyr Tyr Glu Ala Ala Gln Leu Ala Leu Lys
            500                 505                 510

Asn Thr Asp Leu Asp Arg Thr Phe Ala Thr Gly Ile Ser Gly Leu Ser
        515                 520                 525

His Ala Ala Asp Ser Ile Ser Ala Ile Lys Tyr Gly His Val Lys Val
    530                 535                 540

Ile Arg Asp Glu Arg Gly Ile Ala Val Asp Phe Lys Ala Asp Asn Asp
545                 550                 555                 560

Tyr Pro Arg Tyr Gly Asn Asn Asp Asp Arg Ala Asp Asp Ile Ala Lys
                565                 570                 575

Trp Leu Val Lys Glu Leu Tyr Ser Lys Met Asn Thr His His Leu Tyr
            580                 585                 590

Arg Asn Ala Lys Leu Ser Thr Ser Val Leu Thr Ile Thr Ser Asn Val
        595                 600                 605

Val Tyr Gly Lys Asn Thr Gly Thr Thr Pro Asn Gly Arg Gln Lys Gly
    610                 615                 620

Glu Pro Phe Ser Pro Gly Ala Asn Pro Ala Tyr Gly Ala Glu Lys Ser
625                 630                 635                 640

Gly Ala Leu Ala Ser Leu Leu Ser Thr Ala Lys Leu Pro Tyr Arg Tyr
                645                 650                 655

Ala Thr Asp Gly Ile Ser Asn Thr Phe Gly Val Thr Pro Asn Thr Leu
```

```
            660                 665                 670

Gly His Asp Leu Glu Ser Arg Lys Asp Thr Leu Val Asn Met Leu Asp
        675                 680                 685

Gly Tyr Met Lys Asn Asp Gly Met His Leu Asn Ile Asn Val Phe Asn
    690                 695                 700

Lys Asp Thr Leu Ile Asp Ala Gln Lys His Pro Glu Glu Tyr Pro Thr
705                 710                 715                 720

Leu Thr Val Arg Val Ser Gly Tyr Cys Val Tyr Phe Ala Asp Leu Thr
                725                 730                 735

Lys Glu Gln Gln Asp Asp Val Ile Ser Arg Thr Phe Phe Glu Ser Met
            740                 745                 750


<210> SEQ ID NO 51
<211> LENGTH: 2259
<212> TYPE: DNA
<213> ORGANISM: Lactobacillus plantarum
<220> FEATURE:
<221> NAME/KEY: misc_feature
<223> OTHER INFORMATION: JDM1

<400> SEQUENCE: 51

atgattacat cagaaaagac aacaaaacca gcagcttgga aaggtttcaa aggcgggcac     60

tggcaggaag aaatcaacat tcgtgatttt attcaaaata acttcacaca gtacaatggc    120

gacgaaagct tcctggccgg accaacagcc gctactaaga ccttgaatga caaagtctta    180

gaattaaaga aacaagaacg tgccgctggt ggtgtgttgg acgctgatac taaagtcgtt    240

gcaacgatta cttcacacgg ccctggttat attcaaaaag atctcgaaaa gattgttggt    300

ctccagactg acaagccttt gaagcgggcc ttcatgccat ttggtggtat tcgaatggct    360

gatgacgctt tgaaatcata cggttatacc cctgatgaag aaaacgacaa gattttcact    420

gaatatcgca agactcataa ccaaggcgtc ttcgatgttt atactcctga catgcggaaa    480

gcacgtcact acaagatcat caccggacta ccagatgcat acgcacgtgg ccgtctcatt    540

cctgatcttc cacgggtcgc tgtttatggg atcgatcgtt taatggaaga caaagctaat    600

gactttgccc acattggtga tggtgaattg actgatgatg ttattcgcct ccgtgaagaa    660

gttcaagatc aataccgtgc tttagcagat atgaagaaga tggctgccag ttatggctac    720

gatattagca agcctgcaac taatgctcaa gaagctattc aatggatgta cttcgcttac    780

ttagctgcta tcaagaccca aaacggcgct gcaatgtccg ttggccggat tgatacaacg    840

atggacatct tcatccaacg tgacttggac aatggtgttc tggacgaaag ccaagctcaa    900

gaattaattg atcaattcgt catgaaacta cggatggttc ggttcatccg tactgaagaa    960

tacaattctc tcttctctgg tgacccaatc tgggcaacct tatcaatgtg tggtttaggc   1020

gtcgacggtc aacaccatgt gactaagacc gctttccgga ttttaaagac tttggacaac   1080

atgggcgccg caccagaacc aaacatcacg attttatggt cagatcgctt accagaagac   1140

ttcaaacgtt acgcaactga agtttcaatc gacagttcaa ccattcagta tgaaaatgat   1200

gacttgatgc gggtacaatg gggtaccgat tattatggca ttgcttgctg tgtttccgca   1260

caaccaattg ctgatggaat ccagtacttc ggtgcccggg caaacttagc caaagcgatt   1320

ctttatgcca tcaatggtgg ccgcgacgaa attgctggag atcaagttgg ccctgcttac   1380

gaaccaatta cttcagaata catcgattac gacgaattca tgaagaaatt agacaagcaa   1440

atggattggt tagctgacac ttacgtgaac tcactgaatg caattcatta tatgcatgat   1500

aagtactact atgaagctgc ccaattagct ttgaagaata ctgatcttga tcggaccttt   1560
```

```
gcaactggga tttctggctt atcacatgcc gcggattcaa tctcagctat caagtatggt    1620

cacgttaaag taattcgtga cgaacgtggt atcgccgttg acttcaaagc cgacaatgac    1680

tacccacgtt atgggaacaa tgacgatcgc gctgatgaca ttgctaaatg gttagtcaaa    1740

gaattataca gcaagatgaa cacgcatcac ctctatcgga atgccaaact ttcaacttct    1800

gttttgacga ttacctccaa cgttgtttat ggtaagaaca ctggtaccac accaaatggc    1860

cgtcaaaaag gcgaaccatt ctcaccaggt gctaaccctg catacggtgc tgaaaagagt    1920

ggtgcattag cttcacttct ttcaactgcc aaattaccat accgttacgc aactgacggg    1980

atttccaaca cgttcggcgt tacccctaac acgttaggcc atgacctcga atcacggaaa    2040

gacacgttag taaacatgtt agacggttac atgaagaacg atgggatgca cttgaacatc    2100

aacgtcttca ataaagacac tttgattgat gctcagaaac accctgaaga atacccaaca    2160

ttaacggttc gggtttctgg ctactgtgtc tacttcgcag atttaaccaa ggaacaacaa    2220

gatgacgtta tttcacggac attcttcgaa tcaatgtaa                          2259
```

<210> SEQ ID NO 52
<211> LENGTH: 752
<212> TYPE: PRT
<213> ORGANISM: Lactobacillus plantarum
<220> FEATURE:
<221> NAME/KEY: misc_feature
<223> OTHER INFORMATION: JDM1

<400> SEQUENCE: 52

```
Met Ile Thr Ser Glu Lys Thr Thr Lys Pro Ala Ala Trp Lys Gly Phe
1               5                   10                  15

Lys Gly Gly His Trp Gln Glu Glu Ile Asn Ile Arg Asp Phe Ile Gln
            20                  25                  30

Asn Asn Phe Thr Gln Tyr Asn Gly Asp Glu Ser Phe Leu Ala Gly Pro
        35                  40                  45

Thr Ala Ala Thr Lys Thr Leu Asn Asp Lys Val Leu Glu Leu Lys Lys
    50                  55                  60

Gln Glu Arg Ala Ala Gly Gly Val Leu Asp Ala Asp Thr Lys Val Val
65                  70                  75                  80

Ala Thr Ile Thr Ser His Gly Pro Gly Tyr Ile Gln Lys Asp Leu Glu
                85                  90                  95

Lys Ile Val Gly Leu Gln Thr Asp Lys Pro Leu Lys Arg Ala Phe Met
            100                 105                 110

Pro Phe Gly Gly Ile Arg Met Ala Asp Asp Ala Leu Lys Ser Tyr Gly
        115                 120                 125

Tyr Thr Pro Asp Glu Glu Asn Asp Lys Ile Phe Thr Glu Tyr Arg Lys
    130                 135                 140

Thr His Asn Gln Gly Val Phe Asp Val Tyr Thr Pro Asp Met Arg Lys
145                 150                 155                 160

Ala Arg His Tyr Lys Ile Ile Thr Gly Leu Pro Asp Ala Tyr Ala Arg
                165                 170                 175

Gly Arg Leu Ile Pro Asp Leu Pro Arg Val Ala Val Tyr Gly Ile Asp
            180                 185                 190

Arg Leu Met Glu Asp Lys Ala Asn Asp Phe Ala His Ile Gly Asp Gly
        195                 200                 205

Glu Leu Thr Asp Asp Val Ile Arg Leu Arg Glu Glu Val Gln Asp Gln
    210                 215                 220

Tyr Arg Ala Leu Ala Asp Met Lys Lys Met Ala Ala Ser Tyr Gly Tyr
```

-continued

```
225                 230                 235                 240

Asp Ile Ser Lys Pro Ala Thr Asn Ala Gln Glu Ala Ile Gln Trp Met
                245                 250                 255

Tyr Phe Ala Tyr Leu Ala Ala Ile Lys Thr Gln Asn Gly Ala Ala Met
            260                 265                 270

Ser Val Gly Arg Ile Asp Thr Thr Met Asp Ile Phe Ile Gln Arg Asp
        275                 280                 285

Leu Asp Asn Gly Val Leu Asp Glu Ser Gln Ala Gln Glu Leu Ile Asp
    290                 295                 300

Gln Phe Val Met Lys Leu Arg Met Val Arg Phe Ile Arg Thr Glu Glu
305                 310                 315                 320

Tyr Asn Ser Leu Phe Ser Gly Asp Pro Ile Trp Ala Thr Leu Ser Met
                325                 330                 335

Cys Gly Leu Gly Val Asp Gly Gln His His Val Thr Lys Thr Ala Phe
            340                 345                 350

Arg Ile Leu Lys Thr Leu Asp Asn Met Gly Ala Ala Pro Glu Pro Asn
        355                 360                 365

Ile Thr Ile Leu Trp Ser Asp Arg Leu Pro Glu Asp Phe Lys Arg Tyr
    370                 375                 380

Ala Thr Glu Val Ser Ile Asp Ser Ser Thr Ile Gln Tyr Glu Asn Asp
385                 390                 395                 400

Asp Leu Met Arg Val Gln Trp Gly Thr Asp Tyr Tyr Gly Ile Ala Cys
                405                 410                 415

Cys Val Ser Ala Gln Pro Ile Ala Asp Gly Ile Gln Tyr Phe Gly Ala
            420                 425                 430

Arg Ala Asn Leu Ala Lys Ala Ile Leu Tyr Ala Ile Asn Gly Gly Arg
        435                 440                 445

Asp Glu Ile Ala Gly Asp Gln Val Gly Pro Ala Tyr Glu Pro Ile Thr
    450                 455                 460

Ser Glu Tyr Ile Asp Tyr Asp Glu Phe Met Lys Lys Leu Asp Lys Gln
465                 470                 475                 480

Met Asp Trp Leu Ala Asp Thr Tyr Val Asn Ser Leu Asn Ala Ile His
                485                 490                 495

Tyr Met His Asp Lys Tyr Tyr Tyr Glu Ala Ala Gln Leu Ala Leu Lys
            500                 505                 510

Asn Thr Asp Leu Asp Arg Thr Phe Ala Thr Gly Ile Ser Gly Leu Ser
        515                 520                 525

His Ala Ala Asp Ser Ile Ser Ala Ile Lys Tyr Gly His Val Lys Val
    530                 535                 540

Ile Arg Asp Glu Arg Gly Ile Ala Val Asp Phe Lys Ala Asp Asn Asp
545                 550                 555                 560

Tyr Pro Arg Tyr Gly Asn Asn Asp Asp Arg Ala Asp Asp Ile Ala Lys
                565                 570                 575

Trp Leu Val Lys Glu Leu Tyr Ser Lys Met Asn Thr His His Leu Tyr
            580                 585                 590

Arg Asn Ala Lys Leu Ser Thr Ser Val Leu Thr Ile Thr Ser Asn Val
        595                 600                 605

Val Tyr Gly Lys Asn Thr Gly Thr Thr Pro Asn Gly Arg Gln Lys Gly
    610                 615                 620

Glu Pro Phe Ser Pro Gly Ala Asn Pro Ala Tyr Gly Ala Glu Lys Ser
625                 630                 635                 640

Gly Ala Leu Ala Ser Leu Leu Ser Thr Ala Lys Leu Pro Tyr Arg Tyr
                645                 650                 655
```

```
Ala Thr Asp Gly Ile Ser Asn Thr Phe Gly Val Thr Pro Asn Thr Leu
            660                 665                 670

Gly His Asp Leu Glu Ser Arg Lys Asp Thr Leu Val Asn Met Leu Asp
        675                 680                 685

Gly Tyr Met Lys Asn Asp Gly Met His Leu Asn Ile Asn Val Phe Asn
    690                 695                 700

Lys Asp Thr Leu Ile Asp Ala Gln Lys His Pro Glu Glu Tyr Pro Thr
705                 710                 715                 720

Leu Thr Val Arg Val Ser Gly Tyr Cys Val Tyr Phe Ala Asp Leu Thr
                725                 730                 735

Lys Glu Gln Gln Asp Asp Val Ile Ser Arg Thr Phe Phe Glu Ser Met
            740                 745                 750


<210> SEQ ID NO 53
<211> LENGTH: 2445
<212> TYPE: DNA
<213> ORGANISM: Lactobacillus plantarum
<220> FEATURE:
<221> NAME/KEY: misc_feature
<223> OTHER INFORMATION: JDM1

<400> SEQUENCE: 53

atgatcatgt ctgaaacttt aactaaaaca acgacaacta ttaaccactt cggtaaattg     60

acgccaatga tggatcgctt acgcgatagc atcattgatg caaaacctta tgtcgatcca    120

gaacgggcga ttctcacaac cgaaacttat cgacaacacc aagacgaaca agtcgatata    180

ttacgggcta aaatgcttga acacgttctt gataaaatga gtatcttcat tgaagatgat    240

actttaattg ttggtaacca agcacgccaa aatcgttggg caccagtatt ccctgagtat    300

tctatgaatt gggtcattga tgaattagat acatttgaga agcgtcctgg tgacgttttc    360

tatattacgg agaaatctaa ggaagaactt cgtgcgattg cgcctttctg gaaacataat    420

accttggaag accgcggcta cgctagtttt ccagaagcaa gtcgtatttt ttatgattta    480

ggtattattg gagccgatgg taatatcact tctggtgatg gtcacattgc ggtcgactat    540

aaaaacgttg ttaataaggg acttaaatgg tatgaagacc gcattaagac agcacttgct    600

aatcttgacc ttactgattt taaccagcaa aaacaatact atttctataa agcgggccta    660

attgtaatcg atgccattca caattttgct aaacgttacg cccaattagc gtccaagcaa    720

gctcaaaaca cgacatccgc aactcgcaaa gcacaacttg aaaaaatcgc ccaaattcta    780

aacaaggttc cttacgaacc tgcaaattca ttttatgaag cgattcaagc tgtctggtta    840

gttcatctga ccttacaaat cgaatccaac ggtcattctg tctcatatgg tcgtctagat    900

cagtacctag atccattcta tgagcacgat ttaaaaactg gtgctattga cgccaacggt    960

gcaaccgaat tactcacaaa cttatgtctt aagacgttaa cgattaataa agtacgctca   1020

tggcaacata ctgaattttc tgcagggagt cccctctacc aaaacattac gattggtggt   1080

caaacaccag atggtaaaga tgccgttaat ccgacgtcct atctgatttt acgagcaatt   1140

gcgcaagcac atttaccaca acccaactta acggtccgtt atcaccatgg cttaagcgat   1200

aagtttatgc gtgaatgtgt cgaagttatt aaacaaggct taggtatgcc tgcgtttaat   1260

aacgacgaaa ttattattcc gtcgtttatt cgtcgtggcg tcaagaaaga agacgcctat   1320

aattacagtg ccatcggttg tgtcgaaaca gcgatccctg gaaaatgggg ctatcgttgc   1380

accgggatga gcttcattaa cttcccacgc gttctcttac tcattatgaa tggtggcatt   1440

gatcctgaat ctggcaaacg gttattaccc gattatggta agttcactga tatgacttct   1500
```

```
tttgatcaac ttatgactgc ttgggacaaa gcgctccgtg aaatgacacg acaaagtgtg   1560

attatcgaaa atagttgtga tttggctttg gaacaaaatt atcctgatat tctctgctcc   1620

gttttaaccg acgattgtat cggtcgtggt aagaccatta aagaaggtgg cgcggtatac   1680

gactttatca gtggattaca agttggtatt gctaacctag cggactccct agctgcaatc   1740

aagaaacttg tctttgaaga aaagaagttg acaacaaccc aactttggca cgcacttacc   1800

actgattttg cggatgaaga cggtgaaaag attcggcaga tgctcattaa tgatgcccca   1860

aagtatggta acgatgatga ttatgttgat gatttgattg ttgaagctta taaaccatat   1920

attgatgaaa ttgccaagta caaaaaacacg cgctacggtc gcggccctat tggtggcttg   1980

cgttacgcag gaacctcttc tatttcggcc aacgttggtc aagggcacag cactttggct   2040

acaccagatg gtcggcacgc tcggacacca ttagccgaag gttgctcacc agaacatgca   2100

atggatacta atggcccaac tgctgtgttc aaatcagttt ccaagttatc cactaaggac   2160

atcactggtg gcgtattact gaaccaaaag atgtcaccac aaattctacg gagtgatgaa   2220

agctgcatga aattggttgc actactacga accttcttca accgacttca tggttaccat   2280

gtccaataca acattgtttc acgggatacc ttgattgatg cacagaacca tcctgacaag   2340

caccgtgact tgattgttcg ggttgctgga tattccgcct tcttcgtggg cctatccaaa   2400

gaaacccaag atgatattat cgaacggacg gagcagtctc tataa                    2445
```

```
<210> SEQ ID NO 54
<211> LENGTH: 814
<212> TYPE: PRT
<213> ORGANISM: Lactobacillus plantarum
<220> FEATURE:
<221> NAME/KEY: MISC_FEATURE
<223> OTHER INFORMATION: JDM1

<400> SEQUENCE: 54

Met Ile Met Ser Glu Thr Leu Thr Lys Thr Thr Thr Thr Ile Asn His
1               5                   10                  15

Phe Gly Lys Leu Thr Pro Met Met Asp Arg Leu Arg Asp Ser Ile Ile
            20                  25                  30

Asp Ala Lys Pro Tyr Val Asp Pro Glu Arg Ala Ile Leu Thr Thr Glu
        35                  40                  45

Thr Tyr Arg Gln His Gln Asp Glu Gln Val Asp Ile Leu Arg Ala Lys
    50                  55                  60

Met Leu Glu His Val Leu Asp Lys Met Ser Ile Phe Ile Glu Asp Asp
65                  70                  75                  80

Thr Leu Ile Val Gly Asn Gln Ala Arg Gln Asn Arg Trp Ala Pro Val
                85                  90                  95

Phe Pro Glu Tyr Ser Met Asn Trp Val Ile Asp Glu Leu Asp Thr Phe
            100                 105                 110

Glu Lys Arg Pro Gly Asp Val Phe Tyr Ile Thr Glu Lys Ser Lys Glu
        115                 120                 125

Glu Leu Arg Ala Ile Ala Pro Phe Trp Lys His Asn Thr Leu Glu Asp
    130                 135                 140

Arg Gly Tyr Ala Ser Phe Pro Glu Ala Ser Arg Ile Phe Tyr Asp Leu
145                 150                 155                 160

Gly Ile Ile Gly Ala Asp Gly Asn Ile Thr Ser Gly Asp Gly His Ile
                165                 170                 175

Ala Val Asp Tyr Lys Asn Val Val Asn Lys Gly Leu Lys Trp Tyr Glu
            180                 185                 190
```

```
Asp Arg Ile Lys Thr Ala Leu Ala Asn Leu Asp Leu Thr Asp Phe Asn
        195                 200                 205

Gln Gln Lys Gln Tyr Tyr Phe Tyr Lys Ala Gly Leu Ile Val Ile Asp
    210                 215                 220

Ala Ile His Asn Phe Ala Lys Arg Tyr Ala Gln Leu Ala Ser Lys Gln
225                 230                 235                 240

Ala Gln Asn Thr Thr Ser Ala Thr Arg Lys Ala Gln Leu Glu Lys Ile
                245                 250                 255

Ala Gln Ile Leu Asn Lys Val Pro Tyr Glu Pro Ala Asn Ser Phe Tyr
            260                 265                 270

Glu Ala Ile Gln Ala Val Trp Leu Val His Leu Thr Leu Gln Ile Glu
        275                 280                 285

Ser Asn Gly His Ser Val Ser Tyr Gly Arg Leu Asp Gln Tyr Leu Asp
    290                 295                 300

Pro Phe Tyr Glu His Asp Leu Lys Thr Gly Ala Ile Asp Ala Asn Gly
305                 310                 315                 320

Ala Thr Glu Leu Leu Thr Asn Leu Cys Leu Lys Thr Leu Thr Ile Asn
                325                 330                 335

Lys Val Arg Ser Trp Gln His Thr Glu Phe Ser Ala Gly Ser Pro Leu
            340                 345                 350

Tyr Gln Asn Ile Thr Ile Gly Gly Gln Thr Pro Asp Gly Lys Asp Ala
        355                 360                 365

Val Asn Pro Thr Ser Tyr Leu Ile Leu Arg Ala Ile Ala Gln Ala His
    370                 375                 380

Leu Pro Gln Pro Asn Leu Thr Val Arg Tyr His His Gly Leu Ser Asp
385                 390                 395                 400

Lys Phe Met Arg Glu Cys Val Glu Val Ile Lys Gln Gly Leu Gly Met
                405                 410                 415

Pro Ala Phe Asn Asn Asp Glu Ile Ile Ile Pro Ser Phe Ile Arg Arg
            420                 425                 430

Gly Val Lys Lys Glu Asp Ala Tyr Asn Tyr Ser Ala Ile Gly Cys Val
        435                 440                 445

Glu Thr Ala Ile Pro Gly Lys Trp Gly Tyr Arg Cys Thr Gly Met Ser
    450                 455                 460

Phe Ile Asn Phe Pro Arg Val Leu Leu Leu Ile Met Asn Gly Gly Ile
465                 470                 475                 480

Asp Pro Glu Ser Gly Lys Arg Leu Leu Pro Asp Tyr Gly Lys Phe Thr
                485                 490                 495

Asp Met Thr Ser Phe Asp Gln Leu Met Thr Ala Trp Asp Lys Ala Leu
            500                 505                 510

Arg Glu Met Thr Arg Gln Ser Val Ile Ile Glu Asn Ser Cys Asp Leu
        515                 520                 525

Ala Leu Glu Gln Asn Tyr Pro Asp Ile Leu Cys Ser Val Leu Thr Asp
    530                 535                 540

Asp Cys Ile Gly Arg Gly Lys Thr Ile Lys Glu Gly Gly Ala Val Tyr
545                 550                 555                 560

Asp Phe Ile Ser Gly Leu Gln Val Gly Ile Ala Asn Leu Ala Asp Ser
                565                 570                 575

Leu Ala Ala Ile Lys Lys Leu Val Phe Glu Glu Lys Lys Leu Thr Thr
            580                 585                 590

Thr Gln Leu Trp His Ala Leu Thr Thr Asp Phe Ala Asp Glu Asp Gly
        595                 600                 605
```

-continued

```
Glu Lys Ile Arg Gln Met Leu Ile Asn Asp Ala Pro Lys Tyr Gly Asn
    610                 615                 620

Asp Asp Asp Tyr Val Asp Asp Leu Ile Val Glu Ala Tyr Lys Pro Tyr
625                 630                 635                 640

Ile Asp Glu Ile Ala Lys Tyr Lys Asn Thr Arg Tyr Gly Arg Gly Pro
                645                 650                 655

Ile Gly Gly Leu Arg Tyr Ala Gly Thr Ser Ser Ile Ser Ala Asn Val
            660                 665                 670

Gly Gln Gly His Ser Thr Leu Ala Thr Pro Asp Gly Arg His Ala Arg
        675                 680                 685

Thr Pro Leu Ala Glu Gly Cys Ser Pro Glu His Ala Met Asp Thr Asn
    690                 695                 700

Gly Pro Thr Ala Val Phe Lys Ser Val Ser Lys Leu Ser Thr Lys Asp
705                 710                 715                 720

Ile Thr Gly Gly Val Leu Leu Asn Gln Lys Met Ser Pro Gln Ile Leu
                725                 730                 735

Arg Ser Asp Glu Ser Cys Met Lys Leu Val Ala Leu Leu Arg Thr Phe
            740                 745                 750

Phe Asn Arg Leu His Gly Tyr His Val Gln Tyr Asn Ile Val Ser Arg
        755                 760                 765

Asp Thr Leu Ile Asp Ala Gln Asn His Pro Asp Lys His Arg Asp Leu
    770                 775                 780

Ile Val Arg Val Ala Gly Tyr Ser Ala Phe Phe Val Gly Leu Ser Lys
785                 790                 795                 800

Glu Thr Gln Asp Asp Ile Ile Glu Arg Thr Glu Gln Ser Leu
                805                 810
```

<210> SEQ ID NO 55
<211> LENGTH: 2262
<212> TYPE: DNA
<213> ORGANISM: Lactobacillus casei
<220> FEATURE:
<221> NAME/KEY: misc_feature
<223> OTHER INFORMATION: bl23

<400> SEQUENCE: 55

```
atgaaacagc ttgacgaaac caaagttcct aattattggg aaggctttaa cggcggcgac     60

tggcaagaag aaattaatgt gcgcgatttt atcgagcata acctgaacca atatgacggg    120

gacgaaagtt tccttgctgg ccccactgaa gcgacaacag tcctgaacaa tcaggttcta    180

aatttaaaga agcaagaacg tgcaaatggc ggtgttttgg atgctgacaa caatattcca    240

tctacgatca cctcacacgg ccctggttat ttgaacaaag atcttgaaaa gattgttggt    300

gttcagaccg acaagccatt caaacgagca ttcatgccat ttggcggtat tcgaatggct    360

gaagatgcat tggaatctta tggcttcaag acagatcctc aagaacacaa gattttcaat    420

gaatatcgta agacccataa ccaaggtgtc tttgatgctt ataccccctga tatgcgaaag    480

gctcgccatt acaagatcgt gactggcttg ccagacgcat acggccgtgg ccggattgtt    540

tctgatttcc cacggatcgc tgtttacggg atcgatcgtt taatggctga gaagttcaag    600

gattataact tgaccggcga cggcgaaatg actgacgatg taatcaaact gcgtgaagaa    660

atcaatgaac aatatcgtgc cttaaacgac atgaagaaga tggccaagga atatggctat    720

gacatctcgc gtccggcagc taatgcgcaa gaagctgttc agtggatcta ctttggctat    780

ctggctgctg ttaagactca aaacggtgcc gcaatgtccg ttggccggat cgatacggtt    840

attgatgctt atatccaacg cgatatgcgc ttaggcaaat tgaacgaaga acaggcacag    900
```

-continued

```
gaactgattg atcatttggt tatgaaattg cggatggttc gtttcatccg gactgaagaa    960

tataactcac tgttctcagg cgatccaatc tgggcaacct tgtcattggc aggaatgggc   1020

aatgatggcc gtcaccacgt taccaagacg gctttccgtt tcctgaagac tttggacaac   1080

atgggcgcag caccagaacc aaacatcacc ttgctttgga gcgaacgctt gccagaaggc   1140

ttcaaacgct atgcaaccga agtatccatc caaagttcaa ccattcaata tgaaaatgat   1200

gacctgatgc gcaacgaatg ggtaccgat tactacggta ttgcttgctg tgtctcggca   1260

caaccaattg ctgatggcgt tcaatacttt ggtgcccgtg ctaacttagc taagacggtt   1320

ctgtatgcga tcaacggtgg gaaagatgaa attcaggaag cgcaagtagg gcctgaatat   1380

gcaccgatca ccagcgatta cattgattac aaagaattca tgaataagtt cgacaagatg   1440

atggactggc tggccgacac gtatgtcaat gctttgaatg tgattcacta tatgcatgac   1500

aagtattatt atgaagctgc acagctggca ttgaaggata cccaactgaa ccggaccttc   1560

gcaaccggga tttccggcct gtcacacgcg gttgattcca tcagtgcaat caagtatggt   1620

catgtcaagg caattcgcga tgaaaacggt gttgcagttg acttcgttgc tgacaatgat   1680

gactatccac gctatggtaa caacgatgat cgcgctgatg acatcgctaa gtggttggtt   1740

aagaccttct ataacaagat gaacacgcat catctgtatc gcggcgcgaa gttgagtacc   1800

agtgtcctga ccattacctc caacgtggtt tatggtaaga atacagggac aacaccaaac   1860

ggtcgtcaaa aaggcgaacc attctcacca ggtgccaacc cggcatacgg cgcagaaaag   1920

aacggcgcat tggcatcctt gatgtccacc gccaagattc cgtatcatta cgcaactgac   1980

ggcattagta atacgtttgg ggttactccg aacacactgg gccacgatga tgaaactcgt   2040

aaggatacct tggttcacat ggttgacggc tatatggaaa acagcggcat gcatttgaac   2100

atcaacgtct tcaacaagga gaccctgatt gatgctcaga agcacccaga agaataccca   2160

acattgaccg ttcgggtttc tggctactgc gtctacttcg cagatttgac caaggaacaa   2220

caagacgatg tcattgctcg gaccttcttc gaagaaatgt aa                      2262
```

```
<210> SEQ ID NO 56
<211> LENGTH: 753
<212> TYPE: PRT
<213> ORGANISM: Lactobacillus casei
<220> FEATURE:
<221> NAME/KEY: MISC_FEATURE
<223> OTHER INFORMATION: bl23

<400> SEQUENCE: 56

Met Lys Gln Leu Asp Glu Thr Lys Val Pro Asn Tyr Trp Glu Gly Phe
1               5                   10                  15

Asn Gly Gly Asp Trp Gln Glu Glu Ile Asn Val Arg Asp Phe Ile Glu
            20                  25                  30

His Asn Leu Asn Gln Tyr Asp Gly Asp Glu Ser Phe Leu Ala Gly Pro
        35                  40                  45

Thr Glu Ala Thr Thr Val Leu Asn Asn Gln Val Leu Asn Leu Lys Lys
    50                  55                  60

Gln Glu Arg Ala Asn Gly Gly Val Leu Asp Ala Asp Asn Asn Ile Pro
65                  70                  75                  80

Ser Thr Ile Thr Ser His Gly Pro Gly Tyr Leu Asn Lys Asp Leu Glu
                85                  90                  95

Lys Ile Val Gly Val Gln Thr Asp Lys Pro Phe Lys Arg Ala Phe Met
            100                 105                 110
```

-continued

```
Pro Phe Gly Gly Ile Arg Met Ala Glu Asp Ala Leu Glu Ser Tyr Gly
        115                 120                 125

Phe Lys Thr Asp Pro Gln Glu His Lys Ile Phe Asn Glu Tyr Arg Lys
    130                 135                 140

Thr His Asn Gln Gly Val Phe Asp Ala Tyr Thr Pro Asp Met Arg Lys
145                 150                 155                 160

Ala Arg His Tyr Lys Ile Val Thr Gly Leu Pro Asp Ala Tyr Gly Arg
                165                 170                 175

Gly Arg Ile Val Ser Asp Phe Pro Arg Ile Ala Val Tyr Gly Ile Asp
            180                 185                 190

Arg Leu Met Ala Glu Lys Phe Lys Asp Tyr Asn Leu Thr Gly Asp Gly
        195                 200                 205

Glu Met Thr Asp Asp Val Ile Lys Leu Arg Glu Glu Ile Asn Glu Gln
    210                 215                 220

Tyr Arg Ala Leu Asn Asp Met Lys Lys Met Ala Lys Glu Tyr Gly Tyr
225                 230                 235                 240

Asp Ile Ser Arg Pro Ala Ala Asn Ala Gln Glu Ala Val Gln Trp Ile
                245                 250                 255

Tyr Phe Gly Tyr Leu Ala Ala Val Lys Thr Gln Asn Gly Ala Ala Met
            260                 265                 270

Ser Val Gly Arg Ile Asp Thr Val Ile Asp Ala Tyr Ile Gln Arg Asp
        275                 280                 285

Met Arg Leu Gly Lys Leu Asn Glu Glu Gln Ala Gln Glu Leu Ile Asp
    290                 295                 300

His Leu Val Met Lys Leu Arg Met Val Arg Phe Ile Arg Thr Glu Glu
305                 310                 315                 320

Tyr Asn Ser Leu Phe Ser Gly Asp Pro Ile Trp Ala Thr Leu Ser Leu
                325                 330                 335

Ala Gly Met Gly Asn Asp Gly Arg His His Val Thr Lys Thr Ala Phe
            340                 345                 350

Arg Phe Leu Lys Thr Leu Asp Asn Met Gly Ala Ala Pro Glu Pro Asn
        355                 360                 365

Ile Thr Leu Leu Trp Ser Glu Arg Leu Pro Glu Gly Phe Lys Arg Tyr
    370                 375                 380

Ala Thr Glu Val Ser Ile Gln Ser Ser Thr Ile Gln Tyr Glu Asn Asp
385                 390                 395                 400

Asp Leu Met Arg Asn Glu Trp Gly Thr Asp Tyr Tyr Gly Ile Ala Cys
                405                 410                 415

Cys Val Ser Ala Gln Pro Ile Ala Asp Gly Val Gln Tyr Phe Gly Ala
            420                 425                 430

Arg Ala Asn Leu Ala Lys Thr Val Leu Tyr Ala Ile Asn Gly Gly Lys
        435                 440                 445

Asp Glu Ile Gln Glu Ala Gln Val Gly Pro Glu Tyr Ala Pro Ile Thr
    450                 455                 460

Ser Asp Tyr Ile Asp Tyr Lys Glu Phe Met Asn Lys Phe Asp Lys Met
465                 470                 475                 480

Met Asp Trp Leu Ala Asp Thr Tyr Val Asn Ala Leu Asn Val Ile His
                485                 490                 495

Tyr Met His Asp Lys Tyr Tyr Tyr Glu Ala Ala Gln Leu Ala Leu Lys
            500                 505                 510

Asp Thr Gln Leu Asn Arg Thr Phe Ala Thr Gly Ile Ser Gly Leu Ser
        515                 520                 525

His Ala Val Asp Ser Ile Ser Ala Ile Lys Tyr Gly His Val Lys Ala
```

```
    530                 535                 540

Ile Arg Asp Glu Asn Gly Val Ala Val Asp Phe Val Ala Asp Asn Asp
545                 550                 555                 560

Asp Tyr Pro Arg Tyr Gly Asn Asn Asp Asp Arg Ala Asp Asp Ile Ala
                565                 570                 575

Lys Trp Leu Val Lys Thr Phe Tyr Asn Lys Met Asn Thr His His Leu
            580                 585                 590

Tyr Arg Gly Ala Lys Leu Ser Thr Ser Val Leu Thr Ile Thr Ser Asn
        595                 600                 605

Val Val Tyr Gly Lys Asn Thr Gly Thr Thr Pro Asn Gly Arg Gln Lys
    610                 615                 620

Gly Glu Pro Phe Ser Pro Gly Ala Asn Pro Ala Tyr Gly Ala Glu Lys
625                 630                 635                 640

Asn Gly Ala Leu Ala Ser Leu Met Ser Thr Ala Lys Ile Pro Tyr His
                645                 650                 655

Tyr Ala Thr Asp Gly Ile Ser Asn Thr Phe Gly Val Thr Pro Asn Thr
            660                 665                 670

Leu Gly His Asp Asp Glu Thr Arg Lys Asp Thr Leu Val His Met Val
        675                 680                 685

Asp Gly Tyr Met Glu Asn Ser Gly Met His Leu Asn Ile Asn Val Phe
    690                 695                 700

Asn Lys Glu Thr Leu Ile Asp Ala Gln Lys His Pro Glu Glu Tyr Pro
705                 710                 715                 720

Thr Leu Thr Val Arg Val Ser Gly Tyr Cys Val Tyr Phe Ala Asp Leu
                725                 730                 735

Thr Lys Glu Gln Gln Asp Asp Val Ile Ala Arg Thr Phe Phe Glu Glu
            740                 745                 750

Met
```

<210> SEQ ID NO 57
<211> LENGTH: 2262
<212> TYPE: DNA
<213> ORGANISM: Lactobacillus casei
<220> FEATURE:
<221> NAME/KEY: misc_feature
<223> OTHER INFORMATION: ATCC 334

<400> SEQUENCE: 57

```
atgaaacagc ttgacgaaac caaagttcct aattattggg aaggctttaa cggcggcgac      60

tggcaagaag aaattaatgt gcgcgatttt atcgagcata acctgaacca atatgacggg     120

gacgaaagtt tccttgctgg tcccactgaa gcgacaacag tcctgaacaa tcaggttcta     180

aatttaaaga agcaagaacg tgcaaatggc ggtgttttgg atgctgacaa caatattcca     240

tctacgatca cctcacacgg ccctggttat ttgaacaaag atcttgaaaa gattgttggt     300

gttcagaccg acaagccatt caaacgagca ttcatgccat ttggcggtat tcgaatggct     360

gaagatgcat tggaatctta tggcttcaag acagatcctc aagaacacaa gattttcaat     420

gaatatcgta agacccataa ccaaggtgtc tttgatgctt atacccctga tatgcgaaag     480

gctcgccatt acaagatcgt gactggcttg ccagacgcat acggccgcgg ccggattgtt     540

tctgatttcc cacggatcgc tgtttacggg atcgatcgtt taatggctga gaagttcaag     600

gattataact tgaccggcga cggcgaaatg actgacgatg taatcaaatt gcgtgaagaa     660

atcaatgaac aatatcgtgc cttaaacgac atgaagaaga tggccaagga atatggctat     720

gacatctcgc gtccggcagc taatgcgcaa gaagctgttc agtggatcta ctttggctat     780
```

```
ctggctgctg ttaagactca aaacggtgcc gcaatgtccg ttggccggat cgatacggtt    840

attgatgctt atatccaacg cgatatgcgc ttaggcaaat tgaacgaaga acaggcacag    900

gaactgattg atcatttggt tatgaaattg cggatggttc gtttcatccg gactgaagaa    960

tataactcac tgttctcagg cgatccaatc tgggcaacct tgtcattggc aggaatgggc   1020

aatgatggcc gtcaccacgt taccaagacg gctttccgtt tcctgaagac tttggacaac   1080

atgggcgcag caccagaacc aaacatcacc ttgctttgga gcgaacgctt gccagaaggc   1140

tttaaacgct atgcaaccga agtatccatc caaagttcaa ccattcaata tgaaaatgat   1200

gacctgatgc gcaatgaatg gggtaccgat tactacggta ttgcttgctg tgtctcggca   1260

caaccaattg ctgatggcgt tcaatacttt ggtgcccgtg ctaacttagc taagacggtt   1320

ctgtatgcga tcaacggtgg taaagatgaa attcaggaag cgcaagtagg gcctgaatat   1380

gcaccgatca ccagcgatta cattgattac aaagaattca tgaataagtt cgacaagatg   1440

atggactggc tggccgacac gtatgtcaat gctttgaatg tgattcacta tatgcatgac   1500

aagtattatt atgaagctgc acagctggca ttgaaggata cccaactgaa ccggaccttc   1560

gcaaccggga tttccggcct gtcacacgcg gttgattcca tcagtgcaat caagtatggt   1620

catgtcaagg caattcgcga tgaaaatggt gttgcagttg acttcgttgc tgacaatgat   1680

gactatccac gttatggtaa caacgatgat cgcgctgatg acatcgctaa gtggttggtt   1740

aagaccttct ataacaagat gaacacgcat catctgtatc gcggcgcgaa gttgagtacc   1800

agtgtcctga ccattacttc caacgtggtt tatggtaaga atacagggac aacaccaaac   1860

ggtcgtcaaa aaggcgaacc attctcacca ggtgccaacc cggcatacgg cgcagaaaag   1920

aacggcgcat tggcatcctt gatgtccacc gccaagattc cgtatcatta cgcaactgac   1980

ggcattagta atacgtttgg ggttactccg aacacactgg gccacgatga tgaaactcgt   2040

aaggatacct tggttcacat ggttgacggc tatatggaaa acagcggcat gcatttgaac   2100

atcaacgtct tcaacaagga gaccctgatt gatgctcaga agcacccaga agaataccca   2160

acattgaccg ttcgggtttc tggctactgc gtctacttcg cagatttgac caaggaacaa   2220

caagacgatg tcattgctcg gaccttcttc gaagaaatgt aa                      2262
```

```
<210> SEQ ID NO 58
<211> LENGTH: 753
<212> TYPE: PRT
<213> ORGANISM: Lactobacillus casei
<220> FEATURE:
<221> NAME/KEY: MISC_FEATURE
<223> OTHER INFORMATION: ATCC 334

<400> SEQUENCE: 58

Met Lys Gln Leu Asp Glu Thr Lys Val Pro Asn Tyr Trp Glu Gly Phe
1               5                   10                  15

Asn Gly Gly Asp Trp Gln Glu Glu Ile Asn Val Arg Asp Phe Ile Glu
            20                  25                  30

His Asn Leu Asn Gln Tyr Asp Gly Asp Glu Ser Phe Leu Ala Gly Pro
        35                  40                  45

Thr Glu Ala Thr Thr Val Leu Asn Asn Gln Val Leu Asn Leu Lys Lys
    50                  55                  60

Gln Glu Arg Ala Asn Gly Gly Val Leu Asp Ala Asp Asn Asn Ile Pro
65                  70                  75                  80

Ser Thr Ile Thr Ser His Gly Pro Gly Tyr Leu Asn Lys Asp Leu Glu
                85                  90                  95
```

```
Lys Ile Val Gly Val Gln Thr Asp Lys Pro Phe Lys Arg Ala Phe Met
            100                 105                 110

Pro Phe Gly Gly Ile Arg Met Ala Glu Asp Ala Leu Glu Ser Tyr Gly
        115                 120                 125

Phe Lys Thr Asp Pro Gln Glu His Lys Ile Phe Asn Glu Tyr Arg Lys
    130                 135                 140

Thr His Asn Gln Gly Val Phe Asp Ala Tyr Thr Pro Asp Met Arg Lys
145                 150                 155                 160

Ala Arg His Tyr Lys Ile Val Thr Gly Leu Pro Asp Ala Tyr Gly Arg
                165                 170                 175

Gly Arg Ile Val Ser Asp Phe Pro Arg Ile Ala Val Tyr Gly Ile Asp
            180                 185                 190

Arg Leu Met Ala Glu Lys Phe Lys Asp Tyr Asn Leu Thr Gly Asp Gly
        195                 200                 205

Glu Met Thr Asp Asp Val Ile Lys Leu Arg Glu Glu Ile Asn Glu Gln
    210                 215                 220

Tyr Arg Ala Leu Asn Asp Met Lys Lys Met Ala Lys Glu Tyr Gly Tyr
225                 230                 235                 240

Asp Ile Ser Arg Pro Ala Ala Asn Ala Gln Glu Ala Val Gln Trp Ile
                245                 250                 255

Tyr Phe Gly Tyr Leu Ala Ala Val Lys Thr Gln Asn Gly Ala Ala Met
            260                 265                 270

Ser Val Gly Arg Ile Asp Thr Val Ile Asp Ala Tyr Ile Gln Arg Asp
        275                 280                 285

Met Arg Leu Gly Lys Leu Asn Glu Glu Gln Ala Gln Glu Leu Ile Asp
    290                 295                 300

His Leu Val Met Lys Leu Arg Met Val Arg Phe Ile Arg Thr Glu Glu
305                 310                 315                 320

Tyr Asn Ser Leu Phe Ser Gly Asp Pro Ile Trp Ala Thr Leu Ser Leu
                325                 330                 335

Ala Gly Met Gly Asn Asp Gly Arg His His Val Thr Lys Thr Ala Phe
            340                 345                 350

Arg Phe Leu Lys Thr Leu Asp Asn Met Gly Ala Ala Pro Glu Pro Asn
        355                 360                 365

Ile Thr Leu Leu Trp Ser Glu Arg Leu Pro Glu Gly Phe Lys Arg Tyr
    370                 375                 380

Ala Thr Glu Val Ser Ile Gln Ser Ser Thr Ile Gln Tyr Glu Asn Asp
385                 390                 395                 400

Asp Leu Met Arg Asn Glu Trp Gly Thr Asp Tyr Tyr Gly Ile Ala Cys
                405                 410                 415

Cys Val Ser Ala Gln Pro Ile Ala Asp Gly Val Gln Tyr Phe Gly Ala
            420                 425                 430

Arg Ala Asn Leu Ala Lys Thr Val Leu Tyr Ala Ile Asn Gly Gly Lys
        435                 440                 445

Asp Glu Ile Gln Glu Ala Gln Val Gly Pro Glu Tyr Ala Pro Ile Thr
    450                 455                 460

Ser Asp Tyr Ile Asp Tyr Lys Glu Phe Met Asn Lys Phe Asp Lys Met
465                 470                 475                 480

Met Asp Trp Leu Ala Asp Thr Tyr Val Asn Ala Leu Asn Val Ile His
                485                 490                 495

Tyr Met His Asp Lys Tyr Tyr Tyr Glu Ala Ala Gln Leu Ala Leu Lys
            500                 505                 510
```

```
Asp Thr Gln Leu Asn Arg Thr Phe Ala Thr Gly Ile Ser Gly Leu Ser
        515                 520                 525

His Ala Val Asp Ser Ile Ser Ala Ile Lys Tyr Gly His Val Lys Ala
    530                 535                 540

Ile Arg Asp Glu Asn Gly Val Ala Val Asp Phe Val Ala Asp Asn Asp
545                 550                 555                 560

Asp Tyr Pro Arg Tyr Gly Asn Asn Asp Asp Arg Ala Asp Asp Ile Ala
                565                 570                 575

Lys Trp Leu Val Lys Thr Phe Tyr Asn Lys Met Asn Thr His His Leu
            580                 585                 590

Tyr Arg Gly Ala Lys Leu Ser Thr Ser Val Leu Thr Ile Thr Ser Asn
        595                 600                 605

Val Val Tyr Gly Lys Asn Thr Gly Thr Thr Pro Asn Gly Arg Gln Lys
    610                 615                 620

Gly Glu Pro Phe Ser Pro Gly Ala Asn Pro Ala Tyr Gly Ala Glu Lys
625                 630                 635                 640

Asn Gly Ala Leu Ala Ser Leu Met Ser Thr Ala Lys Ile Pro Tyr His
                645                 650                 655

Tyr Ala Thr Asp Gly Ile Ser Asn Thr Phe Gly Val Thr Pro Asn Thr
            660                 665                 670

Leu Gly His Asp Asp Glu Thr Arg Lys Asp Thr Leu Val His Met Val
        675                 680                 685

Asp Gly Tyr Met Glu Asn Ser Gly Met His Leu Asn Ile Asn Val Phe
    690                 695                 700

Asn Lys Glu Thr Leu Ile Asp Ala Gln Lys His Pro Glu Glu Tyr Pro
705                 710                 715                 720

Thr Leu Thr Val Arg Val Ser Gly Tyr Cys Val Tyr Phe Ala Asp Leu
                725                 730                 735

Thr Lys Glu Gln Gln Asp Asp Val Ile Ala Arg Thr Phe Phe Glu Glu
            740                 745                 750

Met
```

<210> SEQ ID NO 59
<211> LENGTH: 2376
<212> TYPE: DNA
<213> ORGANISM: Bifidobacterium adolescentis

<400> SEQUENCE: 59

```
atggcagcag ttgatgcaac ggcggtctcc caggaggaac ttgaggctaa ggcttgggaa      60

ggcttcaccg agggcaactg gcagaaggac attgatgtcc gcgacttcat ccagaagaac     120

tacacgccat atgagggcga cgagtccttc ctggctgacg ccaccgacaa gaccaagcac     180

ctgtggaagt atctggacga caactatctg tccgtggagc gcaagcagcg cgtctacgac     240

gtggacaccc acaccccggc gggcatcgac gccttcccgg ccggctacat cgattccccg     300

gaagtcgaca atgtgattgt cggtctgcag accgatgtgc cgtgcaagcg cgccatgatg     360

ccgaacggcg gctggcgtat ggtcgagcag gccatcaagg aagccggcaa ggagcccgat     420

ccggagatca agaagatctt caccaagtac cgcaagaccc acaacgacgg cgtcttcggc     480

gtctacacca agcagatcaa ggtagctcgc cacaacaaga tcctcaccgg cctgccggat     540

gcctacggcc gtggccgcat catcggcgat taccgtcgtg tggccctgta cggcgtgaac     600

gcgctgatca agttcaagca gcgcgacaag gactccatcc cgtaccgcaa cgacttcacc     660

gagccggaga tcgagcactg gatccgcttc cgtgaggagc atgacgagca gatcaaggcc     720
```

ctgaagcagc tgatcaacct cggcaacgag tacggcctcg acctgtcccg cccggcacag 780
accgcacagg aagccgtgca gtggacctac atgggctacc tcgcctccgt caagagccag 840
gacggcgccg ccatgtcctt cggccgtgtc tccaccttct tcgacgtcta cttcgagcgc 900
gacctgaagg ccggcaagat caccgagacc gacgcacagg agatcatcga taacctggtc 960
atgaagctgc gcatcgtgcg cttcctgcgc accaaggatt acgacgcgat cttctccggc 1020
gatccgtact gggcgacttg gtccgacgcc ggcttcggcg acgacggccg taccatggtc 1080
accaagacct cgttccgtct gctcaacacc ctgaccctcg agcacctcgg acctggcccg 1140
gagccgaaca tcaccatctt ctgggatccg aagctgccgg aagcctacaa gcgcttctgc 1200
gcccgaatct ccatcgacac ctcggccatc cagtacgagt ccgataagga aatccgctcc 1260
cactggggcg acgacgccgc catcgcatgc tgcgtctccc cgatgcgcgt gggcaagcag 1320
atgcagttct tcgccgcccg tgtgaactcc gccaaggccc tgctgtacgc catcaacggc 1380
ggacgcgacg agatgaccgg catgcaggtc atcgacaagg gcgtcatcga cccgatcaag 1440
ccggaagccg atggcacgct ggattacgag aaggtcaagg ccaactacga gaaggccctc 1500
gaatggctgt ccgagaccta tgtgatggct ctgaacatca tccattacat gcatgataag 1560
tacgcttacg agtccatcga gatggctctg cacgacaagg aagtgtaccg caccctcggc 1620
tgcggcatgt ccggcctgtc gatcgcggcc gactccctgt ccgcatgcaa gtacgccaag 1680
gtctacccga tctacaacaa ggacgccaag accacgccgg gccacgagaa cgagtacgtc 1740
gaaggcgccg atgacgatct gatcgtcggc taccgcaccg aaggcgactt cccgctgtac 1800
ggcaacgatg atgaccgtgc cgacgacatc gccaagtggg tcgtctccac cgtcatgggc 1860
caggtcaagc gtctgccggt gtaccgcgac gccgtcccga cccagtccat cctgaccatc 1920
acctccaatg tggaatacgg caaggccacc ggcgccttcc cgtccggcca caagaagggc 1980
accccgtacg ctccgggcgc caacccggag aacggcatgg actcccacgg catgctgccg 2040
tccatgttct ccgtcggcaa gatcgactac aacgacgctc ttgacggcat ctcgctgacc 2100
aacaccatca cccctgatgg tctgggccgc gacgaggaag agcgtatcgg caacctcgtt 2160
ggcatcctgg acgccggcaa cggccacggc ctgtaccacg ccaacatcaa cgtgctgcgc 2220
aaggagcagc tcgaggatgc cgtcgagcat ccggagaagt acccgcacct gaccgtgcgc 2280
gtctccggct acgcggtgaa cttcgtcaag ctcaccaagg aacagcagct cgacgtgatc 2340
tcccgtacgt tccaccaggg cgctgtcgtc gactga 2376

<210> SEQ ID NO 60
<211> LENGTH: 791
<212> TYPE: PRT
<213> ORGANISM: Bifidobacterium adolescentis

<400> SEQUENCE: 60

Met Ala Ala Val Asp Ala Thr Ala Val Ser Gln Glu Glu Leu Glu Ala
1 5 10 15

Lys Ala Trp Glu Gly Phe Thr Glu Gly Asn Trp Gln Lys Asp Ile Asp
20 25 30

Val Arg Asp Phe Ile Gln Lys Asn Tyr Thr Pro Tyr Glu Gly Asp Glu
35 40 45

Ser Phe Leu Ala Asp Ala Thr Asp Lys Thr Lys His Leu Trp Lys Tyr
50 55 60

Leu Asp Asp Asn Tyr Leu Ser Val Glu Arg Lys Gln Arg Val Tyr Asp
65 70 75 80

```
Val Asp Thr His Thr Pro Ala Gly Ile Asp Ala Phe Pro Ala Gly Tyr
                85                  90                  95

Ile Asp Ser Pro Glu Val Asp Asn Val Ile Val Gly Leu Gln Thr Asp
            100                 105                 110

Val Pro Cys Lys Arg Ala Met Met Pro Asn Gly Gly Trp Arg Met Val
        115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Ala Leu Ile Lys Phe Lys Gln Arg
        195                 200                 205

Asp Lys Asp Ser Ile Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Gln Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Val Lys Ser Gln Asp Gly Ala Ala Met Ser Phe Gly
        275                 280                 285

Arg Val Ser Thr Phe Phe Asp Val Tyr Phe Glu Arg Asp Leu Lys Ala
    290                 295                 300

Gly Lys Ile Thr Glu Thr Asp Ala Gln Glu Ile Ile Asp Asn Leu Val
305                 310                 315                 320

Met Lys Leu Arg Ile Val Arg Phe Leu Arg Thr Lys Asp Tyr Asp Ala
                325                 330                 335

Ile Phe Ser Gly Asp Pro Tyr Trp Ala Thr Trp Ser Asp Ala Gly Phe
            340                 345                 350

Gly Asp Asp Gly Arg Thr Met Val Thr Lys Thr Ser Phe Arg Leu Leu
        355                 360                 365

Asn Thr Leu Thr Leu Glu His Leu Gly Pro Gly Pro Glu Pro Asn Ile
    370                 375                 380

Thr Ile Phe Trp Asp Pro Lys Leu Pro Glu Ala Tyr Lys Arg Phe Cys
385                 390                 395                 400

Ala Arg Ile Ser Ile Asp Thr Ser Ala Ile Gln Tyr Glu Ser Asp Lys
                405                 410                 415

Glu Ile Arg Ser His Trp Gly Asp Asp Ala Ala Ile Ala Cys Cys Val
            420                 425                 430

Ser Pro Met Arg Val Gly Lys Gln Met Gln Phe Phe Ala Ala Arg Val
        435                 440                 445

Asn Ser Ala Lys Ala Leu Leu Tyr Ala Ile Asn Gly Gly Arg Asp Glu
    450                 455                 460

Met Thr Gly Met Gln Val Ile Asp Lys Gly Val Ile Asp Pro Ile Lys
465                 470                 475                 480

Pro Glu Ala Asp Gly Thr Leu Asp Tyr Glu Lys Val Lys Ala Asn Tyr
                485                 490                 495

Glu Lys Ala Leu Glu Trp Leu Ser Glu Thr Tyr Val Met Ala Leu Asn
```

```
            500                 505                 510

Ile Ile His Tyr Met His Asp Lys Tyr Ala Tyr Glu Ser Ile Glu Met
        515                 520                 525

Ala Leu His Asp Lys Glu Val Tyr Arg Thr Leu Gly Cys Gly Met Ser
    530                 535                 540

Gly Leu Ser Ile Ala Ala Asp Ser Leu Ser Ala Cys Lys Tyr Ala Lys
545                 550                 555                 560

Val Tyr Pro Ile Tyr Asn Lys Asp Ala Lys Thr Thr Pro Gly His Glu
                565                 570                 575

Asn Glu Tyr Val Glu Gly Ala Asp Asp Asp Leu Ile Val Gly Tyr Arg
            580                 585                 590

Thr Glu Gly Asp Phe Pro Leu Tyr Gly Asn Asp Asp Asp Arg Ala Asp
        595                 600                 605

Asp Ile Ala Lys Trp Val Val Ser Thr Val Met Gly Gln Val Lys Arg
    610                 615                 620

Leu Pro Val Tyr Arg Asp Ala Val Pro Thr Gln Ser Ile Leu Thr Ile
625                 630                 635                 640

Thr Ser Asn Val Glu Tyr Gly Lys Ala Thr Gly Ala Phe Pro Ser Gly
                645                 650                 655

His Lys Lys Gly Thr Pro Tyr Ala Pro Gly Ala Asn Pro Glu Asn Gly
            660                 665                 670

Met Asp Ser His Gly Met Leu Pro Ser Met Phe Ser Val Gly Lys Ile
        675                 680                 685

Asp Tyr Asn Asp Ala Leu Asp Gly Ile Ser Leu Thr Asn Thr Ile Thr
    690                 695                 700

Pro Asp Gly Leu Gly Arg Asp Glu Glu Glu Arg Ile Gly Asn Leu Val
705                 710                 715                 720

Gly Ile Leu Asp Ala Gly Asn Gly His Gly Leu Tyr His Ala Asn Ile
                725                 730                 735

Asn Val Leu Arg Lys Glu Gln Leu Glu Asp Ala Val Glu His Pro Glu
            740                 745                 750

Lys Tyr Pro His Leu Thr Val Arg Val Ser Gly Tyr Ala Val Asn Phe
        755                 760                 765

Val Lys Leu Thr Lys Glu Gln Gln Leu Asp Val Ile Ser Arg Thr Phe
    770                 775                 780

His Gln Gly Ala Val Val Asp
785                 790
```

<210> SEQ ID NO 61
<211> LENGTH: 2415
<212> TYPE: DNA
<213> ORGANISM: Bifidobacterium longum
<220> FEATURE:
<221> NAME/KEY: misc_feature
<223> OTHER INFORMATION: NCC2705

<400> SEQUENCE: 61

```
gtgaagatgc gaaacctaca accccattta aggagtgaca tgaccgcagt ggaaaatgca      60

gctgtctccc aggaggagct cgacgccaag gcgtgggccg gcttcaccga gggcaactgg     120

cagaaggata ttgacgtccg cgacttcatc cagaagaact acaccccgta cgagggcgac     180

gagacattcc tggctcctgc caccgagaag accaagcacc tgtggaagta cctcgacgac     240

aactacctgg ccgtggagcg caagcagcgc gtctacgacg tggacaccca taccccggcc     300

gacgtcgacg ccttcccggc cggctacatc gactccccgg aagtcgataa cgtggtcgtt     360
```

-continued

```
ggcctccaga ccgacgttcc ctgcaagcgc gcgatgatgc cgaacggtgg ctggcgcatg    420
gtcgagcagg ccatcaagga agccggcaag gaaccggatc cggagatcaa gaagatcttc    480
accaagtacc gcaagaccca caacgacggc gtcttcggcg tgtacaccaa gcagatcaag    540
gtcgcccgcc acaacaagat cctcaccggt ctgccggacg cctacggccg tggccgcatc    600
atcggcgact accgccgcgt cgccctgtac ggcgtgaaca agctcatcgc cttcaagaag    660
cgcgacaagg actccgtgcc gtaccgcaac gacttcaccg agccggagat cgagcactgg    720
atccgcttcc gtgaggagca cgacgagcag atcaaggccc tgaagaagct catcaacctc    780
ggcaacgagt acggcctcga cctgtcccgc ccggcccaga ccgcgcagga agccgtgcag    840
tggacctaca tgggctacct ggcctccatc aagtcccagg acggcgccgc catgtccttc    900
ggccgcaact ccgccttcct cgactgctac atcgagcgcg acctccaggc cggcaagatc    960
accgagaccg acgcccagga gctcatcgac aacatcgtca tgaagctgcg catcgtgcgc   1020
ttcctgcgta ccaaggacta cgattcgatc ttctccggcg acccgtactg ggcgacctgg   1080
tccgacgccg gcttcggcga tgacggccgt tcgatggtca ccaagacctc gttccgtctg   1140
ctcaacaccc tgaccctcga gcacctcgga cctggccccg agccgaacat caccatcttc   1200
tgggatccga agctgcctga ggcctacaag cgcttctgcg ccaagatctc catcgacacc   1260
tcggccatcc agtacgagtc cgacaaggag attcgtagcc actggggcga cgacgcggct   1320
atcgcatgct gcgtgtcccc gatgcgtgtc ggcaagcaga tgcagttctt cgccgcccgc   1380
gtgaactccg ccaaggccct gctgtacgcc atcaacggcg gccgcgacga gatgaccggc   1440
atgcaggtca tcgacaaggg cgtgatcgag ccgattaccc cggaggccga cggcaccctg   1500
gactacgaga aggtcaagaa caactacgag aaggctctcg agtggctgtc cgagacctac   1560
gtcatggccc tgaacatcat ccactacatg cacgataagt acgcgtacga gtccatcgag   1620
atggccctgc acgacaagga agtgtaccgc accctcggct gcggcatgtc cggtctgtcc   1680
atcgccgccg actccctcgc cgccgtcaag tacgccaagg tctacccgat ctacaacaag   1740
gacgcgaaga ccctggaagg ccacgagtac gagtacgttg agggcgccga cgacgacctg   1800
atcgtcggct accgcaccga gggcgagttc ccggtctacg gcaacgacga cgaccgcgcc   1860
gacgacatcg ccaagtgggt cgtctccacg gtcatgggcc aggtcaagag gctcccggtc   1920
taccgcggcg ccgtcccgac ccagtccatc ctgacgatca cctccaacgt cgagtacggc   1980
aagaacaccg gttccttccc gtccggccac gccaagggca ccccgtacgc tccgggcgcc   2040
aacccggaga acggcatgga ctcccacggc atgctgccgt ccatgttctc cgtcggcaag   2100
atcgactaca acgacgctct tgacggcatc tcgctgacca acaccatcac ccctgatggc   2160
ctgggccgcg acgaggacga gcgcatcggc aacctggtcg gcatcctgga cgccggcaac   2220
ggccacggcc tctaccacgc gaacatcaac gttctgcgca aggagaccat ggaggacgcc   2280
gtcgagcacc ccgaaaagta cccgcacctg accgtgcgtg tctccggcta cgcggtgaac   2340
ttcgtcaagc tcaccaagga gcagcagctc gacgtcatct cccgtacctt ccaccagggt   2400
gccgtcgtcg actga                                                    2415
```

<210> SEQ ID NO 62
<211> LENGTH: 804
<212> TYPE: PRT
<213> ORGANISM: Bifidobacterium longum
<220> FEATURE:
<221> NAME/KEY: MISC_FEATURE
<223> OTHER INFORMATION: NCC2705

<400> SEQUENCE: 62

Met Lys Met Arg Asn Leu Gln Pro His Leu Arg Ser Asp Met Thr Ala
1               5                   10                  15

Val Glu Asn Ala Ala Val Ser Gln Glu Glu Leu Asp Ala Lys Ala Trp
            20                  25                  30

Ala Gly Phe Thr Glu Gly Asn Trp Gln Lys Asp Ile Asp Val Arg Asp
        35                  40                  45

Phe Ile Gln Lys Asn Tyr Thr Pro Tyr Glu Gly Asp Glu Thr Phe Leu
    50                  55                  60

Ala Pro Ala Thr Glu Lys Thr Lys His Leu Trp Lys Tyr Leu Asp Asp
65                  70                  75                  80

Asn Tyr Leu Ala Val Glu Arg Lys Gln Arg Val Tyr Asp Val Asp Thr
                85                  90                  95

His Thr Pro Ala Asp Val Asp Ala Phe Pro Ala Gly Tyr Ile Asp Ser
            100                 105                 110

Pro Glu Val Asp Asn Val Val Val Gly Leu Gln Thr Asp Val Pro Cys
        115                 120                 125

Lys Arg Ala Met Met Pro Asn Gly Gly Trp Arg Met Val Glu Gln Ala
    130                 135                 140

Ile Lys Glu Ala Gly Lys Glu Pro Asp Pro Glu Ile Lys Lys Ile Phe
145                 150                 155                 160

Thr Lys Tyr Arg Lys Thr His Asn Asp Gly Val Phe Gly Val Tyr Thr
                165                 170                 175

Lys Gln Ile Lys Val Ala Arg His Asn Lys Ile Leu Thr Gly Leu Pro
            180                 185                 190

Asp Ala Tyr Gly Arg Gly Arg Ile Ile Gly Asp Tyr Arg Arg Val Ala
        195                 200                 205

Leu Tyr Gly Val Asn Lys Leu Ile Ala Phe Lys Lys Arg Asp Lys Asp
    210                 215                 220

Ser Val Pro Tyr Arg Asn Asp Phe Thr Glu Pro Glu Ile Glu His Trp
225                 230                 235                 240

Ile Arg Phe Arg Glu Glu His Asp Glu Gln Ile Lys Ala Leu Lys Lys
                245                 250                 255

Leu Ile Asn Leu Gly Asn Glu Tyr Gly Leu Asp Leu Ser Arg Pro Ala
            260                 265                 270

Gln Thr Ala Gln Glu Ala Val Gln Trp Thr Tyr Met Gly Tyr Leu Ala
        275                 280                 285

Ser Ile Lys Ser Gln Asp Gly Ala Ala Met Ser Phe Gly Arg Asn Ser
    290                 295                 300

Ala Phe Leu Asp Cys Tyr Ile Glu Arg Asp Leu Gln Ala Gly Lys Ile
305                 310                 315                 320

Thr Glu Thr Asp Ala Gln Glu Leu Ile Asp Asn Ile Val Met Lys Leu
                325                 330                 335

Arg Ile Val Arg Phe Leu Arg Thr Lys Asp Tyr Asp Ser Ile Phe Ser
            340                 345                 350

Gly Asp Pro Tyr Trp Ala Thr Trp Ser Asp Ala Gly Phe Gly Asp Asp
        355                 360                 365

Gly Arg Ser Met Val Thr Lys Thr Ser Phe Arg Leu Leu Asn Thr Leu
    370                 375                 380

Thr Leu Glu His Leu Gly Pro Gly Pro Glu Pro Asn Ile Thr Ile Phe
385                 390                 395                 400

Trp Asp Pro Lys Leu Pro Glu Ala Tyr Lys Arg Phe Cys Ala Lys Ile
                405                 410                 415

```
Ser Ile Asp Thr Ser Ala Ile Gln Tyr Glu Ser Asp Lys Glu Ile Arg
            420                 425                 430

Ser His Trp Gly Asp Asp Ala Ala Ile Ala Cys Cys Val Ser Pro Met
        435                 440                 445

Arg Val Gly Lys Gln Met Gln Phe Phe Ala Ala Arg Val Asn Ser Ala
    450                 455                 460

Lys Ala Leu Leu Tyr Ala Ile Asn Gly Gly Arg Asp Glu Met Thr Gly
465                 470                 475                 480

Met Gln Val Ile Asp Lys Gly Val Ile Glu Pro Ile Thr Pro Glu Ala
                485                 490                 495

Asp Gly Thr Leu Asp Tyr Glu Lys Val Lys Asn Asn Tyr Glu Lys Ala
            500                 505                 510

Leu Glu Trp Leu Ser Glu Thr Tyr Val Met Ala Leu Asn Ile Ile His
        515                 520                 525

Tyr Met His Asp Lys Tyr Ala Tyr Glu Ser Ile Glu Met Ala Leu His
    530                 535                 540

Asp Lys Glu Val Tyr Arg Thr Leu Gly Cys Gly Met Ser Gly Leu Ser
545                 550                 555                 560

Ile Ala Ala Asp Ser Leu Ala Ala Val Lys Tyr Ala Lys Val Tyr Pro
                565                 570                 575

Ile Tyr Asn Lys Asp Ala Lys Thr Leu Glu Gly His Glu Tyr Glu Tyr
            580                 585                 590

Val Glu Gly Ala Asp Asp Asp Leu Ile Val Gly Tyr Arg Thr Glu Gly
        595                 600                 605

Glu Phe Pro Val Tyr Gly Asn Asp Asp Asp Arg Ala Asp Asp Ile Ala
    610                 615                 620

Lys Trp Val Val Ser Thr Val Met Gly Gln Val Lys Arg Leu Pro Val
625                 630                 635                 640

Tyr Arg Gly Ala Val Pro Thr Gln Ser Ile Leu Thr Ile Thr Ser Asn
                645                 650                 655

Val Glu Tyr Gly Lys Asn Thr Gly Ser Phe Pro Ser Gly His Ala Lys
            660                 665                 670

Gly Thr Pro Tyr Ala Pro Gly Ala Asn Pro Glu Asn Gly Met Asp Ser
        675                 680                 685

His Gly Met Leu Pro Ser Met Phe Ser Val Gly Lys Ile Asp Tyr Asn
    690                 695                 700

Asp Ala Leu Asp Gly Ile Ser Leu Thr Asn Thr Ile Thr Pro Asp Gly
705                 710                 715                 720

Leu Gly Arg Asp Glu Asp Glu Arg Ile Gly Asn Leu Val Gly Ile Leu
                725                 730                 735

Asp Ala Gly Asn Gly His Gly Leu Tyr His Ala Asn Ile Asn Val Leu
            740                 745                 750

Arg Lys Glu Thr Met Glu Asp Ala Val Glu His Pro Glu Lys Tyr Pro
        755                 760                 765

His Leu Thr Val Arg Val Ser Gly Tyr Ala Val Asn Phe Val Lys Leu
    770                 775                 780

Thr Lys Glu Gln Gln Leu Asp Val Ile Ser Arg Thr Phe His Gln Gly
785                 790                 795                 800

Ala Val Val Asp
```

<210> SEQ ID NO 63
<211> LENGTH: 2376
<212> TYPE: DNA

<213> ORGANISM: Bifidobacterium longum
<220> FEATURE:
<221> NAME/KEY: misc_feature
<223> OTHER INFORMATION: DJO10A

<400> SEQUENCE: 63
atgaccgcag tggaaaatgc agctgtctcc caggaggagc tcgacgccaa ggcgtgggcc 60
ggcttcaccg agggcaactg gcagaaggat attgacgtcc gcgacttcat ccagaagaac 120
tacaccccgt acgagggcga cgagacattc ctggctcctg ccaccgagaa gaccaagcac 180
ctgtggaagt acctcgacga caactacctg gccgtggagc gcaagcagcg cgtctacgac 240
gtggacaccc ataccccggc cgacgtcgac gccttcccgg ccggctacat cgactccccg 300
gaagtcgata acgtggtcgt tggcctccag accgacgttc cctgcaagcg cgcgatgatg 360
ccgaacggtg gctggcgcat ggtcgagcag gccatcaagg aagccggcaa ggaaccggat 420
ccggagatca agaagatctt caccaagtac cgcaagaccc acaacgacgg cgtcttcggc 480
gtgtacacca agcagatcaa ggtcgcccgc cacaacaaga tcctcaccgg tctgccggac 540
gcctacggcc gtggccgcat catcggcgac taccgccgcg tcgccctgta cggcgtgaac 600
aagctcatcg ccttcaagaa gcgcgacaag gactccgtgc cgtaccgcaa cgacttcacc 660
gagccggaga tcgagcactg gatccgcttc cgtgaggagc acgacgagca gatcaaggcc 720
ctgaagaagc tcatcaacct cggcaacgag tacggcctcg acctgtcccg cccggcccag 780
accgcgcagg aagccgtgca gtggacctac atgggctacc tggcctccat caagtcccag 840
gacggcgccg ccatgtcctt cggccgcaac tccgccttcc tcgactgcta catcgagcgc 900
gacctccagg ccggcaagat caccgagacc gacgcccagg agctcatcga caacatcgtc 960
atgaagctgc gcatcgtgcg cttcctgcgt accaaggact acgattcgat cttctccggc 1020
gacccgtact gggcgacctg gtccgacgcc ggcttcggcg atgacggccg ttcgatggtc 1080
accaagacct cgttccgtct gctcaacacc ctgaccctcg agcacctcgg acctggcccc 1140
gagccgaaca tcaccatctt ctgggatccg aagctgcctg aggcctacaa gcgcttctgc 1200
gccaagatct ccatcgacac ctcggccatc cagtacgagt ccgacaagga gattcgcagc 1260
cactggggcg acgacgctgc tatcgcctgc tgcgtgtccc cgatgcgtgt cggcaagcag 1320
atgcagttct tcgccgcccg cgtgaactcc gccaaggccc tgctgtacgc catcaacggc 1380
ggccgcgacg agatgaccgg catgcaggtc atcgacaagg gcgtgatcga gccgattacc 1440
ccggaggccg acggcaccct ggactacgag aaggtcaaga acaactacga gaaggctctc 1500
gagtggctgt ccgagaccta cgtcatggcc ctgaacatca tccactacat gcacgataag 1560
tacgcgtacg agtccatcga gatggccctg cacgacaagg aagtgtaccg caccctcggc 1620
tgcggcatgt ccggtctgtc catcgccgcc gactccctcg ccgccgtcaa gtacgccaag 1680
gtctacccga tctacaacaa ggacgcgaag accctggaag gccacgagta cgagtacgtt 1740
gagggcgccg acgacgacct gatcgtcggc taccgcaccg agggcgagtt cccggtctac 1800
ggcaacgacg acgaccgcgc cgacgacatc gccaagtggg tcgtctccac ggtcatgggc 1860
caggtcaaga ggctcccggt ctaccgcggc gccgtcccga cccagtccat cctgacgatc 1920
acctccaacg tcgagtacgg caagaacacc ggttccttcc cgtccggcca cgccaagggc 1980
accccgtacg ctccgggcgc caacccggag aacggcatgg actcccacgg catgctgccg 2040
tccatgttct ccgtcggcaa gatcgactac aacgacgctc ttgacggcat ctcgctgacc 2100
aacaccatca cccctgatgg cctgggccgc gacgaggacg agcgcatcgg caacctggtc 2160

```
ggcatcctgg acgccggcaa cggccacggc ctctaccacg cgaacatcaa cgttctgcgc   2220

aaggagacca tggaggacgc cgtcgagcac cccgaaaagt acccgcacct gaccgtgcgt   2280

gtctccggct acgcggtgaa cttcgtcaag ctcaccaagg agcagcagct cgacgtcatc   2340

tcccgtacct tccaccaggg tgccgtcgtc gactga                             2376


<210> SEQ ID NO 64
<211> LENGTH: 791
<212> TYPE: PRT
<213> ORGANISM: Bifidobacterium longum
<220> FEATURE:
<221> NAME/KEY: MISC_FEATURE
<223> OTHER INFORMATION: DJO10A

<400> SEQUENCE: 64

Met Thr Ala Val Glu Asn Ala Ala Val Ser Gln Glu Glu Leu Asp Ala
1               5                   10                  15

Lys Ala Trp Ala Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

Thr Phe Leu Ala Pro Ala Thr Glu Lys Thr Lys His Leu Trp Lys Tyr
    50                  55                  60

Leu Asp Asp Asn Tyr Leu Ala Val Glu Arg Lys Gln Arg Val Tyr Asp
65                  70                  75                  80

Val Asp Thr His Thr Pro Ala Asp Val Asp Ala Phe Pro Ala Gly Tyr
                85                  90                  95

Ile Asp Ser Pro Glu Val Asp Asn Val Val Val Gly Leu Gln Thr Asp
            100                 105                 110

Val Pro Cys Lys Arg Ala Met Met Pro Asn Gly Gly Trp Arg Met Val
        115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Lys Leu Ile Ala Phe Lys Lys Arg
        195                 200                 205

Asp Lys Asp Ser Val Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Lys Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Ile Lys Ser Gln Asp Gly Ala Ala Met Ser Phe Gly
        275                 280                 285

Arg Asn Ser Ala Phe Leu Asp Cys Tyr Ile Glu Arg Asp Leu Gln Ala
    290                 295                 300

Gly Lys Ile Thr Glu Thr Asp Ala Gln Glu Leu Ile Asp Asn Ile Val
305                 310                 315                 320
```

-continued

```
Met Lys Leu Arg Ile Val Arg Phe Leu Arg Thr Lys Asp Tyr Asp Ser
                325                 330                 335

Ile Phe Ser Gly Asp Pro Tyr Trp Ala Thr Trp Ser Asp Ala Gly Phe
            340                 345                 350

Gly Asp Asp Gly Arg Ser Met Val Thr Lys Thr Ser Phe Arg Leu Leu
        355                 360                 365

Asn Thr Leu Thr Leu Glu His Leu Gly Pro Gly Pro Glu Pro Asn Ile
    370                 375                 380

Thr Ile Phe Trp Asp Pro Lys Leu Pro Glu Ala Tyr Lys Arg Phe Cys
385                 390                 395                 400

Ala Lys Ile Ser Ile Asp Thr Ser Ala Ile Gln Tyr Glu Ser Asp Lys
                405                 410                 415

Glu Ile Arg Ser His Trp Gly Asp Asp Ala Ala Ile Ala Cys Cys Val
            420                 425                 430

Ser Pro Met Arg Val Gly Lys Gln Met Gln Phe Phe Ala Ala Arg Val
        435                 440                 445

Asn Ser Ala Lys Ala Leu Leu Tyr Ala Ile Asn Gly Gly Arg Asp Glu
    450                 455                 460

Met Thr Gly Met Gln Val Ile Asp Lys Gly Val Ile Glu Pro Ile Thr
465                 470                 475                 480

Pro Glu Ala Asp Gly Thr Leu Asp Tyr Glu Lys Val Lys Asn Asn Tyr
                485                 490                 495

Glu Lys Ala Leu Glu Trp Leu Ser Glu Thr Tyr Val Met Ala Leu Asn
            500                 505                 510

Ile Ile His Tyr Met His Asp Lys Tyr Ala Tyr Glu Ser Ile Glu Met
        515                 520                 525

Ala Leu His Asp Lys Glu Val Tyr Arg Thr Leu Gly Cys Gly Met Ser
    530                 535                 540

Gly Leu Ser Ile Ala Ala Asp Ser Leu Ala Ala Val Lys Tyr Ala Lys
545                 550                 555                 560

Val Tyr Pro Ile Tyr Asn Lys Asp Ala Lys Thr Leu Glu Gly His Glu
                565                 570                 575

Tyr Glu Tyr Val Glu Gly Ala Asp Asp Asp Leu Ile Val Gly Tyr Arg
            580                 585                 590

Thr Glu Gly Glu Phe Pro Val Tyr Gly Asn Asp Asp Asp Arg Ala Asp
        595                 600                 605

Asp Ile Ala Lys Trp Val Val Ser Thr Val Met Gly Gln Val Lys Arg
    610                 615                 620

Leu Pro Val Tyr Arg Gly Ala Val Pro Thr Gln Ser Ile Leu Thr Ile
625                 630                 635                 640

Thr Ser Asn Val Glu Tyr Gly Lys Asn Thr Gly Ser Phe Pro Ser Gly
                645                 650                 655

His Ala Lys Gly Thr Pro Tyr Ala Pro Gly Ala Asn Pro Glu Asn Gly
            660                 665                 670

Met Asp Ser His Gly Met Leu Pro Ser Met Phe Ser Val Gly Lys Ile
        675                 680                 685

Asp Tyr Asn Asp Ala Leu Asp Gly Ile Ser Leu Thr Asn Thr Ile Thr
    690                 695                 700

Pro Asp Gly Leu Gly Arg Asp Glu Asp Glu Arg Ile Gly Asn Leu Val
705                 710                 715                 720

Gly Ile Leu Asp Ala Gly Asn Gly His Gly Leu Tyr His Ala Asn Ile
                725                 730                 735

Asn Val Leu Arg Lys Glu Thr Met Glu Asp Ala Val Glu His Pro Glu
```

-continued

```
            740                 745                 750

Lys Tyr Pro His Leu Thr Val Arg Val Ser Gly Tyr Ala Val Asn Phe
        755                 760                 765

Val Lys Leu Thr Lys Glu Gln Gln Leu Asp Val Ile Ser Arg Thr Phe
    770                 775                 780

His Gln Gly Ala Val Val Asp
785                 790
```

<210> SEQ ID NO 65
<211> LENGTH: 2379
<212> TYPE: DNA
<213> ORGANISM: Bifidobacterium animalis
<220> FEATURE:
<221> NAME/KEY: misc_feature
<223> OTHER INFORMATION: DSM 10140

<400> SEQUENCE: 65

```
atgtcagcaa ttgaaaacgt ggccgaggtg tccccggaag ccatcaagga acaggcttgg     60

gaggggttcg ttcccggcaa ctgggagaag gacatcgacg ttcgtgactt cattcagaag    120

aactacacgc cttacgaggg tgatgaatcg ttcctcgcgg atgcgaccga caagacgaag    180

tacctgtgga agtacctcga cgacaactat ctggcggtgg agcgcaagca gcgtgtctat    240

gatgtggaca cccacacgcc ggcggatatc gacgccttcc cggctggcta tatcgattcc    300

ccggagatcg acaatgtgat cgtcggcctg cagaccgatg agccatgcaa gcgagccatg    360

atgccgaatg gcggttggcg catggtggag caggccatca aggaggccgg caaggagccg    420

gacccggcga tcaagaagat cttcaccaag taccgcaaga cgcataacga cggtgtgttc    480

ggcgtctata cgaagaacat caaagtggca cgccacaaca agattctcac cggcctgccg    540

gatgcctacg gccgcggccg catcatcggc gactaccgtc gtgtggccct gtatggcgtg    600

gatgcgctga ttaagttcaa gcagcgtgac aaggacgcca tcccgtaccg caacgacttc    660

tcggagaccg agatcgagca ctggatccgt taccgcgagg agcacgacga gcagattaag    720

gctctgaaga agctcatcaa cctaggcaag gaatacggac tcgatttggc gcgccccgcc    780

atgaacgcgc gtgaggccgt gcagtggacc tacatgggct acctcgcctc catcaagagc    840

caggacggcg ccgcgatgag cttcggccgc gtgtcagcgt tcttcgacat ctacttcgag    900

cgcgatctca aggaaggcaa gatcaccgag accgacgccc aggagatcat cgacaatctg    960

gtgatgaagc tgcgcatcgt gcgattcctg cgcaccaagg actacgattc gatcttctcg   1020

ggcgacccct actgggcgac atggtcggat gcaggcttcg gcgacgatgg ccgcaccatg   1080

gtcaccaaga cgtcgttccg tctgctcaac acgctcacgc tcgagcattt gggaccggga   1140

cccgaaccga acatcacgat tttctgggat ccgaagctgc cggaaggcta caagcgtttc   1200

tgcgcccaga tctccattga tacctcggcc atccagtatg aatccgacaa ggagatccgc   1260

aaccattggg gtgacgatgc ggccattgca tgctgcgtct ccccgatgcg tgtgggcaag   1320

caaatgcagt tcttcgcggc tcgcgtgaac tccgccaagg cgctgctcta cgcgatcaac   1380

ggcggccgtg acgagatgac cggcatgcag gtgatcgaca agggcatcat cgagccgatc   1440

cagcccgagg ctgacggcac gctcgattac gagaaggtga aggccaacta tgagaaggcc   1500

ctcgaatggc tttcggagac ctacgtcgaa gcgctgaaca tcattcatta catgcatgac   1560

aagtatgcgt atgagtccat cgagatggcg ctgcacgacc gcgaggtcta ccgcaccctg   1620

ggctgcggca tgtccggcct gtcgatcgcc gccgattcgc tttccgcatg caagtacgcc   1680

aaggtgtacc caatctacaa caaggacgcc aaggacatgc cgggtcacga gtacgaatat   1740
```

gtcgaaggcg cggacgacga tctggtggtc ggctaccgca ccgagggcga gttcccgctt 1800
tacggcaacg acgacgatcg tgccgatgac attgccaagt gggtcgtgtc caccgtcatg 1860
ggccaggtca agcgcctgcc ggtgtatcgt ggtgccgtcc ccacgcagtc gatcctcacg 1920
atcacctcga acgtcgagta tggcaagaac accggatcct tcccgtcggg ccacgccaag 1980
ggaacgccgt acgccccggg cgcgaacccg gagaacggca tggactccca tggcatgctc 2040
ccctcgatgt tctcggtggg caagatcgat tacaacgacg cccttgacgg catctcgctg 2100
acgaacacga tcacacccga cggcctgggc cgcgatgagg acgaacgcat cagcaacctc 2160
gtcggcatcc tcgacgcagg caacggccat ggactgtacc atgcgaacat caacgtgctg 2220
cgcaaggaac agctcgaaga cgccgtggag cacccggaga agtacccgca cctgaccgtg 2280
cgcgtctccg gttacgccgt gaacttcgtc aagcttacga aggaacagca gcttgacgtc 2340
atttcccgca ccttccatca gggcgcggtc gaggactaa 2379

<210> SEQ ID NO 66
<211> LENGTH: 792
<212> TYPE: PRT
<213> ORGANISM: Bifidobacterium animalis
<220> FEATURE:
<221> NAME/KEY: misc_feature
<223> OTHER INFORMATION: DSM 10140

<400> SEQUENCE: 66

Met Ser Ala Ile Glu Asn Val Ala Glu Val Ser Pro Glu Ala Ile Lys
1 5 10 15

Glu Gln Ala Trp Glu Gly Phe Val Pro Gly Asn Trp Glu Lys Asp Ile
20 25 30

Asp Val Arg Asp Phe Ile Gln Lys Asn Tyr Thr Pro Tyr Glu Gly Asp
35 40 45

Glu Ser Phe Leu Ala Asp Ala Thr Asp Lys Thr Lys Tyr Leu Trp Lys
50 55 60

Tyr Leu Asp Asp Asn Tyr Leu Ala Val Glu Arg Lys Gln Arg Val Tyr
65 70 75 80

Asp Val Asp Thr His Thr Pro Ala Asp Ile Asp Ala Phe Pro Ala Gly
85 90 95

Tyr Ile Asp Ser Pro Glu Ile Asp Asn Val Ile Val Gly Leu Gln Thr
100 105 110

Asp Glu Pro Cys Lys Arg Ala Met Met Pro Asn Gly Gly Trp Arg Met
115 120 125

Val Glu Gln Ala Ile Lys Glu Ala Gly Lys Glu Pro Asp Pro Ala Ile
130 135 140

Lys Lys Ile Phe Thr Lys Tyr Arg Lys Thr His Asn Asp Gly Val Phe
145 150 155 160

Gly Val Tyr Thr Lys Asn Ile Lys Val Ala Arg His Asn Lys Ile Leu
165 170 175

Thr Gly Leu Pro Asp Ala Tyr Gly Arg Gly Arg Ile Ile Gly Asp Tyr
180 185 190

Arg Arg Val Ala Leu Tyr Gly Val Asp Ala Leu Ile Lys Phe Lys Gln
195 200 205

Arg Asp Lys Asp Ala Ile Pro Tyr Arg Asn Asp Phe Ser Glu Thr Glu
210 215 220

Ile Glu His Trp Ile Arg Tyr Arg Glu Glu His Asp Glu Gln Ile Lys
225 230 235 240

-continued

```
Ala Leu Lys Lys Leu Ile Asn Leu Gly Lys Glu Tyr Gly Leu Asp Leu
                245                 250                 255

Ala Arg Pro Ala Met Asn Ala Arg Glu Ala Val Gln Trp Thr Tyr Met
            260                 265                 270

Gly Tyr Leu Ala Ser Ile Lys Ser Gln Asp Gly Ala Ala Met Ser Phe
        275                 280                 285

Gly Arg Val Ser Ala Phe Phe Asp Ile Tyr Phe Glu Arg Asp Leu Lys
    290                 295                 300

Glu Gly Lys Ile Thr Glu Thr Asp Ala Gln Glu Ile Ile Asp Asn Leu
305                 310                 315                 320

Val Met Lys Leu Arg Ile Val Arg Phe Leu Arg Thr Lys Asp Tyr Asp
                325                 330                 335

Ser Ile Phe Ser Gly Asp Pro Tyr Trp Ala Thr Trp Ser Asp Ala Gly
            340                 345                 350

Phe Gly Asp Asp Gly Arg Thr Met Val Thr Lys Thr Ser Phe Arg Leu
        355                 360                 365

Leu Asn Thr Leu Thr Leu Glu His Leu Gly Pro Gly Pro Glu Pro Asn
    370                 375                 380

Ile Thr Ile Phe Trp Asp Pro Lys Leu Pro Glu Gly Tyr Lys Arg Phe
385                 390                 395                 400

Cys Ala Gln Ile Ser Ile Asp Thr Ser Ala Ile Gln Tyr Glu Ser Asp
                405                 410                 415

Lys Glu Ile Arg Asn His Trp Gly Asp Asp Ala Ala Ile Ala Cys Cys
            420                 425                 430

Val Ser Pro Met Arg Val Gly Lys Gln Met Gln Phe Phe Ala Ala Arg
        435                 440                 445

Val Asn Ser Ala Lys Ala Leu Leu Tyr Ala Ile Asn Gly Gly Arg Asp
    450                 455                 460

Glu Met Thr Gly Met Gln Val Ile Asp Lys Gly Ile Ile Glu Pro Ile
465                 470                 475                 480

Gln Pro Glu Ala Asp Gly Thr Leu Asp Tyr Glu Lys Val Lys Ala Asn
                485                 490                 495

Tyr Glu Lys Ala Leu Glu Trp Leu Ser Glu Thr Tyr Val Glu Ala Leu
            500                 505                 510

Asn Ile Ile His Tyr Met His Asp Lys Tyr Ala Tyr Glu Ser Ile Glu
        515                 520                 525

Met Ala Leu His Asp Arg Glu Val Tyr Arg Thr Leu Gly Cys Gly Met
    530                 535                 540

Ser Gly Leu Ser Ile Ala Ala Asp Ser Leu Ser Ala Cys Lys Tyr Ala
545                 550                 555                 560

Lys Val Tyr Pro Ile Tyr Asn Lys Asp Ala Lys Asp Met Pro Gly His
                565                 570                 575

Glu Tyr Glu Tyr Val Glu Gly Ala Asp Asp Asp Leu Val Val Gly Tyr
            580                 585                 590

Arg Thr Glu Gly Glu Phe Pro Leu Tyr Gly Asn Asp Asp Asp Arg Ala
        595                 600                 605

Asp Asp Ile Ala Lys Trp Val Val Ser Thr Val Met Gly Gln Val Lys
    610                 615                 620

Arg Leu Pro Val Tyr Arg Gly Ala Val Pro Thr Gln Ser Ile Leu Thr
625                 630                 635                 640

Ile Thr Ser Asn Val Glu Tyr Gly Lys Asn Thr Gly Ser Phe Pro Ser
                645                 650                 655

Gly His Ala Lys Gly Thr Pro Tyr Ala Pro Gly Ala Asn Pro Glu Asn
```

```
            660                 665                 670

Gly Met Asp Ser His Gly Met Leu Pro Ser Met Phe Ser Val Gly Lys
        675                 680                 685

Ile Asp Tyr Asn Asp Ala Leu Asp Gly Ile Ser Leu Thr Asn Thr Ile
    690                 695                 700

Thr Pro Asp Gly Leu Gly Arg Asp Glu Asp Glu Arg Ile Ser Asn Leu
705                 710                 715                 720

Val Gly Ile Leu Asp Ala Gly Asn Gly His Gly Leu Tyr His Ala Asn
                725                 730                 735

Ile Asn Val Leu Arg Lys Glu Gln Leu Glu Asp Ala Val Glu His Pro
            740                 745                 750

Glu Lys Tyr Pro His Leu Thr Val Arg Val Ser Gly Tyr Ala Val Asn
        755                 760                 765

Phe Val Lys Leu Thr Lys Glu Gln Gln Leu Asp Val Ile Ser Arg Thr
    770                 775                 780

Phe His Gln Gly Ala Val Glu Asp
785                 790


<210> SEQ ID NO 67
<211> LENGTH: 2226
<212> TYPE: DNA
<213> ORGANISM: Clostridium cellulolyticum

<400> SEQUENCE: 67

atggatccat ggagatattt caaaaacgga aattggtccg aggaaataga tgtaagggat     60

tttattatta ataattatat accatataaa ggagatgatt ccttttttaaa aggccctact    120

gaaaagactc aaaaactctg gaaaaaagtc agtggtatcc ttgacgagga aagagagaac    180

ggaggagttc tcgatgttga taccaaaata atatcaacta tcacttcgca tgaacccgga    240

tatattgata aggatttgga aaagattgta ggattgcaga cggataaacc tctaaaaagg    300

ggtataatgc ctttcggtgg tatcaggatg gtagtaaagg gcggagaggc ctacggcaaa    360

aagattgacg aaagtgttgt aaagctattt actgaatata ggaagactca caatgacggt    420

gtttacgatg tctatactcc cgaaatgatg agggcgaaaa aagcaggtat tataaccggg    480

cttcctgatg catacggtag aggaagaata atcggtgatt acagaagagt tgcactgtat    540

ggggttgaca ggcttatcgg agataagcaa aaacaactta caagcctaga aatggattac    600

atggacagtg aaaccataca ggaaagggaa gaaagaaaaa gtcagataaa agctcttgag    660

tacttaaagc aaatggctga aatgtatggc tttgatattt caaggcctgc tgaaaccgca    720

caggaagcat ttcaatggtt gtatttcggt ttcctcggag cagtaaagga gcagaatggt    780

gcggctatga gtcttggaag agtttcaaca ttccttgata tttatataga aagggatatg    840

aaggagggga cacttaccga agaagaggca caggagcttg ttgaccattt tgttatgaag    900

cttagattag taagattcct gagaactcca gagtatgaga aactgttctc aggtgaccct    960

acatggataa ccgaaagcat tggaggtatg ggtcttgacg gacgtactct ggtaacgaag   1020

aattccttca gaatgctgca taccctattt aatctgggtc atgcacccga gcccaatatg   1080

acggtgcttt ggtcggtgca tctgcctgat ggctttaaga aatactgctc atatgtttct   1140

atcaatacaa gctctatcca atacgagagc gatgatataa tgaggtatta ttggggagac   1200

gactacggca tagcatgctg tgtttcagcc atgagaatag gaaagcagat gcagttcttc   1260

ggagcccgct gcaatatggc gaaagctttg ttgtatgcaa ttaacggggg gcgtgatgaa   1320

aaatcgggcg ttcaggtagg acctataatg caggctattg agactgaata tcttgattat   1380
```

```
gatgatgtaa taaagaggtt cgacgcagta ctaacatggg ttgcaagact ttacatcaac   1440

actctgaata taatacacta tatgcatgac aagtacgctt atgaaagact acagatggct   1500

ttgcacgaca aggacatatt aagaacaatg gcctgcggaa tagcaggatt atctgtagtt   1560

gcggattctc tgagtgcaat taaatatgca aaggtaaagg taataagaaa tgaagagggg   1620

cttgccgttg actatgacat agaaggtgat tatccgaaat ttggaaataa cgacgaccgt   1680

gtagacaata tagccgtaat gctggtaaaa agctttatgg agaagctgga aaagcagaga   1740

acctacaggc actctgttcc taccctttca atactgacta ttacatcaaa tgttgtatac   1800

ggagctaaga caggtaatac acctgacgga agaaaagcgg gagaaccctt cggaccgggt   1860

gcaaacccaa tgcacggaag agacttgaac ggtgcacttg cagttcttaa atccatttca   1920

aagctgcctt accagtttgc acaggacggt atatcataca ctttttcaat agtaccaaag   1980

gcacttggaa aagaggaaga tacaaggatc aacaaccttg tgtcactgct tgactcttac   2040

tttaaagaag gcggacatca cattaatatc aatgtatttg agagagaaat gctgctggat   2100

gcaatggatc atcctgaaaa gtacccacag ctcacaatca gggtatccgg ctatgcggta   2160

aactttataa aattgacgag ggaacagcag ctagatgtaa ttaacagaac gatacatgaa   2220

aatata                                                              2226
```

```
<210> SEQ ID NO 68
<211> LENGTH: 742
<212> TYPE: PRT
<213> ORGANISM: Clostridium cellulolyticum

<400> SEQUENCE: 68

Met Asp Pro Trp Arg Tyr Phe Lys Asn Gly Asn Trp Ser Glu Glu Ile
1               5                   10                  15

Asp Val Arg Asp Phe Ile Ile Asn Asn Tyr Ile Pro Tyr Lys Gly Asp
            20                  25                  30

Asp Ser Phe Leu Lys Gly Pro Thr Glu Lys Thr Gln Lys Leu Trp Lys
        35                  40                  45

Lys Val Ser Gly Ile Leu Asp Glu Glu Arg Glu Asn Gly Gly Val Leu
    50                  55                  60

Asp Val Asp Thr Lys Ile Ile Ser Thr Ile Thr Ser His Glu Pro Gly
65                  70                  75                  80

Tyr Ile Asp Lys Asp Leu Glu Lys Ile Val Gly Leu Gln Thr Asp Lys
                85                  90                  95

Pro Leu Lys Arg Gly Ile Met Pro Phe Gly Gly Ile Arg Met Val Val
            100                 105                 110

Lys Gly Gly Glu Ala Tyr Gly Lys Lys Ile Asp Glu Ser Val Val Lys
        115                 120                 125

Leu Phe Thr Glu Tyr Arg Lys Thr His Asn Asp Gly Val Tyr Asp Val
    130                 135                 140

Tyr Thr Pro Glu Met Met Arg Ala Lys Lys Ala Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Arg Leu Ile Gly Asp Lys Gln Lys Gln
            180                 185                 190

Leu Thr Ser Leu Glu Met Asp Tyr Met Asp Ser Glu Thr Ile Gln Glu
        195                 200                 205

Arg Glu Glu Arg Lys Ser Gln Ile Lys Ala Leu Glu Tyr Leu Lys Gln
```

```
    210                 215                 220

Met Ala Glu Met Tyr Gly Phe Asp Ile Ser Arg Pro Ala Glu Thr Ala
225                 230                 235                 240

Gln Glu Ala Phe Gln Trp Leu Tyr Phe Gly Phe Leu Gly Ala Val Lys
                245                 250                 255

Glu Gln Asn Gly Ala Ala Met Ser Leu Gly Arg Val Ser Thr Phe Leu
            260                 265                 270

Asp Ile Tyr Ile Glu Arg Asp Met Lys Glu Gly Thr Leu Thr Glu Glu
        275                 280                 285

Glu Ala Gln Glu Leu Val Asp His Phe Val Met Lys Leu Arg Leu Val
    290                 295                 300

Arg Phe Leu Arg Thr Pro Glu Tyr Glu Lys Leu Phe Ser Gly Asp Pro
305                 310                 315                 320

Thr Trp Ile Thr Glu Ser Ile Gly Gly Met Gly Leu Asp Gly Arg Thr
                325                 330                 335

Leu Val Thr Lys Asn Ser Phe Arg Met Leu His Thr Leu Phe Asn Leu
            340                 345                 350

Gly His Ala Pro Glu Pro Asn Met Thr Val Leu Trp Ser Val His Leu
        355                 360                 365

Pro Asp Gly Phe Lys Lys Tyr Cys Ser Tyr Val Ser Ile Asn Thr Ser
    370                 375                 380

Ser Ile Gln Tyr Glu Ser Asp Asp Ile Met Arg Tyr Tyr Trp Gly Asp
385                 390                 395                 400

Asp Tyr Gly Ile Ala Cys Cys Val Ser Ala Met Arg Ile Gly Lys Gln
                405                 410                 415

Met Gln Phe Phe Gly Ala Arg Cys Asn Met Ala Lys Ala Leu Leu Tyr
            420                 425                 430

Ala Ile Asn Gly Gly Arg Asp Glu Lys Ser Gly Val Gln Val Gly Pro
        435                 440                 445

Ile Met Gln Ala Ile Glu Thr Glu Tyr Leu Asp Tyr Asp Asp Val Ile
    450                 455                 460

Lys Arg Phe Asp Ala Val Leu Thr Trp Val Ala Arg Leu Tyr Ile Asn
465                 470                 475                 480

Thr Leu Asn Ile Ile His Tyr Met His Asp Lys Tyr Ala Tyr Glu Arg
                485                 490                 495

Leu Gln Met Ala Leu His Asp Lys Asp Ile Leu Arg Thr Met Ala Cys
            500                 505                 510

Gly Ile Ala Gly Leu Ser Val Val Ala Asp Ser Leu Ser Ala Ile Lys
        515                 520                 525

Tyr Ala Lys Val Lys Val Ile Arg Asn Glu Glu Gly Leu Ala Val Asp
    530                 535                 540

Tyr Asp Ile Glu Gly Asp Tyr Pro Lys Phe Gly Asn Asn Asp Asp Arg
545                 550                 555                 560

Val Asp Asn Ile Ala Val Met Leu Val Lys Ser Phe Met Glu Lys Leu
                565                 570                 575

Glu Lys Gln Arg Thr Tyr Arg His Ser Val Pro Thr Leu Ser Ile Leu
            580                 585                 590

Thr Ile Thr Ser Asn Val Val Tyr Gly Ala Lys Thr Gly Asn Thr Pro
        595                 600                 605

Asp Gly Arg Lys Ala Gly Glu Pro Phe Gly Pro Gly Ala Asn Pro Met
    610                 615                 620

His Gly Arg Asp Leu Asn Gly Ala Leu Ala Val Leu Lys Ser Ile Ser
625                 630                 635                 640
```

```
Lys Leu Pro Tyr Gln Phe Ala Gln Asp Gly Ile Ser Tyr Thr Phe Ser
                645                 650                 655

Ile Val Pro Lys Ala Leu Gly Lys Glu Glu Asp Thr Arg Ile Asn Asn
            660                 665                 670

Leu Val Ser Leu Leu Asp Ser Tyr Phe Lys Glu Gly Gly His His Ile
        675                 680                 685

Asn Ile Asn Val Phe Glu Arg Glu Met Leu Leu Asp Ala Met Asp His
    690                 695                 700

Pro Glu Lys Tyr Pro Gln Leu Thr Ile Arg Val Ser Gly Tyr Ala Val
705                 710                 715                 720

Asn Phe Ile Lys Leu Thr Arg Glu Gln Gln Leu Asp Val Ile Asn Arg
                725                 730                 735

Thr Ile His Glu Asn Ile
            740


<210> SEQ ID NO 69
<211> LENGTH: 2283
<212> TYPE: DNA
<213> ORGANISM: Escherichia coli

<400> SEQUENCE: 69

atgtccgagc ttaatgaaaa gttagccaca gcctgggaag gttttaccaa aggtgactgg     60

cagaatgaag taaacgtccg tgacttcatt cagaaaaact acactccgta cgagggtgac    120

gagtccttcc tggctggcgc tactgaagcg accaccaccc tgtgggacaa agtaatggaa    180

ggcgttaaac tggaaaaccg cactcacgcg ccagttgact ttgacaccgc tgttgcttcc    240

accatcacct ctcacgacgc tggctacatc aacaagcagc ttgagaaaat cgttggtctg    300

cagactgaag ctccgctgaa acgtgctctt atcccgttcg gtggtatcaa aatgatcgaa    360

ggttcctgca aagcgtacaa ccgcgaactg gatccgatga tcaaaaaaat cttcactgaa    420

taccgtaaaa ctcacaacca gggcgtgttc gacgtttaca ctccggacat cctgcgttgc    480

cgtaaatctg gtgttctgac cggtctgcca gatgcatatg gccgtggccg tatcatcggt    540

gactaccgtc gcgttgcgct gtacggtatc gactacctga tgaaagacaa actggcacag    600

ttcacttctc tgcaggctga tctggaaaac ggcgtaaacc tggaacagac tatccgtctg    660

cgcgaagaaa tcgctgaaca gcaccgcgct ctgggtcaga tgaaagaaat ggctgcgaaa    720

tacggctacg acatctctgg tccggctacc aacgctcagg aagctatcca gtggacttac    780

ttcggctacc tggctgctgt taagtctcag aacggtgctg caatgtcctt cggtcgtacc    840

tccaccttcc tggatgtgta catcgaacgt gacctgaaag ctggcaagat caccgaacaa    900

gaagcgcagg aaatggttga ccacctggtc atgaaactgc gtatggttcg cttcctgcgt    960

actccggaat acgatgaact gttctctggc gacccgatct gggcaaccga atctatcggt   1020

ggtatgggcc tcgacggtcg taccctggtt accaaaaaca gcttccgttt cctgaacacc   1080

ctgtacacca tgggtccgtc tccggaaccg aacatgacca ttctgtggtc tgaaaaactg   1140

ccgctgaact tcaagaaatt cgccgctaaa gtgtccatcg acacctcttc tctgcagtat   1200

gagaacgatg acctgatgcg tccggacttc aacaacgatg actacgctat tgcttgctgc   1260

gtaagcccga tgatcgttgg taaacaaatg cagttcttcg gtgcgcgtgc aaacctggcg   1320

aaaaccatgc tgtacgcaat caacggcggc gttgacgaaa aactgaaaat gcaggttggt   1380

ccgaagtctg aaccgatcaa aggcgatgtc ctgaactatg atgaagtgat ggagcgcatg   1440

gatcacttca tggactggct ggctaaacag tacatcactg cactgaacat catccactac   1500
```

```
atgcacgaca agtacagcta cgaagcctct ctgatggcgc tgcacgaccg tgacgttatc   1560

cgcaccatgg cgtgtggtat cgctggtctg tccgttgctg ctgactccct gtctgcaatc   1620

aaatatgcga aagttaaacc gattcgtgac gaagacggtc tggctatcga cttcgaaatc   1680

gaaggcgaat acccgcagtt tggtaacaat gatccgcgtg tagatgacct ggctgttgac   1740

ctggtagaac gtttcatgaa gaaaattcag aaactgcaca cctaccgtga cgctatcccg   1800

actcagtctg ttctgaccat cacttctaac gttgtgtatg gtaagaaaac gggtaacacc   1860

ccagacggtc gtcgtgctgg cgcgccgttc ggaccgggtg ctaacccgat gcacggtcgt   1920

gaccagaaag gtgcagtagc ctctctgact tccgttgcta aactgccgtt tgcttacgct   1980

aaagatggta tctcctacac cttctctatc gttccgaacg cactgggtaa agacgacgaa   2040

gttcgtaaga ccaacctggc tggtctgatg gatggttact tccaccacga agcatccatc   2100

gaaggtggtc agcacctgaa cgttaacgtg atgaaccgtg aaatgctgct cgacgcgatg   2160

gaaaacccgg aaaaatatcc gcagctgacc atccgtgtat ctggctacgc agtacgtttc   2220

aactcgctga ctaaagaaca gcagcaggac gttattactc gtaccttcac tcaatctatg   2280

taa                                                                 2283
```

<210> SEQ ID NO 70
<211> LENGTH: 760
<212> TYPE: PRT
<213> ORGANISM: Escherichia coli

<400> SEQUENCE: 70

```
Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220
```

-continued

```
Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
    370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
    450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
    610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
```

```
                645                 650                 655

Phe Ala Tyr Ala Lys Asp Gly Ile Ser Tyr Thr Phe Ser Ile Val Pro
            660                 665                 670

Asn Ala Leu Gly Lys Asp Asp Glu Val Arg Lys Thr Asn Leu Ala Gly
        675                 680                 685

Leu Met Asp Gly Tyr Phe His His Glu Ala Ser Ile Glu Gly Gly Gln
    690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
        755                 760


<210> SEQ ID NO 71
<211> LENGTH: 594
<212> TYPE: DNA
<213> ORGANISM: Chlamydomonas reinhardtii
<220> FEATURE:
<221> NAME/KEY: misc_feature
<223> OTHER INFORMATION: PflA1

<400> SEQUENCE: 71

atgttgaagg ctgcgttgcc acgaattatg aacgctgcta gcatgtcttg tgcagctact      60

gggctgcagc gctccggtcc gctggcgatg aacgctgcga ctacatcgcg aacggggccc     120

gcttcagggc ttccgaaaca ttcctggggt gccagtgctc gacgagcatt tgttgcacct     180

gccactatct cggaacggct gcagccgaag ctctcgacga attactcggt ggttctgccg     240

caatacgagc ccacggatcc ctcgggcatc cctgaggttt tcggaaacgt gcattcaaca     300

gaaagcatga gcgcggtgga cggccctggc gtacggtggt ccgcaactac ctcaagccac     360

gcggcggcat caccatcagc ggcggcgagg ccatgctgca gccacacttt gtgtccaccg     420

tgttccaggt tccagggcat tgagctgctg ccgtaccacg tgttgggccg caacaagtgg     480

gaggtcatgg ggctgccgta ccccctggac ggcacgaaca cgccgccgca cgagcaggta     540

cgggccgtga tcaaggtgtt caacgacaac gacgttcccg tcatctgcgc cgag           594


<210> SEQ ID NO 72
<211> LENGTH: 198
<212> TYPE: PRT
<213> ORGANISM: Chlamydomonas reinhardtii
<220> FEATURE:
<221> NAME/KEY: MISC_FEATURE
<223> OTHER INFORMATION: PflA1

<400> SEQUENCE: 72

Met Leu Lys Ala Ala Leu Pro Arg Ile Met Asn Ala Ala Ser Met Ser
1               5                   10                  15

Cys Ala Ala Thr Gly Leu Gln Arg Ser Gly Pro Leu Ala Met Asn Ala
            20                  25                  30

Ala Thr Thr Ser Arg Thr Gly Pro Ala Ser Gly Leu Pro Lys His Ser
        35                  40                  45

Trp Gly Ala Ser Ala Arg Arg Ala Phe Val Ala Pro Ala Thr Ile Ser
    50                  55                  60

Glu Arg Leu Gln Pro Lys Leu Ser Thr Asn Tyr Ser Val Val Leu Pro
65                  70                  75                  80
```

```
Gln Tyr Glu Pro Thr Asp Pro Ser Gly Ile Pro Glu Val Phe Gly Asn
                85                  90                  95

Val His Ser Thr Glu Ser Met Ser Ala Val Asp Gly Pro Gly Val Arg
            100                 105                 110

Trp Ser Ala Thr Thr Ser Ser His Ala Ala Ala Ser Pro Ser Ala Ala
        115                 120                 125

Ala Arg Pro Cys Cys Ser His Thr Leu Cys Pro Pro Cys Ser Arg Phe
    130                 135                 140

Gln Gly Ile Glu Leu Leu Pro Tyr His Val Leu Gly Arg Asn Lys Trp
145                 150                 155                 160

Glu Val Met Gly Leu Pro Tyr Pro Leu Asp Gly Thr Asn Thr Pro Pro
                165                 170                 175

His Glu Gln Val Arg Ala Val Ile Lys Val Phe Asn Asp Asn Asp Val
            180                 185                 190

Pro Val Ile Cys Ala Glu
        195


<210> SEQ ID NO 73
<211> LENGTH: 801
<212> TYPE: DNA
<213> ORGANISM: Neocallimastix frontalis

<400> SEQUENCE: 73

atgccagcta tcgttgatcc aactactatg gattatatgg aagtcaaggg caatgtccat      60

tcaactgaaa gtttggcttg tcttgaaggt ccaggaaaca gattcctttt atttttaaat     120

ggttgtgctg ctcgttgctt atactgtagt aatccagata cttgggatga aactgttggt     180

actccaatga ccgttggcca acttattaag aagattggaa atcttaaaaa ctactatatc     240

aattctgttg gtggtggtgg tgtcactgtt tctggtggtg aaccattaac tcaatttggt     300

ttcttatctt gtttcttata tgctgtcaag aagcacttaa atcttcatac ctgtgttgaa     360

accactggtc aaggttgtac taaggcttgg aattcagttt tacctcatac tgacttatgc     420

ttagtatgta ttaaacatgc tattccagaa aaatacgaac aaattactcg tactaagaaa     480

ttagatagat gtcttaagtt ccttaaggaa ttagaaaaga gaaacattcc atggtggtgt     540

cgttacgttg ttcttccagg ttacactgat tctaaggaag atattgaagc tttaattgaa     600

ttagttaaga acagtccaac ttgtgaaaga attgaattcc ttccataccc cgaattaggt     660

aaaaacaaat gggaagaatt aggtattgaa tatccattaa agaatattaa acaacttaag     720

aaaagtgaaa ttaaatggat ctgtgatatg gtccgtgaag ctttcaagga ccgtaatatt     780

ccagttactg gtgatactta a                                               801


<210> SEQ ID NO 74
<211> LENGTH: 266
<212> TYPE: PRT
<213> ORGANISM: Neocallimastix frontalis

<400> SEQUENCE: 74

Met Pro Ala Ile Val Asp Pro Thr Thr Met Asp Tyr Met Glu Val Lys
1               5                   10                  15

Gly Asn Val His Ser Thr Glu Ser Leu Ala Cys Leu Glu Gly Pro Gly
            20                  25                  30

Asn Arg Phe Leu Leu Phe Leu Asn Gly Cys Ala Ala Arg Cys Leu Tyr
        35                  40                  45

Cys Ser Asn Pro Asp Thr Trp Asp Glu Thr Val Gly Thr Pro Met Thr
```

```
    50                  55                  60

Val Gly Gln Leu Ile Lys Lys Ile Gly Asn Leu Lys Asn Tyr Tyr Ile
65                  70                  75                  80

Asn Ser Val Gly Gly Gly Gly Val Thr Val Ser Gly Gly Glu Pro Leu
                85                  90                  95

Thr Gln Phe Gly Phe Leu Ser Cys Phe Leu Tyr Ala Val Lys Lys His
            100                 105                 110

Leu Asn Leu His Thr Cys Val Glu Thr Thr Gly Gln Gly Cys Thr Lys
        115                 120                 125

Ala Trp Asn Ser Val Leu Pro His Thr Asp Leu Cys Leu Val Cys Ile
    130                 135                 140

Lys His Ala Ile Pro Glu Lys Tyr Glu Gln Ile Thr Arg Thr Lys Lys
145                 150                 155                 160

Leu Asp Arg Cys Leu Lys Phe Leu Lys Glu Leu Glu Lys Arg Asn Ile
                165                 170                 175

Pro Trp Trp Cys Arg Tyr Val Val Leu Pro Gly Tyr Thr Asp Ser Lys
            180                 185                 190

Glu Asp Ile Glu Ala Leu Ile Glu Leu Val Lys Asn Ser Pro Thr Cys
        195                 200                 205

Glu Arg Ile Glu Phe Leu Pro Tyr Pro Glu Leu Gly Lys Asn Lys Trp
    210                 215                 220

Glu Glu Leu Gly Ile Glu Tyr Pro Leu Lys Asn Ile Lys Gln Leu Lys
225                 230                 235                 240

Lys Ser Glu Ile Lys Trp Ile Cys Asp Met Val Arg Glu Ala Phe Lys
                245                 250                 255

Asp Arg Asn Ile Pro Val Thr Gly Asp Thr
            260                 265
```

<210> SEQ ID NO 75
<211> LENGTH: 2496
<212> TYPE: DNA
<213> ORGANISM: Chlamydomonas reinhardtii
<220> FEATURE:
<221> NAME/KEY: misc_feature
<223> OTHER INFORMATION: PflA

<400> SEQUENCE: 75

```
atgttaacac ccttaagcta tcctatcatc aacaccgtct cgtcaagtct gccagcgctt      60

cacgccatga gccagatgct gctggagaag acaatgcgcc ggggcctcgc cacggtctcg     120

gccgcagcga gctccgctgt tggccggccc atccccatgg ctgttaggtc gccgatgcgc     180

tcgatggccg ctgccagcgc ggccgctgag gccctcccgg tggcacccag ccacagctgc     240

gctgctgacc ccgacaagca cccgcacctg cccgaccccc gcccgaagcc ggccgtggac     300

gcgggcatca acgtccagaa gtatgtgcag gacaactaca ccgcttacgc cggcaactcg     360

tccttcctgg ctggccccac tgacaacacc aagaagctgt ggagcgagct ggagaagatg     420

attgccaccg agatcgagaa gggcgtgatg gacgtggatc cctccaagcc ctccaccatc     480

accgccttcc cgcccggcta catcgacaag gacctggaga cggtggtggg gctgcagacc     540

gacgcgccgc tcaagcgcgc catcaagccc ctgggcggcg tcaacatggt caaggcggcg     600

ctggagtcgt acggctacac ccccgacccc gaggtggccc gcctgtacag cacggtgcgc     660

aagacgcaca acagcggcgt gtttgacgcc tacacggacg agatgcgcgc cgcgcgcaag     720

agcggcatcc tgtccggcct gcccgacggc tacggccgcg gccgcatcat cggcgactac     780

cgccgcgtgg cgctgtacgg cgtggacgcg ctgatcaagg ccaagaagac cgacctgaag     840
```

```
cacaacctgc tgggcgtgat ggacgaggag aagatccgcc tgcgcgagga ggtgaacgag    900
cagatccgcg cgctcagcga gctcaaggag atgggcgccg cctacggctt cgacctgagc    960
cgccccgccg ccaactcgcg cgaggcggtg cagtggctgt acttcggcta cctgggcgcc   1020
gtcaaggagc aggacggcgc cgccatgagc ctgggccgca tcgacgcctt cctggacacc   1080
tactttgagc gcgacctcaa ggccggcacc atcactgagg ccgaggtgca ggagctgatc   1140
gaccacttcg tcatgaagct gcgcatcgtg cgccagctgc gcacgcccga gtacaacgcg   1200
ctgtttgccg gcgaccccac ctgggtcacc tgcgtgctgg gcggcactga cgccagcggc   1260
aaggccatgg tcaccaagac cagcttccgc ctgctcaaca ccctgtacaa cctgggcccc   1320
gcgcccgagc ccaacctgac ggtgctgtgg aacgacaacc tgcccgcgcc cttcaaggag   1380
ttctgcgcca aggtgtcgct ggacaccagc tccatccagt acgagtccga caacctcatg   1440
agcaagctgt ttggctccga ctactccatc gcctgctgcg tgtcggccat gcgcgtgggc   1500
aaggacatgc agtactttgg cgcccgcgcc aacctgccca agctgctgct gtacacgctc   1560
aacggcggcc gcgacgaggt gtcgggcgac caggtggggc ccaagttcgc gccggtgcgc   1620
agccccaccg cgccgttgga ctatgaggag gtcaaggcca agatcgagga cggcatggag   1680
tggctggcct ccatgtacgc gaacaccatg aacatcatcc actacatgca cgacaagtac   1740
gactacgagc ggctgcagat ggcgctgcac gacacgcacg tgcgccgcct gctggcgttc   1800
ggcatcagcg gcctgtccgt ggtgaccgac tcgctgtcgg ccatcaagta cgcccaggtg   1860
acgcccgtga ttgacgagcg cggcctcatg acggacttca aggtggaggg cagcttcccc   1920
aagtacggca acgacgatga ccgcgtggac gagatcgccg agtgggtggt gtccaccttc   1980
tccagcaagc tggccaagca gcacacctac cgcaactcgg tgcccacgct gtcggtgctg   2040
accatcacct ccaacgtggt gtacggcaag aagacgggct ccacccccga cggccgcaag   2100
aagggcgagc ccttcgcgcc cggcgccaac ccgctgcacg gccgcgacgc ccacggcgct   2160
ctggcctcgc tcaactcggt ggccaagctg ccctacacca tgtgcctgga cggcatctcc   2220
aacaccttct cgctcatccc ccaggtgctg ggcaggggcg gcgagcacga gcgcgccacc   2280
aacctggcct ccatcctgga cggctacttt gccaacggcg gccaccacat caacgtcaac   2340
gtgctcaacc gctccatgct catggacgcc gtggagcacc ccgagaagta ccccaacctc   2400
accatccgcg tgtccgggta cgctgtgcac ttcgcgcgcc tcacgcgcga gcagcagctg   2460
gaggtgatcg cgcgcacctt ccacgacacc atgtaa                             2496
```

```
<210> SEQ ID NO 76
<211> LENGTH: 831
<212> TYPE: PRT
<213> ORGANISM: Chlamydomonas reinhardtii
<220> FEATURE:
<221> NAME/KEY: MISC_FEATURE
<223> OTHER INFORMATION: PflA

<400> SEQUENCE: 76

Met Leu Thr Pro Leu Ser Tyr Pro Ile Ile Asn Thr Val Ser Ser Ser
1               5                   10                  15

Leu Pro Ala Leu His Ala Met Ser Gln Met Leu Leu Glu Lys Thr Met
            20                  25                  30

Arg Arg Gly Leu Ala Thr Val Ser Ala Ala Ala Ser Ser Ala Val Gly
        35                  40                  45

Arg Pro Ile Pro Met Ala Val Arg Ser Pro Met Arg Ser Met Ala Ala
    50                  55                  60
```

```
Ala Ser Ala Ala Ala Glu Ala Leu Pro Val Ala Pro Ser His Ser Cys
65                  70                  75                  80

Ala Ala Asp Pro Asp Lys His Pro His Leu Pro Asp Pro Arg Pro Lys
                85                  90                  95

Pro Ala Val Asp Ala Gly Ile Asn Val Gln Lys Tyr Val Gln Asp Asn
            100                 105                 110

Tyr Thr Ala Tyr Ala Gly Asn Ser Ser Phe Leu Ala Gly Pro Thr Asp
        115                 120                 125

Asn Thr Lys Lys Leu Trp Ser Glu Leu Glu Lys Met Ile Ala Thr Glu
    130                 135                 140

Ile Glu Lys Gly Val Met Asp Val Asp Pro Ser Lys Pro Ser Thr Ile
145                 150                 155                 160

Thr Ala Phe Pro Pro Gly Tyr Ile Asp Lys Asp Leu Glu Thr Val Val
                165                 170                 175

Gly Leu Gln Thr Asp Ala Pro Leu Lys Arg Ala Ile Lys Pro Leu Gly
            180                 185                 190

Gly Val Asn Met Val Lys Ala Ala Leu Glu Ser Tyr Gly Tyr Thr Pro
        195                 200                 205

Asp Pro Glu Val Ala Arg Leu Tyr Ser Thr Val Arg Lys Thr His Asn
    210                 215                 220

Ser Gly Val Phe Asp Ala Tyr Thr Asp Glu Met Arg Ala Ala Arg Lys
225                 230                 235                 240

Ser Gly Ile Leu Ser Gly Leu Pro Asp Gly Tyr Gly Arg Gly Arg Ile
                245                 250                 255

Ile Gly Asp Tyr Arg Arg Val Ala Leu Tyr Gly Val Asp Ala Leu Ile
            260                 265                 270

Lys Ala Lys Lys Thr Asp Leu Lys His Asn Leu Leu Gly Val Met Asp
        275                 280                 285

Glu Glu Lys Ile Arg Leu Arg Glu Glu Val Asn Glu Gln Ile Arg Ala
    290                 295                 300

Leu Ser Glu Leu Lys Glu Met Gly Ala Ala Tyr Gly Phe Asp Leu Ser
305                 310                 315                 320

Arg Pro Ala Ala Asn Ser Arg Glu Ala Val Gln Trp Leu Tyr Phe Gly
                325                 330                 335

Tyr Leu Gly Ala Val Lys Glu Gln Asp Gly Ala Ala Met Ser Leu Gly
            340                 345                 350

Arg Ile Asp Ala Phe Leu Asp Thr Tyr Phe Glu Arg Asp Leu Lys Ala
        355                 360                 365

Gly Thr Ile Thr Glu Ala Glu Val Gln Glu Leu Ile Asp His Phe Val
    370                 375                 380

Met Lys Leu Arg Ile Val Arg Gln Leu Arg Thr Pro Glu Tyr Asn Ala
385                 390                 395                 400

Leu Phe Ala Gly Asp Pro Thr Trp Val Thr Cys Val Leu Gly Gly Thr
                405                 410                 415

Asp Ala Ser Gly Lys Ala Met Val Thr Lys Thr Ser Phe Arg Leu Leu
            420                 425                 430

Asn Thr Leu Tyr Asn Leu Gly Pro Ala Pro Glu Pro Asn Leu Thr Val
        435                 440                 445

Leu Trp Asn Asp Asn Leu Pro Ala Pro Phe Lys Glu Phe Cys Ala Lys
    450                 455                 460

Val Ser Leu Asp Thr Ser Ser Ile Gln Tyr Glu Ser Asp Asn Leu Met
465                 470                 475                 480
```

-continued

```
Ser Lys Leu Phe Gly Ser Asp Tyr Ser Ile Ala Cys Cys Val Ser Ala
                485                 490                 495

Met Arg Val Gly Lys Asp Met Gln Tyr Phe Gly Ala Arg Ala Asn Leu
            500                 505                 510

Pro Lys Leu Leu Leu Tyr Thr Leu Asn Gly Gly Arg Asp Glu Val Ser
        515                 520                 525

Gly Asp Gln Val Gly Pro Lys Phe Ala Pro Val Arg Ser Pro Thr Ala
    530                 535                 540

Pro Leu Asp Tyr Glu Glu Val Lys Ala Lys Ile Glu Asp Gly Met Glu
545                 550                 555                 560

Trp Leu Ala Ser Met Tyr Ala Asn Thr Met Asn Ile Ile His Tyr Met
                565                 570                 575

His Asp Lys Tyr Asp Tyr Glu Arg Leu Gln Met Ala Leu His Asp Thr
            580                 585                 590

His Val Arg Arg Leu Leu Ala Phe Gly Ile Ser Gly Leu Ser Val Val
        595                 600                 605

Thr Asp Ser Leu Ser Ala Ile Lys Tyr Ala Gln Val Thr Pro Val Ile
    610                 615                 620

Asp Glu Arg Gly Leu Met Thr Asp Phe Lys Val Glu Gly Ser Phe Pro
625                 630                 635                 640

Lys Tyr Gly Asn Asp Asp Asp Arg Val Asp Glu Ile Ala Glu Trp Val
                645                 650                 655

Val Ser Thr Phe Ser Ser Lys Leu Ala Lys Gln His Thr Tyr Arg Asn
            660                 665                 670

Ser Val Pro Thr Leu Ser Val Leu Thr Ile Thr Ser Asn Val Val Tyr
        675                 680                 685

Gly Lys Lys Thr Gly Ser Thr Pro Asp Gly Arg Lys Lys Gly Glu Pro
    690                 695                 700

Phe Ala Pro Gly Ala Asn Pro Leu His Gly Arg Asp Ala His Gly Ala
705                 710                 715                 720

Leu Ala Ser Leu Asn Ser Val Ala Lys Leu Pro Tyr Thr Met Cys Leu
                725                 730                 735

Asp Gly Ile Ser Asn Thr Phe Ser Leu Ile Pro Gln Val Leu Gly Arg
            740                 745                 750

Gly Gly Glu His Glu Arg Ala Thr Asn Leu Ala Ser Ile Leu Asp Gly
        755                 760                 765

Tyr Phe Ala Asn Gly Gly His His Ile Asn Val Asn Val Leu Asn Arg
    770                 775                 780

Ser Met Leu Met Asp Ala Val Glu His Pro Glu Lys Tyr Pro Asn Leu
785                 790                 795                 800

Thr Ile Arg Val Ser Gly Tyr Ala Val His Phe Ala Arg Leu Thr Arg
                805                 810                 815

Glu Gln Gln Leu Glu Val Ile Ala Arg Thr Phe His Asp Thr Met
            820                 825                 830
```

<210> SEQ ID NO 77
<211> LENGTH: 2418
<212> TYPE: DNA
<213> ORGANISM: Piromyces sp. E2

<400> SEQUENCE: 77

```
atggaaagct tagctttatc caatgtcagt gttcttgcta acactgtttc tgttaacgct      60

gttgctgcca ccaaggtcgc tggtgtcaga atggccaagc catcccgcgc tcttcacacc     120

ccagctatga agactactct taagacttct aagaaggtcc cagctatgca agctaagacc     180
```

```
tacgccactc aagctccatg catcaccaac gatgctgctg ccaagagtga aatcgatgtt    240
gaaggttgga ttaagaagca ctacacccca tacgaaggtg atggttcttt ccttgctggt    300
ccaactgaaa agaccaagaa gcttttcgcc aaggctgaag aatacttagc taaggaacgt    360
gccaacggtg gtttatacga tgttgaccca cacactccat ccaccatcac ttcccacaag    420
ccaggttacc ttgacaaaga taacgaagtt atctacggtt accaaactga tgttccactt    480
aagagagcca ttaagccatt cggtggtgtt aacatggtta agaacgctct taaggctgtt    540
aacgttccaa tggacaagga agtcgaacac attttcactg actaccgtaa gactcacaac    600
actgctgtct tcgatcttta ctccaaggaa atgagatctg gtcgttccaa cgctatcatg    660
accggtttac cagatggtta cggtcgtggt cgtattattg gtgattaccg tcgtgttgcc    720
ctttacggta ctgaccgtct tatcgcccaa aagaacaagg ataaggccga actccaaaag    780
agacaaatgg acgaaccaac catgaagctc attggtgaag ttgctgatca agttaaggct    840
cttaagcaac ttactcaaat ggccaagtcc tacggtattg atatctctaa gccagctaag    900
aacgccagag aagctactca atttgtttac tttggttact taggttctat caaggaacaa    960
gatggtgctg ccatgtctct tggtcgtgtt gatgccttcc ttgattgttt ctttgaaaac   1020
gatttaaaga acggtgttat cactgaagct gaagctcaag aaatcattga taaccttatc   1080
cttaagttac gtttcgctcg tcacttacgt accccagaat acaacgactt attcgctggt   1140
gatccaacct gggttactat gtctcttggt ggtatgggat ctgatggtcg taccttagtt   1200
actaagactt ccttccgtgt ccttaacact ctctacaact taggtccagc tccagaacca   1260
aacattactg tcctctggaa caaggctctt ccaaagaact tcaaggactt cgccactaag   1320
gtttctattg atacctcttc catccaatac gaatccgatg ctcttatgtc tgccagattc   1380
ggtgatgact acggtattgc ttgctgtgtc tctgccatga gaattggtaa ggatatgcaa   1440
ttcttcggtg ctcgttgtaa ccttgccaag cttatgcttt acgtccttaa ccacggtaag   1500
gatgaaagaa ctggtaagca agtcggtcca gactttggtc cagttccaga aggtccaatt   1560
ccattcgact ggatgtggga aacctatgac aaggctatgg actggattgc caagctctac   1620
gttaacacca tgaacgttat ccacttctgt cacgaccaat actgttacga atcccttcaa   1680
atggctcttc acgataccga tgtccgtcgt cttatggcct tcggtgttgc tggtctttcc   1740
gttgttgctg attccttctc tgctattaag tacgctaagg ttaccccagt ccgtgatgcc   1800
aagactggtt taactgttga cttcaagatt gaaggtgaat tcccaaaatt cggtaatgat   1860
gatgaccgtg ttgatttctt cgccagaact gttactgaca agcttatcaa caagctcaga   1920
aagaccccaa cctaccgtgg tgctactcac actctttcta ttcttaccat tacctctaac   1980
gtcgtttacg gtaagaagac tggttctact ccagatggtc gtaaggctgg tcaaccattc   2040
gctccaggtt gtaacccaat gcacggtcgt gaattctctg gtgccgttgc ttctctttct   2100
tctgtcgcta aggttaacta cgactcttgt atggatggta tctctaacac cttctctatt   2160
gttccaaaca ctattggtaa gtccttacaa gaacgtcaag gtaacctttc cggtttatta   2220
gatggttact tcaccaaggg tgcccaccac cttaacgtta acgttcttaa gcgtgaaacc   2280
ttagaagacg ccatggccca cccagaaaac tatccaaacc ttactattcg tgtctctggt   2340
tacgctgtca actttgttaa gttaactcca caacaacaaa aggaagttat tgcccgtacc   2400
ttccacgaaa agatgtaa                                                  2418
```

<210> SEQ ID NO 78

<211> LENGTH: 805
<212> TYPE: PRT
<213> ORGANISM: Piromyces sp. E2

<400> SEQUENCE: 78

```
Met Glu Ser Leu Ala Leu Ser Asn Val Ser Val Leu Ala Asn Thr Val
1               5                   10                  15

Ser Val Asn Ala Val Ala Ala Thr Lys Val Ala Gly Val Arg Met Ala
            20                  25                  30

Lys Pro Ser Arg Ala Leu His Thr Pro Ala Met Lys Thr Thr Leu Lys
        35                  40                  45

Thr Ser Lys Lys Val Pro Ala Met Gln Ala Lys Thr Tyr Ala Thr Gln
    50                  55                  60

Ala Pro Cys Ile Thr Asn Asp Ala Ala Ala Lys Ser Glu Ile Asp Val
65                  70                  75                  80

Glu Gly Trp Ile Lys Lys His Tyr Thr Pro Tyr Glu Gly Asp Gly Ser
                85                  90                  95

Phe Leu Ala Gly Pro Thr Glu Lys Thr Lys Lys Leu Phe Ala Lys Ala
            100                 105                 110

Glu Glu Tyr Leu Ala Lys Glu Arg Ala Asn Gly Gly Leu Tyr Asp Val
        115                 120                 125

Asp Pro His Thr Pro Ser Thr Ile Thr Ser His Lys Pro Gly Tyr Leu
    130                 135                 140

Asp Lys Asp Asn Glu Val Ile Tyr Gly Tyr Gln Thr Asp Val Pro Leu
145                 150                 155                 160

Lys Arg Ala Ile Lys Pro Phe Gly Gly Val Asn Met Val Lys Asn Ala
                165                 170                 175

Leu Lys Ala Val Asn Val Pro Met Asp Lys Glu Val Glu His Ile Phe
            180                 185                 190

Thr Asp Tyr Arg Lys Thr His Asn Thr Ala Val Phe Asp Leu Tyr Ser
        195                 200                 205

Lys Glu Met Arg Ser Gly Arg Ser Asn Ala Ile Met Thr Gly Leu Pro
    210                 215                 220

Asp Gly Tyr Gly Arg Gly Arg Ile Ile Gly Asp Tyr Arg Arg Val Ala
225                 230                 235                 240

Leu Tyr Gly Thr Asp Arg Leu Ile Ala Gln Lys Asn Lys Asp Lys Ala
                245                 250                 255

Glu Leu Gln Lys Arg Gln Met Asp Glu Pro Thr Met Lys Leu Ile Gly
            260                 265                 270

Glu Val Ala Asp Gln Val Lys Ala Leu Lys Gln Leu Thr Gln Met Ala
        275                 280                 285

Lys Ser Tyr Gly Ile Asp Ile Ser Lys Pro Ala Lys Asn Ala Arg Glu
    290                 295                 300

Ala Thr Gln Phe Val Tyr Phe Gly Tyr Leu Gly Ser Ile Lys Glu Gln
305                 310                 315                 320

Asp Gly Ala Ala Met Ser Leu Gly Arg Val Asp Ala Phe Leu Asp Cys
                325                 330                 335

Phe Phe Glu Asn Asp Leu Lys Asn Gly Val Ile Thr Glu Ala Glu Ala
            340                 345                 350

Gln Glu Ile Ile Asp Asn Leu Ile Leu Lys Leu Arg Phe Ala Arg His
        355                 360                 365

Leu Arg Thr Pro Glu Tyr Asn Asp Leu Phe Ala Gly Asp Pro Thr Trp
    370                 375                 380

Val Thr Met Ser Leu Gly Gly Met Gly Ser Asp Gly Arg Thr Leu Val
```

```
385                 390                 395                 400

Thr Lys Thr Ser Phe Arg Val Leu Asn Thr Leu Tyr Asn Leu Gly Pro
                405                 410                 415

Ala Pro Glu Pro Asn Ile Thr Val Leu Trp Asn Lys Ala Leu Pro Lys
            420                 425                 430

Asn Phe Lys Asp Phe Ala Thr Lys Val Ser Ile Asp Thr Ser Ser Ile
        435                 440                 445

Gln Tyr Glu Ser Asp Ala Leu Met Ser Ala Arg Phe Gly Asp Asp Tyr
    450                 455                 460

Gly Ile Ala Cys Cys Val Ser Ala Met Arg Ile Gly Lys Asp Met Gln
465                 470                 475                 480

Phe Phe Gly Ala Arg Cys Asn Leu Ala Lys Leu Met Leu Tyr Val Leu
                485                 490                 495

Asn His Gly Lys Asp Glu Arg Thr Gly Lys Gln Val Gly Pro Asp Phe
            500                 505                 510

Gly Pro Val Pro Glu Gly Pro Ile Pro Phe Asp Trp Met Trp Glu Thr
        515                 520                 525

Tyr Asp Lys Ala Met Asp Trp Ile Ala Lys Leu Tyr Val Asn Thr Met
    530                 535                 540

Asn Val Ile His Phe Cys His Asp Gln Tyr Cys Tyr Glu Ser Leu Gln
545                 550                 555                 560

Met Ala Leu His Asp Thr Asp Val Arg Arg Leu Met Ala Phe Gly Val
                565                 570                 575

Ala Gly Leu Ser Val Val Ala Asp Ser Phe Ser Ala Ile Lys Tyr Ala
            580                 585                 590

Lys Val Thr Pro Val Arg Asp Ala Lys Thr Gly Leu Thr Val Asp Phe
        595                 600                 605

Lys Ile Glu Gly Glu Phe Pro Lys Phe Gly Asn Asp Asp Asp Arg Val
    610                 615                 620

Asp Phe Phe Ala Arg Thr Val Thr Asp Lys Leu Ile Asn Lys Leu Arg
625                 630                 635                 640

Lys Thr Pro Thr Tyr Arg Gly Ala Thr His Thr Leu Ser Ile Leu Thr
                645                 650                 655

Ile Thr Ser Asn Val Val Tyr Gly Lys Lys Thr Gly Ser Thr Pro Asp
            660                 665                 670

Gly Arg Lys Ala Gly Gln Pro Phe Ala Pro Gly Cys Asn Pro Met His
        675                 680                 685

Gly Arg Glu Phe Ser Gly Ala Val Ala Ser Leu Ser Ser Val Ala Lys
    690                 695                 700

Val Asn Tyr Asp Ser Cys Met Asp Gly Ile Ser Asn Thr Phe Ser Ile
705                 710                 715                 720

Val Pro Asn Thr Ile Gly Lys Ser Leu Gln Glu Arg Gln Gly Asn Leu
                725                 730                 735

Ser Gly Leu Leu Asp Gly Tyr Phe Thr Lys Gly Ala His His Leu Asn
            740                 745                 750

Val Asn Val Leu Lys Arg Glu Thr Leu Glu Asp Ala Met Ala His Pro
        755                 760                 765

Glu Asn Tyr Pro Asn Leu Thr Ile Arg Val Ser Gly Tyr Ala Val Asn
    770                 775                 780

Phe Val Lys Leu Thr Pro Gln Gln Gln Lys Glu Val Ile Ala Arg Thr
785                 790                 795                 800

Phe His Glu Lys Met
                805
```

<210> SEQ ID NO 79
<211> LENGTH: 2414
<212> TYPE: DNA
<213> ORGANISM: Neocallimastix frontalis

<400> SEQUENCE: 79
gcttagcttt atccaacgtc agtgttcttg ctaacactgt ttctattaac gctgttgctg 60
ccaccaaggt cgctggtgtc agaatggcta aaccaactcg tgctcttcac actccagcta 120
tgaagactac tcttaaggct tccaagaagg ctgctgttcc agtcatgcaa gccaagacct 180
acgctactgc tccagttatc actaacgatg ctgctgccaa gagcgaaatc gatgtcgaag 240
gttggattaa gaagcactat actccatacg aaggtgatgg ttctttcctt gctggtccaa 300
ctgaaaagac taagaagctt ttcgccaagg ctgaagaata cttagccaag gaacgtgcta 360
acggtggttt atacgatgtt gacccacaca ctccatctac tattacctcc cacaagccag 420
gttaccttga caaagaaaac gaagttattt acggttacca aactgatgtt cctcttaaga 480
gagccatcaa gccattcggt ggtgttaaca tggttaagaa cgctcttaag gctgttaatg 540
ttccaatgga caaggaagtc gaacacattt tctctgacta ccgtaagact cacaacactg 600
ctgtcttcga tatctactct aaggaaatga gagctggtcg ttccaacgct atcatgactg 660
gtttaccaga tggttacggt cgtggtcgta ttattggtga ttaccgtcgt gttgcccttt 720
acggtactga ccgtcttatc gcccaaaagg aaaaagataa ggctgaactc caaaagaagc 780
aaatggacga accaaccatg aaattaattg gtgaagttgc tgaccaagtt aaggctctta 840
agcaacttac tcaaatggct aagtcctacg gtattgatat taccaagcca gccaagaacg 900
ccagagaagc tactcaattt gtttacttcg gttacttagg ttctatcaag gaacaagatg 960
gtgctgccat gtctcttggt cgtgttgatg ctttcttaga ttgtttcttt gaaaacgatt 1020
taaagaatgg tgttatcact gaatctgaag ctcaagaaat cattgataac cttatcttaa 1080
agttacgttt cgctcgtcac ttacgtactc cagaatacaa cgacttattc gctggtgatc 1140
caacctgggt tactatgtct cttggtggta tgggtagtga tggtcgtacc ttagttacta 1200
agacttcctt ccgtgttctt aacactcttt acaacttagg tccagctcca gaaccaaaca 1260
tcactgtcct ctggaacaag aaccttccaa agaacttcaa ggacttcgct actaaggttt 1320
ctattgatac ctcttccatt caatacgaat ctgatgccct tatgtccgct agattcggtg 1380
atgattacgg aattgcctgc tgtgtttctg ccatgagaat tggtaaggat atgcaattct 1440
tcggtgctcg ttgtaacctt gctaagctta tgctttacgt ccttaaccat ggtaaggatg 1500
aaagaactgg taagcaagtt ggtccagact tcggtccagt tccagaaggt ccaattccat 1560
tcgactggat gtgggaaact tatgacaagg ctatggattg gattgccaag ctttacgtta 1620
acaccatgaa cgttattcac ttctgtcacg accaatactg ttacgaatct cttcaaatgg 1680
ctcttcacga taccgatgtc cgtcgtctta tggccttcgg tgttgctggt ctttctgttg 1740
ttgctgattc cttctctgct attaagtacg ctaaggttac tccaatccgt gatccaaaga 1800
ccggtttaac tgttgacttc aaggttgaag gtgaattccc aaaattcggt aacgatgatg 1860
accgtgttga cttcttcgcc agaactgtta ctgacaagct tattaacaag ttaagaaaga 1920
ctccaaccta ccgtggtgct acccacactc tttctattct taccattacc tctaacgtcg 1980
tttacggtaa gaagaccggt tctactccag atggtcgtaa ggctggtcaa ccattcgccc 2040
caggttgtaa cccaatgcac ggtcgtgaat tctctggtgc cgttgcttct ctttcttccg 2100

```
ttgctaaggt taactacgat tcttgtatgg atggtatctc taacaccttc tctattgttc   2160

caaacactat cggtaagact ttacaagaac gtcaaggtaa cctttctggt ttattagatg   2220

gttacttcag caagggtgct caccatctta acgttaacgt tcttaagcgt gaaactttag   2280

aagatgccat ggctcaccca gaaaactatc caaaccttac tatccgtgtt tctggttatg   2340

ctgtcaactt cgttaagtta actccagccc aacaaaagga agttattgcc cgtaccttcc   2400

acgaaaagat gtaa                                                     2414


<210> SEQ ID NO 80
<211> LENGTH: 803
<212> TYPE: PRT
<213> ORGANISM: Neocallimastix frontalis

<400> SEQUENCE: 80

Leu Ala Leu Ser Asn Val Ser Val Leu Ala Asn Thr Val Ser Ile Asn
1               5                   10                  15

Ala Val Ala Ala Thr Lys Val Ala Gly Val Arg Met Ala Lys Pro Thr
            20                  25                  30

Arg Ala Leu His Thr Pro Ala Met Lys Thr Thr Leu Lys Ala Ser Lys
        35                  40                  45

Lys Ala Ala Val Pro Val Met Gln Ala Lys Thr Tyr Ala Thr Ala Pro
    50                  55                  60

Val Ile Thr Asn Asp Ala Ala Ala Lys Ser Glu Ile Asp Val Glu Gly
65                  70                  75                  80

Trp Ile Lys Lys His Tyr Thr Pro Tyr Glu Gly Asp Gly Ser Phe Leu
                85                  90                  95

Ala Gly Pro Thr Glu Lys Thr Lys Lys Leu Phe Ala Lys Ala Glu Glu
            100                 105                 110

Tyr Leu Ala Lys Glu Arg Ala Asn Gly Gly Leu Tyr Asp Val Asp Pro
        115                 120                 125

His Thr Pro Ser Thr Ile Thr Ser His Lys Pro Gly Tyr Leu Asp Lys
    130                 135                 140

Glu Asn Glu Val Ile Tyr Gly Tyr Gln Thr Asp Val Pro Leu Lys Arg
145                 150                 155                 160

Ala Ile Lys Pro Phe Gly Gly Val Asn Met Val Lys Asn Ala Leu Lys
                165                 170                 175

Ala Val Asn Val Pro Met Asp Lys Glu Val Glu His Ile Phe Ser Asp
            180                 185                 190

Tyr Arg Lys Thr His Asn Thr Ala Val Phe Asp Ile Tyr Ser Lys Glu
        195                 200                 205

Met Arg Ala Gly Arg Ser Asn Ala Ile Met Thr Gly Leu Pro Asp Gly
    210                 215                 220

Tyr Gly Arg Gly Arg Ile Ile Gly Asp Tyr Arg Arg Val Ala Leu Tyr
225                 230                 235                 240

Gly Thr Asp Arg Leu Ile Ala Gln Lys Glu Lys Asp Lys Ala Glu Leu
                245                 250                 255

Gln Lys Lys Gln Met Asp Glu Pro Thr Met Lys Leu Ile Gly Glu Val
            260                 265                 270

Ala Asp Gln Val Lys Ala Leu Lys Gln Leu Thr Gln Met Ala Lys Ser
        275                 280                 285

Tyr Gly Ile Asp Ile Thr Lys Pro Ala Lys Asn Ala Arg Glu Ala Thr
    290                 295                 300

Gln Phe Val Tyr Phe Gly Tyr Leu Gly Ser Ile Lys Glu Gln Asp Gly
305                 310                 315                 320
```

```
Ala Ala Met Ser Leu Gly Arg Val Asp Ala Phe Leu Asp Cys Phe Phe
                325                 330                 335

Glu Asn Asp Leu Lys Asn Gly Val Ile Thr Glu Ser Glu Ala Gln Glu
            340                 345                 350

Ile Ile Asp Asn Leu Ile Leu Lys Leu Arg Phe Ala Arg His Leu Arg
        355                 360                 365

Thr Pro Glu Tyr Asn Asp Leu Phe Ala Gly Asp Pro Thr Trp Val Thr
    370                 375                 380

Met Ser Leu Gly Gly Met Gly Ser Asp Gly Arg Thr Leu Val Thr Lys
385                 390                 395                 400

Thr Ser Phe Arg Val Leu Asn Thr Leu Tyr Asn Leu Gly Pro Ala Pro
                405                 410                 415

Glu Pro Asn Ile Thr Val Leu Trp Asn Lys Asn Leu Pro Lys Asn Phe
            420                 425                 430

Lys Asp Phe Ala Thr Lys Val Ser Ile Asp Thr Ser Ser Ile Gln Tyr
        435                 440                 445

Glu Ser Asp Ala Leu Met Ser Ala Arg Phe Gly Asp Asp Tyr Gly Ile
    450                 455                 460

Ala Cys Cys Val Ser Ala Met Arg Ile Gly Lys Asp Met Gln Phe Phe
465                 470                 475                 480

Gly Ala Arg Cys Asn Leu Ala Lys Leu Met Leu Tyr Val Leu Asn His
                485                 490                 495

Gly Lys Asp Glu Arg Thr Gly Lys Gln Val Gly Pro Asp Phe Gly Pro
            500                 505                 510

Val Pro Glu Gly Pro Ile Pro Phe Asp Trp Met Trp Glu Thr Tyr Asp
        515                 520                 525

Lys Ala Met Asp Trp Ile Ala Lys Leu Tyr Val Asn Thr Met Asn Val
    530                 535                 540

Ile His Phe Cys His Asp Gln Tyr Cys Tyr Glu Ser Leu Gln Met Ala
545                 550                 555                 560

Leu His Asp Thr Asp Val Arg Arg Leu Met Ala Phe Gly Val Ala Gly
                565                 570                 575

Leu Ser Val Val Ala Asp Ser Phe Ser Ala Ile Lys Tyr Ala Lys Val
            580                 585                 590

Thr Pro Ile Arg Asp Pro Lys Thr Gly Leu Thr Val Asp Phe Lys Val
        595                 600                 605

Glu Gly Glu Phe Pro Lys Phe Gly Asn Asp Asp Asp Arg Val Asp Phe
    610                 615                 620

Phe Ala Arg Thr Val Thr Asp Lys Leu Ile Asn Lys Leu Arg Lys Thr
625                 630                 635                 640

Pro Thr Tyr Arg Gly Ala Thr His Thr Leu Ser Ile Leu Thr Ile Thr
                645                 650                 655

Ser Asn Val Val Tyr Gly Lys Lys Thr Gly Ser Thr Pro Asp Gly Arg
            660                 665                 670

Lys Ala Gly Gln Pro Phe Ala Pro Gly Cys Asn Pro Met His Gly Arg
        675                 680                 685

Glu Phe Ser Gly Ala Val Ala Ser Leu Ser Ser Val Ala Lys Val Asn
    690                 695                 700

Tyr Asp Ser Cys Met Asp Gly Ile Ser Asn Thr Phe Ser Ile Val Pro
705                 710                 715                 720

Asn Thr Ile Gly Lys Thr Leu Gln Glu Arg Gln Gly Asn Leu Ser Gly
                725                 730                 735
```

Leu Leu Asp Gly Tyr Phe Ser Lys Gly Ala His His Leu Asn Val Asn
            740                 745                 750

Val Leu Lys Arg Glu Thr Leu Glu Asp Ala Met Ala His Pro Glu Asn
        755                 760                 765

Tyr Pro Asn Leu Thr Ile Arg Val Ser Gly Tyr Ala Val Asn Phe Val
    770                 775                 780

Lys Leu Thr Pro Ala Gln Gln Lys Glu Val Ile Ala Arg Thr Phe His
785                 790                 795                 800

Glu Lys Met

<210> SEQ ID NO 81
<211> LENGTH: 2619
<212> TYPE: DNA
<213> ORGANISM: Clostridium phytofermentans

<400> SEQUENCE: 81
atgacgaaaa aagtggaatt acagacaact ggattagtag actctctcga agcattaaca 60
gcaaaattta gagagttaaa agaagcacaa gagctctttg ctacctacac tcaagagcaa 120
gtagataaaa tcttctttgc tgctgccatg gctgccaatc agcaacgtat tccgttagca 180
aagatggctg tagaagaaac gggtatgggt attgtagaag ataaagtaat taagaatcat 240
tatgctgcag agtatattta caatgcatac aaagatacaa aaacatgtgg agtggttgaa 300
gaagatccta gcttcggtat caaaaaaatt gcagagccaa tcggcgtagt tgcagctgta 360
atcccaacta ccaatcctac ctccactgct atctttaaaa cattactttg tttaaagact 420
cgtaacgcaa tcatcatcag cccacatcct cgtgctaaga actgtaccat cgcagctgct 480
aaggtagttt tagatgctgc agttgctgca ggtgctcctg ctggtataat tggatggatt 540
gatgttccat cacttgaatt aaccaatgaa gttatgaaaa atgcagacat catccttgca 600
actggtggac ctggtatggt aaaggctgct tattcttctg gtaaaccagc acttggtgtt 660
ggcgcaggta ataccccctgt tattatggat gaaagctgcg atgttcgcct tgcagtaagc 720
tctattattc actctaagac atttgataac ggtatgattt gtgcttccga gcaatccgta 780
attattagtg ataagattta tgaagctgct aagaaagaat tcaaggatcg tggttgccac 840
atctgctccc cagaagagac tcagaagctt cgtgaaacaa tcctaattaa tggtgctctt 900
aacgctaaaa ttgttggaca aagcgctcat acgattgcaa agcttgcagg atttgatgta 960
gcagaagctg ctaagatttt aattggtgaa gtagaatccg ttgaactaga agaacaattt 1020
gcacacgaga aactttctcc agttcttgct atgtacaaat caaaatcctt tgatgatgca 1080
gtaagcaaag ctgctcgtct tgttgcagat ggcggttatg gccatacttc ttccatctat 1140
attaatgtag gtaccggaca agaaaagatt gcaaagtttt ctgatgctat gaagacttgc 1200
cgtattcttg taaatacacc atcctcccat ggtggtatcg gtgaccttta taactttaaa 1260
ttagctccat ctcttactct tggttgtggc tcctggggcg gtaactctgt atcagaaaac 1320
gtaggagtaa agcacttaat caacattaag acagttgctg agaggagaga aaacatgctt 1380
tggtttagag cacctgagaa agtatacttt aagaagggtt gtttaccagt agccctcgca 1440
gaattaaaag atgtaatgaa taaaaagaaa gtattcattg taaccgatgc tttcctttat 1500
aaaaatggct atacaaaatg tgttactgat cagttagatg ctatgggaat tcagcatact 1560
acttactatg atgttgctcc agatccatct ttagctagtg ctacagaagg tgcagaagcg 1620
atgagactct tcgagccaga ctgtattatc gcactcggtg gtggttctgc aatggatgcc 1680
ggaaagatta tgtgggttat gtatgaacac cctgaagtaa acttccttga ccttgcaatg 1740

```
cgtttcatgg atattagaaa gcgtgtttac tccttcccta agatgggcga aaaagcttac   1800

tttatcgcag ttccaacttc ctccggtact ggttctgaag ttacaccatt tgctgttatt   1860

accgatgaga gaactggcgt aaaatatcca cttgcagatt acgaattact tcctaagatg   1920

gctattattg atgccgatat gatgatgaat caacctaagg gattaacttc tgcttccggt   1980

attgatgccc ttacccatgc attagaggca tatgcttcta tcatggctac tgactatacg   2040

gatggtttag cattaaaagc tatgaagaat atcttcgctt accttccaag cgcatatgaa   2100

aatggtgccg ctgatccggt tgcaagagaa aagatggcag atgcttctac cttagctggt   2160

atggcattcg caaatgcatt cttaggaatt tgccactcca tggctcataa attaggtgca   2220

ttccaccact taccacacgg tgtagcaaac gcactcttaa tcaacgaagt aatgcgcttt   2280

aactccgtta gcattcctac aaagatgggt actttctctc aataccaata cccacatgcg   2340

ttagatcgtt atgtagaatg tgcgaacttc ttaggtattg ccggaaagaa cgacaatgag   2400

aaattcgaaa accttcttaa ggcaattgat gaattaaaag aaaaagttgg tatcaagaaa   2460

tccatcaaag aatatggcgt agacgagaaa tatttcttag atactttaga tgctatggtt   2520

gaacaggctt tcgatgatca gtgtactggt gctaacccaa gatatccatt aatgaaggaa   2580

atcaaggaaa tctatcttaa agtgtactac ggtaaataa                           2619
```

<210> SEQ ID NO 82
<211> LENGTH: 872
<212> TYPE: PRT
<213> ORGANISM: Clostridium phytofermentans

<400> SEQUENCE: 82

```
Met Thr Lys Lys Val Glu Leu Gln Thr Thr Gly Leu Val Asp Ser Leu
1               5                   10                  15

Glu Ala Leu Thr Ala Lys Phe Arg Glu Leu Lys Glu Ala Gln Glu Leu
            20                  25                  30

Phe Ala Thr Tyr Thr Gln Glu Gln Val Asp Lys Ile Phe Phe Ala Ala
        35                  40                  45

Ala Met Ala Ala Asn Gln Gln Arg Ile Pro Leu Ala Lys Met Ala Val
    50                  55                  60

Glu Glu Thr Gly Met Gly Ile Val Glu Asp Lys Val Ile Lys Asn His
65                  70                  75                  80

Tyr Ala Ala Glu Tyr Ile Tyr Asn Ala Tyr Lys Asp Thr Lys Thr Cys
                85                  90                  95

Gly Val Val Glu Glu Asp Pro Ser Phe Gly Ile Lys Lys Ile Ala Glu
            100                 105                 110

Pro Ile Gly Val Val Ala Ala Val Ile Pro Thr Thr Asn Pro Thr Ser
        115                 120                 125

Thr Ala Ile Phe Lys Thr Leu Leu Cys Leu Lys Thr Arg Asn Ala Ile
    130                 135                 140

Ile Ile Ser Pro His Pro Arg Ala Lys Asn Cys Thr Ile Ala Ala Ala
145                 150                 155                 160

Lys Val Val Leu Asp Ala Ala Val Ala Ala Gly Ala Pro Ala Gly Ile
                165                 170                 175

Ile Gly Trp Ile Asp Val Pro Ser Leu Glu Leu Thr Asn Glu Val Met
            180                 185                 190

Lys Asn Ala Asp Ile Ile Leu Ala Thr Gly Gly Pro Gly Met Val Lys
        195                 200                 205

Ala Ala Tyr Ser Ser Gly Lys Pro Ala Leu Gly Val Gly Ala Gly Asn
```

```
    210                 215                 220

Thr Pro Val Ile Met Asp Glu Ser Cys Asp Val Arg Leu Ala Val Ser
225                 230                 235                 240

Ser Ile Ile His Ser Lys Thr Phe Asp Asn Gly Met Ile Cys Ala Ser
                245                 250                 255

Glu Gln Ser Val Ile Ile Ser Asp Lys Ile Tyr Glu Ala Ala Lys Lys
            260                 265                 270

Glu Phe Lys Asp Arg Gly Cys His Ile Cys Ser Pro Glu Glu Thr Gln
        275                 280                 285

Lys Leu Arg Glu Thr Ile Leu Ile Asn Gly Ala Leu Asn Ala Lys Ile
    290                 295                 300

Val Gly Gln Ser Ala His Thr Ile Ala Lys Leu Ala Gly Phe Asp Val
305                 310                 315                 320

Ala Glu Ala Ala Lys Ile Leu Ile Gly Glu Val Glu Ser Val Glu Leu
                325                 330                 335

Glu Glu Gln Phe Ala His Glu Lys Leu Ser Pro Val Leu Ala Met Tyr
            340                 345                 350

Lys Ser Lys Ser Phe Asp Asp Ala Val Ser Lys Ala Ala Arg Leu Val
        355                 360                 365

Ala Asp Gly Gly Tyr Gly His Thr Ser Ser Ile Tyr Ile Asn Val Gly
    370                 375                 380

Thr Gly Gln Glu Lys Ile Ala Lys Phe Ser Asp Ala Met Lys Thr Cys
385                 390                 395                 400

Arg Ile Leu Val Asn Thr Pro Ser Ser His Gly Gly Ile Gly Asp Leu
                405                 410                 415

Tyr Asn Phe Lys Leu Ala Pro Ser Leu Thr Leu Gly Cys Gly Ser Trp
            420                 425                 430

Gly Gly Asn Ser Val Ser Glu Asn Val Gly Val Lys His Leu Ile Asn
        435                 440                 445

Ile Lys Thr Val Ala Glu Arg Arg Glu Asn Met Leu Trp Phe Arg Ala
    450                 455                 460

Pro Glu Lys Val Tyr Phe Lys Lys Gly Cys Leu Pro Val Ala Leu Ala
465                 470                 475                 480

Glu Leu Lys Asp Val Met Asn Lys Lys Lys Val Phe Ile Val Thr Asp
                485                 490                 495

Ala Phe Leu Tyr Lys Asn Gly Tyr Thr Lys Cys Val Thr Asp Gln Leu
            500                 505                 510

Asp Ala Met Gly Ile Gln His Thr Thr Tyr Tyr Asp Val Ala Pro Asp
        515                 520                 525

Pro Ser Leu Ala Ser Ala Thr Glu Gly Ala Glu Ala Met Arg Leu Phe
    530                 535                 540

Glu Pro Asp Cys Ile Ile Ala Leu Gly Gly Gly Ser Ala Met Asp Ala
545                 550                 555                 560

Gly Lys Ile Met Trp Val Met Tyr Glu His Pro Glu Val Asn Phe Leu
                565                 570                 575

Asp Leu Ala Met Arg Phe Met Asp Ile Arg Lys Arg Val Tyr Ser Phe
            580                 585                 590

Pro Lys Met Gly Glu Lys Ala Tyr Phe Ile Ala Val Pro Thr Ser Ser
        595                 600                 605

Gly Thr Gly Ser Glu Val Thr Pro Phe Ala Val Ile Thr Asp Glu Arg
    610                 615                 620

Thr Gly Val Lys Tyr Pro Leu Ala Asp Tyr Glu Leu Leu Pro Lys Met
625                 630                 635                 640
```

```
Ala Ile Ile Asp Ala Asp Met Met Met Asn Gln Pro Lys Gly Leu Thr
                645                 650                 655

Ser Ala Ser Gly Ile Asp Ala Leu Thr His Ala Leu Glu Ala Tyr Ala
            660                 665                 670

Ser Ile Met Ala Thr Asp Tyr Thr Asp Gly Leu Ala Leu Lys Ala Met
        675                 680                 685

Lys Asn Ile Phe Ala Tyr Leu Pro Ser Ala Tyr Glu Asn Gly Ala Ala
    690                 695                 700

Asp Pro Val Ala Arg Glu Lys Met Ala Asp Ala Ser Thr Leu Ala Gly
705                 710                 715                 720

Met Ala Phe Ala Asn Ala Phe Leu Gly Ile Cys His Ser Met Ala His
                725                 730                 735

Lys Leu Gly Ala Phe His His Leu Pro His Gly Val Ala Asn Ala Leu
            740                 745                 750

Leu Ile Asn Glu Val Met Arg Phe Asn Ser Val Ser Ile Pro Thr Lys
        755                 760                 765

Met Gly Thr Phe Ser Gln Tyr Gln Tyr Pro His Ala Leu Asp Arg Tyr
    770                 775                 780

Val Glu Cys Ala Asn Phe Leu Gly Ile Ala Gly Lys Asn Asp Asn Glu
785                 790                 795                 800

Lys Phe Glu Asn Leu Leu Lys Ala Ile Asp Glu Leu Lys Glu Lys Val
                805                 810                 815

Gly Ile Lys Lys Ser Ile Lys Glu Tyr Gly Val Asp Glu Lys Tyr Phe
            820                 825                 830

Leu Asp Thr Leu Asp Ala Met Val Glu Gln Ala Phe Asp Asp Gln Cys
        835                 840                 845

Thr Gly Ala Asn Pro Arg Tyr Pro Leu Met Lys Glu Ile Lys Glu Ile
    850                 855                 860

Tyr Leu Lys Val Tyr Tyr Gly Lys
865                 870
```

<210> SEQ ID NO 83
<211> LENGTH: 2676
<212> TYPE: DNA
<213> ORGANISM: Escherichia coli

<400> SEQUENCE: 83

```
atggctgtta ctaatgtcgc tgaacttaac gcactcgtag agcgtgtaaa aaaagcccag      60

cgtgaatatg ccagtttcac tcaagagcaa gtagacaaaa tcttccgcgc cgccgctctg     120

gctgctgcag atgctcgaat cccactcgcg aaaatggccg ttgccgaatc cggcatgggt     180

atcgtcgaag ataaagtgat caaaaaccac tttgcttctg aatatatcta caacgcctat     240

aaagatgaaa aaacctgtgg tgttctgtct gaagacgaca cttttggtac catcactatc     300

gctgaaccaa tcggtattat ttgcggtatc gttccgacca ctaacccgac ttcaactgct     360

atcttcaaat cgctgatcag tctgaagacc cgtaacgcca ttatcttctc cccgcacccg     420

cgtgcaaaag atgccaccaa caaagcggct gatatcgttc tgcaggctgc tatcgctgcc     480

ggtgctccga aagatctgat cggctggatc gatcaacctt ctgttgaact gtctaacgca     540

ctgatgcacc acccagacat caacctgatc ctcgcgactg gtggtccggg catggttaaa     600

gccgcataca gctccggtaa accagctatc ggtgtaggcg cgggcaacac tccagttgtt     660

atcgatgaaa ctgctgatat caaacgtgca gttgcatctg tactgatgtc caaaaccttc     720

gacaacggcg taatctgtgc ttctgaacag tctgttgttg ttgttgactc tgtttatgac     780
```

```
gctgtacgtg aacgttttgc aacccacggc ggctatctgt tgcagggtaa agagctgaaa    840
gctgttcagg atgttatcct gaaaaacggt gcgctgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcggtag aaaaagcaga gaaactggtt   1080
gctatgggcg gtatcggtca tacctcttgc ctgtacactg accaggataa ccaaccggct   1140
cgcgtttctt acttcggtca gaaaatgaaa acggcgcgta tcctgattaa caccccagcg   1200
tctcagggtg gtatcggtga cctgtataac ttcaaactcg caccttccct gactctgggt   1260
tgtggttctt ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctccct gccaatcgcg ctggatgaag tgattactga tggccacaaa   1440
cgtgcgctca tcgtgactga ccgcttcctg ttcaacaatg gttatgctga tcagatcact   1500
tccgtactga aagcagcagg cgttgaaact gaagtcttct tcgaagtaga agcggacccg   1560
accctgagca tcgttcgtaa aggtgcagaa ctggcaaact ccttcaaacc agacgtgatt   1620
atcgcgctgg gtggtggttc cccgatggac gccgcgaaga tcatgtgggt tatgtacgaa   1680
catccggaaa ctcacttcga agagctggcg ctgcgcttta tggatatccg taaacgtatc   1740
tacaagttcc cgaaaatggg cgtgaaagcg aaaatgatcg ctgtcaccac cacttctggt   1800
acaggttctg aagtcactcc gtttgcggtt gtaactgacg acgctactgg tcagaaatat   1860
ccgctggcag actatgcgct gactccggat atggcgattg tcgacgccaa cctggttatg   1920
gacatgccga agtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac cacgaagggt ctaaaaatcc ggtagcgcgt   2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcatt cgatgaccag   2520
tgcaccggcg ctaacccgcg ttacccgctg atctccgagc tgaaacagat tctgctggat   2580
acctactacg gtcgtgatta tgtagaaggt gaaactgcag cgaagaaaga agctgctccg   2640
gctaaagctg agaaaaaagc gaaaaaatcc gcttaa                             2676
```

<210> SEQ ID NO 84
<211> LENGTH: 891
<212> TYPE: PRT
<213> ORGANISM: Escherichia coli

<400> SEQUENCE: 84

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30
```

```
Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
```

```
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880
```

Ala Lys Ala Glu Lys Lys Ala Lys Lys Ser Ala
885 890

<210> SEQ ID NO 85
<211> LENGTH: 2865
<212> TYPE: DNA
<213> ORGANISM: Chlamydomonas reinhardtii
<220> FEATURE:
<221> NAME/KEY: misc_feature
<223> OTHER INFORMATION: AdhE

<400> SEQUENCE: 85
atgatgtcct ccagcctcgt ctctggcaag agggttgccg tgccctctgc tgccaagccc 60
tgtgctgctg tgccgctgcc ccgcgtggcc ggtcgccgga ctgctgcacg cgttgtctgc 120
gaggctgctc cctctggcgc cgcccctgcc agccccaagg ctgaggctgc tgcgcccgtt 180
gccgctgccc cggccacccc ccatgctgag gtgaagaagg agcgcgcccc agccaccgat 240
gaggcgctga cggagctgaa ggcgctgctg aagcgcgccc agaccgccca ggcgcagtac 300
tccacctaca cccaggagca ggtggacgag atcttccgcg ccgccgccga ggccgccaac 360
gccgcccgta tccccctggc caagatggcc gtggaggaga cccgcatggg cgtggctgag 420
gacaaggtgg tgaagaacca cttcgcctcc gagttcatct acaacaagta caagcacact 480
aagacctgcg gcgtcatcga gcacgacccc gccggcggca tccagaaggt ggctgagccc 540
gtgggcgtca ttgccggtat cgtgcccacc accaacccca cctccaccgc catcttcaag 600
tcgctgctgt cgctcaagac ccgcaacgcg ctggtgctgt gcccgcaccc ccgcgccgcc 660
aagagcacca tcgccgccgc gcgcatcgtg cgtgacgccg ccgtggccgc cggcgcgccg 720
cccaacatca tcagctgggt ggagacgccc tcgctgccgg tgtcccaggc gctgatgcag 780
gcgactgaga tcaacctcat cctggccacc ggtggcccgg ccatggtgcg cgccgcctac 840
tcgtccggca acccgtcgct gggtgtgggc gccggcaaca ccccggccct gattgacgag 900
actgccgacg tggccatggc cgtgtcctcc atcctgctgt ccaagacctt tgacaacggc 960
gtcatctgcg cctcggagca gtcggtggtg gtggtggcca aggcctacga cgccgtgcgc 1020
accgagttcg tgcgccgcgg ggcctacttc ctgaccgagg acgacaaggt caaggtccgc 1080
gccggtgtgg ttgtggacgg caagctgaac cccaacattg tgggccagtc catccccaag 1140
ctggcggccc tgttcggcat caaggtgccc cagggcacca aggtgctcat cggcgaggtg 1200
gagaagatcg gccccgagga ggcgctgtcg caggagaagc tgtgccccat cctggccatg 1260
taccgggcgc ccgactacga ccacggcgtc aagatggcct gcgagctcat catgtacggc 1320
ggcgccggcc acacctcggt gctgtacacc aacccgctca acaacgccca catccagcag 1380
taccagagcg cggtcaagac cgtgcgcatc ctcatcaaca cccccgcctc gcagggcgcc 1440
attggtgacc tgtacaactt ccacctggac ccctccctca ccctgggctg cggcacctgg 1500
ggctccacct cggtgtccac caacgtgggc ccgcagcacc tgctgaacat caagaccgtc 1560
accgcgcgcc gcgagaacat gctgtggttc cgcgtgccgc ccaagatcta cttcaagggc 1620
ggctgcctgg aggtggcgct gaccgatctg cgtggcaaat cgcgcgcttt cattgtcacg 1680
gacaagccgc tttttgacat gggatacgcc gacaaggtca cccacatcct ggacagcatt 1740
aacgtgcacc accaggtgtt ctaccacgtg acccccgacc cgaccctggc ctgcattgag 1800
gcgggtctga aggagatcct ggagttcaag cccgatgtca tcatcgcgct gggtggtggc 1860
tcgcccatgg acgccgccaa gatcatgtgg ctgatgtacg agtgccccga cacccgcttc 1920

```
gacggcctgg ccatgcgctt catggacatc cgcaagcgcg tgtacgaggt gccggagctg   1980

ggcaagaagg ccaccatggt gtgcatcccc accaccagtg gcaccggctc ggaggtgacg   2040

cccttctcgg tggtcaccga cgagcgcctg ggcgccaagt accccctggc cgattacgcc   2100

ctgaccccca gcatggccat tgtggacccc cagctggtgc tcaacatgcc caagaagctg   2160

accgcctggg gcggcattga cgcgctcacg cacgcgctgg agagctacgt gtccatctgc   2220

gccaccgact acaccaaggg tctgtcgcgc gaggccatca gcctgctgtt caagtacctg   2280

ccccgcgcct acgccaacgg ctccaacgac tacctggcgc gtgagaaggt gcactacgcc   2340

gccacgattg ccggcatggc cttcgccaac gccttcctgg gcatctgcca ctccatggcg   2400

cacaagctgg gcgccgccta ccacgtgcct cacggcctgg ccaacgccgc gctgatcagc   2460

cacgtcatcc gctacaacgc caccgacatg cccgccaagc aggccgcctt cccgcagtac   2520

gagtacccca ccgccaagca ggactacgcc gacctggcca acatgctggg cctgggcggc   2580

aacacggtgg acgagaaggt gatcaagctg attgaggcgg tggaggagct caaggccaag   2640

gtggacatcc cgcccaccat caaggagatc ttcaacgacc ccaaggtgga cgccgacttc   2700

ctggcgaacg tggacgccct ggccgaggac gccttcgacg accagtgcac gggcgccaac   2760

ccgcgctacc cgctcatggc cgacctgaag cagctctacc tggacgccca cgccgcgccc   2820

atcctgcccg tcaagaccct ggagttcttc tccaagatca actaa                   2865
```

<210> SEQ ID NO 86
<211> LENGTH: 954
<212> TYPE: PRT
<213> ORGANISM: Chlamydomonas reinhardtii
<220> FEATURE:
<221> NAME/KEY: MISC_FEATURE
<223> OTHER INFORMATION: AdhE

<400> SEQUENCE: 86

```
Met Met Ser Ser Ser Leu Val Ser Gly Lys Arg Val Ala Val Pro Ser
1               5                   10                  15

Ala Ala Lys Pro Cys Ala Ala Val Pro Leu Pro Arg Val Ala Gly Arg
            20                  25                  30

Arg Thr Ala Ala Arg Val Val Cys Glu Ala Ala Pro Ser Gly Ala Ala
        35                  40                  45

Pro Ala Ser Pro Lys Ala Glu Ala Ala Ala Pro Val Ala Ala Ala Pro
    50                  55                  60

Ala Thr Pro His Ala Glu Val Lys Lys Glu Arg Ala Pro Ala Thr Asp
65                  70                  75                  80

Glu Ala Leu Thr Glu Leu Lys Ala Leu Leu Lys Arg Ala Gln Thr Ala
                85                  90                  95

Gln Ala Gln Tyr Ser Thr Tyr Thr Gln Glu Gln Val Asp Glu Ile Phe
            100                 105                 110

Arg Ala Ala Ala Glu Ala Ala Asn Ala Ala Arg Ile Pro Leu Ala Lys
        115                 120                 125

Met Ala Val Glu Glu Thr Arg Met Gly Val Ala Glu Asp Lys Val Val
    130                 135                 140

Lys Asn His Phe Ala Ser Glu Phe Ile Tyr Asn Lys Tyr Lys His Thr
145                 150                 155                 160

Lys Thr Cys Gly Val Ile Glu His Asp Pro Ala Gly Gly Ile Gln Lys
                165                 170                 175

Val Ala Glu Pro Val Gly Val Ile Ala Gly Ile Val Pro Thr Thr Asn
            180                 185                 190
```

-continued

```
Pro Thr Ser Thr Ala Ile Phe Lys Ser Leu Leu Ser Leu Lys Thr Arg
        195                 200                 205

Asn Ala Leu Val Leu Cys Pro His Pro Arg Ala Ala Lys Ser Thr Ile
    210                 215                 220

Ala Ala Ala Arg Ile Val Arg Asp Ala Ala Val Ala Ala Gly Ala Pro
225                 230                 235                 240

Pro Asn Ile Ile Ser Trp Val Glu Thr Pro Ser Leu Pro Val Ser Gln
                245                 250                 255

Ala Leu Met Gln Ala Thr Glu Ile Asn Leu Ile Leu Ala Thr Gly Gly
            260                 265                 270

Pro Ala Met Val Arg Ala Ala Tyr Ser Ser Gly Asn Pro Ser Leu Gly
        275                 280                 285

Val Gly Ala Gly Asn Thr Pro Ala Leu Ile Asp Glu Thr Ala Asp Val
    290                 295                 300

Ala Met Ala Val Ser Ser Ile Leu Leu Ser Lys Thr Phe Asp Asn Gly
305                 310                 315                 320

Val Ile Cys Ala Ser Glu Gln Ser Val Val Val Val Ala Lys Ala Tyr
                325                 330                 335

Asp Ala Val Arg Thr Glu Phe Val Arg Arg Gly Ala Tyr Phe Leu Thr
            340                 345                 350

Glu Asp Asp Lys Val Lys Val Arg Ala Gly Val Val Val Asp Gly Lys
        355                 360                 365

Leu Asn Pro Asn Ile Val Gly Gln Ser Ile Pro Lys Leu Ala Ala Leu
    370                 375                 380

Phe Gly Ile Lys Val Pro Gln Gly Thr Lys Val Leu Ile Gly Glu Val
385                 390                 395                 400

Glu Lys Ile Gly Pro Glu Glu Ala Leu Ser Gln Glu Lys Leu Cys Pro
                405                 410                 415

Ile Leu Ala Met Tyr Arg Ala Pro Asp Tyr Asp His Gly Val Lys Met
            420                 425                 430

Ala Cys Glu Leu Ile Met Tyr Gly Gly Ala Gly His Thr Ser Val Leu
        435                 440                 445

Tyr Thr Asn Pro Leu Asn Asn Ala His Ile Gln Gln Tyr Gln Ser Ala
    450                 455                 460

Val Lys Thr Val Arg Ile Leu Ile Asn Thr Pro Ala Ser Gln Gly Ala
465                 470                 475                 480

Ile Gly Asp Leu Tyr Asn Phe His Leu Asp Pro Ser Leu Thr Leu Gly
                485                 490                 495

Cys Gly Thr Trp Gly Ser Thr Ser Val Ser Thr Asn Val Gly Pro Gln
            500                 505                 510

His Leu Leu Asn Ile Lys Thr Val Thr Ala Arg Arg Glu Asn Met Leu
        515                 520                 525

Trp Phe Arg Val Pro Pro Lys Ile Tyr Phe Lys Gly Gly Cys Leu Glu
    530                 535                 540

Val Ala Leu Thr Asp Leu Arg Gly Lys Ser Arg Ala Phe Ile Val Thr
545                 550                 555                 560

Asp Lys Pro Leu Phe Asp Met Gly Tyr Ala Asp Lys Val Thr His Ile
                565                 570                 575

Leu Asp Ser Ile Asn Val His His Gln Val Phe Tyr His Val Thr Pro
            580                 585                 590

Asp Pro Thr Leu Ala Cys Ile Glu Ala Gly Leu Lys Glu Ile Leu Glu
        595                 600                 605

Phe Lys Pro Asp Val Ile Ile Ala Leu Gly Gly Gly Ser Pro Met Asp
```

```
    610                 615                 620

Ala Ala Lys Ile Met Trp Leu Met Tyr Glu Cys Pro Asp Thr Arg Phe
625                 630                 635                 640

Asp Gly Leu Ala Met Arg Phe Met Asp Ile Arg Lys Arg Val Tyr Glu
                645                 650                 655

Val Pro Glu Leu Gly Lys Lys Ala Thr Met Val Cys Ile Pro Thr Thr
            660                 665                 670

Ser Gly Thr Gly Ser Glu Val Thr Pro Phe Ser Val Val Thr Asp Glu
        675                 680                 685

Arg Leu Gly Ala Lys Tyr Pro Leu Ala Asp Tyr Ala Leu Thr Pro Ser
    690                 695                 700

Met Ala Ile Val Asp Pro Gln Leu Val Leu Asn Met Pro Lys Lys Leu
705                 710                 715                 720

Thr Ala Trp Gly Gly Ile Asp Ala Leu Thr His Ala Leu Glu Ser Tyr
                725                 730                 735

Val Ser Ile Cys Ala Thr Asp Tyr Thr Lys Gly Leu Ser Arg Glu Ala
            740                 745                 750

Ile Ser Leu Leu Phe Lys Tyr Leu Pro Arg Ala Tyr Ala Asn Gly Ser
        755                 760                 765

Asn Asp Tyr Leu Ala Arg Glu Lys Val His Tyr Ala Ala Thr Ile Ala
    770                 775                 780

Gly Met Ala Phe Ala Asn Ala Phe Leu Gly Ile Cys His Ser Met Ala
785                 790                 795                 800

His Lys Leu Gly Ala Ala Tyr His Val Pro His Gly Leu Ala Asn Ala
                805                 810                 815

Ala Leu Ile Ser His Val Ile Arg Tyr Asn Ala Thr Asp Met Pro Ala
            820                 825                 830

Lys Gln Ala Ala Phe Pro Gln Tyr Glu Tyr Pro Thr Ala Lys Gln Asp
        835                 840                 845

Tyr Ala Asp Leu Ala Asn Met Leu Gly Leu Gly Gly Asn Thr Val Asp
    850                 855                 860

Glu Lys Val Ile Lys Leu Ile Glu Ala Val Glu Glu Leu Lys Ala Lys
865                 870                 875                 880

Val Asp Ile Pro Pro Thr Ile Lys Glu Ile Phe Asn Asp Pro Lys Val
                885                 890                 895

Asp Ala Asp Phe Leu Ala Asn Val Asp Ala Leu Ala Glu Asp Ala Phe
            900                 905                 910

Asp Asp Gln Cys Thr Gly Ala Asn Pro Arg Tyr Pro Leu Met Ala Asp
        915                 920                 925

Leu Lys Gln Leu Tyr Leu Asp Ala His Ala Ala Pro Ile Leu Pro Val
    930                 935                 940

Lys Thr Leu Glu Phe Phe Ser Lys Ile Asn
945                 950


<210> SEQ ID NO 87
<211> LENGTH: 2658
<212> TYPE: DNA
<213> ORGANISM: Piromyces sp. E2

<400> SEQUENCE: 87

atgtccggat tacaaatgtt ccaaaacctt tctctttacg gtagtctcgc cgaaatcgat      60

actagcgaaa agcttaacga agctatggac aaattaactg ctgcccaaga acaattcaga     120

gaatacaacc aagaacaagt tgacaaaatc ttcaaggctg ttgctttagc tgcttctcaa     180
```

-continued

```
aaccgtgttg ctttcgctaa gtacgcacac gaagaaaccc aaaagggtgt tttcgaagat    240
aaggttatca agaacgaatt cgctgctgat tacatttacc acaagtactg caatgacaag    300
accgccggta tcattgaata tgatgaagcc aatggtctta tggaaattgc tgaaccagtt    360
ggtccagttg ttggtattgc tccagttact aacccaactt ctactatcat ctacaagtct    420
ttaattgcct taaagacccg taactgtatt atcttctcac cacatccagg agctcacaag    480
gcctctgttt tcgttgttaa ggtcttacac caagctgctg ttaaggctgg tgccccagaa    540
aactgtattc aaatcatctt cccaaagatg gatttaacta ctgaattatt acaccaccaa    600
aagactcgtt tcatttgggc tactggtggt ccaggtttag ttcacgcctc ttacacttct    660
ggtaagccag ctcttggtgg tggtccaggt aatgctccag ctcttattga tgaaacttgt    720
gatatgaacg aagctgttgg ttctatcgtt gtttctaaga ctttcgattg tggtatgatc    780
tgtgccactg aaaacgctgt tgtcgttgtc gaatctgtct acgaaaactt cgttgctacc    840
atgaagaagc gtggtgccta cttcatgact ccagaagaaa ccaagaaggc ttctaacctt    900
cttttcggag aaggtatgag attaaatgct aaggctgttg gtcaaactgc caagacttta    960
gctgaaatgg ccggtttcga agtcccagaa aacaccgttg ttctctgtgg tgaagcttct   1020
gaagttaaat tcgaagaacc aatggctcac gaaaagttaa ctactatcct cggtatctac   1080
aaggctaagg actttgacga tggtgtcaga ttatgtaagg aattagttac tttcggtggt   1140
aagggtcaca ctgctgttct ctacaccaac caaaacaaca aggaccgtat tgaaaagtac   1200
caaaacgaag ttccagcctt ccacatctta gttgacatgc catcttccct cggttgtatt   1260
ggtgatatgt acaacttccg tcttgctcca gctcttacca ttacttgtgg tactatgggt   1320
ggtggttcct cctctgataa cattggtcca aagcacttac ttaacatcaa gcgtgttggt   1380
atgagacgcg aaaacatgct tggttcaag attccaaagt ctgtctactt caagcgtgct   1440
atcctttctg aagctttatc tgacttacgt gacacccaca agcgtgctat cattattacc   1500
gatagaacta tgactatgtt aggtcaaact gacaagatca ttaaggcttg tgaaggtcat   1560
ggtatggtct gcactgtcta cgataaggtt gtcccagatc caactatcaa gtgtattatg   1620
gaaggtgtta atgaaatgaa cgtcttcaag ccagatttag ctattgctct tggtggtggt   1680
tctgctatgg atgccgctaa gatgatgcgt ttattctacg aatacccaga ccaagactta   1740
caagatattg ctactcgttt cgtcgatatc cgtaagcgtg ttgttggttg tccaaagctt   1800
ggtagactta ttaagactct tgtctgtatc ccaactacct ctggtactgg tgccgaagtt   1860
actccattcg ctgtcgttac ctctgaagaa ggtcgtaagt acccattagt cgactacgaa   1920
cttactccag atatggctat tgttgatcca gaattcgctg ttggtatgcc aaagcgttta   1980
acttcttgga ctggtattga tgctcttacc cacgccattg aatcttacgt ttctattatg   2040
gctactgact tcactagacc atactctctc cgtgctgttg gtcttatctt cgaatccctt   2100
tcccttgctt acaacaacgg taaggatatt gaagctcgtg aaaagatgca caatgcttct   2160
gctattgctg gtatggcctt tgccaacgct ttccttggtt gttgtcactc tgttgctcac   2220
caacttggtt ccgtctacca cattccacac ggtcttgcca acgctttaat gctttctcac   2280
atcattaagt acaacgctac tgactctcca gttaagatgg gtaccttccc acaatacaag   2340
tacccacaag ctatgcgtca ctacgctgaa attgctgaac tcttattacc accaactcaa   2400
gttgttaaga tgactgatgt tgataaggtt caatacttaa ttgaccgtgt tgaacaatta   2460
aaggctgacg ttggtattcc aaagtctatt aaggaaactg gaatggttac tgaagaagac   2520
ttcttcaaca aggttgacca agttgctatc atggccttcg atgaccaatg tactggtgct   2580
```

```
aacccacgtt acccattagt ttctgaatta aaacaattaa tgattgatgc ctggaacggt   2640

gttgtcccaa agctctaa                                                 2658


<210> SEQ ID NO 88
<211> LENGTH: 885
<212> TYPE: PRT
<213> ORGANISM: Piromyces sp. E2

<400> SEQUENCE: 88

Met Ser Gly Leu Gln Met Phe Gln Asn Leu Ser Leu Tyr Gly Ser Leu
1               5                   10                  15

Ala Glu Ile Asp Thr Ser Glu Lys Leu Asn Glu Ala Met Asp Lys Leu
            20                  25                  30

Thr Ala Ala Gln Glu Gln Phe Arg Glu Tyr Asn Gln Glu Gln Val Asp
        35                  40                  45

Lys Ile Phe Lys Ala Val Ala Leu Ala Ala Ser Gln Asn Arg Val Ala
    50                  55                  60

Phe Ala Lys Tyr Ala His Glu Glu Thr Gln Lys Gly Val Phe Glu Asp
65                  70                  75                  80

Lys Val Ile Lys Asn Glu Phe Ala Ala Asp Tyr Ile Tyr His Lys Tyr
                85                  90                  95

Cys Asn Asp Lys Thr Ala Gly Ile Ile Glu Tyr Asp Glu Ala Asn Gly
            100                 105                 110

Leu Met Glu Ile Ala Glu Pro Val Gly Pro Val Val Gly Ile Ala Pro
        115                 120                 125

Val Thr Asn Pro Thr Ser Thr Ile Ile Tyr Lys Ser Leu Ile Ala Leu
    130                 135                 140

Lys Thr Arg Asn Cys Ile Ile Phe Ser Pro His Pro Gly Ala His Lys
145                 150                 155                 160

Ala Ser Val Phe Val Val Lys Val Leu His Gln Ala Ala Val Lys Ala
                165                 170                 175

Gly Ala Pro Glu Asn Cys Ile Gln Ile Ile Phe Pro Lys Met Asp Leu
            180                 185                 190

Thr Thr Glu Leu Leu His His Gln Lys Thr Arg Phe Ile Trp Ala Thr
        195                 200                 205

Gly Gly Pro Gly Leu Val His Ala Ser Tyr Thr Ser Gly Lys Pro Ala
    210                 215                 220

Leu Gly Gly Gly Pro Gly Asn Ala Pro Ala Leu Ile Asp Glu Thr Cys
225                 230                 235                 240

Asp Met Asn Glu Ala Val Gly Ser Ile Val Val Ser Lys Thr Phe Asp
                245                 250                 255

Cys Gly Met Ile Cys Ala Thr Glu Asn Ala Val Val Val Val Glu Ser
            260                 265                 270

Val Tyr Glu Asn Phe Val Ala Thr Met Lys Lys Arg Gly Ala Tyr Phe
        275                 280                 285

Met Thr Pro Glu Glu Thr Lys Lys Ala Ser Asn Leu Leu Phe Gly Glu
    290                 295                 300

Gly Met Arg Leu Asn Ala Lys Ala Val Gly Gln Thr Ala Lys Thr Leu
305                 310                 315                 320

Ala Glu Met Ala Gly Phe Glu Val Pro Glu Asn Thr Val Val Leu Cys
                325                 330                 335

Gly Glu Ala Ser Glu Val Lys Phe Glu Glu Pro Met Ala His Glu Lys
            340                 345                 350
```

```
Leu Thr Thr Ile Leu Gly Ile Tyr Lys Ala Lys Asp Phe Asp Asp Gly
        355                 360                 365

Val Arg Leu Cys Lys Glu Leu Val Thr Phe Gly Gly Lys Gly His Thr
    370                 375                 380

Ala Val Leu Tyr Thr Asn Gln Asn Asn Lys Asp Arg Ile Glu Lys Tyr
385                 390                 395                 400

Gln Asn Glu Val Pro Ala Phe His Ile Leu Val Asp Met Pro Ser Ser
                405                 410                 415

Leu Gly Cys Ile Gly Asp Met Tyr Asn Phe Arg Leu Ala Pro Ala Leu
            420                 425                 430

Thr Ile Thr Cys Gly Thr Met Gly Gly Gly Ser Ser Ser Asp Asn Ile
        435                 440                 445

Gly Pro Lys His Leu Leu Asn Ile Lys Arg Val Gly Met Arg Arg Glu
    450                 455                 460

Asn Met Leu Trp Phe Lys Ile Pro Lys Ser Val Tyr Phe Lys Arg Ala
465                 470                 475                 480

Ile Leu Ser Glu Ala Leu Ser Asp Leu Arg Asp Thr His Lys Arg Ala
                485                 490                 495

Ile Ile Ile Thr Asp Arg Thr Met Thr Met Leu Gly Gln Thr Asp Lys
            500                 505                 510

Ile Ile Lys Ala Cys Glu Gly His Gly Met Val Cys Thr Val Tyr Asp
        515                 520                 525

Lys Val Val Pro Asp Pro Thr Ile Lys Cys Ile Met Glu Gly Val Asn
    530                 535                 540

Glu Met Asn Val Phe Lys Pro Asp Leu Ala Ile Ala Leu Gly Gly Gly
545                 550                 555                 560

Ser Ala Met Asp Ala Ala Lys Met Met Arg Leu Phe Tyr Glu Tyr Pro
                565                 570                 575

Asp Gln Asp Leu Gln Asp Ile Ala Thr Arg Phe Val Asp Ile Arg Lys
            580                 585                 590

Arg Val Val Gly Cys Pro Lys Leu Gly Arg Leu Ile Lys Thr Leu Val
        595                 600                 605

Cys Ile Pro Thr Thr Ser Gly Thr Gly Ala Glu Val Thr Pro Phe Ala
    610                 615                 620

Val Val Thr Ser Glu Glu Gly Arg Lys Tyr Pro Leu Val Asp Tyr Glu
625                 630                 635                 640

Leu Thr Pro Asp Met Ala Ile Val Asp Pro Glu Phe Ala Val Gly Met
                645                 650                 655

Pro Lys Arg Leu Thr Ser Trp Thr Gly Ile Asp Ala Leu Thr His Ala
            660                 665                 670

Ile Glu Ser Tyr Val Ser Ile Met Ala Thr Asp Phe Thr Arg Pro Tyr
        675                 680                 685

Ser Leu Arg Ala Val Gly Leu Ile Phe Glu Ser Leu Ser Leu Ala Tyr
    690                 695                 700

Asn Asn Gly Lys Asp Ile Glu Ala Arg Glu Lys Met His Asn Ala Ser
705                 710                 715                 720

Ala Ile Ala Gly Met Ala Phe Ala Asn Ala Phe Leu Gly Cys Cys His
                725                 730                 735

Ser Val Ala His Gln Leu Gly Ser Val Tyr His Ile Pro His Gly Leu
            740                 745                 750

Ala Asn Ala Leu Met Leu Ser His Ile Ile Lys Tyr Asn Ala Thr Asp
        755                 760                 765

Ser Pro Val Lys Met Gly Thr Phe Pro Gln Tyr Lys Tyr Pro Gln Ala
```

```
    770                 775                 780

Met Arg His Tyr Ala Glu Ile Ala Glu Leu Leu Leu Pro Pro Thr Gln
785                 790                 795                 800

Val Val Lys Met Thr Asp Val Asp Lys Val Gln Tyr Leu Ile Asp Arg
                805                 810                 815

Val Glu Gln Leu Lys Ala Asp Val Gly Ile Pro Lys Ser Ile Lys Glu
            820                 825                 830

Thr Gly Met Val Thr Glu Glu Asp Phe Phe Asn Lys Val Asp Gln Val
        835                 840                 845

Ala Ile Met Ala Phe Asp Asp Gln Cys Thr Gly Ala Asn Pro Arg Tyr
    850                 855                 860

Pro Leu Val Ser Glu Leu Lys Gln Leu Met Ile Asp Ala Trp Asn Gly
865                 870                 875                 880

Val Val Pro Lys Leu
                885
```

<210> SEQ ID NO 89
<211> LENGTH: 2200
<212> TYPE: DNA
<213> ORGANISM: Saccharomyces cerevisiae
<220> FEATURE:
<221> NAME/KEY: misc_feature
<223> OTHER INFORMATION: GPDI locus
<220> FEATURE:
<221> NAME/KEY: misc_feature
<222> LOCATION: (522)..(1698)
<223> OTHER INFORMATION: coding sequence

<400> SEQUENCE: 89

```
tacaaacgca acacgaaaga acaaaaaaag aagaaaacag aaggccaaga cagggtcaat     60

gagactgttg tcctcctact gtccctatgt ctctggccga tcacgcgcca ttgtccctca    120

gaaacaaatc aaacacccac accccgggca cccaaagtcc ccacccacac caccaatacg    180

taaacggggc gccccctgca ggccctcctg cgcgcggcct cccgccttgc ttctctcccc    240

ttccttttct tttccagttt ttccctattt tgtccctttt tccgcacaac aagtatcaga    300

atgggttcat caaatctatc caacctaatt cgcacgtaga ctggcttggt attggcagtt    360

tcgtagttat atatatacta ccatgagtga aactgttacg ttaccttaaa ttctttctcc    420

ctttaatttt cttttatctt actctcctac ataagacatc aagaaacaat tgtatattgt    480

acaccccccc cctccacaaa cacaaatatt gataatataa agatgtctgc tgctgctgat    540

agattaaact taacttccgg ccacttgaat gctggtagaa agagaagttc ctcttctgtt    600

tctttgaagg ctgccgaaaa gcctttcaag gttactgtga ttggatctgg taactggggt    660

actactattg ccaaggtggt tgccgaaaat tgtaagggat acccagaagt tttcgctcca    720

atagtacaaa tgtgggtgtt cgaagaagag atcaatggtg aaaaattgac tgaaatcata    780

aatactagac atcaaaacgt gaaatacttg cctggcatca ctctacccga caatttggtt    840

gctaatccag acttgattga ttcagtcaag gatgtcgaca tcatcgtttt caacattcca    900

catcaatttt tgccccgtat ctgtagccaa ttgaaaggtc atgttgattc acacgtcaga    960

gctatctcct gtctaaaggg ttttgaagtt ggtgctaaag gtgtccaatt gctatcctct   1020

tacatcactg aggaactagg tattcaatgt ggtgctctat ctggtgctaa cattgccacc   1080

gaagtcgctc aagaacactg gtctgaaaca acagttgctt accacattcc aaaggatttc   1140

agaggcgagg gcaaggacgt cgaccataag gttctaaagg ccttgttcca cagaccttac   1200

ttccacgtta gtgtcatcga agatgttgct ggtatctcca tctgtggtgc tttgaagaac   1260
```

-continued

```
gttgttgcct taggttgtgg tttcgtcgaa ggtctaggct ggggtaacaa cgcttctgct   1320

gccatccaaa gagtcggttt gggtgagatc atcagattcg gtcaaatgtt tttcccagaa   1380

tctagagaag aaacatacta ccaagagtct gctggtgttg ctgatttgat caccacctgc   1440

gctggtggta gaaacgtcaa ggttgctagg ctaatggcta cttctggtaa ggacgcctgg   1500

gaatgtgaaa aggagttgtt gaatggccaa tccgctcaag gtttaattac ctgcaaagaa   1560

gttcacgaat ggttggaaac atgtggctct gtcgaagact tcccattatt tgaagccgta   1620

taccaaatcg tttacaacaa ctacccaatg aagaacctgc cggacatgat tgaagaatta   1680

gatctacatg aagattagat ttattggaga aagataacat atcatacttt cccccacttt   1740

tttcgaggct cttctatatc atattcataa attagcatta tgtcatttct cataactact   1800

ttatcacgtt agaaattact tattattatt aaattaatac aaaatttagt aaccaaataa   1860

atataaataa atatgtatat ttaaatttta aaaaaaaaat cctatagagc aaaaggattt   1920

tccattataa tattagctgt acacctcttc cgcatttttt gagggtggtt acaacaccac   1980

tcattcagag gctgtcggca cagttgcttc tagcatctgg cgtccgtatg tatgggtgta   2040

ttttaaataa taaacaaagt gccacacctt caccaattat gtctttaaga aatggacaag   2100

ttccaaagag cttgcccaag gctcgacaag gatgtacttt ggaatatcta tattcaagta   2160

cgtggcgcgc atatgtttga gtgtgcacac aataaaggtt                         2200
```

<210> SEQ ID NO 90
<211> LENGTH: 1060
<212> TYPE: DNA
<213> ORGANISM: Saccharomyces cerevisiae
<220> FEATURE:
<221> NAME/KEY: misc_feature
<223> OTHER INFORMATION: gpd1 delta mutation
<220> FEATURE:
<221> NAME/KEY: misc_feature
<222> LOCATION: (523)..(542)
<223> OTHER INFORMATION: coding sequence
<220> FEATURE:
<221> NAME/KEY: misc_feature
<222> LOCATION: (543)..(558)
<223> OTHER INFORMATION: coding sequence not deleted

<400> SEQUENCE: 90

```
tacaaacgca acacgaaaga acaaaaaaag aagaaaacag aaggccaaga cagggtcaat     60

gagactgttg tcctcctact gtccctatgt ctctggccga tcacgcgcca ttgtccctca    120

gaaacaaatc aaacacccac accccgggca cccaaagtcc ccacccacac caccaatacg    180

taaacggggc gccccctgca ggccctcctg cgcgcggcct cccgccttgc ttctctcccc    240

ttccttttct ttttccagtt ttccctattt tgtccctttt tccgcacaac aagtatcaga    300

atgggttcat caaatctatc caacctaatt cgcacgtaga ctggcttggt attggcagtt    360

tcgtagttat atatatacta ccatgagtga aactgttacg ttaccttaaa ttctttctcc    420

ctttaatttt cttttatctt actctcctac ataagacatc aagaaacaat tgtatattgt    480

acaccccccc cctccacaaa cacaaatatt gataatataa agatgtctgc tgctgctgat    540

agtctacatg aagattagat ttattggaga aagataacat atcatacttt cccccacttt    600

tttcgaggct cttctatatc atattcataa attagcatta tgtcatttct cataactact    660

ttatcacgtt agaaattact tattattatt aaattaatac aaaatttagt aaccaaataa    720

atataaataa atatgtatat ttaaatttta aaaaaaaaat cctatagagc aaaaggattt    780

tccattataa tattagctgt acacctcttc cgcatttttt gagggtggtt acaacaccac    840
```

tcattcagag gctgtcggca cagttgcttc tagcatctgg cgtccgtatg tatgggtgta 900
ttttaaataa taaacaaagt gccacacctt caccaattat gtctttaaga aatggacaag 960
ttccaaagag cttgcccaag gctcgacaag gatgtacttt ggaatatcta tattcaagta 1020
cgtggcgcgc atatgtttga gtgtgcacac aataaaggtt 1060

<210> SEQ ID NO 91
<211> LENGTH: 2369
<212> TYPE: DNA
<213> ORGANISM: Saccharomyces cerevisiae
<220> FEATURE:
<221> NAME/KEY: misc_feature
<223> OTHER INFORMATION: GPD2 locus
<220> FEATURE:
<221> NAME/KEY: misc_feature
<222> LOCATION: (487)..(1806)
<223> OTHER INFORMATION: coding sequence

<400> SEQUENCE: 91
atagccatca tgcaagcgtg tatcttctaa gattcagtca tcatcattac cgagtttgtt 60
ttccttcaca tgatgaagaa ggtttgagta tgctcgaaac aataagacga cgatggctct 120
gccattgtta tattacgctt ttgcggcgag gtgccgatgg gttgctgagg ggaagagtgt 180
ttagcttacg gacctattgc cattgttatt ccgattaatc tattgttcag cagctcttct 240
ctaccctgtc attctagtat tttttttttt ttttttggt tttactttt tttcttcttg 300 cctttttttc ttgttacttt ttttctagtt ttttttcctt ccactaagct ttttccttga 360
tttatccttg ggttcttctt tctactcctt tagatttttt ttttatatat taatttttaa 420
gtttatgtat tttggtagat tcaattctct ttccctttcc ttttccttcg ctccccttcc 480
ttatcaatgc ttgctgtcag aagattaaca agatacacat tccttaagcg aacgcatccg 540
gtgttatata ctcgtcgtgc atataaaatt ttgccttcaa gatctacttt cctaagaaga 600
tcattattac aaacacaact gcactcaaag atgactgctc atactaatat caaacagcac 660
aaacactgtc atgaggacca tcctatcaga agatcggact ctgccgtgtc aattgtacat 720
ttgaaacgtg cgcccttcaa ggttacagtg attggttctg gtaactgggg gaccaccatc 780
gccaaagtca ttgcggaaaa cacagaattg cattcccata tcttcgagcc agaggtgaga 840
atgtgggttt ttgatgaaaa gatcggcgac gaaaatctga cggatatcat aaatacaaga 900
caccagaacg ttaaatatct acccaatatt gacctgcccc ataatctagt ggccgatcct 960
gatcttttac actccatcaa gggtgctgac atccttgttt tcaacatccc tcatcaattt 1020
ttaccaaaca tagtcaaaca attgcaaggc cacgtggccc ctcatgtaag ggccatctcg 1080
tgtctaaaag ggttcgagtt gggctccaag ggtgtgcaat tgctatcctc ctatgttact 1140
gatgagttag gaatccaatg tggcgcacta tctggtgcaa acttggcacc ggaagtggcc 1200
aaggagcatt ggtccgaaac caccgtggct taccaactac caaaggatta tcaaggtgat 1260
ggcaaggatg tagatcataa gattttgaaa ttgctgttcc acagacctta cttccacgtc 1320
aatgtcatcg atgatgttgc tggtatatcc attgccggtg ccttgaagaa cgtcgtggca 1380
cttgcatgtg gtttcgtaga aggtatggga tggggtaaca atgcctccgc agccattcaa 1440
aggctgggtt taggtgaaat tatcaagttc ggtagaatgt tttcccaga atccaaagtc 1500 gagacctact atcaagaatc cgctggtgtt gcagatctga tcaccacctg ctcaggcggt 1560
agaaacgtca aggttgccac atacatggcc aagaccggta agtcagcctt ggaagcagaa 1620
aaggaattgc ttaacggtca atccgcccaa gggataatca catgcagaga agttcacgag 1680
tggctacaaa catgtgagtt gacccaagaa ttcccattat tcgaggcagt ctaccagata 1740
gtctacaaca acgtccgcat ggaagaccta ccggagatga ttgaagagct agacatcgat 1800
gacgaataga cactctcccc ccccctcccc ctctgatctt tcctgttgcc tctttttccc 1860
ccaaccaatt tatcattata cacaagttct acaactacta ctagtaacat tactacagtt 1920
attataattt tctattctct ttttctttaa gaatctatca ttaacgttaa tttctatata 1980
tacataacta ccattataca cgctattatc gtttacatat cacatcaccg ttaatgaaag 2040
atacgacacc ctgtacacta acacaattaa ataatcgcca taaccttttc tgttatctat 2100
agcccttaaa gctgtttctt cgagcttttt cactgcagta attctccaca tgggcccagc 2160
cactgagata agagcgctat gttagtcact actgacggct ctccagtcat ttatgtgatt 2220
ttttagtgac tcatgtcgca tttggcccgt ttttttccgc tgtcgcaacc tatttccatt 2280
aacggtgccg tatggaagag tcatttaaag gcaggagaga gagattactc atcttcattg 2340
gatcagattg atgactgcgt acggcagat 2369

<210> SEQ ID NO 92
<211> LENGTH: 1024
<212> TYPE: DNA
<213> ORGANISM: Saccharomyces cerevisiae
<220> FEATURE:
<221> NAME/KEY: misc_feature
<223> OTHER INFORMATION: gpd2 delta mutation

<400> SEQUENCE: 92
atagccatca tgcaagcgtg tatcttctaa gattcagtca tcatcattac cgagtttgtt 60
ttccttcaca tgatgaagaa ggtttgagta tgctcgaaac aataagacga cgatggctct 120
gccattgtta tattacgctt ttgcggcgag gtgccgatgg gttgctgagg ggaagagtgt 180
ttagcttacg gacctattgc cattgttatt ccgattaatc tattgttcag cagctcttct 240
ctaccctgtc attctagtat tttttttttt tttttttggt tttacttttt tttcttcttg 300
cctttttttc ttgttacttt ttttctagtt tttttttcctt ccactaagct tttccttga 360 tttatccttg ggttcttctt tctactcctt tagatttttt ttttatatat taatttttaa 420
gtttatgtat tttggtagat tcaattctct ttccctttcc ttttccttcg ctccccttcc 480
ttatcctctg atctttcctg ttgcctcttt ttcccccaac caatttatca ttatacacaa 540
gttctacaac tactactagt aacattacta cagttattat aattttctat tctctttttc 600
tttaagaatc tatcattaac gttaatttct atatatacat aactaccatt atacacgcta 660
ttatcgttta catatcacat caccgttaat gaaagatacg acaccctgta cactaacaca 720
attaaataat cgccataacc ttttctgtta tctatagccc ttaaagctgt ttcttcgagc 780
tttttcactg cagtaattct ccacatgggc ccagccactg agataagagc gctatgttag 840
tcactactga cggctctcca gtcatttatg tgatttttta gtgactcatg tcgcatttgg 900
cccgtttttt tccgctgtcg caacctattt ccattaacgg tgccgtatgg aagagtcatt 960
taaaggcagg agagagagat tactcatctt cattggatca gattgatgac tgcgtacggc 1020
agat 1024

<210> SEQ ID NO 93
<211> LENGTH: 3180
<212> TYPE: DNA
<213> ORGANISM: Saccharomyces cerevisiae
<220> FEATURE:
<221> NAME/KEY: misc_feature
<223> OTHER INFORMATION: FDH1 locus
<220> FEATURE:
<221> NAME/KEY: misc_feature
<222> LOCATION: (880)..(2007)
<223> OTHER INFORMATION: coding sequence

<400> SEQUENCE: 93

```
tatttttcta tagatattta cactccgcaa gtgcaaaaaa aaagcattat cgctaacgat      60

caagaggaac tgagacctta ttagttgtct ttgttggcgt aacataaatt tcttaggaaa     120

agagaaaatt atctcgaagg caaaaataaa ccaagcctcg agtttaatgg ttttctaaaa     180

aacactttaa aaacagatcg ccataaaagg agaagctccg taggagaccg ttttcgaaac     240

ctatgtagaa ataaagggaa agctccaacg gtttggataa atctttagaa gcatagagtt     300

tatacaacat tcagtacgaa atgtactctc gaaacgttct cttttcacgg tgcttagtag     360

cagaaaaaag tgtcggaaat tacctatttt gtcaccactc gaggataggc ttgaaagaga     420

gttttaaccc caacttttct attttgcact tgtttggcta tggtttaaaa cattctgttt     480

ggaccaacag cccaagcggc ttatcccttt tcttttttc ccttataatc gggaatttcc     540

ttactaggaa ggcaccgata ctagaactcc gaatgaaaaa gacatgccag taataaaact     600

attttgatgt tatgcggaat atactattct tggattattc actgttaact aaaagttgga     660

gaaatcactc tgcactgtca atcattgaaa aaaagaacat ataaaagggc acaaaattga     720

gtctttttta atgagttctt gctgaggaaa gtttagttaa tatatcattt acgtaaaata     780

tgcatattct tgtattgtgc tttttttatt cattttaagc aggaacaatt tacaagtatt     840

gcaacgctaa tcaaatcaaa ataacagctg aaaattaata tgtcgaaggg aaaggttttg     900

ctggttcttt acgaaggtgg taagcatgct gaagagcagg aaaagttatt ggggtgtatt     960

gaaaatgaac ttggtatcag aaatttcatt gaagaacagg gatacgagtt ggttactacc    1020

attgacaagg accctgagcc aacctcaacg gtagacaggg agttgaaaga cgctgaaatt    1080

gtcattacta cgcccttttt ccccgcctac atctcgagaa acaggattgc agaagctcct    1140

aacctgaagc tctgtgtaac cgctggcgtc ggttcagacc atgtcgattt agaagctgca    1200

aatgaacgga aaatcacggt caccgaagtt actggttcta acgtcgtttc tgtcgcagag    1260

cacgttatgg ccacaatttt ggttttgata agaaactata atggtggtca tcaacaagca    1320

attaatggtg agtgggatat tgccggcgtg gctaaaaatg agtatgatct ggaagacaaa    1380

ataatttcaa cggtaggtgc cggtagaatt ggatataggg ttctggaaag attggtcgca    1440

tttaatccga agaagttact gtactacgac taccaggaac tacctgcgga agcaatcaat    1500

agattgaacg aggccagcaa gcttttcaat ggcagaggtg atattgttca gagagtagag    1560

aaattggagg atatggttgc tcagtcagat gttgttacca tcaactgtcc attgcacaag    1620

gactcaaggg gtttattcaa taaaaagctt atttcccaca tgaaagatgg tgcatacttg    1680

gtgaataccg ctagaggtgc tatttgtgtc gcagaagatg ttgccgaggc agtcaagtct    1740

ggtaaattgg ctggctatgg tggtgatgtc tgggataagc aaccagcacc aaaagaccat    1800

ccctggagga ctatggacaa taaggaccac gtgggaaacg caatgactgt tcatatcagt    1860

ggcacatctc tggatgctca aaagaggtac gctcagggag taaagaacat cctaaatagt    1920

tacttttcca aaaagtttga ttaccgtcca caggatatta ttgtgcagaa tggttcttat    1980

gccaccagag cttatggaca gaagaaataa gagtgattat gagtatttgt gagcagaagt    2040

tttccggtct ccttttgttc ttgttttggc gtattctcca ctattcgtcc atagcacatt    2100

tataccttag ctaaatattt tgtaaagcaa aattttcgtt atctcttaaa aaatagaaga    2160
```

gcggtttatt aatatcaaat aattgaaact gctgatatgg tagctatata caaaatctgc 2220
tgtcaaaatt tggcagtaaa cgatcttcac ggtagcggtt caaataaaga ggaaaagtct 2280
ttctccctta ctgtttttct ggaatttggc tcgtcgttaa taacagaact aaagatacag 2340
taaaaggaga gatcgcaatc aacttcatta attgtaacag tagcataatc acaactgatc 2400
atctacacta taaacagttt ttatttctaa ttatgggcgc ctggccggct caaacattgt 2460
gcttttaaga ctccaaaagt atctgctgca gaaaagagcc atataatgtt aagtgttcag 2520
ggataggtta tcgcttacta cttcaaacgt ttcgaaggaa agccagggaa gcctatatct 2580
gattccctgt ttcataatcc aatgcagcca ctagcttata attatttgaa ctatttgtcg 2640
aacatcacag taataaaatc cccagaaagt tccacttgct gcatattggc acctgttgat 2700
tcactctcca tcactttttt gttagccgcc cagcctagaa agtctttaaa tacatctgaa 2760
attttttttt ttttaacagt gcacccgtgc atcatacctc atgcaaggta cctttttttc 2820
tcaaaggtat tgtcttccat tgaagtggca ctatggcatg atgaaccctg agcatttctg 2880
aattcaacag aaccaaattg tccagaaata aatctgtccg acatgaatta tgaaactttt 2940
tttcaattaa gtgaagagaa ttttgcagcg tcttaccatt attttgaccc attggtcgca 3000
tgtttgcgct ttgacttcga gaaccatgtt aaagcttact tgtacgacaa ccaatgaagt 3060
atattacggc agttttttttg gactgggtca aaaaaagtgt tgcataatca aatcaggaac 3120
acattaaaat gttgtaaaat ttgtcttagt atcacctgag tggttattca ttacgtacta 3180

<210> SEQ ID NO 94
<211> LENGTH: 1630
<212> TYPE: DNA
<213> ORGANISM: Saccharomyces cerevisiae
<220> FEATURE:
<221> NAME/KEY: misc_feature
<223> OTHER INFORMATION: fdh1 delta mutation

<400> SEQUENCE: 94
tatttttcta tagatattta cactccgcaa gtgcaaaaaa aaagcattat cgctaacgat 60
caagaggaac tgagacctta ttagttgtct ttgttggcgt aacataaatt tcttaggaaa 120
agagaaaatt atctcgaagg caaaaataaa ccaagcctcg agtttaatgg ttttctaaaa 180
aacactttaa aaacagatcg ccataaaagg agaagctccg taggagaccg ttttcgaaac 240
ctatgtagaa ataaagggaa agctccaacg gtttggataa atctttagaa gcatagagtt 300
tatacaacat tcagtacgaa atgtactctc gaaacgttct cttttcacgg tgcttagtag 360
cagaaaaaag tgtcggaaat tacctatttt gtcaccactc gaggataggc ttgaaagaga 420
gttttaaccc caactttttct attttgcact tgtttggcta tggtttaaaa cattctgttt 480
ggaccaacag cccaagcggc ttatcccttt tcttttttttc ccttataatc gggaatttcc 540
ttactaggaa ggcaccgata ctagaactcc gaatgaaaaa gacatgccag taataaaact 600
attttgatgt tatgcggaat atactattct tggattattc actgttaact aaaagttgga 660
gaaatcactc tgcactgtca tggcagtaaa cgatcttcac ggtagcggtt caaataaaga 720
ggaaaagtct ttctccctta ctgtttttct ggaatttggc tcgtcgttaa taacagaact 780
aaagatacag taaaaggaga gatcgcaatc aacttcatta attgtaacag tagcataatc 840
acaactgatc atctacacta taaacagttt ttatttctaa ttatgggcgc ctggccggct 900
caaacattgt gcttttaaga ctccaaaagt atctgctgca gaaaagagcc atataatgtt 960
aagtgttcag ggataggtta tcgcttacta cttcaaacgt ttcgaaggaa agccagggaa 1020

```
gcctatatct gattccctgt ttcataatcc aatgcagcca ctagcttata attatttgaa   1080

ctatttgtcg aacatcacag taataaaatc cccagaaagt tccacttgct gcatattggc   1140

acctgttgat tcactctcca tcactttttt gttagccgcc cagcctagaa agtctttaaa   1200

tacatctgaa attttttttt ttttaacagt gcacccgtgc atcatacctc atgcaaggta   1260

cctttttttc tcaaaggtat tgtcttccat tgaagtggca ctatggcatg atgaaccctg   1320

agcatttctg aattcaacag aaccaaattg tccagaaata aatctgtccg acatgaatta   1380

tgaaactttt tttcaattaa gtgaagagaa ttttgcagcg tcttaccatt attttgaccc   1440

attggtcgca tgtttgcgct ttgacttcga gaaccatgtt aaagcttact tgtacgacaa   1500

ccaatgaagt atattacggc agtttttttg gactgggtca aaaaaagtgt tgcataatca   1560

aatcaggaac acattaaaat gttgtaaaat ttgtcttagt atcacctgag tggttattca   1620

ttacgtacta                                                          1630
```

<210> SEQ ID NO 95
<211> LENGTH: 2668
<212> TYPE: DNA
<213> ORGANISM: Saccharomyces cerevisiae
<220> FEATURE:
<221> NAME/KEY: misc_feature
<223> OTHER INFORMATION: FDH2 locus
<220> FEATURE:
<221> NAME/KEY: misc_feature
<222> LOCATION: (801)..(1929)
<223> OTHER INFORMATION: coding sequence

<400> SEQUENCE: 95

```
tgtcgagaca atgtcattgc aagttatata aacattgtaa tacatcacct cgatgaaaga     60

gaaactggaa tgatagatct ctttttctca aaatttcgtt aatatgtaat aataaggttc    120

ctgatgtaat ttgtttttgt acaaattatt ttagattctg gaggttcaaa taaaatatat    180

attacagcca acgattaggg gggacaagac ttgattacac atttttcgtt ggtaacttga    240

ctcttttatg aaaagaaaac attaagttga aggtgcacgc ttgaggcgct cctttttcat    300

ggtgcttagc agcagatgaa agtgtcagaa gttacctatt ttgtcaccat ttgagaataa    360

gcttgaaaga aagttgtaac cccaactttt ctatcttgca cttgtttgga ccaacagcca    420

aacggcttat cccttttctt ttcccttata atcgggaatt tccttactag gaaggcaccg    480

atactataac tccgaatgaa aaagacatgc cagtaataaa aataattgat gttatgcgga    540

atatactatt cttggattat tcactgttaa ctaaaagttg gagaaatcac tctgcactgt    600

caatcattga aaaaaagaac atataaaagg gcacaaaatc gagtcttttt taatgagttc    660

ttgctgagga aaatttagtt aatatatcat ttacataaaa catgcatatt attgtgttgt    720

actttcttta ttcattttaa gcaggaataa ttacaagtat tgcaacgcta atcaaatcga    780

aataacagct gaaaattaat atgtcgaagg gaaaggtttt gctggttctt tatgaaggtg    840

gtaagcatgc tgaagagcag gaaaagttat tggggtgtat tgaaaatgaa cttggtatca    900

gaaatttcat tgaagaacag ggatacgagt tggttactac cattgacaag gaccctgagc    960

caacctcaac ggtagacagg gagttgaaag acgctgaaat tgtcattact acgccctttt   1020

tccccgccta catctcgaga aacaggattg cagaagctcc taacctgaag ctctgtgtaa   1080

ccgctggcgt cggttcagac catgtcgatt tagaagctgc aaatgaacgg aaaatcacgg   1140

tcaccgaagt tactggttct aacgtcgttt ctgtcgcaga gcacgttatg gccacaattt   1200

tggttttgat aagaaactat aatggtggtc atcaataagc aattaatggt gagtgggata   1260
```

ttgccggcgt ggctaaaaaa tgagtatgat ctggaagaca aaataatttc aacggtaggt 1320
gccggtagaa ttggatatag ggttctggaa agattggtcg catttaatcc gaagaagtta 1380
ctgtactacg actaccagga actacctgcg gaagcaatca atagattgaa cgaggccagc 1440
aagcttttca atggcagagg tgatattgtt cagagagtag agaaattgga ggatatggtt 1500
gctcagtcag atgttgttac catcaactgt ccattgcaca aggactcaag gggtttattc 1560
aataaaaagc ttatttccca catgaaagat ggtgcatact tggtgaatac cgctagaggt 1620
gctatttgtg tcgcagaaga tgttgccgag gcagtcaagt ctggtaaatt ggctggctat 1680
ggtggtgatg tctgggataa gcaaccagca ccaaaagacc atccctggag gactatggac 1740
aataaggacc acgtgggaaa cgcaatgact gttcatatca gtggcacatc tctgcatgct 1800
caaaagaggt acgctcaggg agtaaagaac atcctaaata gttacttttc caaaaagttt 1860
gattaccgtc cacaggatat tattgtgcag aatggttctt atgccaccag agcttatgga 1920
cagaagaaat aagagtgatt atgagtattt gtgagcagaa gttttccggt ctccttttgt 1980
tcttgttttg gcgtattctc cactattcgt ccatagcaca tttatacctt agctaaatat 2040
tttgtaaagc aaaattttcg ttatctctta aaaaatagaa gagcggttta ttaatatcaa 2100
ataattgaaa ctgctgatat ggtagctata tacaaaatct gctgtcaaaa tttggcagta 2160
aacgatcttc acggtagcgg ttcaaataaa gaggaaaagt ccttctccct tactgttttt 2220
ctggaatttg gctcgtcgtt aataacagaa ctaaagatac agtaaaagga gagatcgcaa 2280
tcaacttcat taattgtaac agtagcataa tcacaactgg ttatctgcgt tatagacaat 2340
tcttactcac aatgatgggc gcttagttgg ctgtaaacgt cgctttttaa aactccgaaa 2400
agttaccgct acagaaaaaa accataaatg tatgctagtt gcgcagagag gtttagggtc 2460
caaaatttac taccctgtcg ctcactacag cgactgtccc gaattaagcc cgaagagacg 2520
cagaactgtt gtatgaacct catgaaacca ctgatcttga agatttagac cttcagaatc 2580
gttttcaatt agaagtatac aagaagtctt tgtacaataa tgtcaagaca gagctctgaa 2640
ttatagttca gccttgttat tttttttt 2668

<210> SEQ ID NO 96
<211> LENGTH: 1539
<212> TYPE: DNA
<213> ORGANISM: Saccharomyces cerevisiae
<220> FEATURE:
<221> NAME/KEY: misc_feature
<222> LOCATION: (801)..(1539)
<223> OTHER INFORMATION: deleted coding sequence

<400> SEQUENCE: 96
tgtcgagaca atgtcattgc aagttatata aacattgtaa tacatcacct cgatgaaaga 60
gaaactggaa tgatagatct ctttttctca aaatttcgtt aatatgtaat aataaggttc 120
ctgatgtaat ttgtttttgt acaaattatt ttagattctg gaggttcaaa taaaatatat 180
attacagcca acgattaggg gggacaagac ttgattacac atttttcgtt ggtaacttga 240
ctcttttatg aaaagaaaac attaagttga aggtgcacgc ttgaggcgct cctttttcat 300
ggtgcttagc agcagatgaa agtgtcagaa gttacctatt ttgtcaccat ttgagaataa 360
gcttgaaaga aagttgtaac ccccaacttt ctatcttgca cttgtttgga ccaacagcca 420
aacggcttat cccttttctt ttcccttata atcgggaatt tccttactag gaaggcaccg 480
atactataac tccgaatgaa aaagacatgc cagtaataaa aataattgat gttatgcgga 540

-continued

```
atatactatt cttggattat tcactgttaa ctaaaagttg gagaaatcac tctgcactgt    600

caatcattga aaaaaagaac atataaaagg gcacaaaatc gagtcttttt taatgagttc    660

ttgctgagga aaatttagtt aatatatcat ttacataaaa catgcatatt attgtgttgt    720

actttcttta ttcattttaa gcaggaataa ttacaagtat tgcaacgcta atcaaatcga    780

aataacagct gaaaattaat taagagtgat tatgagtatt tgtgagcaga agttttccgg    840

tctccttttg ttcttgtttt ggcgtattct ccactattcg tccatagcac atttatacct    900

tagctaaata ttttgtaaag caaaattttc gttatctctt aaaaaataga agagcggttt    960

attaatatca aataattgaa actgctgata tggtagctat atacaaaatc tgctgtcaaa   1020

atttggcagt aaacgatctt cacggtagcg gttcaaataa agaggaaaag tccttctccc   1080

ttactgtttt tctggaattt ggctcgtcgt taataacaga actaaagata cagtaaaagg   1140

agagatcgca atcaacttca ttaattgtaa cagtagcata atcacaactg gttatctgcg   1200

ttatagacaa ttcttactca caatgatggg cgcttagttg gctgtaaacg tcgcttttta   1260

aaactccgaa aagttaccgc tacagaaaaa aaccataaat gtatgctagt tgcgcagaga   1320

ggtttagggt ccaaaattta ctaccctgtc gctcactaca gcgactgtcc cgaattaagc   1380

ccgaagagac gcagaactgt tgtatgaacc tcatgaaacc actgatcttg aagatttaga   1440

ccttcagaat cgttttcaat tagaagtata caagaagtct ttgtacaata atgtcaagac   1500

agagctctga attatagttc agccttgtta tttttttt                           1539
```

<210> SEQ ID NO 97
<211> LENGTH: 2863
<212> TYPE: DNA
<213> ORGANISM: Saccharomyces cerevisiae
<220> FEATURE:
<221> NAME/KEY: misc_feature
<223> OTHER INFORMATION: GPD1 at GPD2 locus
<220> FEATURE:
<221> NAME/KEY: misc_feature
<222> LOCATION: (941)..(2113)
<223> OTHER INFORMATION: inserted CDP1

<400> SEQUENCE: 97

```
agtaactgtg acgatatcaa ctcttttttt attatgtaat aagcaaacaa gcacgaatgg     60

ggaaagccta tgtgcaatca ccaaggtcgt cccttttttc ccatttgcta atttagaatt    120

taaagaaacc aaaagaatga agaaagaaaa caaatactag ccctaaccct gacttcgttt    180

ctatgataat accctgcttt aatgaacggt atgccctagg gtatatctca ctctgtacgt    240

tacaaactcc ggttatttta tcggaacatc cgagcacccg cgccttcctc aacccaggca    300

ccgcccccag gtaaccgtgc gcgatgagct aatcctgagc catcacccac cccacccgtt    360

gatgacagca attcgggagg gcgaaaaata aaaactggag caaggaatta ccatcaccgt    420

caccatcacc atcatatcgc cttagcctct agccatagcc atcatgcaag cgtgtatctt    480

ctaagattca gtcatcatca ttaccgagtt tgttttcctt cacatgatga agaaggtttg    540

agtatgctcg aaacaataag acgacgatgg ctctgccatt gttatattac gcttttgcgg    600

cgaggtgccg atgggttgct gaggggaaga gtgtttagct tacggaccta ttgccattgt    660

tattccgatt aatctattgt tcagcagctc ttctctaccc tgtcattcta gtattttttt    720

ttttttttt tggttttact tttttttctt cttgcctttt tttcttgtta cttttttttct    780

agttttttt ccttccacta agctttttcc ttgatttatc cttgggttct tctttctact    840

cctttagatt ttttttttat atattaattt ttaagtttat gtattttggt agattcaatt    900
```

-continued

```
ctctttccct ttcctttcc ttcgctcccc ttccttatca atgtctgctg ctgctgatag    960
attaaactta acttccggcc acttgaatgc tggtagaaag agaagttcct cttctgtttc   1020
tttgaaggct gccgaaaagc ctttcaaggt tactgtgatt ggatctggta actggggtac   1080
tactattgcc aaggtggttg ccgaaaattg taagggatac ccagaagttt tcgctccaat   1140
agtacaaatg tgggtgttcg aagaagagat caatggtgaa aaattgactg aaatcataaa   1200
tactagacat caaaacgtga aatacttgcc tggcatcact ctacccgaca atttggttgc   1260
taatccagac ttgattgatt cagtcaagga tgtcgacatc atcgttttca acattccaca   1320
tcaatttttg ccccgtatct gtagccaatt gaaaggtcat gttgattcac acgtcagagc   1380
tatctcctgt ctaaagggtt ttgaagttgg tgctaaaggt gtccaattgc tatcctctta   1440
catcactgag gaactaggta ttcaatgtgg tgctctatct ggtgctaaca ttgccaccga   1500
agtcgctcaa gaacactggt ctgaaacaac agttgcttac cacattccaa aggatttcag   1560
aggcgagggc aaggacgtcg accataaggt tctaaaggcc ttgttccaca gaccttactt   1620
ccacgttagt gtcatcgaag atgttgctgg tatctccatc tgtggtgctt tgaagaacgt   1680
tgttgcctta ggttgtggtt tcgtcgaagg tctaggctgg ggtaacaacg cttctgctgc   1740
catccaaaga gtcggtttgg gtgagatcat cagattcggt caaatgtttt tcccagaatc   1800
tagagaagaa acatactacc aagagtctgc tggtgttgct gatttgatca ccacctgcgc   1860
tggtggtaga aacgtcaagg ttgctaggct aatggctact tctggtaagg acgcctggga   1920
atgtgaaaag gagttgttga atggccaatc cgctcaaggt ttaattacct gcaaagaagt   1980
tcacgaatgg ttggaaacat gtggctctgt cgaagacttc ccattatttg aagccgtata   2040
ccaaatcgtt tacaacaact acccaatgaa gaacctgccg gacatgattg aagaattaga   2100
tctacatgaa gattagacac tctccccccc cctccccctc tgatctttcc tgttgcctct   2160
ttttccccca accaatttat cattatacac aagttctaca actactacta gtaacattac   2220
tacagttatt ataattttct attctctttt tctttaagaa tctatcatta acgttaattt   2280
ctatatatac ataactacca ttatacacgc tattatcgtt tacatatcac atcaccgtta   2340
atgaaagata cgacaccctg tacactaaca caattaaata atcgccataa ccttttctgt   2400
tatctatagc ccttaaagct gtttcttcga gctttttcac tgcagtaatt ctccacatgg   2460
gcccagccac tgagataaga gcgctatgtt agtcactact gacggctctc cagtcattta   2520
tgtgattttt tagtgactca tgtcgcattt ggcccgtttt tttccgctgt cgcaacctat   2580
ttccattaac ggtgccgtat ggaagagtca tttaaaggca ggagagagag attactcatc   2640
ttcattggat cagattgatg actgcgtacg gcagatagtg taatctgagc agttgcgaga   2700
cccagactgg cactgtctca atagtatatt aatgggcata cattcgtact cccttgttct   2760
tgcccacagt tctctctctc tttacttctt gtatcttgtc tccccattgt gcagcgataa   2820
ggaacattgt tctaatatac acggatacaa aagaaataca cat                     2863
```

<210> SEQ ID NO 98
<211> LENGTH: 12394
<212> TYPE: DNA
<213> ORGANISM: Saccharomyces cerevisiae
<220> FEATURE:
<221> NAME/KEY: misc_feature
<223> OTHER INFORMATION: M2158 AADH integrations at the GPD1 locus

<400> SEQUENCE: 98

```
tagattcttt tcgaatttgt ggtgaagata ggaaagttgg tacagttctc catcaatttt     60
```

-continued

```
ccatattttg ctaaaaactc ccttgcatgt ctctttgcat tcatttctcc tgtatacggg    120
ttcaacacat caatcgaatt ttgcaaagtt gtctccattt ctagaagact ttcatcggga    180
ataaaaaatt catatccatt attcaaaaac gataatgatc cctcgtactt acctgtgtaa    240
ttggatattt tataccatac ttcaaaaata tccttggcct cacttctggt aggatacctt    300
tcgccatgtc tgccaatcat ttgaacttgc gttaatctac aaccttcagg aatatcagtg    360
ggtataccgt agttagcggg aaaggagaaa tatggcgcag accctccaag aaagggaaac    420
agactcttct gagagccaat tagttcaata tccgcaaaac ttctgagtgg gatggagagt    480
gccttagata atagaacacc taaacaaatg gcaaaaataa cgggcttcac cattgttcct    540
gtatggtgta ttagaacata gctgaaaata cttctgcctc aaaaaagtgt taaaaaaaag    600
aggcattata tagaggtaaa gcctacaggc gcaagataac acatcaccgc tctccccccct    660
ctcatgaaaa gtcatcgcta aagaggaaca ctgaaggttc ccgtaggttg tctttggcac    720
aaggtagtac atggtaaaaa ctcaggatgg aataattcaa attcaccaat ttcaacgtcc    780
cttgtttaaa aagaaaagaa tttttctctt taaggtagca ctaatgcatt atcgatgatg    840
taaccattca cacaggttat ttagcttttg atccttgaac cattaattaa cccagaaata    900
gaaattaccc aagtggggct ctccaacaca atgagaggaa aggtgacttt ttaagggggc    960
cagaccctgt taaaaacctt tgatggctat gtaataatag taaattaagt gcaaacatgt   1020
aagaaagatt ctcggtaacg accatacaaa tattgggcgt gtggcgtagt cggtagcgcg   1080
ctcccttagc atgggagagg tctccggttc gattccggac tcgtccaaat tattttttac   1140
tttccgcggt gccgagatgc agacgtggcc aactgtgtct gccgtcgcaa aatgatttga   1200
attttgcgtc gcgcacgttt ctcacgtaca taataagtat tttcatacag ttctagcaag   1260
acgaggtggt caaaatagaa gcgtcctatg ttttacagta caagacagtc catactgaaa   1320
tgacaacgta cttgactttt cagtattttc tttttctcac agtctggtta tttttgaaag   1380
cgcacgaaat atatgtaggc aagcattttc tgagtctgct gacctctaaa attaatgcta   1440
ttgtgcacct tagtaaccca aggcaggaca gttaccttgc gtggtgttac tatggccgga   1500
agcccgaaag agttatcgtt actccgatta ttttgtacag ctgatgggac cttgccgtct   1560
tcattttttt tttttttcac ctatagagcc gggcagagct gcccggctta actaagggcc   1620
ggaaaaaaaa cggaaaaaag aaagccaagc gtgtagacgt agtataacag tatatctgac   1680
acgcacgtga tgaccacgta atcgcatcgc ccctcacctc tcacctctca ccgctgactc   1740
agcttcacta aaaaggaaaa tatatactct ttcccaggca aggtgacagc ggtccccgtc   1800
tcctccacaa aggcctctcc tggggtttga gcaagtctaa gtttacgtag cataaaaatt   1860
ctcggattgc gtcaaataat aaaaaaagta accccacttc tacttctaca tcggaaaaac   1920
attccattca catatcgtct ttggcctatc ttgttttgtc ctcggtagat caggtcagta   1980
caaacgcaac acgaaagaac aaaaaaagaa gaaaacagaa ggccaagaca gggtcaatga   2040
gactgttgtc ctcctactgt ccctatgtct ctggccgatc acgcgccatt gtccctcaga   2100
aacaaatcaa acacccacac cccgggcacc caaagtcccc acccacacca ccaatacgta   2160
aacggggcgc cccctgcagg ccctcctgcg cgcggcctcc cgccttgctt ctctcccctt   2220
ccttttcttt ttccagtttt ccctattttg tccctttttc cgcacaacaa gtatcagaat   2280
gggttcatca aatctatcca acctaattcg cacgtagact ggcttggtat tggcagtttc   2340
gtagttatat atatactacc atgagtgaaa ctgttacgtt accttaaatt ctttctccct   2400
ttaattttct tttatcttac tctcctacat aagacatcaa gaaacaattg tatattgtac   2460
```

-continued

```
acccccccccc tccacaaaca caaatattga taatataaag atggctgtta ctaatgtcgc   2520
tgaacttaac gcactcgtag agcgtgtaaa aaaagcccag cgtgaatatg ccagtttcac   2580
tcaagagcaa gtagacaaaa tcttccgcgc cgccgctctg gctgctgcag atgctcgaat   2640
cccactcgcg aaaatggccg ttgccgaatc cggcatgggt atcgtcgaag ataaagtgat   2700
caaaaaccac tttgcttctg aatatatcta caacgcctat aaagatgaaa aaacctgtgg   2760
tgttctgtct gaagacgaca cttttggtac catcactatc gctgaaccaa tcggtattat   2820
ttgcggtatc gttccgacca ctaacccgac ttcaactgct atcttcaaat cgctgatcag   2880
tctgaagacc cgtaacgcca ttatcttctc cccgcacccg cgtgcaaaag atgccaccaa   2940
caaagcggct gatatcgttc tgcaggctgc tatcgctgcc ggtgctccga aagatctgat   3000
cggctggatc gatcaacctt ctgttgaact gtctaacgca ctgatgcacc acccagacat   3060
caacctgatc ctcgcgactg gtggtccggg catggttaaa gccgcataca gctccggtaa   3120
accagctatc ggtgtaggcg cgggcaacac tccagttgtt atcgatgaaa ctgctgatat   3180
caaacgtgca gttgcatctg tactgatgtc caaaaccttc gacaacggcg taatctgtgc   3240
ttctgaacag tctgttgttg ttgttgactc tgtttatgac gctgtacgtg aacgttttgc   3300
aacccacggc ggctatctgt tgcagggtaa agagctgaaa gctgttcagg atgttatcct   3360
gaaaaacggt gcgctgaacg cggctatcgt tggtcagcca gcctataaaa ttgctgaact   3420
ggcaggcttc tctgtaccag aaaacaccaa gattctgatc ggtgaagtga ccgttgttga   3480
tgaaagcgaa ccgttcgcac atgaaaaact gtccccgact ctggcaatgt accgcgctaa   3540
agatttcgaa gacgcggtag aaaaagcaga gaaactggtt gctatgggcg gtatcggtca   3600
tacctcttgc ctgtacactg accaggataa ccaaccggct cgcgtttctt acttcggtca   3660
gaaaatgaaa acggcgcgta tcctgattaa caccccagcg tctcagggtg gtatcggtga   3720
cctgtataac ttcaaactcg caccttccct gactctgggt tgtggttctt ggggtggtaa   3780
ctccatctct gaaaacgttg gtccgaaaca cctgatcaac aagaaaaccg ttgctaagcg   3840
agctgaaaac atgttgtggc acaaacttcc gaaatctatc tacttccgcc gtggctccct   3900
gccaatcgcg ctggatgaag tgattactga tggccacaaa cgtgcgctca tcgtgactga   3960
ccgcttcctg ttcaacaatg gttatgctga tcagatcact tccgtactga aagcagcagg   4020
cgttgaaact gaagtcttct tcgaagtaga agcggacccg accctgagca tcgttcgtaa   4080
aggtgcagaa ctggcaaact ccttcaaacc agacgtgatt atcgcgctgg gtggtggttc   4140
cccgatggac gccgcgaaga tcatgtgggt tatgtacgaa catccggaaa ctcacttcga   4200
agagctggcg ctgcgcttta tggatatccg taaacgtatc tacaagttcc cgaaaatggg   4260
cgtgaaagcg aaaatgatcg ctgtcaccac cacttctggt acaggttctg aagtcactcc   4320
gtttgcggtt gtaactgacg acgctactgg tcagaaatat ccgctggcag actatgcgct   4380
gactccggat atggcgattg tcgacgccaa cctggttatg gacatgccga agtccctgtg   4440
tgctttcggt ggtctggacg cagtaactca cgccatggaa gcttatgttt ctgtactggc   4500
atctgagttc tctgatggtc aggctctgca ggcactgaaa ctgctgaaag aatatctgcc   4560
agcgtcctac cacgaagggt ctaaaaatcc ggtagcgcgt gaacgtgttc acagtgcagc   4620
gactatcgcg ggtatcgcgt ttgcgaacgc cttcctgggt gtatgtcact caatggcgca   4680
caaactgggt tcccagttcc atattccgca cggtctggca aacgccctgc tgatttgtaa   4740
cgttattcgc tacaatgcga acgacaaccc gaccaagcag actgcattca gccagtatga   4800
```

-continued

```
ccgtccgcag gctcgccgtc gttatgctga aattgccgac cacttgggtc tgagcgcacc   4860
gggcgaccgt actgctgcta agatcgagaa actgctggca tggctggaaa cgctgaaagc   4920
tgaactgggt attccgaaat ctatccgtga agctggcgtt caggaagcag acttcctggc   4980
gaacgtggat aaactgtctg aagatgcatt cgatgaccag tgcaccggcg ctaacccgcg   5040
ttacccgctg atctccgagc tgaaacagat tctgctggat acctactacg gtcgtgatta   5100
tgtagaaggt gaaactgcag cgaagaaaga agctgctccg gctaaagctg agaaaaaagc   5160
gaaaaaatcc gcttaagtcg agagcttttg attaagcctt ctagtccaaa aaacacgttt   5220
ttttgtcatt tatttcattt tcttagaata gtttagttta ttcattttat agtcacgaat   5280
gttttatgat tctatatagg gttgcaaaca agcatttttc attttatgtt aaaacaattt   5340
caggtttacc ttttattctg cttgtggtga cgcgtgtatc cgcccgctct tttggtcacc   5400
catgtattta attgcataaa taattcttaa aagtggagct agtctatttc tatttacata   5460
cctctcattt ctcatttcct cctaatgtgt caatgatcat attcttaact ggaccgatct   5520
tattcgtcag attcaaacca aaagttctta gggctaccac aggaggaaaa ttagtgtgat   5580
ataatttaaa taatttatcc gccattccta atagaacgtt gttcgacgga tatctttctg   5640
cccaaaaggg ttctaagctc aatgaagagc caatgtctaa acctcgttac attgaaaata   5700
cagtaaatgg ttccaccatt attatgttgg tcttgtttag tatggccgat cggcgtgtgt   5760
tttgtttgca ccttttatat agtagaagaa tatttgtctt aattcttatt agtactgcaa   5820
cctaaccact aattatcaac aattattgga ttatataaag gaggtaaatt gccggattaa   5880
aatcaaatat cattcatcaa caagtattca tattgtcggc atatttttac atgcggtgta   5940
agtatttgga tcgtattctt atagtgtcaa tacctcgaag cagcgtttca agtaccagac   6000
gtatgtagga actttttaac gtcgagtccg taagatttga tcagtattaa aaaaatctag   6060
ataaatgagt ggtacaaata aaaacatcat taaaaatcgt taaataaaaa agtatgaaga   6120
tcatctatta aagtattagt agccattagc cttaaaaaaa tcagtgctag tttaagtata   6180
atctcgggcg cgccggccga ggcggttaag cggatttttt cgctttttc tcagctttag    6240
ccggagcagc ttctttcttc gctgcagttt caccttctac ataatcacga ccgtagtagg   6300
tatccagcag aatctgtttc agctcggaga tcagcgggta acgcgggtta gcgccggtgc   6360
actggtcatc gaatgcatct tcagacagtt tatccacgtt cgccaggaag tctgcttcct   6420
gaacgccagc ttcacggata gatttcggaa tacccagttc agctttcagc gtttccagcc   6480
atgccagcag tttctcgatc ttagcagcag tacggtcgcc cggtgcgctc agacccaagt   6540
ggtcggcaat ttcagcataa cgacggcgag cctgcggacg gtcatactgg ctgaatgcag   6600
tctgcttggt cgggttgtcg ttcgcattgt agcgaataac gttacaaatc agcagggcgt   6660
ttgccagacc gtgcggaata tggaactggg aacccagttt gtgcgccatt gagtgacata   6720
cacccaggaa ggcgttcgca aacgcgatac ccgcgatagt cgctgcactg tgaacacgtt   6780
cacgcgctac cggattttta gacccttcgt ggtaggacgc tggcagatat tctttcagca   6840
gtttcagtgc ctgcagagcc tgaccatcag agaactcaga tgccagtaca gaaacataag   6900
cttccatggc gtgagttact gcgtccagac caccgaaagc acacagggac ttcggcatgt   6960
ccataaccag gttggcgtcg acaatcgcca tatccggagt cagcgcatag tctgccagcg   7020
gatatttctg accagtagcg tcgtcagtta caaccgcaaa cggagtgact tcagaacctg   7080
taccagaagt ggtggtgaca gcgatcattt tcgctttcac gcccattttc gggaacttgt   7140
agatacgttt acggatatcc ataaagcgca gcgccagctc ttcgaagtga gtttccggat   7200
```

```
gttcgtacat aacccacatg atcttcgcgg cgtccatcgg ggaaccacca cccagcgcga   7260
taatcacgtc tggtttgaag gagtttgcca gttctgcacc tttacgaacg atgctcaggg   7320
tcgggtccgc ttctacttcg aagaagactt cagtttcaac gcctgctgct ttcagtacgg   7380
aagtgatctg atcagcataa ccattgttga acaggaagcg gtcagtcacg atgagcgcac   7440
gtttgtggcc atcagtaatc acttcatcca gcgcgattgg cagggagcca cggcggaagt   7500
agatagattt cggaagtttg tgccacaaca tgttttcagc tcgcttagca acggttttct   7560
tgttgatcag gtgtttcgga ccaacgtttt cagagatgga gttaccaccc caagaaccac   7620
aacccagagt cagggaaggt gcgagtttga agttatacag gtcaccgata ccaccctgag   7680
acgctggggt gttaatcagg atacgcgccg ttttcatttt ctgaccgaag taagaaacgc   7740
gagccggttg gttatcctgg tcagtgtaca ggcaagaggt atgaccgata ccgcccatag   7800
caaccagttt ctctgctttt tctaccgcgt cttcgaaatc tttagcgcgg tacattgcca   7860
gagtcgggga cagtttttca tgtgcgaacg gttcgctttc atcaacaacg gtcacttcac   7920
cgatcagaat cttggtgttt tctggtacag agaagcctgc cagttcagca attttatagg   7980
ctggctgacc aacgatagcc gcgttcagcg caccgttttt caggataaca tcctgaacag   8040
ctttcagctc tttaccctgc aacagatagc cgccgtgggt tgcaaaacgt tcacgtacag   8100
cgtcataaac agagtcaaca acaacaacag actgttcaga agcacagatt acgccgttgt   8160
cgaaggtttt ggacatcagt acagatgcaa ctgcacgttt gatatcagca gtttcatcga   8220
taacaactgg agtgttgccc gcgcctacac cgatagctgg tttaccggag ctgtatgcgg   8280
ctttaaccat gcccggacca ccagtcgcga ggatcaggtt gatgtctggg tggtgcatca   8340
gtgcgttaga cagttcaaca gaaggttgat cgatccagcc gatcagatct ttcggagcac   8400
cggcagcgat agcagcctgc agaacgatat cagccgcttt gttggtggca tcttttgcac   8460
gcgggtgcgg ggagaagata atggcgttac gggtcttcag actgatcagc gatttgaaga   8520
tagcagttga agtcgggtta gtggtcggaa cgataccgca aataataccg attggttcag   8580
cgatagtgat ggtaccaaaa gtgtcgtctt cagacagaac accacaggtt ttttcatctt   8640
tataggcgtt gtagatatat tcagaagcaa agtggttttt gatcacttta tcttcgacga   8700
tacccatgcc ggattcggca acggccattt tcgcgagtgg gattcgagca tctgcagcag   8760
ccagagcggc ggcgcggaag attttgtcta cttgctcttg agtgaaactg gcatattcac   8820
gctgggcttt ttttacacgc tctacgagtg cgttaagttc agcgacatta gtaacagcca   8880
taattcttaa ttaactttga tatgattttg tttcagattt tttatataaa agctttccca   8940
aatagtgcta aagtgaactt agatttttttg gtacctgttt cgaaattaaa aatagaaaaa   9000
tttctctccc tatattgtta ttcttacttc aaatttgttt atcgtttatt tactaggcga   9060
gacttgagta gacgacaatc caaatagaat taacagattt tattggtaga aagcaataat   9120
attctttaga tggttgagaa taaagaagta aaaaaaccag taaagagaaa aagaaaagga   9180
agaaaattaa agaaaaagga tgattacaca agaagataat aaaaaaactc ctttattaag   9240
agcggaagaa tttaataatg aagatgggaa taagcaaaac aaaaacaaag aagggaaaaa   9300
aaataaaaaa tcgtatttat ttatttaaaa aatcatgttg atgacgacaa tggaaaaaaa   9360
aaaccgattt cactttctca tccttatatt tttcaaaggt tgatgcaagt cgatctcaaa   9420
tcggataacg ctgccaactg ggaaattccg caattccgca agaaaaaaaa aaatgtgaaa   9480
acgtgattgc atttttttaca ggtcctaaag gatttagccc acatatcaag agggtggcag   9540
```

-continued

```
taattgcact gattaagcat tcgtcagcat taggcgaatg tgtgcatgaa tattgccagt   9600
gtgctcgata ttagagagta cattgaagaa tattgtaccg gattatgtac aataactttg   9660
ttaatgagat attaattttc ttttttacta gccgctatcc catgcacgat gctaaatttc   9720
aagaagaaac tgagatttaa aaaattagtg gaagctgata aaacggacta taatggtgta   9780
tggattgagg aatctcgaca tgtttttcca tcgttttcaa cgatgactgt aacccgtaga   9840
ttgaaccagg catgccaaag ttagttagat cagggtaaaa attatagatg aggtatttat   9900
tggagaaaga taacatatca tactttcccc cactttttc gaggctcttc tatatcatat   9960
tcataaatta gcattatgtc atttctcata actactttat cacgttagaa attacttatt  10020
attattaaat taatacaaaa tttagtaacc aaataaatat aaataaatat gtatatttaa  10080
attttaaaaa aaaaatccta tagagcaaaa ggattttcca ttataatatt agctgtacac  10140
ctcttccgca ttttttgagg gtggttacaa caccactcat tcagaggctg tcggcacagt  10200
tgcttctagc atctggcgtc cgtatgtatg ggtgtatttt aaataataaa caaagtgcca  10260
caccttcacc aattatgtct ttaagaaatg gacaagttcc aaagagcttg cccaaggctc  10320
gacaaggatg tactttggaa tatctatatt caagtacgtg gcgcgcatat gtttgagtgt  10380
gcacacaata aaggttttta gatattttgc ggcgtcctaa gaaaataagg ggtttcttaa  10440
aaaataacaa tagcaaacaa agttccttac gatgatttca gatgtgaata gcatggtcat  10500
gatgagtata tacgttttta taaataatta aaagtttcc tcttgtctgt tttttttgttg  10560
gctcgtggtt gttctcgaaa aaggagagtt ttcattttcg aaataggtga ttatcatcat  10620
gttgttatca ccccacgacg aagataatac ggagctcacc gttttctttt tttttccctt  10680
tggctgaaat ttcccaccag aacaaacgtg acaaaattat ctttgaatcc aaagtagctt  10740
atatatatac gtagaagtgt ttcgagacac acatccaaat acgaggttgt tcaatttaaa  10800
cccaagaata cataaaaaaa atatagatat attaacttag taaacaatga ctgcaagcac  10860
accatccaat gtcatgacat tgttcttgtt aaggcatgga caaagtgaat tgaatcacga  10920
gaatatattc tgtggttgga ttgacgctaa gctaaccgaa aaaggtaaag aacaagctcg  10980
tcattctgcc gagctaatcg aacaatattg taaagctaat aatttgagat taccccagat  11040
tggttacacc tcacgtttaa ttaggaccca acagaccata gaaacgatgt gtgaagaatt  11100
taagttaaag ccacaactgc aggttgttta cgactttaat aaaatcaaac ttggagacga  11160
atttggcagt gatgacaagg ataatatgaa aatcccgatt cttcaaactt ggaggctaaa  11220
tgaacgtcat tacggttcct ggcagggcca gaggaaaccg aatgttttaa aagaatatgg  11280
taaggataaa tatatgttca ttaggagaga ttacgagggt aagccaccac ctgtagatct  11340
tgaccgtgag atgattcaac aagaaaatga gaagggctct tctactgggt acgaattcaa  11400
ggagccaaac agacaaataa aatatgaatt ggaatgcagc aatcatgaca ttgtattacc  11460
ggattccgaa tctcttcgtg aagtggttta tagattgaat ccttttctac aaaatgtcat  11520
attaaaatta gccaatcaat atgatgaatc ttcatgcctg attgtgggcc atggaagttc  11580
agtgagatcg ctactgaaaa ttctggaggg tatatcagat gatgacatca agaatgttga  11640
tattccaaat ggtatcccct tagtcgttga attagataag aataatggtc ttaagtttat  11700
cagaaaattc tacctagatc ctgaatctgc taagatcaat gctgagaaag tccgtaatga  11760
gggtttcata aaaaatcctt aagggggggta agtatataat ataattgtgt attttccgaa  11820
gtataatgaa aaccaataga aaacttatta taagtccaat gaggtacttt aaaaatgtga  11880
tatttataag aacattcctg aatgcagata tatgatatat attgtaaata tatatagatg  11940
```

```
tgtatatgta tttccatttt gtgtgaggtt ttcttctttt atctcctata taatttgtaa  12000
ccttaattaa cccatgacat aaccaatatt agcctttgca aattttgtaa cttcttgacg  12060
ttgttctaac gacaaatctt catgcttcga ttttatatgc cttgttaaag catccagtct  12120
cgaaaacgtc ttctgatagc cctcagatcc aagaattttt atacactccg agcaacggaa  12180
gacaatcttc cttttagcgt gaatggtatt ttggtgtctc gttaaatcat aggaccttga  12240
aaattgggca ccacacggtt catttgtaat gagattcatt atctgacacg taaatatttc  12300
gttattaccg tcagaagatg acgtatgggc cgatggtgat gcagtcgaag gtttcgaatt  12360
cgaatttgta gatgaatgtg aagataagtg cttc                              12394
```

<210> SEQ ID NO 99
<211> LENGTH: 13300
<212> TYPE: DNA
<213> ORGANISM: Escherichia coli
<220> FEATURE:
<221> NAME/KEY: misc_feature
<223> OTHER INFORMATION: M2158 AADH integrations at the GPD1 locus

<400> SEQUENCE: 99

```
cagaattggt gatattcttc attatcccct cgacatcttt acttttgatc agctttgtgt     60
atagcgggat atccgattgg aacttggctt cagcaacaaa cttgccaaag tggattctcc    120
tactcaagct ttgcaaacat tctatatctc tagtggcaac agaaccgaag ttattcttat    180
catcaccatc tcttttcgaa attaatggta taatcttttc aatataaact ttttttattt    240
tatcattgta attaacttct ggggcataag gcgccaaaat ttgtgggtag ttaatgctcg    300
gtaagaatga tttctgaatc ttgtcaggaa agaagggagt ttcatcaggt gattcgaatc    360
ttctgatgcg agaatgcgca atttcaagat ttgaaagagc ccaatccaag aaagatcctt    420
taaaattcgg aatttctaaa cctggatggt ttgcctcata aactgaagga catgtggcga    480
aatgcgacct ctcaataaat ttgaagatga tcgaatcctc cattctaact aattcatctc    540
taatattttg tagatttaaa acagtttctg gttttgtgaa atccatatct tataccaatt    600
ttatgcagga tgctgagtgc tatttgttag caaaacggaa tcgatgtttc aacttttcaa    660
tacttttttt cttcttttct tcgaacttcg aagattatag agatccattg aaaatttacg    720
ataaaggaaa tgcaacacga agtttgaaaa aaagttgata ttgaaaaaaa aaaaaaaaga    780
gaaccaaaaa aaaattaaaa aacgtgaaaa cgatggttta acaacttttt tcgaatttgg    840
tatacgtgga aaaacgaatg tatagatgca tttttaaaga atatatataa aatttagtaa    900
ttgtattccg cgagcggcgc aataggtgat ttcatttagc tgctttcagt ttgcgtatca    960
tttcttcatt gatcttggct tctctatcta aatcctcttt cgacttgtaa agtccccaag   1020
ttctaaacca taagaaccgc ctcaatctgg aaaatttgtc agtatcaaga ccataattcg   1080
tgtatgactg aatcaaatgt aatccacttt cgtcatgagt aaattcggcc ttgctcagag   1140
actcctggat tttggctaac aacgcagtcc cttcgatgca tatagctagg ccacaaatta   1200
tgccaataac ggtccatggg ttgatgtttt cttgaattct ttcgtttttc atgctatttg   1260
cgtcttccca agtcccagcg ttccagtatt catactgcgc gttagagtgg tagccataag   1320
agccggcata ttggtaattt tcagtattaa cgttagaacg tggtgaatac gatgtggtcc   1380
agccttgcct cgttgtgtca tatacgatct ttttctttgg gtcacaaaga atatcatatg   1440
cttgagagat gactttaaat ctatgtagtt tttcgcttga tgttagcagc agcggtgatt   1500
tactatcact gttggtaacc ttttctgagc taaatatttg aatgttatcg gaatggtcag   1560
```

-continued

```
ggtggtacaa ttttacataa cgatgatatt ttttttttaa cgacttcttg tccagtttag   1620
gatttccaga tccggccttt ggaatgccaa aaatatcata gggagttgga tctgccaact   1680
caggccattg ttcatccctt atcgtaagtt ttctattgcc atttttatcg ttcgctgtag   1740
catacttagc tataaaagtg atttgtgggg gacacttttc tacacatgat aagtgccact   1800
tgaataaaaa tgggtatacg aacttatggt gtagcataac aaatatattg caagtagtga   1860
cctatggtgt gtagatatac gtacagttag ttacgagcct aaagacacaa cgtgtttgtt   1920
aattatactg tcgctgtaat atcttctctt ccattatcac cggtcattcc ttgcaggggc   1980
ggtagtaccc ggagaccctg aacttttctt tttttttttg cgaaattaaa aagttcattt   2040
tcaattcgac aatgagatct acaagccatt gttttatgtt gatgagagcc agcttaaaga   2100
gttaaaaatt tcatagctac tagtcttcta ggcgggttat ctactgatcc gagcttccac   2160
taggatagca cccaaacacc tgcatatttg gacgaccttt acttacacca ccaaaaacca   2220
ctttcgcctc tcccgcccct gataacgtcc actaattgag cgattacctg agcggtcctc   2280
ttttgtttgc agcatgagac ttgcatactg caaatcgtaa gtagcaacgt ctcaaggtca   2340
aaactgtatg gaaaccttgt cacctcactt aattctagct agcctaccct gcaagtcaag   2400
aggtctccgt gattcctagc cacctcaagg tatgcctctc cccggaaact gtggcctttt   2460
ctggcacaca tgatctccac gatttcaaca tataaatagc ttttgataat ggcaatatta   2520
atcaaattta ttttacttct ttcttgtaac atctctcttg taatccctta ttccttctag   2580
ctatttttca taaaaaacca agcaactgct tatcaacaca caaacactaa atcaaaatgg   2640
ctgttactaa tgtcgctgaa cttaacgcac tcgtagagcg tgtaaaaaaa gcccagcgtg   2700
aatatgccag tttcactcaa gagcaagtag acaaaatctt ccgcgccgcc gctctggctg   2760
ctgcagatgc tcgaatccca ctcgcgaaaa tggccgttgc cgaatccggc atgggtatcg   2820
tcgaagataa agtgatcaaa aaccactttg cttctgaata tatctacaac gcctataaag   2880
atgaaaaaac ctgtggtgtt ctgtctgaag acgacacttt tggtaccatc actatcgctg   2940
aaccaatcgg tattatttgc ggtatcgttc cgaccactaa cccgacttca actgctatct   3000
tcaaatcgct gatcagtctg aagacccgta acgccattat cttctccccg cacccgcgtg   3060
caaaagatgc caccaacaaa gcggctgata tcgttctgca ggctgctatc gctgccggtg   3120
ctccgaaaga tctgatcggc tggatcgatc aaccttctgt tgaactgtct aacgcactga   3180
tgcaccaccc agacatcaac ctgatcctcg cgactggtgg tccgggcatg gttaaagccg   3240
catacagctc cggtaaacca gctatcggtg taggcgcggg caacactcca gttgttatcg   3300
atgaaactgc tgatatcaaa cgtgcagttg catctgtact gatgtccaaa accttcgaca   3360
acggcgtaat ctgtgcttct gaacagtctg ttgttgttgt tgactctgtt tatgacgctg   3420
tacgtgaacg ttttgcaacc cacggcggct atctgttgca gggtaaagag ctgaaagctg   3480
ttcaggatgt tatcctgaaa aacggtgcgc tgaacgcggc tatcgttggt cagccagcct   3540
ataaaattgc tgaactggca ggcttctctg taccagaaaa caccaagatt ctgatcggtg   3600
aagtgaccgt tgttgatgaa agcgaaccgt tcgcacatga aaaactgtcc ccgactctgg   3660
caatgtaccg cgctaaagat ttcgaagacg cggtagaaaa agcagagaaa ctggttgcta   3720
tgggcggtat cggtcatacc tcttgcctgt acactgacca ggataaccaa ccggctcgcg   3780
tttcttactt cggtcagaaa atgaaaacgg cgcgtatcct gattaacacc ccagcgtctc   3840
agggtggtat cggtgacctg tataacttca aactcgcacc ttccctgact ctgggttgtg   3900
```

-continued

```
gttcttgggg tggtaactcc atctctgaaa acgttggtcc gaaacacctg atcaacaaga   3960
aaaccgttgc taagcgagct gaaaacatgt tgtggcacaa acttccgaaa tctatctact   4020
tccgccgtgg ctccctgcca atcgcgctgg atgaagtgat tactgatggc cacaaacgtg   4080
cgctcatcgt gactgaccgc ttcctgttca acaatggtta tgctgatcag atcacttccg   4140
tactgaaagc agcaggcgtt gaaactgaag tcttcttcga agtagaagcg gacccgaccc   4200
tgagcatcgt tcgtaaaggt gcagaactgg caaactcctt caaaccagac gtgattatcg   4260
cgctgggtgg tggttccccg atggacgccg cgaagatcat gtgggttatg tacgaacatc   4320
cggaaactca cttcgaagag ctggcgctgc gctttatgga tatccgtaaa cgtatctaca   4380
agttcccgaa aatgggcgtg aaagcgaaaa tgatcgctgt caccaccact tctggtacag   4440
gttctgaagt cactccgttt gcggttgtaa ctgacgacgc tactggtcag aaatatccgc   4500
tggcagacta tgcgctgact ccggatatgg cgattgtcga cgccaacctg gttatggaca   4560
tgccgaagtc cctgtgtgct ttcggtggtc tggacgcagt aactcacgcc atggaagctt   4620
atgtttctgt actggcatct gagttctctg atggtcaggc tctgcaggca ctgaaactgc   4680
tgaaagaata tctgccagcg tcctaccacg aagggtctaa aaatccggta gcgcgtgaac   4740
gtgttcacag tgcagcgact atcgcgggta tcgcgtttgc gaacgccttc ctgggtgtat   4800
gtcactcaat ggcgcacaaa ctgggttccc agttccatat tccgcacggt ctggcaaacg   4860
ccctgctgat ttgtaacgtt attcgctaca atgcgaacga caacccgacc aagcagactg   4920
cattcagcca gtatgaccgt ccgcaggctc gccgtcgtta tgctgaaatt gccgaccact   4980
tgggtctgag cgcaccgggc gaccgtactg ctgctaagat cgagaaactg ctggcatggc   5040
tggaaacgct gaaagctgaa ctgggtattc cgaaatctat ccgtgaagct ggcgttcagg   5100
aagcagactt cctggcgaac gtggataaac tgtctgaaga tgcattcgat gaccagtgca   5160
ccggcgctaa cccgcgttac ccgctgatct ccgagctgaa acagattctg ctggatacct   5220
actacggtcg tgattatgta gaaggtgaaa ctgcagcgaa gaaagaagct gctccggcta   5280
aagctgagaa aaaagcgaaa aaatccgctt aagtcgagag cttttgatta agccttctag   5340
tccaaaaaac acgttttttt gtcatttatt tcattttctt agaatagttt agtttattca   5400
ttttatagtc acgaatgttt tatgattcta tatagggttg caaacaagca tttttcattt   5460
tatgttaaaa caatttcagg tttacctttt attctgcttg tggtgacgcg tgtatccgcc   5520
cgctcttttg gtcacccatg tatttaattg cataaataat tcttaaaagt ggagctagtc   5580
tatttctatt tacatacctc tcatttctca tttcctccta atgtgtcaat gatcatattc   5640
ttaactggac cgatcttatt cgtcagattc aaaccaaaag ttcttagggc taccacagga   5700
ggaaaattag tgtgatataa tttaaataat ttatccgcca ttcctaatag aacgttgttc   5760
gacggatatc tttctgccca aaagggttct aagctcaatg aagagccaat gtctaaacct   5820
cgttacattg aaaatacagt aaatggttcc accattatta tgttggtctt gtttagtatg   5880
gccgatcggc gtgtgttttg tttgcacctt ttatatagta gaagaatatt tgtcttaatt   5940
cttattagta ctgcaaccta accactaatt atcaacaatt attggattat ataaaggagg   6000
taaattgccg gattaaaatc aaatatcatt catcaacaag tattcatatt gtcggcatat   6060
ttttacatgc ggtgtaagta tttggatcgt attcttatag tgtcaatacc tcgaagcagc   6120
gtttcaagta ccagacgtat gtaggaactt tttaacgtcg agtccgtaag atttgatcag   6180
tattaaaaaa atctagataa atgagtggta caaataaaaa catcattaaa aatcgttaaa   6240
taaaaaagta tgaagatcat ctattaaagt attagtagcc attagcctta aaaaaatcag   6300
```

```
tgctagttta agtataatct cgggcgcgcc ggccgaggcg gttaagcgga tttttcgct   6360
tttttctcag ctttagccgg agcagcttct ttcttcgctg cagtttcacc ttctacataa   6420
tcacgaccgt agtaggtatc cagcagaatc tgtttcagct cggagatcag cgggtaacgc   6480
gggttagcgc cggtgcactg gtcatcgaat gcatcttcag acagtttatc cacgttcgcc   6540
aggaagtctg cttcctgaac gccagcttca cggatagatt tcggaatacc cagttcagct   6600
ttcagcgttt ccagccatgc cagcagtttc tcgatcttag cagcagtacg gtcgcccggt   6660
gcgctcagac ccaagtggtc ggcaatttca gcataacgac ggcgagcctg cggacggtca   6720
tactggctga atgcagtctg cttggtcggg ttgtcgttcg cattgtagcg aataacgtta   6780
caaatcagca gggcgtttgc cagaccgtgc ggaatatgga actgggaacc cagtttgtgc   6840
gccattgagt gacatacacc caggaaggcg ttcgcaaacg cgatacccgc gatagtcgct   6900
gcactgtgaa cacgttcacg cgctaccgga tttttagacc cttcgtggta ggacgctggc   6960
agatattctt tcagcagttt cagtgcctgc agagcctgac catcagagaa ctcagatgcc   7020
agtacagaaa cataagcttc catggcgtga gttactgcgt ccagaccacc gaaagcacac   7080
agggacttcg gcatgtccat aaccaggttg gcgtcgacaa tcgccatatc cggagtcagc   7140
gcatagtctg ccagcggata tttctgacca gtagcgtcgt cagttacaac cgcaaacgga   7200
gtgacttcag aacctgtacc agaagtggtg gtgacagcga tcattttcgc tttcacgccc   7260
atttcggga acttgtagat acgtttacgg atatccataa agcgcagcgc cagctcttcg   7320
aagtgagttt ccggatgttc gtacataacc cacatgatct tcgcggcgtc catcggggaa   7380
ccaccaccca gcgcgataat cacgtctggt ttgaaggagt ttgccagttc tgcaccttta   7440
cgaacgatgc tcagggtcgg gtccgcttct acttcgaaga agacttcagt ttcaacgcct   7500
gctgctttca gtacggaagt gatctgatca gcataaccat tgttgaacag gaagcggtca   7560
gtcacgatga gcgcacgttt gtggccatca gtaatcactt catccagcgc gattggcagg   7620
gagccacggc ggaagtagat agatttcgga agtttgtgcc acaacatgtt ttcagctcgc   7680
ttagcaacgg ttttcttgtt gatcaggtgt ttcggaccaa cgttttcaga gatggagtta   7740
ccaccccaag aaccacaacc cagagtcagg gaaggtgcga gtttgaagtt atacaggtca   7800
ccgataccac cctgagacgc tggggtgtta atcaggatac gcgccgtttt catttctga   7860
ccgaagtaag aaacgcgagc cggttggtta tcctggtcag tgtacaggca agaggtatga   7920
ccgataccgc ccatagcaac cagtttctct gctttttcta ccgcgtcttc gaaatcttta   7980
gcgcggtaca ttgccagagt cggggacagt tttcatgtg cgaacggttc gctttcatca   8040
acaacggtca cttcaccgat cagaatcttg gtgttttctg gtacagagaa gcctgccagt   8100
tcagcaattt tataggctgg ctgaccaacg atagccgcgt tcagcgcacc gtttttcagg   8160
ataacatcct gaacagcttt cagctcttta ccctgcaaca gatagccgcc gtgggttgca   8220
aaacgttcac gtacagcgtc ataaacagag tcaacaacaa caacagactg ttcagaagca   8280
cagattacgc cgttgtcgaa ggttttggac atcagtacag atgcaactgc acgtttgata   8340
tcagcagttt catcgataac aactggagtg ttgcccgcgc ctacaccgat agctggttta   8400
ccggagctgt atgcggcttt aaccatgccc ggaccaccag tcgcgaggat caggttgatg   8460
tctgggtggt gcatcagtgc gttagacagt tcaacagaag gttgatcgat ccagccgatc   8520
agatctttcg gagcaccggc agcgatagca gcctgcagaa cgatatcagc cgctttgttg   8580
gtggcatctt ttgcacgcgg gtgcggggag aagataatgg cgttacgggt cttcagactg   8640
```

-continued

```
atcagcgatt tgaagatagc agttgaagtc gggttagtgg tcggaacgat accgcaaata   8700
ataccgattg gttcagcgat agtgatggta ccaaaagtgt cgtcttcaga cagaacacca   8760
caggtttttt catctttata ggcgttgtag atatattcag aagcaaagtg gtttttgatc   8820
actttatctt cgacgatacc catgccggat tcggcaacgg ccattttcgc gagtgggatt   8880
cgagcatctg cagcagccag agcggcggcg cggaagattt tgtctacttg ctcttgagtg   8940
aaactggcat attcacgctg ggcttttttt acacgctcta cgagtgcgtt aagttcagcg   9000
acattagtaa cagccataat tcttaattaa ctttgatatg attttgtttc agatttttta   9060
tataaaagct ttcccaaata gtgctaaagt gaacttagat tttttggtac ctgtttcgaa   9120
attaaaaata gaaaaatttc tctccctata ttgttattct tacttcaaat ttgtttatcg   9180
tttatttact aggcgagact tgagtagacg acaatccaaa tagaattaac agattttatt   9240
ggtagaaagc aataatattc tttagatggt tgagaataaa gaagtaaaaa aaccagtaaa   9300
gagaaaaaga aaaggaagaa aattaaagaa aaaggatgat tacacaagaa gataataaaa   9360
aaactccttt attaagagcg gaagaattta ataatgaaga tgggaataag caaaacaaaa   9420
acaaagaagg gaaaaaaaat aaaaaatcgt atttatttat ttaaaaaatc atgttgatga   9480
cgacaatgga aaaaaaaaac cgatttcact ttctcatcct tatatttttc aaaggttgat   9540
gcaagtcgat ctcaaatcgg ataacgctgc caactgggaa attccgcaat tccgcaagaa   9600
aaaaaaaaat gtgaaaacgt gattgcattt tttacaggtc ctaaaggatt tagcccacat   9660
atcaagaggg tggcagtaat tgcactgatt aagcattcgt cagcattagg cgaatgtgtg   9720
catgaatatt gccagtgtgc tcgatattag agagtacatt gaagaatatt gtaccggatt   9780
atgtacaata actttgttaa tgagatatta attttctttt ttactagccg ctatcccatg   9840
cacgatgcta aatttcaaga agaaactgag atttaaaaaa ttagtggaag ctgataaaac   9900
ggactataat ggtgtatgga ttgaggaatc tcgacatgtt tttccatcgt tttcaacgat   9960
gactgtaacc cgtagattga accaggcatg ccaaagttag ttagatcagg gtaaaaatta  10020
tagatgaggt ttaattaaac aagcacgcag cacgctgtat ttacgtattt aattttatat  10080
atttgtgcat acactactag ggaagacttg aaaaaaacct aggaaatgaa aaaacgacac  10140
aggaagtccc gtatttacta ttttttcctt ccttttgatg gggcagggcg gaaatagagg  10200
ataggataag cctactgctt agctgtttcc gtctctactt cggtagttgt ctcaattgtc  10260
gtttcagtat tacctttaga gccgctagac gatggttgag ctatttgttg agggaaaact  10320
aagttcatgt aacacacgca taacccgatt aaactcatga atagcttgat tgcaggaggc  10380
tggtccattg gagatggtgc cttattttcc ttataggcaa cgatgatgtc ttcgtcggtg  10440
ttcaggtagt agtgtacact ctgaatcagg gagaaccagg caatgaactt gttcctcaag  10500
aaaatagcgg ccataggcat ggattggtta accacaccag atatgcttgg tgtggcagaa  10560
tatagtcctt ttggtggcgc aattttcttg tacctgtggt agaaagggag cggttgaact  10620
gttagtatat attggcaata tcagcaaatt tgaaagaaaa ttgtcggtga aaaacatacg  10680
aaacacaaag gtcgggcctt gcaacgttat tcaaagtcat tgtttagttg aggaggtagc  10740
agcggagtat atgtattcct tttttttgcc tatggatgtt gtaccatgcc cattctgctc  10800
aagcttttgt taaaattatt tttcagtatt ttttcttcca tgttgcgcgt tacgagaaca  10860
gaagcgacag ataaccgcaa tcatacaact agcgctactg cggggtgtaa aaagcacaag  10920
aactaagcca agatcacaac agttatcgat aaaatagcag tgtttgcatg gccattgaga  10980
aggacaacat tggcgtgcgc gccaatgttg tctcaccatg tagctccaaa cgagttgtaa  11040
```

```
gagacggacc gctcacgctt ccgaagcggt cagaaaacgc ttcccagtat gcagttgacc  11100
tacattcaac ctgcaaatat tgctttgctt caagaaatga ttacacagac gtctattttc  11160
ttctacataa tgcacgaaac ttgggcattt agtcatgtag ccgcctagcg agcctgggtg  11220
ccgtcctatc tcctttgttc gtgcaaagag acaggaacac acactgcgtt ctcttgcggc  11280
cggtctggcg gactcagggg tgcggcgttt gcttaaccgg agggaataat aaaatcgggg  11340
tgacgcaagt atgaagtcat gtgtgcttag caattacgta gagggattag aaataatagt  11400
gtgcggttat cggaaccggc tcttgttccc gtttagagca acccaggtgc aggcgtactt  11460
taaagtattt tctttctttt ttttcctgct acttacgcta ggagctgccg cagctgcaaa  11520
gccgacgtcg gagaggcagg tgatcttcgg ctcggccgac aaatcccctg gatatcattg  11580
gcctgtcgag gtatcggccg cgtggaacta ccgggaatta ctatgcaaaa caattggaaa  11640
tctggtagga aaaccttgtt ctagaacttg gcgattgctg acaaagaaga aaagggccta  11700
ttgttgctgc ctcttttgtt gttcttcctc gtattgtctt gccggtgttc tttgtgtctt  11760
ttgtgtgtag gttcttacta ttatagtgct ctttgctatt atattttctt cgttttcact  11820
ttgcgtaatg taacggtctt aaacaaagtt tttttttttt cgctcttgca ttttcctttt  11880
ctgctctatc ttatttgcta attgtagttt cagaagtttt acttaaatat agcactattt  11940
tccagtttta atgtttcttc tcattgcttt cttttataat tttcgcatat aattatacat  12000
ttacggtgtc ttaactctcc ctcttcaccc ctcattattc cagaaaatac taatacttct  12060
tcacacaaaa gaacgcagtt agacaatcaa caatgaatcc taaatcctct acacctaaga  12120
ttccaagacc caagaacgca tttattctgt tcagacagca ctaccacagg atcttaatag  12180
acgaatggac cgctcaaggt gtggaaatac cccataattc aaacatttct aaaattattg  12240
gtacgaagtg gaagggctta caaccggaag ataaggcaca ctgggaaaat ctagcggaga  12300
aggagaaact agaacatgaa aggaagtatc ctgaatacaa atacaagccg gtaagaaagt  12360
ctaagaagaa gcaactactt ttgaaggaaa tcgagcaaca gcagcagcaa caacagaaag  12420
aacagcagca gcagaaacag tcacaaccgc aattacaaca gccctttaac aacaatatag  12480
ttcttatgaa aagagcacat tctctttcac catcttcctc ggtgtcaagc tcgaacagct  12540
atcagttcca attgaacaat gatcttaaga ggttgcctat tccttctgtt aatacttcta  12600
actatatggt ctccagatct ttaagtggac tacctttgac gcatgataag acggcaagag  12660
acctaccaca gctgtcatct caactaaatt ctattccata ttactcagct ccacacgacc  12720
cttcaacgag acatcattac ctcaacgtcg ctcaagctca accaagggct aactcgaccc  12780
ctcaattgcc ctttatttca tccattatca acaacagcag tcaaacaccg gtaactacaa  12840
ctaccacatc cacaacaact gcgacatctt ctcctgggaa attctcctct tctccgaact  12900
cctctgtact ggagaacaac agattaaaca gtatcaacaa ttcaaatcaa tatttacctc  12960
cccctctatt accttctctg caagattttc aactggatca gtaccagcag ctaaagcaga  13020
tgggaccaac ttatattgtc aaaccactgt ctcacaccag gaacaatcta ttgtccacaa  13080
ctacccctac gcatcatcac attcctcata taccaaacca aaacattcct ctacatcaaa  13140
ttataaactc aagcaacact gaggtcaccg ctaaaactag cctagtttct ccgaaatgat  13200
tttttttttc catttcttct ttccgttata ttatattata ctatattccc tttaactaaa  13260
aatttatgca tttggctcct gtttaataaa agtttaaatc                        13300
```

<210> SEQ ID NO 100

<211> LENGTH: 910
<212> TYPE: PRT
<213> ORGANISM: Bifidobacterium adolescentis

<400> SEQUENCE: 100

```
Met Ala Asp Ala Lys Lys Lys Glu Glu Pro Thr Lys Pro Thr Pro Glu
1               5                   10                  15

Glu Lys Leu Ala Ala Ala Glu Ala Glu Val Asp Ala Leu Val Lys Lys
            20                  25                  30

Gly Leu Lys Ala Leu Asp Glu Phe Glu Lys Leu Asp Gln Lys Gln Val
        35                  40                  45

Asp His Ile Val Ala Lys Ala Ser Val Ala Ala Leu Asn Lys His Leu
    50                  55                  60

Val Leu Ala Lys Met Ala Val Glu Glu Thr His Arg Gly Leu Val Glu
65                  70                  75                  80

Asp Lys Ala Thr Lys Asn Ile Phe Ala Cys Glu His Val Thr Asn Tyr
                85                  90                  95

Leu Ala Gly Gln Lys Thr Val Gly Ile Ile Arg Glu Asp Asp Val Leu
            100                 105                 110

Gly Ile Asp Glu Ile Ala Glu Pro Val Gly Val Val Ala Gly Val Thr
        115                 120                 125

Pro Val Thr Asn Pro Thr Ser Thr Ala Ile Phe Lys Ser Leu Ile Ala
    130                 135                 140

Leu Lys Thr Arg Cys Pro Ile Ile Phe Gly Phe His Pro Gly Ala Gln
145                 150                 155                 160

Asn Cys Ser Val Ala Ala Ala Lys Ile Val Arg Asp Ala Ala Ile Ala
                165                 170                 175

Ala Gly Ala Pro Glu Asn Cys Ile Gln Trp Ile Glu His Pro Ser Ile
            180                 185                 190

Glu Ala Thr Gly Ala Leu Met Lys His Asp Gly Val Ala Thr Ile Leu
        195                 200                 205

Ala Thr Gly Gly Pro Gly Met Val Lys Ala Ala Tyr Ser Ser Gly Lys
    210                 215                 220

Pro Ala Leu Gly Val Gly Ala Gly Asn Ala Pro Ala Tyr Val Asp Lys
225                 230                 235                 240

Asn Val Asp Val Val Arg Ala Ala Asn Asp Leu Ile Leu Ser Lys His
                245                 250                 255

Phe Asp Tyr Gly Met Ile Cys Ala Thr Glu Gln Ala Ile Ile Ala Asp
            260                 265                 270

Lys Asp Ile Tyr Ala Pro Leu Val Lys Glu Leu Lys Arg Arg Lys Ala
        275                 280                 285

Tyr Phe Val Asn Ala Asp Glu Lys Ala Lys Leu Glu Gln Tyr Met Phe
    290                 295                 300

Gly Cys Thr Ala Tyr Ser Gly Gln Thr Pro Lys Leu Asn Ser Val Val
305                 310                 315                 320

Pro Gly Lys Ser Pro Gln Tyr Ile Ala Lys Ala Ala Gly Phe Glu Ile
                325                 330                 335

Pro Glu Asp Ala Thr Ile Leu Ala Ala Glu Cys Lys Glu Val Gly Glu
            340                 345                 350

Asn Glu Pro Leu Thr Met Glu Lys Leu Ala Pro Val Gln Ala Val Leu
        355                 360                 365

Lys Ser Asp Asn Lys Glu Gln Ala Phe Glu Met Cys Glu Ala Met Leu
    370                 375                 380

Lys His Gly Ala Gly His Thr Ala Ala Ile His Thr Asn Asp Arg Asp
```

-continued

```
385                 390                 395                 400

Leu Val Arg Glu Tyr Gly Gln Arg Met His Ala Cys Arg Ile Ile Trp
                405                 410                 415

Asn Ser Pro Ser Ser Leu Gly Gly Val Gly Asp Ile Tyr Asn Ala Ile
            420                 425                 430

Ala Pro Ser Leu Thr Leu Gly Cys Gly Ser Tyr Gly Gly Asn Ser Val
        435                 440                 445

Ser Gly Asn Val Gln Ala Val Asn Leu Ile Asn Ile Lys Arg Ile Ala
    450                 455                 460

Arg Arg Asn Asn Asn Met Gln Trp Phe Lys Ile Pro Ala Lys Thr Tyr
465                 470                 475                 480

Phe Glu Pro Asn Ala Ile Lys Tyr Leu Arg Asp Met Tyr Gly Ile Glu
                485                 490                 495

Lys Ala Val Ile Val Cys Asp Lys Val Met Glu Gln Leu Gly Ile Val
            500                 505                 510

Asp Lys Ile Ile Asp Gln Leu Arg Ala Arg Ser Asn Arg Val Thr Phe
        515                 520                 525

Arg Ile Ile Asp Tyr Val Glu Pro Glu Pro Ser Val Glu Thr Val Glu
    530                 535                 540

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575

Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
        595                 600                 605

Ala Lys Leu Val Cys Ile Pro Thr Ser Ser Gly Thr Gly Ser Glu Val
    610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
        675                 680                 685

Phe Thr Asp Gly Met Ala Leu His Ala Ala Lys Leu Val Trp Asp Asn
    690                 695                 700

Leu Ala Glu Ser Val Asn Gly Glu Pro Gly Glu Glu Lys Thr Arg Ala
705                 710                 715                 720

Gln Glu Lys Met His Asn Ala Ala Thr Met Ala Gly Met Ala Phe Gly
                725                 730                 735

Ser Ala Phe Leu Gly Met Cys His Gly Met Ala His Thr Ile Gly Ala
            740                 745                 750

Leu Cys His Val Ala His Gly Arg Thr Asn Ser Ile Leu Leu Pro Tyr
        755                 760                 765

Val Ile Arg Tyr Asn Gly Ser Val Pro Glu Glu Pro Thr Ser Trp Pro
    770                 775                 780

Lys Tyr Asn Lys Tyr Ile Ala Pro Glu Arg Tyr Gln Glu Ile Ala Lys
785                 790                 795                 800

Asn Leu Gly Val Asn Pro Gly Lys Thr Pro Glu Glu Gly Val Glu Asn
                805                 810                 815
```

```
Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
        835                 840                 845

Ile Asp Gln Ile Gly Met Arg Ala Tyr Glu Asp Gln Cys Ala Pro Ala
    850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910


<210> SEQ ID NO 101
<211> LENGTH: 870
<212> TYPE: PRT
<213> ORGANISM: Bacillus coagulans

<400> SEQUENCE: 101

Met Ala Ile Asp Glu Lys Val Val Gly Lys Ser Ala Gln Ile Thr Glu
1               5                   10                  15

Met Val Asp Ser Leu Val Ala Lys Gly Gln Lys Ala Leu Arg Glu Phe
            20                  25                  30

Met Glu Leu Asp Gln Ala Gln Val Asp Asn Ile Val Lys Gln Met Ala
        35                  40                  45

Leu Ala Gly Leu Glu Gln His Met Val Leu Ala Lys Met Ala Val Glu
    50                  55                  60

Glu Thr Gly Arg Gly Val Tyr Glu Asp Lys Met Thr Lys Asn Leu Phe
65                  70                  75                  80

Ala Thr Glu Tyr Ile Tyr His Asn Ile Lys Tyr Asn Lys Thr Val Gly
                85                  90                  95

Ile Ile Asp Glu Asn Asn Asn Glu Gly Ile Val Lys Phe Ala Glu Pro
            100                 105                 110

Val Gly Val Ile Ala Gly Val Thr Pro Val Thr Asn Pro Thr Ser Thr
        115                 120                 125

Thr Met Phe Lys Ala Leu Ile Ala Ile Lys Thr Arg Asn Pro Ile Ile
    130                 135                 140

Phe Ala Phe His Pro Ser Ala Gln Lys Cys Ser Ser His Ala Ala Lys
145                 150                 155                 160

Val Met Leu Asp Ala Ala Val Lys Ala Gly Ala Pro Glu Asn Cys Ile
                165                 170                 175

Gln Trp Ile Glu Lys Pro Ala Ile Glu Ala Thr Gln Gln Leu Met Asn
            180                 185                 190

His Ser Gly Ile Ser Leu Ile Leu Ala Thr Gly Gly Ser Gly Met Val
        195                 200                 205

Lys Ser Ala Tyr Ser Ser Gly Lys Pro Ala Leu Gly Val Gly Pro Gly
    210                 215                 220

Asn Val Pro Cys Tyr Ile Glu Lys Ser Ala Asp Ile Lys Arg Ala Val
225                 230                 235                 240

Asn Asp Leu Ile Leu Ser Lys Thr Phe Asp Asn Gly Met Ile Cys Ala
                245                 250                 255

Ser Glu Gln Ala Val Ile Ile Asp Lys Glu Ile Tyr Asp Asn Val Lys
            260                 265                 270

Asn Glu Leu Ile Ala Asn Gln Cys Tyr Phe Leu Asn Glu Ala Glu Lys
```

```
        275                 280                 285

Lys Lys Val Glu Lys Thr Val Ile Asn Glu Lys Thr Gln Ser Val Asn
    290                 295                 300

Ser Ala Ile Val Gly Lys Pro Ala Tyr Glu Ile Ala Lys Met Ala Gly
305                 310                 315                 320

Val Asn Val Pro Glu Asp Thr Lys Ile Leu Ile Ala Glu Leu Thr Gly
                325                 330                 335

Val Gly Pro Asp Tyr Pro Leu Ser Arg Glu Lys Leu Ser Pro Val Leu
            340                 345                 350

Ala Cys Tyr Lys Ala Asn Ser Thr Lys Gln Gly Phe Glu Phe Ala Glu
        355                 360                 365

Ala Met Leu Glu Phe Gly Gly Leu Gly His Ser Ala Val Ile His Ser
    370                 375                 380

Thr Asn Asp Glu Val Ile Glu Gln Tyr Gly Leu Lys Met Lys Ala Gly
385                 390                 395                 400

Arg Ile Ile Val Asn Ser Pro Ser Ser Gln Gly Ala Ile Gly Asp Ile
                405                 410                 415

Tyr Asn Ala Tyr Met Pro Ser Leu Thr Leu Gly Cys Gly Thr Phe Gly
            420                 425                 430

Gly Asn Ser Val Ser Thr Asn Val Gly Val Ile Asn Leu Tyr Asn Val
        435                 440                 445

Lys Thr Met Ala Lys Arg Arg Val Asn Met Gln Trp Phe Lys Ile Pro
    450                 455                 460

Pro Arg Val Tyr Phe Glu Lys Asn Ser Val Gln Tyr Leu Glu Lys Met
465                 470                 475                 480

Pro Asp Ile Ser Ser Ala Phe Ile Val Thr Asp Pro Asp Met Val Arg
                485                 490                 495

Leu Gly Phe Val Glu Lys Val Leu Tyr Tyr Leu Arg Lys Arg Pro Asp
            500                 505                 510

Tyr Val His Cys Glu Ile Phe Ser Glu Val Glu Pro Asp Pro Ser Ile
        515                 520                 525

Glu Thr Val Arg Lys Gly Ala Ala Ala Met Ala Ser Phe Gln Pro Asp
    530                 535                 540

Val Ile Ile Ala Leu Gly Gly Gly Ser Ala Met Asp Ala Ala Lys Gly
545                 550                 555                 560

Met Trp Leu Phe Tyr Glu His Pro Glu Val Asp Phe Asn Glu Leu Lys
                565                 570                 575

Gln Lys Phe Met Asp Ile Arg Lys Arg Val Ala Lys Phe Pro Lys Leu
            580                 585                 590

Gly Glu Lys Ala Gln Leu Val Cys Ile Pro Thr Thr Ser Gly Thr Gly
        595                 600                 605

Ser Glu Val Thr Ser Phe Ala Val Ile Ser Asp Lys Lys Asn Asn Thr
    610                 615                 620

Lys Tyr Pro Leu Ala Asp Tyr Glu Leu Thr Pro Asp Val Ala Ile Ile
625                 630                 635                 640

Asp Pro Gln Phe Val Met Thr Val Pro Lys Ser Val Thr Ala Asp Thr
                645                 650                 655

Gly Met Asp Val Leu Thr His Ala Ile Glu Ala Tyr Val Ser Asn Met
            660                 665                 670

Ala Asn Asp Tyr Thr Asp Gly Leu Ala Ile Lys Ala Ile Gln Leu Val
        675                 680                 685

His Glu Tyr Leu Pro Lys Ala Tyr Ala Asn Gly Asn Asp Ala Leu Ala
    690                 695                 700
```

```
Arg Glu Lys Met His Asn Ala Ser Thr Leu Ala Gly Met Ala Phe Ser
705                 710                 715                 720

Asn Ala Phe Leu Gly Ile Asn His Ser Leu Ala His Lys Ile Gly Ala
            725                 730                 735

Glu Phe His Ile Pro His Gly Arg Ala Asn Ala Ile Leu Leu Pro His
            740                 745                 750

Val Ile Arg Tyr Asn Ala Gln Lys Pro Lys Lys Phe Ala Ala Phe Pro
        755                 760                 765

Lys Tyr Glu His Phe Ile Ala Asp Gln Arg Tyr Ala Glu Ile Ala Arg
    770                 775                 780

Val Leu Gly Leu Pro Ala Ser Thr Thr Glu Glu Gly Val Glu Ser Leu
785                 790                 795                 800

Cys Gln Glu Ile Ile Arg Met Cys Lys Leu Phe Asn Ile Pro Leu Ser
            805                 810                 815

Leu Lys Ala Ala Gly Val Asn Arg Ala Asp Phe Glu Lys Arg Val Ala
            820                 825                 830

Ile Ile Ala Asp Arg Ala Phe Glu Asp Gln Cys Thr Pro Ala Asn Pro
        835                 840                 845

Lys Leu Pro Leu Val Ser Glu Leu Glu Asp Ile Leu Arg Lys Ala Phe
    850                 855                 860

Glu Gly Val Glu Ala Lys
865                 870


<210> SEQ ID NO 102
<211> LENGTH: 867
<212> TYPE: PRT
<213> ORGANISM: Bacillus licheniformis

<400> SEQUENCE: 102

Met Ala Ile Glu Glu Lys Asn Met Lys Gln Lys Gln Asn Ala Ser Asn
1               5                   10                  15

Met Ile Asp Gln Leu Val Glu Lys Gly Leu Lys Ala Leu Glu Glu Phe
            20                  25                  30

Arg Ser Phe Asp Gln Glu Gln Ile Asp Glu Ile Val Lys Gln Met Ala
        35                  40                  45

Leu Ala Gly Leu Asp Gln His Met Pro Leu Ala Lys Leu Ala Val Glu
    50                  55                  60

Glu Thr Lys Arg Gly Val Tyr Glu Asp Lys Ile Ile Lys Asn Met Phe
65                  70                  75                  80

Ala Thr Glu Tyr Val Tyr His His Ile Lys Tyr Asp Lys Thr Val Gly
                85                  90                  95

Ile Ile Asn Glu Asn Glu His Asp Gly Val Ile Glu Ile Ala Glu Pro
            100                 105                 110

Val Gly Val Ile Ala Gly Val Thr Pro Val Thr Asn Pro Thr Ser Thr
        115                 120                 125

Thr Met Phe Lys Ser Leu Ile Ser Ile Lys Thr Arg Asn Pro Ile Val
    130                 135                 140

Phe Ala Phe His Pro Ser Ala Gln Lys Cys Ser Arg Glu Ala Ala Arg
145                 150                 155                 160

Ile Leu Arg Asp Ala Ala Val Lys Ala Gly Ala Pro Asp Asn Cys Ile
                165                 170                 175

Gln Trp Ile Glu Thr Pro Ser Leu Asp Ala Thr Gln Ala Leu Met Thr
            180                 185                 190

His Pro Asn Val Ser Leu Ile Leu Ala Thr Gly Gly Ala Gly Met Val
```

```
        195                 200                 205

Lys Ser Ala Tyr Ser Ser Gly Lys Pro Ala Leu Gly Val Gly Pro Gly
    210                 215                 220

Asn Val Pro Cys Tyr Ile Glu Lys Ser Ala Asn Leu Lys Gln Ala Val
225                 230                 235                 240

Asn Asp Leu Ile Leu Ser Lys Thr Phe Asp Asn Gly Met Ile Cys Ala
                245                 250                 255

Ser Glu Gln Ala Val Ile Ile Asp Lys Gly Ile Tyr Ser Asp Val Lys
            260                 265                 270

Ala Glu Met Thr Arg Asn Asn Cys Tyr Phe Leu Asn Lys Thr Glu Lys
        275                 280                 285

Ser Lys Val Glu Lys Leu Val Ile Asn Glu Asn Thr Cys Ala Val Asn
    290                 295                 300

Ala Asp Ile Val Gly Met Pro Ala Phe Lys Ile Ala Glu Met Ala Gly
305                 310                 315                 320

Ile Lys Val Pro Gln Asp Thr Lys Ile Leu Ile Ala Glu Leu Glu Gly
                325                 330                 335

Val Gly Pro Asp Asp Pro Leu Ser Arg Glu Lys Leu Ser Pro Val Leu
            340                 345                 350

Ala Cys Tyr Lys Val Ser Gly Leu Glu Glu Gly Leu Lys Arg Ala Glu
        355                 360                 365

Glu Met Leu Ala Phe Gly Gly Thr Gly His Ser Ala Val Ile His Thr
    370                 375                 380

Asn Asp Gln Glu Ala Val Lys Glu Phe Gly Leu Arg Met Lys Ala Gly
385                 390                 395                 400

Arg Ile Ile Val Asn Ala Pro Ser Ser Gln Gly Ala Ile Gly Asp Ile
                405                 410                 415

Tyr Asn Ala Tyr Met Pro Ser Leu Thr Leu Gly Cys Gly Thr Tyr Gly
            420                 425                 430

Gly Asn Ser Val Ser Ser Asn Val Gly Ala Val His Leu Ile Asn Thr
        435                 440                 445

Lys Lys Val Ala Lys Arg Asn Val Asn Met Gln Trp Phe Lys Val Pro
    450                 455                 460

Pro Lys Ile Tyr Phe Glu Lys His Ala Thr Gln Tyr Leu Ala Lys Met
465                 470                 475                 480

Pro Asp Ile Ser Lys Ala Phe Ile Val Thr Asp Pro Gly Met Val Lys
                485                 490                 495

Leu Gly Tyr Val Asp Arg Ala Leu His Tyr Leu Arg Arg Arg Pro Asp
            500                 505                 510

Tyr Val His Cys Glu Ile Phe Ser Asp Val Glu Pro Asp Pro Ser Ile
        515                 520                 525

Glu Thr Val Met Asn Gly Val Asp Met Met Ala Lys Phe Gln Pro Asp
    530                 535                 540

Val Ile Ile Ala Leu Gly Gly Gly Ser Ala Met Asp Ala Ala Lys Gly
545                 550                 555                 560

Met Trp Met Phe Tyr Glu His Pro Asp Ala Glu Phe Phe Gly Leu Lys
                565                 570                 575

Gln Lys Phe Leu Asp Ile Arg Lys Arg Ile Val Lys Tyr Pro Lys Leu
            580                 585                 590

Gly Gly Lys Ala Lys Phe Val Ala Ile Pro Thr Thr Ser Gly Thr Gly
        595                 600                 605

Ser Glu Val Thr Ser Phe Ser Val Ile Thr Asp Lys Glu Thr Asn Thr
    610                 615                 620
```

Lys Tyr Pro Leu Ala Asp Tyr Glu Leu Thr Pro Asp Val Ala Ile Ile
625 630 635 640

Asp Pro Gln Phe Val Met Thr Val Pro Lys His Ile Thr Ala Asp Thr
645 650 655

Gly Met Asp Val Leu Thr His Ala Ile Glu Ser Tyr Val Ser Cys Met
660 665 670

Ala Asn Asp Tyr Thr Asp Gly Leu Ala Met Lys Ala Ile Gln Leu Ile
675 680 685

Phe Glu Tyr Leu Pro Arg Ala Tyr Lys Asn Gly Ser Asp Glu Leu Ala
690 695 700

Arg Glu Lys Val His Asn Ala Ser Thr Ile Ala Gly Met Ala Phe Ser
705 710 715 720

Asn Ala Phe Leu Gly Ile Asn His Ser Leu Ala His Lys Leu Gly Ala
725 730 735

Glu Phe Gln Ile Ala His Gly Arg Ala Asn Ala Ile Leu Leu Pro His
740 745 750

Val Ile Arg Tyr Asn Ala Ala Lys Pro Lys Lys Phe Thr Ala Phe Pro
755 760 765

Lys Tyr Ser His Phe Ile Ala Asp Gln Arg Tyr Ala Glu Ile Ala Arg
770 775 780

Thr Leu Gly Leu Pro Ala Lys Thr Thr Ala Glu Gly Val Glu Ser Leu
785 790 795 800

Ile Gln Glu Ile Ile Ser Leu Ala Lys Glu Leu Lys Ile Pro Met Ser
805 810 815

Ile Lys Gln Asn Gly Val Asp Ala Ala Ala Phe Glu Ser Lys Val Asp
820 825 830

Leu Met Ala Glu Arg Ala Phe Glu Asp Gln Cys Thr Thr Ala Asn Pro
835 840 845

Lys Leu Pro Leu Val Ser Glu Leu Ala Glu Ile Tyr Arg Ser Ala Tyr
850 855 860

Lys Gly Val
865

<210> SEQ ID NO 103
<211> LENGTH: 866
<212> TYPE: PRT
<213> ORGANISM: Enterococcus faecium

<400> SEQUENCE: 103

Met Met Ala Lys Val Met Glu Lys Glu Lys Thr Lys Thr Ile Asp Val
1 5 10 15

Gln Ala Met Ile Asp Gly Leu Ala Glu Lys Ala Asn Val Ala Leu Lys
20 25 30

Glu Met Glu Ser Phe Asp Gln Glu Lys Val Asp His Ile Val His Glu
35 40 45

Met Ala Met Ala Ala Leu Asp Gln His Met Pro Leu Ala Lys Met Ala
50 55 60

Val Glu Glu Thr Gly Arg Gly Val Tyr Glu Asp Lys Ala Ile Lys Asn
65 70 75 80

Met Tyr Ala Ser Glu Tyr Ile Trp His Asn Ile Lys His Asp Lys Thr
85 90 95

Val Gly Val Ile Asn Glu Asp Val Gln Lys Gly Leu Ile Glu Ile Ala
100 105 110

Glu Pro Val Gly Val Val Cys Gly Val Thr Pro Thr Thr Asn Pro Thr

```
        115                 120                 125

Ser Thr Thr Ile Phe Lys Ser Met Ile Ala Leu Lys Thr Arg Asn Pro
    130                 135                 140

Ile Val Phe Ala Phe His Pro Ser Ala Gln Lys Ser Ser Ala Glu Ala
145                 150                 155                 160

Ala Arg Val Val Arg Asp Ala Ala Ile Ala Ala Gly Ala Pro Glu Asn
                165                 170                 175

Cys Ile Gln Trp Ile Glu His Pro Ser Ile Glu Ala Thr Ser Met Leu
            180                 185                 190

Met Asn His Pro Gly Ile Ala Ile Val Leu Ala Thr Gly Gly Ala Gly
        195                 200                 205

Met Val Lys Ser Ala Tyr Ser Thr Gly Lys Pro Ala Leu Gly Val Gly
    210                 215                 220

Pro Gly Asn Val Pro Ala Tyr Ile Glu Lys Thr Ala Lys Ile Lys Arg
225                 230                 235                 240

Ala Val Asn Asp Leu Ile Val Ser Lys Thr Phe Asp Asn Gly Met Ile
                245                 250                 255

Cys Ala Ser Glu Gln Ala Val Ile Val Asp Lys Glu Ile Tyr Ala Ala
            260                 265                 270

Val Lys Ala Glu Phe Gln Ala His Gln Val Tyr Ile Val Lys Pro Asp
        275                 280                 285

Glu Leu Gln Lys Leu Glu Asp Ala Val Met Asn Glu Gly Lys Tyr Ala
    290                 295                 300

Val Asn Pro Ser Ile Val Gly His Ser Ala Met Glu Ile Ala Lys Leu
305                 310                 315                 320

Ala Gly Ile Ser Val Pro Lys Gly Thr Lys Met Leu Ile Ala Glu Leu
                325                 330                 335

Glu Gly Val Gly Pro Asp Tyr Pro Leu Ser Arg Glu Lys Leu Ser Pro
            340                 345                 350

Val Leu Ala Met Ile Lys Ala Asn Asn Thr Asp His Ala Phe Asp Leu
        355                 360                 365

Cys Glu Gly Met Leu Asn Leu Gly Gly Leu Gly His Thr Ala Val Ile
    370                 375                 380

His Ser Glu Asn Glu Glu Leu His Val Lys Phe Gly Leu Arg Met Lys
385                 390                 395                 400

Ala Cys Arg Ile Leu Val Asn Thr Pro Ser Ala Glu Gly Gly Ile Gly
                405                 410                 415

Asp Ile Tyr Asn Glu Met Ile Pro Ser Leu Thr Leu Gly Cys Gly Ser
            420                 425                 430

Tyr Gly Lys Asn Ser Val Ser Arg Asn Val Ser Ala Val Asn Leu Ile
        435                 440                 445

Asn Val Lys Thr Val Ala Lys Arg Arg Asn Asn Met Gln Trp Phe Lys
    450                 455                 460

Leu Pro Pro Lys Ile Phe Phe Glu Lys Asn Ser Leu Leu Tyr Leu Glu
465                 470                 475                 480

Lys Met Glu Asn Val Glu Arg Val Met Ile Val Cys Asp Pro Gly Met
                485                 490                 495

Val Gln Phe Gly Tyr Cys Asp Thr Val Arg Glu Val Leu Ser Arg Arg
            500                 505                 510

Lys Asn Asp Val Lys Ile Glu Val Phe Ser Glu Val Glu Pro Asn Pro
        515                 520                 525

Ser Thr Asn Thr Val Tyr Ala Gly Thr Lys Leu Met Ala Asp Phe Lys
    530                 535                 540
```

Pro Asp Thr Val Ile Ala Leu Gly Gly Gly Ser Ala Met Asp Ala Ala
545                 550                 555                 560

Lys Gly Met Trp Met Phe Tyr Glu His Pro Asp Thr Ser Phe Phe Gly
            565                 570                 575

Ala Lys Gln Lys Phe Leu Asp Ile Arg Lys Arg Thr Tyr Lys Ile Asp
        580                 585                 590

Lys Pro Glu Lys Thr Gln Phe Val Cys Ile Pro Thr Thr Ser Gly Thr
            595                 600                 605

Gly Ser Glu Val Thr Pro Phe Ala Val Ile Thr Asp Ser Glu Thr His
        610                 615                 620

Val Lys Tyr Pro Leu Ala Asp Tyr Ala Leu Thr Pro Asp Val Ala Ile
625                 630                 635                 640

Val Asp Pro Gln Phe Val Met Ser Val Pro Ala Ser Val Thr Ala Asp
                645                 650                 655

Thr Gly Met Asp Val Leu Thr His Ala Ile Glu Ser Tyr Val Ser Val
            660                 665                 670

Met Ala Ser Asp Tyr Thr Arg Gly Leu Ser Leu Gln Ala Ile Lys Leu
        675                 680                 685

Val Phe Asp Tyr Leu Glu Lys Ser Val Lys Thr Pro Asp Met Glu Ser
            690                 695                 700

Arg Glu Lys Met His Asn Ala Ser Thr Met Ala Gly Met Ala Phe Ala
705                 710                 715                 720

Asn Ala Phe Leu Gly Ile Cys His Ser Val Ala His Lys Ile Gly Gly
                725                 730                 735

Glu Tyr Gly Ile Pro His Gly Arg Thr Asn Ala Ile Leu Leu Pro His
            740                 745                 750

Ile Ile Arg Tyr Asn Ala Lys Asp Pro Gln Lys His Ala Met Phe Pro
        755                 760                 765

Lys Tyr Asp Tyr Phe Arg Ala Asp Thr Asp Tyr Ala Asp Ile Ala Lys
            770                 775                 780

Phe Leu Gly Leu Lys Gly Glu Thr Thr Glu Glu Leu Val Glu Ala Leu
785                 790                 795                 800

Ala Thr Ala Val Tyr Glu Leu Gly Asn Ser Val Gly Ile Asn Met Ser
                805                 810                 815

Leu Lys Ala Gln Gly Val Thr Gln Glu Thr Leu Asp Thr Thr Val Asp
            820                 825                 830

Arg Met Ala Glu Leu Ala Tyr Glu Asp Gln Cys Thr Thr Ala Asn Pro
        835                 840                 845

Lys Glu Pro Leu Ile Ser Glu Leu Lys Gln Ile Ile Ile Asp Ala Tyr
    850                 855                 860

Asn Gly
865

<210> SEQ ID NO 104
<211> LENGTH: 3300
<212> TYPE: DNA
<213> ORGANISM: Saccharomyces cerevisiae
<220> FEATURE:
<221> NAME/KEY: misc_feature
<222> LOCATION: (601)..(2610)
<223> OTHER INFORMATION: coding sequence

<400> SEQUENCE: 104
aacgcggctg atgcttttat ttaggaagga atacttacat tatcatgaga acattgtcaa      60
gggcattctg atacgggcct tccatcgcaa gaaaaaggca gcaacggact gagggacgga     120

-continued

```
gagagttacg gcataagaag tagtaggaga gcagagtgtc ataaagttat attattctcg    180
tcctaaagtc aattagttct gttgcgcttg acaatatatg tcgtgtaata ccgtccctta    240
gcagaagaaa gaaagacgga tccatatatg ttaaaatgct tcagagatgt ttctttaatg    300
tgccgtccaa caaaggtatc ttctgtagct tcctctattt tcgatcagat ctcatagtga    360
gaaggcgcaa ttcagtagtt aaaagcgggg aacagtgtga atccggagac ggcaagattg    420
cccggccctt tttgcggaaa agataaaaca agatatattg cactttttcc accaagaaaa    480
acaggaagtg gattaaaaaa tcaacaaagt ataacgccta ttgtcccaat aagcgtcggt    540
tgttcttctt tattatttta ccaagtacgc tcgagggtac attctaatgc attaaaagac    600
atgagtaatc ctcaaaaagc tctaaacgac tttctgtcca gtgaatctgt tcatacacat    660
gatagttcta ggaaacaatc taataagcag tcatccgacg aaggacgctc ttcatcacaa    720
ccttcacatc atcactctgg tggtactaac aacaataata acaataataa taataataat    780
aacagtaaca acaacaacaa cggcaacgat gggggaaatg atgacgacta tgattatgaa    840
atgcaagatt atagaccttc tccgcaaagt gcgcggccta ctcccacgta tgttccacaa    900
tattctgtag aaagtgggac tgctttcccg attcaagagg ttattcctag cgcatacatt    960
aacacacaag atataaacca taaagataac ggtccgccga gtgcaagcag taatagagca   1020
ttcaggccta gagggcagac cacagtgtcg gccaacgtgc ttaacattga agatttttac   1080
aaaaatgcag acgatgcgca taccatcccg gagtcacatt tatcgagaag gagaagtagg   1140
tcgagggcta cgagtaatgc tgggcacagt gccaatacag gcgccacgaa tggcaggact   1200
actggtgccc aaactaatat ggaaagcaat gaatcaccac gtaacgtccc cattatggtg   1260
aagccaaaga cattatacca gaaccctcaa acacctacag tcttgccctc cacataccat   1320
ccaattaata aatggtcttc cgtcaaaaac acttatttga aggaattttt agccgagttt   1380
atgggaacaa tggttatgat tattttcggt agtgctgttg tttgtcaggt caatgttgct   1440
gggaaaatac agcaggacaa tttcaacgtg gctttggata accttaacgt taccgggtct   1500
tctgcagaaa cgatagacgc tatgaagagt ttaacatcct tggtttcatc cgttgcgggc   1560
ggtacctttg atgatgtggc attgggctgg gctgctgccg tggtgatggg ctatttctgc   1620
gctggtggta gtgccatctc aggtgctcat ttgaatccgt ctattacatt agccaatttg   1680
gtgtatagag gttttcccct gaagaaagtt ccttattact ttgctggaca attgatcggt   1740
gccttcacag gcgctttgat cttgtttatt tggtacaaaa gggtgttaca agaggcatat   1800
agcgattggt ggatgaatga aagtgttgcg ggaatgtttt gcgtttttcc aaagccttat   1860
ctaagttcag gacggcaatt tttttccgaa tttttatgtg gagctatgtt acaagcagga   1920
acatttgcgc tgaccgatcc ttatacgtgt ttgtcctctg atgttttccc attgatgatg   1980
tttattttga ttttcattat caatgcttcc atggcttatc agacaggtac agcaatgaat   2040
ttggctcgtg atctgggccc acgtcttgca ctatatgcag ttggatttga tcataaaatg   2100
ctttgggtgc atcatcatca tttcttttgg gttcccatgg taggcccatt tattggtgcg   2160
ttaatggggg ggttggttta cgatgtctgt atttatcagg gtcatgaatc tccagtcaac   2220
tggtctttac cagtttataa ggaaatgatt atgagagcct ggtttagaag gcctggttgg   2280
aagaagagaa atagagcaag aagaacatcg gacctgagtg acttctcata caataacgat   2340
gatgatgagg aatttggaga aagaatggct cttcaaaaga caaagaccaa gtcatctatt   2400
tcagacaacg aaaatgaagc aggagaaaag aaagtgcaat ttaaatctgt tcagcgcggc   2460
```

aaaagaacgt ttggtggtat accaacaatt cttgaagaag aagattccat tgaaactgct 2520
tcgctaggtg cgacgacgac tgattctatt gggttatccg acacatcatc agaagattcg 2580
cattatggta atgctaagaa ggtaacatga gaaaacagac aagaaaaaga aacaaataat 2640
atagactgat agaaaaaaat actgcttact accgccggta taatatatat atatatatat 2700
atttacatag atgattgcat agtgttttaa aaagctttcc taggttaagc tatgaatctt 2760
cataacctaa ccaactaaat atgaaaatac tgacccatcg tcttaagtaa gttgacatga 2820
actcagcctg gtcacctact atacatgatg tatcgcatgg atggaaagaa taccaaacgc 2880
taccttccag gttaatgata gtatccaaac ctagttggaa tttgccttga acatcaagca 2940
gcgattcgat atcagttggg agcatcaatt tggtcattgg aataccatct atgcttttct 3000
cctcccatat tcgcaaaagt agtaagggct cgttatatac ttttgaatat gtaagatata 3060
attctatatg atttagtaat ttattttcta tacgctcagt atttttctgc agttgtcgag 3120
taggtattaa acgcaaaaga agtccatcct tttcatcatt caaatggaca tcttggcaaa 3180
gggcccagtt atggaaaatc tgggagtcat acaacgattg cagttggcta tgccactcct 3240
ggtaaggaat catcaagtct gataattctg ttttttagcc cttttttttt ttttttcatg 3300

<210> SEQ ID NO 105
<211> LENGTH: 1326
<212> TYPE: DNA
<213> ORGANISM: Saccharomyces cerevisiae
<220> FEATURE:
<221> NAME/KEY: misc_feature
<223> OTHER INFORMATION: fps1 delta mutaion
<220> FEATURE:
<221> NAME/KEY: misc_feature
<222> LOCATION: (602)..(636)
<223> OTHER INFORMATION: coding sequence

<400> SEQUENCE: 105
aacgcggctg atgcttttat ttaggaagga atacttacat tatcatgaga acattgtcaa 60
gggcattctg atacgggcct tccatcgcaa gaaaaaggca gcaacggact gagggacgga 120
gagagttacg gcataagaag tagtaggaga gcagagtgtc ataaagttat attattctcg 180
tcctaaagtc aattagttct gttgcgcttg acaatatatg tcgtgtaata ccgtccctta 240
gcagaagaaa gaaagacgga tccatatatg ttaaaatgct tcagagatgt ttctttaatg 300
tgccgtccaa caaaggtatc ttctgtagct tcctctattt tcgatcagat ctcatagtga 360
gaaggcgcaa ttcagtagtt aaaagcgggg aacagtgtga atccggagac ggcaagattg 420
cccggccctt tttgcggaaa agataaaaca agatatattg cactttttcc accaagaaaa 480
acaggaagtg gattaaaaaa tcaacaaagt ataacgccta ttgtcccaat aagcgtcggt 540
tgttcttctt tattatttta ccaagtacgc tcgagggtac attctaatgc attaaaagac 600
gattcgcatt atggtaatgc taagaaggta acatgagaaa acagacaaga aaaagaaaca 660
aataatatag actgatagaa aaaaatactg cttactaccg ccggtataat atatatatat 720
atatatattt acatagatga ttgcatagtg ttttaaaaag ctttcctagg ttaagctatg 780
aatcttcata acctaaccaa ctaaatatga aaatactgac ccatcgtctt aagtaagttg 840
acatgaactc agcctggtca cctactatac atgatgtatc gcatggatgg aaagaatacc 900
aaacgctacc ttccaggtta atgatagtat ccaaacctag ttggaatttg ccttgaacat 960
caagcagcga ttcgatatca gttgggagca tcaatttggt cattggaata ccatctatgc 1020
ttttctcctc ccatattcgc aaaagtagta agggctcgtt atatactttt gaatatgtaa 1080

```
gatataattc tatatgattt agtaatttat tttctatacg ctcagtattt ttctgcagtt    1140

gtcgagtagg tattaaacgc aaaagaagtc catccttttc atcattcaaa tggacatctt    1200

ggcaaagggc ccagttatgg aaaatctggg agtcatacaa cgattgcagt tggctatgcc    1260

actcctggta aggaatcatc aagtctgata attctgtttt ttagcccttt tttttttttt    1320

ttcatg                                                                1326
```

<210> SEQ ID NO 106
<211> LENGTH: 53
<212> TYPE: PRT
<213> ORGANISM: Saccharomyces fibuligera
<220> FEATURE:
<221> NAME/KEY: MISC_FEATURE
<223> OTHER INFORMATION: Sf GA (AE9)

<400> SEQUENCE: 106

```
Asp Asn Lys Asn Arg Tyr Lys Ile Asn Gly Asn Tyr Lys Ala Gly Cys
1               5                   10                  15

Asn Ser Lys Lys His Ile Val Glu Ser Pro Gln Leu Ser Ser Arg Gly
            20                  25                  30

Gly Cys Cys Asp His Ile Asp Asp Asn Gly Gln Leu Thr Glu Glu Ile
        35                  40                  45

Asn Arg Tyr Thr Gly
    50
```

<210> SEQ ID NO 107
<211> LENGTH: 34
<212> TYPE: PRT
<213> ORGANISM: Bifidobacterium adolescentis
<220> FEATURE:
<221> NAME/KEY: MISC_FEATURE
<223> OTHER INFORMATION: Ba pflA

<400> SEQUENCE: 107

```
Cys Gln Asn Pro Asp Thr Trp Lys Met Arg Asp Gly Lys Pro Val Tyr
1               5                   10                  15

Tyr Glu Gly Leu Thr Ser Ser Glu Glu Asn Val Glu Asn Asn Ala Lys
            20                  25                  30

Ile Cys
```

<210> SEQ ID NO 108
<211> LENGTH: 58
<212> TYPE: PRT
<213> ORGANISM: Bifidobacterium adolescentis
<220> FEATURE:
<221> NAME/KEY: MISC_FEATURE
<223> OTHER INFORMATION: Ba pflB

<400> SEQUENCE: 108

```
Trp Glu Gly Phe Thr Glu Gly Asn Trp Gln Lys Asp Ile Asp Val Arg
1               5                   10                  15

Asp Cys Lys Gln Arg Asp Lys Asp Ser Ile Pro Tyr Arg Asn Asp Phe
            20                  25                  30

Thr Glu Cys Pro Glu Cys Cys Asn Thr Ile Thr Pro Asp Gly Leu Gly
        35                  40                  45

Arg Asp Glu Glu Glu Glu Arg Ile Gly Asn
    50                  55
```

<210> SEQ ID NO 109
<211> LENGTH: 53
<212> TYPE: PRT

<213> ORGANISM: Bifidobacterium adolescentis

<400> SEQUENCE: 109

Asp Ala Lys Lys Lys Glu Glu Pro Thr Lys Pro Thr Pro Glu Glu Lys
1               5                   10                  15

Leu Cys Cys Lys Asn Leu Gly Val Asn Pro Gly Lys Thr Pro Glu Glu
            20                  25                  30

Gly Val Glu Asn Cys Gly Ser Tyr Gly Gly Asn Ser Val Ser Gly Val
        35                  40                  45

Asn Gln Ala Val Asn
    50

<210> SEQ ID NO 110
<211> LENGTH: 29
<212> TYPE: DNA
<213> ORGANISM: Artificial Sequence
<220> FEATURE:
<223> OTHER INFORMATION: Primer X11824

<400> SEQUENCE: 110
aagcctacag gcgcaagata acacatcac 29

<210> SEQ ID NO 111
<211> LENGTH: 59
<212> TYPE: DNA
<213> ORGANISM: Artificial Sequence
<220> FEATURE:
<223> OTHER INFORMATION: Primer X15546

<400> SEQUENCE: 111
ggacgaggca agctaaacag atctctagac ctactttata ttatcaatat ttgtgtttg 59

<210> SEQ ID NO 112
<211> LENGTH: 26
<212> TYPE: DNA
<213> ORGANISM: Artificial Sequence
<220> FEATURE:
<223> OTHER INFORMATION: Primer X15380

<400> SEQUENCE: 112
taggtctaga gatctgttta gcttgc 26

<210> SEQ ID NO 113
<211> LENGTH: 23
<212> TYPE: DNA
<213> ORGANISM: Artificial Sequence
<220> FEATURE:
<223> OTHER INFORMATION: Primer X15382

<400> SEQUENCE: 113
gagactacat gatagtccaa aga 23

<210> SEQ ID NO 114
<211> LENGTH: 59
<212> TYPE: DNA
<213> ORGANISM: Artificial Sequence
<220> FEATURE:
<223> OTHER INFORMATION: Primer X15547

<400> SEQUENCE: 114
ccgtttcttt tctttggact atcatgtagt ctcatttatt ggagaaagat aacatatca 59

<210> SEQ ID NO 115
<211> LENGTH: 35

<212> TYPE: DNA
<213> ORGANISM: Artificial Sequence
<220> FEATURE:
<223> OTHER INFORMATION: Primer X11829

<400> SEQUENCE: 115
ctcagcattg atcttagcag attcaggatc taggt 35

<210> SEQ ID NO 116
<211> LENGTH: 29
<212> TYPE: DNA
<213> ORGANISM: Artificial Sequence
<220> FEATURE:
<223> OTHER INFORMATION: Primer X11816

<400> SEQUENCE: 116
gcagtcatca ggatcgtagg agataagca 29

<210> SEQ ID NO 117
<211> LENGTH: 59
<212> TYPE: DNA
<213> ORGANISM: Artificial Sequence
<220> FEATURE:
<223> OTHER INFORMATION: Primer X15548

<400> SEQUENCE: 117
ggacgaggca agctaaacag atctctagac ctatgataag gaaggggagc gaaggaaaa 59

<210> SEQ ID NO 118
<211> LENGTH: 59
<212> TYPE: DNA
<213> ORGANISM: Artificial Sequence
<220> FEATURE:
<223> OTHER INFORMATION: Primer X15549

<400> SEQUENCE: 118
ccgtttcttt tctttggact atcatgtagt ctcctctgat ctttcctgtt gcctctttt 59

<210> SEQ ID NO 119
<211> LENGTH: 30
<212> TYPE: DNA
<213> ORGANISM: Artificial Sequence
<220> FEATURE:
<223> OTHER INFORMATION: Primer X11821

<400> SEQUENCE: 119
tcacaagagt gtgcagaaat aggaggtgga 30

<210> SEQ ID NO 120
<211> LENGTH: 30
<212> TYPE: DNA
<213> ORGANISM: Artificial Sequence
<220> FEATURE:
<223> OTHER INFORMATION: X16096

<400> SEQUENCE: 120
catggtgctt agcagcagat gaaagtgtca 30

<210> SEQ ID NO 121
<211> LENGTH: 59
<212> TYPE: DNA
<213> ORGANISM: Artificial Sequence
<220> FEATURE:
<223> OTHER INFORMATION: Primer X15554

<400> SEQUENCE: 121
ggacgaggca agctaaacag atctctagac ctaattaatt ttcagctgtt atttcgatt 59

<210> SEQ ID NO 122
<211> LENGTH: 59
<212> TYPE: DNA
<213> ORGANISM: Artificial Sequence
<220> FEATURE:
<223> OTHER INFORMATION: Primer X15555

<400> SEQUENCE: 122
ccgtttcttt tctttggact atcatgtagt ctcgagtgat tatgagtatt tgtgagcag 59

<210> SEQ ID NO 123
<211> LENGTH: 30
<212> TYPE: DNA
<213> ORGANISM: Artificial Sequence
<220> FEATURE:
<223> OTHER INFORMATION: Primer X11845

<400> SEQUENCE: 123
ttacttgtga aactgtctcc gctatgtcag 30

<210> SEQ ID NO 124
<211> LENGTH: 25
<212> TYPE: DNA
<213> ORGANISM: Artificial Sequence
<220> FEATURE:
<223> OTHER INFORMATION: Primer X15559

<400> SEQUENCE: 124
ggaaggcacc gatactagaa ctccg 25

<210> SEQ ID NO 125
<211> LENGTH: 59
<212> TYPE: DNA
<213> ORGANISM: Artificial Sequence
<220> FEATURE:
<223> OTHER INFORMATION: Primer X15550

<400> SEQUENCE: 125
gggacgaggc aagctaaaca gatctctaga cctaattaat tttcagctgt tattttgat 59

<210> SEQ ID NO 126
<211> LENGTH: 59
<212> TYPE: DNA
<213> ORGANISM: Artificial Sequence
<220> FEATURE:
<223> OTHER INFORMATION: Primer X15552

<400> SEQUENCE: 126
ccgtttcttt tctttggact atcatgtagt ctcgagtgat tatgagtatt tgtgagcag 59

<210> SEQ ID NO 127
<211> LENGTH: 31
<212> TYPE: DNA
<213> ORGANISM: Artificial Sequence
<220> FEATURE:
<223> OTHER INFORMATION: Primer X15553

<400> SEQUENCE: 127
accagcgtct ggtggacaaa cggccttcaa c 31

<210> SEQ ID NO 128
<211> LENGTH: 24
<212> TYPE: DNA
<213> ORGANISM: Artificial Sequence
<220> FEATURE:
<223> OTHER INFORMATION: Primer X15556

<400> SEQUENCE: 128
ccactcgagg ataggcttga aaga 24

<210> SEQ ID NO 129
<211> LENGTH: 59
<212> TYPE: DNA
<213> ORGANISM: Artificial Sequence
<220> FEATURE:
<223> OTHER INFORMATION: Primer X15870

<400> SEQUENCE: 129
ctaatcaaat caaaataaca gctgaaaatt aatgagtgat tatgagtatt tgtgagcag 59

<210> SEQ ID NO 130
<211> LENGTH: 59
<212> TYPE: DNA
<213> ORGANISM: Artificial Sequence
<220> FEATURE:
<223> OTHER INFORMATION: Primer X15871

<400> SEQUENCE: 130
aaaacttctg ctcacaaata ctcataatca ctcattaatt ttcagctgtt attttgatt 59

<210> SEQ ID NO 131
<211> LENGTH: 59
<212> TYPE: DNA
<213> ORGANISM: Artificial Sequence
<220> FEATURE:
<223> OTHER INFORMATION: Primer X17243

<400> SEQUENCE: 131
tagttagatc agggtaaaaa ttatagatga ggtattaatt ttcagctgtt atttcgatt 59

<210> SEQ ID NO 132
<211> LENGTH: 59
<212> TYPE: DNA
<213> ORGANISM: Artificial Sequence
<220> FEATURE:
<223> OTHER INFORMATION: Primer X16738

<400> SEQUENCE: 132
ctaatcaaat cgaaataaca gctgaaaatt aatacctcat ctataatttt taccctgat 59

<210> SEQ ID NO 133
<211> LENGTH: 59
<212> TYPE: DNA
<213> ORGANISM: Artificial Sequence
<220> FEATURE:
<223> OTHER INFORMATION: Primer X16620

<400> SEQUENCE: 133
tcggatcagt agataacccg cctagaagac taggttacat tgaaaataca gtaaatggt 59

<210> SEQ ID NO 134
<211> LENGTH: 59
<212> TYPE: DNA
<213> ORGANISM: Artificial Sequence
<220> FEATURE:
<223> OTHER INFORMATION: Primer X16621

<400> SEQUENCE: 134
tggtggaacc atttactgta ttttcaatgt aacctagtct tctaggcggg ttatctact 59

<210> SEQ ID NO 135
<211> LENGTH: 59
<212> TYPE: DNA
<213> ORGANISM: Artificial Sequence
<220> FEATURE:
<223> OTHER INFORMATION: Primer X13208

<400> SEQUENCE: 135
ccgaaatatt ccacggttta gaaaaaaatc ggaggtttag acattggctc ttcattgag 59

<210> SEQ ID NO 136
<211> LENGTH: 59
<212> TYPE: DNA
<213> ORGANISM: Artificial Sequence
<220> FEATURE:
<223> OTHER INFORMATION: Primer X13209

<400> SEQUENCE: 136
aagctcaatg aagagccaat gtctaaacct ccgatttttt tctaaaccgt ggaatattt 59

<210> SEQ ID NO 137
<211> LENGTH: 59
<212> TYPE: DNA
<213> ORGANISM: Artificial Sequence
<220> FEATURE:
<223> OTHER INFORMATION: Primer X17242

<400> SEQUENCE: 137
acatcatctt ttaacttgaa tttattctct agctttcaat cattggagca atcatttta 59

<210> SEQ ID NO 138
<211> LENGTH: 59
<212> TYPE: DNA
<213> ORGANISM: Artificial Sequence
<220> FEATURE:
<223> OTHER INFORMATION: Primer X17241

<400> SEQUENCE: 138
gtccatgtaa aatgattgct ccaatgattg aaagctagag aataaattca agttaaaag 59

<210> SEQ ID NO 139
<211> LENGTH: 60
<212> TYPE: DNA
<213> ORGANISM: Artificial Sequence
<220> FEATURE:
<223> OTHER INFORMATION: Primer X16744

<400> SEQUENCE: 139
aaaaacttct gctcacaaat actcataatc actcctactt attcccttcg agattatatc 60

<210> SEQ ID NO 140
<211> LENGTH: 59
<212> TYPE: DNA
<213> ORGANISM: Artificial Sequence
<220> FEATURE:
<223> OTHER INFORMATION: Primer X17244

<400> SEQUENCE: 140
gttcctagat ataatctcga agggaataag taggagtgat tatgagtatt tgtgagcag 59

<210> SEQ ID NO 141
<211> LENGTH: 30
<212> TYPE: DNA
<213> ORGANISM: Artificial Sequence
<220> FEATURE:
<223> OTHER INFORMATION: Primer X11845

<400> SEQUENCE: 141
ttacttgtga aactgtctcc gctatgtcag 30

<210> SEQ ID NO 142
<211> LENGTH: 26
<212> TYPE: DNA
<213> ORGANISM: Artificial Sequence
<220> FEATURE:
<223> OTHER INFORMATION: Primer X15473

<400> SEQUENCE: 142
agtcatcagg atcgtaggag ataagc 26

<210> SEQ ID NO 143
<211> LENGTH: 59
<212> TYPE: DNA
<213> ORGANISM: Artificial Sequence
<220> FEATURE:
<223> OTHER INFORMATION: Primer X17460

<400> SEQUENCE: 143
agaagataat atttttatat aattatatta atcctaatct tcatgtagat ctaattctt 59

<210> SEQ ID NO 144
<211> LENGTH: 59
<212> TYPE: DNA
<213> ORGANISM: Artificial Sequence
<220> FEATURE:
<223> OTHER INFORMATION: Primer X17459

<400> SEQUENCE: 144
cctttccttt tccttcgctc cccttcctta tcaatggcag acgcaaagaa gaaggaaga 59

<210> SEQ ID NO 145
<211> LENGTH: 59
<212> TYPE: DNA
<213> ORGANISM: Artificial Sequence
<220> FEATURE:
<223> OTHER INFORMATION: Primer X17289

<400> SEQUENCE: 145
gtccatgtaa aatgattgct ccaatgattg aaagttacat tgaaaataca gtaaatggt 59

<210> SEQ ID NO 146
<211> LENGTH: 59
<212> TYPE: DNA
<213> ORGANISM: Artificial Sequence
<220> FEATURE:
<223> OTHER INFORMATION: Primer X17290

<400> SEQUENCE: 146
tggtggaacc atttactgta ttttcaatgt aactttcaat cattggagca atcatttta 59

<210> SEQ ID NO 147
<211> LENGTH: 58
<212> TYPE: DNA
<213> ORGANISM: Artificial Sequence
<220> FEATURE:
<223> OTHER INFORMATION: Primer X15735

<400> SEQUENCE: 147
catcttttaa cttgaattta ttctctagcc tagtcttcta ggcgggttat ctactgat 58

<210> SEQ ID NO 148

<211> LENGTH: 59
<212> TYPE: DNA
<213> ORGANISM: Artificial Sequence
<220> FEATURE:
<223> OTHER INFORMATION: Primer X15736

<400> SEQUENCE: 148
agataacccg cctagaagac taggctagag aataaattca agttaaaaga tgatgttga 59

<210> SEQ ID NO 149
<211> LENGTH: 59
<212> TYPE: DNA
<213> ORGANISM: Artificial Sequence
<220> FEATURE:
<223> OTHER INFORMATION: Primer X17457

<400> SEQUENCE: 149
tgggggaaaa agaggcaaca ggaaagatca gagctactta ttcccttcga gattatatc 59

<210> SEQ ID NO 150
<211> LENGTH: 60
<212> TYPE: DNA
<213> ORGANISM: Artificial Sequence
<220> FEATURE:
<223> OTHER INFORMATION: Primer X17458

<400> SEQUENCE: 150
gttcctagat ataatctcga agggaataag tagctctgat ctttcctgtt gcctcttttt 60

<210> SEQ ID NO 151
<211> LENGTH: 26
<212> TYPE: DNA
<213> ORGANISM: Artificial Sequence
<220> FEATURE:
<223> OTHER INFORMATION: Primer X15476

<400> SEQUENCE: 151
gtagatctgc ccagaatgat gacgtt 26

<210> SEQ ID NO 152
<211> LENGTH: 23
<212> TYPE: DNA
<213> ORGANISM: Artificial Sequence
<220> FEATURE:
<223> OTHER INFORMATION: Primer X17826

<400> SEQUENCE: 152
tcgctaacga tcaagaggaa ctg 23

<210> SEQ ID NO 153
<211> LENGTH: 22
<212> TYPE: DNA
<213> ORGANISM: Artificial Sequence
<220> FEATURE:
<223> OTHER INFORMATION: Primer X16944

<400> SEQUENCE: 153
tacacgtgca tttggaccta tc 22

<210> SEQ ID NO 154
<211> LENGTH: 20
<212> TYPE: DNA
<213> ORGANISM: Artificial Sequence
<220> FEATURE:
<223> OTHER INFORMATION: Primer 17413

<400> SEQUENCE: 154
ggattcttcg agagctaaga 20

<210> SEQ ID NO 155
<211> LENGTH: 27
<212> TYPE: DNA
<213> ORGANISM: Artificial Sequence
<220> FEATURE:
<223> OTHER INFORMATION: Primer 15810

<400> SEQUENCE: 155
gacttgcagg gtaggctagc tagaatt 27

<210> SEQ ID NO 156
<211> LENGTH: 20
<212> TYPE: DNA
<213> ORGANISM: Artificial Sequence
<220> FEATURE:
<223> OTHER INFORMATION: Primer 17834

<400> SEQUENCE: 156
gctgcttcga ggtattgaca 20

<210> SEQ ID NO 157
<211> LENGTH: 24
<212> TYPE: DNA
<213> ORGANISM: Artificial Sequence
<220> FEATURE:
<223> OTHER INFORMATION: Primer 14554

<400> SEQUENCE: 157
ggctcttcat tgagcttaga accc 24

<210> SEQ ID NO 158
<211> LENGTH: 21
<212> TYPE: DNA
<213> ORGANISM: Artificial Sequence
<220> FEATURE:
<223> OTHER INFORMATION: Primer 16291

<400> SEQUENCE: 158
aactggaccg atcttattcg t 21

<210> SEQ ID NO 159
<211> LENGTH: 25
<212> TYPE: DNA
<213> ORGANISM: Artificial Sequence
<220> FEATURE:
<223> OTHER INFORMATION: Primer 15229

<400> SEQUENCE: 159
agtccactgc ggagtcattt caaag 25

<210> SEQ ID NO 160
<211> LENGTH: 25
<212> TYPE: DNA
<213> ORGANISM: Artificial Sequence
<220> FEATURE:
<223> OTHER INFORMATION: Primer 16503

<400> SEQUENCE: 160
ctgccagcga attcgactct gcaat 25

<210> SEQ ID NO 161
<211> LENGTH: 30
<212> TYPE: DNA

<213> ORGANISM: Artificial Sequence
<220> FEATURE:
<223> OTHER INFORMATION: Primer 11317

<400> SEQUENCE: 161
cagtcgctgt agtgagcgac agggtagtaa 30

<210> SEQ ID NO 162
<211> LENGTH: 19
<212> TYPE: DNA
<213> ORGANISM: Artificial Sequence
<220> FEATURE:
<223> OTHER INFORMATION: Primer 16241

<400> SEQUENCE: 162
ctttgcatta gcatgcgta 19

<210> SEQ ID NO 163
<211> LENGTH: 23
<212> TYPE: DNA
<213> ORGANISM: Artificial Sequence
<220> FEATURE:
<223> OTHER INFORMATION: Primer 16946

<400> SEQUENCE: 163
taggtcgaga ccagaatgca tgt 23

<210> SEQ ID NO 164
<211> LENGTH: 22
<212> TYPE: DNA
<213> ORGANISM: Artificial Sequence
<220> FEATURE:
<223> OTHER INFORMATION: Primer 16939

<400> SEQUENCE: 164
atgctgatgc atgtccacaa ag 22

<210> SEQ ID NO 165
<211> LENGTH: 23
<212> TYPE: DNA
<213> ORGANISM: Artificial Sequence
<220> FEATURE:
<223> OTHER INFORMATION: Primer 16940

<400> SEQUENCE: 165
ccttatcagt caattgagga aag 23

<210> SEQ ID NO 166
<211> LENGTH: 23
<212> TYPE: DNA
<213> ORGANISM: Artificial Sequence
<220> FEATURE:
<223> OTHER INFORMATION: Primer 16807

<400> SEQUENCE: 166
gcgatgagct aatcctgagc cat 23

<210> SEQ ID NO 167
<211> LENGTH: 24
<212> TYPE: DNA
<213> ORGANISM: Artificial Sequence
<220> FEATURE:
<223> OTHER INFORMATION: Primer 14567

<400> SEQUENCE: 167
tggttccacc attattatgt tggt 24

<210> SEQ ID NO 168
<211> LENGTH: 20
<212> TYPE: DNA
<213> ORGANISM: Artificial Sequence
<220> FEATURE:
<223> OTHER INFORMATION: Primer 17834

<400> SEQUENCE: 168
gctgcttcga ggtattgaca 20

<210> SEQ ID NO 169
<211> LENGTH: 25
<212> TYPE: DNA
<213> ORGANISM: Artificial Sequence
<220> FEATURE:
<223> OTHER INFORMATION: Primer 14557

<400> SEQUENCE: 169
ctaaaccgtg gaatatttcg gatat 25

<210> SEQ ID NO 170
<211> LENGTH: 23
<212> TYPE: DNA
<213> ORGANISM: Artificial Sequence
<220> FEATURE:
<223> OTHER INFORMATION: Primer 16640

<400> SEQUENCE: 170
cctcatcagc tctggaacaa cga 23

<210> SEQ ID NO 171
<211> LENGTH: 24
<212> TYPE: DNA
<213> ORGANISM: Artificial Sequence
<220> FEATURE:
<223> OTHER INFORMATION: Primer 14552

<400> SEQUENCE: 171
gatccgagct tccactagga tagc 24

<210> SEQ ID NO 172
<211> LENGTH: 22
<212> TYPE: DNA
<213> ORGANISM: Artificial Sequence
<220> FEATURE:
<223> OTHER INFORMATION: Primer 17586

<400> SEQUENCE: 172
gcagtatgca agtctcatgc tg 22

<210> SEQ ID NO 173
<211> LENGTH: 23
<212> TYPE: DNA
<213> ORGANISM: Artificial Sequence
<220> FEATURE:
<223> OTHER INFORMATION: Primer 16806

<400> SEQUENCE: 173
gaacttgcag gcaccgatct tca 23

<210> SEQ ID NO 174
<211> LENGTH: 27
<212> TYPE: DNA
<213> ORGANISM: Artificial Sequence
<220> FEATURE:

<223> OTHER INFORMATION: Primer 13092

<400> SEQUENCE: 174
ccacaccata gacttcagcc ttcttag 27

<210> SEQ ID NO 175
<211> LENGTH: 22
<212> TYPE: DNA
<213> ORGANISM: Artificial Sequence
<220> FEATURE:
<223> OTHER INFORMATION: Primer 17586

<400> SEQUENCE: 175
gcagtatgca agtctcatgc tg 22

<210> SEQ ID NO 176
<211> LENGTH: 25
<212> TYPE: DNA
<213> ORGANISM: Artificial Sequence
<220> FEATURE:
<223> OTHER INFORMATION: Primer 10871

<400> SEQUENCE: 176
cgttcgctgt agcatactta gctat 25

<210> SEQ ID NO 177
<211> LENGTH: 24
<212> TYPE: DNA
<213> ORGANISM: Artificial Sequence
<220> FEATURE:
<223> OTHER INFORMATION: Primer 14554

<400> SEQUENCE: 177
ggctcttcat tgagcttaga accc 24

<210> SEQ ID NO 178
<211> LENGTH: 21
<212> TYPE: DNA
<213> ORGANISM: Artificial Sequence
<220> FEATURE:
<223> OTHER INFORMATION: Primer 16291

<400> SEQUENCE: 178
aactggaccg atcttattcg t 21

<210> SEQ ID NO 179
<211> LENGTH: 21
<212> TYPE: DNA
<213> ORGANISM: Artificial Sequence
<220> FEATURE:
<223> OTHER INFORMATION: Primer 17887

<400> SEQUENCE: 179
actgcctcat tgatggtggt a 21

<210> SEQ ID NO 180
<211> LENGTH: 23
<212> TYPE: DNA
<213> ORGANISM: Artificial Sequence
<220> FEATURE:
<223> OTHER INFORMATION: Primer 16640

<400> SEQUENCE: 180
cctcatcagc tctggaacaa cga 23

<210> SEQ ID NO 181
<211> LENGTH: 23
<212> TYPE: DNA
<213> ORGANISM: Artificial Sequence
<220> FEATURE:
<223> OTHER INFORMATION: Primer 16509

<400> SEQUENCE: 181
gtatgattgc ggttatctgt cgc 23

<210> SEQ ID NO 182
<211> LENGTH: 22
<212> TYPE: DNA
<213> ORGANISM: Artificial Sequence
<220> FEATURE:
<223> OTHER INFORMATION: Primer 13246

<400> SEQUENCE: 182
cctatggatg ttgtaccatg cc 22

<210> SEQ ID NO 183
<211> LENGTH: 28
<212> TYPE: DNA
<213> ORGANISM: Artificial Sequence
<220> FEATURE:
<223> OTHER INFORMATION: Primer 13095

<400> SEQUENCE: 183
ccaatatctt gcagtccatc ctcgtcgc 28

<210> SEQ ID NO 184
<211> LENGTH: 31
<212> TYPE: DNA
<213> ORGANISM: Artificial Sequence
<220> FEATURE:
<223> OTHER INFORMATION: Primer X18868

<400> SEQUENCE: 184
gccaaagtgg attctcctac tcaagctttg c 31

<210> SEQ ID NO 185
<211> LENGTH: 59
<212> TYPE: DNA
<213> ORGANISM: Artificial Sequence
<220> FEATURE:
<223> OTHER INFORMATION: Primer X18844

<400> SEQUENCE: 185
tcggatcagt agataacccg cctagaagac tagtagctat gaaattttta actctttaa 59

<210> SEQ ID NO 186
<211> LENGTH: 59
<212> TYPE: DNA
<213> ORGANISM: Artificial Sequence
<220> FEATURE:
<223> OTHER INFORMATION: Primer X18845

<400> SEQUENCE: 186
agccagctta aagagttaaa aatttcatag ctactagtct tctaggcggg ttatctact 59

<210> SEQ ID NO 187
<211> LENGTH: 59
<212> TYPE: DNA
<213> ORGANISM: Artificial Sequence
<220> FEATURE:
<223> OTHER INFORMATION: Primer X15464

-continued

```
<400> SEQUENCE: 187

gtccatgtaa aatgattgct ccaatgattg aaagaggttt agacattggc tcttcattg      59


<210> SEQ ID NO 188
<211> LENGTH: 59
<212> TYPE: DNA
<213> ORGANISM: Artificial Sequence
<220> FEATURE:
<223> OTHER INFORMATION: Primer X15465

<400> SEQUENCE: 188

ctaagctcaa tgaagagcca atgtctaaac ctctttcaat cattggagca atcattta      59


<210> SEQ ID NO 189
<211> LENGTH: 59
<212> TYPE: DNA
<213> ORGANISM: Artificial Sequence
<220> FEATURE:
<223> OTHER INFORMATION: Primer X11750

<400> SEQUENCE: 189

ataaaattaa atacgtaaat acagcgtgct gcgtgctcga tttttttcta aaccgtgga      59


<210> SEQ ID NO 190
<211> LENGTH: 26
<212> TYPE: DNA
<213> ORGANISM: Artificial Sequence
<220> FEATURE:
<223> OTHER INFORMATION: Primer X15479

<400> SEQUENCE: 190

agcacgcagc acgctgtatt tacgta                                          26


<210> SEQ ID NO 191
<211> LENGTH: 30
<212> TYPE: DNA
<213> ORGANISM: Artificial Sequence
<220> FEATURE:
<223> OTHER INFORMATION: Primer X18869

<400> SEQUENCE: 191

agatcctgtg gtagtgctgt ctgaacagaa                                      30
```

METHODS FOR THE IMPROVEMENT OF PRODUCT YIELD AND PRODUCTION IN A MICROORGANISM THROUGH THE ADDITION OF ALTERNATE ELECTRON ACCEPTORS

CROSS REFERENCE TO RELATED APPLICATION

The present invention application is a continuation of U.S. application Ser. No. 14/110,075, filed Mar. 21, 2014, which is a 371 National Stage Application of International Application No. PCT/US2012/032443, filed Apr. 5, 2012, which claims the benefit of U.S. Provisional Application No. 61/472,085. The entire contents of each are incorporated herein by reference in their entirety.

BACKGROUND OF THE INVENTION

Sequence Listing

This application contains a sequence listing which is submitted under 37 CFR §1.821(c) in an electronic form as the text file 177CRFSeqList.txt, created on Apr. 30, 2015, the size of which is 437,476 bytes and the content of which is incorporated by reference.

The conversion of biomass, such as corn, sugarcane or other energy crops, as well as simple sugars, to ethanol is routinely completed through the use of yeast fermentation. However, during yeast metabolism a major byproduct of fermentation is glycerol. Glycerol is formed during anaerobic growth as a way for the yeast to balance its redox state and regenerate $NAD^+$ used as a cofactor during glycolysis. It has been shown that the function of glycerol is likely not as a metabolite itself but rather as an electron sink capturing electrons allowing further growth-linked metabolism to continue. As glycerol is a byproduct with low value, it can be an undesirable by-product of fermentation. It would be beneficial to reduce or eliminate this by-product and further direct more carbon towards desired end-products, such as ethanol.

Several strategies are available in the art for the conversion of glycerol to higher value products though biochemical or other means, but relatively little has been demonstrated for the removal or reduction of glycerol and improvement of overall sugar yield to ethanol or other desired end-products of metabolism. Through engineering of alternate pathways, potentially with the simultaneous reduction or deletion of the glycerol pathway, alternate or replacement electron acceptors for the regeneration of $NAD^+$ can be used during yeast metabolism. Such alternate or replacement electron acceptors could be molecules such as formate or hydrogen.

The elimination of glycerol synthesis genes has been demonstrated but removal of this pathway completely blocked anaerobic growth of the yeast, preventing useful application during an industrial process. Ansell, R., et al., *EMBO J.* 16:2179-87 (1997); Pahlman, A-K., et al., *J. Biol. Chem.* 276:3555-63 (2001); Guo, Z P., et al., *Metab. Eng.* 13:49-59 (2011). Other methods to bypass glycerol formation require the co-utilization of additional carbon sources, such as xylose or acetate, to serve as electron acceptors. Lidén, G., et al., *Appl. Env. Microbiol.* 62:3894-96 (1996); Medina, V. G., et al., *Appl. Env. Microbiol.* 76:190-195 (2010). By incorporating a formate pathway as an alternate electron acceptor, glycerol formation can be bypassed and ethanol yield can be increased. The engineering of a pyruvate formate lyase from *E. coli*, which is capable of converting pyruvate to formate, has been done to increase formate production. Waks, Z., and Silver, P. A., *Appl. Env. Microbiol.* 75:1867-1875 (2009). Formate engineering in Waks and Silver was done, however, to provide a source of formate in *S. cerevisiae* for the production of hydrogen by a secondary microorganism, *E. coli*. Waks and Silver did not combine formate production with the removal of glycerol formation, and the use of formate as an alternate electron acceptor for the reduction of glycerol was not proposed or evaluated. Thus, despite prior efforts to bypass and/or eliminate glycerol production, there exists a need for the engineering of alternate or replacement electron acceptors in a cell to direct more carbon towards desired end-products, such as ethanol.

The importance of engineering alternate or replacement electron acceptors is exemplified in the process of corn mash fermentation. About 16 billion gallons of corn-based ethanol are produced annually, so even small increases in ethanol yield, such as 5-10%, can translate into an extra billion or so gallons of ethanol over current yields. Ethanol production from corn mash typically results in glycerol yields ranging from 10-12 g/L. See Yang, R. D., et al., "Pilot plant studies of ethanol production from whole ground corn, corn flour, and starch," Fuel Alcohol U.S.A., Feb. 13-16, 1982 (reported glycerol levels to be as high as 7.2% w/w of initial sugar consumed in normal corn mash fermentations or approximately 1.4 g/100 mL using 20% sugar). By reducing or eliminating the glycerol yield in the production of ethanol from corn and re-engineering metabolic processes, increased ethanol yields can be achieved. Additional benefits may be gained in the production of ethanol from corn. Corn mash is a nutrient rich medium, in some cases containing lipid and protein content that can be >3% of the total fermentation volume. As a result of the energy contained in these components, even higher ethanol yields may be achieved than what is predicted using, for example, pure sugar. The additional increases can come from the metabolism of lipids or amino acids in the corn mash medium. The recombinant cells and methods of the invention enable increasing ethanol yields from biomass fermentation by reducing or eliminating glycerol.

BRIEF SUMMARY OF THE INVENTION

The invention is generally directed to the reduction or removal of glycerol production in a host cell and to the engineering of an alternate electron acceptor for the regeneration of $NAD^+$.

One aspect of the invention relates to a recombinant microorganism comprising: a deletion of one or more native enzymes that function to produce glycerol and/or regulate glycerol synthesis; and one or more native and/or heterologous enzymes that function in one or more engineered metabolic pathways to convert a carbohydrate source to ethanol, wherein said one or more native and/or heterologous enzymes is activated, upregulated or downregulated. In some embodiments, the recombinant microorganism produces less glycerol than a control recombinant microorganism without deletion of said one or more native enzymes that function to produce glycerol and/or regulate glycerol synthesis. In some embodiments, the carbohydrate source is biomass. In some embodiments, the biomass comprises a lignocellulosic material selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, agave, and combinations thereof. In some embodiments, the biomass is corn mash or corn starch.

In particular aspects, the one or more native enzymes that function to produce glycerol are encoded by a gpd1 polynucleotide, a gpd2 polynucleotide, or both a gpd1 polynucleotide and a gpd2 polynucleotide. In certain embodiments, the recombinant microorganism further comprises a native and/or heterologous gpd1 polynucleotide operably linked to a native gpd2 promoter polynucleotide. In other aspects, the one or more native enzymes that function to produce glycerol are encoded by a gpp1 polynucleotide, a gpp2 polynucleotide, or both a gpp1 polynucleotide and a gpp2 polynucleotide.

In particular aspects, the one or more native enzymes that function to regulate glycerol synthesis are encoded by an fps1 polynucleotide.

In further aspects, the engineered metabolic pathways comprise conversion of pyruvate to acetyl-CoA and formate. In certain embodiments, pyruvate is converted to acetyl-CoA and formate by a pyruvate formate lyase (PFL). In some embodiments, the PFL is of prokaryotic or eukaryotic origin. In some embodiments, PFL is from one or more of a *Bifidobacteria*, an *Escherichia*, a *Thermoanaerobacter*, a *Clostridia*, a *Streptococcus*, a *Lactobacillus*, a *Chlamydomonas*, a *Piromyces*, a *Neocallimastix*, or a *Bacillus* species. In some embodiments, PFL is from one or more of a *Bacillus licheniformis*, a *Streptococcus thermophilus*, a *Lactobacillus plantarum*, a *Lactobacillus casei*, a *Bifidobacterium adolescentis*, a *Clostridium cellulolyticum*, a *Escherichia coli*, a *Chlamydomonas reinhardtii* PflA, a *Piromyces* sp. E2, or a *Neocallimastix frontalis*. In one embodiment, PFL is from a *Bifidobacterium adolescentis*.

In additional aspects, the engineered metabolic pathways comprise conversion of acetyl-CoA to ethanol. In certain embodiments, acetyl-CoA is converted to acetaldehyde by an acetaldehyde dehydrogenase and acetaldehyde is converted to ethanol by an alcohol dehydrogenase. In certain embodiments, acetyl-CoA is converted to ethanol by a bifunctional acetaldehyde/alcohol dehydrogenase. In some embodiments, the acetaldehyde dehydrogenase, alcohol dehydrogenase, or bifuntional acetaldehyde/alcohol dehydrogenase is of prokaryotic or eukaryotic origin. In one embodiment, acetaldehyde dehydrogenase is from *C. phytofermentans*. In some embodiments, bifunctional acetaldehyde/alcohol dehydrogenase is from an *Escherichia*, a *Clostridia*, a *Chlamydomonas*, a *Piromyces*, or a *Bifidobacteria* species. In some embodiments, bifunctional acetaldehyde/alcohol dehydrogenase is from *Escherichia coli, Clostridium phytofermentans, Chlamydomonas reinhardtii, Piromyces* sp. E2, or *Bifidobacterium adolescentis*. In one embodiment, bifunctional acetaldehyde/alcohol dehydrogenase is from a *Bifidobacterium adolescentis* or *Piromyces* sp. E2.

In further aspects, the recombinant microorganism comprises a deletion of one or more native enzymes encoded by an fdh1 polynucleotide, an fdh2 polynucleotide, or both an fdh1 polynucleotide and an fdh2 polynucleotide.

In certain embodiments, the carbohydrate source for the recombinant microorganism is lignocellulose. In certain embodiments, the recombinant microorganism produces ethanol. In certain embodiments, the recombinant microorganism produces formate.

In certain embodiments, the recombinant microorganism is selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utliis, Arxula adeninivorans, Pichia stipitis, Debaryomyces hansenii, Debaryomyces polymorphus, Schizosaccharomyces pombe, Candida albicans, and Schwanniomyces occidentalis*. In one embodiment, the recombinant microorganism is *Saccharomyces cerevisiae*.

In certain embodiments, the recombinant microorganism comprises one or more native enzymes that function to produce glycerol encoded by both a gpd1 polynucleotide and a gpd2 polynucleotide, an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to produce glycerol encoded by both a gpp1 polynucleotide and a gpp2 polynucleotide, an engineered metabolic pathway that comprises conversion of pyruvate to acetyl-CoA and formate by a pyruvate formate lyase. In further embodiments, one engineered metabolic pathway of the recombinant microorganism converts acetyl-CoA to ethanol by a bifunctional acetaldehyde/alcohol dehydrogenase and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to regulate glycerol synthesis encoded by an fps1 polynucleotide, an engineered metabolic pathway that comprises conversion of pyruvate to acetyl-CoA and formate by a pyruvate formate lyase. In further embodiments, one engineered metabolic pathway of the recombinant microorganism converts acetyl-CoA to ethanol by a bifunctional acetaldehyde/alcohol dehydrogenase and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to regulate glycerol synthesis encoded by an fps1 polynucleotide and one or more native enzymes that function to produce glycerol encoded by both a gpd1 polynucleotide and a gpd2 polynucleotide, and an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to regulate glycerol synthesis encoded by an fps1 polynucleotide, an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, and the recombinant microorganism further comprises a deletion of one or more native enzymes encoded by both an fdh1 polynucleotide and an fdh2 polynucleotide.

In certain embodiments, the recombinant microorganism comprises one or more native enzymes that function to produce glycerol encoded by both a gpd1 polynucleotide and a gpd2 polynucleotide, an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, and the recombinant microorganism further comprises a native and/or heterologous gpd1 polynucleotide operably linked to a native gpd2 promoter polynucleotide.

In certain embodiments, the recombinant microorganism comprises one or more native enzymes that function to produce glycerol encoded by both a gpd1 polynucleotide and a gpd2 polynucleotide, and an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide and a deletion of one or more native enzymes encoded by both an fdh1 polynucleotide and an fdh2 polynucleotide.

In certain embodiments, the recombinant microorganism comprises one or more native enzymes that function to produce glycerol encoded by both a gpd1 polynucleotide and a gpd2 polynucleotide and one or more native enzymes that function to regulate glycerol synthesis encoded by an fps1 polynucleotide, and an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide.

In certain embodiments, the recombinant microorganism comprises one or more native enzymes that function to produce glycerol encoded by both a gpd1 polynucleotide and a gpd2 polynucleotide and one or more native enzymes that function to regulate glycerol synthesis encoded by an fps1 polynucleotide, and an engineered metabolic pathway that comprises conversion of pyruvate to acetyl-CoA and formate by a pyruvate formate lyase and an engineered metabolic pathway that comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide and a deletion of one or more native enzymes encoded by both an fdh1 polynucleotide and an fdh2 polynucleotide.

In some embodiments, the deletion of one or more native enzymes that function to produce glycerol and/or regulate glycerol synthesis in the recombinant microorganism reduces glycerol formation by: more than about 10% of the glycerol produced by a recombinant microorganism without a deletion of one or more native enzymes that function to produce glycerol and/or regulate glycerol synthesis; more than about 20% of the glycerol produced by a recombinant microorganism without a deletion of one or more native enzymes that function to produce glycerol and/or regulate glycerol synthesis; more than about 30% of the glycerol produced by a recombinant microorganism without a deletion of one or more native enzymes that function to produce glycerol and/or regulate glycerol synthesis; more than about 40% of the glycerol produced by a recombinant microorganism without a deletion of one or more native enzymes that function to produce glycerol and/or regulate glycerol synthesis; more than about 50% of the glycerol produced by a recombinant microorganism without a deletion of one or more native enzymes that function to produce glycerol and/or regulate glycerol synthesis; more than about 60% of the glycerol produced by a recombinant microorganism without a deletion of one or more native enzymes that function to produce glycerol and/or regulate glycerol synthesis; more than about 70% of the glycerol produced by a recombinant microorganism without a deletion of one or more native enzymes that function to produce glycerol and/or regulate glycerol synthesis; more than about 80% of the glycerol produced by a recombinant microorganism without a deletion of one or more native enzymes that function to produce glycerol and/or regulate glycerol synthesis; more than about 90% of the glycerol produced by a recombinant microorganism without a deletion of one or more native enzymes that function to produce glycerol and/or regulate glycerol synthesis; more than about 95% of the glycerol produced by a recombinant microorganism without a deletion of one or more native enzymes that function to produce glycerol and/or regulate glycerol synthesis; or more than about 99% of the glycerol produced by a recombinant microorganism without a deletion of one or more native enzymes that function to produce glycerol and/or regulate glycerol synthesis.

In some embodiments, the recombinant microorganism produces an amount of formate selected from: at least about 0.012 g/L in 24 hours; at least about 0.022 g/L in 48 hours; or at least about 2.5 g/L in 142 hours.

In some embodiments, the recombinant microorganism produces a formate yield selected from: at least about 0.05-fold more formate than is produced by a recombinant microorganism without activation, upregulation, or downregulation of one or more native and/or heterologous enzymes; at least about 0.1-fold more formate than is produced by a recombinant microorganism without activation, upregulation, or downregulation of one or more native and/or heterologous enzymes; at least about 0.5-fold more formate than is produced by a recombinant microorganism without activation, upregulation, or downregulation of one or more native and/or heterologous enzymes; at least about 1.0-fold more formate than is produced by a recombinant microorganism without activation, upregulation, or downregulation of one or more native and/or heterologous enzymes; at least about 5.0-fold more formate than is produced by a recombinant microorganism without activation, upregulation, or downregulation of one or more native and/or heterologous enzymes; at least about 10.0-fold more formate than is produced by a recombinant microorganism without activation, upregulation, or downregulation of one or more native and/or heterologous enzymes; at least about 20.0-fold more formate than is produced by a recombinant microorganism without activation, upregulation, or downregulation of one or more native and/or heterologous enzymes; at least about 30.0-fold more formate than is produced by a recombinant microorganism without activation, upregulation, or downregulation of one or more native and/or heterologous enzymes; at least about 40.0-fold more formate than is produced by a recombinant microorganism without activation, upregulation, or downregulation of one or more native and/or heterologous enzymes; at least about 50.0-fold more formate than is produced by a recombinant microorganism without activation, upregulation, or downregulation of one or more native and/or heterologous enzymes; at least about 75.0-fold more formate than is produced by a recombinant microorganism without activation, upregulation, or downregulation of one or more native and/or heterologous enzymes; or at least about 100-fold more formate than is produced by a recombinant microorganism without activation, upregulation, or downregulation of one or more native and/or heterologous enzymes.

In some embodiments, the recombinant microorganism produces an ethanol yield selected from: at least about 1% more ethanol than is produced by a recombinant microorganism without activation, upregulation, or downregulation of one or more native and/or heterologous enzymes; at least about 2% more ethanol than is produced by a recombinant microorganism without activation, upregulation, or downregulation of one or more native and/or heterologous enzymes; at least about 3% more ethanol than is produced by a recombinant microorganism without activation, upregulation, or downregulation of one or more native and/or heterologous enzymes; at least about 4% more ethanol than is produced by a recombinant microorganism without activation, upregulation, or downregulation of one or more native and/or heterologous enzymes; at least about 5% more ethanol than is produced by a recombinant microorganism without activation, upregulation, or downregulation of one or more native and/or heterologous enzymes; at least about 10% more ethanol than is produced by a recombinant microorganism without activation, upregulation, or downregulation of one or more native and/or heterologous enzymes; at least about 20% more ethanol than is produced by a recombinant microorganism without activation, upregulation, or downregulation of one or more native and/or heterologous enzymes; at least about 30% more ethanol than is produced by a recombinant microorganism without activation, upregulation, or downregulation of one or more native and/or heterologous enzymes; at least about 40% more ethanol than is produced by a recombinant microorganism without activation, upregulation, or downregulation of one or more native and/or heterologous enzymes; at least about 50% more ethanol than is produced by a recombinant microorganism without activation, upregulation, or downregulation of one or more native and/or heterologous enzymes; at least about 60% more ethanol than is produced by a recombinant microorganism without activation, upregulation, or downregulation of one or more native and/or heterologous enzymes; at least about 70% more ethanol than is produced by a recombinant microorganism without activation, upregulation, or downregulation of one or more native and/or heterologous enzymes; at least about 80% more ethanol than is produced by a recombinant microorganism without activation, upregulation, or downregulation of one or more native and/or heterologous enzymes; at least about 90% more ethanol than is produced by a recombinant microorganism without activation, upregulation, or downregulation of one or more native and/or heterologous enzymes; at least about 95% more ethanol than is produced by a recombinant microorganism without activation, upregulation, or downregulation of one or more native and/or heterologous enzymes; or at least about 99% more ethanol than is produced by a recombinant microorganism without activation, upregulation, or downregulation of one or more native and/or heterologous enzymes.

In some embodiments, the conversion of the carbohydrate source to ethanol by the recombinant microorganism, or the enzymes engineered therein, is under anaerobic conditions.

In some embodiments, the recombinant microorganism has an acetate uptake (g/L) under anaerobic conditions selected from: at least about 1% more acetate uptake than that taken up by a recombinant microorganism without activation, upregulation, or downregulation of one or more native and/or heterologous enzymes; at least about 10% more acetate uptake than that taken up by a recombinant microorganism without activation, upregulation, or downregulation of one or more native and/or heterologous enzymes; at least about 20% more acetate uptake than that taken up by a recombinant microorganism without activation, upregulation, or downregulation of one or more native and/or heterologous enzymes; at least about 30% more acetate uptake than that taken up by a recombinant microorganism without activation, upregulation, or downregulation of one or more native and/or heterologous enzymes; at least about 40% more acetate uptake than that taken up by a recombinant microorganism without activation, upregulation, or downregulation of one or more native and/or heterologous enzymes; at least about 50% more acetate uptake than that taken up by a recombinant microorganism without activation, upregulation, or downregulation of one or more native and/or heterologous enzymes; at least about 60% more acetate uptake than that taken up by a recombinant microorganism without activation, upregulation, or downregulation of one or more native and/or heterologous enzymes; at least about 70% more acetate uptake than that taken up by a recombinant microorganism without activation, upregulation, or downregulation of one or more native and/or heterologous enzymes; at least about 80% more acetate uptake than that taken up by a recombinant microorganism without activation, upregulation, or downregulation of one or more native and/or heterologous enzymes; and at least about 90% more acetate uptake than that taken up by a recombinant microorganism without activation, upregulation, or downregulation of one or more native and/or heterologous enzymes.

In some embodiments, the recombinant microorganism produces more ethanol at a slower glucose utilization rate compared to a recombinant microorganism without deletion of one or more native enzymes that function to produce glycerol and/or regulate glycerol synthesis, wherein the glucose utilization rate is selected from: at least about 1% less glucose used per hour than that used by a recombinant microorganism without activation, upregulation, or downregulation of one or more native and/or heterologous enzymes; at least about 5% less glucose used per hour than that used by a recombinant microorganism without activation, upregulation, or downregulation of one or more native and/or heterologous enzymes; at least about 10% less glucose used per hour than that used by a recombinant microorganism without activation, upregulation, or downregulation of one or more native and/or heterologous enzymes; at least about 20% less glucose used per hour than that used by a recombinant microorganism without activation, upregulation, or downregulation of one or more native and/or heterologous enzymes; at least about 30% less glucose used per hour than that used by a recombinant microorganism without activation, upregulation, or downregulation of one or more native and/or heterologous enzymes; at least about 40% less glucose used per hour than that used by a recombinant microorganism without activation, upregulation, or downregulation of one or more native and/or heterologous enzymes; at least about 50% less glucose used per hour than that used by a recombinant microorganism without activation, upregulation, or downregulation of one or more native and/or heterologous enzymes; at least about 60% less glucose used per hour than that used by a recombinant microorganism without activation, upregulation, or downregulation of one or more native and/or heterologous enzymes; at least about 70% less glucose used per hour than that used by a recombinant microorganism without activation, upregulation, or downregulation of one or more native and/or heterologous enzymes; at least about 80% less glucose used per hour than that used by a recombinant microorganism without activation, upregulation, or downregulation of one or more native and/or heterologous enzymes; and at least about 90% less glucose used per hour than that used by a recombinant microorganism without activation, upregulation, or downregulation of one or more native and/or heterologous enzymes.

Another aspect of the invention relates to a recombinant microorganism comprising: one or more heterologous enzymes that function to regulate glycerol synthesis, wherein said one or more heterologous enzymes is activated, upregulated or downregulated; and one or more native and/or heterologous enzymes that function in one or more engineered metabolic pathways to convert a carbohydrate source to ethanol, wherein said one or more native and/or heterologous enzymes is activated, upregulated or downregulated. In certain embodiments, the one or more heterologous enzymes that function to regulate glycerol synthesis are encoded by an fps1 polynucleotide. In one embodiment, the fps1 polynucleotide is from *Escherichia coli.*

In some embodiments, one of the engineered metabolic pathways of the above recombinant microorganism comprises conversion of pyruvate to acetyl-CoA and formate. In certain embodiments, pyruvate is converted to acetyl-CoA and formate by a pyruvate formate lyase (PFL). In some embodiments, PFL is of prokaryotic or eukaryotic origin. In some embodiments, PFL is from one or more of a *Bifidobacteria*, an *Escherichia*, a *Thermoanaerobacter*, a *Clostridia*, a *Streptococcus*, a *Lactobacillus*, a *Chlamydomonas*, a *Piromyces*, a *Neocallimastix*, or a *Bacillus* species. In some embodiments, the PFL is from one or more of a *Bacillus licheniformis*, a *Streptococcus thermophilus*, a *Lactobacillus plantarum*, a *Lactobacillus casei*, a *Bifidobacterium adolescentis*, a *Clostridium cellulolyticum*, a *Escherichia coli*, a *Chlamydomonas reinhardtii* PflA, a *Piromyces* sp. E2, or a *Neocallimastix frontalis*. In one embodiment, PFL is from a *Bifidobacterium adolescentis.*

In some embodiments, one of said engineered metabolic pathways of the above recombinant microorganism comprises conversion of acetyl-CoA to ethanol. In some embodiments, acetyl-CoA is converted to acetaldehyde by an acetaldehyde dehydrogenase and acetaldehyde is converted to ethanol by an alcohol dehydrogenase. In other embodiments, acetyl-CoA is converted to ethanol by a bifunctional acetaldehyde/alcohol dehydrogenase. In some embodiments, the acetaldehyde dehydrogenase, alcohol dehydrogenase, or bifuntional acetaldehyde/alcohol dehydrogenase is of prokaryotic or eukaryotic origin. In one embodiment, acetaldehyde dehydrogenase is from *C. phytofermentans*. In certain embodiments, the bifunctional acetaldehyde/alcohol dehydrogenase is from an *Escherichia*, a *Clostridia*, a *Chlamydomonas*, a *Piromyces*, or a *Bifidobacteria* species. In some embodiments, the bifunctional acetaldehyde/alcohol dehydrogenase is from *Escherichia coli, Clostridium phytofermentans, Chlamydomonas reinhardtii, Piromyces* sp. E2, or *Bifidobacterium adolescentis*. In one embodiment, the bifunctional acetaldehyde/alcohol dehydrogenase is from a *Bifidobacterium adolescentis* or *Piromyces* sp. E2.

In further aspects, the recombinant microorganism comprises a deletion of one or more native enzymes encoded by an fdh1 polynucleotide, an fdh2 polynucleotide, or both an fdh1 polynucleotide and an fdh2 polynucleotide.

In some embodiments, the recombinant microorganism produces ethanol. In other embodiments, the recombinant microorganism produces formate. In some embodiments, the recombinant microorganism is selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utliis, Arxula adeninivorans, Pichia stipitis, Debaryomyces hansenii, Debaiyomyces polymorphus, Schizosaccharomyces pombe, Candida albicans*, and *Schwanniomyces occidentalis*. In one embodiment, the recombinant microorganism is *Saccharomyces cerevisiae.*

In some embodiments, the recombinant microorganisms of the invention further comprise one or more native and/or heterologous enzymes that function in one or more engineered metabolic pathways to convert xylose to xylulose-5-phosphate and/or arabinose to xylulose-5-phosphate, wherein the one or more native and/or heterologous enzymes are activated, upregulated or downregulated.

In some embodiments, the recombinant microorganisms of the invention further comprise one or more native and/or heterologous enzymes which encodes a saccharolytic enzyme, including amylases, cellulases, hemicellulases, cellulolytic and amylolytic accessory enzymes, inulinases, levanases, and pentose sugar utilizing enzymes. In one aspect, the saccharolytic enzyme is an amylase, where the amylase is selected from *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum* or *Arabidopsis thaliana*. In another aspect, the saccharolytic enzyme is an amylase from *S. fibuligera* glucoamylase (glu-0111-CO).

Another aspect of the invention relates to a method for decreasing cellular glycerol comprising contacting biomass with a recombinant microorganism of the invention. A further aspect of the invention relates to a method for increasing cytosolic formate comprising contacting biomass with a recombinant microorganism of the invention. Another aspect of the invention relates to a process for converting biomass to ethanol comprising contacting biomass with a recombinant microorganism of the invention. In some embodiments, the biomass comprises lignocellulosic biomass. In some embodiments, the lignocellulosic biomass is selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, agave, and combinations thereof. In some embodiments, the biomass is corn mash or corn starch.

In another aspect, the present invention also describes industrial yeast strains that express enzymes for the production of fuel ethanol from corn starch.

BRIEF DESCRIPTION OF THE DRAWINGS/FIGURES

DETAILED DESCRIPTION OF THE INVENTION

Definitions

Figure 1:
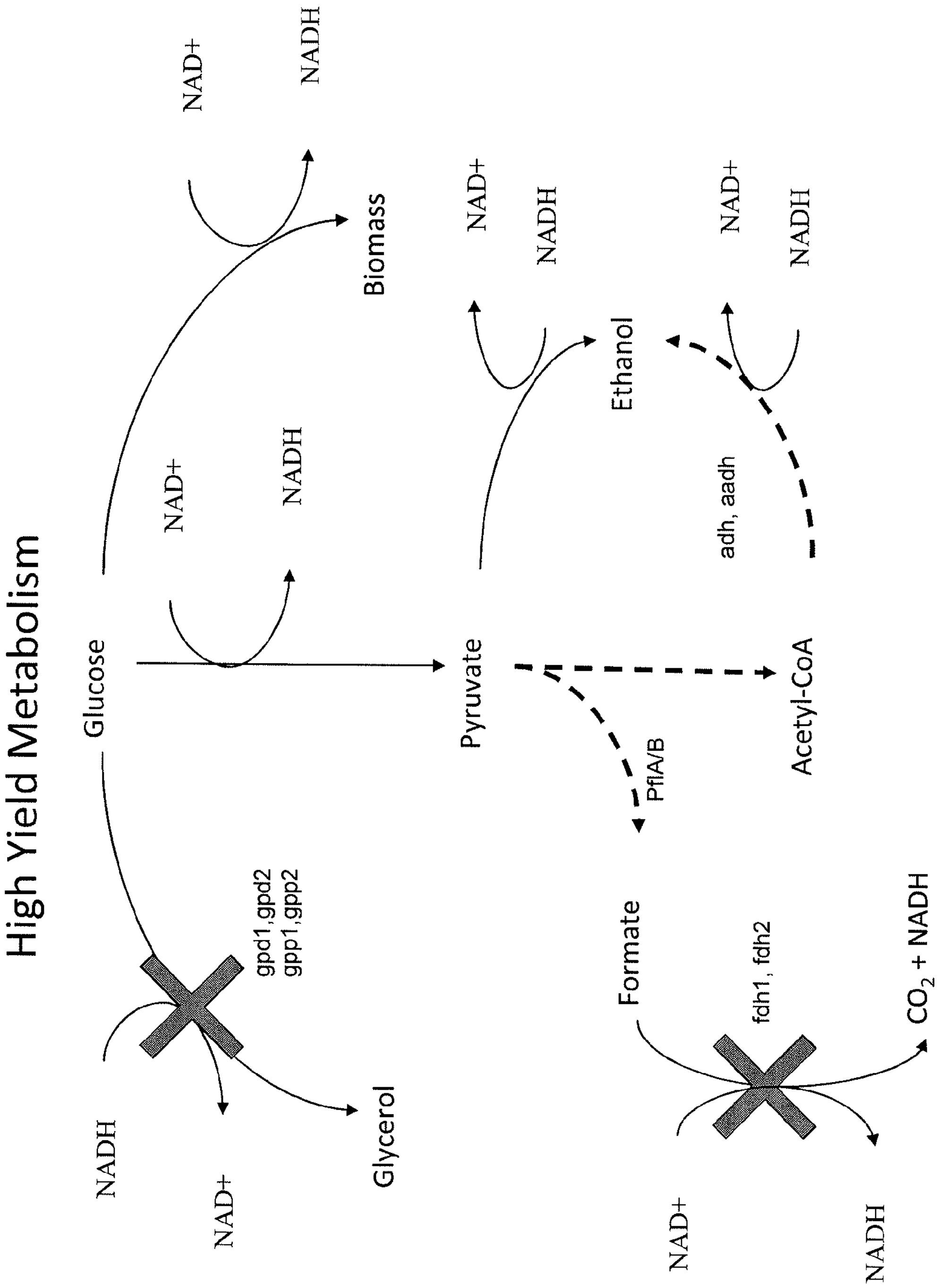
FIG. 1 shows a schematic of high yield metabolism.
Figure 2:
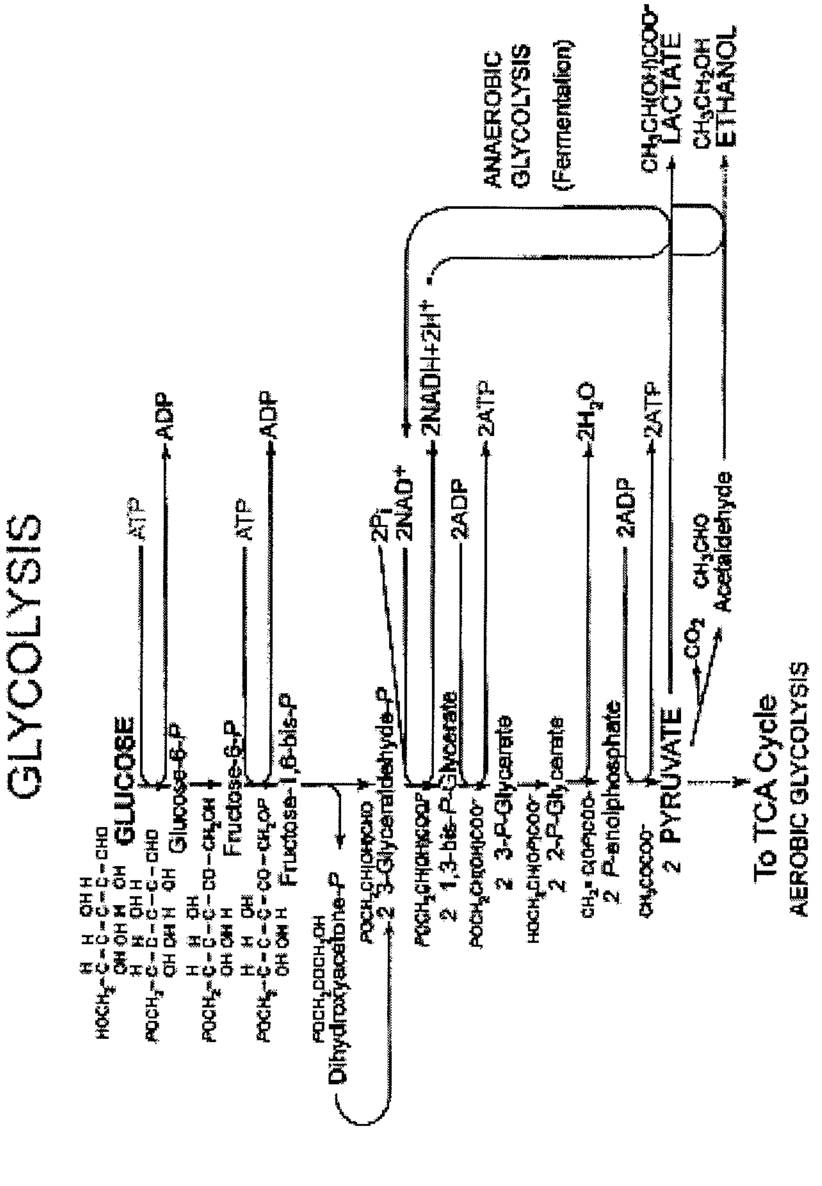
FIG. 2 depicts the glycolysis pathway.
Figure 3:
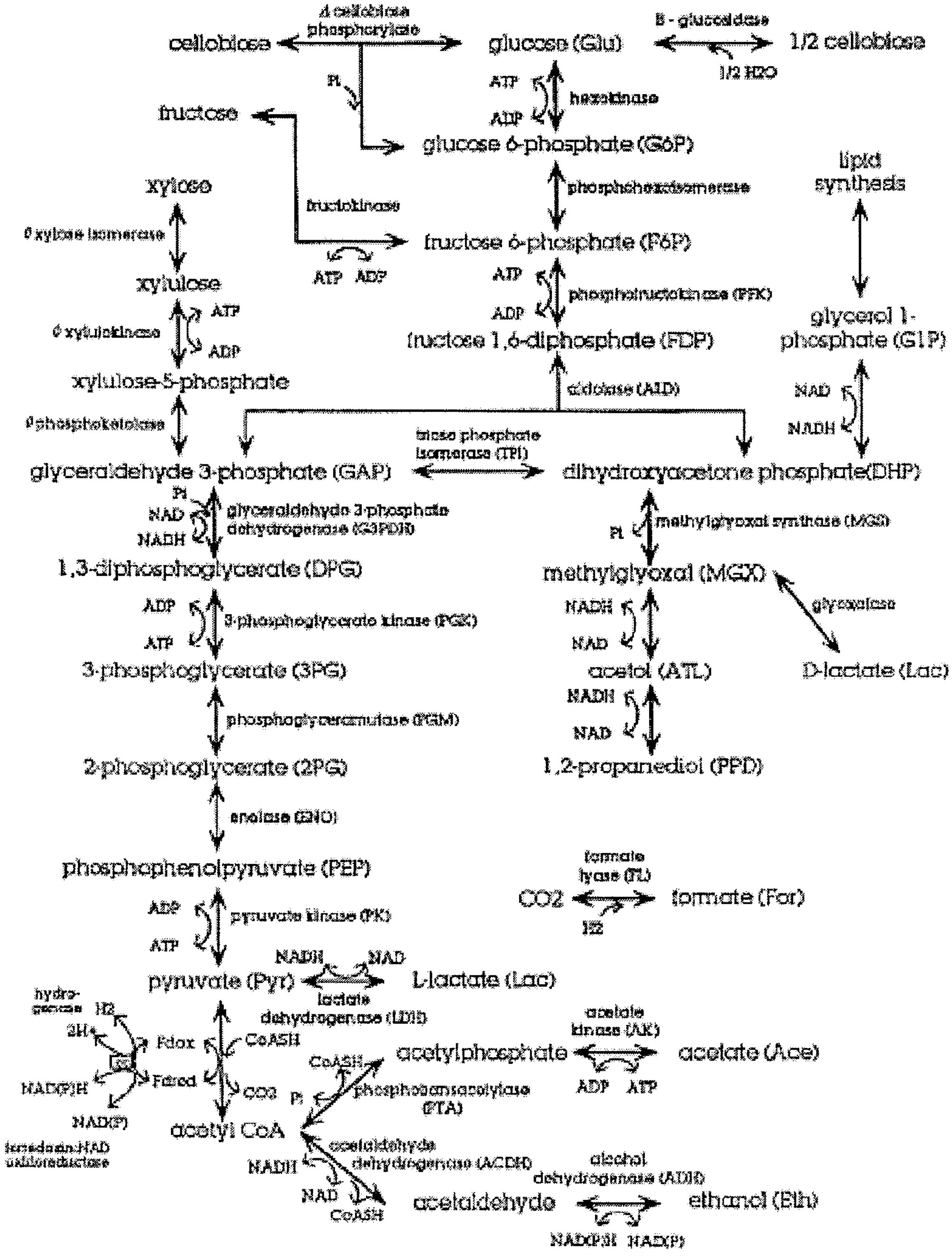
FIG. 3 shows a schematic of the glycolysis/fermentation pathway.
Figure 4:
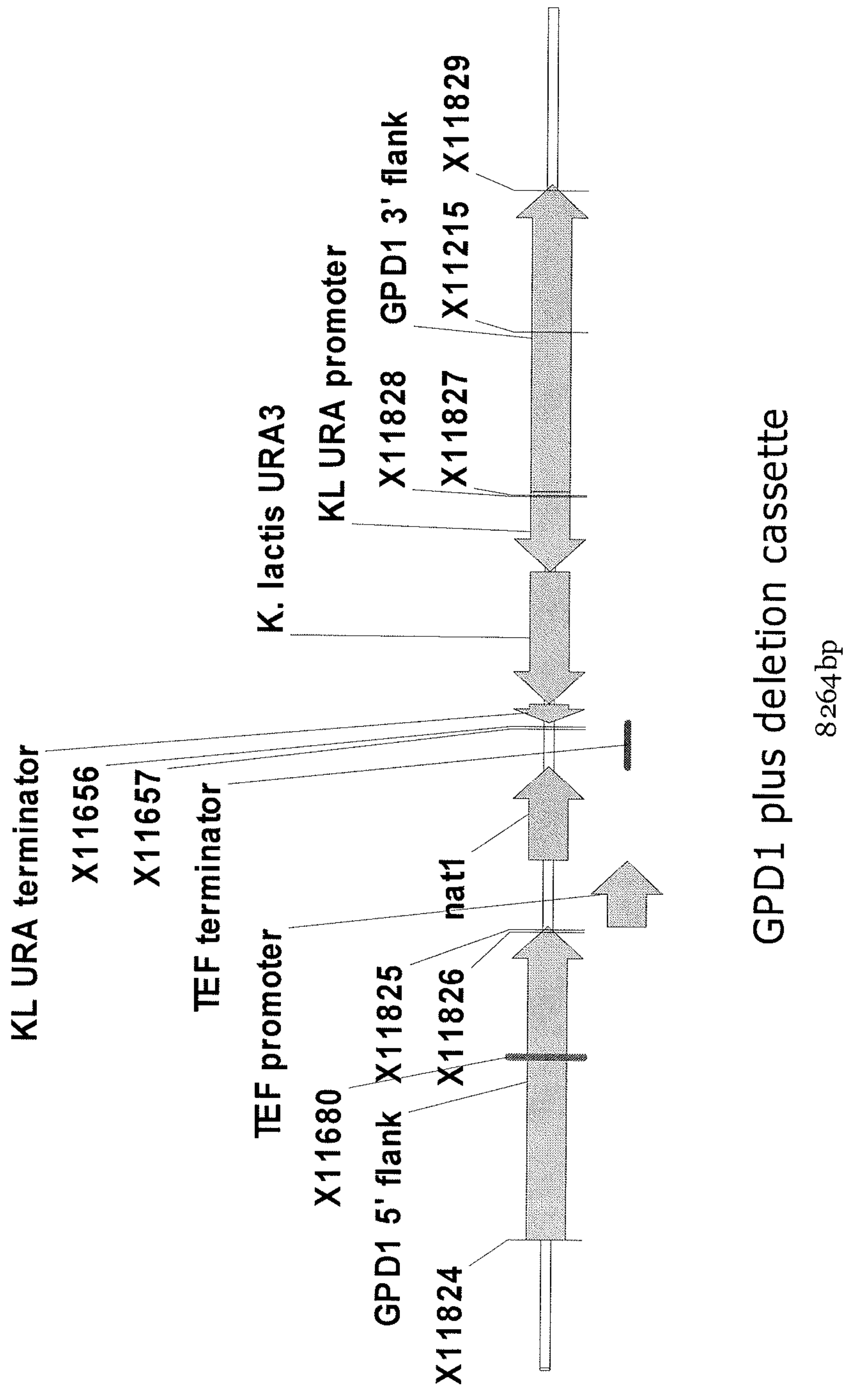
FIG. 4 shows a map depicting location of primers used to make marked deletion of GPD1.
Figure 5:
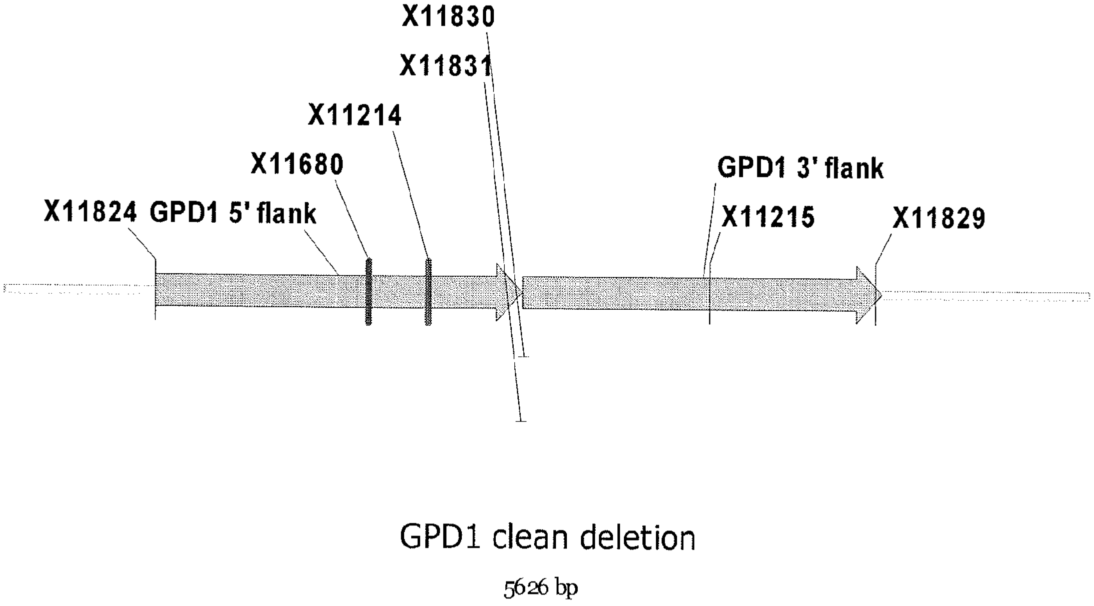
FIG. 5 shows a map depicting location of primers used to remove marker from GPD1 locus.
Figure 6:
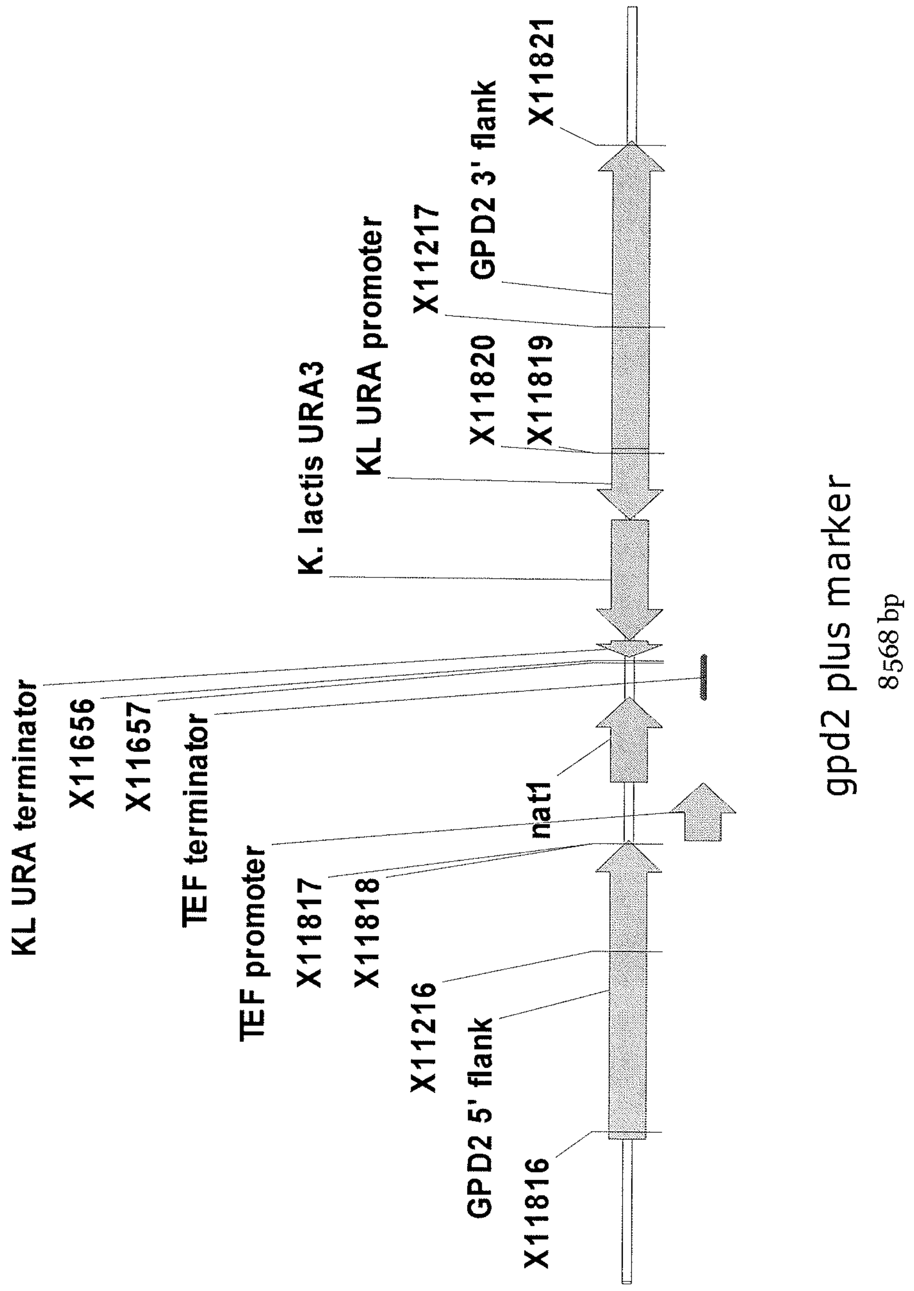
FIG. 6 shows a map depicting location of primers used to make marked deletion of GPD2.
Figure 7:
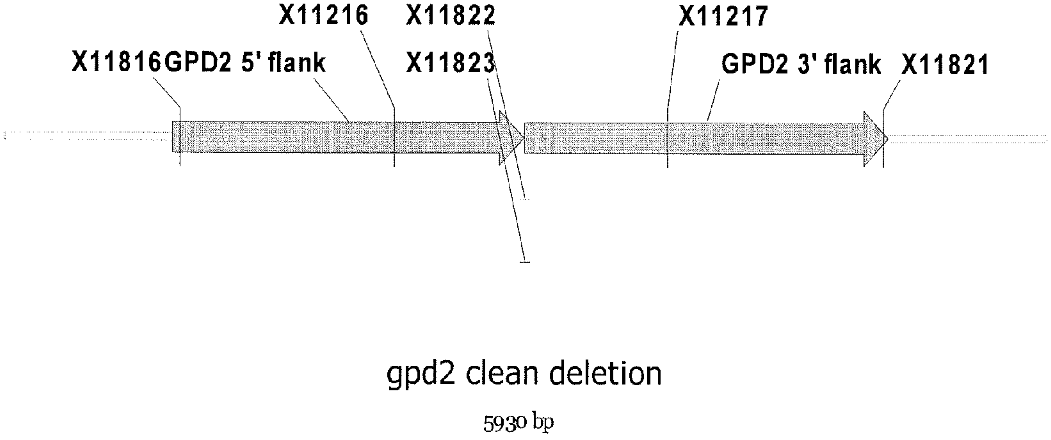
FIG. 7 shows a map depicting location of primers used to remove marker from GPD2 locus.
Figure 8:
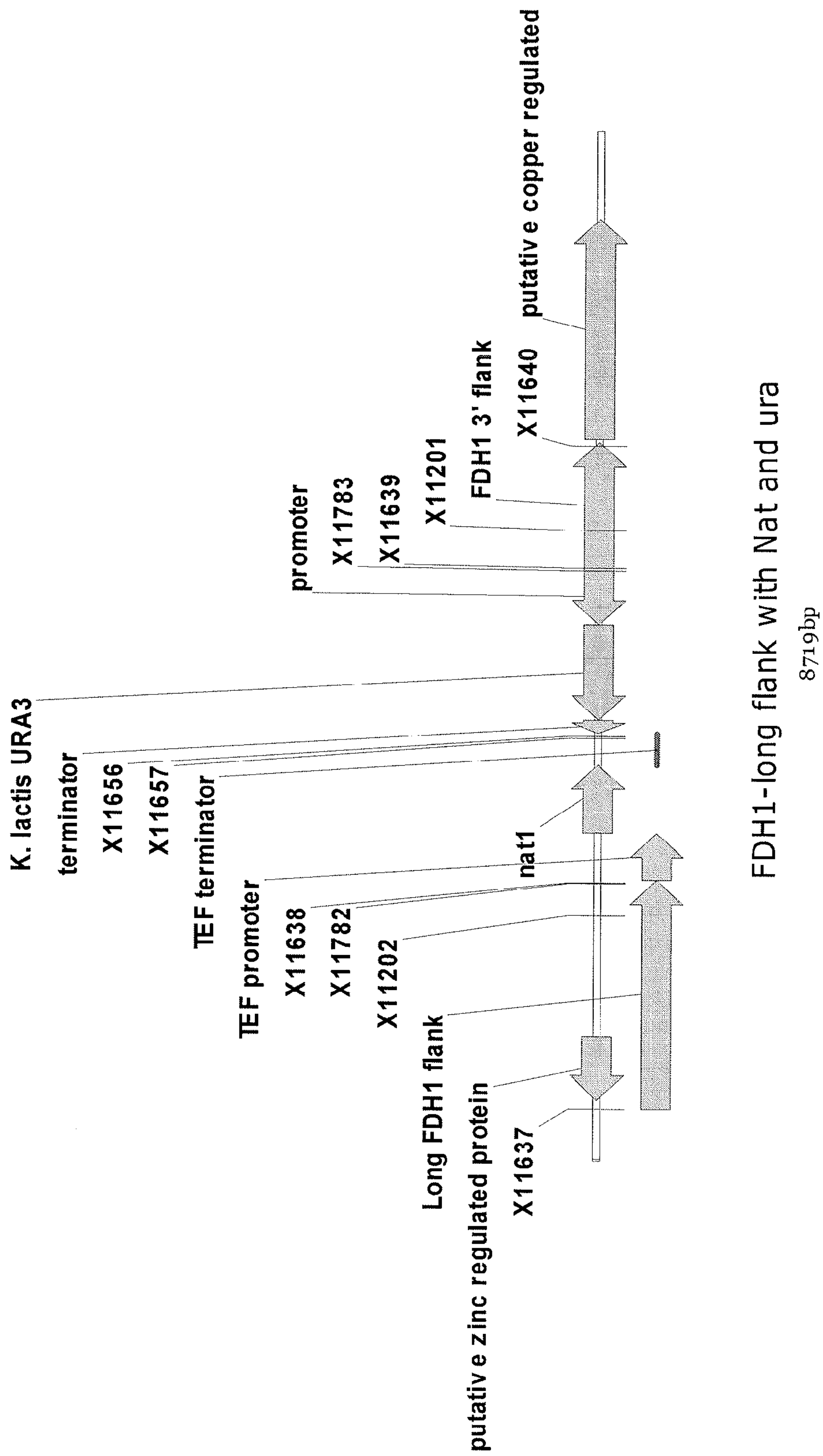
FIG. 8 shows a map depicting location of primers used to make marked deletion of FDH1.
Figure 9:
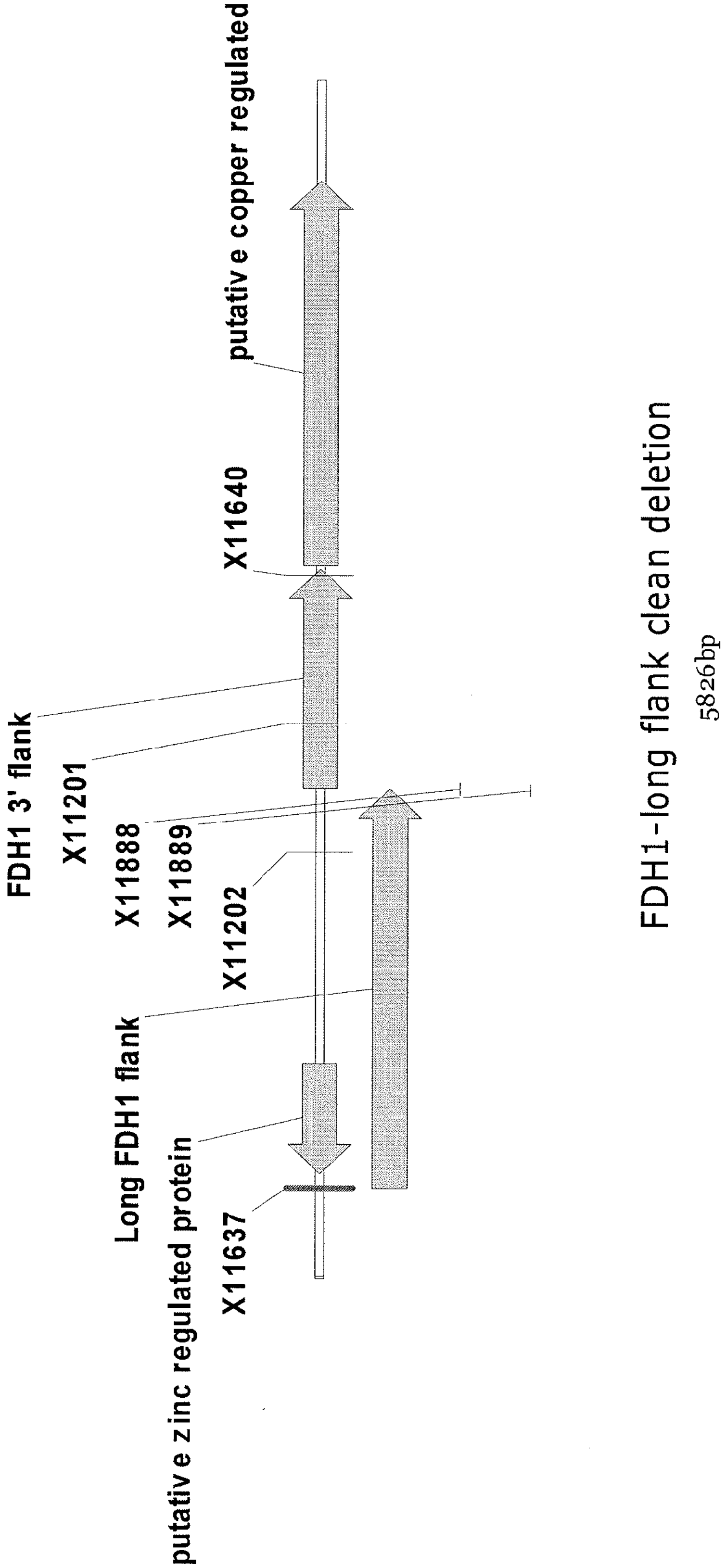
FIG. 9 shows a map depicting location of primers used to remove marker from FDH1 locus.
Figure 10:
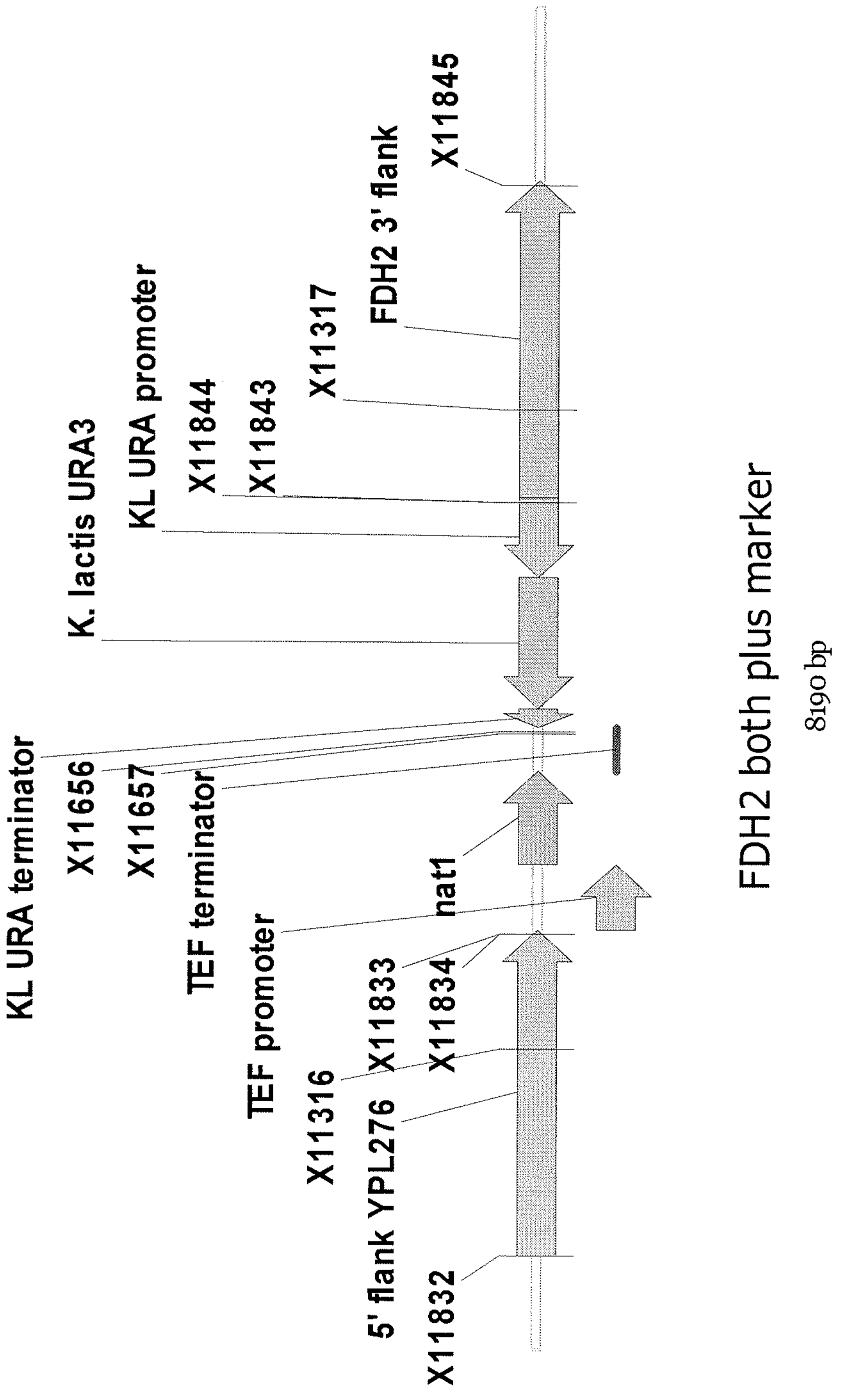
FIG. 10 shows a map depicting location of primers used to make marked deletion of FDH2.
Figure 11:
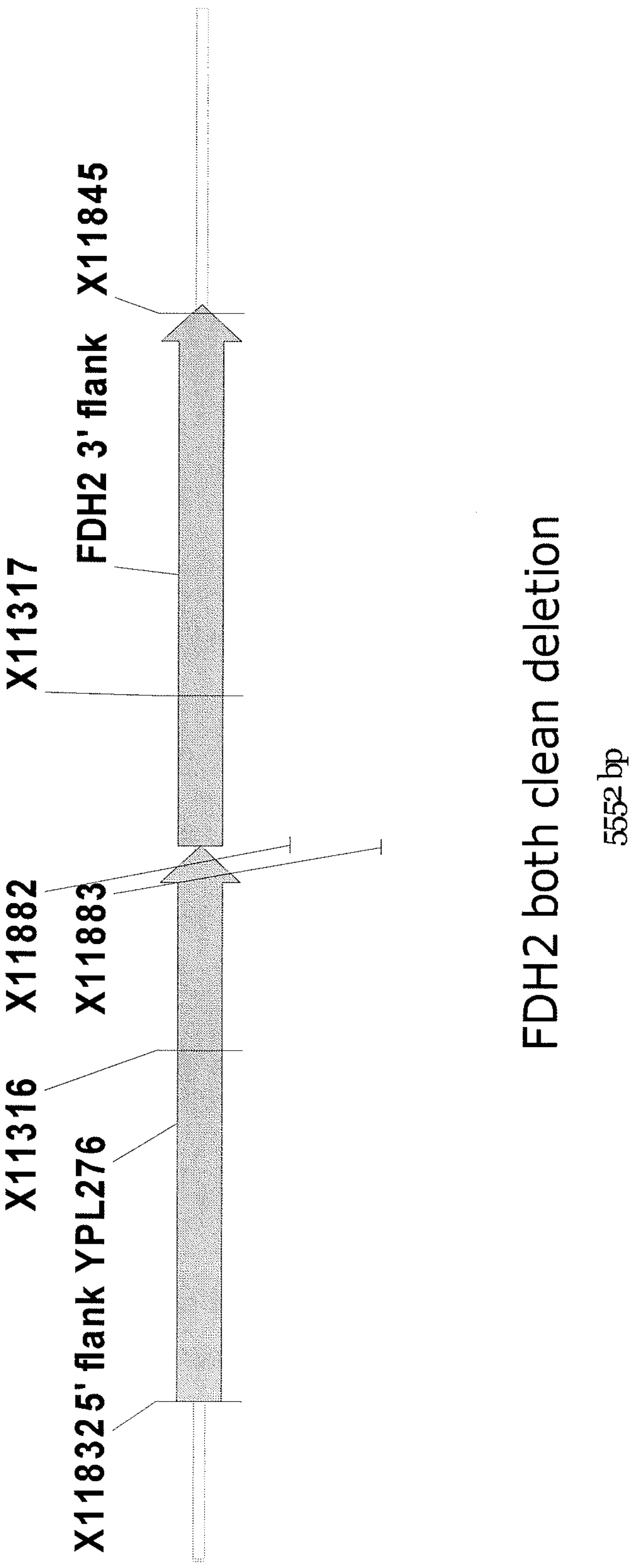
FIG. 11 shows a map depicting location of primers used to remove marker from FDH2 locus.

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes.

The term "heterologous polynucleotide" is intended to include a polynucleotide that encodes one or more polypeptides or portions or fragments of polypeptides. A heterologous polynucleotide may be derived from any source, e.g., eukaryotes, prokaryotes, viruses, or synthetic polynucleotide fragments.

The terms "promoter" or "surrogate promoter" is intended to include a polynucleotide that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. In certain embodiments, the gene or polynucleotide is involved in at least one step in the bioconversion of biomass to, e.g., ethanol. Accordingly, the term is intended to include any gene encoding a polypeptide, such as the enzymes acetate kinase (ACK), phosphotransacetylase (PTA), lactate dehydrogenase (LDH), pyruvate formate lyase (PFL), aldehyde dehydrogenase (ADH) and/or alcohol dehydrogenase (ADH), acetyl-CoA transferase (ACS), acetaldehyde dehydrogenase (ACDH), acetaldehyde/alcohol dehydrogenase (AADH), glycerol-3-phosphate dehydrogenase (GPD), glycerol 3-phosphatase (GPP), acetyl-CoA synthetase, thiolase, CoA transferase, acetoacetate decarboxylase, alcohol acetyltransferase enzymes in the D-xylose pathway, such as xylose isomerase and xylulokinase, enzymes in the L-arabinose pathway, such as L-arabinose isomerase and L-ribulose-5-phosphate 4-epimerase. The term gene is also intended to cover all copies of a particular gene, e.g., all of the DNA sequences in a cell encoding a particular gene product.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more genes is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product, e.g., a polypeptide, of an expressed gene.

The term "increased expression" is intended to include an alteration in gene expression at least at the level of increased mRNA production and, preferably, at the level of polypeptide expression. The term "increased production" is intended to include an increase in the amount of a polypeptide expressed, in the level of the enzymatic activity of the polypeptide, or a combination thereof, as compared to the native production of, or the enzymatic activity, of the polypeptide.

The terms "activity," "activities," "enzymatic activity," and "enzymatic activities" are used interchangeably and are intended to include any functional activity normally attributed to a selected polypeptide when produced under favorable conditions. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "xylanolytic activity" is intended to include the ability to hydrolyze glycosidic linkages in oligopentoses and polypentoses.

The term "arabinolytic activity" is intended to include the ability to hydrolyze glycosidic linkages in oligopentoses and polypentoses.

The term "cellulolytic activity" is intended to include the ability to hydrolyze glycosidic linkages in oligohexoses and polyhexoses. Cellulolytic activity may also include the ability to depolymerize or debranch cellulose and hemicellulose.

As used herein, the term "lactate dehydrogenase" or "LDH" is intended to include the enzymes capable of converting pyruvate into lactate. It is understood that LDH can also catalyze the oxidation of hydroxybutyrate. LDH includes those enzymes that correspond to Enzyme Commission Number 1.1.1.27.

As used herein the term "alcohol dehydrogenase" or "ADH" is intended to include the enzymes capable of converting acetaldehyde into an alcohol, such as ethanol. ADH also includes the enzymes capable of converting acetone to isopropanol. ADH includes those enzymes that correspond to Enzyme Commission Number 1.1.1.1.

As used herein, the term "phosphotransacetylase" or "PTA" is intended to include the enzymes capable of converting acetyl-phosphate into acetyl-CoA. PTA includes those enzymes that correspond to Enzyme Commission Number 2.3.1.8.

As used herein, the term "acetate kinase" or "ACK" is intended to include the enzymes capable of converting acetate into acetyl-phosphate. ACK includes those enzymes that correspond to Enzyme Commission Number 2.7.2.1.

As used herein, the term "pyruvate formate lyase" or "PFL" is intended to include the enzymes capable of converting pyruvate into acetyl-CoA and formate. PFL includes those enzymes that correspond to Enzyme Commission Number 2.3.1.54.

As used herein, the term "formate dehydrogenase" or "FDH" is intended to include the enzymes capable of converting formate and $NAD^+$ to NADH and $CO_2$. FDH includes those enzymes that correspond to Enzyme Commission Number 1.2.1.2.

As used herein, the term "acetaldehyde dehydrogenase" or "ACDH" is intended to include the enzymes capable of converting acetyl-CoA to acetaldehyde. ACDH includes those enzymes that correspond to Enzyme Commission Number 1.2.1.3.

As used herein, the term "acetaldehyde/alcohol dehydrogenase" is intended to include the enzymes capable of converting acetyl-CoA to ethanol. Acetaldehyde/alcohol dehydrogenase includes those enzymes that correspond to Enzyme Commission Numbers 1.2.1.10 and 1.1.1.1.

As used herein, the term "glycerol-3-phosphate dehydrogenase" or "GPD" is intended to include the enzymes capable of converting dihydroxyacetone phosphate to glycerol-3-phosphate. GPD includes those enzymes that correspond to Enzyme Commission Number 1.1.1.8.

As used herein, the term "glycerol 3-phosphatase" or "GPP" is intended to include the enzymes capable of converting glycerol 3-phosphate to glycerol. GPP includes those enzymes that correspond to Enzyme Commission Number 3.1.3.21.

As used herein, the term "acetyl-CoA synthetase" or "ACS" is intended to include the enzymes capable of converting acetate to acetyl-CoA. Acetyl-CoA synthetase includes those enzymes that correspond to Enzyme Commission Number 6.2.1.1.

As used herein, the term "thiolase" is intended to include the enzymes capable of converting acetyl-CoA to acetoacetyl-CoA. Thiolase includes those enzymes that correspond to Enzyme Commission Number 2.3.1.9.

As used herein, the term "CoA transferase" is intended to include the enzymes capable of converting acetate and acetoacetyl-CoA to acetoacetate and acetyl-CoA. CoA transferase includes those enzymes that correspond to Enzyme Commission Number 2.8.3.8.

As used herein, the term "acetoacetate decarboxylase" is intended to include the enzymes capable of converting acetoacetate to acetone and carbon dioxide. Acetoacetate decarboxylase includes those enzymes that correspond to Enzyme Commission Number 4.1.1.4.

As used herein, the term "alcohol acetyltransferase" is intended to include the enzymes capable of converting acetyl-CoA and ethanol to ethyl acetate. Alcohol acetyltransferase includes those enzymes that correspond to Enzyme Commission Number 2.3.1.84.

The term "pyruvate decarboxylase activity" is intended to include the ability of a polypeptide to enzymatically convert pyruvate into acetaldehyde and carbon dioxide (e.g., "pyruvate decarboxylase" or "PDC"). Typically, the activity of a selected polypeptide encompasses the total enzymatic activity associated with the produced polypeptide, comprising, e.g., the superior substrate affinity of the enzyme, thermostability, stability at different pHs, or a combination of these attributes. PDC includes those enzymes that correspond to Enzyme Commission Number 4.1.1.1.

The term "ethanologenic" is intended to include the ability of a microorganism to produce ethanol from a carbohydrate as a fermentation product. The term is intended to include, but is not limited to, naturally occurring ethanologenic organisms, ethanologenic organisms with naturally occurring or induced mutations, and ethanologenic organisms which have been genetically modified.

The terms "fermenting" and "fermentation" are intended to include the enzymatic process (e.g., cellular or acellular, e.g., a lysate or purified polypeptide mixture) by which ethanol is produced from a carbohydrate, in particular, as a product of fermentation.

The term "secreted" is intended to include the movement of polypeptides to the periplasmic space or extracellular milieu. The term "increased secretion" is intended to include situations in which a given polypeptide is secreted at an increased level (i.e., in excess of the naturally-occurring amount of secretion). In certain embodiments, the term "increased secretion" refers to an increase in secretion of a given polypeptide that is at least about 10% or at least about 100%, 200%, 300%, 400%, 500%, 600%, 700%, 800%, 900%, 1000%, or more, as compared to the naturally-occurring level of secretion.

The term "secretory polypeptide" is intended to include any polypeptide(s), alone or in combination with other polypeptides, that facilitate the transport of another polypeptide from the intracellular space of a cell to the extracellular milieu. In certain embodiments, the secretory polypeptide(s) encompass all the necessary secretory polypeptides sufficient to impart secretory activity to a Gram-negative or Gram-positive host cell or to a yeast host cell. Typically, secretory proteins are encoded in a single region or locus that may be isolated from one host cell and transferred to another host cell using genetic engineering. In certain embodiments, the secretory polypeptide(s) are derived from any bacterial cell having secretory activity or any yeast cell having secretory activity. In certain embodiments, the secretory polypeptide(s) are derived from a host cell having Type II secretory activity. In certain embodiments, the host cell is a thermophilic bacterial cell. In certain embodiments, the host cell is a yeast cell.

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from or based on a sequence associated with the indicated polynucleotide source.

The term "recombinant microorganism" or "recombinant host cell" is intended to include progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

By "thermophilic" is meant an organism that thrives at a temperature of about 45° C. or higher.

By "mesophilic" is meant an organism that thrives at a temperature of about 20-45° C.

The term "organic acid" is art-recognized. "Organic acid," as used herein, also includes certain organic solvents such as ethanol. The term "lactic acid" refers to the organic acid 2-hydroxypropionic acid in either the free acid or salt form. The salt form of lactic acid is referred to as "lactate" regardless of the neutralizing agent, i.e., calcium carbonate or ammonium hydroxide. The term "acetic acid" refers to the organic acid methanecarboxylic acid, also known as ethanoic acid, in either free acid or salt form. The salt form of acetic acid is referred to as "acetate."

Certain embodiments of the present invention provide for the "insertion," (e.g., the addition, integration, incorporation, or introduction) of certain genes or particular polynucleotide sequences within thermophilic or mesophilic microorganisms, which insertion of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

Certain embodiments of the present invention provide for the "inactivation" or "deletion" of certain genes or particular polynucleotide sequences within thermophilic or mesophilic microorganisms, which "inactivation" or "deletion" of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

The term "consolidated bioprocessing" or "CBP" refers to biomass processing schemes involving enzymatic or microbial hydrolysis that commonly involve four biologically mediated transformations: (1) the production of saccharolytic enzymes (amylases, cellulases, and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called CBP, which is distinguished from other less highly integrated configurations in that it does not involve a dedicated process step for cellulase and/or hemicellulase production.

The term "CBP organism" is intended to include microorganisms of the invention, e.g., microorganisms that have properties suitable for CBP.

In one aspect of the invention, the genes or particular polynucleotide sequences are inserted to activate the activity for which they encode, such as the expression of an enzyme. In certain embodiments, genes encoding enzymes in the metabolic production of ethanol, e.g., enzymes that metabolize pentose and/or hexose sugars, may be added to a mesophilic or thermophilic organism. In certain embodiments of the invention, the enzyme may confer the ability to metabolize a pentose sugar and be involved, for example, in the D-xylose pathway and/or L-arabinose pathway.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the terms "deletion," "partial deletion," "substantial deletion," or "complete deletion." In certain embodiments, strains of thermophilic or mesophilic microorganisms of interest may be engineered by site directed homologous recombination to knockout the production of organic acids. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Similarly, the enzymes of the invention as described herein can be endogenous to the native strain of the microorganism, and can thus be understood to be referred to as "native" or "endogenous."

The term "upregulated" means increased in activity, e.g., increase in enzymatic activity of the enzyme as compared to activity in a native host organism.

The term "downregulated" means decreased in activity, e.g., decrease in enzymatic activity of the enzyme as compared to activity in a native host organism.

The term "activated" means expressed or metabolically functional.

The term "adapted for growing" means selection of an organism for growth under conditions in which the organism does not otherwise grow or in which the organism grows slowly or minimally. Thus, an organism that is said to be adapted for growing under the selected condition, grows better than an organism that has not been adapted for growing under the selected conditions. Growth can be measured by any methods known in the art, including, but not limited to, measurement of optical density or specific growth rate.

The term "carbohydrate source" is intended to include any source of carbohydrate including, but not limited to, biomass or carbohydrates, such as a sugar or a sugar alcohol. "Carbohydrates" include, but are not limited to, monosaccharides (e.g., glucose, fructose, galactose, xylose, arabinose, or ribose), sugar derivatives (e.g., sorbitol, glycerol, galacturonic acid, rhamnose, xylitol), disaccharides (e.g., sucrose, cellobiose, maltose, or lactose), oligosaccharides (e.g., xylooligomers, cellodextrins, or maltodextrins), and polysaccharides (e.g., xylan, cellulose, starch, mannan, alginate, or pectin).

As used herein, an "amylolytic enzyme" can be any enzyme involved in amylase digestion, metabolism and/or hydrolysis. The term "amylase" refers to an enzyme that breaks starch down into sugar. Amylase is present in human saliva, where it begins the chemical process of digestion. Foods that contain much starch but little sugar, such as rice and potato, taste slightly sweet as they are chewed because amylase turns some of their starch into sugar in the mouth. The pancreas also makes amylase (α-amylase) to hydrolyse dietary starch into disaccharides and trisaccharides which are converted by other enzymes to glucose to supply the body with energy. Plants and some bacteria also produce amylase. All amylases are glycoside hydrolases and act on α-1,4-glycosidic bonds. Some amylases, such as γ-amylase (glucoamylase), also act on α-1,6-glycosidic bonds. Amylase enzymes include α-amylase (EC 3.2.1.1), β-amylase (EC 3.2.1.2), and γ-amylase (EC 3.2.1.3). The α-amylases are calcium metalloenzymes, unable to function in the absence of calcium. By acting at random locations along the starch chain, α-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase. In animals, it is a major digestive enzyme and its optimum pH is about 6.7-7.0. Another form of amylase, β-amylase is also synthesized by bacteria, fungi, and plants. Working from the non-reducing end, β-amylase catalyzes the hydrolysis of the second α-1,4 glycosidic bond, cleaving off two glucose units (maltose) at a time. Many microbes produce amylase to degrade extracellular starches. In addition to cleaving the last α(1-4)glycosidic linkages at the nonreducing end of amylose and amylopectin, yielding glucose, γ-amylase will cleave α(1-6) glycosidic linkages. Another amylolytic enzyme is alpha-glucosidase that acts on maltose and other short malto-oligosaccharides produced by alpha-, beta-, and gamma-amylases, converting them to glucose. Another amylolytic enzyme is pullulanase. Pullulanase is a specific kind of glucanase, an amylolytic exoenzyme, that degrades pullulan. Pullulan is regarded as a chain of maltotriose units linked by alpha-1,6-glycosidic bonds. Pullulanase (EC 3.2.1.41) is also known as pullulan-6-glucanohydrolase (Debranching enzyme). Another amylolytic enzyme, isopullulanase, hydrolyses pullulan to isopanose (6-alpha-maltosylglucose).

Isopullulanase (EC 3.2.1.57) is also known as pullulan 4-glucanohydrolase. An "amylase" can be any enzyme involved in amylase digestion, metabolism and/or hydrolysis, including α-amylase, -amylase, glucoamylase, pullulanase, isopullulanase, and alpha-glucosidase.

As used herein, a "saccharolytic enzyme" can be any enzyme involved in carbohydrate digestion, metabolism and/or hydrolysis, including amylases, cellulases, hemicellulases, cellulolytic and amylolytic accessory enzymes, inulinases, levanases, and pentose sugar utilizing enzymes.

Biomass

Biomass can include any type of biomass known in the art or described herein. For example, biomass can include, but is not limited to, starch, sugar, and lignocellulosic materials. Starch materials can include, but are not limited to, mashes such as corn, wheat, rye, barley, rice, or milo. Sugar materials can include, but are not limited to, sugar beets, artichoke tubers, sweet sorghum, or cane. The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants, and sugar-processing residues. The terms "hemicellulosics," "hemicellulosic portions," and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan, inter alia), pectins (e.g., homogalacturonans, rhamnogalacturonan I and II, and xylogalacturonan), and proteoglycans (e.g., arabinogalactan-protein, extensin, and proline-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Paper sludge is also a viable feedstock for lactate or acetate production. Paper sludge is solid residue arising from pulping and paper-making, and is typically removed from process wastewater in a primary clarifier. At a disposal cost of $30/wet ton, the cost of sludge disposal equates to $5/ton of paper that is produced for sale. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

Glycerol Reduction

Anaerobic growth conditions require the production of endogenouse electron acceptors, such as the coenzyme nicotinamide adenine dinucleotide ($NAD^+$). In cellular redox reactions, the $NAD^+$/NADH couple plays a vital role as a reservoir and carrier of reducing equivalents. Ansell, R., et al., *EMBO J.* 16:2179-87 (1997). Cellular glycerol production, which generates an $NAD^+$, serves as a redox valve to remove excess reducing power during anaerobic fermentation in yeast. Glycerol production is, however, an energetically wasteful process that expends ATP and results in the loss of a reduced three-carbon compound. Ansell, R., et al., *EMBO J.* 16:2179-87 (1997). To generate glycerol from a starting glucose molecule, glycerol 3-phosphate dehydrogenase (GPD) reduces dihydroxyacetone phosphate to glycerol 3-phosphate and glycerol 3-phosphatase (GPP) dephosphorylates glycerol 3-phosphate to glycerol. Despite being energetically wasteful, glycerol production is a necessary metabolic process for anaerobic growth as deleting GPD activity completely inhibits growth under anaeroblic conditions. See Ansell, R., et al., *EMBO J.* 16:2179-87 (1997).

GPD is encoded by two isogenes, gpd1 and gpd2. GPD1 encodes the major isoform in anaerobically growing cells, while GPD2 is required for glycerol production in the absence of oxygen, which stimulates its expression. Pahlman, A-K., et al., *J. Biol. Chem.* 276:3555-63 (2001). The first step in the conversion of dihydroxyacetone phosphate to glycerol by GPD is rate controlling. Guo, Z. P., et al., *Metab. Eng.* 13:49-59 (2011). GPP is also encoded by two isogenes, gpp1 and gpp2. The deletion of GPP genes arrests growth when shifted to anaerobic conditions, demonstrating that GPP is important for cellular tolerance to osmotic and anaerobic stress. See Pahlman, A-K., et al., *J. Biol. Chem.* 276:3555-63 (2001).

Because glycerol is a major by-product of anaerobic production of ethanol, many efforts have been made to delete cellular production of glycerol. However, because of the reducing equivalents produced by glycerol synthesis, deletion of the glycerol synthesis pathway cannot be done without compensating for this valuable metabolic function. Attempts to delete glycerol production and engineer alternate electron acceptors have been made. Lidén, G., et al., *Appl. Env. Microbiol.* 62:3894-96 (1996); Medina, V. G., et al., *Appl. Env. Microbiol.* 76:190-195 (2010). Lidén and Medina both deleted the gpd1 and gpd2 genes and attempted to bypass glycerol formation using additional carbon sources. Lidén engineered a xylose reductase from *Pichia stipitis* into an *S. cerevisiae* gpd1/2 deletion strain. The xylose reductase activity facilitated the anaerobic growth of the glycerol-deleted strain in the presence of xylose. See Lidén, G., et al., *Appl. Env. Microbiol.* 62:3894-96 (1996). Medina engineered an acetylaldehyde dehydrogenase, mhpF, from *E. coli* into an *S. cerevisiae* gpd1/2 deletion strain to convert acetyl-CoA to acetaldehyde. The acetylaldehyde dehydrogenase activity facilitated the anaerobic growth of the glycerol-deletion strain in the presence of acetic acid but not in the presence of glucose as the sole source of carbon. Medina, V. G., et al., *Appl. Env. Microbiol.* 76:190-195 (2010); see also EP 2277989. Medina noted several issues with the mhpF-containing strain that needed to be addressed before implementing industrially, including significantly reduced growth and product formation rates than yeast comprising GPD1 and GPD2.

Additional attempts to redirect flux from glycerol to ethanol have included the engineering of a non-phosphorylating NADP+-dependent glyceraldehydes-3-phosphate dehydrogenase (GAPN) into yeast, either with or without the simultaneous knockout of GPD1. Bro, C., et al., *Metab. Eng.* 8:102-111 (2006); U.S. Patent Appl. Pub. No. US2006/0257983; Guo, Z. P., et al., *Metab. Eng.* 13:49-59 (2011). However, other cellular mechanisms exist to control the production and accumulation of glycerol, including glycerol exporters such as FPS1, that do not require the engineering of alternate NADP+/NADPH coupling or deletion of glycerol synthesis genes. Tamás, M. J., et al., *Mol. Microbiol.* 31:1087-1004 (1999).

FPS1 is a channel protein located in the plasma membrane that controls the accumulation and release of glycerol in yeast osmoregulation. Null mutants of this strain accumulate large amounts of intracellular glycerol, grow much slower than wild-type, and consume the sugar substrate at a slower rate. Tamás, M. J., et al., *Mol. Microbiol.* 31:1087-1004 (1999). Despite slower growth under anaerobic conditions, an fps1Δ strain can serve as an alternative to eliminating $NAD^+$-dependant glycerol activity. An fps1Δ strain has reduced glycerol formation yet has a completely functional $NAD^+$-dependant glycerol synthesis pathway. Alternatively, rather than deleting endogenous FPS1, constitutively active mutants of FPS1 or homologs from other organisms can be used to regulate glycerol synthesis while keep the $NAD^+$-dependant glycerol activity intact. In embodiments of the invention that modulate FPS1, the recombinant host cells can still synthesize and retain glycerol and achieve improved robustness relative to strains that are unable to make glycerol.

An example FPS1 sequence from *S. cerevisiae* is shown below.

*S. cerevisiae* FPS1 (nucleotide; coding sequence underlined; SEQ ID NO: 1):

```
ttgacggcagttctcatagcatctcaaagcaatagcagtgcaaaagtaca
taaccgtaggaaggtacgcggtaggtatttgagttcgttggtggttatcc
tccgcaaggcgcttcggcggttatttgttgatagtcgaagaacaccaaaa
aaaatgctgttattgctttctccgtaaacaataaaacccggtagcgggat
aacgcggctgatgcttttatttaggaaggaatacttacattatcatgaga
acattgtcaagggcattctgatacgggccttccatcgcaagaaaaaggca
gcaacggactgagggacggagagagttacggcataagaagtagtaggaga
gcagagtgtcataaagttatattattctcgtcctaaagtcaattagttct
gttgcgcttgacaatatatgtcgtgtaataccgtcccttagcagaagaaa
gaaagacggatccatatatgttaaaatgcttcagagatgtttctttaatg
tgccgtccaacaaaggtatcttctgtagcttcctctattttcgatcagat
ctcatagtgagaaggcgcaattcagtagttaaaagcggggaacagtgtga
atccggagacggcaagattgcccggcccttttttgcggaaaagataaaaca
agatatattgcacttttccaccaagaaaaacaggaagtggattaaaaaat
caacaaagtataacgcctattgtcccaataagcgtcggttgttcttcttt
attattttaccaagtacgctcgagggtacattctaatgcattaaaagaca
tgagtaatcctcaaaaagctctaaacgactttctgtccagtgaatctgtt
catacacatgatagttctaggaaacaatctaataagcagtcatccgacga
aggacgctcttcatcacaaccttcacatcatcactctggtggtactaaca
acaataataacaataataataataataataacagtaacaacaacaacaac
ggcaacgatggggaaatgatgacgactatgattatgaaatgcaagatta
tagaccttctccgcaaagtgcgcggcctactcccacgtatgttccacaat
attctgtagaaagtgggactgctttcccgattcaagaggttattcctagc
```

-continued gcatacattaacacacaagatataaaccataaagataacggtccgccgag
tgcaagcagtaatagagcattcaggcctagagggcagaccacagtgtcgg
ccaacgtgcttaacattgaagattttacaaaaatgcagacgatgcgcat
accatcccggagtcacatttatcgagaaggagaagtaggtcgagggctac
gagtaatgctgggcacagtgccaatacaggcgccacgaatggcaggacta
ctggtgcccaaactaatatggaaagcaatgaatcaccacgtaacgtcccc
attatggtgaagccaaagacattataccagaaccctcaaacacctacagt
cttgccctccacataccatccaattaataaatggtcttccgtcaaaaaca
cttatttgaaggaatttttagccgagtttatgggaacaatggttatgatt
attttcggtagtgctgttgtttgtcaggtcaatgttgctgggaaaataca
gcaggacaatttcaacgtggctttggataaccttaacgttaccgggtctt
ctgcagaaacgatagacgctatgaagagtttaacatccttggtttcatcc
gttgcgggcggtacctttgatgatgtggcattgggctgggctgctgccgt
ggtgatgggctatttctgcgctggtggtagtgccatctcaggtgctcatt
tgaatccgtctattacattagccaatttggtgtatagaggttttcccctg
aagaaagttccttattactttgctggacaattgatcggtgccttcacagg
cgctttgatcttgtttatttggtacaaaagggtgttacaagaggcatata
gcgattggtggatgaatgaaagtgttgcgggaatgttttgcgtttttcca
aagccttatctaagttcaggacggcaatttttttccgaattttatgtgg
agctatgttacaagcaggaacatttgcgctgaccgatccttatacgtgtt
tgtcctctgatgttttcccattgatgatattattttgattttcattatca
atgcttccatggcttatcagacaggtacagcaatgaatttggctcgtgat
ctgggcccacgtcttgcactatatgcagttggatttgatcataaaatgct
ttgggtgcatcatcatcatttcttttgggttcccatggtaggcccattta
ttggtgcgttaatgggggggttggtttacgatgtctgtatttatcagggt
catgaatctccagtcaactggtctttaccagtttataaggaaatgattat
gagagcctggtttagaaggcctggttggaagaagagaaatagagcaagaa
gaacatcggacctgagtgacttctcatacaataacgatgatgatgaggaa
tttggagaaagaatggctcttcaaaagacaaagaccaagtcatctatttc
agacaacgaaaatgaagcaggagaaaagaaagtgcaatttaaatctgttc
agcgcggcaaaagaacgtttggtggtataccaacaattcttgaagaagaa
gattccattgaaactgcttcgctaggtgcgacgacgactgattctattgg
gttatccgacacatcatcagaagattcgcattatggtaatgctaagaagg
taacatgagaaaacagacaagaaaaagaaacaaataatatagactgatag
aaaaaaatactgcttactaccgccggtataatatatatatatatatatat
ttacatagatgattgcatagtgttttaaaaagctttcctaggttaagcta
tgaatcttcataacctaaccaactaaatatgaaaatactgacccatcgtc
ttaagtaagttgacatgaactcagcctggtcacctactatacatgatgta
tcgcatggatggaaagaataccaaacgctaccttccaggttaatgatagt
atccaaacctagttggaatttgccttgaacatcaagcagcgattcgatat
cagttgggagcatcaatttggtcattggaataccatctatgcttttctcc
tcccatattcgcaaaagtagtaagggctcgttatatacttttgaatatgt
aagatataattctatatgatttagtaatttattttctatacgctcagtat
ttttctgcagttgtcgagtaggtattaaacgcaaaagaagtccatccttt
tcatcattcaaatggacatcttggcaaagggcccagttatggaaaatctg
ggagtcatacaacgattgcagttggctatgccactcctggtaaggaatca
tcaagtctgataattctgtttatagcccttttttttttttttcatggtg
ttctcttctcattgcttttcaattttaagttcgttacctttcatatagag
tttcttaacagaaatttcacaacgaaaatataattaactacaggca

*S. cerevisiae* FPS1 (amino acid; SEQ ID NO:2):

Pyruvate Formate Lyase (PFL)

The conversion of the pyruvate to acetyl-CoA and formate is performed by pyruvate formate lyase (PFL). In *E. coli*, PFL is the primary enzyme responsible for the production of formate. PFL is a dimer of PflB that requires the activating enzyme PflAE, which is encoded by pflA, radical S-adenosylmethionine, and a single electron donor. See Waks, Z., and Silver, P. A., *Appl. Env. Microbiol.* 75:1867-1875 (2009). Waks and Silver engineered strains of *S. cerevisiae* to secrete formate by the addition of PFL and AdhE from *E. coli* and deletion of endogenous formate dehydrogenases and to produce hydrogen in a two-step process using *E. coli*. Waks and Silver, however, did not combine formate production with the removal of glycerol formation, and the use of formate as an alternate electron acceptor for the reduction of glycerol was not proposed or evaluated.

PFL enzymes for use in the recombinant host cells of the invention can come from a bacterial or eukaryotic source. Examples of bacterial PFL include, but are not limited to, *Bacillus licheniformis* DSM13, *Bacillus licheniformis* ATCC14580, *Streptococcus thermophilus* CNRZ1066, *Streptococcus thermophilus* LMG18311, *Streptococcus thermophilus* LMD-9, *Lactobacillus plantarum* WCFS1 (Gene Accession No. 1p_2598), *Lactobacillus plantarum* WCFS1 (Gene Accession No. 1p_3313), *Lactobacillus plantarum* JDM1 (Gene Accession No. JDM1_2695), *Lactobacillus plantarum* JDM1 (Gene Accession No. JDM1_2087), *Lactobacillus casei* b123, *Lactobacillus casei* ATCC 334, *Bifidobacterium adolescentis, Bifidobacterium longum* NCC2705, *Bifidobacterium longum* DJO10A, *Bifidobacterium animalis* DSM 10140, *Clostridium cellulolyticum*, or *Escherichia coli*. Additional PFL enzymes may be from the PFL1 family, the RNR pfl superfamily, or the PFL2 superfamily.

pflA Sequences from Bacteria Include:

*Bacillus licheniformis* DSM13 (nucleotide; SEQ ID NO:3):

*Bacillus licheniformis* DSM13 (amino acid; SEQ ID NO:4):

*Bacillus licheniformis* ATCC14580 (nucleotide; SEQ ID NO:5):

*Bacillus licheniformis* ATCC14580 (amino acid; SEQ ID NO:6):

*Streptococcus thermophilus* CNRZ1066 (nucleotide; SEQ ID N0:7):

*Streptococcus thermophilus* CNRZ1066 (amino acid; SEQ ID NO:8):

*Streptococcus thermophilus* LMG18311 (nucleotide; SEQ ID N0:9):

*Streptococcus thermophilus* LMG18311 (amino acid; SEQ ID NO:10):

*Streptococcus thermophilus* LMD-9 (nucleotide; SEQ ID NO:11):

*Streptococcus thermophilus* LMD-9 (amino acid; SEQ ID NO:12):

*Lactobacillus plantarum* WCFS1 (Gene Accession No: 1p_2596) (nucleotide; SEQ ID NO:13):

*Lactobacillus plantarum* WCFS1 (Gene Accession No: 1p_2596) (amino acid; SEQ ID NO:14):

*Lactobacillus plantarum* WCFS1 (Gene Accession No: 1p_3314) (nucleotide; SEQ ID NO:15):

*Lactobacillus plantarum* WCFS1 (Gene Accession No: 1p_3314) (amino acid; SEQ ID NO:16):

*Lactobacillus plantarum* JDM1 (Gene Accession No: JDM1_2660) (nucleotide; SEQ ID NO:17):

*Lactobacillus plantarum* JDM1 (Gene Accession No: JDM1_2660) (amino acid; SEQ ID NO:18):

*Lactobacillus plantarum* JDM1 (Gene Accession No: JDM1_2085) (nucleotide; SEQ ID NO:19):

*Lactobacillus plantarum* JDM1 (Gene Accession No: JDM1_2085) (amino acid; SEQ ID NO:20):

*Lactobacillus casei* b123 (nucleotide; SEQ ID NO:21):

*Lactobacillus casei* b123 (amino acid; SEQ ID NO:22):

*Lactobacillus casei* ATCC 334 (nucleotide; SEQ ID NO:23):

*Lactobacillus casei* ATCC 334 (amino acid; SEQ ID NO:24):

*Bifidobacterium adolescentis* (nucleotide; SEQ ID NO:25):

*Bifidobacterium adolescentis* (amino acid; SEQ ID NO:26):

*Bifidobacterium longum* NCC2705 (nucleotide; SEQ ID NO:27):

*Bifidobacterium longum* NCC2705 (amino acid; SEQ ID NO:28):

*Bifidobacterium longum* DJO10A (nucleotide; SEQ ID NO:29):

*Bifidobacterium longum* DJO10A (amino acid; SEQ ID NO:30):

*Bifidobacterium animalis* DSM 10140 (nucleotide; SEQ ID NO:31):

*Bifidobacterium animalis* DSM 10140 (amino acid; SEQ ID NO:32):

*Clostridium cellulolyticum* (nucleotide; SEQ ID NO:33):

*Clostridium cellulolyticum* (amino acid; SEQ ID NO:34):

*Escherichia coli* (nucleotide; SEQ ID NO:35):

*Escherichia coli* (amino acid; SEQ ID NO:36):

pflB sequences from bacteria include:

*Bacillus licheniformis* DSM13 (nucleotide; SEQ ID NO:37):

*Bacillus licheniformis* DSM13 (amino acid; SEQ ID NO:38):

*Bacillus licheniformis* ATCC14580 (nucleotide; SEQ ID NO:39):

*Bacillus licheniformis* ATCC14580 (amino acid; SEQ ID NO:40):

*Streptococcus thermophilus* CNRZ1066 (nucleotide; SEQ ID NO:41):

*Streptococcus thermophilus* CNRZ1066 (amino acid; SEQ ID NO:42):

*Streptococcus thermophilus* LMG18311 (nucleotide; SEQ ID NO:43):

*Streptococcus thermophilus* LMG18311 (amino acid; SEQ ID NO:44):

*Streptococcus thermophilus* LMD-9 (nucleotide; SEQ ID NO:45):

*Streptococcus thermophilus* LMD-9 (amino acid; SEQ ID NO:46):

*Lactobacillus plantarum* WCFS1 (Gene Accession No. 1p_2598) (nucleotide; SEQ ID NO:47):

*Lactobacillus plantarum* WCFS1 (Gene Accession No. 1p_2598) (amino acid; SEQ ID NO:48):

*Lactobacillus plantarum* WCFS1 (Gene Accession No: 1p_3313) (nucleotide; SEQ ID NO:49):

*Lactobacillus plantarum* WCFS1 (Gene Accession No: 1p_3313) (amino acid; SEQ ID NO:50):

*Lactobacillus plantarum* JDM1 (Gene Accession No: JDM12695) (nucleotide; SEQ ID NO:51):

*Lactobacillus plantarum* JDM1 (Gene Accession No: JDM12695) (amino acid; SEQ ID NO:52):

*Lactobacillus plantarum* JDM1 (Gene Accession No: JDM1_2087) (nucleotide; SEQ ID NO:53):

*Lactobacillus plantarum* JDM1 (Gene Accession No: JDM1_2087) (amino acid; SEQ ID NO:54):

*Lactobacillus casei* b123 (nucleotide; SEQ ID NO:55):

*Lactobacillus casei* b123 (amino acid; SEQ ID NO:56):

*Lactobacillus casei* ATCC 334 (nucleotide; SEQ ID NO:57):

*Lactobacillus casei* ATCC 334 (amino acid; SEQ ID NO:58):

*Bifidobacterium adolescentis* (nucleotide; SEQ ID NO:59):

*Bifidobacterium adolescentis* (amino acid; SEQ ID NO:60):

*Bifidobacterium longum* NCC2705 (nucleotide; SEQ ID NO:61):

*Bifidobacterium longum* NCC2705 (amino acid; SEQ ID NO:62):

*Bifidobacterium longum* DJO10A (nucleotide; SEQ ID NO:63):

*Bifidobacterium longum* DJO10A (amino acid; SEQ ID NO:64):

*Bifidobacterium animalis* DSM 10140 (nucleotide; SEQ ID NO:65):

*Bifidobacterium animalis* DSM 10140 (amino acid; SEQ ID NO:66):

*Clostridium cellulolyticum* (nucleotide; SEQ ID NO:67):

*Clostridium cellulolyticum* (amino acid; SEQ ID NO:68):

*Escherichia coli* (nucleotide; SEQ ID NO:69):

*Escherichia coli* (amino acid; SEQ ID NO:70):

Examples of eukaryotic PFL include, but are not limited to, *Chlamydomonas reinhardtii* PflA1, *Piromyces* sp. E2, or *Neocallimastix frontalis, Acetabularia acetabulum, Haematococcus pluvialis, Volvox carteri, Ostreococcus tauri, Ostreococcus lucimarinus, Micromonas pusilla, Micromonas* sp., *Porphyra haitanensis*, and *Cyanophora paradoxa*), an opisthokont (*Amoebidium parasiticum*), an amoebozoan (*Mastigamoeba balamuthi*), a stramenopile (*Thalassiosira pseudonana* (2)) and a haptophyte (*Prymnesium parvum*), *M. pusilla, Micromonas* sp. *O. tauri* and *O. lucimarinus*) an amoebozoan (*M. balamuthi*), and a stramenopile (*T. pseudonana*). See Stairs, C. W., et al., "Eukaryotic pyruvate formate lyase and its activating enzyme were acquired laterally from a firmicute," Mol. Biol. and Evol., published on-line on Feb. 3, 2011, at http://mbe.oxfordjournals.org/.

pflA sequences from eukaryotes include:

*Chlamydomonas reinhardtii* PflA1 (nucleotide; SEQ ID N0:71):

*Chlamydomonas reinhardtii* PflA1 (amino acid; SEQ ID N0:72):

*Neocallimastix frontalis* (nucleotide; SEQ ID N0:73):

*Neocallimastix frontalis* (amino acid; SEQ ID N0:74):

pfl1 sequences from eukaryotes include:

*Chlamydomonas reinhardtii* PflA (nucleotide; SEQ ID N0:75):

*Chlamydomonas reinhardtii* PflA (amino acid; SEQ ID N0:76):

*Piromyces* sp. E2 (nucleotide; SEQ ID N0:77):

*Piromyces* sp. E2 (amino acid; SEQ ID N0:78):

*Neocallimastix frontalis* (nucleotide—partial CDS, missing start; SEQ ID NO:79):

*Neocallimastix frontalis* (amino acid—partial CDS, missing start; SEQ ID NO:80):

Acetaldehyde/Alcohol Dehydrogenases

Engineering of acetaldehyde dehydrogenases, alcohol dehydrogenases, and/or bifunctional acetylaldehyde/alcohol dehydrogenases into a cell can increase the production of ethanol. However, because the production of ethanol is redox neutral, an acetaldehyde/alcohol dehydrogenase activity cannot serve as an alternative for the redox balancing that the production of glycerol provides to a cell in anaerobic metabolism. When Medina attempted to express an acetylaldehyde dehydrogenase, mhpF, from *E. coli* in an *S. cerevisiae* gpd1/2 deletion strain, the strain did not grow under anaerobic conditions in the presence of glucose as the sole source of carbon. Medina, V. G., et al., *Appl. Env. Microbiol.* 76:190-195 (2010); see also EP 2277989. Rather, the anaerobic growth of the glycerol-deletion strain required the presence of acetic acid. However, an acetylaldehyde dehydrogenase has not been expressed in combination with PFL or with the recombinant host cells of the invention. Additionally, replacing the endogenous acetylaldehyde dehydrogenase activity with either an improved acetaldehyde dehydrogenase or using a bifunctional acetaldehyde/alcohol dehydrogenase (AADH) can positively affect the in vivo kinetics of the reaction providing for improved growth of the host strain.

AADH enzymes for use in the recombinant host cells of the invention can come from a bacterial or eukaryotic source. Examples of bacterial AADH include, but are not limited to, *Clostridium phytofermentans, Escherichia coli, Bacillus coagulans, Bacillus lentus, Bacillus licheniformis, Bacillus pumilus, Bacillus subtilis, Bacteroides amylophilus, Bacteroides capillosus, Bacteroides ruminocola, Bacteroides suis, Bifidobacterium adolescentis, Bifidobacterium animalis, Bifidobacterium bifidum, Bifidobacterium infantis, Bifidobacterium longum, Bifidobacterium thermophilum, Lactobacillus acidophilus, Lactobacillus brevis, Lactobacillus buchneri* (cattle only), *Lactobacillus bulgaricus, Lactobacillus casei, Lactobacillus cellobiosus, Lactobacillus curvatus, Lactobacillus delbruekii, Lactobacillus farciminis* (swine only), *Lactobacillus fermentum, Lactobacillus helveticus, Lactobacillus lactis, Lactobacillus plantarum, Lactobacillus reuterii, Leuconostoc mesenteroides, Pediococcus acidilacticii, Pediococcus pentosaceus, Propionibacterium acidpropionici* (cattle only), *Propionibacterium freudenreichii, Propionibacterium shermanii, Enterococcus cremoris, Enterococcus diacetylactis, Enterococcus faecium, Enterococcus intermedius, Enterococcus lactis*, or *Enterococcus thermophilus*

AdhE bacterial sequences include:

*Clostridium phytofermentans* (nucleotide; SEQ ID NO:81):

*Clostridium phytofermentans* (amino acid; SEQ ID NO:82):

*Escherichia coli* (nucleotide; SEQ ID NO:83):

*Escherichia coli* (amino acid; SEQ ID NO:84):

*Bifidobacterium adolescentis* (amino acid; SEQ ID NO:100):

*Bacillus coagulans* (amino acid; SEQ ID NO:101):

*Bacillus licheniformis* (amino acid; SEQ ID NO: 102):

*Enterococcus faecium* TX1330 (amino acid; SEQ ID NO:103):

Examples of eukaryotic AdhE include, but are not limited to, *Chlamydomonas reinhardtii* AdhE, *Piromyces* sp. E2, or *Neocallimastix frontalis.*

AdhE sequences from eukaryotes include:

*Chlamydomonas reinhardtii* AdhE (nucleotide; SEQ ID NO:85):

*Chlamydomonas reinhardtii* AdhE (amino acid; SEQ ID NO:86):

*Piromyces* sp. E2 (nucleotide; SEQ ID NO:87):

*Piromyces* sp. E2 (amino acid; SEQ ID NO:88):

Consolidated Bioprocessing

Consolidated bioprocessing (CBP) is a processing strategy for cellulosic biomass that involves consolidating into a single process step four biologically-mediated events: enzyme production, hydrolysis, hexose fermentation, and pentose fermentation. Implementing this strategy requires development of microorganisms that both utilize cellulose, hemicellulosics, and other biomass components while also producing a product of interest at sufficiently high yield and concentrations. The feasibility of CBP is supported by kinetic and bioenergetic analysis. See van Walsum and Lynd (1998) *Biotech. Bioeng.* 58:316.

CBP offers the potential for lower cost and higher efficiency than processes featuring dedicated saccharolytic enzyme production. The benefits result in part from avoided capital costs, substrate and other raw materials, and utilities associated with saccharolytic enzyme production. In addition, several factors support the realization of higher rates of hydrolysis, and hence reduced reactor volume and capital investment using CBP, including enzyme-microbe synergy and the use of thermophilic organisms and/or complexed saccharolytic systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring saccharolytic microorganisms to improve product-related properties, such as yield and titer; and engineering non-saccharolytic organisms that exhibit high product yields and titers to express a heterologous saccharolytic enzyme system enabling starch, cellulose, and, hemicellulose utilization.

Starch and Cellulose Degradation

The degradation of starch into component sugar units proceeds via amylolytic enzymes. Amylase is an example of an amylolytic enzyme that is present in human saliva, where it begins the chemical process of digestion. The pancreas also makes amylase (alpha amylase) to hydrolyze dietary starch into disaccharides and trisaccharides which are converted by other enzymes to glucose to supply the body with energy. Plants and some bacteria also produce amylases. Amylases are glycoside hydrolases and act on α-1,4-glycosidic bonds.

Several amylolytic enzymes are implicated in starch hydrolysis. Alpha-amylases (EC 3.2.1.1) (alternate names: 1,4-α-D-glucan glucanohydrolase; glycogenase) are calcium metalloenzymes, i.e., completely unable to function in the absence of calcium. By acting at random locations along the starch chain, alpha-amylase breaks down long-chain carbohydrates, ultimately yielding maltotriose and maltose from amylose, or maltose, glucose and "limit dextrin" from amylopectin. Because it can act anywhere on the substrate, alpha-amylase tends to be faster-acting than beta-amylase.

Another form of amylase, beta-amylase (EC 3.2.1.2) (alternate names: 1,4-α-D-glucan maltohydrolase; glycogenase; saccharogen amylase) catalyzes the hydrolysis of the second α-1,4 glycosidic bond, cleaving off two glucose units (maltose) at a time. The third amylase is gamma-amylase (EC 3.2.1.3) (alternate names: Glucan 1,4-α-glucosidase; amyloglucosidase; Exo-1,4-α-glucosidase; glucoamylase; lysosomal α-glucosidase; 1,4-α-D-glucan glucohydrolase). In addition to cleaving the last α(1-4)glycosidic linkages at the nonreducing end of amylose and amylopectin, yielding glucose, gamma-amylase will cleave α(1-6) glycosidic linkages.

A fourth enzyme, alpha-glucosidase, acts on maltose and other short malto-oligosaccharides produced by alpha-, beta-, and gamma-amylases, converting them to glucose.

Three major types of enzymatic activities degrade native cellulose. The first type is endoglucanases (1,4-β-D-glucan 4-glucanohydrolases; EC 3.2.1.4). Endoglucanases cut at random in the cellulose polysaccharide chain of amorphous cellulose, generating oligosaccharides of varying lengths and consequently new chain ends. The second type are exoglucanases, including cellodextrinases (1,4-β-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. The third type are β-glucosidases (β-glucoside glucohydrolases; EC 3.2.1.21). β-Glucosidases hydrolyze soluble cellodextrins and cellobiose to glucose units.

Even though yeast strains expressing enzymes for the production of fuel ethanol from whole grain or starch have been previously disclosed, the application has not been commercialized in the grain-based fuel ethanol industry, due to the relatively poor ability of the resulting strains to produce/tolerate high levels of ethanol. For example, U.S. Pat. No. 7,226,776 discloses that a polysaccharase enzyme expressing ethanologen can make ethanol directly from carbohydrate polymers, but the maximal ethanol titer demonstrated is 3.9 g/l. U.S. Pat. No. 5,422,267 discloses the use of a glucoamylase in yeast for production of alcoholic beverages; however, no commercially relevant titers of ethanol are disclosed.

Heterologous Saccharolytic Enzymes

According to one aspect of the present invention, the expression of heterologous saccharolytic enzymes the recombinant microorganisms of the invention can be used advantageously to produce products such as ethanol from biomass sources. For example, cellulases from a variety of sources can be heterologously expressed to successfully increase efficiency of ethanol production. The saccharolytic enzymes can be from fungi, yeast, bacteria, plant, protozoan or termite sources. In some embodiments, the saccharolytic enzyme is from *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum* or *Arabidopsis thaliana.*

In some embodiments, the cellulase for expression in the recombinant microorganisms of the invention is any cellulase disclosed in Table 4 or Table 7 in copending International Appl. No. PCT/US2011/039192, incorporated by reference herein, or any cellulase suitable for expression in an appropriate host cell. In other embodiments, the amylase for expression in the recombinant microorganisms of the invention is any amylase such as alpha-amylases, beta-amylases, glucoamylases, alpha-glucosidases, pullulanase, or isopullulanase paralogues or orthologues, any amylase disclosed in Tables 15-19, preferably in Table 19, in copending International Appl. No. PCT/US2011/039192, incorporated by reference herein, or any amylase suitable for expression in an appropriate host cell. In some embodiments of the invention, multiple saccharolytic enzymes from a single organism are co-expressed in the same recombinant microorganism. In some embodiments of the invention, multiple saccharolytic enzymes from different organisms are co-expressed in the same recombinant microorganism. In particular, saccharolytic enzymes from two, three, four, five, six, seven, eight, nine or more organisms can be co-expressed in the same recombinant microorganism. Similarly, the invention can encompass co-cultures of yeast strains, wherein the yeast strains express different saccharolytic enzymes. Co-cultures can include yeast strains expressing heterologous saccharolytic enzymes from the same organisms or from different organisms. Co-cultures can include yeast strains expressing saccharolytic enzymes from two, three, four, five, six, seven, eight, nine or more organisms.

Lignocellulases for expression in the recombinant microorganisms of the present invention include both endoglucanases and exoglucanases. Other lignocellulases for expression in the recombinant microorganisms of the invention include accesory enzymes which can act on the lignocellulosic material. The lignocellulases can be, for example, endoglucanases, glucosidases, cellobiohydrolases, xylanases, glucanases, xylosidases, xylan esterases, arabinofuranosidases, galactosidases, cellobiose phosphorylases, cellodextrin phosphorylases, mannanases, mannosidases, xyloglucanases, endoxylanases, glucuronidases, acetylxylanesterases, arabinofuranohydrolases, swollenins, glucuronyl esterases, expansins, pectinases, and feruoyl esterases. In some embodiments, the lignocellulases of the invention can be any suitable enzyme for digesting the desired lignocellulosic material.

In certain embodiments of the invention, the lignocellulase can be an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase paralogue or orthologue. In particular embodiments, the lignocellulase is derived from any species named in Tables 4 and 7, in copending International Appl. No. PCT/US2011/039192, incorporated by reference herein.

Xylose Metabolism

Xylose is a five-carbon monosaccharide that can be metabolized into useful products by a variety of organisms. There are two main pathways of xylose metabolism, each unique in the characteristic enzymes they utilize. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR, encoded by the XYL1 gene, is responsible for the reduction of xylose to xylitol and is aided by cofactors NADH or NADPH. Xylitol is then oxidized to xylulose by XDH, which is expressed through the XYL2 gene, and accomplished exclusively with the cofactor $NAD^+$. Because of the varying cofactors needed in this pathway and the degree to which they are available for usage, an imbalance can result in an overproduction of xylitol byproduct and an inefficient production of desirable ethanol. Varying expression of the XR and XDH enzyme levels have been tested in the laboratory in the attempt to optimize the efficiency of the xylose metabolism pathway.

The other pathway for xylose metabolism is called the "Xylose Isomerase" (XI) pathway. Enzyme XI is responsible for direct conversion of xylose into xylulose, and does not proceed via a xylitol intermediate. Both pathways create xylulose, although the enzymes utilized are different. After production of xylulose both the XR-XDH and XI pathways proceed through the enzyme xylulokinase (XK), encoded on gene XKS1, to further modify xylulose into xylulose-5-phosphate where it then enters the pentose phosphate pathway for further catabolism.

Studies on flux through the pentose phosphate pathway during xylose metabolism have revealed that limiting the speed of this step may be beneficial to the efficiency of fermentation to ethanol. Modifications to this flux that may improve ethanol production include a) lowering phosphoglucose isomerase activity, b) deleting the GND1 gene, and c) deleting the ZWF1 gene (Jeppsson et al., *Appl. Environ. Microbiol.* 68:1604-09 (2002)). Since the pentose phosphate pathway produces additional NADPH during metabolism, limiting this step will help to correct the already evident imbalance between NAD(P)H and NAD cofactors and reduce xylitol byproduct. Another experiment comparing the two xylose metabolizing pathways revealed that the XI pathway was best able to metabolize xylose to produce the greatest ethanol yield, while the XR-XDH pathway reached a much faster rate of ethanol production (Karhumaa et al., *Microb Cell Fact.* 2007 Feb. 5; 6:5). See also International Publication No. WO2006/009434, incorporated herein by reference in its entirety.

In some embodiments, the recombinant microorganisms of the invention have the ability to metabolize xylose using one or more of the above enzymes.

Arabinose Metabolism

Arabinose is a five-carbon monosaccharide that can be metabolized into useful products by a variety of organisms. L-Arabinose residues are found widely distributed among many heteropolysaccharides of different plant tissues, such as arabinans, arabinogalactans, xylans and arabinoxylans. *Bacillus* species in the soil participate in the early stages of plant material decomposition, and *B. subtilis* secretes three enzymes, an endo-arabanase and two arabinosidases, capable of releasing arabinosyl oligomers and L-arabinose from plant cell.

Three pathways for L-arabinose metabolism in microorganisms have been described. Many bacteria, including *Escherichia coli*, use arabinose isomerase (AraA; E.C. 5.3.1.4), ribulokinase (AraB; E.C. 2.7.1.16), and ribulose phosphate epimerase (AraD; E.C. 5.1.3.4) to sequentially convert L-arabinose to D-xylulose-5-phosphate through L-ribulose and L-ribulose 5-phosphate. See, e.g., Sa-Nogueira I, et al., *Microbiology* 143:957-69 (1997). The D-xylulose-5-phosphate then enters the pentose phosphate pathway for further catabolism. In the second pathway, L-arabinose is converted to L-2-keto-3-deoxyarabonate (L-KDA) by the consecutive action of enzymes arabinose dehydrogenase (ADH), arabinolactone (AL), and arabinonate dehydratase (AraC). See, e.g., Watanabe, S, et al., *J. Biol. Chem.* 281: 2612-2623 (2006). L-KDA can be further metabolized in two alternative pathways: 1) L-KDA conversion to 2-ketoglutarate via 2-ketoglutaric semialdehyde (KGSA) by L-KDA dehydratase and KGSA dehydrogenase or 2) L-KDA conversion to pyruvate and glycolaldehyde by L-KDA aldolase. In the third, fungal pathway, L-arabinose is converted to D-xylulose-5-phosphate through L-arabinitol, L-xylulose, and xylitol, by enzymes such as NAD(P)H-dependent aldose reductase (AR), L-arabinitol 4-dehydrogenase (ALDH), L-xylulose reductase (LXR), xylitol dehydrogenase (XylD), and xylulokinase (XylB). These, and additional proteins involved in arabinose metabolism and regulation may be found at http://www.nmpdr.org/FIG/wiki/rest.cgi/NmpdrPlugin/SeedViewer?page=Subsystems;su bsystem=L-Arabinose_utilization, visited Mar. 21, 2011, which is incorporated by reference herein in its entirety.

AraC protein regulates expression of its own synthesis and the other genes of the Ara system. See Schleif, R., *Trends Genet.* 16(12):559-65 (2000). In the *E. coli*, the AraC protein positively and negatively regulates expression of the proteins required for the uptake and catabolism of the sugar L-arabinose. Homologs of AraC, such as regulatory proteins RhaR and RhaS of the rhamnose operon, have been identified that contain regions homologous to the DNA-binding domain of AraC (Leal, T. F. and de Sa-Nogueira, I., *FEMS Microbiol Lett.* 241(1):41-48 (2004)). Such arabinose regulatory proteins are referred to as the AraC/XylS family. See also, Mota, L. J., et al., *Mol. Microbiol.* 33(3):476-89 (1999); Mota, L. J., et al., *J Bacteriol.* 183(14):4190-201 (2001).

In *E. coli*, the transport of L-arabinose across the *E. coli* cytoplasmic membrane requires the expression of either the high-affinity transport operon, araFGH, a binding protein-dependent system on the low-affinity transport operon, araE, a proton symporter. Additional arabinose transporters include those identified from *K. marxianus* and *P. guilliermondii*, disclosed in U.S. Pat. No. 7,846,712, which is incorporated by reference herein.

In some embodiments, the recombinant microorganisms of the invention have the ability to metabolize arabinose using one or more of the above enzymes.

Microorganisms

The present invention includes multiple strategies for the development of microorganisms with the combination of substrate-utilization and product-formation properties required for CBP. The "native cellulolytic strategy" involves engineering naturally occurring cellulolytic microorganisms to improve product-related properties, such as yield and titer. The "recombinant cellulolytic strategy" involves engineering natively non-cellulolytic organisms that exhibit high product yields and titers to express a heterologous cellulase system that enables cellulose utilization or hemicellulose utilization or both.

Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. For example, under aerobic conditions pyruvate may be oxidized to acetyl coenzyme A (acetyl-CoA), which then enters the tricarboxylic acid cycle (TCA), which in turn generates synthetic precursors, $CO_2$, and reduced cofactors. The cofactors are then oxidized by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidized in reactions involving the reduction of organic substrates to products, such as lactate and ethanol. In addition, ATP is regenerated from the production of organic acids, such as acetate, in a process known as substrate level phosphorylation. Therefore, the fermentation products of glycolysis and pyruvate metabolism include a variety of organic acids, alcohols and $CO_2$.

Most facultative anaerobes metabolize pyruvate aerobically via pyruvate dehydrogenase (PDH) and the tricarboxylic acid cycle (TCA). Under anaerobic conditions, the main energy pathway for the metabolism of pyruvate is via pyruvate-formate-lyase (PFL) pathway to give formate and acetyl-CoA. Acetyl-CoA is then converted to acetate, via phosphotransacetylase (PTA) and acetate kinase (ACK) with the co-production of ATP, or reduced to ethanol via acetaldehyde dehydrogenase (ACDH) and alcohol dehydrogenase (ADH). In order to maintain a balance of reducing equivalents, excess NADH produced from glycolysis is re-oxidized to NAD by lactate dehydrogenase (LDH) during the reduction of pyruvate to lactate. NADH can also be re-oxidized by ACDH and ADH during the reduction of acetyl-CoA to ethanol, but this is a minor reaction in cells with a functional LDH.

Host Cells

Host cells useful in the present invention include any prokaryotic or eukaryotic cells; for example, microorganisms selected from bacterial, algal, and yeast cells. Among host cells thus suitable for the present invention are microorganisms, for example, of the genera *Aeromonas, Aspergillus, Bacillus, Escherichia, Kluyveromyces, Pichia, Rhodococcus, Saccharomyces* and *Streptomyces*.

In some embodiments, the host cells are microorganisms. In one embodiment the microorganism is a yeast. According to the present invention the yeast host cell can be, for example, from the genera *Saccharomyces, Kluyveromyces, Candida, Pichia, Schizosaccharomyces, Hansenula, Kloeckera, Schwanniomyces*, and *Yarrowia*. Yeast species as host cells may include, for example, *S. cerevisiae, S. bulderi, S. barnetti, S. exiguus, S. uvarum, S. diastaticus, K lactis, K marxianus*, or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In another embodiment, the yeast is a thermotolerant *Saccharomyces cerevisiae*. The selection of an appropriate host is deemed to be within the scope of those skilled in the art from the teachings herein.

In some embodiments, the host cell is an oleaginous cell. The oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. According to the present invention, the oleaginous host cell can be an oleaginous microalgae host cell. For example, the oleaginous microalgea host cell can be from the genera *Thraustochytrium* or *Schizochytrium*. Biodiesel could then be produced from the triglyceride produced by the oleaginous organisms using conventional lipid transesterification processes. In some particular embodiments, the oleaginous host cells can be induced to secrete synthesized lipids. Embodiments using oleaginous host cells are advantegeous because they can produce biodiesel from lignocellulosic feedstocks which, relative to oilseed substrates, are cheaper, can be grown more densely, show lower life cycle carbon dioxide emissions, and can be cultivated on marginal lands.

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

Thermotolerant host cells can include, for example, *Issatchenkia orientalis, Pichia mississippiensis, Pichia mexicana, Pichia farinosa, Clavispora opuntiae, Clavispora lusitaniae, Candida mexicana, Hansenula polymorpha* and *Kluyveromyces* host cells. In some embodiments, the thermotolerant cell is an *S. cerevisiae* strain, or other yeast strain, that has been adapted to grow in high temperatures, for example, by selection for growth at high temperatures in a cytostat.

In some particular embodiments, the host cell is a *Kluyveromyces* host cell. For example, the *Kluyveromyces* host cell can be a *K. lactis, K. marxianus, K. blattae, K. phaffii, K. yarrowii, K. aestuarii, K. dobzhanskii, K. wickerhamii K. thermotolerans*, or *K. waltii* host cell. In one embodiment, the host cell is a *K. lactis*, or *K. marxianus* host cell. In another embodiment, the host cell is a *K. marxianus* host cell.

In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments of the present invention, the thermotolterant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the host cell has the ability to metabolize xylose. Detailed information regarding the development of the xylose-utilizing technology can be found in the following publications: Kuyper M et al. *FEMS Yeast Res.* 4: 655-64 (2004), Kuyper M et al. *FEMS Yeast Res.* 5:399-409 (2005), and Kuyper M et al. *FEMS Yeast Res.* 5:925-34 (2005), which are herein incorporated by reference in their entirety. For example, xylose-utilization can be accomplished in *S. cerevisiae* by heterologously expressing the xylose isomerase gene, XylA, e.g., from the anaerobic fungus *Piromyces* sp. E2, overexpressing five *S. cerevisiae* enzymes involved in the conversion of xylulose to glycolytic intermediates (xylulokinase, ribulose 5-phosphate isomerase, ribulose 5-phosphate epimerase, transketolase and transaldolase) and deleting the GRE3 gene encoding aldose reductase to minimise xylitol production.

In some embodiments, the host cell has the ability to metabolize arabinose. For example, arabinose-utilization can be accomplished by heterologously expressing, e.g., one or more of arabinose isomerase, ribulokinase, or ribulose phosphate epimerase.

The host cells can contain antibiotic markers or can contain no antibiotic markers.

In certain embodiments, the host cell is a microorganism that is a species of the genera *Thermoanaerobacterium, Thermoanaerobacter, Clostridium, Geobacillus, Saccharococcus, Paenibacillus, Bacillus, Caldicellulosiruptor, Anaerocellum*, or *Anoxybacillus*. In certain embodiments, the host cell is a bacterium selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter the rmohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, and Anaerocellum thermophilum*. In certain embodiments, the host cell is *Clostridium thermocellum, Clostridium cellulolyticum*, or *Thermoanaerobacterium saccharolyticum*.

Codon Optimized Polynucleotides

The polynucleotides encoding heterologous cellulases can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at http://www.kazusa.or.jp/codon/ (visited Feb. 28, 2011), and these tables can be adapted in a number of ways. See Nakamura, Y., et al. "Codon usage tabulated from the international DNA sequence databases: status for the year 2000," *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNII Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at www.entelechon.com/2008/10/backtranslation-tool/ (visited Feb. 28, 2011) and the "backtranseq" function available at emboss.bioinformatics.nl/cgi-bin/emboss/backtranseq (visited Feb. 28, 2011). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

Transposons

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extrachromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker(s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce more ethanol, or less lactic acid and/or more acetate.

Native Cellulolytic Strategy

Naturally occurring cellulolytic microorganisms are starting points for CBP organism development via the native strategy. Anaerobes and facultative anaerobes are of particular interest. The primary objective is to engineer the metabolization of biomass to solvents, including but not limited to, acetone, isopropanol, ethyl acetate, or ethanol. Metabolic engineering of mixed-acid fermentations in relation to, for example, ethanol production, has been successful in the case of mesophilic, non-cellulolytic, enteric bacteria. Recent developments in suitable gene-transfer techniques allow for this type of work to be undertaken with cellulolytic bacteria.

Recombinant Cellulolytic Strategy

Non-cellulolytic microorganisms with desired product-formation properties are starting points for CBP organism development by the recombinant cellulolytic strategy. The primary objective of such developments is to engineer a heterologous cellulase system that enables growth and fermentation on pretreated lignocellulose. The heterologous production of cellulases has been pursued primarily with bacterial hosts producing ethanol at high yield (engineered strains of *E. coli, Klebsiella oxytoca*, and *Zymomonas mobilis*) and the yeast *Saccharomyces cerevisiae*. Cellulase expression in strains of *K. oxytoca* resulted in increased hydrolysis yields—but not growth without added cellulase—for microcrystalline cellulose, and anaerobic growth on amorphous cellulose. Although dozens of saccharolytic enzymes have been functionally expressed in *S. cerevisiae*, anaerobic growth on cellulose as the result of such expression has not been definitively demonstrated.

Aspects of the present invention relate to the use of thermophilic or mesophilic microorganisms as hosts for modification via the native cellulolytic strategy. Their potential in process applications in biotechnology stems from their ability to grow at relatively high temperatures with attendant high metabolic rates, production of physically and chemically stable enzymes, and elevated yields of end products. Major groups of thermophilic bacteria include eubacteria and archaebacteria. Thermophilic eubacteria include: phototropic bacteria, such as cyanobacteria, purple bacteria, and green bacteria; Gram-positive bacteria, such as *Bacillus, Clostridium*, Lactic acid bacteria, and *Actinomyces*; and other eubacteria, such as *Thiobacillus, Spirochete, Desulfotomaculum*, Gram-negative aerobes, Gram-negative anaerobes, and *Thermotoga*. Within archaebacteria are considered Methanogens, extreme thermophiles (an art-recognized term), and *Thermoplasma*. In certain embodiments, the present invention relates to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus, Thermoproteus* (rod-shaped), *Thermofilum* (rod-shaped), *Pyrodictium, Acidianus, Sulfolobus, Pyrobaculum, Pyrococcus, Thermodiscus, Staphylothermus, Desulfurococcus, Archaeoglobus*, and *Methanopyrus*. Some examples of thermophilic or mesophilic (including bacteria, procaryotic microorganism, and fungi), which may be suitable for the present invention include, but are not limited to: *Clostridium thermosulfurogenes, Clostridium cellulolyticum, Clostridium thermocellum, Clostridium thermohydrosulfuricum, Clostridium thermoaceticum, Clostridium thermosaccharolyticum, Clostridium tartarivorum, Clostridium the rmocellulaseum, Clostridium phytofermentans, Clostridium straminosolvens, Thermoanaerobacterium thermosaccarolyticum, Thermoanaerobacterium saccharolyticum, Thermobacteroides acetoethylicus, Thermoanaerobium brockii, Methanobacterium thermoautotrophicum, Anaerocellum thermophilium, Pyrodictium occultum, Thermoproteus neutrophilus, Thermofilum librum, Thermothrix thioparus, Desulfovibrio thermophilus, Thermoplasma acidophilum, Hydrogenomonas thermophilus, Thermomicrobium roseum, Thermus flavas, Thermus ruber, Pyrococcus jitriosus, Thermus aquaticus, Thermus thermophilus, Chloroflexus aurantiacus, Thermococcus litoralis, Pyrodictium abyssi, Bacillus stearothermophilus, Cyanidium caldarium, Mastigocladus laminosus, Chlamydothrix calidissima, Chlamydothrix penicillata, Thiothrix carnea, Phormidium tenuissimum, Phormidium geysericola, Phormidium subterraneum, Phormidium bijahensi, Oscillatoria filiformis, Synechococcus lividus, Chloroflexus aurantiacus, Pyrodictium brockii, Thiobacillus thiooxidans, Sulfolobus acidocaldarius, Thiobacillus thermophilica, Bacillus stearothermophilus, Cercosukifer hamathensis, Vahlkampfia reichi, Cyclidium citrullus, Dactylaria gallopava, Synechococcus lividus, Synechococcus elongatus, Synechococcus minervae, Synechocystis aquatilus, Aphanocapsa thermalis, Oscillatoria terebriformis, Oscillatoria amphibia, Oscillatoria germinata, Oscillatoria okenii, Phormidium laminosum, Phormidium parparasiens, Symploca thermalis, Bacillus acidocaldarias, Bacillus coagulans, Bacillus thermocatenalatus, Bacillus licheniformis, Bacillus pamilas, Bacillus macerans, Bacillus circulans, Bacillus laterosporus, Bacillus brevis, Bacillus subtilis, Bacillus sphaericus, Desulfotomaculum nigrificans, Streptococcus thermophilus, Lactobacillus thermophilus, Lactobacillus bulgaricus, Bifidobacterium thermophilum, Streptomyces fragmentosporus, Streptomyces the rmonitrificans, Streptomyces thermovulgaris, Pseudonocardia thermophila, Thermoactinomyces vulgaris, Thermoactinomyces sacchari, Thermoactinomyces candidas, Thermomonospora curvata, Thermomonospora viridis, Thermomonospora citrina, Microbispora thermodiastatica, Microbispora aerata, Microbispora bispora, Actinobifida dichotomica, Actinobifida chromogena, Micropolyspora caesia, Micropolyspora faeni, Micropolyspora cectivugida, Micropolyspora cabrobrunea, Micropolyspora thermovirida, Micropolyspora viridinigra, Methanobacterium thermoautothropicum, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus*, variants thereof, and/or progeny thereof.

In particular embodiments, the present invention relates to thermophilic bacteria selected from the group consisting of *Clostridium cellulolyticum, Clostridium thermocellum*, and *Thermoanaerobacterium saccharolyticum.*

In certain embodiments, the present invention relates to thermophilic bacteria selected from the group consisting of *Fervidobacterium gondwanense, Clostridium thermolacticum, Moorella* sp., and *Rhodothermus marinus.*

In certain embodiments, the present invention relates to thermophilic bacteria of the genera *Thermoanaerobacterium* or *Thermoanaerobacter*, including, but not limited to, species selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brockii,* variants thereof, and progeny thereof.

In certain embodiments, the present invention relates to microorganisms of the genera *Geobacillus, Saccharococcus, Paenibacillus, Bacillus*, and *Anoxybacillus*, including, but not limited to, species selected from the group consisting of: *Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis*, variants thereof, and progeny thereof.

In certain embodiments, the present invention relates to mesophilic bacteria selected from the group consisting of *Saccharophagus degradans; Flavobacterium johnsoniae; Fibrobacter succinogenes; Clostridium hungatei; Clostridium phytofermentans; Clostridium cellulolyticum; Clostridium aldrichii; Clostridium termitididis; Acetivibrio cellulolyticus; Acetivibrio ethanolgignens; Acetivibrio multivorans; Bacteroides cellulosolvens; and Alkalibacter saccharofomentans*, variants thereof and progeny thereof.

Organism Development Via the Native Cellulolytic Strategy

One approach to organism development for CBP begins with organisms that naturally utilize cellulose, hemicellulose and/or other biomass components, which are then genetically engineered to enhance product yield and tolerance. For example, *Clostridium thermocellum* is a thermophilic bacterium that has among the highest rates of cellulose utilization reported. Other organisms of interest are xylose-utilizing thermophiles such as *Thermoanaerobacterium saccharolyticum* and *Thermoanaerobacterium* the *thermosaccharolyticum*. Organic acid production may be responsible for the low concentrations of produced ethanol generally associated with these organisms. Thus, one objective is to eliminate production of acetic and lactic acid in these organisms via metabolic engineering. Substantial efforts have been devoted to developing gene transfer systems for the above-described target organisms and multiple *C. thermocellum* isolates from nature have been characterized. See McLaughlin et al. (2002) *Environ. Sci. Technol.* 36:2122. Metabolic engineering of thermophilic, saccharolytic bacteria is an active area of interest, and knockout of lactate dehydrogenase in *T. saccharolyticum* has recently been reported. See Desai et al. (2004) *Appl. Microbiol. Biotechnol.* 65:600. Knockout of acetate kinase and phosphotransacetylase in this organism is also possible.

Organism Development Via the Recombinant Cellulolytic Strategy

An alternative approach to organism development for CBP involves conferring the ability to grow on lignocellulosic materials to microorganisms that naturally have high product yield and tolerance via expression of a heterologous cellulasic system and perhaps other features. For example, *Saccharomyces cerevisiae* has been engineered to express over two dozen different saccharolytic enzymes. See Lynd et al. (2002) *Microbiol. Mol. Biol. Rev.* 66:506.

Whereas cellulosic hydrolysis has been approached in the literature primarily in the context of an enzymatically-oriented intellectual paradigm, the CBP processing strategy requires that cellulosic hydrolysis be viewed in terms of a microbial paradigm. This microbial paradigm naturally leads to an emphasis on different fundamental issues, organisms, cellulasic systems, and applied milestones compared to those of the enzymatic paradigm. In this context, *C. thermocellum* has been a model organism because of its high growth rate on cellulose together with its potential utility for CBP.

In certain embodiments, organisms useful in the present invention may be applicable to the process known as simultaneous saccharification and fermentation (SSF), which is intended to include the use of said microorganisms and/or one or more recombinant hosts (or extracts thereof, including purified or unpurified extracts) for the contemporaneous degradation or depolymerization of a complex sugar (i.e., cellulosic biomass) and bioconversion of that sugar residue into ethanol by fermentation.

Ethanol Production

According to the present invention, a recombinant microorganism can be used to produce ethanol from biomass, which is referred to herein as lignocellulosic material, lignocellulosic substrate, or cellulosic biomass. Methods of producing ethanol can be accomplished, for example, by contacting the biomass with a recombinant microorganism as described herein, and as described in commonly owned U.S. Patent Application Publication No. 2011/0189744 A1, U.S. Patent Application Publication No. 2011/0312054 A1, U.S. Patent Application Publication No. 2012/0003701, International Appl. No. PCT/US2009/065571, International Appl. No. PCT/US2009/069443, International Appl. No. PCT/US2009/064128, International Appl. No. PCT/IB2009/005881, and PCT/US2009/065571, the contents of each are incorporated by reference herein.

Numerous cellulosic substrates can be used in accordance with the present invention. Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

In some embodiments, the invention is directed to a method for hydrolyzing a cellulosic substrate, for example a cellulosic substrate as described above, by contacting the cellulosic substrate with a recombinant microorganism of the invention. In some embodiments, the invention is directed to a method for hydrolyzing a cellulosic substrate, for example a cellulosic substrate as described above, by contacting the cellulosic substrate with a co-culture comprising yeast cells expressing heterologous cellulases.

In some embodiments, the invention is directed to a method for fermenting cellulose. Such methods can be accomplished, for example, by culturing a host cell or co-culture in a medium that contains insoluble cellulose to allow saccharification and fermentation of the cellulose.

The production of ethanol can, according to the present invention, be performed at temperatures of at least about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C. In some embodiments of the present invention, the thermotolterant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, methods of producing ethanol can comprise contacting a cellulosic substrate with a recombinant microorganism or co-culture of the invention and additionally contacting the cellulosic substrate with externally produced cellulase enzymes. Exemplary externally produced cellulase enzymes are commercially available and are known to those of skill in the art.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter.

In some embodiments, the host cells of the present invention can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter more than a control strain (e.g., a wild-type strain) and grown under the same conditions. In some embodiments, the ethanol can be produced in the absence of any externally added cellulases.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein. The U.S. Department of Energy (DOE) provides a method for calculating theoretical ethanol yield. Accordingly, if the weight percentages are known of C6 sugars (i.e., glucan, galactan, mannan), the theoretical yield of ethanol in gallons per dry ton of total C6 polymers can be determined by applying a conversion factor as follows:

(1.11 pounds of C6 sugar/pound of polymeric sugar)×(0.51 pounds of ethanol/pound of sugar)×(2000 pounds of ethanol/ton of C6 polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

And if the weight percentages are known of C5 sugars (i.e., xylan, arabinan), the theoretical yield of ethanol in gallons per dry ton of total C5 polymers can be determined by applying a conversion factor as follows:

(1.136 pounds of C5 sugar/pound of C5 polymeric sugar)×(0.51 pounds of ethanol/pound of sugar)×(2000 pounds of ethanol/ton of C5 polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

It follows that by adding the theoretical yield of ethanol in gallons per dry ton of the total C6 polymers to the theoretical yield of ethanol in gallons per dry ton of the total C5 polymers gives the total theoretical yield of ethanol in gallons per dry ton of feedstock.

Applying this analysis, the DOE provides the following examples of theoretical yield of ethanol in gallons per dry ton of feedstock: corn grain, 124.4; corn stover, 113.0; rice straw, 109.9; cotton gin trash, 56.8; forest thinnings, 81.5; harwood sawdust, 100.8; bagasse, 111.5; and mixed paper, 116.2. It is important to note that these are theoretical yields. The DOE warns that depending on the nature of the feedstock and the process employed, actual yield could be anywhere from 60% to 90% of theoretical, and further states that "achieving high yield may be costly, however, so lower yield processes may often be more cost effective." (Ibid.)

EXEMPLIFICATION

The invention now being generally described, it will be more readily understood by reference to the following examples, which are included merely for purposes of illustration of certain aspects and embodiments of the present invention, and are not intended to limit the invention.

Example 1

Improving Ethanol Yield Through Engineering of Alternate Electron Acceptors

The present Example describes pathways to reduce or eliminate glycerol by engineering alternate electron acceptors in a yeast cell. Glycerol is an undesired by-product of sugar metabolism during anaerobic growth in yeast. The amount of glycerol produced during anaeroblic growth on glucose has been empirically determined by Medina, V G, et al., *Appl. Env. Microbiol.* 76:190-95 (2010):

56 mmol glucose→1 g biomass+88 mmol ethanol+95 mmol $CO_2$+11 mmol glycerol+1.7 mmol acetate Assuming glycerol production is primarily for the regeneration of $NAD^+$ for the continuation of glycolysis, a half reaction for glycerol production is (Medina, V G, et al., *Appl. Env. Microbiol.* 76:190-95 (2010)):

0.5 glucose+NADH+$H^+$+ATP→glycerol+$NAD^+$+ADP+$P_i$

The following pathways describe engineering an alternate electron acceptor for glycerol in the above half reaction, engineering an increase in ethanol yield during anaerobic growth on glucose by using improved enzyme activities for converting glucose to ethanol, and/or deleting endogenous glycerol-producing or glycerol-regulating genes.

1.1 Engineering of a Formate Pathway in Yeast

Production of formate from glucose can provide similar reducing equivalents as glycerol, as shown in the following half reaction:

0.5 glucose+NADH+$H^+$+ADP+$P_i$→formate+$NAD^+$+ATP+ethanol

In addition to balancing the redox constraints of the cell, this pathway provides increased ATP yield and results in an overall anaerobic growth equation of:

56 mmol glucose→1 g biomass+99 mmol ethanol+95 mmol $CO_2$+11 mmol formate+1.7 mmol acetate Engineering in a formate pathway as an alternate electron acceptor to glycerol results in an increase of 12.5% in the theoretical yield of ethanol. Enzymes than can be targeted to engineer such an increase include pyruvate formate lyase (PFL) and formate dehydrogenase (FDH). See FIG. 1.

1.1.1 Expression of PFL

The conversion of pyruvate to acetyl-CoA and formate is performed by PFL. Thus, to produce formate in yeast, a PFL can be expressed. PFLs are common in bacteria from a variety of sources. Vigorous hydrogen producing bacteria, such as from a *clostridium, thermoanaerobacterium*, or other anaerobic bacteria will likely result in an increased productivity. Examples of PFL include, but are not limited, *Bacillus licheniformis, Streptococcus thermophilus, Lactobacillus plantarum, Lactobacillus casei, Bifidobacterium adolescentis, Clostridium cellulolyticum, Escherichia coli, Chlamydomonas reinhardtii* PflA, *Piromyces* sp. E2, or *Neocallimastix frontalis*. See Example 4 and Table 1 below.

1.1.2 Deletion of FDH

To prevent yeast from converting formate to $CO_2$ and NADH, endogeneous FDH genes can be deleted or downregulated. Deleting or downregulating fdh1, fdh2, or both genes can enhance the redox balance and ethanol yield of the recombinant microorganisms of the invention.

1.2 Improving Conversion of Acetyl-CoA to Ethanol

To improve the conversion of acetyl-CoA to ethanol, endogenous yeast genes can be replaced or complimented with either an improved acetaldehyde dehydrogenase (e.g., from *C. phytofermentans* or other source) to convert acetyl-CoA to acetaldehyde, or a bifunctional acetaldehyde/alcohol dehydrogenase (AADH) to convert acetyl-CoA to acetaldehyde and acetaldehyde to ethanol. By engineering in one or more such enzymes, the in vivo kinetics of the conversion of acetyl-CoA to ethanol can be increased, providing for improved growth of the host strain. The bi-functional alcohol/aldehyde dehydrogenase can come from a variety of microbial sources, including but not limited to *E. coli, C. acetobutylicum, T. saccharolyticum, C. thermocellum, C. phytofermentans, Piromyces* SP E2, or *Bifidobacterium adolescentis.*

1.3 Deletion or Downregulation of Glycerol Pathway

Deleting or altering expression of glycerol formation genes will reduce or block endogenous production of glycerol and may enhance acetate uptake. Deletion of gpd1, gpd2, or both genes and/or deletion of gpp1, gpp2, or both genes may be used to eliminate glycerol formation and enhance ethanol yield. However, the complete elimination of glycerol may not be practical for an industrial process. See Guo, Z P., et al., *Metab. Eng.* 13:49-59 (2011). Thus, rather than the complete removal of any one, all, or some combination of these glycerol formation genes, one or more of these genes can be altered or downregulated to reduce glycerol formation and enhance ethanol yield.

Example 2

Deletion or Downregulation of Glycerol-Regulating Gene FPS1 to Improve Ethanol Yield Instead of, or in addition to, downregulating glycerol production through deletion or alteration of glycerol-forming genes, glycerol production can be downregulated by deletion or alteration of a glycerol-regulating gene. FPS1 is an aquaglyceroporin responsible for efflux of glycerol. An fps1Δ strain has reduced glycerol formation yet has a completely functional $NAD^+$-dependant glycerol synthesis pathway. In addition to deletion of FPS1, constitutively active mutants of FPS1 or homologs from other organisms can be expressed to alter glycerol production. Because such FPS1 deletion or alteration strains can still synthesize and retain glycerol, improved robustness may be observed relative to strains that are unable to make glycerol.

Null mutants of an fps1Δ strain grow much slower anaerobically than wild-type due to intracellular glycerol accumulation. Tamás, M. J., et al., *Molecular Microbiol.* 31(4):1087-1104 (1999). However, preliminary data indicates that expression of a *B. adolescentis* bifunctional AADH in conjunction with *B. adolescentis* PFL in an fps1Δ strain can enable anaerobic growth of fps1Δ strain (see Example 7 and FIGS. 22 and 24). Additionally, significantly improved osmotic tolerance was also observed when FPS1 was deleted in glycerol mutant strains containing ADH and PFL alone. Increased resistance to osmotic stress was determined by observation of improved growth of the fps1Δ mutant on several different high osmolarity media including 1M sodium chloride, 1M sorbitol, and 1M xylitol. The fps1Δ mutant was created by marker recycle resulting in a deletion of a large region of the FPS1 coding sequence (sequence of native and deletion below).

Sequence of FPS1 locus (coding sequence is underlined; SEQ ID NO:104):

```
aacgcggctgatgcttttatttaggaaggaatacttacattatcatgaga
acattgtcaagggcattctgatacgggccttccatcgcaagaaaaaggca
gcaacggactgagggacggagagagttacggcataagaagtagtaggaga
gcagagtgtcataaagttatattattctcgtcctaaagtcaattagttct
gttgcgcttgacaatatatgtcgtgtaataccgtcccttagcagaagaaa
gaaagacggatccatatatgttaaaatgcttcagagatgtttctttaatg
tgccgtccaacaaaggtatcttctgtagcttcctctattttcgatcagat
ctcatagtgagaaggcgcaattcagtagttaaaagcggggaacagtgtga
atccggagacggcaagattgcccggcccttttgcggaaaagataaaacaa
gatatattgcactttttccaccaagaaaaacaggaagtggattaaaaat
caacaaagtataacgcctattgtcccaataagcgtcggttgttatcttta
ttattttaccaagtacgctcgagggtacattctaatgcattaaaagacat
gagtaatcctcaaaaagctctaaacgactactgtccagtgaatctgttca
tacacatgatagttctaggaaacaatctaataagcagtcatccgacgaag
gacgctcttcatcacaaccttcacatcatcactctggtggtactaacaac
aataataacaataataataataataataacagtaacaacaacaacaacgg
caacgatgggggaaatgatgacgactatgattatgaaatgcaagattata
gaccttctccgcaaagtgcgcggcctactcccacgtatgttccacaatat
tctgtagaaagtgggactgctttcccgattcaagaggttattcctagcgc
atacattaacacacaagatataaaccataaagataacggtccgccgagtg
caagcagtaatagagcattcaggcctagagggcagaccacagtgtcggcc
aacgtgcttaacattgaagattttacaaaaatgcagacgatgcgcatac
catcccggagtcacatttatcgagaaggagaagtaggtcgagggctacga
gtaatgctgggcacagtgccaatacaggcgccacgaatggcaggactact
ggtgcccaaactaatatggaaagcaatgaatcaccacgtaacgtccccat
tatggtgaagccaaagacattataccagaaccctcaaacacctacagtca
gccctccacataccatccaattaataaatggtcttccgtcaaaaacactt
atttgaaggaatattagccgagtttatgggaacaatggttatgattatat
cggtagtgctgttgtagtcaggtcaatgttgctgggaaaatacagcagga
caatttcaacgtggctttggataaccttaacgttaccgggtcttctgcag
aaacgatagacgctatgaagagtttaacatccttggtttcatccgttgcg
ggcggtaccatgatgatgtggcattgggctgggctgctgccgtggtgatg
ggctatttactgcgctggtggtagtgccatctcaggtgctcatttgaatc
cgtctattacattagccaatttggtgtatagaggttttcccctgaagaaa
gttccttattactttgctggacaattgatcggtgccacacaggcgctttg
atcttgtttatttggtacaaaagggtgttacaagaggcatatagcgattg
gtggatgaatgaaagtgttgcgggaatgttttgcgtttttccaaagcctt
atctaagacaggacggcaatttttttccgaatttttatgtggagctatgt
tacaagcaggaacatttgcgctgaccgatccttatacgtgtttgtcctct
```

-continued gatgttttcccattgatgatgtttattttgattttcattatcaatgcttc
catggcttatcagacaggtacagcaatgaatttggctcgtgatctgggcc
cacgtcttgcactatatgcagttggatttgatcataaaatgctttgggtg
catcatcatcatttcttttgggttcccatggtaggcccatttattggtgc
gttaatgggggggttggtttacgatgtctgtatttatcagggtcatgaat
ctccagtcaactggtctttaccagtttataaggaaatgattatgagagcc
tggtttagaaggcctggttggaagaagagaaatagagcaagaagaacatc
ggacctgagtgacttctcatacaataacgatgatgatgaggaatttggag
aaagaatggctcttcaaaagacaaagaccaagtcatctatttcagacaac
gaaaatgaagcaggagaaaagaaagtgcaatttaaatctgttcagcgcgg
caaaagaacgtttggtggtataccaacaattcttgaagaagaagattcca
ttgaaactgcttcgctaggtgcgacgacgactgattctattgggttatcc
gacacatcatcagaagattcgcattatggtaatgctaagaaggtaacatg
agaaaacagacaagaaaaagaaacaaataatatagactgatagaaaaaaa
tactgcttactaccgccggtataatatatatatatatatatatttacata
gatgattgcatagtgttttaaaaagctttcctaggttaagctatgaatct
tcataacctaaccaactaaatatgaaaatactgacccatcgtcttaagta
agttgacatgaactcagcctggtcacctactatacatgatgtatcgcatg
gatggaaagaataccaaacgctaccttccaggttaatgatagtatccaaa
cctagaggaatttgccagaacatcaagcagcgattcgatatcagttggga
gcatcaatttggtcattggaataccatctatgcttactcctcccatattc
gcaaaagtagtaagggctcgttatatacttttgaatatgtaagatataat
tctatatgatttagtaatttattttctatacgctcagtatttactgcagt
tgtcgagtaggtattaaacgcaaaagaagtccatccttttcatcattcaa
atggacatcttggcaaagggcccagttatggaaaatctgggagtcataca
acgattgcagttggctatgccactcctggtaaggaatcatcaagtctgat
aattctgtttttagccatttttttttttttttcatg Sequence of fps1Δ mutation (part of the fps1 coding sequence was not deleted (underlined) and the region that was deleted is represented by a Δ; SEQ ID NO:105):

aacgcggctgatgcttttatttaggaaggaatacttacattatcatgaga
acattgtcaagggcattctgatacgggccttccatcgcaagaaaaaggca
gcaacggactgagggacggagagagttacggcataagaagtagtaggaga
gcagagtgtcataaagttatattattctcgtcctaaagtcaattagttct
gttgcgcttgacaatatatgtcgtgtaataccgtcccttagcagaagaaa
gaaagacggatccatatatgttaaaatgcttcagagatgtttctttaatg
tgccgtccaacaaaggtatcttctgtagcttcctctattttcgatcagat
ctcatagtgagaaggcgcaattcagtagttaaaagcggggaacagtgtga
atccggagacggcaagattgcccggcccttttttgcggaaaagataaaaca
agatatattgcactttttccaccaagaaaaacaggaagtggattaaaaaa
tcaacaaagtataacgcctattgtcccaataagcgtcggttgttcttctt -continued tattattttaccaagtacgctcgagggtacattctaatgcattaaaagac
Δgattcgcattatggtaatgctaagaaggtaacatgagaaaacagacaag
aaaaagaaacaaataatatagactgatagaaaaaaatactgcttactacc
gccggtataatatatatatatatatatatttacatagatgattgcatagt
gttttaaaaagctttcctaggttaagctatgaatcttcataacctaacca
actaaatatgaaaatactgacccatcgtcttaagtaagttgacatgaact
cagcctggtcacctactatacatgatgtatcgcatggatggaaagaatac
caaacgctaccttccaggttaatgatagtatccaaacctagttggaattt
gccttgaacatcaagcagcgattcgatatcagttgggagcatcaatttgg
tcattggaataccatctatgcttttctcctcccatattcgcaaaagtagt
aagggctcgttatatacttttgaatatgtaagatataattctatatgatt
tagtaatttattttctatacgctcagtatttttctgcagttgtcgagtag
gtattaaacgcaaaagaagtccatccttttcatcattcaaatggacatct
tggcaaagggcccagttatggaaaatctgggagtcatacaacgattgcag
ttggctatgccactcctggtaaggaatcatcaagtctgataattctgttt
tttagcccttttttttttttttcatg

Example 3

Generating Yeast Strains with a Deleted or Downregulated Glycerol-Production Pathway To create yeast strains with altered glycerol production, endogenous glycerol-producing or regulating genes can either be deleted or downregulated, by generating the following genetic backgrounds:

| | Haploid Strains | Diploid Strains |
|---|---|---|
| Glycerol Elimination Background | gpd1Δ gpd2Δ fdh1Δ fdh2Δ<br>fdh1Δ fdh2Δ fps1Δ<br>gpd1Δ gpd2Δ fdh1Δ fdh2Δ fps1Δ<br>gpd1Δ gpd2Δ fps1Δ<br>gpd1Δ gpd2Δ | gpd1Δ/gpd1Δ gpd2Δ/gpd2Δ fdh1Δ/fdh1Δ fdh2Δ/fdh2Δ<br>fdh1Δ/fdh1Δ fdh2Δ/fdh2Δ fps1Δ/fps1Δ<br>gpd1Δ/gpd1Δ gpd2Δ/gpd2Δ fdh1Δ/fdh1Δ fdh2Δ/fdh2Δ fps1Δ/fps1Δ<br>gpd1Δ/gpd1Δ gpd2Δ/gpd2Δ fps1Δ/fps1Δ<br>gpd1Δ/gpd1Δ gpd2Δ/gpd2Δ |
| Glycerol Reduction Background | gpd1Δ gpd2Δ::GPD1 fdh1Δ fdh2Δ<br>gpd1Δ gpd2Δ::GPD1<br>gpd1Δ gpd2Δ::GPD1 fdh1Δfdh2Δ fps1Δ<br>gpd1Δ gpd2Δ::GPD1 fps1Δ<br>gpd1Δ: GPD2 gpd2Δ<br>gpd1::GPD2 gpd2Δ fdh1Δfdh2Δ | gpd1Δ/gpd1Δ gpd2Δ/gpd2Δ::GPD1/GPD1 fdh1Δ/fdh1Δ fdh2Δ/fdh2Δ<br>gpd1Δ/gpd1Δ gpd2Δ/gpd2Δ::GPD1/GPD1<br>gpd1Δ/gpd1Δ gpd2Δ/gpd2Δ::GPD1/GPD1 fdh1Δ/fdh1Δ fdh2Δ/fdh2Δ fps1Δ/fps1Δ<br>gpd1Δ/gpd1Δ gpd2Δ/gpd2Δ::GPD1/GPD1 fps1Δ/fps1Δ<br>gpd1Δ/gpd1Δ::GPD2/GPD2 gpd2Δ/gpd2Δ<br>gpd1Δ/gpd1Δ::GPD2/GPD2 gpd2Δ/gpd2Δ fdh1Δ/fdh1Δ fdh2Δ/fdh2Δ |

Strains in the glycerol elimination background were created by deleting one or more of the following genes: gpd1, gpd2, fdh1, fdh2, and/or fps1. Strains in the glycerol reduction background have been created by deleting one or more of the following genes: gpd1, gpd2, fdh1, fdh2, and/or fps1, and by expressing GPD1 under the control of the gpd2 promoter (designated gpd2Δ::GPD1). These strains in which GPD1 is expressed from the gpd2 promoter make a smaller amount of glycerol relative to a wild-type strain.

3.1 Generation of Glycerol-Elimination Strain gpd1Δ gpd2Δ fdh1Δ fdh2Δ

To produce glycerol-elimination strain gpd1Δ gpd2Δ fdh1Δ fdh2Δ, the following methods were used. All genetic modifications were generated using positive selections to insert genetic elements and negative selections to remove genetic elements. See FIGS. 4-11. The genetic elements were amplified by PCR and transformed into host strains, followed by selection and screening for the desired modification. The sequence of native gpd1, gpd2, fdh1, fdh2 from *S. cerevisiae*, and resulting loci following deletion, are listed below.

Sequence of GPD1 locus (coding sequence is underlined; SEQ ID NO:89):

```
tacaaacgcaacacgaaagaacaaaaaaagaagaaaacagaaggccaaga
cagggtcaatgagactgttgtcctcctactgtccctatgtctctggccga
tcacgcgccattgtccctcagaaacaaatcaaacacccacaccccgggca
cccaaagtccccacccacaccaccaatacgtaaacggggcgccccctgca
ggccctcctgcgcgcggcctcccgccttgcttctctccccttccttttct
ttttccagttttccctattttgtccctttttccgcacaacaagtatcaga
atgggttcatcaaatctatccaacctaattcgcacgtagactggcttggt
attggcagtttcgtagttatatatatactaccatgagtgaaactgttacg
ttaccttaaattctttctccctttaattttcttttatcttactctcctac
ataagacatcaagaaacaattgtatattgtacaccccccccctccacaaa
cacaaatattgataatataaagatgtctgctgctgctgatagattaaact
taacttccggccacttgaatgctggtagaaagagaagttcctcttctgtt
tctttgaaggctgccgaaaagcctttcaaggttactgtgattggatctgg
taactggggtactactattgccaaggtggttgccgaaaattgtaagggat
acccagaagttttcgctccaatagtacaaatgtgggtgttcgaagaagag
atcaatggtgaaaaattgactgaaatcataaatactagacatcaaaacgt
gaaatacttgcctggcatcactctacccgacaatttggttgctaatccag
acttgattgattcagtcaaggatgtcgacatcatcgttttcaacattcca
catcaatttttgccccgtatctgtagccaattgaaaggtcatgttgattc
acacgtcagagctatctcctgtctaaagggttttgaagttggtgctaaag
gtgtccaattgctatcctcttacatcactgaggaactaggtattcaatgt
ggtgctctatctggtgctaacattgccaccgaagtcgctcaagaacactg
gtctgaaacaacagttgcttaccacattccaaaggatttcagaggcgagg
gcaaggacgtcgaccataaggttctaaaggccttgttccacagaccttac
ttccacgttagtgtcatcgaagatgttgctggtatctccatctgtggtgc
tttgaagaacgttgttgccttaggttgtggtttcgtcgaaggtctaggct
ggggtaacaacgcttctgctgccatccaaagagtcggtttgggtgagatc
atcagattcggtcaaatgtttttcccagaatctagagaagaaacatacta
```

-continued

```
ccaagagtctgctggtgttgctgatttgatcaccacctgcgctggtggta
gaaacgtcaaggttgctaggctaatggctacttctggtaaggacgcctgg
gaatgtgaaaaggagttgttgaatggccaatccgctcaaggtttaattac
ctgcaaagaagttcacgaatggttggaaacatgtggctctgtcgaagact
tcccattatttgaagccgtataccaaatcgtttacaacaactacccaatg
aagaacctgccggacatgattgaagaattagatctacatgaagattagat
ttattggagaaagataacatatcatactttcccccactttttttcgaggct
cttctatatcatattcataaattagcattatgtcatttctcataactact
ttatcacgttagaaattacttattattattaaattaatacaaaatttagt
aaccaaataaatataaataaatatgtatatttaaattttaaaaaaaaat
cctatagagcaaaaggattttccattataatattagctgtacacctcttc
cgcatttttttgagggtggttacaacaccactcattcagaggctgtcggca
cagttgcttctagcatctggcgtccgtatgtatgggtgtattttaaataa
taaacaaagtgccacaccttcaccaattatgtctttaagaaatggacaag
ttccaaagagcttgcccaaggctcgacaaggatgtactttggaatatcta
tattcaagtacgtggcgcgcatatgtttgagtgtgcacacaataaaggtt
```

Sequence of gpd1 Δ mutation (part of the gpd1 coding sequence was not deleted (underlined) and the region that was deleted is represented by a Δ; SEQ ID NO:90):

```
tacaaacgcaacacgaaagaacaaaaaaagaagaaaacagaaggccaaga
cagggtcaatgagactgttgtcctcctactgtccctatgtctctggccga
tcacgcgccattgtccctcagaaacaaatcaaacacccacaccccgggca
cccaaagtccccacccacaccaccaatacgtaaacggggcgccccctgca
ggccctcctgcgcgcggcctcccgccttgcttctctccccttccttttct
ttttccagttttccctattttgtccctttttccgcacaacaagtatcaga
atgggttcatcaaatctatccaacctaattcgcacgtagactggcttggt
attggcagtttcgtagttatatatatactaccatgagtgaaactgttacg
ttaccttaaattaaattctttccctttaattttcttttatcttactctcc
tacataagacatcaagaaacaattgtatattgtacaccccccccctccac
aaacacaaatattgataatataaagatgtctgctgctgctgatagΔtcta
catgaagattagatttattggagaaagataacatatcatactttcccccca
ctttttttcgaggctcttctatatcatattcataaattagcattatgtcat
ttctcataactactttatcacgttagaaattacttattattattaaatta
atacaaaatttagtaaccaaataaatataaataaatatgtatatttaaat
tttaaaaaaaaaatcctatagagcaaaaggattttccattataatattag
ctgtacacctcttccgcatttttttgagggtggttacaacaccactcattc
agaggctgtcggcacagttgcttctagcatctggcgtccgtatgtatggg
tgtattttaaataataaacaaagtgccacaccttcaccaattatgtcttt
aagaaatggacaagttccaaagagcttgcccaaggctcgacaaggatgta
ctttggaatatctatattcaagtacgtggcgcgcatatgtttgagtgtgc
acacaataaaggtt
```

Sequence of GPD2 locus (coding sequence is underlined; SEQ ID NO:91):

atagccatcatgcaagcgtgtatcttctaagattcagtcatcatcattac
cgagtttgttttccttcacatgatgaagaaggtttgagtatgctcgaaac
aataagacgacgatggctctgccattgttatattacgcttttgcggcgag
gtgccgatgggttgctgaggggaagagtgtttagcttacggacctattgc
cattgttattccgattaatctattgttcagcagctcttctctaccctgtc
attctagtattttttttttttttttttggttttactttttttttcttcttg
ccttttttttcttgttactttttttctagttttttttccttccactaagct
ttttccttgatttatccttgggttcttctttctactcctttagattttttt
ttttatatattaatttttaagtttatgtattttggtagattcaattctct
ttccctttccttttccttcgctccccttccttatcaatgcttgctgtcag
aagattaacaagatacacattccttaagcgaacgcatccggtgttatata
ctcgtcgtgcatataaaattttgccttcaagatctactttcctaagaaga
tcattattacaaacacaactgcactcaaagatgactgctcatactaatat
caaacagcacaaacactgtcatgaggaccatcctatcagaagatcggact
ctgccgtgtcaattgtacatttgaaacgtgcgcccttcaaggttacagtg
attggttctggtaactgggggaccaccatcgccaaagtcattgcggaaaa
cacagaattgcattcccatatcttcgagccagaggtgagaatgtgggttt
ttgatgaaaagatcggcgacgaaaatctgacggatatcataaatacaaga
caccagaacgttaaatatctacccaatattgacctgccccataatctagt
ggccgatcctgatcttttactccatcaagggtgctgacatccttgttttc
aacatccctcatcaatttttaccaaacatagtcaaacaattgcaaggcca
cgtggcccctcatgtaagggccatctcgtgtctaaaagggttcgagttgg
gctccaagggtgtgcaattgctatcctcctatgttactgatgagttagga
atccaatgtggcgcactatctggtgcaaacttggcaccggaagtggccaa
ggagcattggtccgaaaccaccgtggcttaccaactaccaaaggattatc
aaggtgatggcaaggatgtagatcataagattttgaaattgctgttccac
agaccttacttccacgtcaatgtcatcgatgatgttgctggtatatccat
tgccggtgccttgaagaacgtcgtggcacttgcatgtggtttcgtagaag
gtatgggatggggtaacaatgcctccgcagccattcaaaggctgggttta
ggtgaaattatcaagttcggtagaatgtttttcccagaatccaaagtcga
gacctactatcaagaatccgctggtgttgcagatctgatcaccacctgct
caggcggtagaaacgtcaaggttgccacatacatggccaagaccggtaag
tcagccttggaagcagaaaaggaattgcttaacggtcaatccgcccaagg
gataatcacatgcagagaagttcacgagtggctacaaacatgtgagttga
cccaagaattcccattattcgaggcagtctaccagatagtctacaacaac
gtccgcatggaagacctaccggagatgattgaagagctagacatcgatga
cgaatagacactctcccccccccctcccccctctgatctttcctgttgcctc
tttttcccccaaccaatttatcattatacacaagttctacaactactact
agtaacattactacagttattataattttctattctctttttctttaaga -continued atctatcattaacgttaatttctatatatacataactaccattatacacg
ctattatcgtttacatatcacatcaccgttaatgaaagatacgacaccct
gtacactaacacaattaaataatcgccataaccttttctgttatctatag
ccataaagctgtttcttcgagctttttcactgcagtaattctccacatgg
gcccagccactgagataagagcgctatgttagtcactactgacggctctc
cagtcatttatgtgatttttttagtgactcatgtcgcatttggcccgtttt
tttccgctgtcgcaacctatttccattaacggtgccgtatggaagagtca
tttaaaggcaggagagagagagattactcatcttcattggatcagattgatg
actgcgtacggcagat Sequence of gpd2Δ mutation (the entire coding sequence was deleted, which is represented by a Δ; SEQ ID NO:92):

atagccatcatgcaagcgtgtatcttctaagattcagtcatcatcattac
cgagtttgttttccttcacatgatgaagaaggtttgagtatgctcgaaac
aataagacgacgatggctctgccattgttatattacgcttttgcggcgag
gtgccgatgggttgctgaggggaagagtgtttagcttacggacctattgc
cattgttattccgattaatctattgttcagcagctcttctctaccagtca
ttctagtattttttttttttttttttggttttactttttttttcttcttgc
cttttttttcttgttactttttttctagttttttttccttccactaagctt
tttccttgatttatccttgggttcttctttctactcctttagatttttttt
tttatatattaatttttaagtttatgtattttggtagattcaattctctt
tccctttccttttccttcgctccccttccttatcΔctctgatctttcctg
ttgcctctttttcccccaaccaatttatcattatacacaagttctacaac
tactactagtaacattactacagttattataattttctattctctttttc
tttaagaatctatcattaacgttaatttctatatatacataactaccatt
atacacgctattatcgtttacatatcacatcaccgttaatgaaagatacg
acaccctgtacactaacacaattaaataatcgccataaccttttctgtta
tctatagcccttaaagctgtttcttcgagctttttcactgcagtaattct
ccacatgggcccagccactgagataagagcgctatgttagtcactactga
cggctctccagtcatttatgtgatttttttagtgactcatgtcgcatttgg
cccgtttttttccgctgtcgcaacctatttccattaacggtgccgtatgg
aagagtcatttaaaggcaggagagagagagattactcatcttcattggatca
gattgatgactgcgtacggcagat Sequence of FDH1 locus (coding sequence is underlined; SEQ ID NO:93):

tatttttctatagatatttacactccgcaagtgcaaaaaaaaagcattat
cgctaacgatcaagaggaactgagaccttattagttgtctttgttggcgt
aacataaatttcttaggaaaagagaaaattatctcgaaggcaaaaataaa
ccaagcctcgagtttaatggttttctaaaaaacactttaaaaacagatcg
ccataaaaggagaagctccgtaggagaccgttttcgaaacctatgtagaa
ataaagggaaagctccaacggtttggataaatctttagaagcatagagtt -continued tatacaacattcagtacgaaatgtactctcgaaacgttctcttttcacgg
tgcttagtagcagaaaaaagtgtcggaaattacctattagtcaccactcg
aggataggcttgaaagagagttttaaccccaacttttctattttgcactt
gtttggctatggtttaaaacattctgtttggaccaacagcccaagcggct
tatccctttttcttttttacccttataatcgggaatttccttactaggaagg
caccgatactagaactccgaatgaaaaagacatgccagtaataaaactat
tttgatgttatgcggaatatactattcttggattattcactgttaactaa
aagttggagaaatcactctgcactgtcaatcattgaaaaaaagaacatat
aaaagggcacaaaattgagtctttttttaatgagttcttgctgaggaaagt
ttagttaatatatcatttacgtaaaatatgcatattcttgtattgtgctt
tttttattcattttaagcaggaacaatttacaagtattgcaacgctaatc
aaatcaaaataacagctgaaaattaatatgtcgaagggaaaggttttgct
ggttctttacgaaggtggtaagcatgctgaagagcaggaaaagttattgg
ggtgtattgaaaatgaacttggtatcagaaatttcattgaagaacaggga
tacgagttggttactaccattgacaaggaccctgagccaacctcaacggt
agacagggagttgaaagacgctgaaattgtcattactacgcccttttttcc
ccgcctacatctcgagaaacaggattgcagaagctcctaacctgaagctc
tgtgtaaccgctggcgtcggttcagaccatgtcgatttagaagctgcaaa
tgaacggaaaatcacggtcaccgaagttactggttctaacgtcgtttctg
tcgcagagcacgttatggccacaattttggttttgataagaaactataat
ggtggtcatcaacaagcaattaatggtgagtgggatattgccggcgtggc
taaaaatgagtatgatctggaagacaaaataatttcaacggtaggtgccg
gtagaattggatatagggttctggaaagattggtcgcatttaatccgaag
aagttactgtactacgactaccaggaactacctgcggaagcaatcaatag
attgaacgaggccagcaagcttttcaatggcagaggtgatattgttcaga
gagtagagaaattggaggatatggttgctcagtcagatgttgttaccatc
aactgtccattgcacaaggactcaagggggtttattcaataaaaagcttat
ttcccacatgaaagatggtgcatacttggtgaataccgctagaggtgcta
tttgtgtcgcagaagatgttgccgaggcagtcaagtctggtaaattggct
ggctatggtggtgatgtctgggataagcaaccagcaccaaaagaccatcc
ctggaggactatggacaataaggaccacgtgggaaacgcaatgactgttc
atatcagtggcacatctctggatgctcaaaagaggtacgctcagggagta
aagaacatcctaaatagttacttttccaaaaagtttgattaccgtccaca
ggatattattgtgcagaatggttcttatgccaccagagcttatggacaga
agaaataagagtgattatgagtatttgtgagcagaagttttccggtctcc
ttttgttcttgttttggcgtattctccactattcgtccatagcacattta
taccttagctaaatattttgtaaagcaaaattttcgttatctcttaaaaa
atagaagagcggtttattaatatcaaataattgaaactgctgatatggta
gctatatacaaaatctgctgtcaaaatttggcagtaaacgatcttcacgg
tagcggttcaaataaagaggaaaagtctttctcccttactgtttttctgg
aatttggctcgtcgttaataacagaactaaagatacagtaaaaggagaga -continued tcgcaatcaacttcattaattgtaacagtagcataatcacaactgatcat
ctacactataaacagtttttatttctaattatgggcgcctggccggctca
aacattgtgcttttaagactccaaaagtatctgctgcagaaaagagccat
ataatgttaagtgttcagggataggttatcgcttactacttcaaacgttt
cgaaggaaagccagggaagcctatatctgattccctgtttcataatccaa
tgcagccactagcttataattatttgaactatttgtcgaacatcacagta
ataaaatccccagaaagttccacttgctgcatattggcacctgttgattc
actctccatcactttttttgttagccgcccagcctagaaagtctttaaata
catctgaaatttttttttttttaacagtgcacccgtgcatcatacctcat
gcaaggtacctttttttctcaaaggtattgtcttccattgaagtggcact
atggcatgatgaaccctgagcatttctgaattcaacagaaccaaattgtc
cagaaataaatctgtccgacatgaattatgaaactttttttcaattaagt
gaagagaattttgcagcgtcttaccattattttgacccattggtcgcatg
tttgcgctttgacttcgagaaccatgttaaagcttacttgtacgacaacc
aatgaagtatattacggcagtttttttggactgggtcaaaaaaagtgttg
cataatcaaatcaggaacacattaaaatgttgtaaaatttgtcttagtat
cacctgagtggttattcattacgtacta Sequence of fdh1Δ mutation (the entire coding sequence was deleted, which is represented by a Δ; SEQ ID NO:94):

tatttttctatagatatttacactccgcaagtgcaaaaaaaaagcattat
cgctaacgatcaagaggaactgagaccttattagttgtctttgttggcgt
aacataaatttcttaggaaaagagaaaattatctcgaaggcaaaaataaa
ccaagcctcgagtttaatggttttctaaaaaacactttaaaaacagatcg
ccataaaaggagaagctccgtaggagaccgttttcgaaacctatgtagaa
ataaagggaaagctccaacggtttggataaatctttagaagcatagagtt
tatacaacattcagtacgaaatgtactctcgaaacgttctatttcacggt
gcttagtagcagaaaaaagtgtcggaaattacctattttgtcaccactcg
aggataggcttgaaagagagttttaaccccaacttttctattttgcactt
gtttggctatggtttaaaacattctgtttggaccaacagcccaagcggct
tatcccttttcttttttttcccttataatcgggaatttccttactaggaag
gcaccgatactagaactccgaatgaaaaagacatgccagtaataaaacta
ttttgatgttatgcggaatatactattcttggattattcactgttaacta
aaagttggagaaatcactctgcactgtcaΔtggcagtaaacgatcttcac
ggtagcggttcaaataaagaggaaaagtctttctcccttactgtttttct
ggaatttggctcgtcgttaataacagaactaaagatacagtaaaaggaga
gatcgcaatcaacttcattaattgtaacagtagcataatcacaactgatc
atctacactataaacagtttttatttctaattatgggcgcctggccggct
caaacattgtgcttttaagactccaaaagtatctgctgcagaaaagagcc
atataatgttaagtgttcagggataggttatcgcttactacttcaaacgt
ttcgaaggaaagccagggaagcctatatctgattccctgtttcataatcc -continued aatgcagccactagcttataattatttgaactatagtcgaacatcacagt
aataaaatccccagaaagttccacttgctgcatattggcacctgttgatt
cactctccatcactttttttgttagccgcccagcctagaaagtctttaaat
acatctgaaattttttttttttaacagtgcacccgtgcatcatacctca
tgcaaggtaccttttttctcaaaggtattgtcttccattgaagtggcac
tatggcatgatgaaccctgagcatactgaattcaacagaaccaaattgtc
cagaaataaatctgtccgacatgaattatgaaactttttttcaattaagt
gaagagaattttgcagcgtcttaccattattttgacccattggtcgcatg
tttgcgctttgacttcgagaaccatgttaaagcttacttgtacgacaacc
aatgaagtatattacggcagtttttttggactgggtcaaaaaaagtgttg
cataatcaaatcaggaacacattaaaatgttgtaaaatttgtcttagtat
cacctgagtggttattcattacgtacta Sequence of FDH2 locus (coding sequence is underlined; SEQ ID NO:95):

tgtcgagacaatgtcattgcaagttatataaacattgtaatacatcacct
cgatgaaagagaaactggaatgatagatctctttttctcaaaatttcgtt
aatatgtaataataaggttcctgatgtaatttgtttttgtacaaattatt
ttagattctggaggttcaaataaaatatatattacagccaacgattaggg
gggacaagacttgattacacatttttcgttggtaacttgactcttttatg
aaaagaaaacattaagttgaaggtgcacgcttgaggcgctccttttttcat
ggtgcttagcagcagatgaaagtgtcagaagttacctattttgtcaccat
ttgagaataagcttgaaagaaagttgtaaccccaacttttctatcttgca
cttgtttggaccaacagccaaacggcttatccctttttctttttcccttata
atcgggaatttccttactaggaaggcaccgatactataactccgaatgaa
aaagacatgccagtaataaaaataattgatgttatgcggaatatactatt
cttggattattcactgttaactaaaagttggagaaatcactctgcactgt
caatcattgaaaaaaaagaacatataaaagggcacaaaatcgagtcttttt
taatgagttcttgctgaggaaaatttagttaatatatcatttacataaaa
catgcatattattgtgttgtactttctttattcattttaagcaggaataa
ttacaagtattgcaacgctaatcaaatcgaaataacagctgaaaattaat
atgtcgaagggaaaggttttgctggttctttatgaaggtggtaagcatgc
tgaagagcaggaaaagttattggggtgtattgaaaatgaacttggtatca
gaaatttcattgaagaacagggatacgagttggttactaccattgacaag
gaccctgagccaacctcaacggtagacagggagttgaaagacgctgaaat
tgtcattactacgcccttttttccccgcctacatctcgagaaacaggattg
cagaagctcctaacctgaagctctgtgtaaccgctggcgtcggttcagac
catgtcgatttagaagctgcaaatgaacggaaaatcacggtcaccgaagt
tactggttctaacgtcgtttctgtcgcagagcacgttatggccacaattt
tggttttgataagaaactataatggtggtcatcaataagcaattaatggt
gagtgggatattgccggcgtggctaaaaaatgagtatgatctggaagaca
aaataatttcaacggtaggtgccggtagaattggatatagggttctggaa
agattggtcgcatttaatccgaagaagttactgtactacgactaccagga
actacctgcggaagcaatcaatagattgaacgaggccagcaagcttttca
atggcagaggtgatattgttcagagagtagagaaattggaggatatggtt
gctcagtcagatgttgttaccatcaactgtccattgcacaaggactcaag
gggtttattcaataaaaagcttatttcccacatgaaagatggtgcatact
tggtgaataccgctagaggtgctatttgtgtcgcagaagatgttgccgag
gcagtcaagtctggtaaattggctggctatggtggtgatgtctgggataa
gcaaccagcaccaaaagaccatccctggaggactatggacaataaggacc
acgtgggaaacgcaatgactgttcatatcagtggcacatctctgcatgct
caaaagaggtacgctcagggagtaaagaacatcctaaatagttacttttc
caaaaagtttgattaccgtccacaggatattattgtgcagaatggttctt
atgccaccagagcttatggacagaagaaataagagtgattatgagtattt
gtgagcagaagttttccggtctcctttttgttcttgttttggcgtattctc
cactattcgtccatagcacatttataccttagctaaatattttgtaaagc
aaaattttcgttatctcttaaaaaatagaagagcggtttattaatatcaa
ataattgaaactgctgatatggtagctatatacaaaatctgctgtcaaaa
tttggcagtaaacgatcttcacggtagcggttcaaataaagaggaaaagt
ccttctcccttactgtttttctggaatttggctcgtcgttaataacagaa
ctaaagatacagtaaaaggagagatcgcaatcaacttcattaattgtaac
agtagcataatcacaactggttatctgcgttatagacaattcttactcac
aatgatgggcgcttagttggctgtaaacgtcgcttttttaaaactccgaaa
agttaccgctacagaaaaaaaccataaatgtatgctagttgcgcagagag
gtttagggtccaaaatttactaccctgtcgctcactacagcgactgtccc
gaattaagcccgaagagacgcagaactgttgtatgaacctcatgaaacca
ctgatcttgaagatttagaccttcagaatcgttttcaattagaagtatac
aagaagtctttgtacaataatgtcaagacagagctctgaattatagttca
gccttgttatttttttt Sequence of fdh2Δ mutation (the entire coding sequence was deleted, which is represented by a Δ; SEQ ID NO:96):

tgtcgagacaatgtcattgcaagttatataaacattgtaatacatcacct
cgatgaaagagaaactggaatgatagatctctttttctcaaaatttcgtt
aatatgtaataataaggttcctgatgtaatttgtttttgtacaaattatt
ttagattctggaggttcaaataaaatatatattacagccaacgattaggg
gggacaagacttgattacacatttttcgttggtaacttgactcttttatg
aaaagaaaacattaagttgaaggtgcacgcttgaggcgctccttttttcat
ggtgcttagcagcagatgaaagtgtcagaagttacctattttgtcaccat
ttgagaataagcttgaaagaaagttgtaaccccaacttttctatcttgca
cttgtttggaccaacagccaaacggcttatccctttttctttttcccttata
atcgggaatttccttactaggaaggcaccgatactataactccgaatgaa -continued

```
aaagacatgccagtaataaaaataattgatgttatgcggaatatactatt
cttggattattcactgttaactaaaagttggagaaatcactctgcactgt
caatcattgaaaaaaagaacatataaagggcacaaaatcgagtcttttt
taatgagttcttgctgaggaaaatttagttaatatatcatttacataaaa
catgcatattattgtgttgtactttctttattcattttaagcaggaataa
ttacaagtattgcaacgctaatcaaatcgaaataacagctgaaaattaat
Δtaagagtgattatgagtatttgtgagcagaagttttccggtctcctttt
gttcttgttttggcgtattctccactattcgtccatagcacatttatacc
ttagctaaatattttgtaaagcaaaattttcgttatctcttaaaaaatag
aagagcggtttattaatatcaaataattgaaactgctgatatggtagcta
tatacaaaatctgctgtcaaaatttggcagtaaacgatcttcacggtagc
ggttcaaataaagaggaaaagtccttctcccttactgtttttctggaatt
tggctcgtcgttaataacagaactaaagatacagtaaaaggagagatcgc
aatcaacttcattaattgtaacagtagcataatcacaactggttatctgc
gttatagacaattcttactcacaatgatgggcgcttagttggctgtaaac
gtcgctttttaaaactccgaaaagttaccgctacagaaaaaaaccataaa
tgtatgctagttgcgcagagaggtttagggtccaaaatttactaccctgt
cgctcactacagcgactgtcccgaattaagcccgaagagacgcagaactg
ttgtatgaacctcatgaaaccactgatcttgaagatttagaccttcagaa
tcgttttcaattagaagtatacaagaagtctttgtacaataatgtcaaga
cagagctctgaattatagttcagccttgttatttttttt
```

3.2 Generation of Glycerol-Reduced Strain Comprising gpd2Δ::GPD1

Glycerol-reduction strain gpd2Δ::GPD1, was constructed as described above. The sequence of gpd1Δ/gpd1Δ gpd2Δ/gpd2Δ::GPD1/GPD1 is provided below.

Sequence of GPD1 at GPD2 locus (inserted GPD1 is underlined; SEQ ID NO:97):

```
agtaactgtgacgatatcaactctttttttattatgtaataagcaaacaa
gcacgaatggggaaagcctatgtgcaatcaccaaggtcgtccctttttc
ccatttgctaatttagaatttaaagaaaccaaaagaatgaagaaagaaaa
caaatactagccctaaccctgacttcgtttctatgataataccctgcttt
aatgaacggtatgccctagggtatatctcactctgtacgttacaaactcc
ggttattttatcggaacatccgagcacccgcgccttcctcaacccaggca
ccgcccccaggtaaccgtgcgcgatgagctaatcctgagccatcacccac
cccacccgttgatgacagcaattcgggagggcgaaaaataaaaactggag
caaggaattaccatcaccgtcaccatcaccatcatatcgccttagcctct
agccatagccatcatgcaagcgtgtatcttctaagattcagtcatcatca
ttaccgagtttgttttccttcacatgatgaagaaggtttgagtatgctcg
aaacaataagacgacgatggctctgccattgttatattacgcttttgcgg
cgaggtgccgatgggttgctgaggggaagagtgtttagcttacggaccta
ttgccattgttattccgattaatctattgttcagcagctcttctctaccc
```

-continued

```
tgtcattctagtatttttttttttttttttttggttttactttttttttct
tcttgccttttttcttgttacttttttttctagtttttttttccttccact
aagcttttttccttgatttatccttgggttcttctttctactcctttagat
ttttttttatatattaattttaagtttatgtattttggtagattcaatt
ctctttccctttccttttccttcgctccccttccttatcaatgtctgctg
ctgctgatagattaaacttaacttccggccacttgaatgctggtagaaag
agaagttcctcttctgtttctttgaaggctgccgaaaagcctttcaaggt
tactgtgattggatctggtaactggggtactactattgccaaggtggttg
ccgaaaattgtaagggatacccagaagttttcgctccaatagtacaaatg
tgggtgttcgaagaagagatcaatggtgaaaaattgactgaaatcataaa
tactagacatcaaaacgtgaaatacttgcctggcatcactctacccgaca
atttggttgctaatccagacttgattgattcagtcaaggatgtcgacatc
atcgttttcaacattccacatcaatttttgccccgtatctgtagccaatt
gaaaggtcatgttgattcacacgtcagagctatctcctgtctaaagggtt
ttgaagttggtgctaaaggtgtccaattgctatcctcttacatcactgag
gaactaggtattcaatgtggtgctctatctggtgctaacattgccaccga
agtcgctcaagaacactggtctgaaacaacagttgcttaccacattccaa
aggatttcagaggcgagggcaaggacgtcgaccataaggttctaaaggcc
ttgttccacagaccttacttccacgttagtgtcatcgaagatgttgctgg
tatctccatctgtggtgctttgaagaacgttgagccttaggttgtggttt
cgtcgaaggtctaggctggggtaacaacgcttctgctgccatccaaagag
tcggtttgggtgagatcatcagattcggtcaaatgtttttcccagaatct
agagaagaaacatactaccaagagtctgctggtgttgctgatttgatcac
cacctgcgctggtggtagaaacgtcaaggttgctaggctaatggctactt
ctggtaaggacgcctgggaatgtgaaaaggagttgttgaatggccaatcc
gctcaaggtttaattacctgcaaagaagttcacgaatggttggaaacatg
tggctctgtcgaagacttcccattatttgaagccgtataccaaatcgttt
acaacaactacccaatgaagaacctgccggacatgattgaagaattagat
ctacatgaagattagacactctccccccccctcccccctctgatattcctg
ttgcctctttttcccccaaccaatttatcattatacacaagttctacaa
ctactactagtaacattactacagttattataatttctattctcttttt
cttaagaatctatcattaacgttaatttctatatatacataactaccatt
atacacgctattatcgtttacatatcacatcaccgttaatgaaagatacg
acaccctgtacactaacacaattaaataatcgccataacctttctgtta
tctatagcccttaaagctgtttcttcgagctttttcactgcagtaattct
ccacatgggcccagccactgagataagagcgctatgttagtcactactga
cggctctccagtcatttatgtgatttttagtgactcatgtcgcatttgg
cccgtttttttccgctgtcgcaacctatttccattaacggtgccgtatgg
aagagtcatttaaaggcaggagagagagattactcatcttcattggatca
gattgatgactgcgtacggcagatagtgtaatctgagcagttgcgagacc
cagactggcactgtctcaatagtatattaatgggcatacattcgtactcc
```

-continued

```
cttgttcttgcccacagttctctctctctttacttcttgtatcttgtctc

cccattgtgcagcgataaggaacattgttctaatatacacggatacaaaa

gaaatacacat
```

Example 4

Cloning and Characterization of PFL and AADH Enzymes

Figure 22:
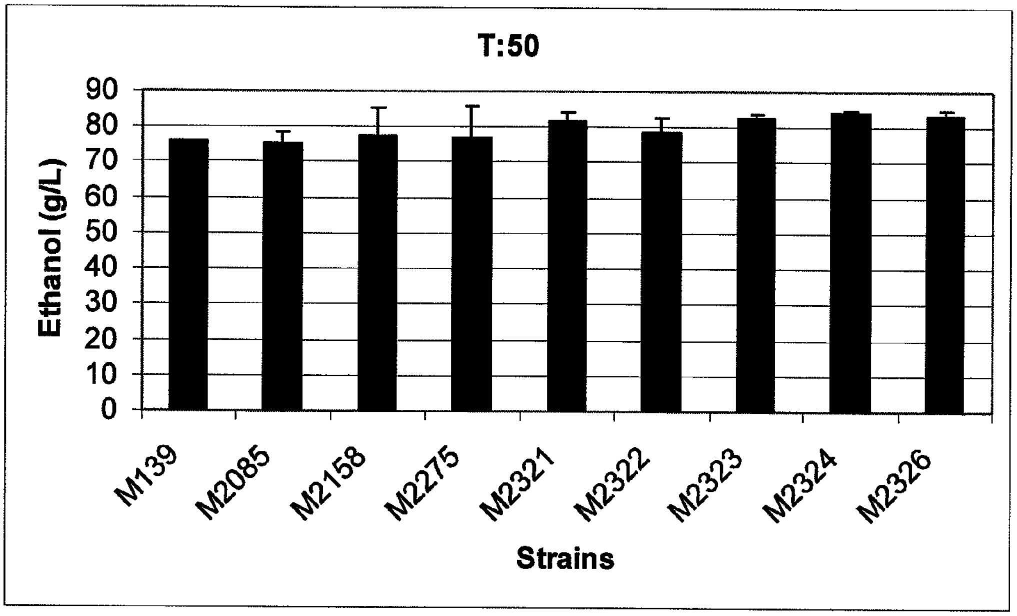
FIG. 22 shows a graph of ethanol production (g/L) of strains of the invention after 50 hours of fermentation.

To identify PFL enzymes for use in the strains of the invention, several PFL enzymes were identified for cloning and functional analysis. See Table 1. Functionality was determined by plasmid based expression of each PFL in the fcyΔ::ADHE gpd1Δ . . . . ADHE gpd2Δfdh1Δfdh2Δ (M2158) background. FIG. 22 shows fermentation performance in 20% corn mash. A PFL was determined to be functional based on the presence or absence of a yield increase over M2085. The *C. cellulolyticum* PFL was determined to be non-functional based on data shown in FIG. 13. The strain listed as M1992 +pMU2481 is M2085 plus a plasmid expressing the *C. cellulolyticum* PFL. This strain does not appear to make formate.

TABLE 1

| Analysis of PFL Enzymes | | |
|---|---|---|
| Organism | Functional | SEQ ID NOs: |
| *Bacillus licheniformis* ATCC__14580 | nd | 6 and 40 |
| *Streptococcus thermophilus* LMD__9 | nd | 12 and 46 |
| *Lactobacillus plantarum* WCFS1 (lp__3314 and lp__3313) | nd | 16 and 50 |
| *Lactobacillus casei* ATCC__334 | yes | 24 and 58 |
| *Bifidobacterium adolescentis* | yes | 26 and 60 |
| *Clostridium cellulolyticum* | no | 34 and 68 |
| *Escherichia coli* | yes | 36 and 70 |
| *Chlamydomonas reinhardtii* PflA | yes | 72 and 76 |
| *Piromyces* sp. E2 | yes | 78 |
| *Neocallimastix frontalis* | yes | 74 and 80 |

Figure 12:
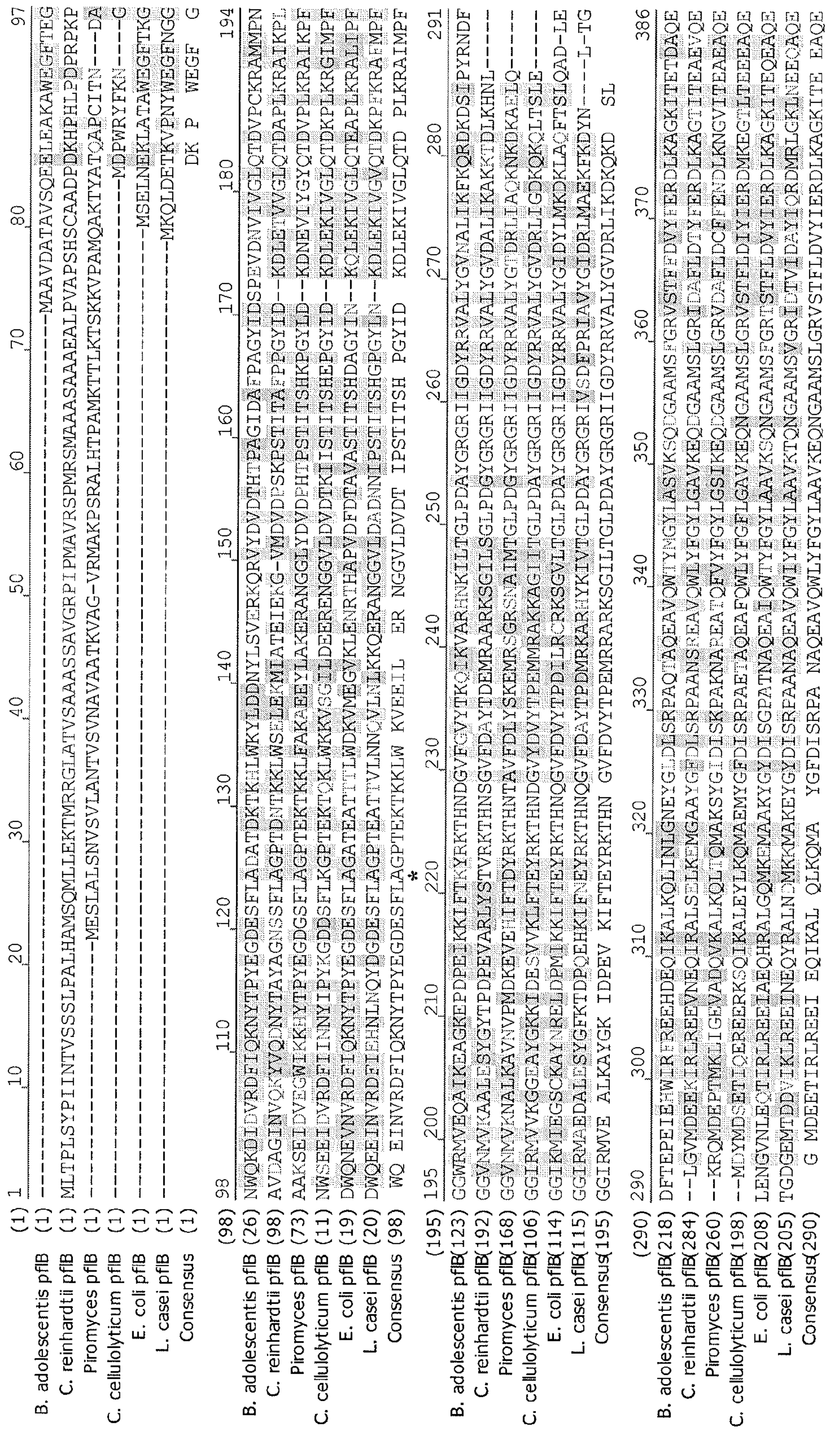
FIG. 12 shows an alignment of PFL enzymes from various organisms.

As shown in Example 7, eight of nine PFL enzymes that were tested can enable the glycerol elimination and glycerol reduction technologies described herein. An alignment of six of these PFL enzymes is shown in FIG. 12. Four of the residues are absent in *C. cellulolyticum* yet conserved among the other PFL enzymes (indicated with asterisks in FIG. 12). There is an insertion of 18 amino acids at position 640 of the *B. adolescentis* PFL, which is not present in the other PFL enzymes. The eukaryotic PFLs (*Piromyces* and *Chlamydomonas*) have an N-terminal extension which has been reported to be involved in mitochondrial targeting. Deletion of this sequence may improve the performance of these enzymes in *S. cerevisiae*. These differences may provide insights into identifying additional PFL enzymes for use in the strains of the invention.

To identify AADH enzymes for use in the strains of the invention, several AADH enzymes were identified for cloning and functional analysis. See Table 2. Functionality was determined though analysis of the data listed in Table 3 below and shown in FIG. 20. An AADH enzyme was determined to be functional if a strain containing the genotype gpd1Δgpd2Δ plus a given AADH, had a faster anaerobic growth rate than strain gpd1Δgpd2Δ (FIG. 20) and there was evidence for acetate consumption (Table 3).

TABLE 2

| Analysis of AADH Enzymes | | |
|---|---|---|
| Organism | Functional | SEQ ID NO: |
| *Escherichia coli* | yes | 84 |
| *Clostridium phytofermentans* | yes | 82 |
| *Chlamydomonas reinhardtii* | yes | 86 |
| *Piromyces* sp. E2 | yes | 88 |
| *Bifidobacterium adolescentis* | yes | 100 |

Figure 20:
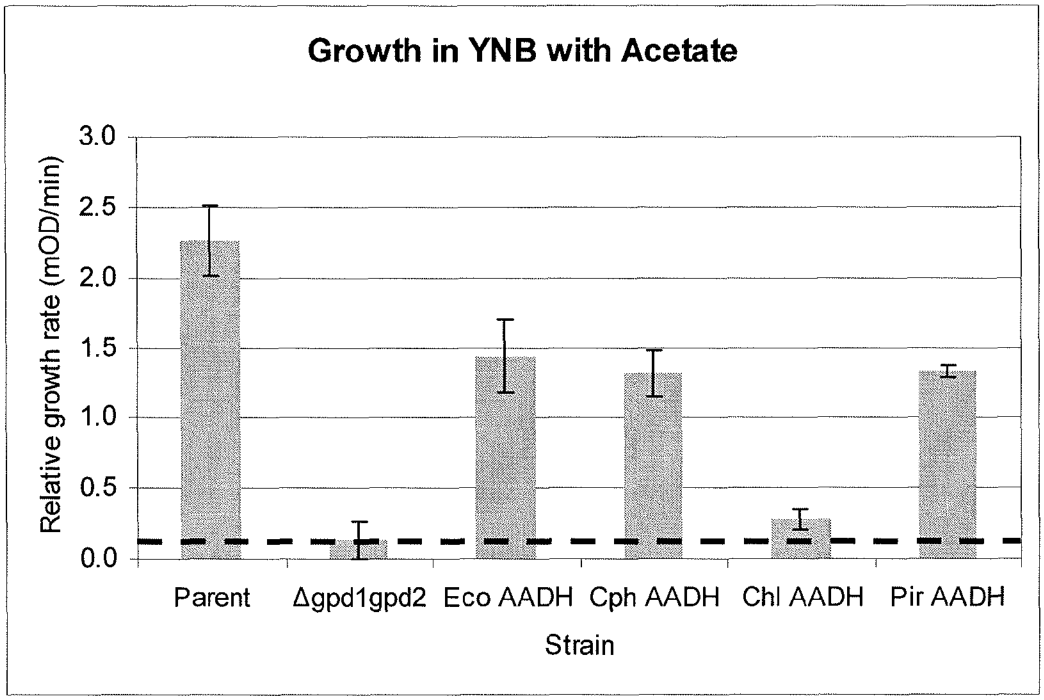
FIG. 20 shows a graph of the relative growth rate (mOD/min) of strains of the invention.

When glycerol deletion strains are grown anaerobically, they are not capable of growth or fermentation and cannot consume sugar during glycolysis. However, if these glycerol deletion strains are complemented with an AADH, the strains are able to grow with the supplementation of acetate in the media. FIG. 20 shows the growth rates of the parental strain, the glycerol deletion strain, and four glycerol deletion strains expressing AADHs from *Escherichia coli* (Eco), *Clostridium phytofermentans* (Cph), *Chlamydomonas reinhardtii* (Chl), and *Piromyces* sp. E2 (Pir). As shown in FIG. 20, all four genes can restore growth levels above the glycerol deletion strain (as noted by the dotted line) indicating a functional AADH.

The product yields and conversion of acetate by the strains above, as well as additional strains, are shown in Table 3. The glycerol deletion strain was unable to consume sugar or produce ethanol. The parent strain produced glycerol and ethanol but was unable to convert the acetate in the media, initially present at ~2 g/L, giving an ethanol yield of 0.41 g/g glucose, consistent with anaerobic ethanol yields. The glycerol deletion strains complemented with AADHs, however, were able to consume glucose and produce ethanol without producing glycerol, or the glycerol production was significantly decreased compared to the parent strain (Chl AADH). See Table 3. In these glycerol deletion mutants, the acetate levels were also reduced, resulting in higher ethanol yields (calculated as grams ethanol produced per gram consumed glucose) than was achieved by the parent strain.

TABLE 3

| Product Yields and Acetate Conversion of Glycerol Deletion Strains Expressing AADH | | | | | |
|---|---|---|---|---|---|
| Strain | Glycerol[a] | Acetate Uptake[a] | Ethanol[a] | Ethanol Yield[b] | Growth rate ($hr^{-1}$) |
| Parent M139 | 1.37 | 0.14 | 10.41 | 0.42 | 0.27 |
| Δgpd1Δgpd2 M2032 | 0.00 | 0.00 | 0.00 | 0.00 | 0.01 |
| Eco AADH M1991 | 0.00 | 0.62 | 11.39 | 0.46 | 0.17 |
| Cph AADH M1991 | 0.00 | 0.66 | 11.21 | 0.45 | 0.18 |
| Chl AADH M1991 | 0.00 | 0.32 | 9.04 | 0.47 | 0.04 |
| Pir AADH M1991 | 0.00 | 0.68 | 11.17 | 0.45 | 0.17 |
| Bad AADH M1991 | 0.00 | 0.67 | 10.95 | 0.44 | 0.18 |
| Eco mhpF M1991 | 0.00 | 0.03 | 0.50 | 0.02 | 0.06 |
| Cph ADH (1428) M1991 | 0.00 | 0.60 | 11.29 | 0.45 | 0.19 |
| Cph ADH (2642) M1991 | 0.00 | 0.74 | 11.22 | 0.45 | 0.20 |
| Tsac AADH M1991 | 0.00 | 0.59 | 11.89 | 0.48 | 0.16 |

[a]grams per liter

[b]gram ethanol produced per gram sugar consumed

Example 5

Expression of PFL and AADH and Detection of Formate

To examine the expression of formate in a yeast strain of the invention, *E. coli* PFL was cloned and expressed in an FDH deletion strain. Strain M1992+pMU2483 has deletions of FDH1 and FDH2 and a plasmid expressing the *E. coli* PflA and PflB. This strain was constructed by transforming strain M1992 (fdh1Δfdh2Δ) with plasmids expressing either *C. cellulolyticum* PFL (pMU2481) or *E. coli* PFL (pMU2483).

Figure 13:
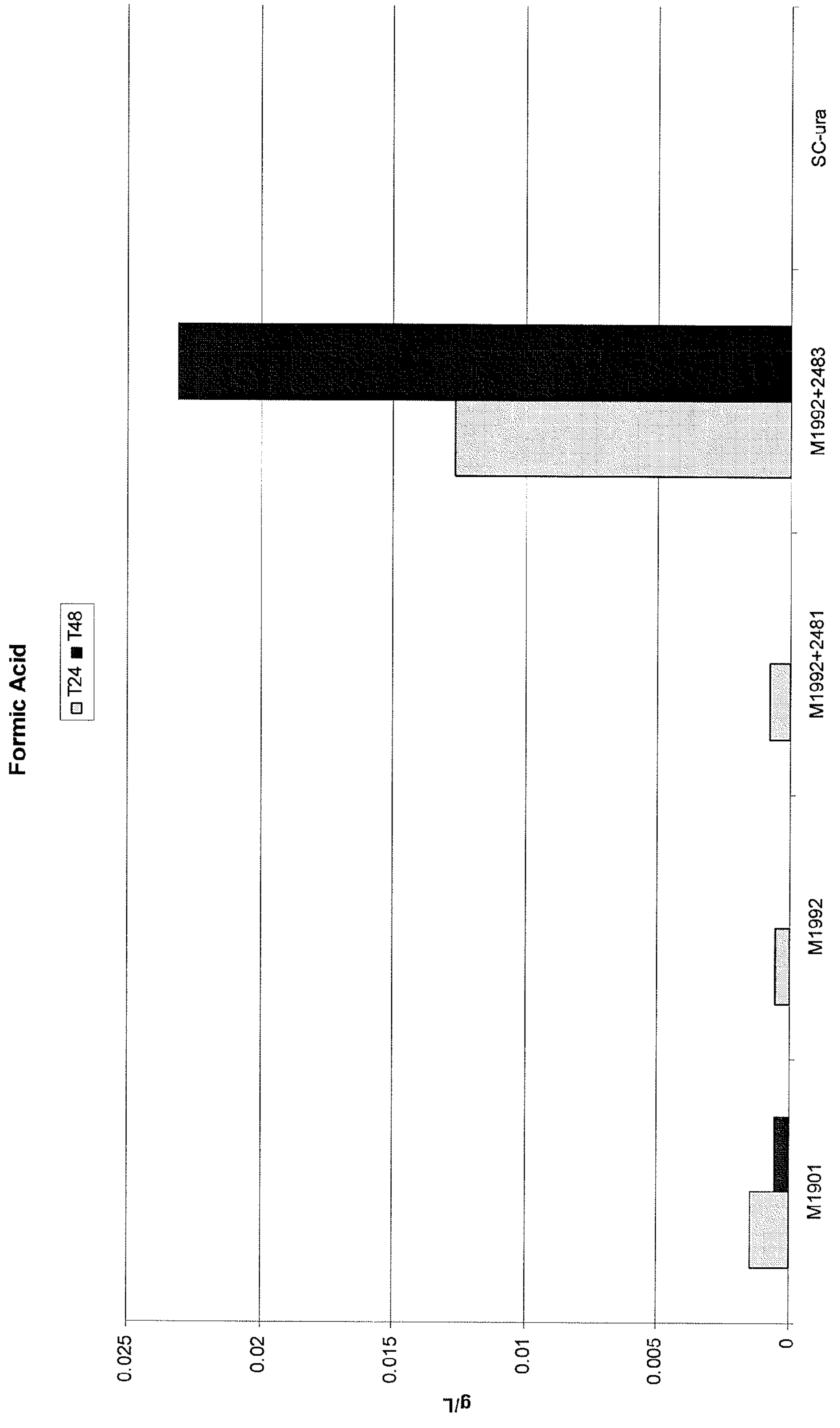
FIG. 13 shows a graph of formate production over 48 hours.

The strains were grown in YNB medium buffered with HEPES at pH 6.5, and formate was measured using a formate detection kit from Megazymes (Cat. No. K-FORM), according to manufacturer's specifications. As shown in FIG. 13, approximately 0.0125 g/L and 0.023 g/L formate was measured after 24 hours and 48 hours of growth, respectively. Similar results have been achieved by overexpressing an *E. coli* PFL in *S. cerevesiae*. Waks and Silver, *Appl. Env. Microbiol.* 75:1867-75 (2009).

Figure 26:
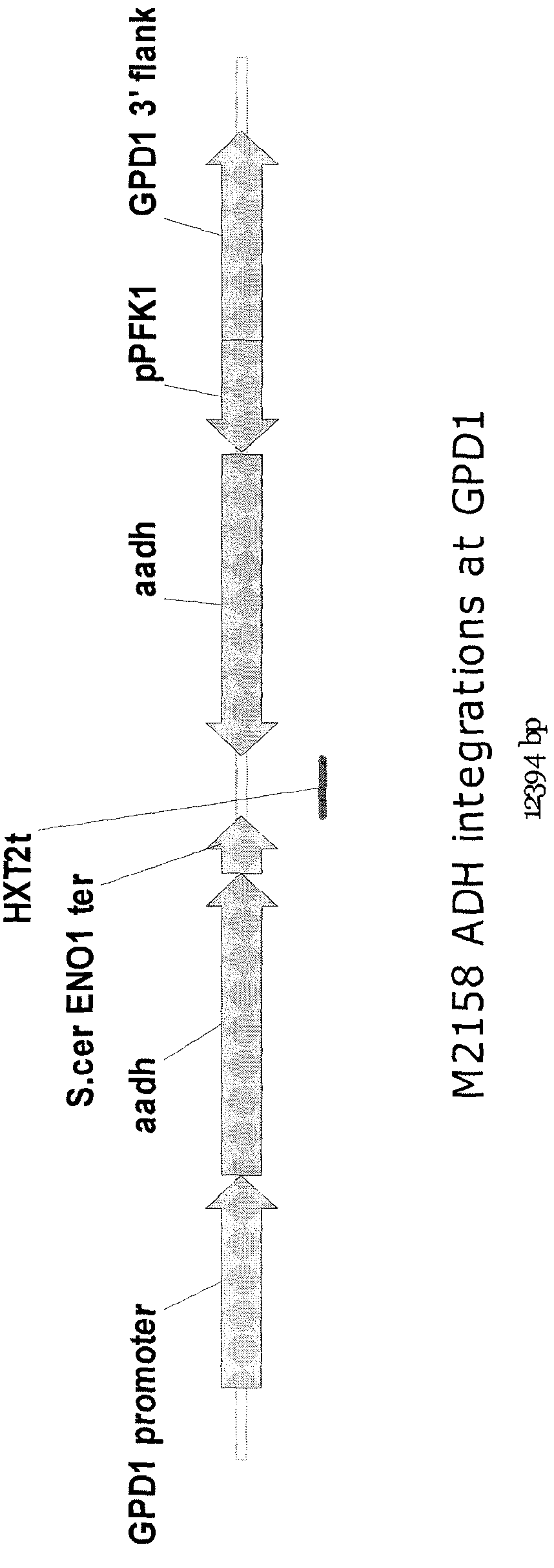
FIG. 26 shows a diagram depicting integration of *E. coli* AADHs at the GPD1 locus.
Figure 27:
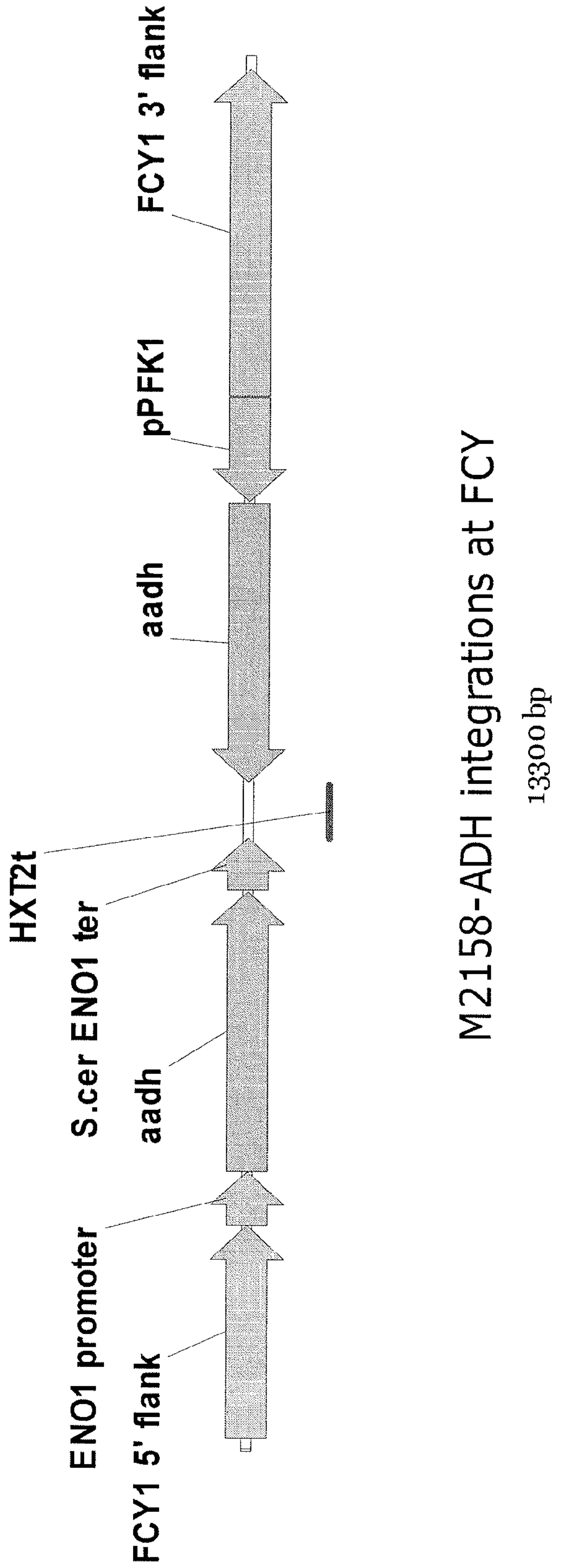
FIG. 27 shows a diagram depicting integration of *E. coli* AADHs at the FCY1 locus

PFL was also co-expressed in a strain expressing AADH. See FIG. 14. M2085 is a background strain with the genotype gpd1 Δgpd2Δfdh1Δfdh2Δ and M2032 has the genotype gpd1 Δgpd2Δ. Both of these strains are unable to grow anaerobically even in the presence of acetate. M2158 was created by integrating multiple copies of *E. coli* AADHs at the GPD1 and FCY1 locus in the M2085 background. The integration schemes are shown in FIGS. 26 and 27 and the corresponding nucleotide sequences for M2158 are listed below. One copy of AADH is driven by the native GPD1 promoter. See FIG. 26. The second copy is oriented in the reverse direction and is driven by the phosphofructokinase promoter. See FIG. 26. For AADH integration in FCY1, one copy is driven by the ENO1 promoter and a second copy is driven by the PFK1 promoter. See FIG. 27. M2182 was created by transforming a vector expressing the *B. adolescentis* PFLs into the M2158 background.

Sequence of M2158 AADH integrations at the GPD1 locus (nucleotide; SEQ ID NO:98):

```
tagattcttttcgaatttgtggtgaagataggaaagttggtacagttctc
catcaattttccatattttgctaaaactcccttgcatgtctctttgcat
tcatttctcctgtatacgggttcaacacatcaatcgaattttgcaaagtt
gtctccatttctagaagactttcatcgggaataaaaaattcatatccatt
attcaaaaacgataatgatccctcgtacttacctgtgtaattggatattt
tataccatacttcaaaaatatccttggcctcacttctggtaggatacctt
tcgccatgtctgccaatcatttgaacttgcgttaatctacaaccttcagg
aatatcagtgggtataccgtagttagcgggaaaggagaaatatggcgcag
accctccaagaaagggaaacagactcttctgagagccaattagttcaata
tccgcaaaacttctgagtgggatggagagtgccttagataatagaacacc
taaacaaatggcaaaaataacgggcttcaccattgttcctgtatggtgta
ttagaacatagctgaaaatacttctgcctcaaaaaagtgttaaaaaaaag
aggcattatatagaggtaaagcctacaggcgcaagataacacatcaccgc
tctccccccctctcatgaaaagtcatcgctaaagaggaacactgaaggttc
```

-continued

```
ccgtaggttgtctttggcacaaggtagtacatggtaaaaactcaggatgg
aataattcaaattcaccaatttcaacgtcccttgtttaaaaagaaaagaa
tttttctctttaaggtagcactaatgcattatcgatgatgtaaccattca
cacaggttatttagcttttgatccttgaaccattaattaacccagaaata
gaaattacccaagtggggctctccaacacaatgagaggaaaggtgacttt
ttaagggggccagaccctgttaaaaacctttgatggctatgtaataatag
taaattaagtgcaaacatgtaagaaagattctcggtaacgaccatacaaa
tattgggcgtgtggcgtagtcggtagcgcgctcccttagcatgggagagg
tctccggttcgattccggactcgtccaaattatttttactttccgcggt
gccgagatgcagacgtggccaactgtgtctgccgtcgcaaaatgatttga
attttgcgtcgcgcacgtttctcacgtacataataagtattttcatacag
actagcaagacgaggtggtcaaaatagaagcgtcctatgttttacagtac
aagacagtccatactgaaatgacaacgtacttgacttttcagtattttct
ttttctcacagtctggttatttttgaaagcgcacgaaatatatgtaggca
agcattttctgagtctgctgacctctaaaattaatgctattgtgcacctt
agtaacccaaggcaggacagttaccttgcgtggtgttactatggccggaa
gcccgaaagagttatcgttactccgattattttgtacagctgatgggacc
ttgccgtcttcatttttttttttttcacctatagagccgggcagagctg
cccggcttaactaagggccggaaaaaaaacggaaaaaagaaagccaagcg
tgtagacgtagtataacagtatatctgacacgcacgtgatgaccacgtaa
tcgcatcgcccctcacctctcacctctcaccgctgactcagcttcactaa
aaaggaaaatatatactattcccaggcaaggtgacagcggtccccgtctc
ctccacaaaggcctctcctggggtttgagcaagtctaagtttacgtagca
taaaaattctcggattgcgtcaaataataaaaaaagtaaccccacttcta
cttctacatcggaaaaacattccattcacatatcgtctttggcctatctt
gttttgtcctcggtagatcaggtcagtacaaacgcaacacgaaagaacaa
aaaaagaagaaaacagaaggccaagacagggtcaatgagactgttgtcct
cctactgtccctatgtctctggccgatcacgcgccattgtccctcagaaa
caaatcaaacacccacaccccgggcacccaaagtccccacccacaccacc
aatacgtaaacggggcgcccccctgcaggccctcctgcgcgcggcctcccg
ccttgcttctctccccttcctttttctttttccagttttccctattttgtc
cctttttccgcacaacaagtatcagaatgggttcatcaaatctatccaac
ctaattcgcacgtagactggcttggtattggcagtttcgtagttatatat
atactaccatgagtgaaactgttacgttaccttaaattctttctcccttt
aattttcttttatcttactctcctacataagacatcaagaaacaattgta
tattgtacacccccccccctccacaaacacaaatattgataatataaagat
ggctgttactaatgtcgctgaacttaacgcactcgtagagcgtgtaaaaa
aagcccagcgtgaatatgccagtttcactcaagagcaagtagacaaaatc
ttccgcgccgccgctctggctgctgcagatgctcgaatcccactcgcgaa
aatggccgttgccgaatccggcatgggtatcgtcgaagataaagtgatca
aaaaccactttgcttctgaatatatctacaacgcctataaagatgaaaaa
```

-continued acctgtggtgttctgtctgaagacgacacttttggtaccatcactatcgc tgaaccaatcggtattatttgcggtatcgttccgaccactaacccgactt caactgctatcttcaaatcgctgatcagtctgaagacccgtaacgccatt atcttctccccgcacccgcgtgcaaaagatgccaccaacaaagcggctga tatcgttctgcaggctgctatcgctgccggtgctccgaaagatctgatcg gctggatcgatcaaccttctgttgaactgtctaacgcactgatgcaccac ccagacatcaacctgatcctcgcgactggtggtccgggcatggttaaagc cgcatacagctccggtaaaccagctatcggtgtaggcgcgggcaacactc cagttgttatcgatgaaactgctgatatcaaacgtgcagttgcatctgta ctgatgtccaaaaccttcgacaacggcgtaatctgtgcttctgaacagtc tgttgttgttgttgactctgtttatgacgctgtacgtgaacgttttgcaa cccacggcggctatctgttgcagggtaaagagctgaaagctgttcaggat gttatcctgaaaaacggtgcgctgaacgcggctatcgttggtcagccagc ctataaaattgctgaactggcaggcttctctgtaccagaaaacaccaaga ttctgatcggtgaagtgaccgttgttgatgaaagcgaaccgttcgcacat gaaaaactgtccccgactctggcaatgtaccgcgctaaagatttcgaaga cgcggtagaaaaagcagagaaactggttgctatgggcggtatcggtcata cctcttgcctgtacactgaccaggataaccaaccggctcgcgtttcttac ttcggtcagaaaatgaaaacggcgcgtatcctgattaacaccccagcgtc tcagggtggtatcggtgacctgtataacttcaaactcgcaccttccctga ctctgggttgtggttcttggggtggtaactccatctctgaaaacgttggt ccgaaacacctgatcaacaagaaaaccgttgctaagcgagctgaaaacat gttgtggcacaaacttccgaaatctatctacttccgccgtggctccctgc caatcgcgctggatgaagtgattactgatggccacaaacgtgcgctcatc gtgactgaccgcttcctgttcaacaatggttatgctgatcagatcacttc cgtactgaaagcagcaggcgttgaaactgaagtcttcttcgaagtagaag cggacccgaccctgagcatcgttcgtaaaggtgcagaactggcaaactcc ttcaaaccagacgtgattatcgcgctgggtggtggaccccgatggacgcc gcgaagatcatgtgggttatgtacgaacatccggaaactcacttcgaaga gctggcgctgcgctttatggatatccgtaaacgtatctacaagttcccga aaatgggcgtgaaagcgaaaatgatcgctgtcaccaccacttctggtaca ggttctgaagtcactccgtttgcggttgtaactgacgacgctactggtca gaaatatccgctggcagactatgcgctgactccggatatggcgattgtcg acgccaacctggttatggacatgccgaagtccctgtgtgctttcggtggt ctggacgcagtaactcacgccatggaagcttatgtttctgtactggcatc tgagttctctgatggtcaggctctgcaggcactgaaactgctgaaagaat atctgccagcgtcctaccacgaagggtctaaaaatccggtagcgcgtgaa cgtgttcacagtgcagcgactatcgcgggtatcgcgtttgcgaacgcctt cctgggtgtatgtcactcaatggcgcacaaactgggttcccagttccata ttccgcacggtctggcaaacgccctgctgatttgtaacgttattcgctac aatgcgaacgacaacccgaccaagcagactgcattcagccagtatgaccg tccgcaggctcgccgtcgttatgctgaaattgccgaccacttgggtctga gcgcaccgggcgaccgtactgctgctaagatcgagaaactgctggcatgg ctggaaacgctgaaagctgaactgggtattccgaaatctatccgtgaagc tggcgttcaggaagcagacttcctggcgaacgtggataaactgtctgaag atgcattcgatgaccagtgcaccggcgctaacccgcgttacccgctgatc tccgagctgaaacagattctgctggatacctactacggtcgtgattatgt agaaggtgaaactgcagcgaagaaagaagctgctccggctaaagctgaga aaaaagcgaaaaaatccgcttaagtcgagagcttttgattaagccttcta gtccaaaaaacacgtttttttgtcatttatttcattttcttagaatagtt tagtttattcattttatagtcacgaatgttttatgattctatatagggtt gcaaacaagcatttttcattttatgttaaaacaatttcaggtttaccttt tattctgcttgtggtgacgcgtgtatccgcccgctcttttggtcacccat gtatttaattgcataaataattcttaaaagtggagctagtctatttctat ttacatacctctcatttctcatttcctcctaatgtgtcaatgatcatatt cttaactggaccgatcttattcgtcagattcaaaccaaaagttcttaggg ctaccacaggaggaaaattagtgtgatataatttaaataatttatccgcc attcctaatagaacgttgttcgacggatatctttctgcccaaaagggttc taagctcaatgaagagccaatgtctaaacctcgttacattgaaaatacag taaatggttccaccattattatgttggtcttgtttagtatggccgatcgg cgtgtgttttgtttgcaccttttatatagtagaagaatatttgtataatt cttattagtactgcaacctaaccactaattatcaacaattattggattat ataaaggaggtaaattgccggattaaaatcaaatatcattcatcaacaag tattcatattgtcggcatatttttacatgcggtgtaagtatttggatcgt attcttatagtgtcaatacctcgaagcagcgtttcaagtaccagacgtat gtaggaactttttaacgtcgagtccgtaagatttgatcagtattaaaaaa atctagataaatgagtggtacaaataaaaacatcattaaaaatcgttaaa taaaaaagtatgaagatcatctattaaagtattagtagccattagcctta aaaaaatcagtgctagtttaagtataatctcgggcgcgccggccgaggcg gttaagcggatttttcgctttttctcagctttagccggagcagcttct ttcttcgctgcagtttcaccttctacataatcacgaccgtagtaggtatc cagcagaatctgtttcagctcggagatcagcgggtaacgcgggttagcgc cggtgcactggtcatcgaatgcatcttcagacagtttatccacgttcgcc aggaagtctgcttcctgaacgccagcttcacggatagatttcggaatacc cagttcagctttcagcgtttccagccatgccagcagtttctcgatcttag cagcagtacggtcgcccggtgcgctcagacccaagtggtcggcaatttca gcataacgacggcgagcctgcggacggtcatactggctgaatgcagtctg cttggtcgggttgtcgttcgcattgtagcgaataacgttacaaatcagca gggcgtttgccagaccgtgcggaatatggaactgggaacccagtttgtgc gccattgagtgacatacacccaggaaggcgttcgcaaacgcgatacccgc gatagtcgctgcactgtgaacacgttcacgcgctaccggatttttagacc cttcgtggtaggacgctggcagatattctttcagcagtttcagtgcctgc -continued agagcctgaccatcagagaactcagatgccagtacagaaacataagcttc catggcgtgagttactgcgtccagaccaccgaaagcacacagggacttcg gcatgtccataaccaggttggcgtcgacaatcgccatatccggagtcagc gcatagtctgccagcggatatttctgaccagtagcgtcgtcagttacaac cgcaaacggagtgacttcagaacctgtaccagaagtggtggtgacagcga tcattttcgctttcacgcccattttcgggaacttgtagatacgtttacgg atatccataaagcgcagcgccagctcttcgaagtgagtttccggatgttc gtacataacccacatgatcttcgcggcgtccatcggggaaccaccaccca gcgcgataatcacgtctggtttgaaggagtttgccagttctgcaccttta cgaacgatgctcagggtcgggtccgcttctacttcgaagaagacttcagt ttcaacgcctgctgctttcagtacggaagtgatctgatcagcataaccat tgttgaacaggaagcggtcagtcacgatgagcgcacgtttgtggccatca gtaatcacttcatccagcgcgattggcagggagccacggcggaagtagat agatttcggaagtttgtgccacaacatgttttcagctcgcttagcaacgg ttttcttgttgatcaggtgtttcggaccaacgttttcagagatggagtta ccaccccaagaaccacaacccagagtcagggaaggtgcgagtttgaagtt atacaggtcaccgataccaccctgagacgctggggtgttaatcaggatac gcgccgttttcattttctgaccgaagtaagaaacgcgagccggttggtta tcctggtcagtgtacaggcaagaggtatgaccgataccgcccatagcaac cagtttctctgctttttctaccgcgtcttcgaaatctttagcgcggtaca ttgccagagtcggggacagtttttcatgtgcgaacggttcgctttcatca acaacggtcacttcaccgatcagaatcttggtgttttctggtacagagaa gcctgccagttcagcaattttataggctggctgaccaacgatagccgcgt tcagcgcaccgtttttcaggataacatcctgaacagctttcagctcttta ccctgcaacagatagccgccgtgggttgcaaaacgttcacgtacagcgtc ataaacagagtcaacaacaacaacagactgttcagaagcacagattacgc cgttgtcgaaggttttggacatcagtacagatgcaactgcacgtttgata tcagcagtttcatcgataacaactggagtgttgcccgcgcctacaccgat agctggtttaccggagctgtatgcggctttaaccatgcccggaccaccag tcgcgaggatcaggttgatgtctgggtggtgcatcagtgcgttagacagt tcaacagaaggttgatcgatccagccgatcagatctttcggagcaccggc agcgatagcagcctgcagaacgatatcagccgctttgttggtggcatctt ttgcacgcgggtgcggggagaagataatggcgttacgggtcttcagactg atcagcgatttgaagatagcagttgaagtcgggttagtggtcggaacgat accgcaaataataccgattggttcagcgatagtgatggtaccaaaagtgt cgtcttcagacagaacaccacaggtttttcatctttataggcgttgtag atatattcagaagcaaagtggtttttgatcactttatcttcgacgatacc catgccggattcggcaacggccattttcgcgagtgggattcgagcatctg cagcagccagagcggcggcgcggaagattttgtctacttgctcttgagtg aaactggcatattcacgctgggctttttttacacgctctacgagtgcgtt aagttcagcgacattagtaacagccataattcttaattaactttgatatg -continued attttgtttcagatttttatataaaagctttcccaaatagtgctaaagt gaacttagatttttggtacctgtttcgaaattaaaaatagaaaaatttc tctccctatattgttattcttacttcaaatttgtttatcgtttatttact aggcgagacttgagtagacgacaatccaaatagaattaacagattttatt ggtagaaagcaataatattctttagatggttgagaataaagaagtaaaaa aaccagtaaagagaaaaagaaaaggaagaaaattaaagaaaaaggatgat tacacaagaagataataaaaaaactcctttattaagagcggaagaattta ataatgaagatgggaataagcaaaacaaaaacaaagaagggaaaaaaaat aaaaaatcgtatttatttatttaaaaaatcatgttgatgacgacaatgga aaaaaaaaaccgatttcactttctcatccttatatttttcaaaggttgat gcaagtcgatctcaaatcggataacgctgccaactgggaaattccgcaat tccgcaagaaaaaaaaaaatgtgaaaacgtgattgcatttttttacaggtc ctaaaggatttagcccacatatcaagagggtggcagtaattgcactgatt aagcattcgtcagcattaggcgaatgtgtgcatgaatattgccagtgtgc tcgatattagagagtacattgaagaatattgtaccggattatgtacaata actttgttaatgagatattaattttcttttttactagccgctatcccatg cacgatgctaaatttcaagaagaaactgagatttaaaaaattagtggaag ctgataaaacggactataatggtgtatggattgaggaatctcgacatgtt tttccatcgttttcaacgatgactgtaacccgtagattgaaccaggcatg ccaaagttagttagatcagggtaaaaattatagatgaggtatttattgga gaaagataacatatcatactttcccccactttttttcgaggctcttctata tcatattcataaattagcattatgtcatttctcataactactttatcacg ttagaaattacttattattattaaattaatacaaaatttagtaaccaaat aaatataaataaatatgtatatttaaatttaaaaaaaaaatcctataga gcaaaaggattttccattataatattagctgtacacctatccgcattttt tgagggtggttacaacaccactcattcagaggctgtcggcacagttgctt ctagcatctggcgtccgtatgtatgggtgtattttaaataataaacaaag tgccacaccttcaccaattatgtctttaagaaatggacaagttccaaaga gcttgcccaaggctcgacaaggatgtactttggaatatctatattcaagt acgtggcgcgcatatgtttgagtgtgcacacaataaaggtttttagatat tttgcggcgtcctaagaaaataaggggtttcttaaaaaataacaatagca aacaaagttccttacgatgatttcagatgtgaatagcatggtcatgatga gtatatacgtttttataaataattaaaagttttcctcttgtctgtttttt tgttggctcgtggttgttctcgaaaaaggagagttttcattttcgaaata ggtgattatcatcatgttgttatcaccccacgacgaagataatacggagc tcaccgttttcttttttttttcctttggctgaaatttcccaccagaacaaa cgtgacaaaattatctttgaatccaaagtagcttatatatatacgtagaa gtgtttcgagacacacatccaaatacgaggttgttcaatttaaacccaag aatacataaaaaaaatatagatatattaacttagtaaacaatgactgcaa gcacaccatccaatgtcatgacattgttcttgttaaggcatggacaaagt gaattgaatcacgagaatatattctgtggttggattgacgctaagctaac -continued cgaaaaaggtaaagaacaagctcgtcattctgccgagctaatcgaacaat attgtaaagctaataatttgagattaccccagattggttacacctcacgt ttaattaggacccaacagaccatagaaacgatgtgtgaagaatttaagtt aaagccacaactgcaggttgtttacgactttaataaaatcaaacttggag acgaatttggcagtgatgacaaggataatatgaaaatcccgattatcaaa cttggaggctaaatgaacgtcattacggttcctggcagggccagaggaaa ccgaatgttttaaaagaatatggtaaggataaatatatgttcattaggag agattacgagggtaagccaccacctgtagatcttgaccgtgagatgattc aacaagaaaatgagaagggctcttctactgggtacgaattcaaggagcca aacagacaaataaaatatgaattggaatgcagcaatcatgacattgtatt accggattccgaatctcttcgtgaagtggtttatagattgaatccattct acaaaatgtcatattaaaattagccaatcaatatgatgaatcttcatgcc tgattgtgggccatggaagttcagtgagatcgctactgaaaattctggag ggtatatcagatgatgacatcaagaatgttgatattccaaatggtatccc cttagtcgttgaattagataagaataatggtcttaagtttatcagaaaat tctacctagatcctgaatctgctaagatcaatgctgagaaagtccgtaat gagggtttcataaaaaatccttaagggggggtaagtatataatataattgt gtattttccgaagtataatgaaaaccaatagaaaacttattataagtcca atgaggtactttaaaaatgtgatatttataagaacattcctgaatgcaga tatatgatatatattgtaaatatatatagatgtgtatatgtatttccatt ttgtgtgaggttttcttcttttatctcctatataatttgtaaccttaatt aacccatgacataaccaatattagcctttgcaaattttgtaacttcttga cgttgttctaacgacaaatcttcatgcttcgattttatatgccttgttaa agcatccagtctcgaaaacgtcttctgatagccctcagatccaagaattt ttatacactccgagcaacggaagacaatcttccttttagcgtgaatggta ttttggtgtctcgttaaatcataggaccttgaaaattgggcaccacacgg ttcatttgtaatgagattcattatctgacacgtaaatatttcgttattac cgtcagaagatgacgtatgggccgatggtgatgcagtcgaaggtttcgaa ttcgaatttgtagatgaatgtgaagataagtgcttc Sequence of M2158 AADH integrations at the GPD1 locus (nucleotide; SEQ ID NO:99):

cagaattggtgatattcttcattatcccctcgacatctttacttttgatc agctttgtgtatagcgggatatccgattggaacttggcttcagcaacaaa cttgccaaagtggattctcctactcaagctttgcaaacattctatatctc tagtggcaacagaaccgaagttattcttatcatcaccatctcttttcgaa attaatggtataatcttttcaatataaacttatttattttatcattgtaa ttaacttctggggcataaggcgccaaaatttgtgggtagttaatgctcgg taagaatgatttctgaatcttgtcaggaaagaagggagtttcatcaggtg attcgaatcttctgatgcgagaatgcgcaatttcaagatttgaaagagcc caatccaagaaagatcctttaaaattcggaatttctaaacctggatggtt -continued tgcctcataaactgaaggacatgtggcgaaatgcgacctctcaataaatt tgaagatgatcgaatcctccattctaactaattcatctctaatattttgt agatttaaaacagtttctggttttgtgaaatccatatcttataccaattt tatgcaggatgctgagtgctatttgttagcaaaacggaatcgatgtttca acttttcaatactttttttcttcttttcttcgaacttcgaagattataga gatccattgaaaatttacgataaaggaaatgcaacacgaagtttgaaaaa aagttgatattgaaaaaaaaaaaaaaagagaaccaaaaaaaaattaaaaa acgtgaaaacgatggtttaacaactttttttcgaatttggtatacgtggaa aaacgaatgtatagatgcattttttaaagaatatatataaaatttagtaat tgtattccgcgagcggcgcaataggtgatttcatttagctgctttcagtt tgcgtatcatttcttcattgatcttggcttctctatctaaatcctctttc gacttgtaaagtccccaagttctaaaccataagaaccgcctcaatctgga aaatttgtcagtatcaagaccataattcgtgtatgactgaatcaaatgta atccactttcgtcatgagtaaattcggccttgctcagagactcctggatt ttggctaacaacgcagtcccttcgatgcatatagctaggccacaaattat gccaataacggtccatgggttgatgttttcttgaattctttcgtttttca tgctatttgcgtcttcccaagtcccagcgttccagtattcatactgcgcg ttagagtggtagccataagagccggcatattggtaattttcagtattaac gttagaacgtggtgaatacgatgtggtccagccttgcctcgttgtgtcat atacgatctttttctttgggtcacaaagaatatcatatgcttgagagatg actttaaatctatgtagtttttcgcttgatgttagcagcagcggtgattt actatcactgttggtaaccttttctgagctaaatatttgaatgttatcgg aatggtcagggtggtacaattttacataacgatgatattttttttttaac gacttcttgtccagtttaggatttccagatccggcctttggaatgccaaa aatatcatagggagttggatctgccaactcaggccattgttcatcccta tcgtaagttttctattgccatttttatcgttcgctgtagcatacttagct ataaaagtgatttgtgggggacacttttctacacatgataagtgccactt gaataaaaatgggtatacgaacttatggtgtagcataacaaatatattgc aagtagtgacctatggtgtgtagatatacgtacagttagttacgagccta aagacacaacgtgtttgttaattatactgtcgctgtaatatcttctcttc cattatcaccggtcattccttgcaggggcggtagtacccggagaccctga acttttcttttttttttgcgaaattaaaaagttcattttcaattcgaca atgagatctacaagccattgttttatgttgatgagagccagcttaaagag ttaaaaatttcatagctactagtcttctaggcgggttatctactgatccg agcttccactaggatagcacccaaacacctgcatatttggacgaccttta cttacaccaccaaaaaccactttcgcctctcccgcccctgataacgtcca ctaattgagcgattacctgagcggtcctcttttgtttgcagcatgagact tgcatactgcaaatcgtaagtagcaacgtctcaaggtcaaaactgtatgg aaaccttgtcacctcacttaattctagctagcctaccctgcaagtcaaga ggtctccgtgattcctagccacctcaaggtatgcctctccccggaaactg tggccttttctggcacacatgatctccacgatttcaacatataaatagct -continued

```
tttgataatggcaatattaatcaaatttattttacttctttcttgtaaca
tctctcttgtaatcccttattccttctagctatttttcataaaaaaccaa
gcaactgcttatcaacacacaaacactaaatcaaaatggctgttactaat
gtcgctgaacttaacgcactcgtagagcgtgtaaaaaaagcccagcgtga
atatgccagtttcactcaagagcaagtagacaaaatcttccgcgccgccg
ctctggctgctgcagatgctcgaatcccactcgcgaaaatggccgttgcc
gaatccggcatgggtatcgtcgaagataaagtgatcaaaaaccactttgc
ttctgaatatatctacaacgcctataaagatgaaaaaacctgtggtgttc
tgtctgaagacgacacttttggtaccatcactatcgctgaaccaatcggt
attatttgcggtatcgttccgaccactaacccgacttcaactgctatctt
caaatcgctgatcagtctgaagacccgtaacgccattatcttctccccgc
acccgcgtgcaaaagatgccaccaacaaagcggctgatatcgttctgcag
gctgctatcgctgccggtgctccgaaagatctgatcggctggatcgatca
accttctgttgaactgtctaacgcactgatgcaccacccagacatcaacc
tgatcctcgcgactggtggtccgggcatggttaaagccgcatacagctcc
ggtaaaccagctatcggtgtaggcgcgggcaacactccagttgttatcga
tgaaactgctgatatcaaacgtgcagttgcatctgtactgatgtccaaaa
ccttcgacaacggcgtaatctgtgcttctgaacagtctgttgttgttgtt
gactctgtttatgacgctgtacgtgaacgttttgcaacccacggcggcta
tctgttgcagggtaaagagctgaaagctgttcaggatgttatcctgaaaa
acggtgcgctgaacgcggctatcgttggtcagccagcctataaaattgct
gaactggcaggcttctctgtaccagaaaacaccaagattctgatcggtga
agtgaccgttgttgatgaaagcgaaccgttcgcacatgaaaaactgtccc
cgactctggcaatgtaccgcgctaaagatttcgaagacgcggtagaaaaa
gcagagaaactggttgctatgggcggtatcggtcatacctcttgcctgta
cactgaccaggataaccaaccggctcgcgtttcttacttcggtcagaaaa
tgaaaacggcgcgtatcctgattaacaccccagcgtctcagggtggtatc
ggtgacctgtataacttcaaactcgcaccttccctgactctgggttgtgg
ttcttggggtggtaactccatctctgaaaacgttggtccgaaacacctga
tcaacaagaaaaccgttgctaagcgagctgaaaacatgttgtggcacaaa
cttccgaaatctatctacttccgccgtggctccctgccaatcgcgctgga
tgaagtgattactgatggccacaaacgtgcgctcatcgtgactgaccgct
tcctgttcaacaatggttatgctgatcagatcacttccgtactgaaagca
gcaggcgttgaaactgaagtcttcttcgaagtagaagcggacccgaccct
gagcatcgttcgtaaaggtgcagaactggcaaactccttcaaaccagacg
tgattatcgcgctgggtggtggttccccgatggacgccgcgaagatcatg
tgggttatgtacgaacatccggaaactcacttcgaagagctggcgctgcg
ctttatggatatccgtaaacgtatctacaagttcccgaaaatgggcgtga
aagcgaaaatgatcgctgtcaccaccacttctggtacaggttctgaagtc
actccgtttgcggttgtaactgacgacgctactggtcagaaatatccgct
ggcagactatgcgctgactccggatatggcgattgtcgacgccaacctgg
```

-continued

```
ttatggacatgccgaagtccctgtgtgctttcggtggtctggacgcagta
actcacgccatggaagcttatgtttctgtactggcatctgagttctctga
tggtcaggctctgcaggcactgaaactgctgaaagaatatctgccagcgt
cctaccacgaagggtctaaaaatccggtagcgcgtgaacgtgttcacagt
gcagcgactatcgcgggtatcgcgtttgcgaacgccttcctgggtgtatg
tcactcaatggcgcacaaactgggttcccagttccatattccgcacggtc
tggcaaacgccctgctgatttgtaacgttattcgctacaatgcgaacgac
aacccgaccaagcagactgcattcagccagtatgaccgtccgcaggctcg
ccgtcgttatgctgaaattgccgaccacttgggtctgagcgcaccgggcg
accgtactgctgctaagatcgagaaactgctggcatggctggaaacgctg
aaagctgaactgggtattccgaaatctatccgtgaagctggcgttcagga
agcagacttcctggcgaacgtggataaactgtctgaagatgcattcgatg
accagtgcaccggcgctaacccgcgttacccgctgatctccgagctgaaa
cagattctgctggatacctactacggtcgtgattatgtagaaggtgaaac
tgcagcgaagaaagaagctgctccggctaaagctgagaaaaaagcgaaaa
aatccgcttaagtcgagagcttttgattaagccttctagtccaaaaaaca
cgtttttttgtcatttatttcattttcttagaatagtttagtttattcat
tttatagtcacgaatgttttatgattctatatagggttgcaaacaagcat
ttttcattttatgttaaaacaatttcaggtttacttttattctgcttgt
ggtgacgcgtgtatccgcccgctcttttggtcacccatgtatttaattgc
ataaataattcttaaaagtggagctagtctatttctatttacatacctct
catttctcatttcctcctaatgtgtcaatgatcatattcttaactggacc
gatcttattcgtcagattcaaaccaaaagttcttagggctaccacaggag
gaaaattagtgtgatataatttaaataatttatccgccattcctaataga
acgttgttcgacggatatctttctgcccaaaagggttctaagctcaatga
agagccaatgtctaaacctcgttacattgaaaatacagtaaatggttcca
ccattattatgttggtcttgtttagtatggccgatcggcgtgtgttttgt
ttgcaccattttatatagtagaagaatatttgtcttaattcttattagta
ctgcaacctaaccactaattatcaacaattattggattatataaaggagg
taaattgccggattaaaatcaaatatcattcatcaacaagtattcatatt
gtcggcatatttttacatgcggtgtaagtatttggatcgtattcttatag
tgtcaatacctcgaagcagcgtttcaagtaccagacgtatgtaggaactt
tttaacgtcgagtccgtaagatttgatcagtattaaaaaaatctagataa
atgagtggtacaaataaaaacatcattaaaaatcgttaaataaaaaagta
tgaagatcatctattaaagtattagtagccattagccttaaaaaaatcag
tgctagtttaagtataatctcgggcgcgccggccgaggcggttaagcgga
tttttcgctttttctcagctttagccggagcagcttctttcttcgctg
cagtttcaccttctacataatcacgaccgtagtaggtatccagcagaatc
tgtttcagctcggagatcagcgggtaacgcgggttagcgccggtgcactg
gtcatcgaatgcatcttcagacagtttatccacgttcgccaggaagtctg
cttcctgaacgccagcttcacggatagatttcggaatacccagttcagct
```

-continued

```
ttcagcgtttccagccatgccagcagtttctcgatcttagcagcagtacg
gtcgcccggtgcgctcagacccaagtggtcggcaatttcagcataacgac
ggcgagcctgcggacggtcatactggctgaatgcagtctgcttggtcggg
ttgtcgttcgcattgtagcgaataacgttacaaatcagcagggcgtttgc
cagaccgtgcggaatatggaactgggaacccagtttgtgcgccattgagt
gacatacacccaggaaggcgttcgcaaacgcgatacccgcgatagtcgct
gcactgtgaacacgttcacgcgctaccggatttttagacccttcgtggta
ggacgctggcagatattctttcagcagtttcagtgcctgcagagcctgac
catcagagaactcagatgccagtacagaaacataagcttccatggcgtga
gttactgcgtccagaccaccgaaagcacacagggacttcggcatgtccat
aaccaggttggcgtcgacaatcgccatatccggagtcagcgcatagtctg
ccagcggatatttctgaccagtagcgtcgtcagttacaaccgcaaacgga
gtgacttcagaacctgtaccagaagtggtggtgacagcgatcattttcgc
tttcacgcccattttcgggaacttgtagatacgtttacggatatccataa
agcgcagcgccagctcttcgaagtgagtttccggatgttcgtacataacc
cacatgatcttcgcggcgtccatcggggaaccaccacccagcgcgataat
cacgtctggtttgaaggagtttgccagttctgcacctttacgaacgatgc
tcagggtcgggtccgcttctacttcgaagaagacttcagtttcaacgcct
gctgctttcagtacggaagtgatctgatcagcataaccattgttgaacag
gaagcggtcagtcacgatgagcgcacgtttgtggccatcagtaatcactt
catccagcgcgattggcagggagccacggcggaagtagatagatttcgga
agtttgtgccacaacatgttttcagctcgcttagcaacggttttcttgtt
gatcaggtgtttcggaccaacgttttcagagatggagttaccaccccaag
aaccacaacccagagtcagggaaggtgcgagtttgaagttatacaggtca
ccgataccaccctgagacgctggggtgttaatcaggatacgcgccgtttt
cattttctgaccgaagtaagaaacgcgagccggttggttatcctggtcag
tgtacaggcaagaggtatgaccgataccgcccatagcaaccagtttctct
gcatttctaccgcgtcttcgaaatctttagcgcggtacattgccagagtc
ggggacagtttttcatgtgcgaacggttcgctttcatcaacaacggtcac
ttcaccgatcagaatcttggtgttttctggtacagagaagcctgccagtt
cagcaattttataggctggctgaccaacgatagccgcgttcagcgcaccg
tttttcaggataacatcctgaacagctttcagctctttaccctgcaacag
atagccgccgtgggttgcaaaacgttcacgtacagcgtcataaacagagt
caacaacaacaacagactgttcagaagcacagattacgccgttgtcgaag
gttttggacatcagtacagatgcaactgcacgtttgatatcagcagtttc
atcgataacaactggagtgttgcccgcgcctacaccgatagctggtttac
cggagctgtatgcggctttaaccatgcccggaccaccagtcgcgaggatc
aggttgatgtctgggtggtgcatcagtgcgttagacagttcaacagaagg
ttgatcgatccagccgatcagatctttcggagcaccggcagcgatagcag
cctgcagaacgatatcagccgctttgttggtggcatcttttgcacgcggg
tgcggggagaagataatggcgttacgggtcttcagactgatcagcgattt
```

-continued

```
gaagatagcagttgaagtcgggttagtggtcggaacgataccgcaaataa
taccgattggttcagcgatagtgatggtaccaaaagtgtcgtcttcagac
agaacaccacaggtttttcatctttataggcgttgtagatatattcaga
agcaaagtggtttttgatcactttatcttcgacgatacccatgccggatt
cggcaacggccattttcgcgagtgggattcgagcatctgcagcagccaga
gcggcggcgcggaagattttgtctacttgctcttgagtgaaactggcata
ttcacgctgggctttttttacacgctctacgagtgcgttaagttcagcga
cattagtaacagccataattcttaattaactttgatatgattttgtttca
gatttttatataaaagctttcccaaatagtgctaaagtgaacttagatt
ttttggtacctgtttcgaaattaaaaatagaaaaatttctctccctatat
tgttattcttacttcaaatttgtttatcgtttatttactaggcgagactt
gagtagacgacaatccaaatagaattaacagattttattggtagaaagca
ataatattctttagatggttgagaataaagaagtaaaaaaaccagtaaag
agaaaaagaaaaggaagaaaattaaagaaaaaggatgattacacaagaag
ataataaaaaaactcctttattaagagcggaagaatttaataatgaagat
gggaataagcaaaacaaaaacaaagaagggaaaaaaaatcaaaaaatcgta
tttatttatttaaaaaatcatgttgatgacgacaatggaaaaaaaaaacc
gatttcactttctcatccttatatttttcaaaggttgatgcaagtcgatc
tcaaatcggataacgctgccaactgggaaattccgcaattccgcaagaaa
aaaaaaatgtgaaaacgtgattgcatttttttacaggtcctaaaggattt
agcccacatatcaagagggtggcagtaattgcactgattaagcattcgtc
agcattaggcgaatgtgtgcatgaatattgccagtgtgctcgatattaga
gagtacattgaagaatattgtaccggattatgtacaataactttgttaat
gagatattaatttttcttttttactagccgctatcccatgcacgatgctaa
atttcaagaagaaactgagatttaaaaaattagtggaagctgataaaacg
gactataatggtgtatggattgaggaatctcgacatgtttttccatcgtt
ttcaacgatgactgtaacccgtagattgaaccaggcatgccaaagttagt
tagatcagggtaaaaattatagatgaggtttaattaaacaagcacgcagc
acgctgtatttacgtatttaattttatatatttgtgcatacactactagg
gaagacttgaaaaaaacctaggaaatgaaaaaacgacacaggaagtcccg
tatttactatttttttccttccttttgatggggcagggcggaaatagagga
taggataagcctactgcttagctgtttccgtctctacttcggtagttgtc
tcaattgtcgtttcagtattacctttagagccgctagacgatggttgagc
tatttgttgagggaaaactaagttcatgtaacacacgcataacccgatta
aactcatgaatagcttgattgcaggaggctggtccattggagatggtgcc
ttattttccttataggcaacgatgatgtcttcgtcggtgttcaggtagta
gtgtacactctgaatcagggagaaccaggcaatgaacttgttcctcaaga
aaatagcggccataggcatggattggttaaccacaccagatatgcttggt
gtggcagaatatagtccttttggtggcgcaattttcttgtacctgtggta
gaaagggagcggttgaactgttagtatatattggcaatatcagcaaattt
gaaagaaaattgtcggtgaaaaacatacgaaacacaaaggtcgggccttg
```

Figure 14:
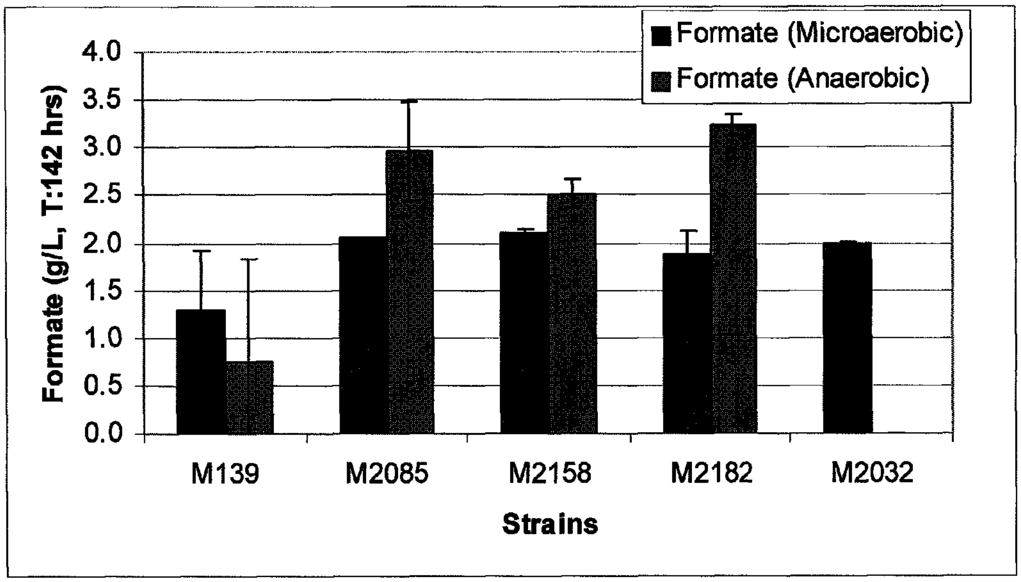
FIG. 14 shows a graph of formate production at the end of 142 hours in microaerobic and anaerobic conditions.

-continued caacgttattcaaagtcattgtttagttgaggaggtagcagcggagtata tgtattcctttttttgcctatggatgttgtaccatgcccattctgctca agcttttgttaaaattattttcagtatttttcttccatgttgcgcgtt acgagaacagaagcgacagataaccgcaatcatacaactagcgctactgc ggggtgtaaaaagcacaagaactaagccaagatcacaacagttatcgata aaatagcagtgtttgcatggccattgagaaggacaacattggcgtgcgcg ccaatgttgtctcaccatgtagctccaaacgagttgtaagagacggaccg ctcacgcttccgaagcggtcagaaaacgcttcccagtatgcagttgacct acattcaacctgcaaatattgctttgcttcaagaaatgattacacagacg tctatttcttctacataatgcacgaaacttgggcatttagtcatgtagc cgcctagcgagcctgggtgccgtcctatctcctttgttcgtgcaaagaga caggaacacacactgcgttctcttgcggccggtctggcggactcaggggt gcggcgtttgcttaaccggagggaataataaaatcggggtgacgcaagta tgaagtcatgtgtgcttagcaattacgtagagggattagaaataatagtg tgcggttatcggaaccggctcttgttcccgtttagagcaacccaggtgca ggcgtactttaaagtatttcttcttttttttcctgctacttacgctag gagctgccgcagctgcaaagccgacgtcggagaggcaggtgatcttcggc tcggccgacaaatcccctggatatcattggcctgtcgaggtatcggccgc gtggaactaccgggaattactatgcaaaacaattggaaatctggtaggaa aaccttgttctagaacttggcgattgctgacaaagaagaaaagggcctat tgttgctgcctcttttgttgttcttcctcgtattgtcttgccggtgttct ttgtgtcttttgtgtgtaggttcttactattatagtgctctttgctatta tattttcttcgttttcactttgcgtaatgtaacggtcttaaacaaagttt tttttttttcgctcttgcattttcctttctgctctatcttatttgctaa ttgtagtttcagaagttttacttaaatatagcactattttccagttttaa tgtttcttctcattgctttcttttataattttcgcatataattatacatt tacggtgtcttaactctccctcttcacccctcattattccagaaaatact aatacttcttcacacaaaagaacgcagttagacaatcaacaatgaatcct aaatcctctacacctaagattccaagacccaagaacgcatttattctgtt cagacagcactaccacaggatcttaatagacgaatggaccgctcaaggtg tggaaataccccataattcaaacatttctaaaattattggtacgaagtgg aagggcttacaaccggaagataaggcacactgggaaaatctagcggagaa ggagaaactagaacatgaaaggaagtatcctgaatacaaatacaagccgg taagaaagtctaagaagaagcaactacttttgaaggaaatcgagcaacag cagcagcaacaacagaaagaacagcagcagcagaaacagtcacaaccgca attacaacagccctttaacaacaatatagttcttatgaaaagagcacatt ctctttcaccatcttcctcggtgtcaagctcgaacagctatcagttccaa ttgaacaatgatcttaagaggttgcctattccttctgttaatacttctaa ctatatggtctccagatctttaagtggactacctttgacgcatgataaga cggcaagagacctaccacagctgtcatctcaactaaattctattccatat tactcagctccacacgacccttcaacgagacatcattacctcaacgtcgc -continued tcaagctcaaccaagggctaactcgacccctcaattgccctttatttcat ccattatcaacaacagcagtcaaacaccggtaactacaactaccacatcc acaacaactgcgacatcttctcctgggaaattctcctcttctccgaactc ctctgtactggagaacaacagattaaacagtatcaacaattcaaatcaat atttacctccccctctattaccttctctgcaagattttcaactggatcag taccagcagctaaagcagatgggaccaacttatattgtcaaaccactgtc tcacaccaggaacaatctattgtccacaactacccctacgcatcatcaca ttcctcatataccaaaccaaaacattcctctacatcaaattataaactca agcaacactgaggtcaccgctaaaactagcctagtttctccgaaatgatt ttttttttccatttcttctttccgttatattatattatactatattccct ttaactaaaaatttatgcatttggctcctgtttaataaaagtttaaatc These strains were grown in YPD containing 50 g/L glucose under anaerobic and microaerobic conditions, and formate was measured over 142 hours. As shown in FIG. 14, at the end of 142 hours, strains containing the heterologous PFL and AADH made more formate than the wildtype strain M139.

Example 6

Expression of PFL and AADH and Detection of Ethanol

The purpose of this Example is to determine whether formate production can confer anaerobic growth on fdh, gpd, and/or fps deletion strains. Yeast strains containing an fdh1Δfdh2Δgpd1Δgpd2Δ genetic background (M2025) were transformed with vectors expressing PflA/B cassettes from *C. cellulolyticum* (TB274) and *E. coli* (TB275). Each of these strains also contained a second construct expressing the *E. coli* AdhE. YPD medium was prepared and added to hungate tubes, oxygen was purged with nitrogen, and the tubes were autoclaved for 20 minutes. A pre-culture of TB274 and TB275 was prepared overnight in YPD medium containing antibiotics which select for maintenance of both plasmids. A pre-culture of M1901, the parent strain of M2025, and M2025 itself were prepared in YPD and included as positive and negative controls, respectively. A strain referred to as TB267 was created which contains only the bifunctional ADH plasmid. This strain was prepared in YPD plus antibiotic to select for the plasmid. This strain controls for the potential effect of ADH or other electron acceptors that may be present in YPD medium.

Figure 15:
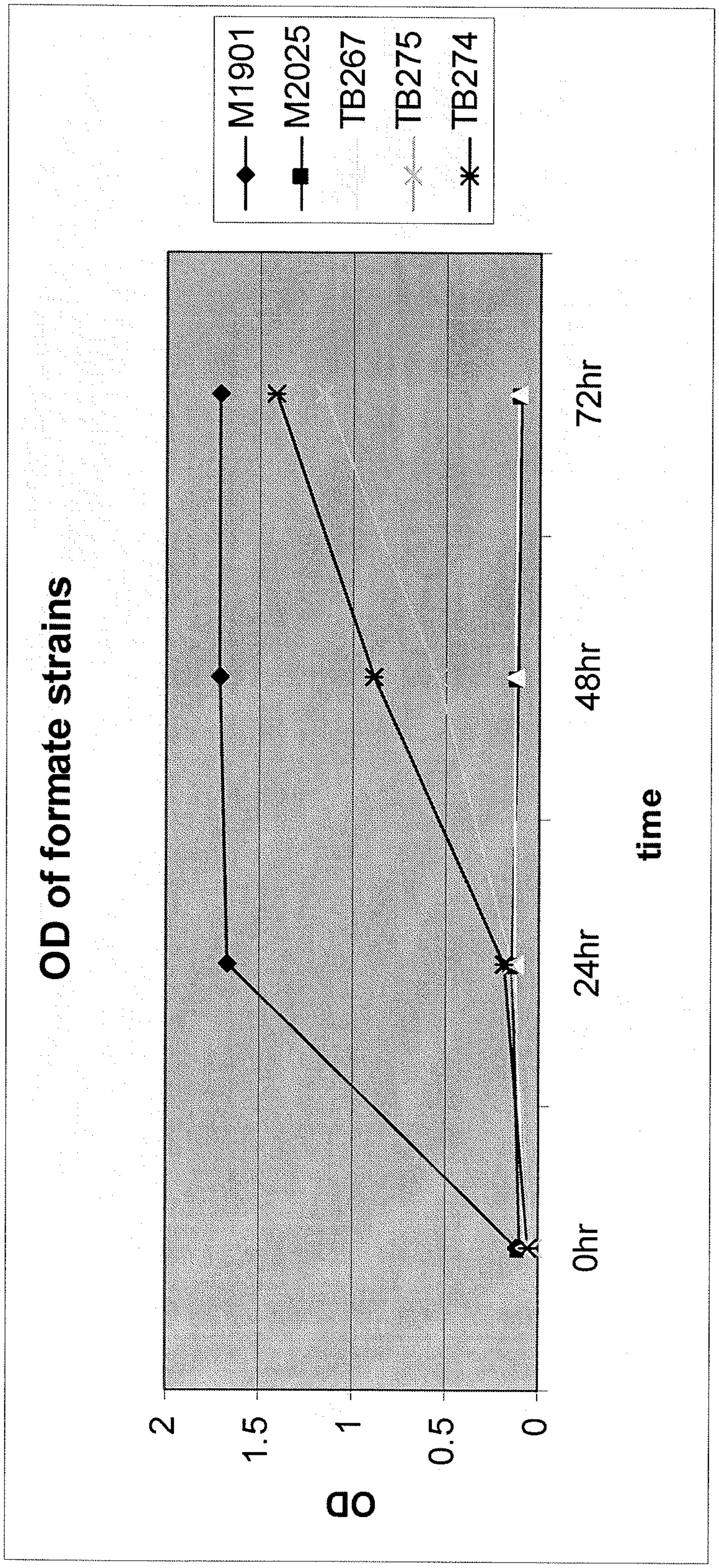
FIG. 15 shows a graph of the growth of strains of the invention over 72 hours as measured by OD.

All strains were inoculated to final OD's of about 0.05 or below. The OD of each culture was measured at 0, 24, 48, and 72 hours (FIG. 15), and samples were prepared and submitted for HPLC determination of metabolite levels. As expected, the M1901 strain grew fairly quickly, consuming all the sugar substrate by 24 hours. The M2025 and TB267 strains, which are unable to make glycerol, did not show a significant increase in OD during this experiment. The TB274 and TB275 strains, which express both PFL and ADH, were able to grow after a 24 hour lag time. See FIG. 15. These data indicate that the introduced metabolic pathway in TB274 and TB275 does not block cellular growth.

Figure 16:
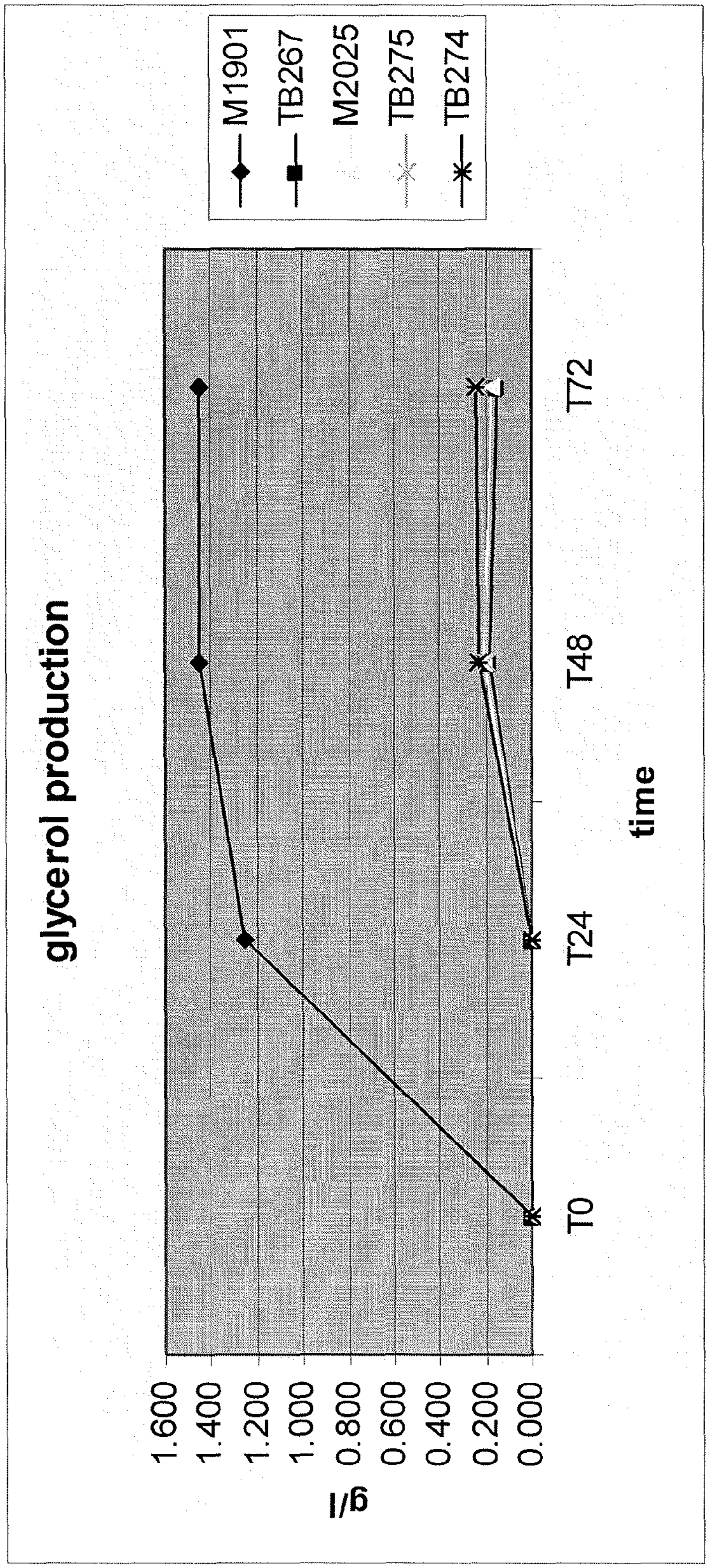
FIG. 16 shows a graph of glycerol production (g/L) of strains of the invention over 72 hours.

The production of glycerol in these strains is shown in FIG. 16. The anaerobic growth of M1901 was accompanied by glycerol production as expected. A trace amount of glycerol was observed in the PflA/B containing strains TB274 and TB275, but this was at or below the level of the negative controls which did not grow. See FIG. 16. These data, in conjunction with the OD data, indicate that the expression of PflA/B and AdhE allowed for anaerobic growth of M2025 without associated glycerol production.

Figure 17:
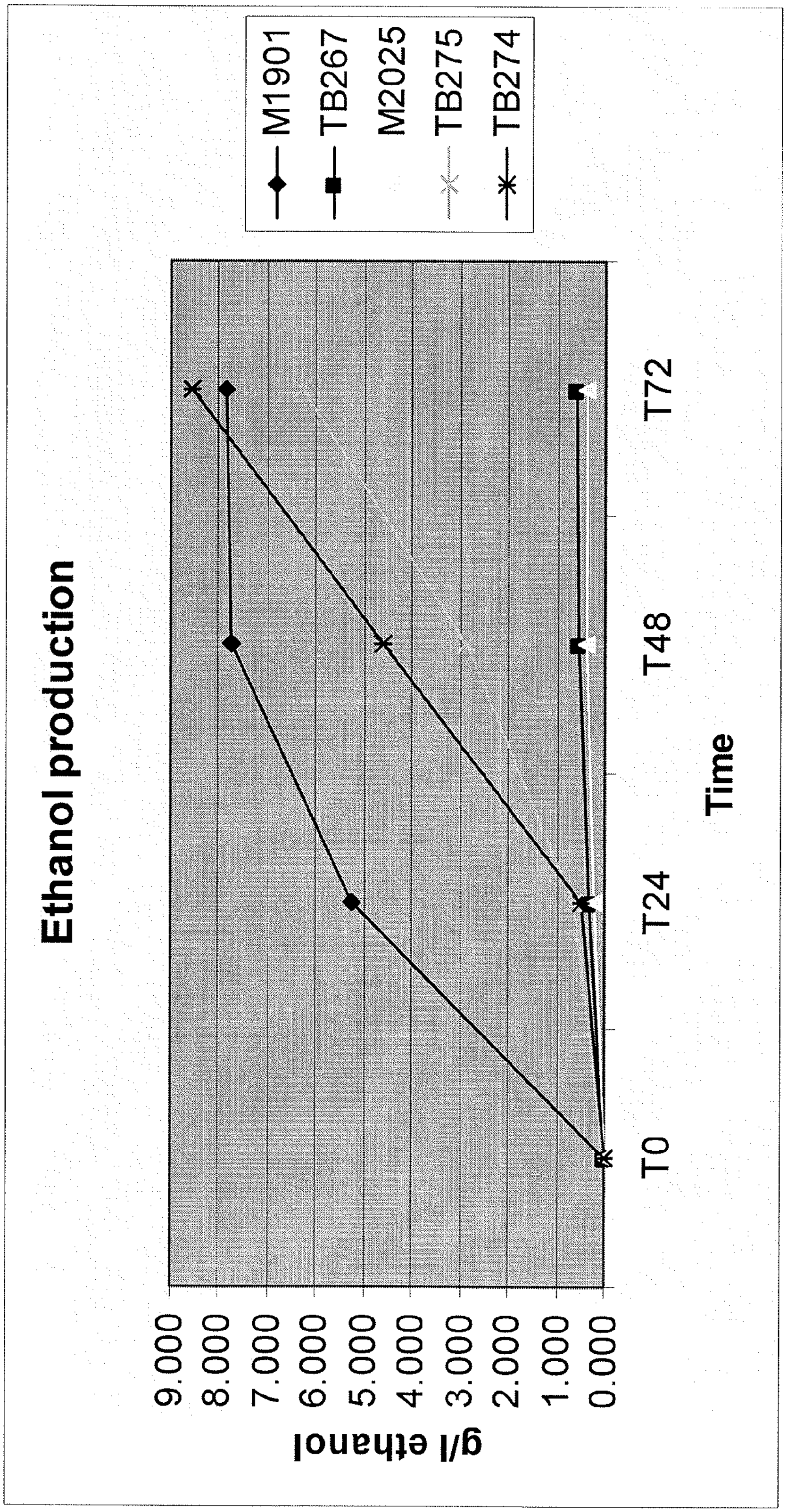
FIG. 17 shows a graph of ethanol production (g/L) of strains of the invention over 72 hours.
Figure 18:
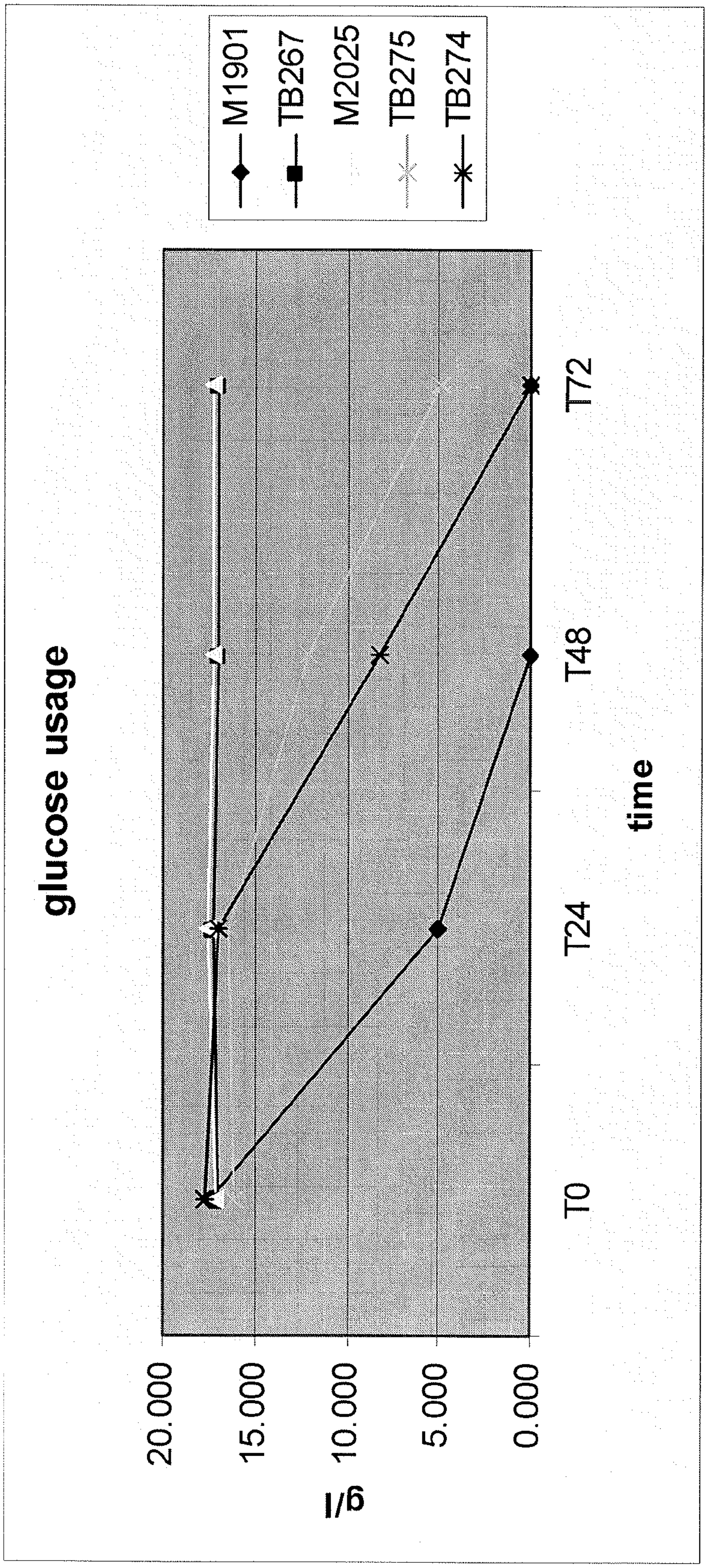
FIG. 18 shows a graph of glucose utilization (g/L) of strains of the invention over 72 hours.

The production of ethanol and glucose concentration are shown in FIGS. 17 and 18, respectively. Both M1901 and TB274 consumed all the sugar, but about 5 g/L glucose remained in the TB275 fermentation. See FIG. 18. TB274 had an 11% increase in ethanol yield in comparison to M1901. See FIG. 17. The increase in yield was higher than expected and likely came partially at the expense of biomass, although this was not determined.

Strains containing PFL and AADH were compared to other strains engineered to express AADH. A description of these strains appears in Table 4.

TABLE 4

Genetic Backgrounds for PFL Expression

| Strain Name | Genetic Background |
|---|---|
| M139 | wt control |
| M2085 | gdp1Δ gpd2Δ fdh1Δ fdh2Δ |
| M2158 | gdp1Δ gpd2Δ fdh1Δ fdh2Δ + AADH |
| M2182 | gdp1Δ gpd2Δ fdh1Δ fdh2Δ + AADH and PFL |

Figure 19:
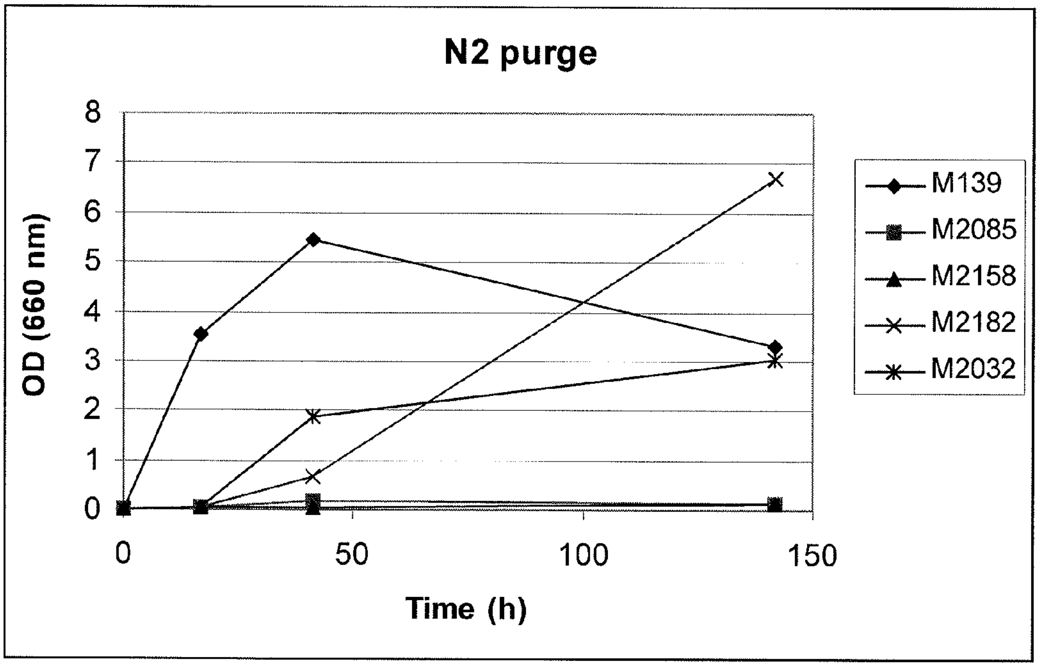
FIG. 19 shows a graph of the growth of a strain of the invention over 142 hours as measured by OD.

These five strains were tested in nitrogen purged bottles. As shown in FIG. 19, strain M2182 which has both PFL and AADH expression cassettes in a gdp1Δ gpd2Δ fdh1Δfdh2Δ background, had a faster growth rate and reached a higher OD than M2158, which contains only the bifunctional ADH activity and did not appear to grow at all. See FIG. 19. These data show that a strain expressing both PFL and AADH activities grows better than the other engineered functionalities. Similar improvements over these other engineered functionalities are also observed in corn mash fermentations (see Example 7 below).

Example 7

Production of Ethanol from Corn Mash

The purpose of this experiment was to determine whether PFLs cloned from the organisms listed below in Table 5 could provide for increased ethanol yield when used in fermentation of 20% corn mash. A total of nine PFLs have been tested for function in yeast. Of these, only the *C. cellulolyticum* PFL had no positive effect on growth of glycerol synthesis mutants in corn mash fermentations. Additionally, no formate was observed in formate assays when using a strain containing *C. cellulolyticum* PFL. This strain was not tested for performance on corn mash fermentation.

Eight PFLs were tested for functionality in strain M2158 which has the *E. coli* AADH integrated on the chromosome of a gpd1Δ gpd2Δ fdh1Δ fdh2Δ background (M2085) or M2275, which is identical to M2158 except that it also has the gpd2Δ::GPD1 glycerol reduction mutation. Two separate corn mash fermentation experiments were performed using 20% solids in a baffled shake flask using the strains listed in Table 5. Performance of the strains was evaluated by HPLC analysis of metabolites.

TABLE 5

Genetic Backgrounds for Corn Mash Fermentations

| Strain Name | Genetic Background |
|---|---|
| M139 | wt control |
| M2085 | gpd1Δ gpd2Δ fdh1Δ fdh2Δ |
| M2158 | integrated AADH |
| M2180 | M2158 + *B. lichenformis* PFL |
| M2181 | M2158 + *L. planatarum* PFL |
| M2182 | M2158 + *B. adolescentis* PFL |
| M2183 | M2158 + *S. thermophilus* PFL |
| M2184 | M2158 + *E. coli* PFL |
| M2321 | M2158 + *L. casei* PFL |
| M2322 | M2158 + *C. reinhardtii* PFL |
| M2323 | M2158 + *Piromyces* PFL |
| M2324 | M2158 + *E. coli* PFL |
| M2275 | M2158 + gpdΔ::GPD1 |
| M2326 | M2275 + *B. adolescentis* PFL |

Figure 21:
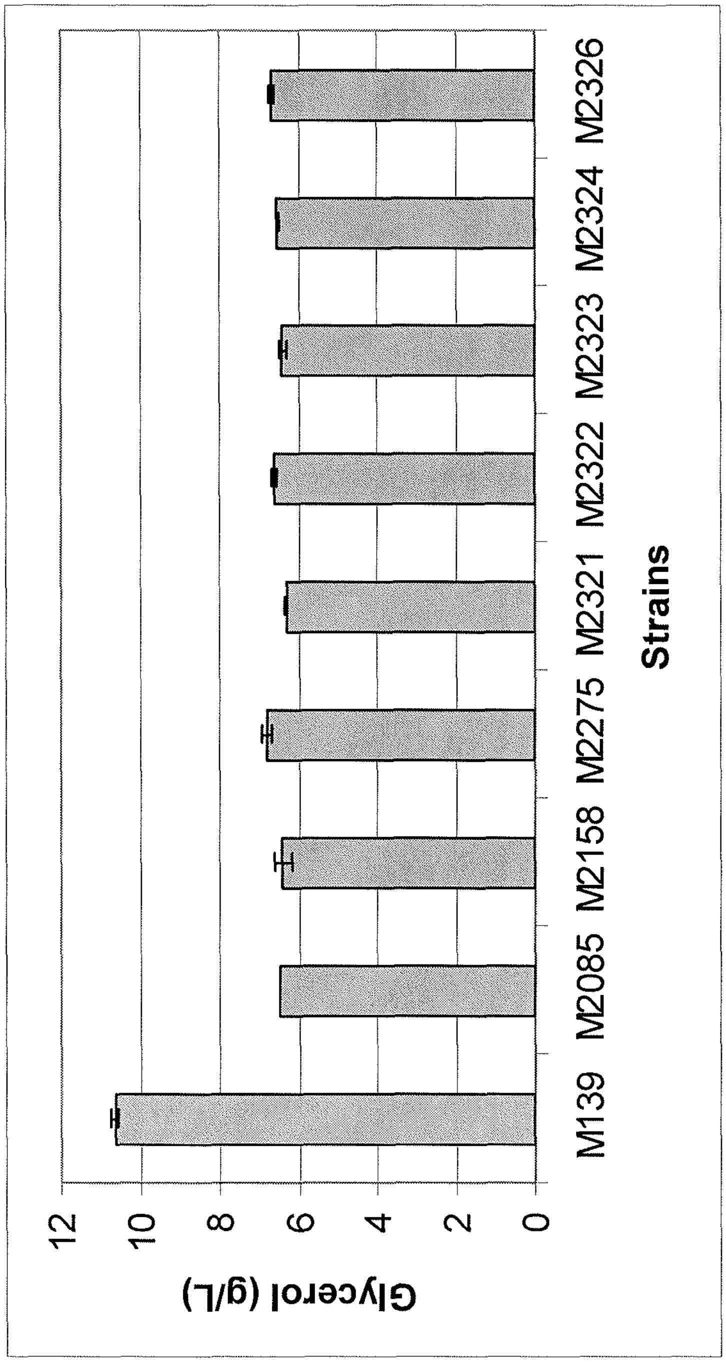
FIG. 21 shows a graph of ethanol production (g/L) of strains of the invention after 50 hours of fermentation.
Figure 23:
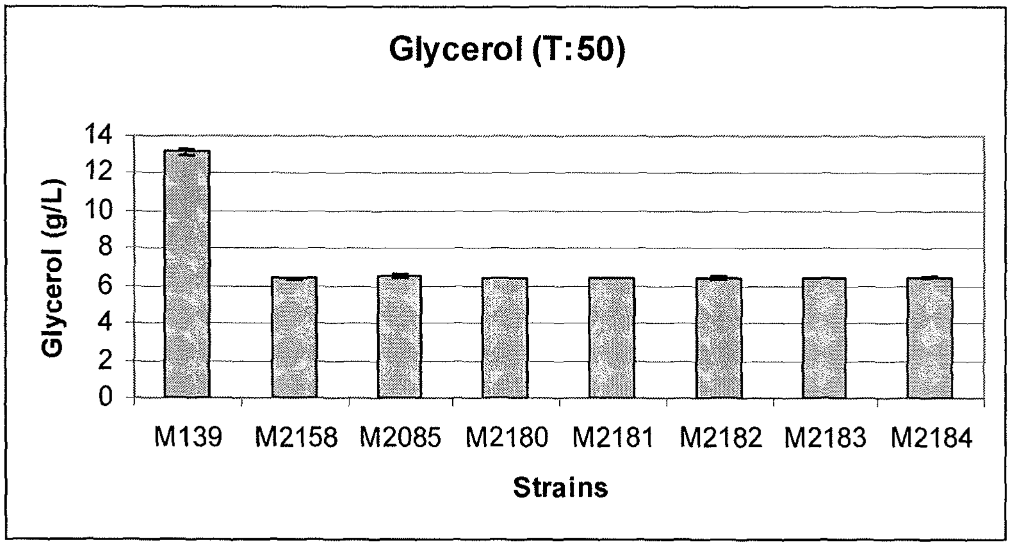
FIG. 23 shows a graph of glycerol production (g/L) of strains of the invention after 50 hours of fermentation.
Figure 24:
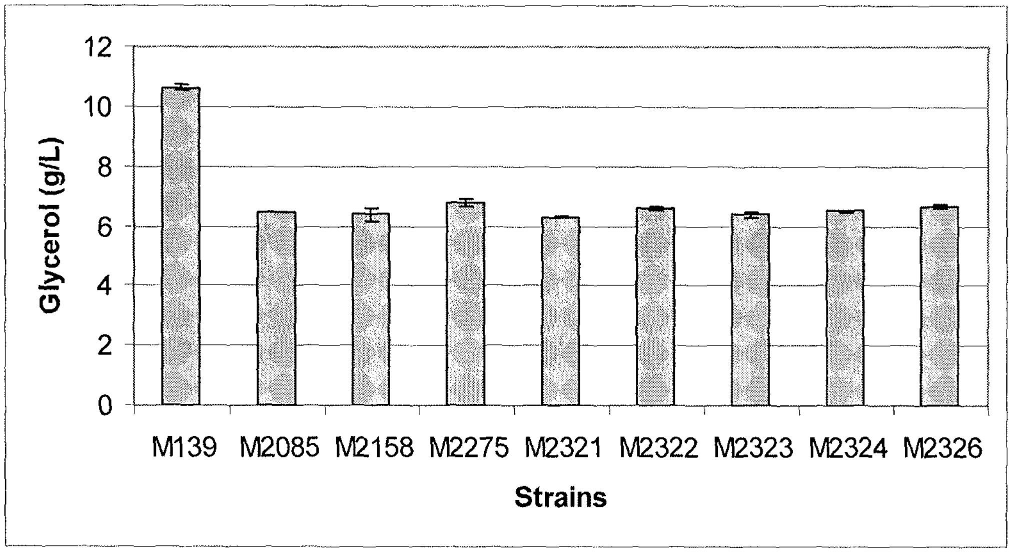
FIG. 24 shows a graph of glycerol production (g/L) of strains of the invention after 50 hours of fermentation.
Figure 25:
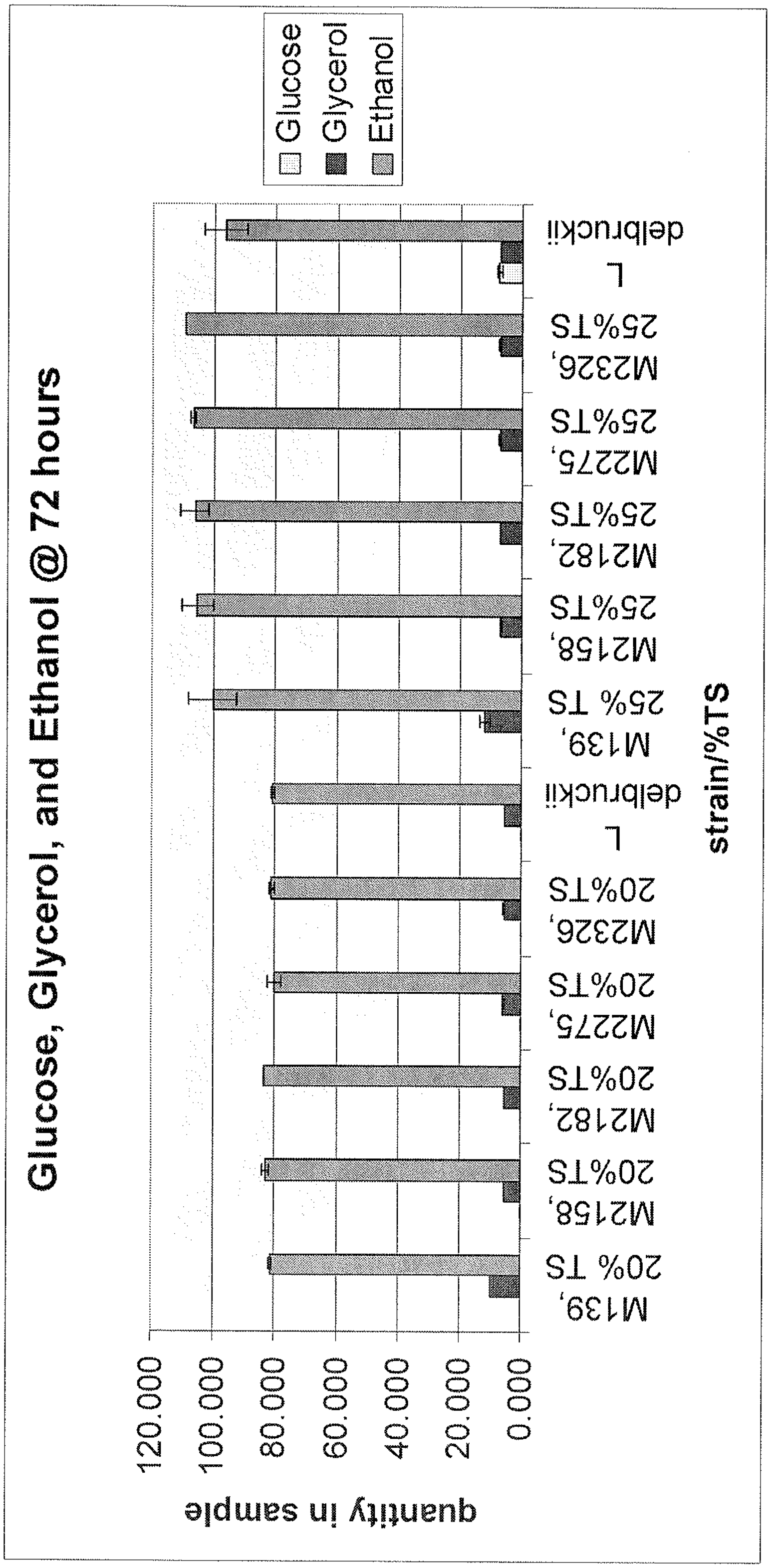
FIG. 25 shows a graph of glucose utilization (g/L), glycerol production (g/L), and ethanol production (g/L) after 72 hours of fermentation.

As shown in FIGS. 21 and 22, the addition of PFL improves the ethanol yield of strains containing only AADH. FIGS. 23 and 24 show that these strains do not make glycerol as expected. The approximately 4 g/L glycerol observed is already in the industrial mash substrate used for this experiment. FIG. 25 demonstrates a 9% increase in ethanol yield with strain M2326, which is a glycerol reduction strain.

Example 8

The following example demonstrates the creation of the *Saccharomyces cerevisiae* strain M3625. The genotype of strain M3625 is: Δgpd2::*B. adolescentis* pflA/pflB/adhE Δfdh1Δfdh2::*B. adolescentis* pflA/pflB/adhE fcy1Δ::*S. fibuligera* glucoamylase (glu-0111-CO). Strain M2390 is referred to as Ethanol Red (new) from LaSaffre (pahc.com/Phibro/Performance-Products/Catalog/23/Ethanol-Red.html).

The genetic modification techniques utilized to develop *Saccharomyces cerevisiae* strain M3625 relied upon directed integration to insert the genes for *Bifidobacterium adolescentis* pflA, pflB, AdhE and *S. fibuligera* glu-0111-CO at specific and known sites within the yeast chromosome. The directed integration approach creates transgenic strains with integration events that are stable and easy to characterize. Chromosomal integration, by its very nature, reduces the probability of any mobilization of the heterologous DNA and enhances strain stability relative to other approaches.

The MX cassettes are the most commonly used engineering tool when an insertion or deletion of a genetic element is desired at a given chromosomal loci (Wach A, et al., *Yeast* 10(13):1793-1808 (1994)). A recyclable MX cassette contains one or more markers which enable both dominant and negative selection (Goldstein, A. L. and McCusker, J. H., *Yeast* 15:1541-1553 (1999); Ito-Harashima, S. and McCusker, J. H., Yeast 21:53-61 (2004)). The dominant marker enables selection for the modification and the counter selectable marker enables subsequent removal of the marker system via Cre-Lox mediated recombination (Güldener, Ulrich, et al., Nucleic Acids Research (1996) 24 (13) 2519-2524) or recombination between duplicated homologous regions flanking the cassette. Since the markers are removed, they can be reused during subsequent engineering steps and ensures no undesirable foreign genetic material remains in the strain.

To create stable homozygous integrations in M3625, two new HSV-thymidine kinase (TDK) based MX cassettes were developed. Expression of thymidine kinase in *S. cerevisiae* results in sensitivity to the compound fluoro-deoxyuracil (FUDR). The cellular toxicity of FUDR is dependent on the presence of two enzymes involved in pyrimidine metabolism: thymidine kinase (Tdk) and thymidilate synthetase (ThyA). Tdk converts FUDR to fluoro-dUMP (F-dUMP) which is a covalent inhibitor of ThyA and the basis for counter selection in a variety of eukaryotic organisms (Czako, M., and L. Marton, (1994) Plant Physiol 104:1067-1071; Gardiner, D. M., and B. J. Howlett, (2004) Curr Genet 45:249-255; Khang, C. H., et al., (2005) Fungal Genet Biol 42:483-492; Szybalski, W. (1992) Bioessays 14:495-500).

Figure 28:
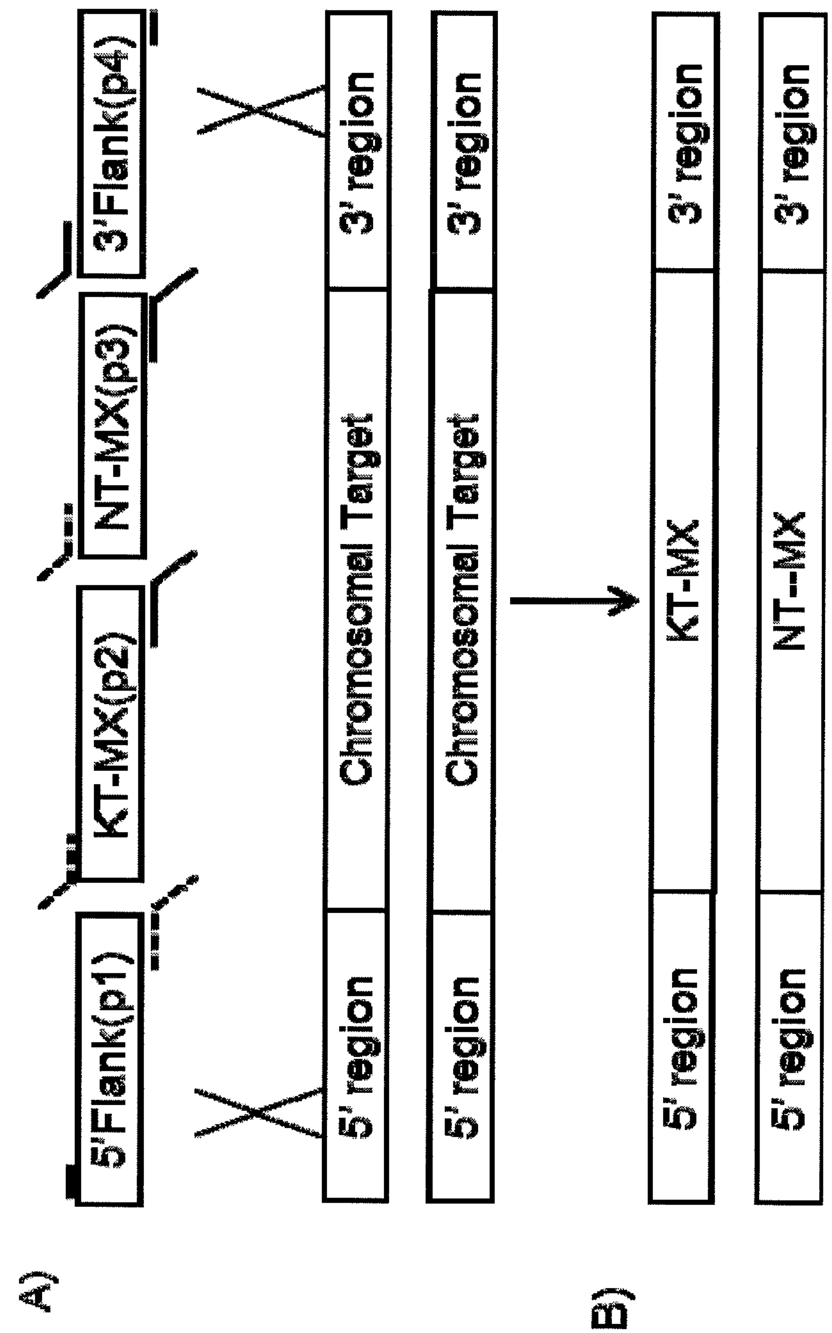
FIG. 28 shows a schematic diagram of a strategy for PCR construction and integration of KT-MX and NT-MX integration cassettes into both chromosomes of a target loci.

The HSV-TDK expression cassette was independently fused to two commonly used dominant selectable markers which confer resistance to the drugs G418 (Kan) or nourseothricin (Nat) (Goldstein, A. L. and McCusker, J. H., Yeast 15:1541-1553 (1999)). Transformation of both double expression cassettes, referred to as KT-MX and NT-MX, enables positive selection for integration into both chromosomes as illustrated in FIG. 28A. The transformed deletion assembly contains four PCR products, a 5'flank(p1) which is homologous upstream of the target site, KT-MX cassette (p2), NT-MX cassette(p3), and a 3' flank(p4) homologous downstream of the target site. Each component is amplified individually using primers which create homologous overlapping extensions of each PCR product. See Tables 7 and 8. The bent dashed lines in FIG. 28A represent homology between the KT/NT-MX cassettes and the 5' flank and the bent solid lines represent homology with the 3' flank. For each round of engineering, PCR amplicons of upstream and downstream regions flanking the target site are designed to contain homologous tails for both the KT-MX and NT-MX cassettes. Both the flanks and the markers are transformed followed by selection on YPD medium containing both G418 and Nat. See FIG. 28B. FIG. 28B shows a schematic of the chromosome after replacement of the target site with KT-MX and NT-MX.

Figure 29:
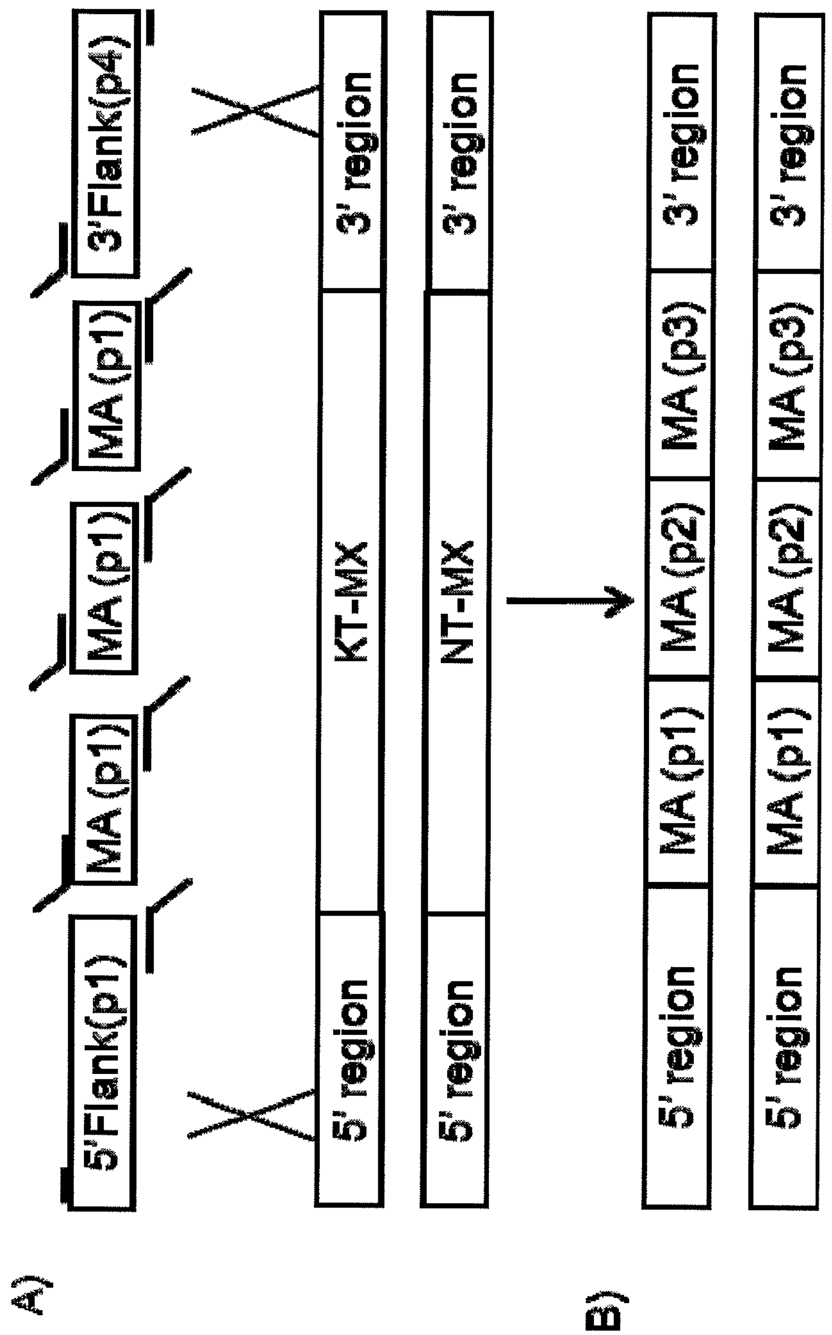
FIG. 29 shows a schematic diagram of strategy used to replace integrated KT-MX and NT-MX selection cassettes with a Mascoma Assembly on both chromosomes of a target loci.

After each engineering step taken in the construction of M3625, all markers are subsequently deleted and/or replaced with a desired expression cassette (Mascoma Assembly) resulting in a strain free of antibiotic markers (FIG. 29). FIG. 29 demonstrates that the transformed Mascoma Assembly contains a quantity of PCR products which is dependent on the desired engineering event (pX), a 5'flank(p1) which homologous upstream of the target site and a 3' flank (p4) homologous downstream of the target site. Each component is amplified individually using primers which create homologous overlapping extensions. The overlapping bent lines in FIG. 29 represent homology at the end of those PCR products. FIG. 29B shows a schematic of a chromosome following selection on FUDR and replacement of genetic markers with the Mascoma assembly. Confirmation of marker removal was evaluated by southern blot, PCR and dilution plating onto selective medium as described below.

Four loci were modified during the construction of M3625. The integration procedure strategy described above was used at the FDH1, GPD1 and GPD2 loci using the Mascoma Assemblies listed in Table 6. Detailed molecular maps depicting the components of each Mascoma Assembly are provided in FIGS. 30-37.

TABLE 6

Genetic modifications contained in M3625.

| Target Locus | Locus Modification | Cassette ID | Cassette Description |
|---|---|---|---|
| FDH1 | Clean Deletion | MA0370 | Clean Deletion of FDH1 |
| FDH2 | Replaced with expression cassette | MA0280 | 2 copies of pflA/B and 4 copies of adhE |
| GPD2 | Replaced with expression cassette | MA0289 | 2 copies of pflA/B and 4 copies of adhE |
| FCY1 | Replaced with expression cassette | MA0317 | Four copies of Glucoamylase |

TABLE 7

Primers used for the creation of strain M3625.

| Target Locus | PCR Product 1; Primer Pair | PCR Product 2; Primer Pair | PCR Product 3; Primer Pair |
|---|---|---|---|
| GPD1 | GPD1 5' Flank; X11824/X15546 | pAGTEF-kan/nat-pHXT2-TDK; X15380/X15382 | GPD1 3' Flank; X15547/X11829 |
| GPD2 | GPD2 5' Flank; X11816/X15548 | pAGTEF-kan/nat-pHXT2-TDK; X15380/X15382 | GPD2 3' flank; X15549/X11821 |
| FDH2 | FDH2 5' Flank; X16096/X15554 | pAGTEF-kan/nat-pHXT2-TDK; X15380/X15382 | FDH2 3' flank; X15555/X11845 |
| FDH1 | FHD1 5' Flank; X15559/X15550 | pAGTEF-kan/nat-pHXT2-TDK; X15380/X15382 | FDH1 3' flank; X15552/X15553 |

TABLE 8

Sequences of Primers used for creation of strain M3625

| Primer | Sequence | SEQ ID NO |
|---|---|---|
| X11824 | aagcctacaggcgcaagataacacatcac | 110 |
| X15546 | ggacgaggcaagctaaacagatctctagacctactttatattatcaatatttgtgtttg | 111 |
| X15380 | taggtctagagatctgtttagcttgc | 112 |
| X15382 | gagactacatgatagtccaaaga | 113 |
| X15547 | ccgtttcttttctttggactatcatgtagtctcatttattggagaaagataacatatca | 114 |
| X11829 | ctcagcattgatcttagcagattcaggatctaggt | 115 |
| X11816 | gcagtcatcaggatcgtaggagataagca | 116 |

TABLE 8-continued

Sequences of Primers used for creation of strain M3625

| Primer | Sequence | SEQ ID NO |
|---|---|---|
| X15548 | ggacgaggcaagctaaacagatctctagacctatgataaggaaggggagcg aaggaaaa | 117 |
| X15549 | ccgtttcttttctttggactatcatgtagtctcctctgatctttcctgttgcctctttt | 118 |
| X11821 | tcacaagagtgtgcagaaataggaggtgga | 119 |
| X16096 | catggtgcttagcagcagatgaaagtgtca | 120 |
| X15554 | ggacgaggcaagctaaacagatctctagacctaattaattttcagctgttatttcgatt | 121 |
| X15555 | ccgtttcttttctttggactatcatgtagtctcgagtgattatgagtatttgtgagcag | 122 |
| X11845 | ttacttgtgaaactgtctccgctatgtcag | 123 |
| X15559 | ggaaggcaccgatactagaactccg | 124 |
| X15550 | gggacgaggcaagctaaacagatctctagacctaattaattttcagctgttattttgat | 125 |
| X15552 | ccgtttcttttctttggactatcatgtagtctcgagtgattatgagtatttgtgagcag | 126 |
| X15553 | accagcgtctggtggacaaacggccttcaac | 127 |

Genotyping and Sequencing of MA0370

Figure 30:
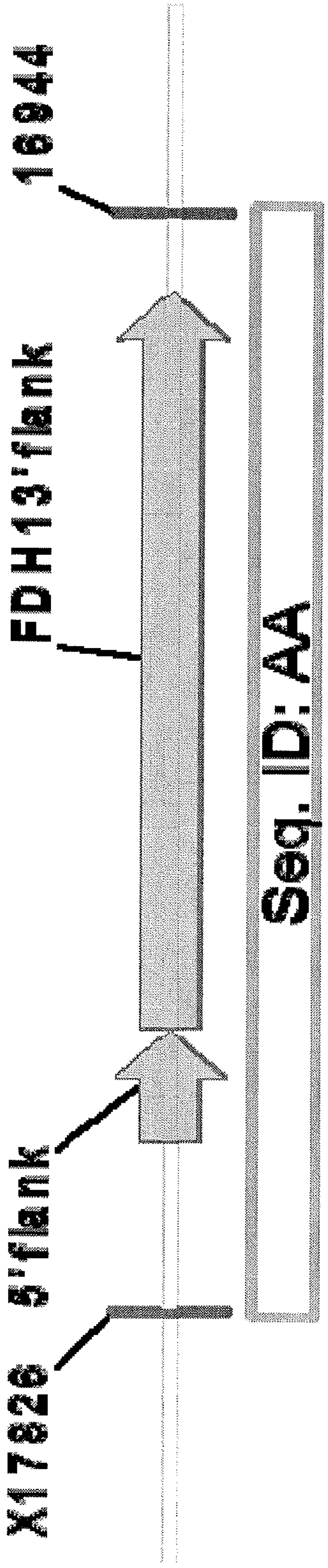
FIG. 30 shows a molecular map and genotyping of MA0370 integrated at the FDH1 site of M3625.
Figure 31:
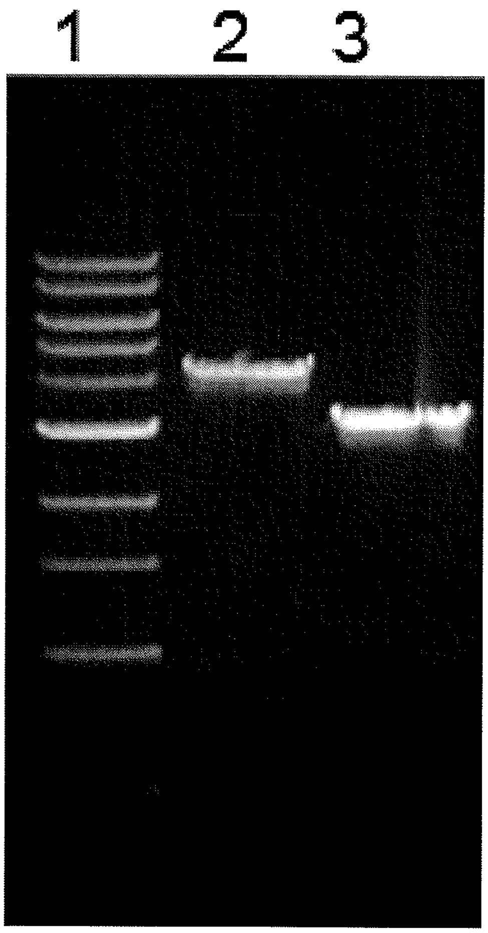
FIG. 31 shows an image of an agarose gel containing PCR products used to genotype and sequence the MA0370 site.

To confirm that FDH1 was deleted after insertion of MA370, PCR products were amplified from M2390 and M3625 genomic DNA using primers X17826 and X16944. The expected results are listed in Table 10 and the sequences of the primers used are listed in Table 11. A molecular map depicting the MA0370 integration site is shown in FIG. 30. The molecular map depicts the location of flanks used to remove the KT-MX and NT-MX markers and the position of primers used for genotyping. See FIG. 30 (5' flank, *S. cerevisiae* FDH1 upstream flanking region; 3' flank—*S. cerevisiae* FDH1 downstream flanking region. Region AA—amplified and sequenced chromosomal DNA region). Primer pair X15556/X15871 was used for the FDH1 5' Flank and primer pair X15870/X15553 was used for the FHD1 3' Flank to create the assembly shown in FIG. 30. Sequences for the primers for assembly used are found in Table 9. An agarose gel image showing PCR products used to determine genotype is shown in FIG. 31 (lane 1: 1 KB ladder; lane 2: M2390 (X17826/X16944); lane 3: M3625 (X17826/X16944)) (see Table 11).

TABLE 9

Primers used to create the MA0370 integration site.

| Primer | Sequence | SEQ ID NO |
|---|---|---|
| X15556 | ccactcgaggataggcttgaaaga | 128 |
| X15870 | ctaatcaaatcaaaataacagctgaaaattaatgagtgattatgagta tttgtgagcag | 129 |
| X15871 | aaaacttctgctcacaaatactcataatcactcattaattttcagctgttattt tgatt | 130 |
| X15553 | accagcgtctggtggacaaacggccttcaac | 127 |

In order to determine the exact DNA sequence of the M3625 MA0370 site, region AA was amplified from genomic DNA of M3625 strain in 5 independent PCR reactions. All PCR products were purified and sequenced by the Sanger method at the Dartmouth College Sequencing facility.

TABLE 10

Primers and summary of results of MA0370 genotyping.

| Lane | Template DNA | Primers | Expected size(bp) | Correct Size Observed |
|---|---|---|---|---|
| 1 | 1 KB ladder | N/A | N/A | N/A |
| 2 | M2390 | X17826/X16944 | 4386 bp | yes |
| 3 | M3625 | X17826/X16944 | 3237 | yes |

TABLE 11

Sequence of primers used for MA0370 genotyping.

| Primer | Sequence | SEQ ID NO |
|---|---|---|
| X17826 | tcgctaacgatcaagaggaactg | 152 |
| X16944 | tacacgtgcatttggacctatc | 153 |

Genotyping and Sequencing of MA0280

Figure 32:
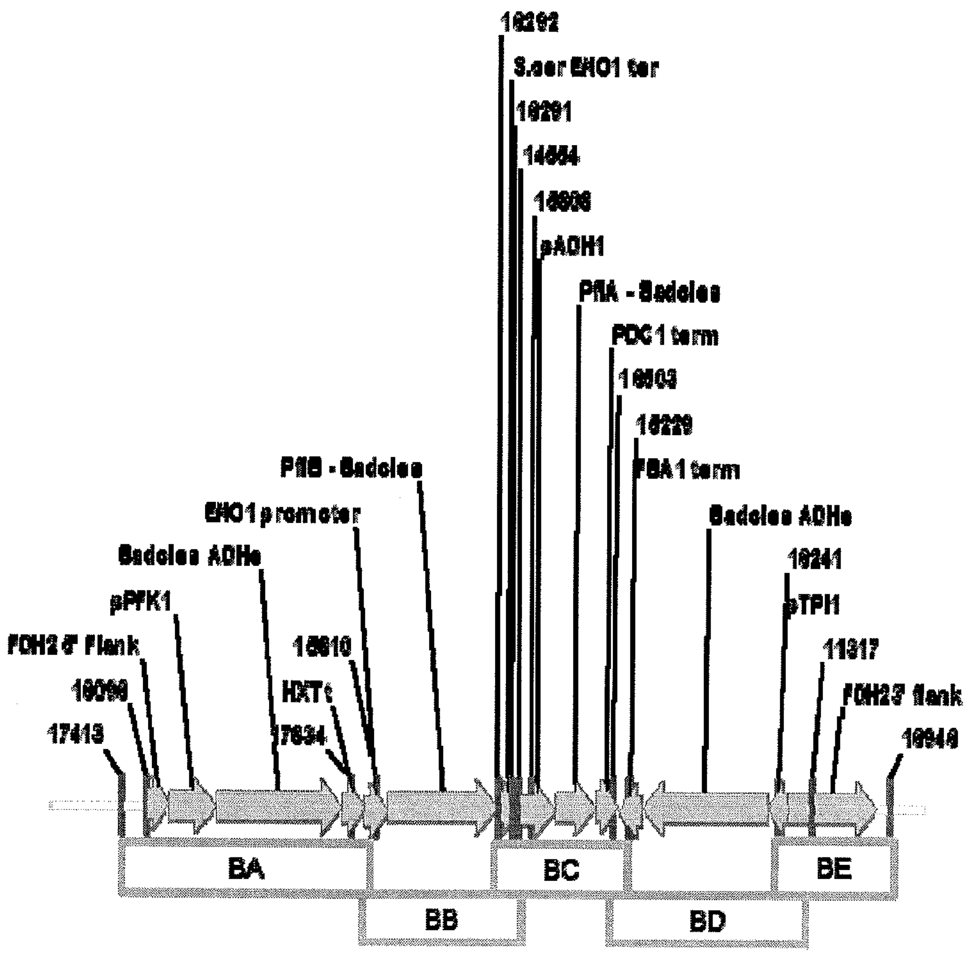
FIG. 32 shows a molecular map and genotyping of MA0280 integrated at the FDH2 site of M3625.

To confirm that MA280 was inserted at the FDH2 site, PCR products were amplified from M3625 genomic DNA. The primers and expected genotyping results are listed in Table 13. Sequences of the primers used for genotyping and sequencing MA0280 are listed in Table 14. A molecular map depicting the MA0280 integration site is shown in FIG. 32.

Figure 33:
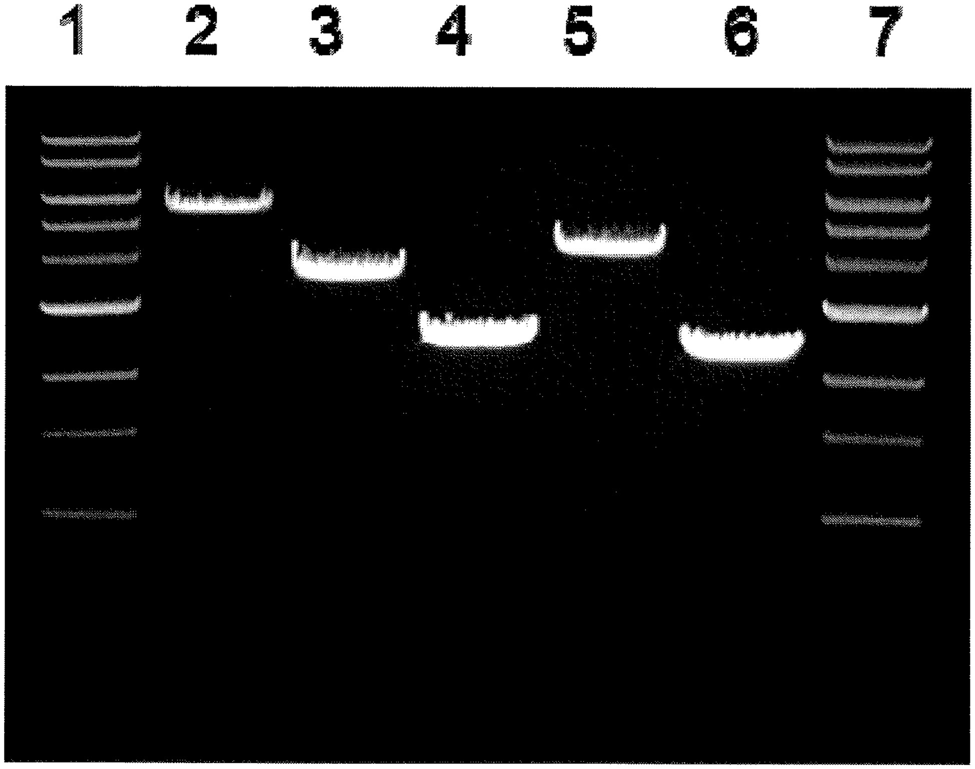
FIG. 33 shows an image of an agarose gel containing PCR products used to genotype and sequence the MA0280 site.

The molecular map depicts the location of flanks used to replace the KT-MX and NT-MX markers and insert the MA0280 expression cassette. The position of primers used for genotyping for genotyping are indicated on the map. See FIG. 32 (Feature description on map of MA0280 site of the M3625 strain; FDH2 5' flank—*S. cerevisiae* FDH2 upstream flanking region; PFK1p—*S. cerevisiae* PFK1 gene promoter; ADHE—*Bifidobacterium adolescentis* ADHE coding gene; HXT2t-*S. cerevisiae* HXT2 gene terminator; ENO1p—*S. cerevisiae* ENO1 gene promoter; PFLB—*Bifidobacterium adolescentis* PFLB coding gene; ENO1t—*S. cerevisiae* ENO1 gene terminator; ADH1p—*S. cerevisiae* ADH1 gene promoter; PFLA—*Bifidobacterium adolescentis* PFLA coding gene; PDC1t—*S. cerevisiae* PDC1 gene terminator; FBA1t—*S. cerevisiae* FBA1 gene terminator; TPI1p—*S. cerevisiae* TPI1 gene promoter; FDH2 3' flank—*S. cerevisiae* FDH2 downstream flanking region. Regions BA-BE, amplified and sequenced chromosomal DNA regions). Primer pair X16096/X17243 was used for the FDH2 5' Flank, primer pair X16738/X16620 was used for pPFK1-ADH-HXT2, primer pair X16621/X13208 was used for pENO1-PFL-ENO1t, primer pair X13209/X17242 was used for pADH1-PFL-PDC1t, primer pair X17241/X16744 was used for pTPI-ADH-FBA1trc, and primer pair X17244/X11845 was used for the FDH2 5' Flank to create the assembly shown in FIG. 32. Sequences for the primers used to create the assembly shown in FIG. 32 are found in Table 12. An agarose gel image showing PCR products used to genotype and sequence the MA0280 site is shown in FIG. 33 (lane 1: 1 KB ladder; lane 2*: M*3625 (17413/15810); lane 3*: M*3625 (17834/14554); lane 4*: M*3625 (16291/15229); lane 5*: M*3625 (16503/11317); lane 6: (16241/16946) lane 7: 1 KB ladder) (see Table 14).

TABLE 12

Primers used to create the MA0280 integration site.

| Primer | Sequence | SEQ ID NO |
|---|---|---|
| X16096 | catggtgcttagcagcagatgaaagtgtca | 120 |
| X17243 | tagttagatcagggtaaaaattatagatgaggtattaattttcagct gttatttcgatt | 131 |
| X16738 | ctaatcaaatcgaaataacagctgaaaattaatacctcatctataat ttttaccctgat | 132 |
| X16620 | tcggatcagtagataacccgcctagaagactaggttacattgaaa atacagtaaatggt | 133 |
| X16621 | tggtggaaccatttactgtattttcaatgtaacctagtcttctaggcg ggttatctact | 134 |
| X13208 | ccgaaatattccacggtttagaaaaaaatcggaggtttagacattg gctcttcattgag | 135 |
| X13209 | aagctcaatgaagagccaatgtctaaacctccgatttttttctaaac cgtggaatattt | 136 |
| X17242 | acatcatcttttaacttgaatttattctctagctttcaatcattggagc aatcattta | 137 |
| X17241 | gtccatgtaaaatgattgctccaatgattgaaagctagagaataa attcaagttaaaag | 138 |
| X16744 | aaaaacttctgctcacaaatactcataatcactcctacttattcccttc gagattatatc | 139 |
| X17244 | gttcctagatataatctcgaagggaataagtaggagtgattatgagta tttgtgagcag | 140 |
| X11845 | ttacttgtgaaactgtctccgctatgtcag | 141 |

In order to determine exact DNA sequence of the M3625 MA0280 site, regions BA-BE were amplified from genomic DNA of M3625 strain in 5 independent PCR reactions. All PCR products were purified and sequenced by the Sanger method at the Dartmouth College Sequencing facility.

TABLE 13

Primers and summary of results of MA0280 genotyping.

| Lane | Template DNA | Primers | Expected size(bp) | Correct Size Observed |
|---|---|---|---|---|
| 1 | 1 KB ladder | N/A | N/A | N/A |
| 2 | M3625 | 17413/15810 | 5567 | Yes |
| 3 | M3625 | 17834/14554 | 3686 | Yes |
| 4 | M3625 | 16291/15229 | 2569 | Yes |
| 5 | M3625 | 16503/11317 | 4352 | yes |
| 6 | M3625 | 16241/16946 | 2478 | yes |
| 7 | 1 KB ladder | N/A | N/A | N/A |

TABLE 14

| Sequence of primers used for genotyping MA0280. | | |
|---|---|---|
| Primer | Sequence | SEQ ID NO |
| 17413 | ggattcttcgagagctaaga | 154 |
| 15810 | gacttgcagggtaggctagctagaatt | 155 |
| 17834 | gctgcttcgaggtattgaca | 156 |
| 14554 | ggctcttcattgagcttagaaccc | 157 |
| 16291 | aactggaccgatcttattcgt | 158 |
| 15229 | agtccactgcggagtcatttcaaag | 159 |
| 16503 | ctgccagcgaattcgactctgcaat | 160 |
| 11317 | cagtcgctgtagtgagcgacagggtagtaa | 161 |
| 16241 | ctttgcattagcatgcgta | 162 |
| 16946 | taggtcgagaccagaatgcatgt | 163 |

Genotyping and Sequencing of MA0289

Figure 34:
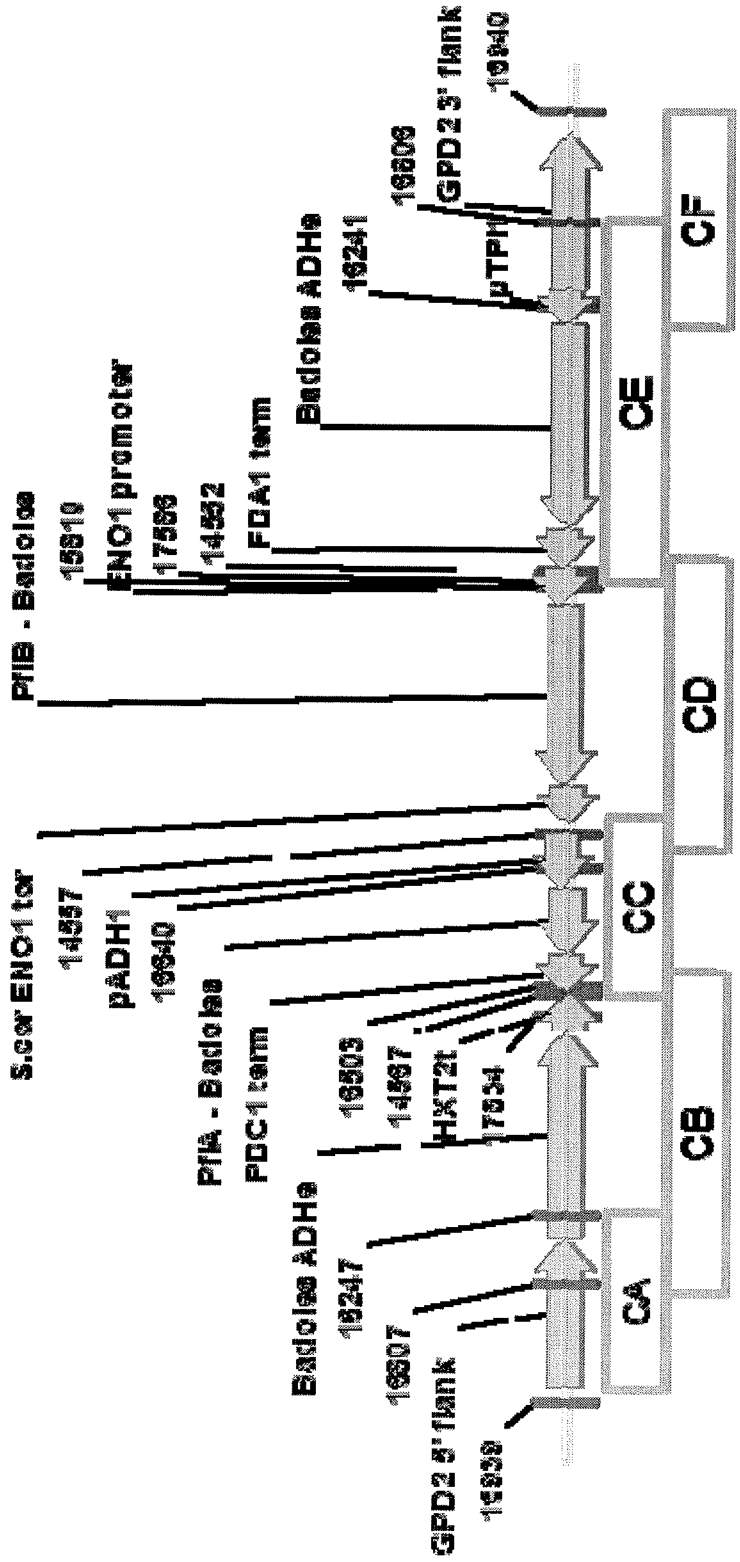
FIG. 34 shows a molecular map and genotyping of MA0289 integrated at the GPD2 site of M3625.
Figure 35:
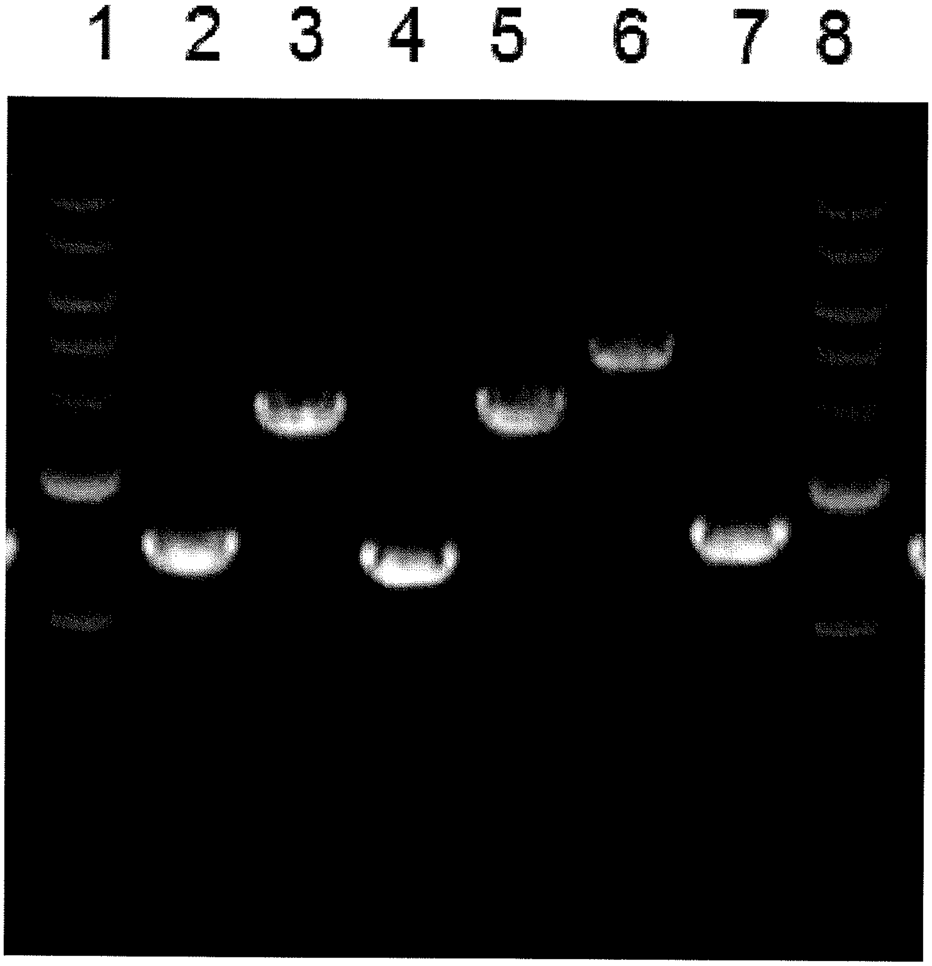
FIG. 35 shows an image of an agarose gel containing PCR products used to genotype and sequence the MA0370 site.

To confirm that MA0289 was inserted at the GPD2 site, PCR products were amplified from M3625 genomic DNA. The primers and expected genotyping results are listed in Table 16. Sequences for the primers used for genotyping MA0289 are listed in Table 17. A molecular map depicting the MA0289 integration site is shown in FIG. 34. The molecular map depicts the location of flanks used to replace the KT-MX and NT-MX markers and insert the MA0280 expression cassette. The position of primers used for genotyping are indicated on the map. See FIG. 34 (Feature description on map of MA0280 site of the M3625 strain; GPD2 5' flank—*S. cerevisiae* GPD2 upstream flanking region; ADHE—*Bifidobacterium adolescentis* ADHE coding gene; HXT2t—*S. cerevisiae* HXT2 gene terminator; PDC1t—*S. cerevisiae* PDC1 gene terminator; PFLA—*Bifidobacterium adolescentis* PFLA coding gene; ADH1p—*S. cerevisiae* ADH1 gene promoter; ENO1t—*S. cerevisiae* ENO1 gene terminator; PFLB—*Bifidobacterium adolescentis* PFLB coding gene; ENO1p—*S. cerevisiae* ENO1 gene promoter; FBA1t—*S. cerevisiae* FBA1 gene terminator; TPI1p—*S. cerevisiae* TPI1 gene promoter; GPD2 3' flank—*S. cerevisiae* GPD2 downstream flanking region; Regions CA-CF—amplified and sequenced chromosomal DNA regions). Primer pair X15473/X17460 was used for the GPD2 5' Flank, primer pair X17459/X17289 was used for ADH-HXT2, primer pair X17290/X13209 was used for pADH1-PFL-PDC1trc, primer pair X13208/X15735 was used for pENO1-PFL-ENO1trc, primer pair X15736/X17457 was used for pTPI-ADH-FBA1trc, and primer pair X17458/X15476 was used for the GPD2 3' Flank to create the assembly shown in FIG. 34. Sequences for the primers used to create the assembly shown in FIG. 34 are found in Table 15. An agarose gel image showing PCR products used to genotype and sequence the MA0280 site is shown in FIG. 35 (lane 1: 1 KB ladder; lane 2*: M*3625 (17413/15810); lane 3*: M*3625 (17834/14554); lane 4*: M*3625 (16291/15229); lane 5*: M*3625 (16503/11317); lane 6: (16241/16946); lane 7: 1 KB ladder).

TABLE 15

| Primers used to create the MA0289 integration site. | | |
|---|---|---|
| Primer | Sequence | SEQ ID NO |
| X15473 | agtcatcaggatcgtaggagataagc | 142 |
| X17460 | agaagataatatttttatataattatattaatcctaatcttcatgtag atctaattctt | 143 |
| X17459 | cctttccttttccttcgctccccttccttatcaatggcagacgcaa agaagaaggaaga | 144 |
| X17289 | gtccatgtaaaatgattgctccaatgattgaaagttacattgaaa atacagtaaatggt | 145 |
| X17290 | tggtggaaccatttactgtattttcaatgtaactttcaatcattgga gcaatcatttta | 146 |
| X13208 | ccgaaatattccacggtttagaaaaaaatcggaggtttagacattg gctcttcattgag | 135 |
| X13209 | aagctcaatgaagagccaatgtctaaacctccgatttttttctaaac cgtggaatattt | 136 |
| X15735 | catcttttaacttgaatttattctctagcctagtcttctaggcgggttat ctactgat | 147 |
| X15736 | agataacccgcctagaagactaggctagagaataaattcaagtta aaagatgatgttga | 148 |
| X17457 | tgggggaaaaagaggcaacaggaaagatcagagctacttattc ccttcgagattatatc | 149 |
| X17458 | gttcctagatataatctcgaagggaataagtagctctgatctttcct gttgcctcttttt | 150 |
| X15476 | gtagatctgcccagaatgatgacgtt | 151 |

In order to determine exact DNA sequence of the M3625 MA0289 site, regions CA-CF were amplified from genomic DNA of M3625 strain in 5 independent PCR reactions. All PCR products were purified and sequenced by the Sanger method at the Dartmouth College Sequencing facility.

TABLE 16

Primers and summary of results of MA0289 genotyping.

| Lane | Template DNA | Primers | Expected size(bp) | Correct Size Observed |
|---|---|---|---|---|
| 1 | 1 KB ladder | N/A | N/A | N/A |
| 2 | M3625 | 16939/16940 | 2477 | Yes |
| 3 | M3625 | 16807/14567 | 3831 | Yes |
| 4 | M3625 | 17834/14557 | 2478 | Yes |
| 5 | M3625 | 16640/14552 | 3978 | yes |
| 6 | M3625 | 17586/16806 | 4789 | yes |
| 7 | 1 KB ladder | N/A | N/A | N/A |

TABLE 17

Sequence of primers used for genotyping MA0289.

| Primer | Sequence | SEQ ID NO |
|---|---|---|
| 16939 | atgctgatgcatgtccacaaag | 164 |
| 16940 | ccttatcagtcaattgaggaaag | 165 |
| 16807 | gcgatgagctaatcctgagccat | 166 |
| 14567 | tggttccaccattattatgttggt | 167 |
| 17834 | gctgcttcgaggtattgaca | 168 |
| 14557 | ctaaaccgtggaatatttcggatat | 169 |
| 16640 | cctcatcagctctggaacaacga | 170 |
| 14552 | gatccgagcttccactaggatagc | 171 |

TABLE 17-continued

Sequence of primers used for genotyping MA0289.

| Primer | Sequence | SEQ ID NO |
|---|---|---|
| 17586 | gcagtatgcaagtctcatgctg | 172 |
| 16806 | gaacttgcaggcaccgatcttca | 173 |

Genotyping and Sequencing of MA0317

Figure 36:
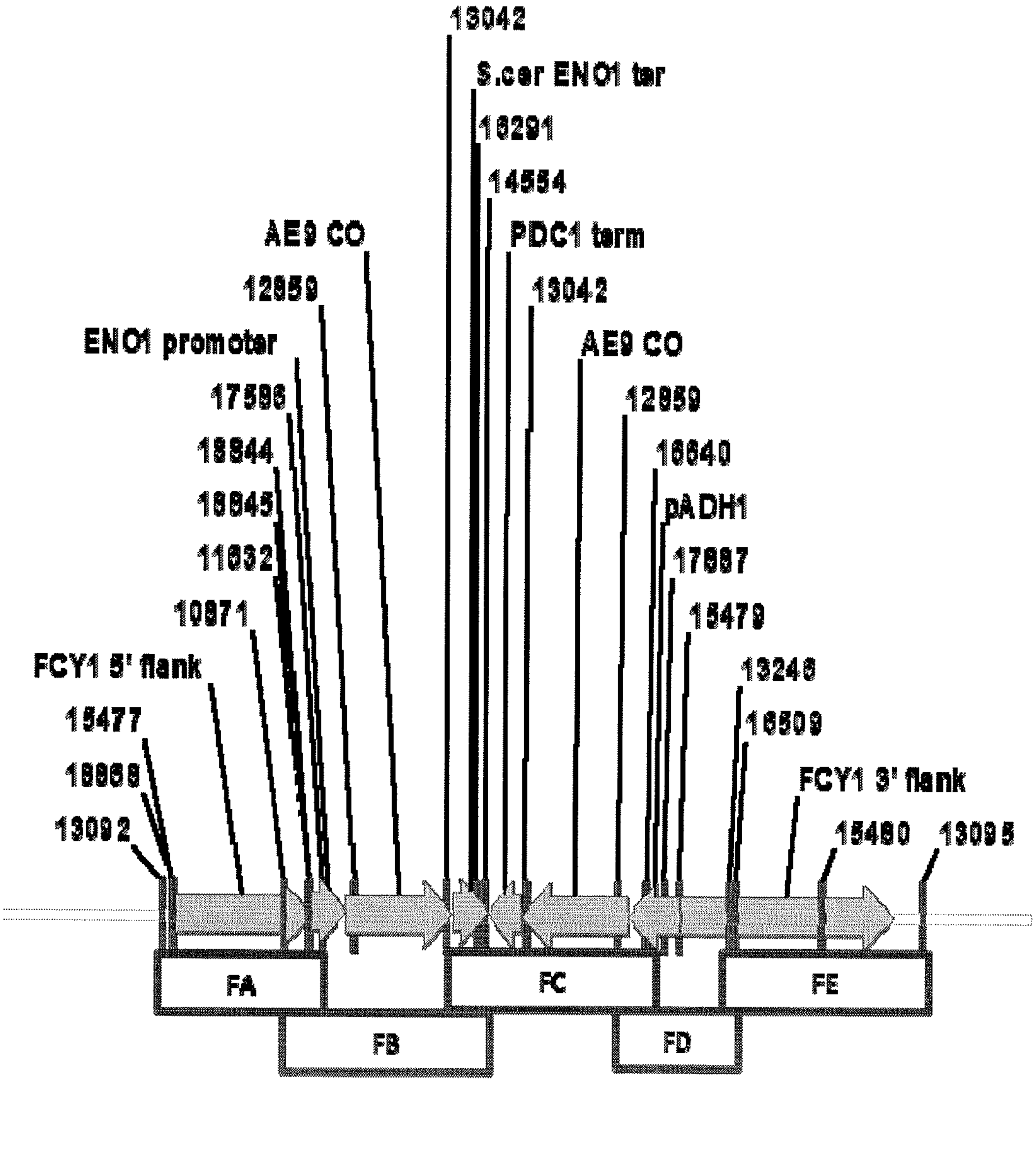
FIG. 36 shows a molecular map and genotyping of MA0317 integrated at the FCY1 site of M3625.
Figure 37:
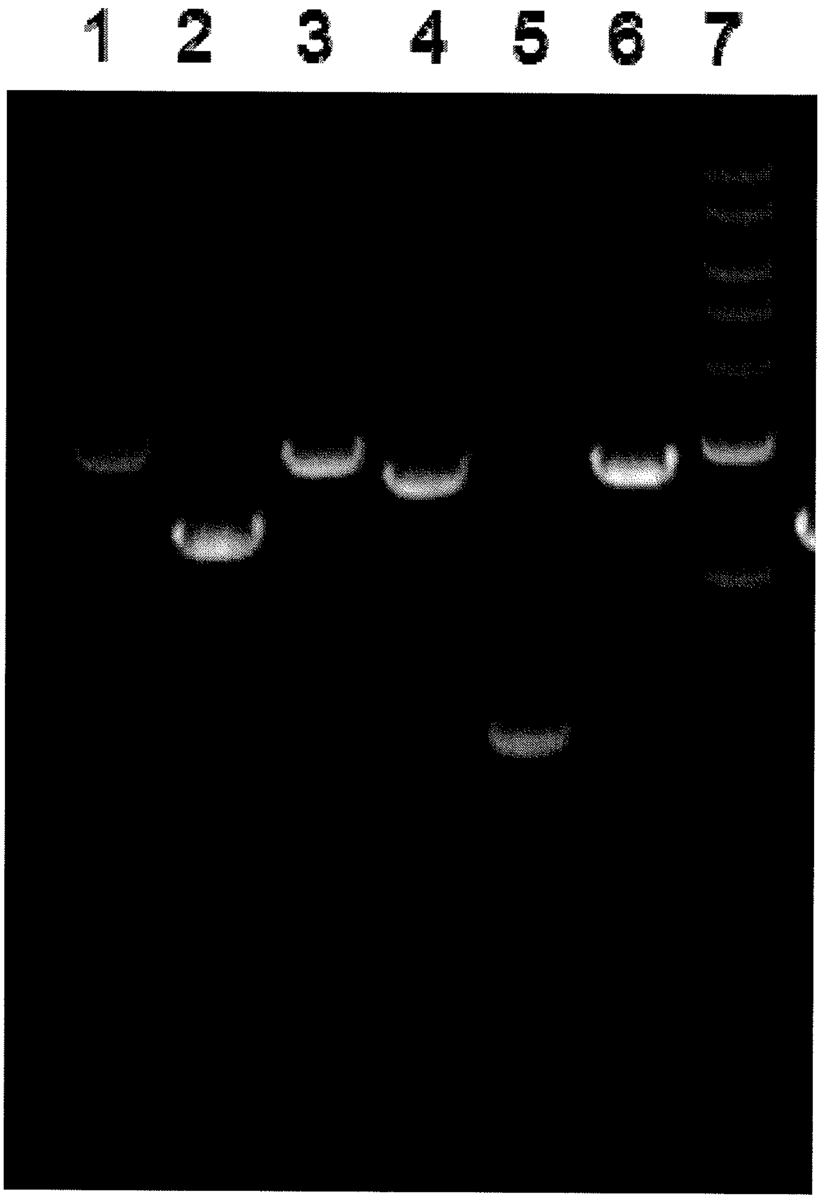
FIG. 37 shows an image of an agarose gel containing PCR products used to genotype and sequence the MA0317 site.

To confirm that MA0317 was inserted at the FCY1 site, PCR products were amplified from M3625 genomic DNA. The primers and expected genotyping results are listed in Table 19. Sequences for the primers used to genotype MA0317 are listed in Table 20. A molecular map depicting the MA0317 integration site is shown in FIG. 36. The molecular map depicts the location of flanks used to replace the FCY1 gene with MA0317 and the position or primers used for genotyping. See FIG. 36 (Feature description on the map of MA0371 site of M3625; FCY1 5' flank—*S. cerevisiae* FCY1 upstream flanking region; ENO1p—*S. cerevisiae* ENO1 gene promoter; AE9 —*S. fibuligera* glu 0111 coding gene; ENO1t—*S. cerevisiae* ENO1 gene terminator; PDC1t—*S. cerevisiae* PDC1 terminator; ADH1p—*S. cerevisiae* ADH1 gene promoter; FCY1 3' flank—*S. cerevisiae* FCY1 downstream flanking region; Regions FA-FE, amplified and sequenced chromosomal DNA regions). Primer pair X18868/X18844 was used for the FCY 5' Flank, primer pair X18845/X15464 was used for pENO-AE9-ENO1t, primer pair X15465/X11750 was used for pADH1-AE9-PDC1t, and primer pair X15479/X18869 was used for the FCY 3' Flank to create the assembly shown in FIG. 36. Sequences for the primers used to create the assembly shown in FIG. 36 are found in Table 18. An agarose gel image showing PCR products used to determine genotype is shown in FIG. 37 (lane 1: 1 KB ladder; lane 2: *M*3625 (13092/17586); lane 3: *M*3625 (10871/14554); lane 4: *M*3625 (16291/17887); lane 5: *M*3625 (16640/16509); lane 6: *M*3625 (13246/13095); lane 7: 1 KB ladder).

TABLE 18

Primers used to create the MA0317 integration site.

| Primer | Sequence | SEQ ID NO |
|---|---|---|
| X18868 | gccaaagtggattctcctactcaagctttgc | 184 |
| X18844 | tcggatcagtagataacccgcctagaagactagtagctatgaaatttttaactctttaa | 185 |
| X18845 | agccagcttaaagagttaaaaatttcatagctactagtcttctaggcgggttatctact | 186 |
| X15464 | gtccatgtaaaatgattgctccaatgattgaaagaggtttagacattggctcttcattg | 187 |
| X15465 | ctaagctcaatgaagagccaatgtctaaacctctttcaatcattggagcaatcatttta | 188 |
| X11750 | ataaaattaaatacgtaaatacagcgtgctgcgtgctcgatttttttctaaaccgtgga | 189 |
| X15479 | agcacgcagcacgctgtatttacgta | 190 |
| X18869 | agatcctgtggtagtgctgtctgaacagaa | 191 |

In order to determine exact DNA sequence of the M3625 MA0317 site, regions FA-FE were amplified from genomic DNA of M3625 strain in 5 independent PCR reactions. All PCR products were purified and sequenced by the Sanger method at the Dartmouth College Sequencing facility.

TABLE 19

Primers and summary of results of MA0317 genotyping.

| Lane | Template DNA | Primers | Expected size(bp) | Correct Size Observed |
|---|---|---|---|---|
| 1 | 1 KB ladder | N/A | N/A | N/A |
| 2 | M3625 | 13092/17586 | 2368 | yes |
| 3 | M3625 | 10871/14554 | 2966 | yes |
| 4 | M3625 | 16291/17887 | 2778 | yes |
| 5 | M3625 | 16640/16509 | 1334 | yes |
| 6 | M3625 | 13246/13095 | 2863 | yes |
| 7 | 1 KB ladder | N/A | N/A | N/A |

TABLE 20

Sequence of primers used for genotyping MA0317.

| Primer | Sequence | SEQ ID NO |
|---|---|---|
| 13092 | ccacaccatagacttcagccttcttag | 174 |
| 17586 | gcagtatgcaagtctcatgctg | 175 |
| 10871 | cgttcgctgtagcatacttagctat | 176 |
| 14554 | ggctcttcattgagcttagaaccc | 177 |
| 16291 | aactggaccgatcttattcgt | 178 |
| 17887 | actgcctcattgatggtggta | 179 |
| 16640 | cctcatcagctctggaacaacga | 180 |
| 16509 | gtatgattgcggttatctgtcgc | 181 |
| 13246 | cctatggatgttgtaccatgcc | 182 |
| 13095 | ccaatatcttgcagtccatcctcgtcgc | 183 |

Figure 38:
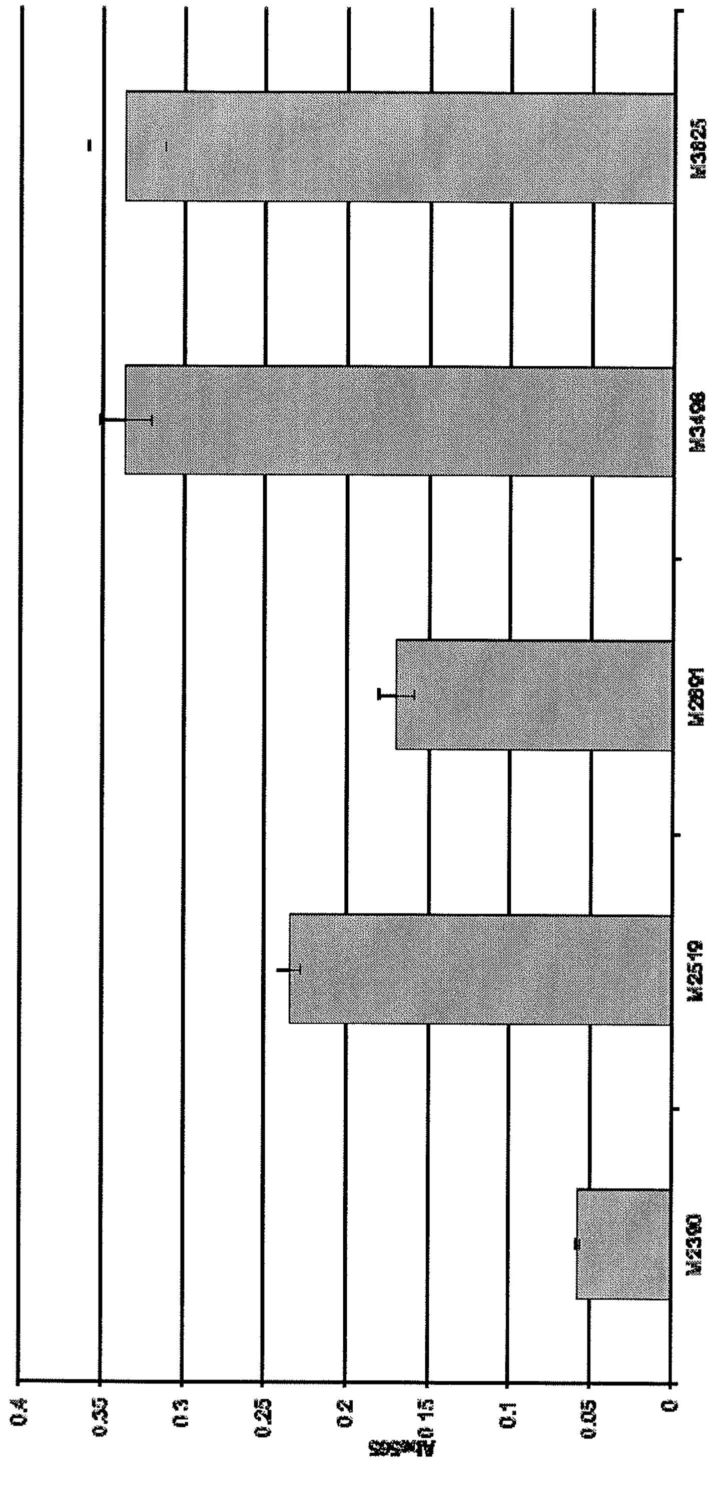
FIG. 38 shows a graph depicting the results of a starch assay performed with strains M2390, M2519, M2691, M3498, and M3625.

FIG. 38 shows the results of starch assay demonstrating starch degrading activity in M3625. The assay was performed as described in copending International Appl. No. PCT/US2011/039192, incorporated by reference herein in its entirety.

Western Blot Protein Detection:

Anti-PflA, anti-PflB, anti-GA (AE9) and anti-AdhE antibodies:

In an effort to detect the presence of and help characterize a number of enzymes engineered into the yeast strain, polyclonal antibodies were produced in rabbits at Lampire Biological Products, Pipersville, Pa., against synthesized peptides with sequence similarity to the engineered proteins. Table 11 depicts the peptides that were used as immunogens for the rabbits:

TABLE 21

Immunogens used for antibody production

| Protein | Immunogen | SEQ ID NO |
|---|---|---|
| Sf GA (AE9) | intact purified protein<br>DNKNRYKINGNYKAGC<br>NSGKKHIVESPQLSSRGGC<br>CDHIDDNGQLTEEINRYTG | 106 |
| Ba pflA | CQNPDTWKMRDGKPVYYE<br>GLTSSEENVENVAKIC | 107 |
| Ba pflB | WEGFTEGNWQKDIDVRDC<br>KQRDKDSIPYRNDFTECPEC<br>CNTITPDGLGRDEEEERIGN | 108 |
| Ba AdhE | DAKKKEEPTKPTPEEKLC<br>CKNLGVNPGKTPEEGVEN<br>CGSYGGNSVSGVNQAVN | 109 |

For all of the synthesized peptides a terminal Cys was added for conjugation. Both the peptides and the purified GA protein were conjugated to KLH prior to injection into the rabbit. A 50 day protocol was used for antibody production with ELISA monitoring of the various bleeds against the immunogen. After testing these polyclonal antibodies in a Western blot against the lysate from the engineered yeast strains, serum from the positive rabbits was purified using a Protein G column. The purified antibodies were dialyzed into PBS, concentration was determined by absorbance at 280 nm and the antibodies were used for further evaluation of the strains. Upon evaluation by SDS-PAGE, the antibodies appeared to be >90% pure.

Antibodies raised against the synthesized peptides were used in Western blot detection of each engineered protein in cell extracts and culture supernatants as described below.

Strain Growth Conditions:

Cells were plated from freezer stock on YPD (20 g/L peptone, 10 g/L yeast extract, 20 g/L glucose) agar for 48 hours and used to inoculate 25 mL YPD (20 g/L peptone, 10 g/L yeast extract, 20 g/L glucose) in a 50 mL culture tube. Cells were grown aerobically for 8 hours at 35° C. with shaking at 250 rpm, then 1 mL was removed to inoculate a sealed, CO2 purged serum bottle containing 50 mL YPD (20 g/L peptone, 10 g/L yeast extract, 20 g/L glucose) with 7 mg/L ergosterol, 289 mg/L ethanol and 544 mg/L Tween 80. These cultures were then grown anaerobically overnight (~16 h) at 35° C. with shaking at 250 rpm. Cells were harvested by centrifugation and washed with 25 mL deionized water. The resulting wet cell pellets were used for Western blot detection of PflA, PflB and AdhE.

Aerobic cultures used to inoculate the serum bottles were returned to the shaking incubator for an additional 40 hours. At the end of incubation, cells were pelleted by centrifugation and the supernatant was recovered and concentrated ~10× using a 10 kDa molecular weight cut-off (MWCO) filter membrane. The resulting concentrates were used for Western blot detection of extracellular AE9 glucoamylase.

Cell Lysis and Sample Preparation:

For Western blots of PflB and AdhE, cells were homogenized by mechanical disruption with 0.5 mm diameter beads and agitation at 4800 rpm in a bead beater. 100 μL of wet cells were added to homogenization buffer containing 1 mM phenylmethanesulfonylfluoride (PMSF), 2 mM dithiothreitol (DTT) and 1% dimethyl sulfoxide (DMSO) in 100 mM sodium phosphate buffer pH 7.4. Cells were agitated for 6 cycles of 10 seconds each, cooling on ice between cycles. Cell debris was pelleted by centrifugation and supernatant was recovered. 15 μL of the resulting supernatant was added to 15 μl, 2× concentrated SDS-PAGE sample buffer with 50 mM DTT and loaded onto a 4-20% Tris-Glycine SDS-PAGE gel.

For Western blot detection of PflA, cells were lysed by adding 40 μL wet cells to 40 μL 2× concentrated SDS-PAGE sample buffer with 50 mM DTT. The mixture was then incubated at room temperature for 30 minutes, followed by heating at 100° C. for 2 minutes. Cells were pelleted by centrifugation and 30 μL of the supernatant was loaded onto a 4-20% Tris-Glycine SDS-PAGE gel.

For AE9 analysis, 15 μL of concentrated aerobic culture supernatant was added to 15 μL 2× concentrated SDS-PAGE sample buffer with 50 mM DTT and loaded onto a 4-20% Tris-Glycine SDS-PAGE gel.

Following gel electrophoresis, proteins were transferred to a polyvinylidine fluoride (PVDF) membrane and blocked overnight with Tris buffered saline (TBS; 10 mM Tris, 150 mM sodium chloride pH 7.5) containing 2% weight by volume (w/v) bovine serum albumin (BSA). The blocking solution was then removed, and primary peptide antibodies were diluted to approximately 2 μg/mL in Tris buffered saline with Tween 20 (TBST; TBS with 0.1% v/v Tween 20) and added to each membrane. After a 1 hour incubation, the primary antibody was discarded and the membrane was washed for 3 periods of 5 minutes each in 10 mM Tris, 500 mM sodium chloride, 0.1% Tween 20 pH 7.5 (THST). The secondary antibody, goat anti-rabbit with horseradish peroxidase label, was diluted 1:7500 in TBST, added to the blot and incubated for 1 hour. The secondary antibody was then discarded and the blot was again washed with THST for 3 periods of 5 minutes each. The wash solution was then discarded, enhanced chemiluminescence (ECL) substrate was added, and the blot was read by a series of composite exposures using a gel imaging camera.

Figure 39:
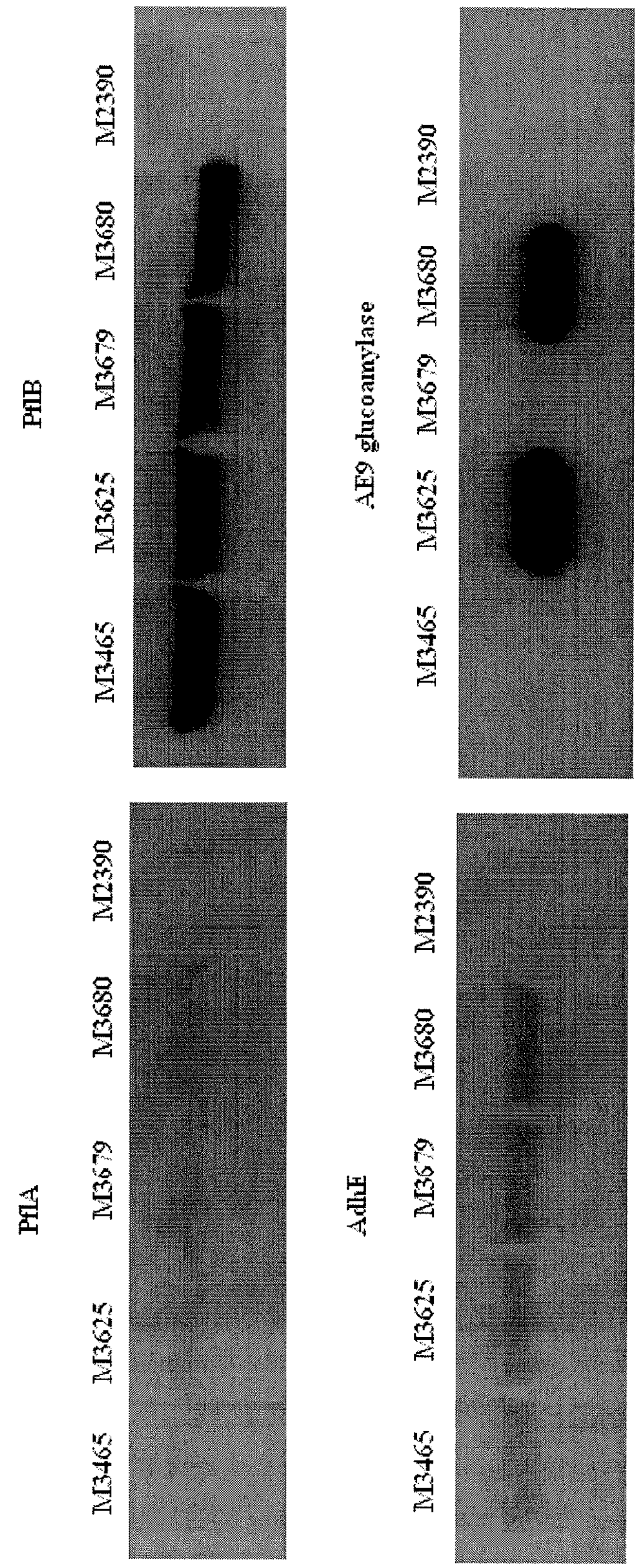
FIG. 39 shows an anti-peptide Western blot analysis of cell extracts (PflA, PflB, AdhE) and aerobic culture supernatants (AE9).

As shown in FIG. 39, for anti-PflA, PflB and AdhE primary antibodies, bands of approximately the correct molecular weight were detected in each experimental strain, whereas no band was detected in the background control strain (M2390). For anti-AE9, bands were detected in strains engineered to express the protein (M3625 and M3680) but were absent in other strains. See FIG. 39. There appeared to be two distinct bands for PflB, which may indicate oxygenic cleavage of the protein due to aerobic cell lysis conditions.

Pyruvate Formate Lyase Activity Assay:

Pyruvate formate lyase (PflB) is activated in the absence of oxygen by Pfl activase (PflA) and catalyzes the reaction of pyruvate and CoA to formate and acetyl-CoA. The activity of PflB was measured in cell extracts by measuring formate production when extracts were added to a reaction mixture containing pyruvate, CoA and DTT.

Strain Growth Conditions:

Cells were plated from freezer stock on YPD (20 g/L peptone, 10 g/L yeast extract, 20 g/L dextrose) agar for 48 hours and used to inoculate 25 mL YPD (20 g/L peptone, 10 g/L yeast extract, 20 g/L dextrose) in a 50 mL culture tube. Cells were grown aerobically for 8 hours at 35° C. with shaking at 250 rpm, then 1 mL was removed to inoculate a sealed, CO2 purged serum bottle containing 50 mL YPD (20 g/L peptone, 10 g/L yeast extract, 20 g/L dextrose) with 7 mg/L ergosterol, 289 mg/L ethanol and 544 mg/L Tween 80. These cultures were then grown anaerobically overnight (~16 h) at 35° C. with shaking at 250 rpm. Cells were harvested by centrifugation and washed with 25 mL deionized water in an anaerobic chamber.

Cell Lysis and Sample Preparation:

Cells were homogenized in an anaerobic chamber by mechanical disruption with 0.5 mm diameter beads and agitation at 4800 rpm in a bead beater. 1004 of wet cells were added to homogenization buffer containing 1 mM PMSF, 2 mM DTT and 1% DMSO in 100 mM sodium phosphate buffer pH 7.4. Cells were agitated for 6 cycles of 10 seconds each, cooling on ice between cycles. Cell debris was pelleted by centrifugation at 14,100×g for 10 minutes and supernatant was recovered and clarified by filtration through a 0.22 μm filter membrane. The resulting extract was used directly in the activity assay.

Pfl Activity Assay:

A 2× concentrated assay substrate mixture consisted of 20 mM sodium pyruvate, 0.11 mM CoA and 20 mM DTT. Reagents were weighed out, brought into an anaerobic chamber and added to 10 mL of 100 mM sodium phosphate buffer pH 7.4 which had been thoroughly degassed. 1004 of cell extract was added to 100 μL of the concentrated assay mixture and incubated at ambient temperature (~29° C.) for 30 minutes. Samples were then removed from the anaerobic chamber and heated in a heating block at 100° C. for 90 seconds followed by cooling on ice to precipitate protein. Precipitate was removed by centrifugation at 15,000×g for 10 minutes. The resulting supernatant was analyzed for formate concentration using the formic acid assay kit available from Megazyme International Ireland, Bray, Co. Wicklow, Ireland.

Remaining cell extracts were diluted 1:8 in 100 mM sodium phosphate buffer pH 7.4 and assayed for total protein content using the BCA total protein determination method. Formate concentrations of the Pfl assay samples were normalized to the total protein concentration of the sample.

Figure 40:
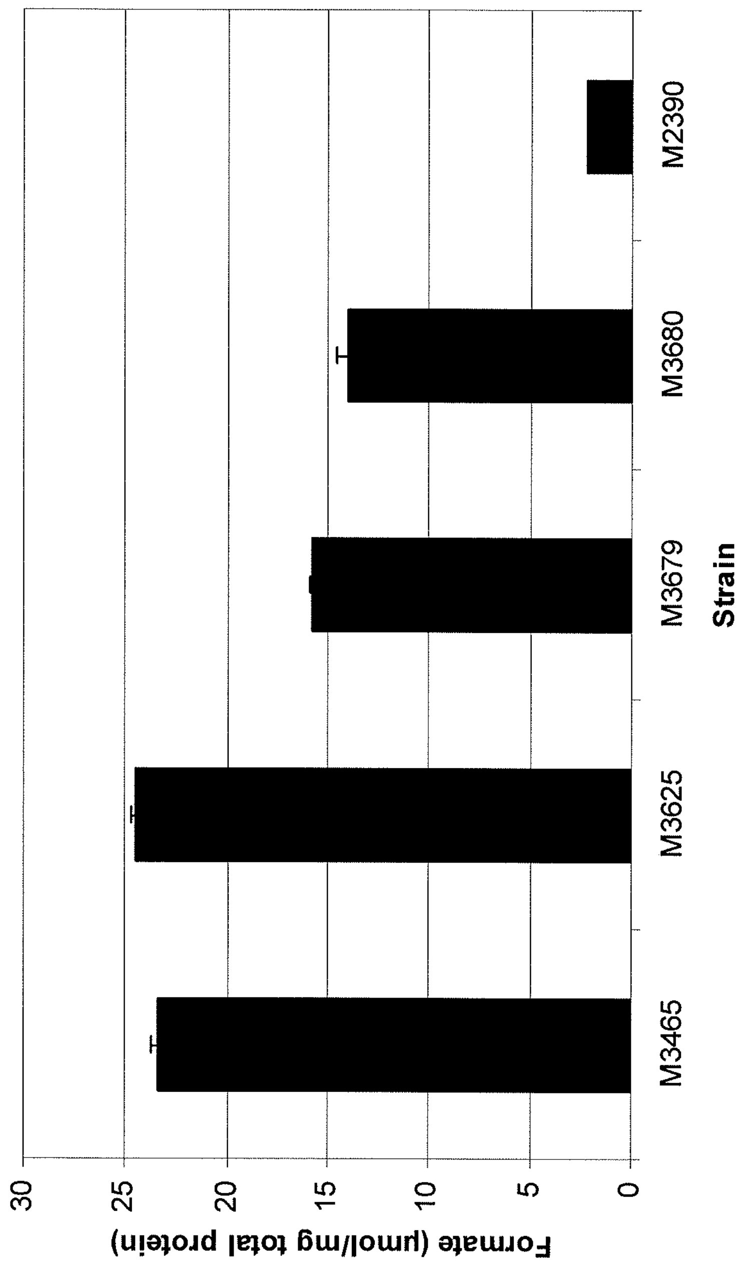
FIG. 40 shows a graph depicting the results of a formate lyase assay performed with engineered strains M3465, M3625, M3679, M3680, and M2390.

As shown in FIG. 40, experimental strains with engineered Pfl activity (M3465, *M*3625, *M*3679, and M3680) showed significantly higher amounts of formate present after incubation with the reaction mixture than the background control strain (M2390).

Alcohol Dehydrogenase E (AdhE) Enzymatic Activity Assays

AdhE is an intracellular bi-functional enzyme catalyzing the formation of ethanol from acetyl-CoA by way of acetaldehyde as an intermediate. This is accomplished by an acetaldehyde dehydrogenase activity and an alcohol dehydrogenase activity working in series. *Saccharomyces cerevisiae* strains have native alcohol dehydrogenase (Adh) activity; the intent of these activity assays is to show that Adh activity is retained by the engineered strains, and an additional acetaldehyde dehydrogenase activity (from AdhE) is present.

Figure 49:
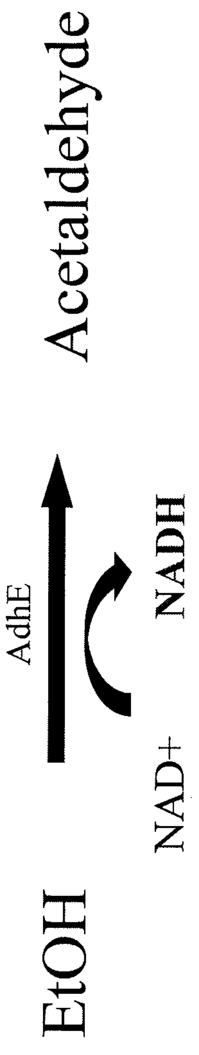
FIG. 49 shows the reverse reaction catalyzed by *Bifidobacterium adolecentis* bifunctional alcohol dehydrogenase (AdhE) in which ethanol is converted to acetaldehyde.

Alcohol Dehydrogenase Activity:

As mentioned above, *Bifidobacterium adolecentis* bifunctional alcohol dehydrogenase (AdhE) has 2 primary functions. One function is the conversion of acetaldehyde to ethanol. This reversible reaction utilizes NADH as a cofactor. In order to evaluate the presence of this enzyme and ensure that it has the desired activity, an assay was developed to evaluate the reverse reaction in which ethanol is converted to acetaldehyde. See FIG. 49. The rate of the reaction is monitored by NADH absorbance at 340 nm.

Strain Growth Conditions:

Strains were patched from freezer stock onto a YPD (20 g/L peptone, 10 g/L yeast extract, 20 g/L dextrose) agar plate and incubated overnight at 35° C. From that plate, 50 mL shake tubes with 25 mL YPD (20 g/L peptone, 10 g/L yeast extract, 20 g/L dextrose) were inoculated and incubated at 35° C., 250 rpm overnight. The cultures were centrifuged at 5000 rpm×5 min at 4 C, washed with deionized (DI) water and centrifuged at 5000 rpm×5 min at 4 C, washed a second time with DI water and centrifuged at 5000 rpm×5 min at 4 C, and then put on ice.

Cell Lysis and Sample Preparation:

100 μL of wet cell pellet was pipetted into a Zymo Research BashingBead 0.5 mm Tubes along with 500 μL 100 mM Na2PO4, 2.5 mM MgCl2, 0.5 mM CaCl2 pH 7.4 buffer and 6 μL 100 mM phenylmethylsulfonyl fluoride (PMSF). The cells were lysed by mechanical disruption using a MP FastPrep-24 set to run at 4.0 m/s for 10 seconds three times with cooling on ice for 10 seconds between each run. This was repeated three times with chilling on ice for one minute in between each run. Each tube was then centrifuged for 10 minutes at 15,000 rpm using an Eppendorf centrifuge 5424. The supernatant was removed and transferred to 2 mL tubes. 1 μL of New England Biolabs DNAse I was added to each tube. The tubes were inverted and placed into an incubator set at 37° C. for 30 min. The tubes were removed from the incubator and the samples were transferred to 0.22 μm filter centrifuge tubes which were centrifuged for 2 min at 10,000 rpm. 504 of sample was pulled and diluted with 450 μL 100 mM $Na_2PO_4$ pH 7.4 in separate sample tubes and then placed on ice.

Alcohol Dehydrogenase Activity Assay:

The assay used to determine alcohol dehydrogenase activity of AdhE was adapted from the method of Vallee, B. L. and Hoch, F. L., *Proc Natl Acad Sci USA* (1955) 41(6): 327-338. 100 μL 0.1M Na4P2O7 pH 9.6 buffer, 32 μL 2M ethanol, and 1.66 μL 0.025M $NAD^+$ were added to each well in a 96 well plate. Once the lysate was added to the reaction mixture, the total volume of reaction was equivalent to 153.66 μL resulting in final concentrations of 65 mM $Na_4P_2O_7$ pH 9.6 buffer, 416.5 mM ethanol, and 0.27 mM $NAD^+$. To begin the reaction, 204, of 1:10 diluted lysate was pipetted into each well and the absorbance at 340 nm was observed and recorded over 1.7 min using Spectramax M2 and Softmax software. Each sample was done in duplicate to ensure reproducibility. Thermo Scientific's BCA Protein Assay Kit was used to measure total protein concentration from the lysate generated. This data was used to normalize the data generated from the actual reaction during analysis.

TABLE 22

Data for alcohol dehydrogenase activity assay

| | Average activity (μmol NADH/min/mg) | Standard Deviation | % CV | % Change | p-value |
|---|---|---|---|---|---|
| M2390 | 599 | 15.6 | 2.6 | | |
| M3465 | 659 | 16.2 | 2.5 | 10 | 0.1942 |
| M3625 | 999.5 | 132 | 13.2 | 66.9 | 0.0108 |
| M3679 | 755 | 82 | 10.9 | 26 | 0.0603 |
| M3680 | 698 | 29.7 | 4.3 | 16.5 | 0.0996 |

Alcohol dehydrogenase activities of engineered strains. p-value was based on a one-tailed T-test.

Figure 41:
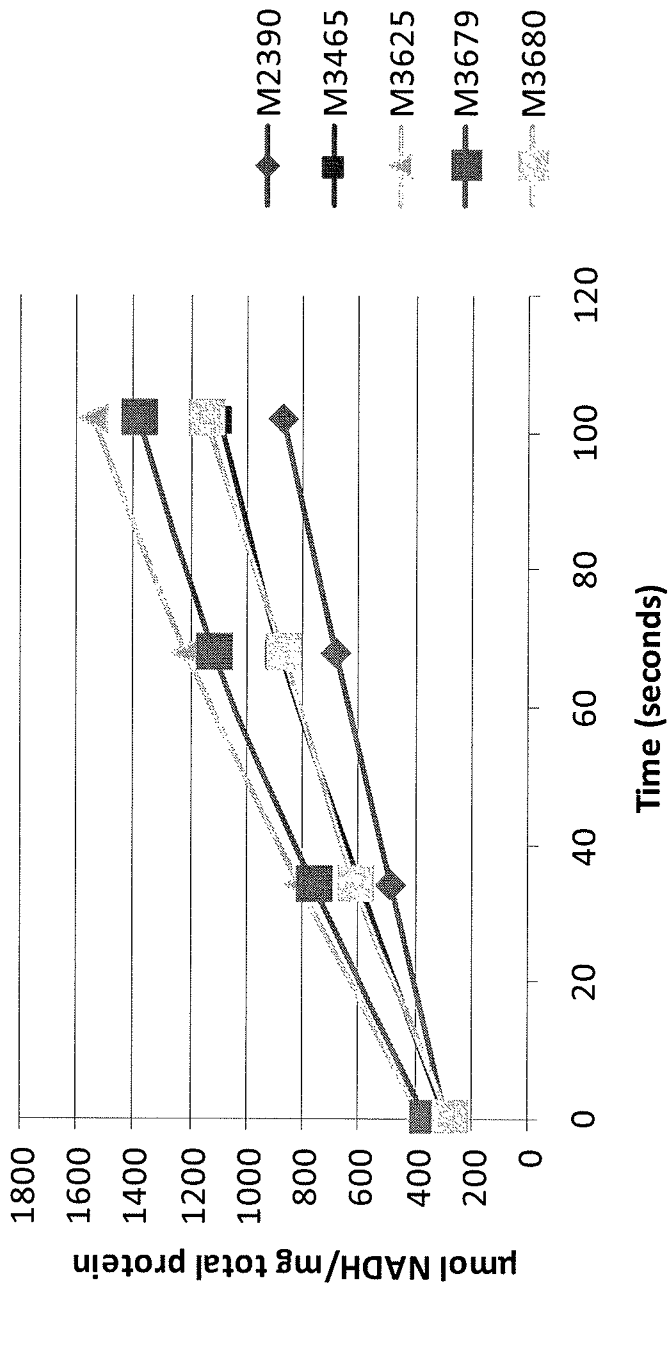
FIG. 41 shows a graph depicting the results of an alcohol dehydrogenase assay performed with engineered strains M3465, M3625, M3679, and M3680.

The background strain, M2390, performed as expected in this assay. Although it did not have AdhE engineered into its genome, it still expressed wild-type alcohol dehydrogenase and thus was active in the alcohol dehydrogenase assay. Other strains with AdhE engineered into their genomes should have expressed the bi-functional enzyme and should have been more active given the total protein concentration was equal in each sample used in the assay. With a p-value of <0.05, *M*3625 demonstrated a statistically significant higher activity than the background strain. However, the other strains have a p-value>0.05 indicating that they are within error of the background strain even though there was an increase in activity as shown by the % change over the background activity. See Table 22. After normalizing the protein concentrations, a graphical representation of the data shows that each strain was more active than the background strain M2390 during a 1.7 minute reaction period. FIG. 41 shows the activity of each strain plotted in μmol NADH/mg total protein vs. time during a 1.7 minute reaction.

Based on these results, the assay showed alcohol dehydrogenase activity in all strains. However, M2390 is less active and slower at converting $NAD^+$ to NADH than the other strains indicating that the engineered AdhE is present in each strain and it appears to be functioning properly.

Figure 50:
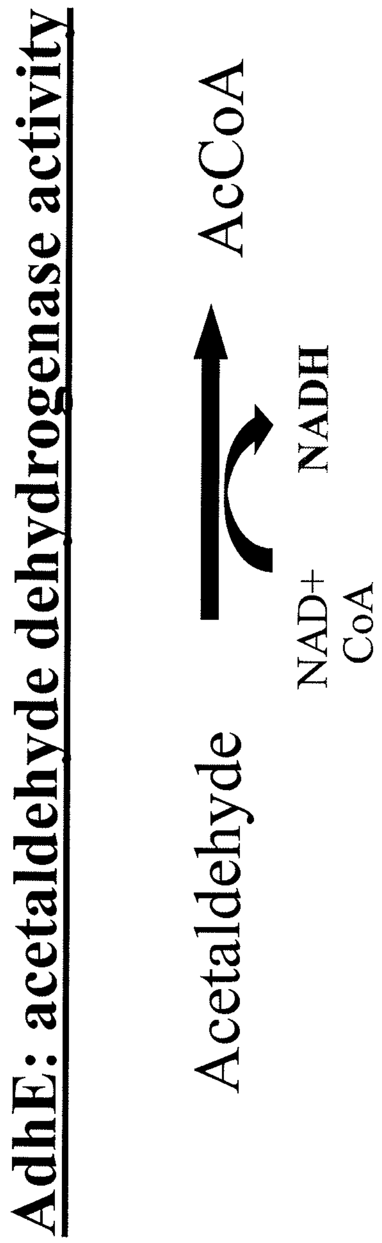
FIG. 50 shows a diagram of the reaction for the conversion of acetaldehyde to acetyl CoA by AdhE.

Acetaldehyde Dehydrogenase Activity:

The second activity of AdhE is the reversible reaction converting acetaldehyde to acetyl coenzyme A. This activity is not native to *Saccharomyces cerevisiae* strains, and should only be present in the engineered strains. In order to evaluate the presence of this enzyme and ensure that it has the desired activity, an assay was developed to measure the conversion of acetaldehyde to acetyl CoA by AdhE. The rate of the reaction is monitored by NADH absorbance at 340 nm. A diagram of the reaction is provided in FIG. 50.

Strain Growth Conditions:

Strains were patched from a freezer stock onto a YPD (20 g/L peptone, 10 g/L yeast extract, 20 g/L dextrose) agar plate and incubated overnight at 35° C. From that plate, 50 mL shake tubes with 25 mL YPD (20 g/L peptone, 10 g/L yeast extract, 20 g/L dextrose) were inoculated and incubated at 35° C., 250 rpm overnight. The cultures were centrifuged at 5000 rpm×5 min at 4° C., washed with DI water and centrifuged at 5000 rpm×5 min at 4 C, washed a second time with DI water and centrifuged at 5000 rpm×5 min at 4° C., and then put on ice.

Cell Lysis and Sample Preparation:

100 μL of wet cell pellet was pipetted into a Zymo Research BashingBead 0.5 mm Tubes along with 5004, 100 mM $Na_2PO_4$, 2.5 mM $MgCl_2$, 0.5 mM $CaCl_2$ pH 7.4 buffer and 6 μL 100 mM phenylmethylsulfonyl fluoride (PMSF). The cells were lysed by mechanical disruption using a MP FastPrep-24 set to run at 4.0 m/s for 10 seconds three times with cooling on ice for 10 seconds between each run. This was repeated three times with chilling on ice for one minute in between each run. Each tube was then centrifuged for 10 minutes at 15,000 rpm using an Eppendorf centrifuge 5424. The supernatant was removed and transferred to 2 mL tubes. 1 μL of New England Biolabs DNAse I was added to each tube. The tubes were inverted and placed into an incubator set at 37° C. for 30 min. The tubes were removed from the incubator and the samples were transferred to 0.22 μm filter centrifuge tubes which were centrifuged for 2 min at 10,000 rpm using the Eppendorf centrifuge 5424. 50 μL of sample was pulled and diluted with 450 μL 100 mM $Na_2PO_4$ pH 7.4 in separate sample tubes and then were placed on ice.

Acetaldehyde Dehydrogenase Activity Assay:

800 μL 50 mM $Na_4P_2O_7$ pH 9.6, 50 μL 0.025M NAD+, 50 μL 1M acetaldehyde, and 50 μL 1:10 diluted lysate were added to a Plastibrand micro UV-cuvette. The cuvette was placed into a Shimadzu UV-1700 set to read absorbance at 340 nm. 50 μL of 2 mM CoA were pipetted into the cuvette which was then mixed by gently pipetting the contents of the cuvette and the absorbance was monitored for 5 minutes. The resulting final concentrations of each reagent were 40 mM $Na_4P_2O_7$ pH 9.6, 1.25 mM $NAD^+$, 50 mM acetaldehyde, and 0.1 mM CoA. Each sample was done in duplicate to ensure reproducibility. Thermo Scientific's BCA Protein Assay Kit was used to measure total protein concentration from the lysate generated. This data was used to normalize the data generated from the actual reaction during analysis.

Data for alcohol dehydrogenase (acetaldehyde dehydrogenase activity) assay is shown in Table 23. Note the lysate used in this assay was the same lysate used in the alcohol dehydrogenase assay detailed in the previous section.

TABLE 23

| Acetaldehyde Dehydrogenase Activity | | | | |
|---|---|---|---|---|
| | Average activity (μmol NADH/min/mg) | Standard Deviation | % CV | p-value |
| M2390 | 0 | 0 | 0.0 | |
| M3465 | 163 | 24 | 14.7 | 0.0054 |
| M3625 | 115 | 7.07 | 6.2 | 0.0009 |
| M3679 | 106 | 9.97 | 9.4 | 0.0022 |
| M3680 | 177 | 7.07 | 4.0 | 0.0004 |

Acetaldehyde dehydrogenase activity. p-value was based on a one-tailed T-test.

The background strain, M2390, performed as expected in this assay. The wild-type strain should have no acetaldehyde dehydrogenase activity, as demonstrated by this assay. The other strains with AdhE engineered into their genomes should have expressed the protein and had acetaldehyde dehydrogenase activity. This activity was observed in all of the engineered strains (M3465, *M*3625, *M*3679, and M3680) with minimal error and a p-value of $<0.05$.

Formate Dehydrogenase Activity

In strains M3465, *M*3625, *M*3679, and M3680 formate dehydrogenase was knocked out of the genome in the hopes to balance redox with the various engineering steps that were undertaken. The background strain, M2390, should have the gene intact. To ensure that the native *Saccharomyces cerevisiae* formate dehydrogenase gene was removed, an enzymatic assay was developed. Formate dehydrogenase catalyzes the conversion of formate to carbon dioxide at the expense of $NAD^+$.

$$\text{Formate} + NAD^+ \xrightarrow{FDH} CO2 + NADH$$

Enzymatic activity can be monitored by measuring NADH formation at 340 nm.

Strain Growth Conditions:

M2390, *M*3465, *M*3625, *M*3679, and M3680 were patched from a freezer stock onto a YPD (20 g/L peptone, 10 g/L yeast extract, 20 g/L dextrose) agar plate and incubated overnight at 35° C. From that plate, 50 mL shake tubes with 25 mL YPD+24 mM Sodium Formate were inoculated and incubated at 35° C., 250 rpm overnight (20 g/L peptone, 10 g/L yeast extract, 20 g/L dextrose). The cultures were centrifuged at 5000 rpm×5 min at 4° C., washed with DI water and centrifuged at 5000 rpm×5 min at 4° C., washed a second time with DI water and centrifuged at 5000 rpm×5 min at 4 C, and then put on ice.

Cell Lysis and Sample Preparation:

100 μL of wet cell pellet was pipetted into a Zymo Research BashingBead 0.5 mm Tubes along with 500 μL 100 mM $Na_2PO_4$, 2.5 mM $MgCl_2$, 0.5 mM $CaCl_2$ pH 7.4 buffer and 6 μL 100 mM phenylmethylsulfonyl fluoride (PMSF). The cells were lysed by mechanical disruption using a MP FastPrep-24 set to run at 4.0 m/s for 10 seconds three times with cooling on ice for 10 seconds between each run. This was repeated three times with chilling on ice for one minute in between each run. Each tube was then centrifuged for 10 minutes at 15,000 rpm using an Eppendorf centrifuge 5424. The supernatant was removed and transferred to 2 mL tubes. 1 μL of New England Biolabs DNAse I was added to each tube. The tubes were inverted and placed into an incubator set at 37° C. for 30 min. The tubes were removed from the incubator and the samples were transferred to 0.22 μm filter centrifuge tubes which were centrifuged for 2 min at 10,000 rpm using the Eppendorf centrifuge 5424.

Formate Dehydrogenase Activity Assay:

800 μL 62.5 mM $K_2PO_4$ pH 7.0, 50 μL 40 mM NAD+, and 50 uL 1M Sodium Formate were added to a Plastibrand micro UV-cuvette. The cuvette was placed into a Shimadzu UV-1700 set to read absorbance at 340 nm and blanked. 100 μL of undiluted lysate sample were pipetted into the cuvette which was then mixed by gently pipetting the contents of the cuvette and the absorbance was monitored for 2.5 minutes. The resulting final concentrations of each reagent were 50 mM Potassium Phosphate, 2 mM NAD+, and 0.05M Sodium Formate. Each sample was done in duplicate to ensure reproducibility.

TABLE 24

| Fdh activity of engineered strains | | | |
|---|---|---|---|
| | Average μmol NADH/min | Standard Deviation | % CV |
| M3631 | 0.03 | 0.00269 | 0.865 |
| M2390 | 0.008 | 0 | 0 |
| M3465 | 0 | 0 | 0 |
| M3625 | 0 | 0 | 0 |
| M3679 | 0 | 0 | 0 |
| M3680 | 0 | 0 | 0 |

As shown in Table 24, the FDH knockout strains (M3465, *M*3625, *M*3679, and M3680) did not exhibit any formate dehydrogenase activity. The background strain, M2390, had minimal activity. The positive control strain, M3631, which overexpresses FDH was active and produced a significant amount of NADH that was observed and recorded.

AE9 glucoamylase activity assay:

*Saccharomycopsis fibuligera* GLU1 glucoamylase (AE9) produces glucose from starch.

Extracellular AE9 glucoamylase activity on raw corn starch was assayed to determine the presence of glucoamylase activity in aerobic culture supernatants of engineered strains. Cells were grown aerobically, removed by centrifugation, and the resulting supernatant was assayed for activity and compared to supernatant from strain M2390, which does not contain AE9.

Cell Growth Conditions:

Cells were plated on YPD (20 g/L peptone, 10 g/L yeast extract, 20 g/L dextrose) agar for 48 hours and used to inoculate 25 mL YPD (20 g/L peptone, 10 g/L yeast extract, 20 g/L glucose) in a 50 mL culture tube. Cells were grown aerobically for 48 hours at 35° C. with shaking at 250 rpm. After 48 hours, cells were removed via centrifugation and the supernatant was recovered.

Sample Preparation:

The recovered aerobic culture supernatant was clarified by filtration through a 0.22 μm filter membrane and concentrated ~10× using a 10 kDa molecular weight cut-off filter. The retained concentrate was then analyzed for AE9 concentration via a phenyl reverse phase (phenyl-RP) HPLC method developed in-house using purified AE9 as a standard. Samples were diluted to an AE9 concentration of 50 μg/mL and used directly in the activity assay.

Glucoamylase Activity Assay:

A 2.2% (weight by volume) corn starch solution was made up in 50 mM sodium acetate buffer pH 5.0. In a 96-well assay plate, 504 of supernatant (adjusted to 50 μg/mL AE9 concentration) was added to 450 μL 2.2% starch.

The plate was incubated at room temperature without shaking, and 50 μL of sample was taken at 1, 2, 5, 10, 30, 120 and 210 minutes. Wells were mixed by pipette aspiration after initial enzyme addition, as well as at each sampling thereafter. Samples were analyzed via 3,5-dinitrosalicylic acid (DNS) method to determine reducing sugars.

Figure 42:
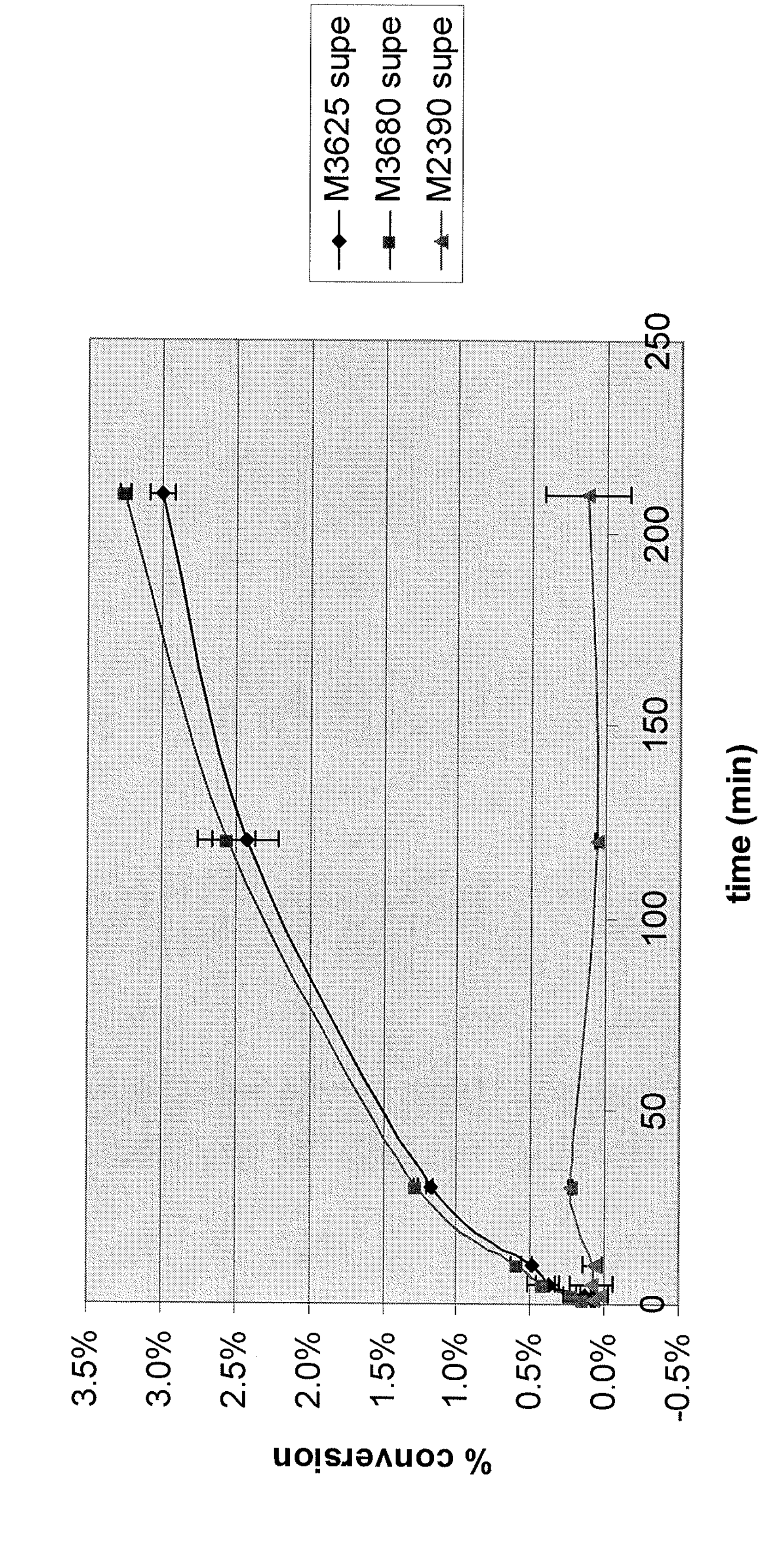
FIG. 42 shows a graph depicting the results of a glucoamylase activity assay performed with engineered strains M3625 and M3680 using 50 μg/mL AE9 on corn starch at room temperature (~25° C.).

As shown in FIG. 42, the aerobic culture supernatants of M3625 and M3680 showed similar activity on raw corn starch, as measured by DNS analysis (Somogyi, M., Notes on Sugar Determination, JBC (200)45 (1952)). Amylolytic activity of M2390 supernatant was negligible in this assay.

The above data show that pflA, pflB and AdhE are present in strain M3625 and have the proper activity. Fdh activity, seen in the background strain as well as in the positive control when fdh was overexpressed, was not present in the engineered strains indicating that this gene was knocked out successfully.

Example 9

Figure 43A:
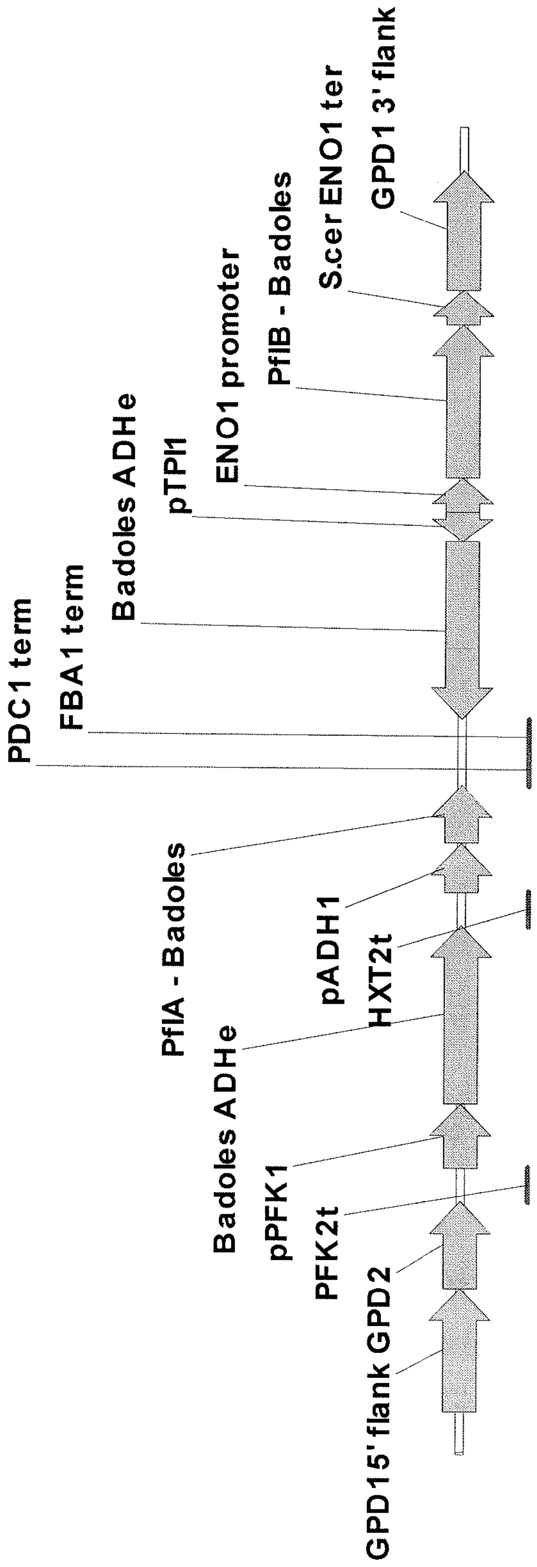
FIG. 43A is a schematic showing insertion of promoters and terminators used to express, GPD2, and *B. adolescentis* pflA, pflB and adhE at the GPD1 locus in M3624 and M3515.
Figure 43B:
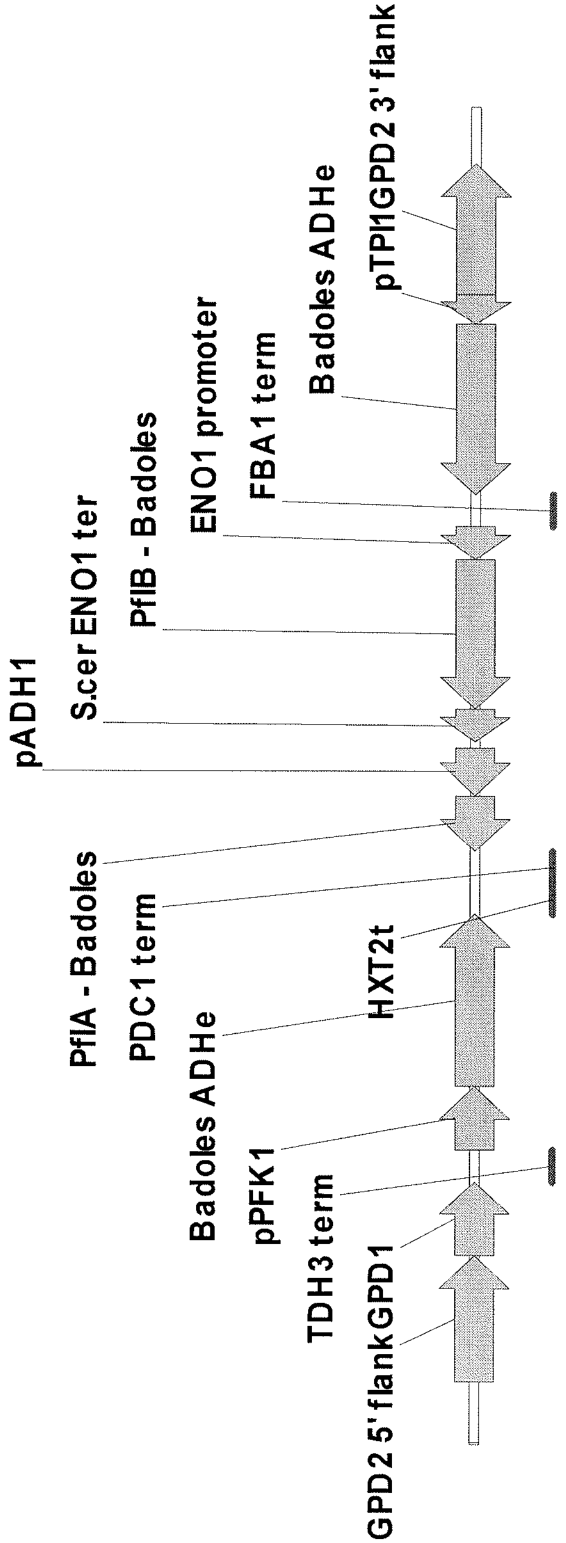
FIG. 43B is a schematic showing insertion of promoters and terminators used to express GPD1 and *B. adolescentis* pflA, pflB and adhE at the GPD2 locus in M3624 and M3515.
Figure 43C:
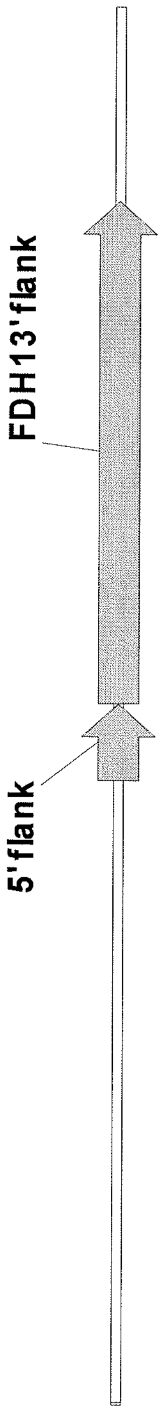
FIG. 43C is a schematic showing deletion of the FDH1 gene in M3624 and M3515.
Figure 43D:
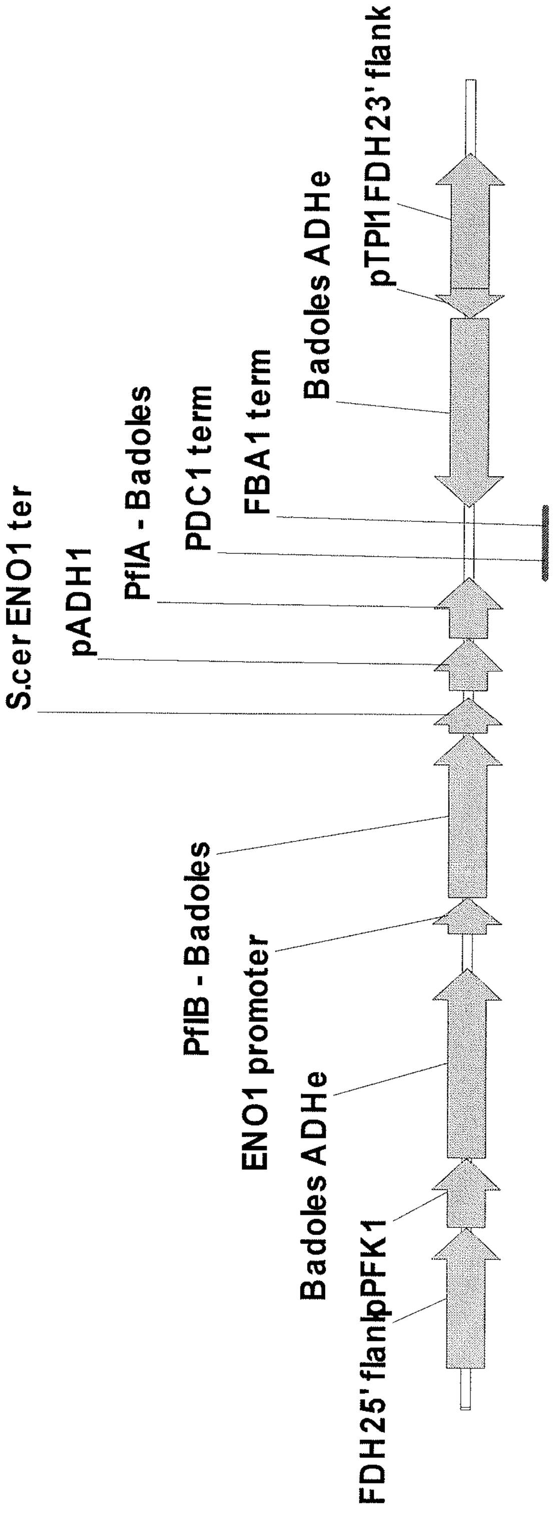
FIG. 43D is a schematic showing insertions of promoters and terminators used to express *B. adolescentis* pflA, pflB and adhE at the FDH2 locus in M3624 and M3515.

The following example demonstrates the ethanol yield of the *Saccharomyces cerevisiae* strain M3624. The genotype of strain M3624 is: Δgpd1::GPD2-*B. adolescentis* pflA/pFlB/adhEΔgpd2::GPD1-*B. adolescentis* pflA/pflB/adhE Δfdh1 Δfdh2::*B. adolescentis* pflA/pflB/adhE. Strain M3624 was created according to the same methods employed above in Example 8. Detailed molecular maps for strain M3624 are shown in FIGS. 43A-D. FIG. 43A shows insertion at the GPD1 locus; GPD2 expressed from the GPD1 promoter; PFK2t-PFK2 terminator; HXT2t-HXT2 terminator; pADH1-ADH1 promoter; PDC1 term-PDC1 terminator; FBA1 term-FBA1 terminator; pTPI1-TPI1 promoter; Scer ENO1 ter-ENO1 terminator. FIG. 43B shows insertion at the GPD2 locus; GPD1 expressed from the GPD2 promoter; TDH3 term-TDH3 terminator; pPFK1-PFK1 promoter; HXT2t-HXT2 terminator; PDC1 term-PDC1 terminator; pADH1-ADH1 promoter; S.cer ENO1 ter-ENO1 terminator; FBA1 term-FBA1 terminator; pTPI1-TPI1 promoter. FIG. 43C shows deletion of the FDH1 gene; flanking regions to create deletion of FDH1. FIG. 43D shows insertion at the FDH2 locus; pPFK1-PFK1 promoter, S.cer ENO1 ter-ENO1 terminator; pADH1-ADh1 promoter; FBA1 term-FBA1 terminator; PDC1 term-PDC1 terminator; pTPI-TPI1 promoter.

Figure 44:
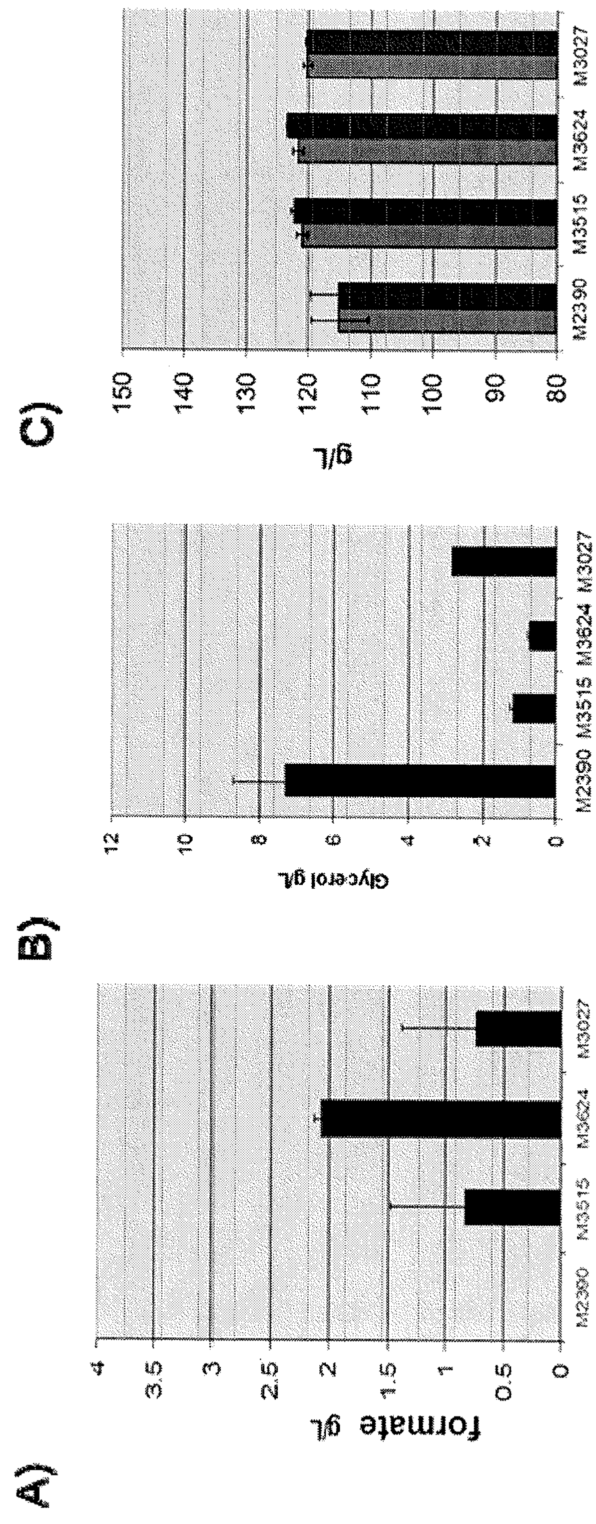
FIG. 44A shows HPLC analysis of formate produced by glycerol reduction strains during fermentation of 28% solids corn mash.
FIG. 44B shows HPLC analysis of glycerol produced by glycerol reduction strains during fermentation of 28% solids corn mash.
FIG. 44C shows HPLC analysis of ethanol produced by glycerol reduction strains during fermentation of 28% solids corn mash.

The data shown in FIG. 44 demonstrates that a 3.4% ethanol yield increase is obtained through reduction of glycerol and production of formate. M2390 is the control strain, M3515 and M3624 are engineered with the genotype Δgpd1::GPD2-*B. adolescenits* pflA/pflB/adhE Δgpd2::GPD1-*B. adolescentis* pflA/PFlB/adhE fdh1Δfdh2Δ::*B. adolescentis* pflA/pflB/adhE. M3027 is engineered with the genotype Δgpd1 Δgpd2::GPD1-*B. adolescentis* pflA/PFlB/adhE fdh1Δfdh2Δ::*B. adolescentis* pflA/pflB/adhE. Panel A shows measurement of formate concentration, panel B shows measurement of glycerol concentration, and panel C shows measurement of ethanol concentration.

Both M3515 and M3624 have been engineered at 4 separate loci. The GPD1 gene is expressed from the GPD2 promoter and the GPD2 gene is expressed from the GPD1 promoter, the FDH1 and FDH2 genes have been deleted. Additionally, the *B. adolescentis* pflA, pflB and adhE genes are expressed as shown in FIGS. 43A, B, and D.

Example 10

Figure 45A:
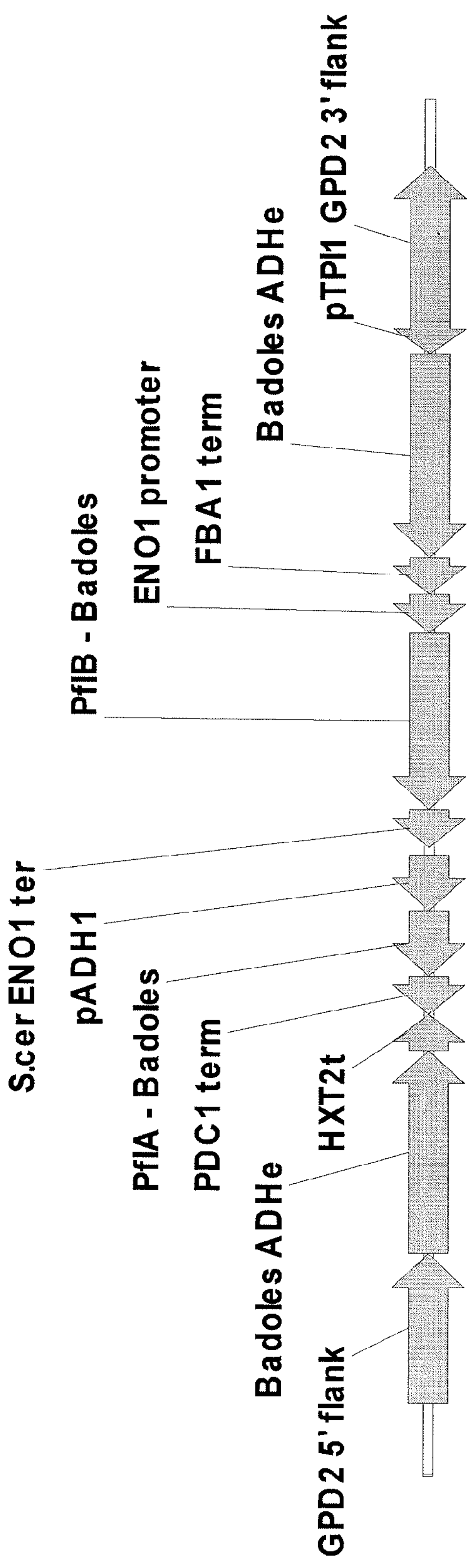
FIG. 45A is a schematic showing insertion of promoters and terminators used to express *B. adolescentis* pflA, pflB and adhE at the GPD2 locus in M3465.
Figure 45B:
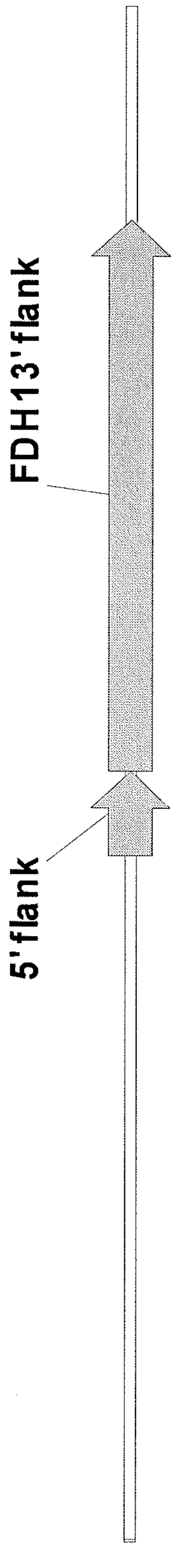
FIG. 45B is a schematic showing deletion of the FDH1 gene in M3465.
Figure 45C:
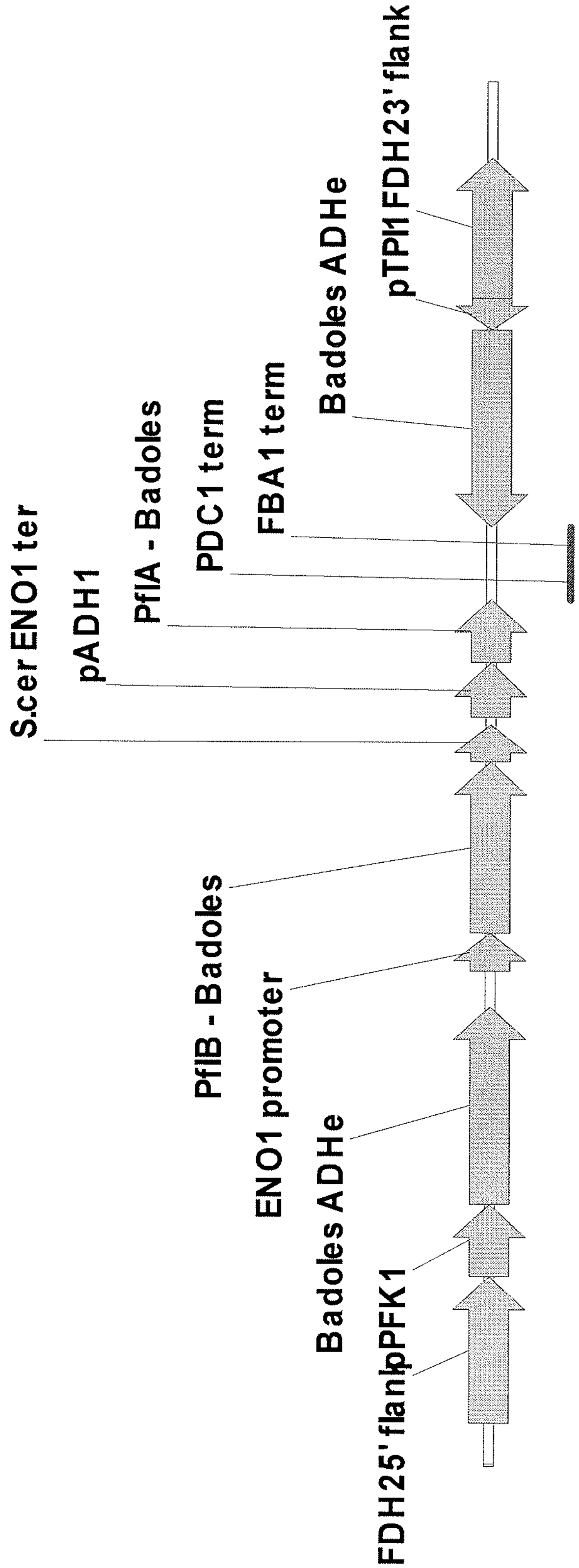
FIG. 45C is a schematic showing insertion of promoters and terminators used to express *B. adolescentis* pflA, pflB and adhE at the FDH2 locus in M3465.
Figure 46A:
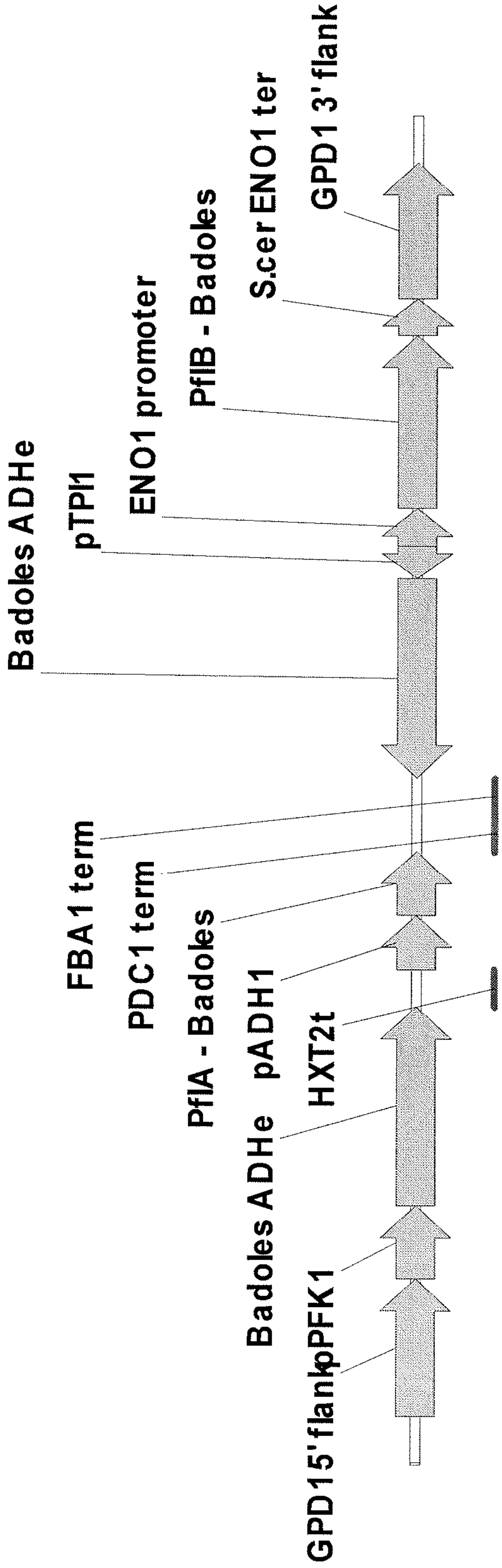
FIG. 46A is a schematic showing insertion of promoters and terminators used to express *B. adolescentis* pflA, pflB and adhE at the GPD1 locus in M3469.
Figure 46B:
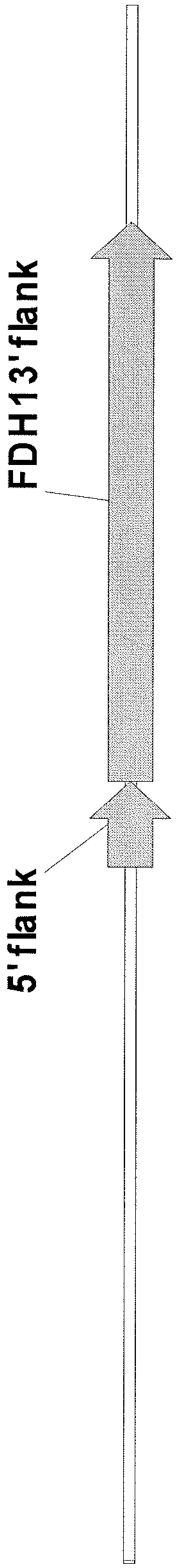
FIG. 46B is a schematic showing deletion of the FDH1 gene in M3469.
Figure 46C:
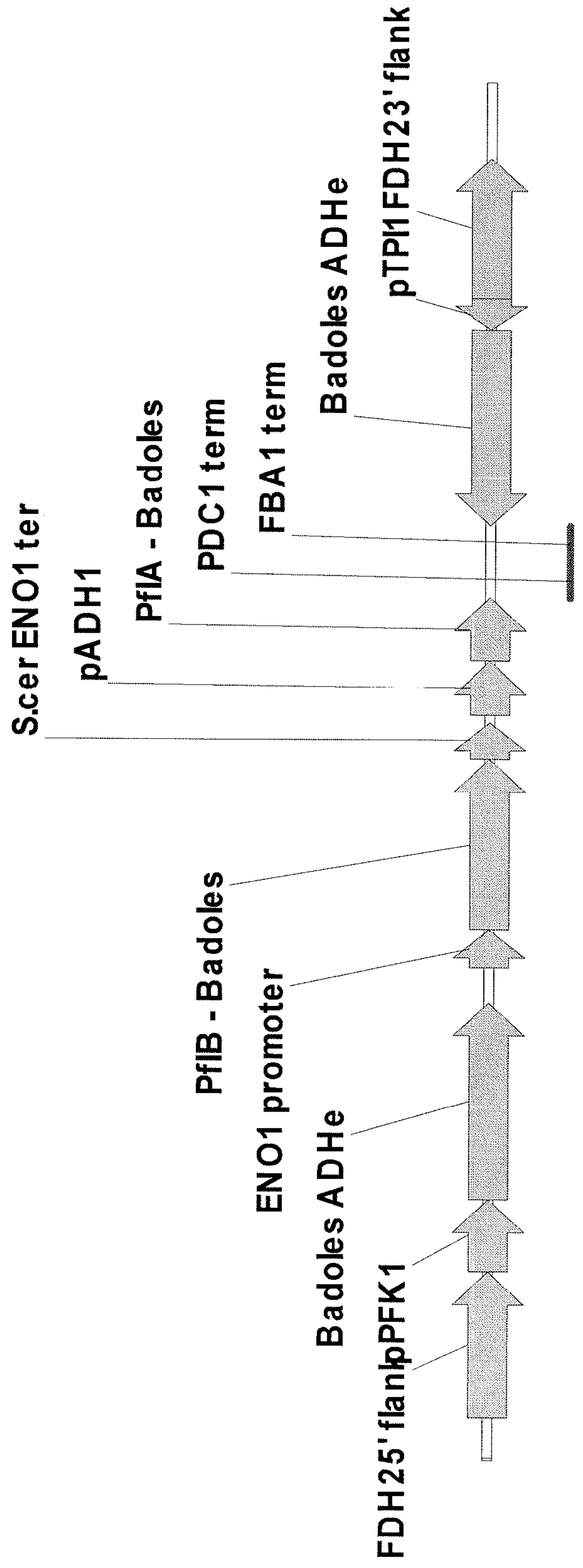
FIG. 46C is a schematic showing insertion of promoters and terminators used to express *B. adolescentis* pflA, pflB and adhE at the FDH2 locus in M3469.

The following example demonstrates the ethanol yield of the *Saccharomyces cerevisiae* strains M3465 and M3469. The genotype of strain M3465 is: Δgpd2::*B. adolescentis* pflA/pflB/adhE Δfdh1Δ fdh2::*B. adolescentis* pflA/pflB/adhE. The genotype of strain M3469 is: Δgpd1::*B. adolescentis* pflA/pflB/adhE fdh1Δ fdh2Δ::*B. adolescentis* pflA/pflB/adhE. Strains M3465 and M3469 were created according to the same methods employed above in Example 8. Detailed molecular maps of strains M3465 and M3469 are shown in FIGS. 45 A-C and 46 A-C, respectively. FIG. 45A shows insertion at the GPD2 locus; pPFK1-PFK1 promoter; HXT2t-HXT2 terminator; PDC1 term-PDC1 terminator; pADH1-ADH1 promoter; S.cer ENOL ter-ENOL terminator; FBA1 term-FBA1 terminator; pTPI1-TPI1 promoter. FIG. 45B shows deletion of the FDH1 gene; flanking regions to create deletion of FDH1. FIG. 45C shows insertion at the FDH2 locus; pPFK1-PFK1 promoter; S.cer ENO1 ter-ENO1 terminator; pADH1-ADh1 promoter; FBA1 term-FBA1 terminator; PDC1 term-PDC1 terminator; pTPI-TPI1 promoter. FIG. 46A shows insertion at the GPD1 locus; pPFK1-PFK1 promoter; HXT2t-HXT2 terminator; PDC1 term-PDC1 terminator; pADH1-ADH1 promoter; S.cer ENO1 ter-ENO1 terminator; FBA1 term-FBA1 terminator; pTPI1-TPI1 promoter. FIG. 46B shows deletion of the FDH1 gene; flanking regions to create deletion of FDH1. FIG. 46C shows insertion at the FDH2 locus; pPFK1-PFK1 promoter, S.cer ENO1 ter-ENO1 terminator; pADH1-ADh1 promoter; FBA1 term-FBA1 terminator; PDC1 term-PDC1 terminator; pTPI-TPI1 promoter.

Figure 47:
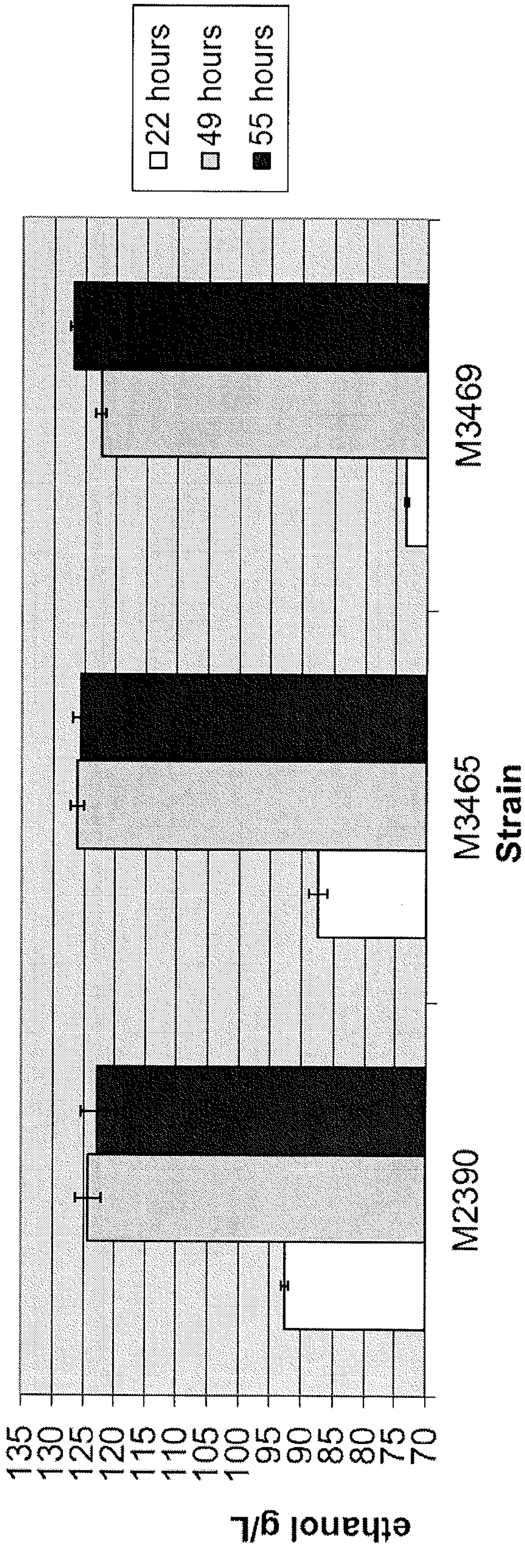
FIG. 47 shows HPLC analysis of ethanol titers produced by glycerol reduction strains during fermentation of 30% solids corn mash.
Figure 48:
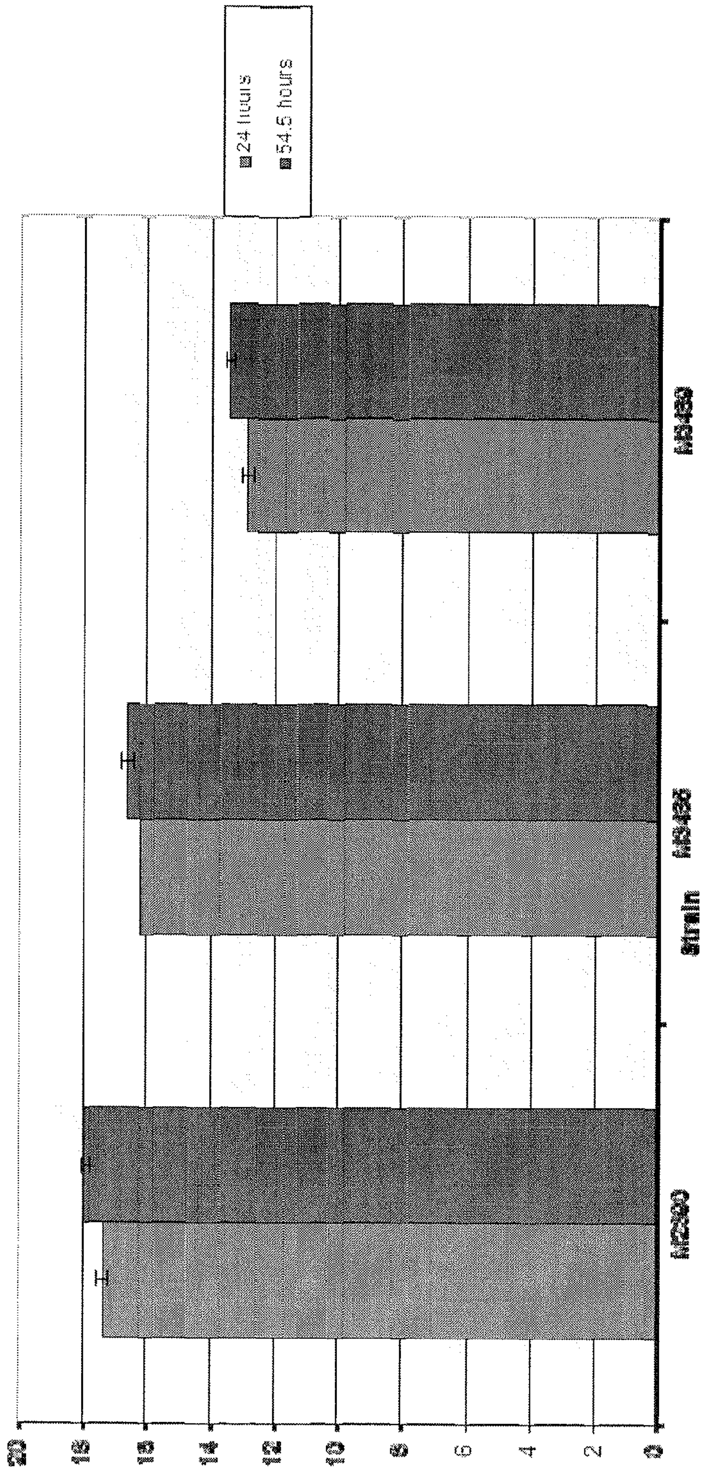
FIG. 48 shows HPLC analysis of glycerol titers produced by glycerol reduction strains during fermentation of 30% solids corn mash.

This example demonstrates that the ethanol yield increase is dependent on the level of glycerol reduction. Fermentation of 30% solids corn mash by M3465, which contains a deletion of the GPD2, FDH1 and FDH2 genes and expression of *B. adolescentis* pflA, pflB and adhE genes from the GPD2 and FDH2 loci, results in a 1.5% increase in ethanol titer. As shown in FIG. 47, fermentation of 30% solids corn mash by M3469, which contains a deletion of the GPD1, FDH1 and FDH2 genes and expression of *B. adolescentis* pflA, pflB and adhE genes from the GPD1 and FDH2 loci, results in a 2.5% increase in ethanol titer. M2390 is the control parent strain. As shown in FIG. 48, fermentation of corn mash by M3465 and M3469 results in ~15% lower glycerol and 30% lower glycerol levels respectively. M2390, represented in FIGS. 47 and 48, is the control strain.

Example 11

Figure 53:
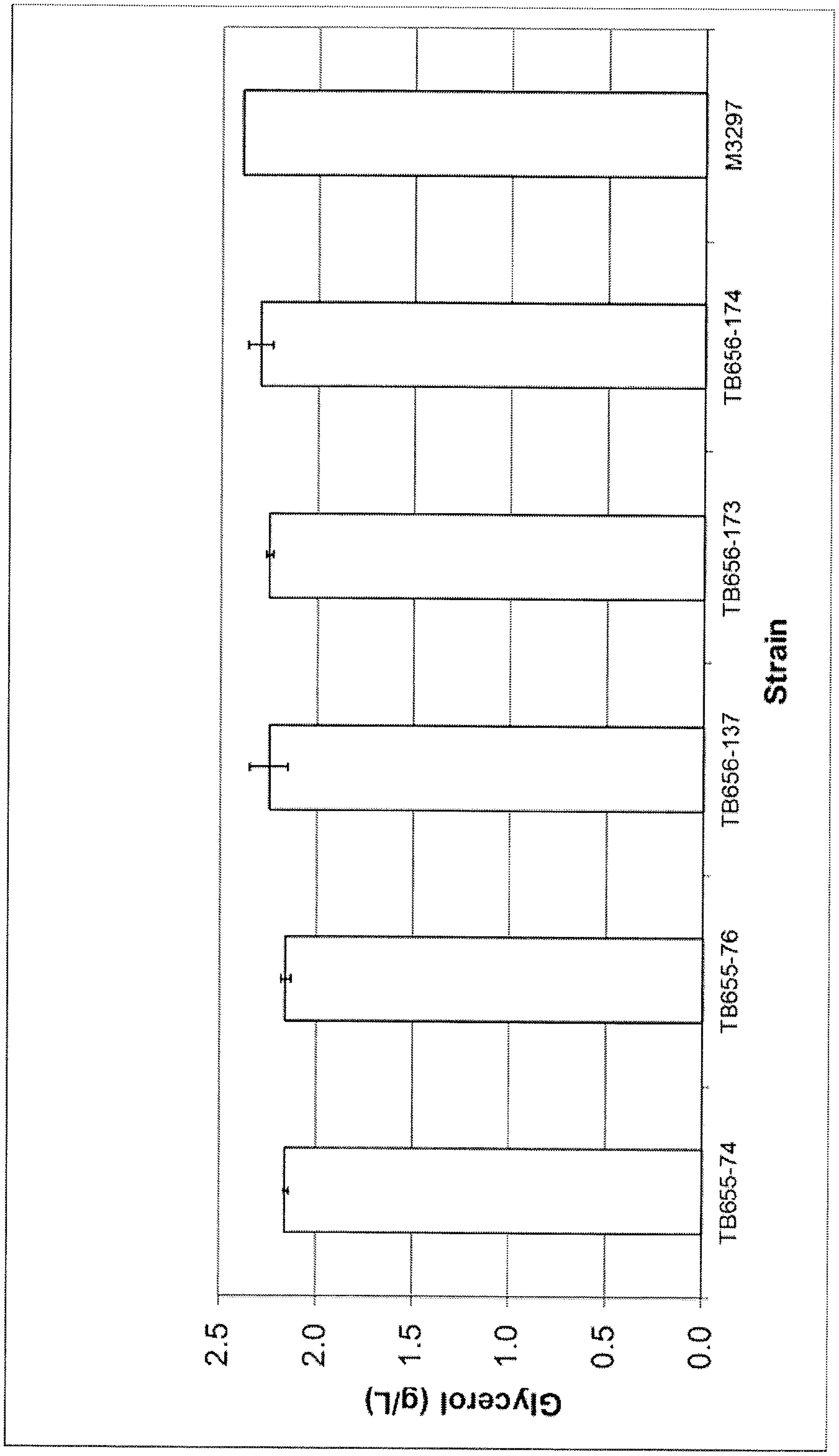
FIG. 53 is a graph depicting decreased glycerol formation in strains TB655 and TB656 compared to strain M3297.
Figure 54:
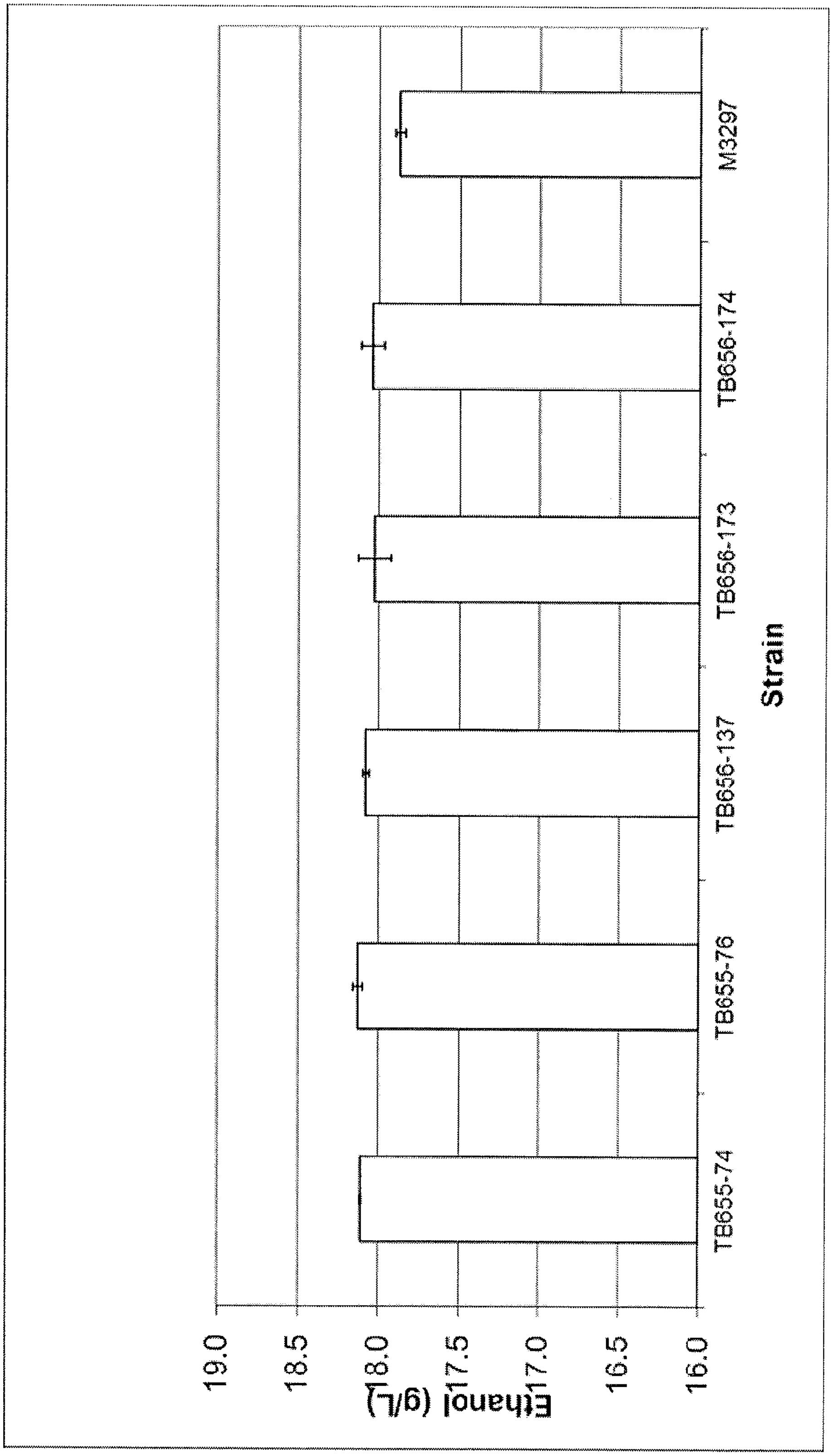
FIG. 54 is a graph depicting increased ethanol yield in strains TB655 and TB656 compared to strain M3297.
Figure 55:
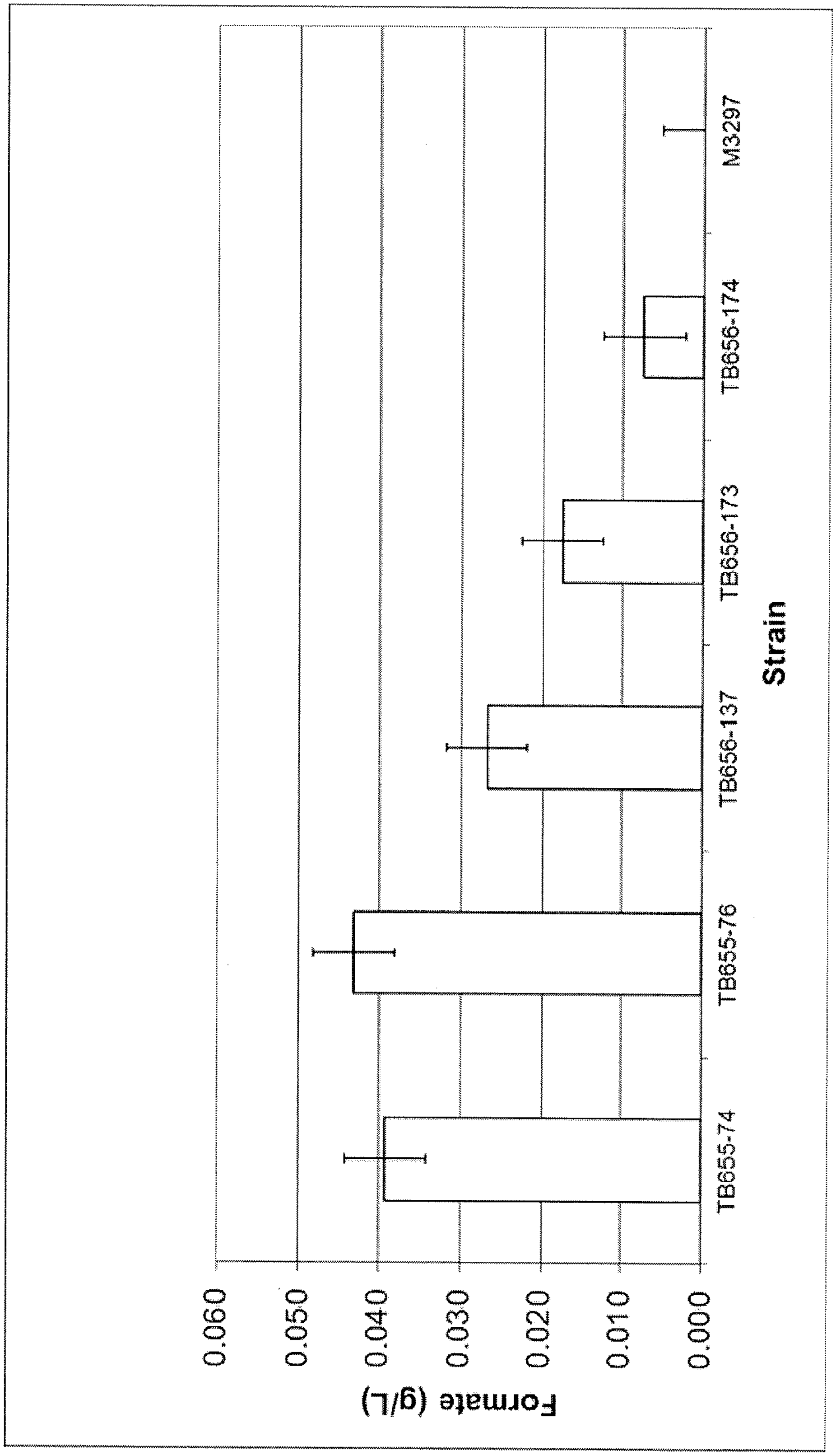
FIG. 55 is a graph depicting formate production in strains TB655, TB656, and M3297.

An alternative way to reduce glycerol formation is through deletion of the glycerol-3-phosphate phosphatase (GPP) genes. *Saccharomyces* contains two copies of these genes, GPP1 and GPP2. The data below demonstrates that expression of *B. adolescentis* pflA, pflB and adhE in backgrounds containing deletions of FDH1, FDH2 and either GPP1 or GPP2 results in decreased glycerol formation (FIG. 53; strain comparison, min buff medium, glucose 40 g/L, anaerobic fermentations, 35° C.-72 hr.) and increased ethanol yield (FIG. 54; strain comparison, min buff medium, glucose 40 g/L, anaerobic fermentations, 35° C.-72 hr.). Production of formate was also observed. See FIG. 55 (strain comparison, min buff medium, glucose 40 g/L, anaerobic fermentations, 35° C.-72 hr.).

Figure 51:
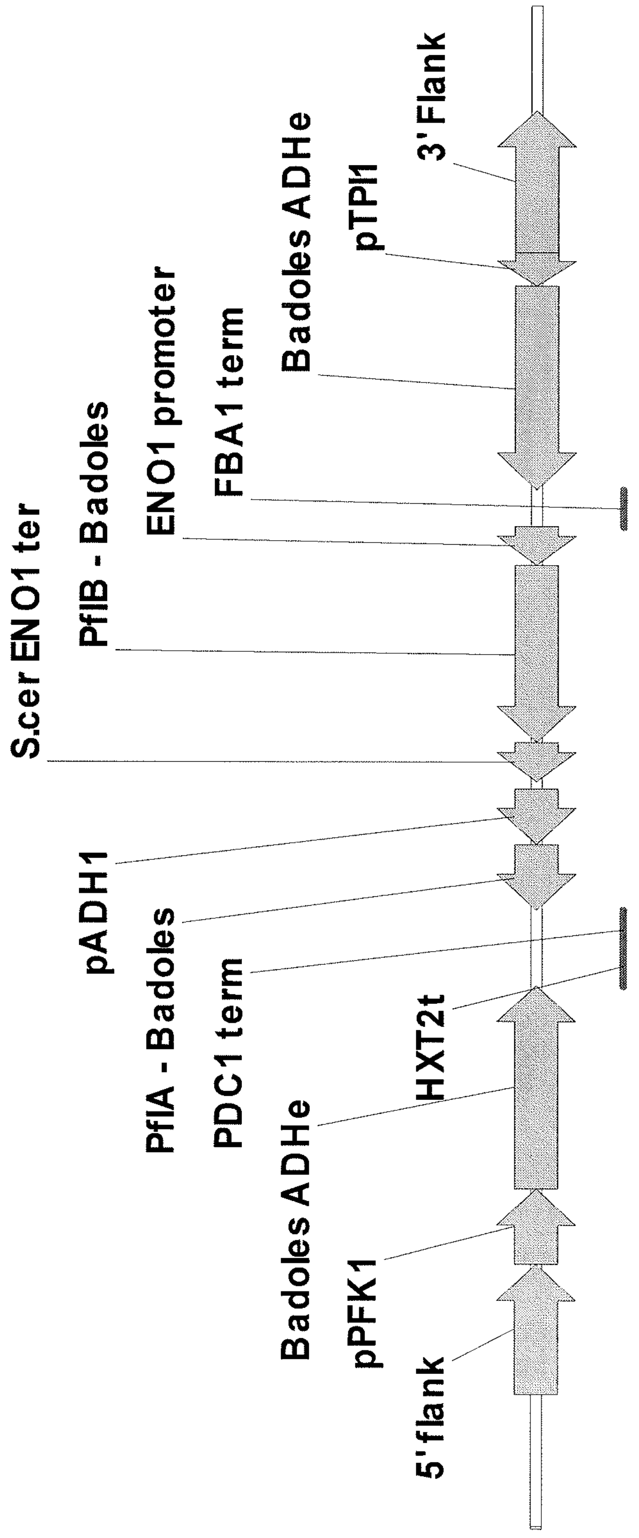
FIG. 51 is a schematic showing insertion of promoters and terminators used to express *B. adolescentis* pflA, pflB and adhE at the GPP1 locus in TB655.
Figure 52:
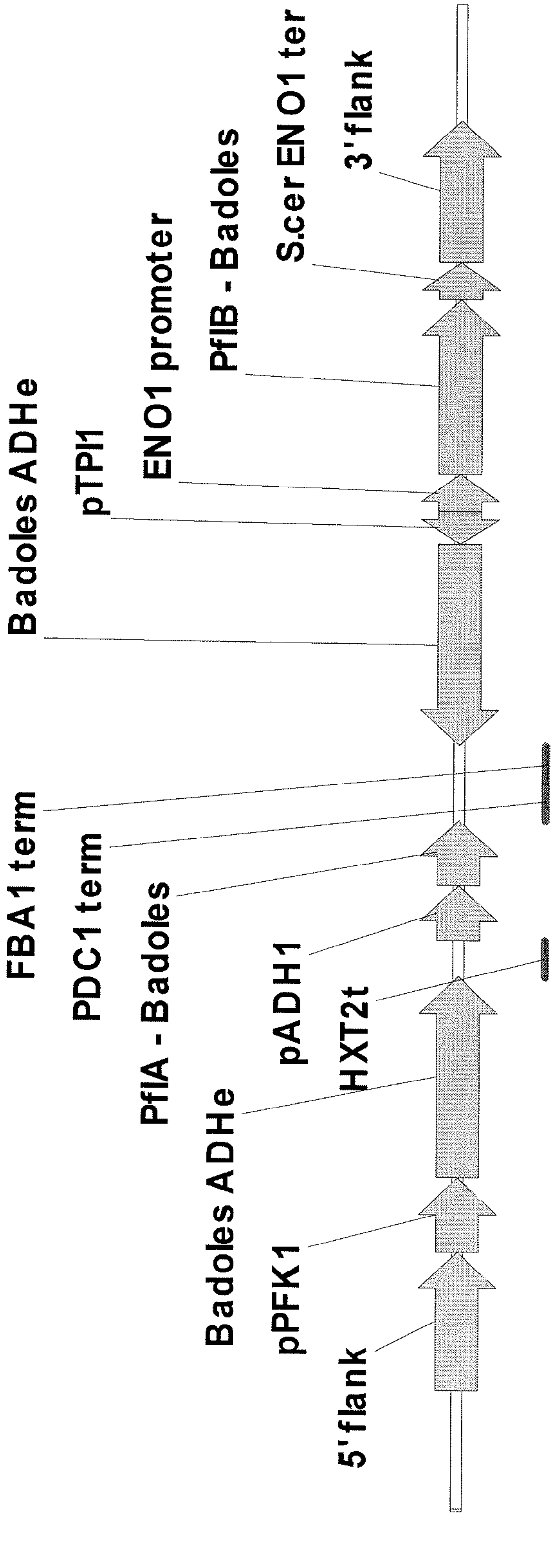
FIG. 52 is a schematic showing insertion of promoters and terminators used to express *B. adolescentis* pflA, pflB and adhE at the GPP2 locus in TB656.

The strains engineered to measure the glycerol formation, ethanol yield, and formate production were the *Saccharomyces cerevisiae* strains M3297, TB655, and TB656. Strains M3297, TB655, and TB656 were created according to the same methods employed above in Example 8. The genotype of strain M3297 is: Δfdh1Δfdh2::pflA/pflB/adhE. This strain contains only deletion in the FDH genes plus expression fo pflA, pflB and AdhE. The genotype of strain TB655 is:

Δfdh1Δfdh2::pflA/pflB/adhEΔgpp1::pflA/pflB/adhE. This strain contains deletion in the FDH genes, expression of pflA, pflB and AdhE, and deletion of GPP1. See FIG. 51. The genotype of strain TB656 is: Δfdh1Δfdh2::pflA/pflB/adhEΔgpp2::pflA/pflB/adhE. This strain contains deletion in the FDH genes, expression of pflA, pflB and AdhE and deletion of GPP1. See FIG. 52.

The amount of ethanol, glycerol, and formate produced by strains TB655 and TB656 was measured using the methods described above. Compared to the control strain M3297, strains TB655 and TB656 demonstrated statistically significant changes in the amount of ethanol, glycerol, and formate produced. Relative to strain M3297, strain TB655 (gpp1 mutant) demonstrated a 1.3% increase in ethanol titer, 10% reduction in glycerol, and 100% more formate produced, whereas strain TB656 (gpp2 mutant) demonstrated a 0.95% increase in ethanol titer, 6.1% reduction in glycerol formation, and 100% more formate produced. These results demonstrate the novel combination of GPP mutation with a metabolic engineering solution to balance redox during anaerobic growth.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant yeast comprising:

(a) a deletion of one or more native enzymes that function to produce glycerol and/or regulate glycerol synthesis, wherein said one or more enzymes is encoded by a gpd1, gpd2, gpp1, gpp2 or fps1 polynucleotide; and (b) one or more native and/or heterologous enzymes that function in one or more engineered metabolic pathways to convert a carbohydrate source to ethanol, wherein one of said metabolic pathways comprises conversion of pyruvate to acetyl-CoA and formate by a pyruvate formate lyase, wherein one of said metabolic pathways comprises conversion of acetyl-CoA to ethanol by an acetaldehyde dehydrogenase, alcohol dehydrogenase, or a bifunctional acetaldehyde/alcohol dehydrogenase, and wherein said one or more native and/or heterologous enzymes is activated, upregulated or downregulated.

2. The recombinant yeast of claim 1, wherein said one or more native enzymes that function to produce glycerol is encoded by both a gpd1 polynucleotide and a gpd2 polynucleotide, and wherein one of said engineered metabolic pathways comprises conversion of acetyl-CoA to ethanol by a bifunctional acetaldehyde/alcohol dehydrogenase, and further comprising a deletion of one or more native enzymes encoded by both an fdh1 polynucleotide and an fdh2 polynucleotide.

3. The recombinant yeast of claim 1, wherein said one or more native enzymes that function to produce glycerol is encoded by both a gpp1 polynucleotide and a gpp2 polynucleotide, and wherein one of said engineered metabolic pathways comprises conversion of acetyl-CoA to ethanol by a bifunctional acetaldehyde/alcohol dehydrogenase, and further comprising a deletion of one or more native enzymes encoded by both an fdh1 polynucleotide and an fdh2 polynucleotide.

4. The recombinant yeast of claim 1, wherein said one or more native enzymes that function to regulate glycerol synthesis is encoded by an fps1 polynucleotide, and wherein one of said engineered metabolic pathways comprises conversion of acetyl-CoA to ethanol by a bifunctional acetaldehyde/alcohol dehydrogenase, and further comprising a deletion of one or more native enzymes encoded by both an fdh1 polynucleotide and an fdh2 polynucleotide.

5. The recombinant yeast of claim 1, wherein said one or more native enzymes that function to regulate glycerol synthesis is encoded by an fps1 polynucleotide and said one or more native enzymes that function to produce glycerol is encoded by both a gpd1 polynucleotide and a gpd2 polynucleotide, wherein one of said engineered metabolic pathways comprises conversion of acetyl-CoA to ethanol by a bifunctional acetaldehyde/alcohol dehydrogenase, and further comprising a deletion of one or more native enzymes encoded by both an fdh1 polynucleotide and an fdh2 polynucleotide.

6. The recombinant yeast of claim 1, wherein said one or more native enzymes that function to produce glycerol is encoded by both a gpd1 polynucleotide and a gpd2 polynucleotide and wherein one of said engineered metabolic pathways comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide.

7. The recombinant yeast of claim 6, further comprising a deletion of one or more native enzymes encoded by both an fdh1 polynucleotide and an fdh2 polynucleotide.

8. The recombinant yeast of claim 1, wherein said one or more native enzymes that function to produce glycerol is encoded by both a gpd1 polynucleotide and a gpd2 polynucleotide and said one or more native enzymes that function to regulate glycerol synthesis is encoded by an fsp1 polynucleotide, and wherein one of said engineered metabolic pathways comprises conversion of acetyl-CoA to ethanol by a bifunctional acetaldehyde/alcohol dehydrogenase, further comprising a native and/or heterologous gpd1 polynucleotide operably linked to a native gpd2 promoter polynucleotide.

9. The recombinant yeast of claim 8, further comprising a deletion of one or more native enzymes encoded by both an fdh1 polynucleotide and an fdh2 polynucleotide.

10. The recombinant yeast of claim 2, wherein one of said engineered metabolic pathways comprises conversion of a carbohydrate source to one or more sugar units by a saccharolytic enzyme.

11. The recombinant yeast of claim 3, wherein one of said engineered metabolic pathways comprises conversion of a carbohydrate source to one or more sugar units by a saccharolytic enzyme.

12. The recombinant yeast of claim 4, wherein one of said engineered metabolic pathways comprises conversion of a carbohydrate source to one or more sugar units by a saccharolytic enzyme.

13. The recombinant yeast of claim 5, wherein one of said engineered metabolic pathways comprises conversion of a carbohydrate source to one or more sugar units by a saccharolytic enzyme.

14. The recombinant yeast of claim 6, wherein one of said engineered metabolic pathways comprises conversion of a carbohydrate source to one or more sugar units by a saccharolytic enzyme.

15. The recombinant yeast of claim 7, wherein one of said engineered metabolic pathways comprises conversion of a carbohydrate source to one or more sugar units by a saccharolytic enzyme.

16. The recombinant yeast of claim 8, wherein one of said engineered metabolic pathways comprises conversion of a carbohydrate source to one or more sugar units by a saccharolytic enzyme.

17. The recombinant yeast of claim 9, wherein one of said engineered metabolic pathways comprises conversion of a carbohydrate source to one or more sugar units by a saccharolytic enzyme.

18. The recombinant yeast of claim 1, wherein said one or more native enzymes that function to produce glycerol is encoded by a gpd2 polynucleotide, and wherein one of said engineered metabolic pathways comprises conversion of acetyl-CoA to ethanol by a bifunctional acetaldehyde/alcohol dehydrogenase and one of said engineered metabolic pathways comprises conversion of a carbohydrate source to one or more sugar units by a saccharolytic enzyme, and further comprising a deletion of one or more native enzymes encoded by both an fdh1 polynucleotide and an fdh2 polynucleotide.

19. The recombinant yeast of claim 1, wherein said yeast is a member of a genus selected from the group consisting of *Saccharomyces, Kluyveromyces, Candida, Pichia, Schizosaccharomyces, Hansenula, Kloeckera, Schwanniomyces*, and *Yarrowia.*

20. The recombinant yeast of claim 1, wherein said yeast is a member of a species selected from the group consisting of *S. cerevisiae, S. bulderi, S. barnetti, S. exiguus, S. uvarum, S. diastaticus, K. lac tis, K. marxianus*, and *K. fragilis.*

21. The recombinant yeast of claim 1, wherein said yeast is selected from the group consisting of *Saccharomyces cerevisiae, Kluyveromyces lactis, Kluyveromyces marxianus, Pichia pastoris, Yarrowia lipolytica, Hansenula polymorphs, Phaffia rhodozyma, Candida utliis, Arxula adeninivorans, Pichia stipitis, Debaryomyces hansenii, Debaryomyces polymmphus, Schizosaccharomyces pombe, Candida albicans*, and *Schwanniomyces occidentalis.*

22. The recombinant yeast of claim 1, wherein said yeast is *Saccharomyces cerevisiae.*

23. The recombinant yeast of claim 1, wherein said pyruvate formate lyase is from one or more of a *Bijidobacteria*, an *Escherichia*, a *Thennoanaerobacter*, a *Clostridia*, a *Streptococcus*, a *Lactobacillus*, a *Chlamydomonas*, a *Piromyces*, a *Neocallimastix*, or a *Bacillus* species.

24. The recombinant yeast of claim 1, wherein said pyruvate formate lyase is from one or more of a *Bacillus lichenifonnis*, a *Streptococcus thermophilus*, a *Lactobacillus plantarum*, a *Lactobacillus casei*, a *Bijidobacteriwn adolescentis*, a *Clostridium cellulolyticum*, a *Escherichia coli*, a *Chlamydomonas reinhardtii* PflA, a *Piromyces* sp. E2, or a *Neocallimastix frontalis.*

25. The recombinant yeast of claim 1, wherein said pyruvate formate lyase is from a *Bifidobacterium adolescentis.*

26. The recombinant yeast of claim 1, wherein said bifunctional acetaldehyde/alcohol dehydrogenase is from an *Escherichia*, a *Clostridia*, a *Chlamydomonas*, a *Piromyces*, or a *Bifidobacteria* species.

27. The recombinant yeast of claim 1, wherein said bifunctional acetaldehyde/alcohol dehydrogenase is from an *Escherichia coli, Clostridium phytofermentans, Chlamydomonas reinhardtii, Piromyces* sp. E2, or *Bifidobacterium adolescentis.*

28. The recombinant yeast of claim 1, wherein said bifunctional acetaldehyde/alcohol dehydrogenase is from a *Bifidobacterium adolescentis* or *Piromyces* sp. E2.

29. The recombinant yeast of claim 1, wherein one of said engineered metabolic pathways comprises conversion of a carbohydrate source to one or more sugar units by a saccharolytic enzyme, and wherein said saccharolytic enzyme is from a microorganism selected from the group consisting of *H. grisea, T aurantiacus, T emersonii, T reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Arabidopsis thaliana*, and *S. fibuligera.*

30. The recombinant yeast of claim 1, wherein said yeast is selected from the group consisting of *Saccharomyces cerevisiae, Kluyveromyces lactis, Kluyveromyces marxianus, Pichia pastoris, Yarrowia lipolytica, Hansenula polymorphs, Phaffia rhodozyma, Candida utliis, Arxula adeninivorans, Pichia stipitis, Debaryomyces hansenii, Debaryomyces polymmphus, Schizosaccharomyces pombe, Candida albicans*, and *Schwanniomyces occidentalis*, wherein said pyruvate formate lyase is from one or more of a *Bacillus lichenifonnis*, a *Streptococcus thermophilus*, a *Lactobacillus plantarum*, a *Lactobacillus casei*, a *Bijidobacteriwn adolescentis*, a *Clostridium cellulolyticum*, a *Escherichia coli*, a *Chlamydomonas reinhardtii* PflA, a *Piromyces* sp. E2, or a *Neocallimastix frontalis*, and wherein said bifunctional acetaldehyde/alcohol dehydrogenase is from an *Escherichia coli, Clostridium phytofermentans, Chlamydomonas reinhardtii, Piromyces* sp. E2, or *Bifidobacterium adolescentis.*

31. The recombinant yeast of claim 30, wherein one of said engineered metabolic pathways comprises conversion of a carbohydrate source to one or more sugar units by a saccharolytic enzyme, and wherein said saccharolytic enzyme is from a microorganism selected from the group consisting of *H. grisea, T aurantiacus, T emersonii, T reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Arabidopsis thaliana*, and *S. fibuligera.*

* * * * *